US007906640B2

(12) United States Patent
Bourgeron et al.

(10) Patent No.: US 7,906,640 B2
(45) Date of Patent: Mar. 15, 2011

(54) POLYNUCLEOTIDE AND PROTEIN INVOLVED IN SYNAPTOGENESIS, VARIANTS THEREOF, AND THEIR THERAPEUTIC AND DIAGNOSTIC USES

(75) Inventors: Thomas Bourgeron, Paris (FR); Stephane Jamain, Paris (FR); Helene Quach, Paris (FR); Catalina Betancur, Paris (FR); Marion Leboyer, Paris (FR); Christopher Gillberg, Goteberg (SE)

(73) Assignees: Institut National de la Sante Et de la Recherche Medicale (INSERM), Paris (FR); Institut Pasteur, Paris (FR); Assistance Publique-Hopitaux de Paris, Paris (FR)

( * ) Notice: Subject to any disclaimer, the term of this patent is extended or adjusted under 35 U.S.C. 154(b) by 234 days.

(21) Appl. No.: 11/931,784

(22) Filed: Oct. 31, 2007

(65) Prior Publication Data

US 2009/0202992 A1 Aug. 13, 2009

Related U.S. Application Data

(63) Continuation of application No. 10/496,011, filed as application No. PCT/FR02/04134 on Dec. 2, 2002, now Pat. No. 7,384,740.

(30) Foreign Application Priority Data

Nov. 30, 2001 (CA) ..................... 2364106

(51) Int. Cl.
*C07H 21/04* (2006.01)
*C07H 21/02* (2006.01)
*C07K 16/18* (2006.01)
*C12Q 1/68* (2006.01)
*G01N 33/53* (2006.01)
(52) U.S. Cl. ........ 536/24.31; 530/387.9; 435/6; 435/7.1
(58) Field of Classification Search ........................ None
See application file for complete search history.

(56) References Cited

FOREIGN PATENT DOCUMENTS

WO 99/55915 11/1999
WO WO 99/55915 * 11/1999

OTHER PUBLICATIONS

U.S. Appl. No. 11/932,220, filed Oct. 31, 2007, Bourgeron, et al.
Anne Philippe, et al., "Genome-wide scan for autism susceptibility genes", Human Molecular Genetics, vol. 8, No. 5, pp. 805-812, 1999.
N. Simon Thomas, et al., "Xp deletions associated with autism in three females", Hum. Genet., vol. 104, pp. 43-48, 1999.
Jeff Milunsky, et al., "Schizophrenia susceptibility gene locus at Xp22.3", Clinical Genetics, vol. 55, pp. 455-460, 1999.
Peter Scheiffele, et al., "Neuroligin expressed in nonneuronal cells triggers presynaptic development in contacting axons", Cell, vol. 101, pp. 657-669.
Konstantin Ichtchenko, et al., "Neuroligin 1: A splice site-specific lingand for β-neurexins", Cell, vol. 81, pp. 435-443, May 5, 1995.
Konstantin Ichtchenko, et al., "Structures, alternatives splicing, and neurexin binding of multiple neuroligins", The Journal of Biological Chemistry, vol. 271, No. 5, pp. 2676-2682, Feb. 2, 1996.
Marc F. Bolliger, et al., "Identification of a novel neuroligin in humans which binds to PSD-95 and has a widespread expression", Biochem. J. vol. 356, pp. 581-588.
Mirta Grifman, et al., "Functional redundancy of acetycholinesterase and neuroligin in mammalian neuritogenesis," Proc. Natl. Acad. Sci. USA, vol. 95, pp. 13935-13940, 1998.
M. Irie, et al., "Binding of neuroligins to PSD-95," Science, vol. 277, pp. 1511-1515, Sep. 5, 1997.
Kazuyo Hirao, et al., "A novel multiple PDZ domain-containing molecule interacting with N-methyl-d-aspartate receptors and neuronal cell adhesion proteins", The journal of Biological Chemistry, vol. 273, No. 33, pp. 21105-21110, Aug. 14, 1998.
Cornelia Kurschner, et al., "CIPP, a novel multivalent PDZ domain protein, selectively interacts with Kir4.0 family members, NMDA receptor subunits, neurexins, and neuroligins", Molecular and Cellular Neuroscience, vol. 11, No. 3, pp. 161-172, 1998.
Kazuhiko Toyooka, et al., "Selective reduction of a PDZ protein, SAP-97, in the prefrontal cortex of patients with chronic schizophrenia", Journal of Neurochemistry, vol. 83, No. 4, pp. 797-806, 2002.
G. Kohler, et al., "Continuous cultures of fused cells secreting antibody of predefined specificity", Nature, vol. 256, pp. 495-497, Aug. 7, 1975.
2003 Nature Publishing Group, vol. 34, pp. 27-29, "Mutations of the X-linked genes encoding neuroligins NLGN3 and NLGN4 are associated with autism".
Robert A Philibert, et al., Gene 246 (2000) pp. 303-310, "The structure and expression of the human neuroligin-3 gene".
Grifman M et al. Functional redundancy of acetylcholinesterase and neuroligin in mammalian neuritogenesis PNAS USA, 1998; 95:13935-13940.
Vincent JB et al. Mutation screenin of X-chromosome neuroligin genes: No mutations in 196 probands. Am J Med Genet B Neuropsychiatric Genet 2004; 129B: 82-84.
Ylisaukko-oja T et al. Analysis of four neuroligin genes as candidates for autism. Eur J Human Genetics, 2005; 13: 1285-1292.
Abdolmaleky HM et al. Genetics and epigenetics in major psychiatric disorders: dilemmas, achievements, applications, and future scope. Am J. Pharmacogenomics, 2005: 5(3): 149-160.
Cline H. Synaptogenesis: A balancing act between excitation and inhibition. Curr Biol. 2004; 15(6): R203-R205.
Dean C & Dresbach T. Neuroligins and neurexins: Linking cell adhesion, synapse formation and cognitive function. Trends Neurosci, 2006; 29(1): 21-29.
Gauthier J et al. NLGN3/NLSG4 Gene mutations are not responsible for autism in the Quebec population. Am J Med Genet B Neuropsychiatric Genet, 2005; 132(1): 74-75.

* cited by examiner

*Primary Examiner* — Elizabeth C. Kemmerer
*Assistant Examiner* — Kimberly A. Ballard
(74) *Attorney, Agent, or Firm* — Oblon, Spivak, McClelland, Maier & Neustadt, L.L.P.

(57) ABSTRACT

The invention relates to a kit for diagnosing autism linked to a mutation in a protein belonging to the family of human neuroligins.

3 Claims, 158 Drawing Sheets
(5 of 158 Drawing Sheet(s) Filed in Color)

FIGURE 4A FIGURE 4B

> gène HNL4X (SEQ ID NO:1)

Contig joins AC019328 (118849-136028); AC079173 (165018-1); AC078956 (144914-173130) (99094-1) (218402-203634) (271472-281661)

>HNL4X Exon1b (10670-10828)
C/EBPalp (10561-10571)
Sp1 (10608-10618)

```
    ttgttgccattacctttttttttttttttttttgtgagacggagtctcgctctatcacccaggctggag        70
    tgcagtggtgtgatctcagctcactgcgacttctgccgccaggtttcaagtgatcctccagcctcagcct      140
    tctgagtagctgggactacaggtgcgcaccacaacaccctgctaattttgtattttttagtagagaggg       210
    ggtctcaccatgttggcccggctgacatcgaactcctgaacctcaagtgatccacctgccttggcctccca     280
    aagtactagaattacaagcgtgagccactgtgcccagccctcagttacatttgaatatgagacaaacaaa      350
    gaaaaaaccagcataattatatctcaaatattgcacaaaacattcttttagtaatgttttttgtgagtcct     420
    atattttagctgttaaatctggcaaccctaggcccagatgtctgtgctaacgtctggtctatctaccac       490
    ttagatagatacttgtgtggttataagctgtatacttgtgtagttataagccgaccacaccacttctccc      560
    agacagcttccttacataagtttcctatgacaaagcccctgtcttaatactgctcatcttctcgaagacg      630
    catttttaaaaaatccattaacacccttttcatattaattagggcacttcctgtgcaagtaacataaacccat    700
    ttaaataagcttaatcaaaagaaaacagaaaaggaaatgtgttcaaggatacaggatgtctcacaggttc     770
    caagggcagtatagcaaaatgaacactgtccactaaaaattcatgtctacccagaacctgggaatgtgac     840
    cttatttggaaacaggggctttgcagatgtaattaaggtaaggatgaagatgagatcataccagattaag     910
    gtgggtcctaaatctaatgagaatgtccttacaagagacagaaaaagacacatgaagacacatacagagg     980
    agaaggccataggggagatggaggcagagactggagtgatgcggccacaagcccagggacgcctggagcca   1050
    ccaggagctgggatagacaggaaggatactcccctaggtcccctggagggagaatggccatgcagacacc    1120
    ttgatctcagacttttgatctctcagaactaggggagagtaaatgtctttggtttaagctgctcagtttaa    1190
    ggtactgtgttacaggaggcctagggaaattcatacaggtaagaatgtgatggggccgggtgtggtagagt   1260
    gcacctgtcatttcagcacttaggggagactgagaagcaggaggatcctgtgaggtcaggagtttgggacc    1330
    agcctgggcaatctagtgagaccctgtctttatactagattggtgcaaaagtaattgcggttttttgccat    1400
    taaaagtaattgcaaaaaccacaccaacttaataaaaaattacaaaaattagctgggcgtggaggcacaca    1470
    cctgtagacccagctactgaggaggctgaggtagcaggtctcttgaacttcgaggttgcagt             1540
    gagctatgataatgccactgcactctagcctgggcaacagagcaagactctgtctctaaaagaaaaacaa    1610
    caagaacagcaaaagaatatgatgaagatgtagaaggatgtgcagcccttctctttgtcattcattacct    1680
    ttctgtcttcatatctactttgtacattgtatataagcttcctccatttttccactggacaaggtggaaaa    1750
    gcatgaccaggaaggccccctaaatttacctgttgcctgtccactcctccatgagagccaccatttgctgtgtg    1820
    tgtggctgtgtccatggactgcagtgtcacagttgtgagccagcttttccagggactgcataccccatagcc   1890
    cggctcagcttagatgctcaaccttggaccaagcaacgtggccacaagatgaaaatccctttgggtggat    1960
    gctactttaactctcagcctggatgaccagataccctaggaggccatgcaaagctgtcctccaggcaagag   2030
    cttctccaactttggcgtttggtgcaaatcaccagagaacatgttaaaacgcagttttgatacagttgat    2100
    ctggggtggggctcaaagttatgcattttttaacaggcttccaggtattaataacacccatgatattaga    2170
    ccgaggactataatttgtttagcaaagtatcaaaactctagatctttttgtatatttgcaggaaaagaac     2240
    aaggtattgcatgggtccaggtgttctttacataattttagtcatgactcttccaggaaaatattaccag    2310
    gctcctaatacaccaatgctttataacagatcaaaccccactcaaaacaatcccattggtatttatacat    2380
    atgttgcatctgctctgtttccacatgtatgcatacacacatgtgtgtacttgtcacatgcaaaacggta    2450
    tttgcaatacattccctgtcttctcaatgaataagacctggaaaaaaccaaaataagtgtttttttaaaaa   2520
    ttccaatacagacctcgagtttgaaagataaaagggaaccattgtcctaggaattttttgtcaacctca     2590
    ttttatttcacctaaaattataaaccacactgcattcaccagaggtggtctatatgcctacataacctatg    2660
    tctaacaccggtcattaacaagaaagaaagctgtttgcttgagctttaataaataaaacacattgatgct    2730
    gcctcttattgtcttaccccccatgttaaatgtctcctttttaaagtacaaaggaagaaaacaggaagagag    2800
    tccatgtgcacacccacaacagagatacaatcaggcataagtcaaccatcctgggaatataaacccctct    2870
    gtattgtatagatatatatagatataaatatagatatagataaatatgtatcaatatatagagataacta    2940
    ttcatatagacagatccatatctctatagatatctatagaagatacagatacgcatatatgtcataga     3010
    tacctatagaagatacagatatctatagagatagatacattgaaacagacatagcaattt            3080
    ctataaacatctatatagagatataaatttatgaatttataagcctatctatatgcctatttctaaatct    3150
    ctctctatatacatgcatatcaataattccaaggtcccaaacttggagaaagatttatgtatatttccat    3220
    acttttaaaagtgtagtgcatgttgtcattcatcaaagcgacatagacattgtaaaagattttcatttta    3290
    aaagtcttaggcaagaacagtggtacagtcgctgcagaatgtcatttaaaaatgaactctattttgggcc    3360
    tcttatttgggattcaatatccttggttttcttacaaaagcaatagttaatggatttctcaccgtcaatg    3430
    aatgtagtgaaatttggagcctgaatctttttaaaaatcagggccgtttaaaagtcatttaggctcat     3500
    catgcccagtgatgaaataataactggggatagaatttaaaataatcaaatggaaggccagcaaagagca    3570
    taactctctactgtggatgcatgttacataattaatggtgtgttacaggtttgaaataacagaagtcaga    3640
    aggacaaaggcttcaagaaaccagaaatagactcttgcccaaagatatctttattcccattcatcaga     3710
    tgcaaaaatcgaattaagggtatgtacaaccttttatcggaaaatatcaatttaaagtatttccttcaa    3780
    gctgtattaatcttataaaatactttccctacaaaaccaatgggaataaacaagagcatctctttatctc    3850
    ctccatctggatttctgtaattatatttacatgtaagaaatgttatatacattcaactatttcaataaaa    3920
    tcttatttaagtgactgacattaattttaaattttatgtaattcagcttcaactggtctggagttttactt   3990
    gctatcattgaaagaaaaaggttgatttagcaactttggagtgtaaaataagacagaatgaattttgctt   4060
    aaccttaagggtgcaaatatttctaaggtttacagcatattactcttatttaatctacgttgttaattac    4130
    cttatattttaaaagactttaaatcctgtttgggaataacatttcttaaatgttttctaaaaaactgagt   4200
    atgttgtttaccctggtttatgatttatacacatatatattttagatattttctagtttacatatatat    4270
```

FIG. 8A-1

```
ctatatgtaaatatctatagctatatctttttatatatctatatctatatatttccatgtgtgtatatag    4340
atagatataggtatcaaaacaagtattatataaatgttactctttgtcctatcatttctcaaatttatta    4410
aacctcatgttctgaactggcctcatataatggtgaccacctaaggcaattatcatcaacatgtttccga    4480
gatattttctaaaatggtgtctacaatagcaaatgaaagtaagaaacaccacaaataaactaacagatg    4550
aataaaaataaagtggaacaatcgttcggatcagaaggggcattgggtaaagaattagctatgtgagggc    4620
aaagactatgtcttatttatccatcttgaatattttgcagagttttgtggaacaagcaacagttctcacat    4690
tcacgcttagtgaatagtgaataaaaatagcaatcagcaaaccacttaacaatgacccaccacaaccctg    4760
ctatttctgaatttaccttatctttttttttcctttcacaggcagactataattatgatttcaacttcct    4830
catcggatccccagtcatgaatctatctaacatattcagctgaaggctgtcaaggatctactgattccac    4900
aatgcagtggtactctcccatcgcccttcactcctaaaatctctgaagaccatgacacagttgactcctg    4970
cctactccttgtggaggttaaagtccttccttgaattccataccacactttctcttaccaaagatcttct    5040
gcagatgggagaatgaccctattttaggttgttatcaagacccctacccagtgtcactttctccaaagatt    5110
tgcctttctcttaagggaacactttctctattttacaccaaaatgttaagtatcatatccataggggtt    5180
gtgcttggatccgtagatcctaccttaagatccctattcaggtcaaatctcctgtcccaaagatctcagg    5250
tctgtgggtcattggtatttctatgatccaccagcacctcattttctttccacacaagtgactctggct    5320
gagtgcactctcattcatcttagccttcccatctcaccacatgaagctatctctagtatcttctcattt    5390
tagggctccatcccattttttgctcaacttctgcaactatgcatatagtcaaatgccactcatagtgaaat    5460
aaaattcatcataactgtgttatttcactaatactgccctaatttatgaatgcagcagcctcgctgtact    5530
cttttgttctagaatgtcccagccctaaatcccctcagagtaagctctctgaaaggtaatctctgctac    5600
catccccgactaacacccataaggattccagccaatgaatattcatcaacctctgtagtccagcctgacc    5670
aatttcttcttattctcctctatgaatcataagaacctatcatcagctcaccaccactcctgttttcagg    5740
gtttaatttgaggattatctaaaaaagcaacctcatgtagcagggtggccccccaaatgcaggttccaag    5810
aactcactcaagacctgctaggtttgaatcctggtgtttagctctagaggcatggatttttgtaaccatct    5880
tcctgggtcatccttgtgcaccttgaacttccaaagcctttgctcacactatatctgtttctcgtctcca    5950
gatattgttaacttggaataatgtcccacccctgctctccaattccccagggaaaccttgttcatctgtg    6020
aaccattttctcagcatcccaataggaagcctgttacgccttctgtatgcttttggagatggcatatgtca    6090
cacattgagttgcatttaaataattaaagagcttaatttatcctcttattagattttaagcaccttctat    6160
actatacatatttctctctctaataatgattagtaattaataacatagtatatattactattgcacgaac    6230
aattattatcctactgaaaatatttctgtttcacttggaccattgtattaggagagtcagtatgaatcag    6300
tagtgcccactggcttccaccagtattgcattcagagttctacgtattgatctcacaggagcttgaacat    6370
aataccagaatgtggttgatggagacactgagatggaaaatcagagagaacaagtagtgtggtatagatt    6440
atttctcatgttccctccagttcttgtaccaaactcagcttatatatctttcttggaaccctacagtttt    6510
atttcattttatgactcccccagctcccacatttcaccatactccacaattagatttaaaatggaagcat    6580
gaagaatgatactcttatctcttccaggaattgtggatctaaacctctgtagctcctctgtctgtgttgc    6650
aatctggtggcccagttgttaaaaattggtgttttgggtcctatcctcctgtaagggattttgga    6720
ttagggaaaatgataatttcataacatcttatattcactttttcttacaatcatgattccacctgtctaa    6790
gatgctttctgactttttcttttttttgagggagggtctcattctgcaacccaggctggagtacagtggc    6860
acgatcatggctcactgcagcctcgacctctctggctcaagtgaccttcccccttcagcctcctgcacta    6930
ccactcccagctagttttttaattttttttatagaaacagggtctcactatgttgccctatttttcaaatta    7000
ttttaaaaaactcctcaatggagtcattcagatagaagtgaaaatgtgaaaatgcttgcctgctctcttcccaggt    7070
cacatatctcagggaagagatctggtacccaaccaatccacccacaagctaagccaagcattcagatttt    7140
gcccaaactctccttcccaatcttactttatcatgctgccttatttagaagtgatgtctcccacatcaa    7210
cttctcttcccttcactacccttcccttccttttccctccttccctttctccttttctctttctctctct    7280
gtgtctctcattcaggacttcatttgttgcatccattcttgcaacaatcttacaaatatttctttttctt    7350
tccacgttggccctcttcaacttgttctccatattgccatcacagtgattgtcctaaaatataaatctga    7420
tcatttcttccctctccctgcagaaaatatgttactggcttccccactgcctactggataaattccacc    7490
ttttcagtatggcactcaaaattcttcacaattaggtctttaatccttccttaccaccttctttttcata    7560
ctcaatgtcatggcattccaaaccctcccctatttctagatctccacacatacagtattgctatgatgtct    7630
ttatccatggcttctttctcaacttcttgacccaatcagtgtctgtgtaccattctttccctactcagaa    7700
agttcttgcaaacccttctttaatcattttcacctccatgggtccctatgaattcatatgtattc    7770
cttgtgcacaccttcttgtaatcatatttttttctcatgcttttggctatcttgtccactagactgtatgc    7840
tttctcaaaaataaatggatgagtttcactcacagatgcatgtcagtgcttaggactgcaccagtgctaa    7910
aaaaaaaacaaccctgaatttatgaataagtcaatgaattaatacattcttggcaaacccatgactttc    7980
tggcctactataaattactgtgttcaaggtgagattctgcttttagtttaggatatagatatctatatata    8050
tgtccatatatctgcagctatatatccatatccatgtatatcactgatttggggaataagctatacttat    8120
taacaatattactatgttaatgggtcttcaatatctatacaataacggaaaaagtacatgcatatttcta    8190
aatatctatccaataattggaacacacacgtatgtatggatggatatatttttttttattattgggtata    8260
gatatctattaatagataagtgtatatttatgtacctatcttgttggtaaaaggtgcttttatacatatt    8330
atttcatttagtctccacaagaaatccacaggaaaggtaatttttaatctcagtttaacagattcacagaa    8400
cataactgacttttacaacaaggcaaagtttgtgaggatagagtcttaacatgaaaccaggtccccaaatt    8470
ggtgtctatcaccttccccattattggtcaggctgcccaaatatccttcacatcaccatggcaggcttca    8540
tgctttggtttactgcctaaagccgaagcaattaggaggatatcctatgtgttgcggacactatcttttt    8610
ccttccataaatgaattaatgggccatgaaataattttaagaaaagctaacttttctggccaagcagaag    8680
aataaaagtaatcaccatgtaatattgttgtgaagactacctggccccacacattaactcagctaatcat    8750
tacagtattacacggtgattatctgttccatttacagatacagaaatggaggcaaacgattaaaatataca    8820
cacctaaggtcacatgcatcttgaacccaagcaatctcattttaaaatccgtgttcattgtcacaacact    8890
ctattatgccctctgatctttgcattgccaatttaaatccaactttctccaactcaactttaagtacagg    8960
ggtcataccccgtcctcgcccccgcaacttgaaactccctgggaaagataacctcctggacccctggaa    9030
atgaagaggcgtatttaaaaacaaatgcctcatcctgggcacaatttccaacattttatccaaatcatgaa    9100
agtataagaataagtaaacaaaaagcctttcatcgatccccctctcaaccataccctgagcataaaacag    9170
gtcctgtactttacagaactgtattccaaatttttgctgctcttaaaaattttttttatatcattgcttcc    9240
caaatgaattacaataacgcagacatagagactgctggagatcgtgacctttaaacagttaaagatgtttg    9310
catatactgcagcatgttggtgtggagggtatctagagagtcctaaaaaagcaaagaggaagaaggttt    9380
```

FIG. 8A-2

```
gctgtacgcgtctggtgcggtggcaccgtttgccatgcccacctgctctatctcccgagtacccgggatc      9450
tctccgttacagctggtttgcattgggattagcagctctttgcatgaggttgtagctgtggatgtggttt      9520
ctgtagtgatggggccgactccggagatctattggctgctggctttgtaaatttcattcagtttggtcca      9590
atggcagagggagagccccggagacagcaggacctctctcctcaatctctcttttttcttgcagaaccgtc      9660
tctctcccttctctgtctcttagcacagagctcttattcagccactagcttggcccttcctgctttcaatt      9730
gtaatgcttgttctgcccgtccacagactattggcggcagaaacaacgaatttcctccaaactaggcggt      9800
gttggtggctcttgcattcctctggatgaggaaatctagttgggggggttccagaaggggaaggctcctgg      9870
gctttcaatacatcctcctgaatcatacctcgtttcgggttccctagaaaaatctggacgtgtaaaaga      9940
actcttaacggccgatgcagctcttccaaagctaaggtaggtgcagttttaagacctgtctctgggacat     10010
tattctcattttaaaaagccgtttaaacattttgacttgcagcaaaggatggaaagcctcactgcagata     10080
cttgagcttcacttcatctgatctttattttttcctttttatgattattaatattattttttggaaaatttg    10150
gacaggactttctcccatctgtctcgctgcatttcttaggtgtgggtgggagtgtagaccttcatacggt     10220
ttttacatgcaacctctccacagaaatatttggtttttattttcacttaaagagaaaaatccagaccaccg    10290
ttgtttggaagcgttttgctgcaatcagctatttgaacggctctggggccgtgtgtgatgtgtttacaaa     10360
gtagcgctgccttccacacaaataaacagaagactgtggcggggagaggaggaaaaaaatatatatgtat    10430
ctgcagtacagggagaagaaggagagaagcggccagggctggagatggtgaaggcaggaagacttctgca    10500
aactgtgaggcatgggaggcttttcttttctttttctctcccccccccaccccccccccttattctttaag    10570
aaaactgtcagctaccaccgcctgggtgctttttgagggggttggggggtgctgttaaccagaaagaa      10640
aaagggaaaaccggcttggttggggtcgcatttaagcgatttttttttcccttccttcatctccgggcctcg  10710
gataagatgacggcttgggtgatgcacgaaataacgcacgtgattgattagacctggcttggcttggcta    10780
gggaacgatccaggcgcgctggagaccccgcgtgaagatgaaatgacggtagctccgggctgcttctgta   10850
aaccggggacgggctccatgcaccccctttcccgtgtgtgtgggtttcgaggcgggtggggaagggtgagc   10920
aagccgcagaaggaggggtagagctggtggttttgcttctttcgggagccttttgagtgtagtctgaacctt    10990
gagggggggcgcgggggggcttgcactgccgccctgggaaccatctctgaactgcccgcttttccgaagga   11060
gcggaaaagttggaagctgcgaggacagactaccggagccctggtctgggtctcggggggatctggagccc  11130
tagtcggtgcccactgagaacacccccttctcggagcgagggtgtcgggggggagtgttaagcctgcggggc  11200
gcacggtccgccagtccccgaggtgggggacgggggaggaggctgaggagtcggttccaataggcgcacca  11270
cctctacagccctggaaaacgcaaccgccacccccttcttccttccaccatcccaagcctctctgctg     11340
tcccgggccgatttcatctcgtctcttcccccgcctccccgcttcccgcctcccaattcccgcgcggct     11410
cggctcagccccttcccactccagtgggcagaactgatggagaagatccgccaagcgcgcagccggcggc   11480
ggaggagacagtgcggggtgggcgagggcttcgagaccacgcagagagagagtgaacttcagtcctgac   11550
ccctccccaaggccgcggctggggcgcccacagcccgcgctggcacccgcgtggcctgacctgcggaagc   11620
gcgagcggggatgaggtagggagaggaggtaggtgcgctcggctgcagatgatgcgtgggtggggggc    11690
ttgctgtgggaggagaggcccaggtccggcctgcgccctccaccccgcggctgctccctccgcctctgg    11760
tttttccaagaggccggtcgctaccccgaggacactctcatccttcagtcagtctcctggacacccttc    11830
ctcctcctgtccctcaacctgacctggctctttcgcccctccgagaaccggtaggctggggtccctcggc    11900
ggggttctcctgggccgcacccgaagctttgcgccccggtatccgggcccagtgctccgtgcaaccctg    11970
ggcccgagcgcacgattccggcgcctgctcgccgccagacagcgcccttttcttcccggagcggcgggg   12040
gcgggagcagggggtcaggccaacccttgcaccccgaggcctgggcccgggccaccctgggaacggat    12110
gttctgcatggagagcgaggggcagccggaggacgtcctccgcatcataccctccccttccccagaagg    12180
cttttttttttttccggactgcggtttcttttctctgccttcttcctctgaacctacggcaggtgtcag     12250
cctctttttgtgtatgtgctgctgctatctcggggatggcggggagggggtgcaggaggcagcgtgaag    12320
gggtcctaggaggttccggcgggttttggcccctgcggtgcgccggggcttgcaactcgcccgggtgct    12390
gggcgcgcgcgtcacgaattcagcctagggctttgggcgagtcgtaggcttgggagtgaggacagaggatcccga 12460
tctgtcatttggacccaacttaagaaatttgggtgggggttgggtgggggttttggaactaagcaggtg    12530
atgttcttgcgagctggatccacaaggtggtagtatggcttcttttattttattttattttatttcta    12600
tttggtcattttttttggggggggcggtggtttgttgttgttgttgttgctcttatcttatgcttttga     12670
aggcatccgttgcccgtagggtttacatcggagcgcgttgcattatattttcttgaaggggtggtgtg    12740
cgtgagctcccatctcagaatcagcccttccggtgatgtgaggaaggcaaaagcaaaaaaaaaaaaaaa    12810
aaaaaaaaaaaaaaagaaaaaagaaagaaaaaaggaaaagaaaaagtttagggagacctcgttatc     12880
ctgacgaagcagaattgccagtttgtgtgggcgttctgcgggcaacatagaagtgcatgcttaagaaatc    12950
cggggtagcttccttctccagctagaaattaaatggccagggtgcaaacacctgactttgatgagaacaa    13020
agcggcagaaactgcaagagacctgcatggtttgaatggacgcactgagcctttcctaggggatggcag    13090
agcggggtgaaatcagatagcaaagaaatctgccgtttttgtggggcagatttggagagtggaaattat    13160
ttcataccctttagttggctgtggggaagatgttagcagtaatccattaaatcctcagcatagatttcct    13230
gtggaaatgagcaaaatgttaagtggggggagggatggctaatggcacatggttgcattaatccctgtatt   13300
tccagaaaaaaatatgaattctgtgtatcctaaaattaagaatacaggaatttcatggagaactctgc    13370
aagcatgtattttctcagattagaaattcagtattttattactcaatgaaatgtagaatgcgtgtgtgtg    13440
tatgtgtgtatacagacatacacacgcattctacatttctacatatatgtgtgtgtgtgtatatat      13510
atatatatatatatatatatatatgccattttaaagatattttcttgacatgtaagaaacataa      13580
tcagggccagttgtagcaagtggaaaattacttcatcagttttaagtcagtagattaaaatgaaggctt    13650
cattttttttttgaaatcagaataataattgcattttcataataatgcctgtgcgtggatgcagttttaaa   13720
gatgctttgatgttttcttctccagtggaagaattgctactttctttgcgttttatttaaataaactaa    13790
tgccgagtatacagttggccctcaaaccagtaacctagctgattttttacccaaacctgagaatgtaacag   13860
atacttgataagggactggtggctgcataaggtagataatgaagttatctgatgctgtgaaatttacaa    13930
gcagactgaaagaatttgaaagttcatagttgttggcctggaatgttgacctgtggtaaatatatagt    14000
ttttttaaaatttgtgaacttggctatttcattgttttgtgtgtagtaattgtggaaagcttatagtctc    14070
tccacaaagatgagagtgttgactgactccgcaacagagacttgcttttggaagtgcagggtctcttta    14140
aaagccatttggaatactgtgcttttatttctagaccacaaccaaaaggttctcaaaaaactaaacattc    14210
aagtgcacgagggaatgacctccgtttaacattctttctttttaattggtacgccacatttcaaacccttt    14280
tgtaatactgttgaatattgccaataatgcaacttgttgagcgaatgattgcattcaaatgaagtagcaa    14350
tatacaaatattttaagtccttagtatcctccttctaaagataggcttatctggttaaaatatacttat    14420
attccaaataaggtgagagttggtcttaagatgtgaatgtcaagtgtaagagacacgattttagtttgta   14490
```

FIG. 8A-3

```
aaccagaatgtattctttctgtactgcttctgccttttaacaatatgtattctattcccaaatggggaa    14560
atatgttcagtttagtttaaatctgttgctcttttttgtgtgtgttttttgtctgagtactgtactttttca    14630
gaggagagacttcgtctcctatttaattatgtgaatggatattcagacagatttgaatagccaccactga    14700
tttcttaaaactcctgagctaccagttttaaatcaaagatacatcttttgcacagtcaattagaggaagtg    14770
agaatcaaaattgaagcccaggctgctgaggcaattaggtcatctgctgtgctctctactaccattcact    14840
caacgaatattttccagttctgtcatttttctctaaacaacctacatttggactttgaaaggctccactg    14910
ttctttgttaagtgaacggcagtgtaggaagccctccctcattttttcttggagcacagtagcacacatga    14980
acaagaaaaaaagaaggtgatagctcctagcagtttgtcattgtgccatttataggctttgaataaatg    15050
tatagatgaaaaggctttccctctgcaggtggttacattaaacaaaaaataagtaaataaaagcctcata    15120
aaatcattacgggagtggaaggttggtggtggaaaacagcccatctacctcgggctgagatttcaaactt    15190
tagacatctcgtgttcagttcacgtgtcccaggtgtgtgcggaacacctccatacaccacatcttcccaa    15260
ggcactctcatcttcccagaaatggtacctgaaggagaacagacctaaccccaacaatactaaaatacgt    15330
atataaaaaactatatatagtaagatatgtatcctactatataatatatatatgtaatacatattatag    15400
taaggtctgcatcatgtatataaaaatacactatatatcttattattatatatatagtgagatgaggtgt    15470
attaatccattctcaggctgctaaaaaagacatacccaagactgggtaatttgtaaaggaaagaggttta    15540
aatgactcacagttcagcatggctggagaggcctcaggaaacttacaatcatggtggaaggggaagcaaa    15610
tacttccttcttcacatgatggcaggaaggagaggaatgagaaccgagtgaaggggggaaaccccttataa    15680
aatcaacagatcttgtgagaacttactcactatcataagaatagcatggggcaaactgcccccatgattc    15750
aattacttcccaccacatccctccacgacacgtggggattatgggagctacaatccaagatgaggtttgg    15820
tggggacaaagccaaaccatatcatgaggtttttattgaatttatttgagacaggaaaagagtaatcctcc    15890
ataatttagaaaggagatgaagtacaatgaacatttaggtcctcattagttgaggaatacatttcaaaga    15960
gagaaatgttaatttcagtatagtgctaatgaaacgatctaggctttcactgctctctggaaatgtggat    16030
aaatgcccagaattttgtttgggtgttttatttaaaatgtatattatataaagaaatcatggtttgtc    16100
aaagtaacagagtgctattttttggcttacaacaggacttttcttagctccacctgttaatatccggtcatca    16170
ttttggttttaagaggctggtacctgattggatgatgaaaacttggatctcaaagccatcaccccagaca    16240
tgtgatttttattaacatctgtgggcatctgtccggctcccacatcaacccttcatccaggctcatttctct    16310
gttgttttttgtttggttgtttgtatgcttggttggggagaggggacacggatttgctaagggcacct    16380
ttttcaggagtgaaacttagcctgtcatataagctgaaaaggaacttgggttgttcaagttgcattact    16450
tggtaagtttttggatcctttaaaaaagaaaggactgaggttactaaaagtgttattggcactgataaaa    16520
gagctatggtgaattgtggtttgttttttgtaaagtgcagaaaaggcctctttggttctgtgatgatggct    16590
gtggtgaagttgcatgcggtgccattttccatgtttagtatttcaacaccaccaatatgtggctctggag    16660
tatgggacgggcaagtccaagaactcagtgaggcatgccgtgtgactccaatggtcagagctgttcagca    16730
tggaactgtggtctcaaaagcatgggggatggggcaaggactgcgctgcaactgagtgcctttaact    16800
tattccactcttcagtactctctgtgactataactctgtgaatgggttaggtggggaaactcacaaaagt    16870
aaatgcatgttttcacaaacaaaatatgtcattgttaactgttttcctaagtgagacaatatgccctcat    16940
gccctgaagctacatggtaagaatggcagtgtgtatgagcgggtgtatacacatacatgtatgcatatgc    17010
taacacattaactaggaactagtctttgctgaaaatgtttttctcagccattgcaacacattagataaaa    17080
gcaaatatatatatatatatatatatatatatatataatataagaaggaaaatgtggttttcca    17150
ttattttcttttctaatcctcatcattca    17180
```

>HNL4 Exon2 (66564-67333)

```
attctcagagggtaattatatagttcgattttaacttcttcaacagaccgactactacagttgatgagca    70
aggagatgaaagtatttgataaacatcatgggagttaatatgattcttgagggaggggagaaggctgcttg    140
tcttaggtaatgcttttgagggtaggtttgtcctagccttgaggtagcaggcttgctctgttggctgaag    210
aagccttaacatgcatgcccgtattgcaaatttacccacatgccaactgtatgctgtgggaagaaatgaa    280
taatgtagatgccattacaggaaattaggcggaacggatagacttagtgcatcagaaccaatgagaagta    350
gacaagacatttagaaaatagcaacagcaatgaaaacaaatataagtaaaccacaatcaaaacccttaca    420
tttgggtttctagttgcctgttaccacagagggttctggttactagctaaaatgtaacccagtaggaagg    490
tcaagacaaggcccctcatgctgtctcaaacagtaacaaacagtaaggatgacccagggagaaaggtaa    560
caagttacatggaagttaaataccagttacctgtgcagagactgaaaacataaagcagacacaggaatgg    630
cagtagtagaaagtggggaaaatctgaattttgttgcagcataaaaccaaccaaccaaccctagtgaggga    700
atcaatacctcaaaaaaaaatcttctgacaatctaggttcatggtagagattaaacggtaccatattat    770
gaggacagaacaataaatcacacatggcttcccatagaatttgtgtgacagtggttgtgtactatgattc    840
agtctgtcatgacaatttcaccagtaaaataaccttccaggatttatttgatatctcaattgataagcct    910
cccgtaagtgaataaccagaatatgaactaatttataaaaattaacttaaaattacacaagaagttatgt    980
gtctagtcatttcacaatcaaatgtatttaggcatttaatctagtaagatcccaaataataaaaaattgt    1050
ttcttttctagaccaacatgtatcctgatgttataaatacatatgtaaattatatacatatatttgtatat    1120
gtaaaatacacatacatttacatatgcatacatagctcactttttattggggagcacatcttcctgaagg    1190
ttttttcaaagaataattattctacctgtaatgctgtagcagtatttgtaaaaagttcaaatgtggctggg    1260
tacagtggctcatgccctgtaattccagcattttgagaggccaaggtgggtaggatcacttgagcccaggac    1330
tttgagaccagtctaggaaacaccatccatacgaaaaaaatttaaaaataagtcaggtgtggtggtgcat    1400
gtctgtagtcccgttactcaggaggctgaggtgtaaggctcacttgaggagtatatcaggagtttgagg    1470
ctgcagtgagctatgacctcactactgcattgcagcctgggcaacagagtgacactccatctcttaaaaa    1540
gaattcaaatgcctcatttatctggacagaatttgattggtgttattctattgctgaataattccaggt    1610
atgcattttaccttttctctattgacttttaaacatagcttatgaaaaacaaacaaacaaaaccaaacaga    1680
gggagttttgcaaaactatatttaaaagtaaaccatactccctcacccctgactccacaaaaatactgttta    1750
atgtagagaaaccacagacggtgcagcccccaaatctggagcatcctcaggtacctgggggcattctgga    1820
gtgaggggctgagcctcagaggcatttggtcacacttgggtggggatgcctcattggctagtgaagaagc    1890
agctgtctcttccatgtagtggtcagttgtggcctctcctggaagggaatttatccagcagtgtgtgttc    1960
ctgaagatgctaatagcaaattatgttcagtgaagccagctgcatcctgttggtcttgctagtcccggga    2030
ttccttgccacagcaggtcagaatggaaggagctgcttatctttcctccttacttcctctccccatccca    2100
```

FIG. 8A-4

```
gctctcatctgacatccttccaacacctatatgacaggaaaaaaattctctctcttcaaattaagaaaaggg    2170
tctggtctgggtacgatggctcatgcctgtaatcccagcactttggaggacgaggtgggtggatcatat       2240
gaggtcaggagttcaagtagtgaaaccccatctctactaaaaatacaaaaattagccaggtgtggtggca      2310
cgtgcctgtagtcccagctactcaggaggctgaggcaggagaatggcttgaactcaggagtcggaggttg      2380
cagtaagctgatatcacgccactgcactccagcctgggcgacagagcaagactctctctcaaaaaaaaaa     2450
aaaaaagtgtttgagtatttactctctccacatctttcagctattctcacttcactcactgggagtagacaggacag  2520
gatggctccagggacagtgctattgttaccttgttatccacttccaatttggaaaggtaaaaatatgctt      2590
cagtgtctactaaattgcctgcattgaatttgaagtacagtttgttgggatactcatgatgaaattggaa      2660
aacagaatcacagattgttaggacttgaatgtacttgagcaatcatttgtattccctcatgtacacaagg      2730
aaattgagtcacagagagtttcagtgatttatcctcatccttttttttttttttgagacggagtttcgc      2800
tttcgttacccacgctggagtgcaatggcgcagtctcggctcaccgcaacctctgcctcccaggttcaag      2870
tgtttctcctgcctcagtctcccaagtagctgggattacaggcacacaccaccactgctggctaattttg     2940
tattttagtagagacagggtttctccatgttggtcagctggtctcgaactcccgacctcaggtgatcca      3010
cctgccttggcctctcaaagtgctgggattacaggcgtgagccaccatgcccggccgtgatttatctcca     3080
taattttaaacactatccctgcaatgaaaaaggaatacccccaatttttaacatatctgcttacgccagt     3150
tcatgacaagcttacaaaattagaagtaattttaaatgggcaaaataaagcaaagtgcattatttaattt      3220
tcaaaacagactttcttattatgcagcagcgatttaaacagataaatcatttctatgaaagggactag       3290
cagagaaagcaggaaaagacatgtcccacattaaaagctgaactgttggtgggactcattttgttta        3360
tgagttatgatgaatgcaccttagctgtttctaacccgctcccattccctgtttttattgtaagtcag       3430
aacccagcatttttacattttttgaagtgttaattaattgcctttgtttaatgcaccttgctgtgtctca    3500
agcattgttaagaaaggataagatctttttcagggatgattctttcctttccttacagggctttgtctgt     3570
gatgagaactttctatacacatatttttcttttaagagacgggtctcactatgttgcgcaggctggtc      3640
tcgaacgcctgggctcaagggatccttcggactgacctcctgaatactgggattactggtgcgagccac      3710
cgcacttggctctatcttctgcaaaaactggtggattctacttctctctccatctatgtttagtcctgg     3780
gagatataatcaagagaaaagaaacatctaccttcattagattaagagtcaaacaaaagggcctagaggc    3850
aaagaggctccacgaccctctttgcgggtgagcctgtgcattgaaatcctcagcttcaaagagacacag     3920
aaggcaaaataggaagttggatttgcaggagttagtctcttggagggtcttgtaaaattgaagggttcac    3990
atatgccctgtcaactctccaagagagagatgacttggtgaaatctgtattttgtgatgattagtctttc    4060
tcagagggctggttcaagggcaaacgaagggcagaataaggacttgcagatgtgttaagaacagaacccg    4130
ctgtgttgtgcgtcaacgacaaaagcccactccactcctgacattcatatttgggtaactgttttttg      4200
cagtgcagacctgtgaaacctggagtattttcagtcacagcttttatcgagatgctttctgttgacctga   4270
gaattaattatggtttgtcaaacagcttgacgaccttgtcagtggtgttttttggttttacaactcccc    4340
atctaaggatttgagaatgccgcagtggataaaactgtgtgactgacgttcattattttttttccacaatg  4410
cttttaaagtaagtgcgctgggaatgctccatttattatgtagaggagaacatttccaaactttaacttt   4480
gttgctgttgcttttgtacactgaggcattgattctgcaggattaaaagaaggtgctgattattccatt    4550
ggtggaaagtttcaggagtggaagccagcagaattgttccactgagatgataattctgactctttgattc  4620
ttacacattgactacttttacaaaatacaaacctgttttaatctttttaaaggacatttgtgcgctactg   4690
ttttcatttttaaaataaccttttaaaaattttaggatagtttcaggtttgctgaaaggttgcaaagat    4760
agtacagagagttactcttttaactccacacgcatatcgcatcttacgtgaccatctgttacacttaagga 4830
accaacattagtacgttactaagaactgacatcacaatttgtttggatttcactggtgtccacctaatgt   4900
cctttttctcttctgaggtaccatctgaaataccacactgcatggatttgccctatttttcttagcctcat 4970
ctagtctgtgacagtttctcagttttccttgtttttcatgaccttaatagtttgaggtattaatgtca    5040
tggagaatgtccaccaactagagccagtctgatgtttagacaggggtatgtgtttgggggaggaaatcc   5110
acagagatgaaggtttccttcatctcaccctagcaacggtgactactgtccagaagacttttgctgctgg  5180
tgttggctttgatcacctggctgacagagagtttgtcacttttctctgctggtaaagttgtactctcccct 5250
ccctgcccaagtctagtctttgaaaccaagtccctaaagtgggggtggggtgggagaagaggcagaatta  5320
agctccactttccggatggtggaatatcgataaattatttggaattcttctctaagaaagatgggtctct  5390
cccctttatttacttaatcaatcatttatatcagtatggacacatggatattttagatatgctttgggct  5460
acattgctgtgacttattccactttatattccttgtggccatgatgtagacaccagagagtctattcact  5530
tgaatagcaagtaaatgagggggactcaatggtaaatgactcttagagaaactctcagccctgcttgttca 5600
tggatgctcagcttgcaaaaacaccttcttccatcaggaaacctcagtggatgggcaaacattacagcgt  5670
ccttgaatatgcttcattgctttaatctacgaacttcctatgcagtaagcaaaaccacccataccacagc  5740
ttaagagtgggctttcctcccaacactcatcctagtgtcttttgataaagaggtataaagttgaaggaa    5810
catgttactaaccagaagacttccagaggacccccattgatcagggtagatgaatggctgtgtgcgtcttg  5880
tcacaaccatcagtattcaaaaggtgatatcatcctcttaacctctatgatgtcttttaacataaaattt  5950
taatatgcatacaggcggttattacttaagcattgcttaagaagcagtctttttttttttaattcatgtaa  6020
ctggatctattctctgaataaggaatataagcaaatcgtagccatttcaaggactcttttttttttttt    6090
taaatggagtcttgctctgtcgcccaggctggagtgcagtggcgcgaccttggctcactgcaacctccac   6160
ctcctggttcaagccattctcctgtctcagcctcccaagtagctgggattacaggtgcccacgagcacac  6230
caggctgattttttgtgttttagtagagatggtgttcaccatgttagccaggctggtctcgaactcctg    6300
acctcagatgagccgcccacctcaacctcctgacgtgggattacagacatgagccactgtgcccagc      6370
ctcaaggaggcttttaagggcaggatgttttttttttcttatggtgaaggaatgaagagtagtatgggaaa 6440
gaaatacagaaactttgaaaaagaaatgtaaaactggatcatcattccataggctagtagttaatagta   6510
aataactgtatagtttgttcaagggattttgtgaatatttaaacacagatgataattctctatctacat   6580
ctacgtgtttacctgcatttatatcatatgtacgtatggacatatatatttgcctgtagatcacatcttt  6650
gtatggtatctgtaccaatattagagtctatagctacagcatatcaataacagtatctattcttatctat  6720
atcttaatcatatcttttgtatctgtacacatatcttttaccgatattcacattatatttctatgtct   6790
agatctatatatatctctatctataccattttgaactttacatttcctacagtatgatagcataagctat  6860
tttaggattattaaaaatcttcataagcattgttttcatggttaattttctcaaaagactatgctttaa    6930
catacccagttctttatatattttttgacatttggcttatttaatgttttgctcctctaatgtatttt    7000
tcttttttttactccacacccctcccgcctctaattttcaaattgggcattcttcattataggggcattgc  7070
ttattttcttttgtatgtttcaaaaaacattctgcattggtctgtacacatttttccctcttgtatccct  7140
tctgtaaacatttgtattcacttgaaacccttatggaatattttactacagaaaatttctggttatgataa  7210
```

FIG. 8A-5

```
aaaaaggcagagaagatagaataaaggatcccatgtgcccatcagttggcttcagcaattatgaatggat      7280
agcctaatctttagtatctaacttcattcatatttccattcttattatgggcatgatgtaattcatttaaa     7350
gatatgtctgtacgttgctctaaaatataggaaccattttattttacacagctgcagaatcttttccatg     7420
cctaaaattatcaacagtagttcctctgtatcatccactataaagttgtaactgtcaaaatgatcttctc     7490
gtagttttgtaactcacgcaaggtcaaggtctagcactgcaataggttgatttgtcttttacatttcttt     7560
taattgatatagcttccctatcttttttatgcacattcttgttgaaaaaactgctctttttactctacatg    7630
aaagtgggttttagaattggaaaatgtagttgtcaagttattttagaaggaacgtgtgtattttccgtaa     7700
tgcacagtcttaagttactaactccttaggagcaaacgctgtgtgacttggtagtgttctacccagaagg     7770
aatgctgctgggtaaatttggccagctacgtgacagctctttggactcagtatatctcagttttatctat    7840
ttttaacaaggttttattttgaagacagggtctcgctctgtcgcccatgctggagtgcagtgatgcaatc    7910
atagctcgatgcggtcttgaacttctgggctcaagcaatcttcccacctcagcctcatattatctagtac    7980
ctggcagagatacagatctgatgagaagcaaagatagagggggtgtcagaaggtagctttttgttgcaccat  8050
tacatacatacacacacacacacacacacacacacacacacacaaacgggcgcacacgcacgcacaaagaat  8120
caactgcaatttttttcctctttgccaacccacagttaagtaaaattattagttctattgaactccacatt   8190
gcatgtgatatttgaatgatagaggctaaagagaggccaaagagggaggattgcttgaggcaggagtt      8260
caagacgagcttcgacaacataatgagaccgcgtttctacagaaaaaaagaaaaaaaatagccagatgtg    8330
atggctcgctcctgtaatcccagctactggagaggctgagcaggaggatggcttgagccgaggagttgg     8400
aggctgcagtgaactctgatagtgccactgcactccagcctgggtgacagagagattctgtctctaaaaa    8470
acaggaaaaatatgactaaagaaaaccaaactaatctaatctatacagttatagatagttggctatcatt    8540
cttatgctaatgtaagtatgcctcattttaagaagagttgtgtgtgtgtatgtgtgtgtatctgtgagtg    8610
tgtgtgtatgcatgatataaatccagacttctaagcgagtatcagggatggtgaactattattagtagat    8680
cattggaacctgttacacaaggatgcactagagaattttacaaactattaaattctgtataatttaaaat    8750
gtgacttgatttactcagatattttaaaaggatgcatgtctcttacaaaacaagatttactaactttggt    8820
gctcttgacgttgaggctggataattcttgttgtggtggctgtcctgtgccttgcgtgatgctgaatgg     8890
tattgctggactcaagcttctaggtgcccgttgtatacacgttcctgtttttaaaaaaaacttatataaat   8960
ttaacgggcacaagtgctgtttgttacatggatatattgcatagtgatgaaatctgggttttagtgta      9030
accaccacccaaataacatacattgtatccattaagtaatttctcattcctcatcatcctaccaccctcc    9100
cacctttttgattctccagggtctattattccactctctgtgtccatgtgtacacattatttagctccca    9170
cttaggagtgaggacatgtggttttctgtttccgagttgtttcacttaaggtaatggcctcca           9240
gttccatccatgctcctgcaaaagagatagtttcgttcttttatggctgaataatatttcgttattcat     9310
atataccacattttctttattcatttatccattgatggatgccagctggattccatatctttgctattg    9380
tgaatagtgcggtattaaacgtatgcgtgcaggtatccttttgacatagcgatttcttttttatttgcgta   9450
gatacccagtagtgggattgctagataagatggtagttctatttttagttctttgaggactctccatact    9520
gttttccatagaacttatactaatttacattcccatcaacagtgttggattccctttctctctgcatc      9590
ctcatcaacctctgttatgttttgagtttgacatccacaatgtctgcagacagtctcagatatcccttg     9660
ggagtaaaatccatcccagttaaaaagctctgttatgaaatgaggtgtacttattccaagttttacatgg    9730
ggaatttcactggtttttgggttctagtagccccgacgtgtatactgggcatgaccagataagataaact    9800
gggcaaagagtgcaatgagagatagtaaccacattattttggaagatgtttttcataaccagaatagact    9870
ttatgaattctatcaattgtaatgagaatcggattgacattgggggacagttaatataacgcacgttatc    9940
cgaaaggaggtggcattgatttatataagtgagagcttacgagaaaacaaagactggaaataaagaaaaa   10010
gaaaatccttgataagtatctgatagaacaaagtgcagaacgaaatgcagctagcttatctaaaattggg   10080
caaaatcatgttccaaatgaaagctcagtagatgggaagagagtatttgaacatttgatgtgaaaaatga   10150
gatttactgttccacagatatgaacacattgatgagagctgtcagttattagaacttattaacatcaatg   10220
ggaacaccagaaatgtgctgcacagaaaatttaaatttaagactgtttgaaaatggtgttatattttctga   10290
actgttacattgattgattaaaattagattatccaacaaaataagaacttttgatattctgtgagtgaat   10360
atgagatgaatttatgtggcagatgtgtttttaaaagatgtattattaaccgcagagattcagaattaat   10430
gtcgccaaccccaaagaatgcagtataacatttgtcataagtgacctcataataggttattttataatat    10500
cgttttttaattttgataataaatggacacctttttacatctttaataataaaaggatatatgcaaaaccag  10570
ttattttttattccaatgttaataaaatagcaataagcctcatttcatttgaagcaccaactttcactcca   10640
tatcaaatttctaaaagtctgggagatactcaccaactagtcaagaagattttcattctataaaattgta    10710
taatgcagtgaatcctgttcttttcccatatgcatttatttaatattttatatttgatacaaggaatctat   10780
attattttcattaagccactcataaacgtaagtgttttacttcttcttgggtacattttttaaaaatttgg   10850
ttacattttttgagatgttgatgccatggttaaaatattccaactaagtaatgggatggggtttacaataag  10920
tttttgctctacaaggaaataggtcaataaatcaggctccagccaattataggagaaaaggaaaagttaa   10990
cttattatacattattgcacacagtgtttgatgtatgtatgcaaattgctcccaaatacagtttggttgc   11060
agttgtgctccacattttatggtggatgcagttttgaatatgtgcagagagaatatattctgacctcattc   11130
atcaatgtgatgcaaatgtgtagaaatggcaaggtcatttttgtatgatgataaaatgcctgtttgaaag   11200
taaactcatccacccatccatccaaaggttgcatttctcaattcccaattctaaatatgtctgtgtgtg    11270
tgtgtgtatgtgtgtgtgagagagagagagagaatctagtgcaattttattgttctactttgttcc       11340
aggcttgacatttttagtgattgaaactaaaataccttgattcttaccctctaatttacaaataaaatct   11410
ggtttactgttatggattgaactgtgttacagattgattgttccccaaaaagatattcattctatataatgta 11480
aatgccagcacctcagaatgtgatcttatttgaaataaggtctttgcagatgtaattacaatgaggtg    11550
attaaggtggccccttattccgtacaactggtgtcgtaaccaccatgtgaagacacagacactcacagggt  11620
gaagacggccatctgatgatggaaggttggcatgatgcagctacaaaaagggaatgccaaggattactgg   11690
caactccctgaatttagaagagacaggaaagtatcctcaccaagaaccctcagagggagcatggccaaca   11760
tcatgattttggacttctagacttcagaacttttgagacagtatattcctgtttcctgagacataagcctt  11830
gtgattcttttgatagtaactctaggaaactcatacaccaagacacagagttatttatttaaattcatt    11900
ttttttcatttaaaaatacttatttgacaaagactgtaatatggaaagtgtccagtgtgatgactggatg   11970
tacgtatacattgtgtaacaatgatcacaatcaaattaatgaacatatcactcatagcccatgtggtaca   12040
taatggatgaccctgaagttatgcagccagcttggggcagagctgggtttgaagggcagactcctcaccc   12110
agccacacttgtcttccagaatcactttcacatcgtcatgaggattttagagactccactgctccatgtc   12180
actgcatcaacacattgtggagtgggggtctcataattcattgcaggtgtctgaagatcaacagttggg    12250
tttcccttccctcaactgtaaaatgagtgagttggacctgtctccagggccttttctaagctatatgattt  12320
```

FIG. 8A-6

```
gagaacaatgatcattgtaattaagacgcttgacttgaatactgctcattttaaaccatgattagggata   12390
tgagatgctccgtgtgtttctaaataaacttcattgtgacctggttaagtgttggatatgaattggcaa   12460
gaggaggcttgctagtagaaatggtgtaatttaaaaccccattcacaagtatttacacactgcaagacatc   12530
tagatcctcagaagtcaggtagtatcctaaaagcacagtgtgtaatttatggtagataattgaaattgca   12600
ctgaaattgaacttggtggtggggagtacacttcatagtattcaattttgccttcactttattctatgt   12670
ctgactctcaggaaataggaactgcaacgttgggttctccagtgtattttcaacttcaaacttgtgaat   12740
tgtaaaccattaaacaaatgatcaaacactacatctttccctgctcttgtatggacatagagttttgtta   12810
ttcatgccttctcttttcttatctgggaagagatctttcttaacctttagaaattggattaatgcgaccc   12880
tcttttaacctcacatttgatgtgaatgtcagaacttttgaaacttagctgtgcttttagtacactgatc   12950
actgagtgcccgttgactggcaggcactgggctgctcagtgaggtaggtgaagaagagacaccagctccc   13020
tcctggagtgtgtgctctgctggaggataaagacacttatcaagcaatagcataaatgcttctgacacta   13090
tgactctaatcagagtggcacagccaatgggcatggggctaggagaatatgagaattcgtaggtatgggg   13160
atgctgtcagggttcatgaaaggtcttcccaatgatgagaaaactgcaagttgggaggaggtagaaataa   13230
ctgaaagaaatggttgtagagatgaatacattgggggatgatcgtgttgcagggtgacatctttagtga   13300
taaaagggatagagtttgagctcctgctgcagaccctcagcgatgtgttgtaatggtaagaattggctca   13370
tggtttcctggtttgcctgattgctgcatccacaaaaccatgggttctggggttaattcccatccatttt   13440
gttgctgaatttctcagaatgatagtcttcggtacattgttactgaaaaggggtgctaaacccaatgtct   13510
tcattgcttttgaagcagatggtccagtgtagtgtttctcaaacataagcatcagagtgtcctagaggtc   13580
ttgttaaaggcaaattgctgggatccatcccaggagttctgagtcagcagatctgagatgggaccccata   13650
attccccagttgaagttgccgttactggtcttggatcactcttttagaactactgccttagggtatttc   13720
tgggttacatgtgcacacatgacctgcttaagttttgagctcaacattctgttttattccttcctgttca   13790
gaggccggcatccacagctctgggtctcatcatttgcttttgtcatccagttgtgctctactgatttat   13860
aagttatctttatgttttcagtttcccagtcaattcaagccaatgcatatttattgggcatctaccatgt   13930
gctatggactgtgagggacttaaagattaataacaacaaccataaaaactcattgacgtgctgggcatta   14000
tttatttcccccatggccccccaaatgctaggcttatcattcaaaacactacagcaacttgaaggcagaga   14070
ttgtttctcatttcagggatccacaggtatatggcttctcaaacgaaggtctggtaattccaggctgcat   14140
gcagctattcttcctttaaagactgagaaaccatgcataacatcttttcttccttcttcgtttataca   14210
tttgataactatgtactgacatcttacttgagaaggtcaccatgccagataccgtcagtgatagaaaca   14280
cagataagattcaacctctgatcccagggagactctcagtaaggaagagaaaatgagaaatgaaagtacc   14350
tatactacaaggcatgcacgtcacacattccataagtgggtaaaaacacagaccttggcagcacagaatc   14420
ttgtttccatttgtgtcatttaggacactgcattggttatctattgctgcataaaaaattcttctaaac   14490
cttaggttaaaactgcaaacatttatcatctcatgcatttctatacatcagggatttaggagcagtgtag   14560
ctggccagttctagctcagggtccgtcatgatgttgtggtcaagttgtagacagggcttgcagttttatg   14630
acggtgttggagaatctcacttatgtgtcacttggccaggaggcttcagttcttggccacatgggcttctc   14700
cctagggctagacgtgtgacattaacagctggcttttctggaaagtgaggagagaaagagggaggctgaaa   14770
gagagtctaaggtgaaagccacacacttctagaacttgatcttggaggtgacaccttgtcacttttgcac   14840
ttgatttggaggtgacaccttgtcactttgctacatgctattggttgttcaaatcaaatctggcaccat   14910
gtggatgaggattccaggaaggtgttaattgcaggtgtcagttggccatctcagaagctagactatcacc   14980
agaagctcttccaaaggaggtggcttatgagctgcatagaattttgtcataaggacaaaggagaaagtgt   15050
gaacaaacacataggtacagcaagtgttgaggaatgggctgtgttgtgttgagtgttgtctcaagggcat   15120
gttgagtttgggtgatgaaattgaaatcagatcatttcaggtggtgcaacttgatggtaagccatataga   15190
tgttattctgtaggcaatggggcaatcatattaggacttttgcagaatttatttaaggaatagcagtttca   15260
tgatagtagaggtagggatagaagacagaaggtcagtaatgcaagttgagatctagtttatagattcaact   15330
gtggtagagattgaggaaatggggatggcatgaggctctgcagaggcattggaaggatgatactgataga   15400
atcttgcaaactattggatagaggccaagacaatgaataaccaagcaaggttgcagttatgggtggagtt   15470
gtccagttaagaaaagggagagagttcagaggtaggtgaaggtcagcattattagatgcttttggagacac   15540
atgagactgacagagatgtttactatttttttggtgattataaggtaatcaatagactttgagagatta   15610
ctgttttcagtcttccatattatgttgcttggatgcattttctttttcctgaaacttggcagacata   15680
tccattatcaagacgttttcagaggggcatggtgcctcatgcctgtaaatccagcactttgggaggctga   15750
agcaggattgcttgagctcaggagttggagaccagccggggcaacatggtgaaactcctcatcctcacaca   15820
agtacaaaaattagtcaggcatgcgcagcaatatgcctgtagtcctacctacctcgggaggctgaggtggag   15890
gattgcttgagcctggggaggcggaggctgcagtgagcccagatcacactactgcactccatcttgggtga   15960
cacagtgagaccctgtctcaaaaaaaaaaaaaaaagaaatgaaaagaccttttcaaccattctaatca   16030
taattccaagacctatttgtgtcctgacttcaagagcaggtactcttattgagaaacatttctgtaattg   16100
ttcccacttcccttataccttttttctgacagcaggtggcatccctcagttgtctagctgaccactgg   16170
aagggctgacccctcaacaaacccatatcctgcttggagtttctctataggccctgtcttatttattgct   16240
cctgctttgagtaacttttctccttcctccaaatctattcttctaattttccttcactgctctattaattgaa   16310
ctgacttttctgattgtctgttcctcctgcctttgcagttactgtcgctccctaaattccatcctcgaat   16380
cactcctcttccttccgtactgtcctatgtagctttgcatctactcatggtttgatgattatttccatcg   16450
gagagaccacaggggtctctatcttctgctctcacttctcttccaagttccttcctgcccttacagctcc   16520
cctttcaacaacattgcctatatgctctggccaaaactcaattcagtgttcccaaaattgtcccatcatc   16590
ttcttgccaagcttaccctgtccctgctcatggcatcttctcctctcaattcctcatttcttggatttga   16660
atcccctctctttcccatccccagtgtaaatcactttcagaaataacaggtcctgtcattcttcttctg   16730
agatacatctgtactttccttggtcatcttctcactttatgtgttactatttaatcatatcctgtctat   16800
gacttgtacactctccaatctattttttaaagctattcttcttcatcttcacaaataattgattatgtaa   16870
gactactatctcgttcaaaattcataaacaagcatccactgtgcttcaccacctgccccatctccgccgt   16940
tacaactgcagtcatcattttactcctctgggtgttatacttcatcctccacccaacctgagtatggata   17010
ggaatcactgcatttcacctttgcttttttctgcttcttctcaggctctctttcaaccctggaat   17080
actgttattttcccatctccacaccttattcatgactgagggctaaaatgctgtttcttttcactgctctc   17150
tctaacatgcattgttttgtattcctctgtggtagtcatcaatttccattacagaggccaggagacctgat   17220
actttcttgagtgtgaatttcagtagttgacgtcttgtgtctccagtttcctcagctgttgagggctgtga   17290
gaagagtacctacctcgagggatgtttgcaaaataaataagttaaggtcaggcactgtgggctcatgcctg   17360
taatcccaagcactttgggaggctgaggcaggaggactgcttgatcccaggagttcgagaccagcctgggc   17430
```

FIG. 8A-7

```
aacatagggagaccctgtctgtacaaagaataataataataataataaaaattaggcaggtatgatggca      17500
catgcctgtgatcccagctacttgggaagctgagacaggaggattgcttgagcctgggtattcaaggtta      17570
taatgagctaggattgcaccattgcactccagcgtgtgtgacagagcaagatcttgtaaaaaaaaaaaaa      17640
aaaaaaagaaaaggaaaggaataaattaagcatataaagcacttaaaacaggtatttagaaagtgttga      17710
aggcggccttgacattacttatctttggcccatccttgtctttctccttcgtagtctaaaatgttttaca      17780
aaggactgttttctcatgacactgagaatgaaccccaaattccttttcactgacctattccacttttataca     17850
gtaagcctcttgctcacttctccaccttcatcccaggccatcctcttctcactgaactgctgtcccagtc      17920
ctcttttggttttgtgatctgagtggataccgtgttaggacattttttgtgtgccactccctctgcccaga     17990
gcaccctgtcctgttcccatttaaagtgggttccaccctcgattgtgttcttatttaacccattatttac     18060
tttcttctctgagctcacctgatctcaaaggctttttattctttgtctacttatggatatgtgtggagg      18130
atctgggggggttagtgaattttttctctgcattctctaaacatgtgtattgcatgaatctggaatagatca    18200
gcccttactgggtatttattaaagaaatgagtagttgtaagacactctatagatattcatttaatgaatg     18270
agaaaatcaaatgttgcctggtaaaaacaagtgttaagtcagctatcacagttttctgagatatgcagcc     18340
aagccagggagactgagggaaggatgtcttcattgtaaaatcaacgcactgtaggggaaagttcctctc      18410
tcacctaagggaatatcgatcttccttgattgtttgctttggtatttctaaattagcatgatttaccaaa     18480
aatgtttggatcactcagtacatgcatgtgattttttctaaatggctatctttaaaaaaacttcctcatc     18550
tgtattaatgtccctagagttttttacattttttgcctgtatttcattaaagatgatgtcatagaaaattt    18620
ttgtcaaatttctcattctggtccgtgcctggaagattgacagtgatgcagtctaagaaagttcaggatt     18690
ttgaggtttaatcatttacattctaacactaaagctacaaatctgccgtgcagtgttgcttacttctact     18760
gctcactggatggatgagtctatgtgctttttaaattccttataaagatgtgggtcaaaactagcagtgt     18830
ggtcaataaattaatttcttgagagtttatcagaattgtgggatgatttgggaggagcaaaattgtgtaa     18900
aatcaatcctctatttttaaacttattcttctaaaattctaaatagaatttttttattcattaatatttt     18970
cttgatttcataatgctaaaaattaagtaagatgaatgtttgtgttggagaatgggagcaaatccaagacc      19040
aaaaatcagatgatttattaaatttgcaagttaaaaaaataaatacagtttgaaagattgctctgtttga     19110
ggaaaggacatacaattttgttgagataacttagggtacaaatcaaggtcatttatgttcatttgaacat     19180
tcatattcacatccggaaatatccagaatgactacactaaaacctgcaggtaaattcttttctcagctga     19250
gcataccatattgttgtagttaatcaagaaatctaccaaaattaaatttgtcctcctacttttagttta      19320
gaaatttaggggggtcactgggactcaaaagaaaattcaataaataatggaccatcctagagatacttctt     19390
tttaacttaaaaatccctctgagatatcctcaggttttaaaaataccttttgtattttcctgttttttgtgt    19460
gtgtttgtgtaggcctacatcttcatattagtcatcagtgttgtcagaaccttggctagaatcatagtct     19530
agaccttcttgaggtcactgggtggttggctacattttccacctcttgcttttcatgggtcccactctgag    19600
aaacatgctccttctctctctcctctttcaaggtcatctttgaggacatcttctgaagcttttctga       19670
gatgctgcctcttctgagcacgacactgtctattcttgtatccaccagtataggagctcatgcaatttgta    19740
agcacttgccttaatgatgcgctccctgaaagaccctgaggagagggatcaggtggcgttcatctttagg     19810
atcccttccctgtcctcacagcacattcatggtccacgttcagcaaacacttgtacaatgacatgactta     19880
gggtttctagacaatctgtattgtaatttctgttgatataaagggataacattagcatcatatgaaaagt     19950
cagagttctatcaatgtcatcttgatgaaaatatttatatcgttatatcttatgtcctaggtgtcttctt     20020
gactgactacccagggcgagttggaatggctatgtgcatctctctgaaccccccaaatcttttagttgtaat   20090
gatgaacttacatggagaggcttattcgaaacgtcattatagtgtggatgataaccttcttagtttccac     20160
agctgatattcctccaaagttttgtatgctttgactaatgtattctctttatgctaagctttctttaaaa     20230
tgatatgaatgttccataaatgctgattttttttgtttttgagacagggcttcactctgtcacccaggg      20300
tggagtgcagtggcgtaactacagctcactgcagcctctgctcctgggctcaagcaatcctcccacctca     20370
gcctgtgagtagctgggactacaggcgtgcaccaccaaacctcgctaattttttgtatttttttgtagag     20440
acagagtttcgccatgttgcccaggctggtctcaaattcctgagctgaagcaatcctccctcctcagcct     20510
cccgaagtgctgggattacaggcatgagccaccacgcccgcccccataacgttagtttaattagcacct     20580
ttctgctttagttcatgttgactattgaaaatctatcatcctgctataattaatgttttaaaagatactt     20650
ttagatagtgatcaaaaacttatttattaagtagaatgtaaattattacaaatgatatgaataccatagg      20720
ataaagtttttatatgacaacttagattataaaatgcaattctagccaggcacattggctcatgcctgta     20790
atcccagcactttgggaggcccagcaggcaccaaccgcttgcttccaggagttcgagagcaaccagggca     20860
acatagtgagactccgtctctctataaaaaatacaaaaaaaaaaaaaaaagctgagcatggtggtgcatgc    20930
ctgtagtcccagctattcaggagactgaggtgagaggattgcttgagcctgggaggttgaggctgcagtg     21000
atccaaggttgcaccgttgcactccagtctaggcaacagataaatatgagtacaaatggctgatcatctt     21070
catattaatatgaaattgcatttttttgatacaggatctcgttctgtcttgtggccttctgtaataggtta    21140
tcttgtccaaattctggaataaagtccagaagaattttaatctagataatttattctttaacctttgaaa     21210
tattgtatcagctacatgacaatggcttataactagctctaaataaatgaaataacgtttgcgagagtga     21280
atcacatcactgagaaccaagggaaacatgaaatagtgattattttgaacagagagtgttagtggtctgc     21350
attctgccttgcacccaaatggcatcacctatgggtgtgataaaaagcccctgcctttctctccctcctc     21420
agtgcttgggatttccaacaacagcaaaagagaagccaggaagaatgctgtgttgtgagtaccccagga     21490
agggttttcctttatgaagaggcagacctagttaggaaatacataaccatggactgcaggaaagacagtt     21560
gagtctgcatggaggatagagaccagggaccccataaaaggagaggtggtgaccgaggcctgcaggatgc     21630
atggaaacattcctgacctcaagggcagcaactgtgaacacactcctactaggcagaactagaatggatg     21700
aacagagttcttttcagggagactcaccaggtagatgactacacatgagacacttttttttttttttttt     21770
ttttttttttttttgagacagagtctcgctctgtcgcccaggctggagtgcagtggcgccatctcggctca    21840
ctgcaagctccgcctcccgggttcacgccattctcctgcctcagcctcctgagtagctgagactacaggc     21910
gcccgccaccacgcccggctaattgttttgtattttttagtagagacagggtttaaccgtgttagccagga     21980
cggtcttgatctcctgacctcgtgatccgcccacctcggcctcccgagtagctgggattacaggcgtgag     22050
ccaccgaaacacttcagtgggaatattttgttccatcagattttagcaatatcggatttgaaaataggg     22120
gaagcacacacagatacaattagtttcaccatctcacttgtgtatttaaacaaacctgtaaacaaagcta     22190
agcgaaccaagaaacaaacaaaaccctcaaacctaatacagtaataataggctgggggtggtggctcatga    22260
ctattattaatctcagcactttggtaggctaatacagaagaattgcttgagcccagagttcgagaccagc     22330
ctgggcaaaatagtgagatcctatctctataaagattatttaaaaaattagccaggtttcgaggcatcca     22400
cctgtagtcccaggtacttgggaggctgagaggcaggggatcacctgagcctaggaatttgagattaca      22470
gccagctgtgatcgtgccattgaattccagcctgggtaaaagagtgaggtctgtctccaaagttaataaa    22540
```

```
taagtaaaataataataataattttttaccgtatcacaaaaaatatagccagtcagatacaatgcacacta     22610
attattgtaaaattttctgaaacacacatacatcactaacttgataattgtaaatttaacactgattgga     22680
gggtgtgaacaaaggtatgatcaagtaaaataaatgtataggcaatttcaaagtcttaataatacaattt     22750
caagagctaatattaattgagcatttactatatgcacactcatgcatcatgggactgtgtttggtgctaa     22820
tatcacaaaactttattttttcttccactggtaattttgtcactgttgaaaactgtttcagccatggat     22890
ccccacagtgcgggagattgcgggatgtgggagagaaatgatggtctcaatccccacctgagccagtgtcc     22960
tatggcaggcaggtgaaagccaagccacccagcttgagttctggctccacttttatagttctgtggtgtt     23030
gggcaggttagctaatctgtccctgcattagtgttctcaactaatggggataaagctcacatataccttta     23100
tatgtttttggagacaattaagagttagtatatgtaaagaattcagcaagttagatgctgacccactatg     23170
tacatattagctattataacttattattcggacaaacagctaatgcatgtggagcttaatacctaggtga     23240
cgggttgataggtgcagcaaaccactatggcacacgtttacctatgtaagaaacctgcacattctgaaca     23310
tgtatcccggaacttaaagtaaaataaaaataaaaaataaaaaaataactattattactactattattag     23380
aattgtttggatgaggaggtagcttgatatcttgaaaaaatgcatggtctttggagtcaagataggtctt     23450
actccctgcttcagtgagctgcgttacttaacacctggatatcattttttttcccaatgtaaaataagatg     23520
tcataataactcctgcccttggctgtagaagggtcagtgaagatgaatgttattatgattgttgttaaat     23590
ataaattcatttttacaaatacagtttcatcaacaatatttatgataatgcctattaataacaaaatgtg     23660
ctaggtgttatgagaaatcaaaaacatagttaaaatatgatcttgtcttcctgtaatttaataatgtgct     23730
ggctcattagctatgaaacccaaaggccttatctactttgtattaatattttttcaagcatggaagtaag     23800
cccagaagggtattgagtgatgtatcctcttcttccttaccatctttcctatagatgcaaaatcctgag     23870
tgtgaaaggccacgtggtactctgttagatatctcgcaggtgttacttatcgatggttcttgcttaaaag     23940
tagaaggaggagtgtcgcatgagacgcatcctataaagagagcattccgggtgagatggcaagaaaaact     24010
ccgaatggtcctgagatgataactgatccaatggagatgatatatctgttcagttgacgcaaacataatt     24080
gcggttatacccgtgaatgtaaggcaaaaactgcaattgcgttgcaccaacctaatatatatatctttt     24150
tggagacagggtcttgctctgtcgcccaggctgtagtggtagtggcgatcacagctcactgcagcctca     24220
acctcccaggctcaagtgatcctcccacctcagcttcctgagtccgctgggaccatagacacatgccgcc     24290
acatccagctaattttttgagataagttttcttgcagtagagtcaatggcagtgttgttctgaccttctgcc     24360
acagcaaaacatctctgcaggttgaggattagttcttgcaaataagtgatttctaaatgattgattggtt     24430
cttttcacacattttgcagatttctttttattaaacaagttatatctaatggagaaatacagtgagttgat     24500
gatctccaacaaaactttaatgccaccagatcaatgccaaccagattatgagttgcccattggaaacct     24570
caaggagtcttcattgattttgtattctcaaactgcatgtgtgtgctaaaatggttgcatagagattcca     24640
catgcagccatgcatgtgtgtaggtgctcccactagactagttccttgacttattagggaacaagttaag     24710
aattacttcatgtcatgatcggctagttcttgtaactacccataagaaagcttataaggaatgtcacatt     24780
ggttttgaaacaatatcatctcttttactgatggagagaggtatgttttctttttttttttaaataggg     24850
aacaatgtgctaagatggaaaaaaaaaaatcaagtaggttttccagggaggcatttttttttttttttttt     24920
tttttttgagacggagtctcgttctgtcgcccaggctgggagtgcttgcgatctccgctcactgcaag     24990
ctctgccttccgggttcacgccattctcttgcctcagcctcccgagtagctgggactacaggcgcccgcc     25060
actgcgcccggctaatttttgcatttttagtagagacggggtttcaccgtggtctcgatctcctgacct     25130
cgtgatccgcccacctcggcctcccagagtgctgggattacaggcgtgagccaccgcgcccggcccaggg     25200
aggcatttttaaaggcaccatctcagaaggacgaggcaatggtaagtatcaggaatagttattggcgagt     25270
ccagcacagcagtcaatgactgtgttctggactgcaccgttggactcggggaaccactgtgtggccaggct     25340
gtgggctccggcagttgttcaaaaccctgaacctggagctcagaccagaggggttgtatgggaggctcact     25410
gtcattcattgtaacccctaagaacctcatccttccttgagcccgattgttcccatctgatcagagcttag     25480
atgcaagattgggaagaaaggtggtggagttgggtctgcctggaggacagcccaggtgagtcatgcatg     25550
gctgggagagcagtaggttcattctcaccacctcatttttctaaggggaaacagatccacaagggagggt     25620
cagcccccagatcattggccacacttatgggaaacatgtgctgctgttacgcaggcccccttcattctgtttt     25690
gcatgctctccttgtaaccccctgggcctatcaggacggcaggggtgtcgttggaagaggcatccaagaag     25760
gatctttaggctgcaggatggaagcacacactacagcatgaccttaggtagatggttcattcattaccttt     25830
ttaatatcttcctctttctttgctgtcaaacatgggtaataaaatacctaacctgtcatattataagaag     25900
taattgaggccaggtgcagtgggtcatgcctgtaatcccaacacgttgggaggctgaggagggagaatca     25970
cttgggttcaggagttcgagaccagcctgggccacacagtgagacttcatctctacaaaaaatttaaaaa     26040
ttagccagacatggtgatgcacacctgtagtcccagctacttgggaggctgaggtgggaggatcgcttga     26110
gctcaggagtttgaggctgtgtagctgtgattgctccactccagcctggccaacgagcaagaccc     26180
tgtctcaaagaaaaaaaaaattaggtgaaaacaatgtctatgcaacgctcagtgcctggtgatgtctaag     26250
gaatgcccaaactttctaggtaaggggtagggatgcattgggtgagagtcccattggatgagcatgaat     26320
gggaactcatcaatattgctgaaagtgcctgatccagaattaaaatatttcaacagaaaattcagaggaa     26390
actttagaatgctgaaaaatgccatattggtcagtcttactggttaatcgacttttctgaagtacataca     26460
cacttttttttttatttgagatagaatctcgctctttcatccaggctgtagtgcagtggcagaatttcagc     26530
tcactgcaacctccacctcccaggttcaagtgattctcctgcctcagcctcccggtagctgggattaca     26600
ggcacccactgcaacgctcagctagtttttgtatttttagtaggggtgaggttttaccatgttggccagg     26670
ctggtcttgaactcctgacctcaggtgatctgcctgcttttgcctcccaaagtgctgggattacaggtgt     26740
gagccacaacttccttcccacccagctaattttttgtattttagtagaggcagggtttcaccatgttgac     26810
caggctggtctcgaactcctgacctcaagtgatccatccgctttggcctccaaaagtgctgggattacag     26880
gcatgagccactgcgccagcacacacttcacttttgatcagcccccttttagagcatctgaacttctttt     26950
tccagtcccttgttccacccaggcaatcccaagcctggtgcctcctatctctagcctttgatttaggct     27020
attctgtctgcctgtgtgcaacattcctttccctcctactgaagttctaccccatcctgtgttgcatg     27090
agttgatggataattttgaaaaaataattattggtaatcattaacctctactgacttatttcattgatgc     27160
attttttgagcctggttaaaccaagtctagcagtgctttcggattacttttggtggtgaaaattgtttactt     27230
aaaaaaaaaaaacaatttgaaacaaataaaaagtagaaaagcagtggttcaagctcatttggagtgtcca     27300
aagtgacatgcctggaaatttaggattttgaaataattgtcgtcctcctcatgccacacttcgggt     27370
acatctcataaagtagacaaacacagatgaaggtcacctgtctgactcactgtatgtaaacctctcagaa     27440
attcacccttggctgcactgctcaccggaagtccattttcttctagagtaaagatttgcaatgatctagg     27510
actcaaaaagtccatcttgggccatttgaatgaccccagcatctcattttacccttgtatttgtagccc     27580
ctgcagagtggggttcaaaatgtcagacaggtactactagtacaggcagaggggacactcagaccatgag     27650
```

```
atccttctcactgtctggacattagaaagagagcagagcccaaggaaaagatatgggtagaatactttg      27720
tgatatacagctgtgagcccatgttagtggagatatttcacaattgaaaatctggacccttccccacaaa     27790
ctcaaattttagaaaggttcatctgatgctttcatacatctcaagtaaatggctctgtcttttcatggtt     27860
cagctgcaaatctgaagtctttacaatttgattgcttaaatattggttattgacaaattttcttatcaat    27930
ttgaatgttgtagcttccaaactttttgtcaaattttagaccacaaaggccttttgagtatctctttaatg   28000
attgccagataattttcctatccatggctttctctttacagaataaaacttcagtattttttccttgattc   28070
tagaagattgtcaaggtcatgtcctttatggaactcttgtttccaacaaagttgatttttaaacatctct    28140
ccatatttcctgccataaacaaatactaggttttgttttcaaagataatttgtaatttataaagaaaga     28210
ttaatgctgtcccacctccccatttgatcattaacatacaaattggaagaaaatcatacttggaaaaat     28280
gattgatcagctgtttgctattttatctagtatagatttatttgtcttatcaaaggtaaaacgaataaa     28350
ggtacacatcattttcatcagcatatacagctaaataatcaataatgatacattatgtaaatcccttg      28420
gctcctgaattacacgactttctttttttccattttctttttttttcaacctggatgagtcttaataaata   28490
atcaaggcctgaagtctaagaaatgtttgtcttctctctcacacttacagcctttggaacaggaacccaa    28560
tgcagcattggttgtaattatttcagtagctgcagtgcaaagcacattcaggtgaatataatcagactgt    28630
cctagttccaaggagaagcagtagtaacaggtctggcatcaggctcagagctatagacgagtcacagctt    28700
ataatatgatagactcactttatgaaaccccaaaggaacattatataaagtgcacaatcatgatgagaa     28770
atgagaacttctgaacctaggactttttttaaaattgttttaccatatgcacttaggttcaaactacattt   28840
gaaaccactgggcattatcagtatgtctctgcaagagtcagctactgcttttgcttaattggtagctgca   28910
ttttctcttaagggggggaatgctttggagtgtgttttcctgataatttggagtggtctttgctgaatggt   28980
gatcctaggttggaatttcctacattgtacaccaagaatcagttggctggatgaaaaacaagtgacaaag   29050
ggttttttcctttcccagtattctcaaaatcctcagtaagaactgaaggcatcatgactcttcagtgacat   29120
cagttgtccttgaggagggggtggaggatttcgtggagacacacataggcctgataatgaggacatctatg   29190
ctgtaatccagctctgctgctaattagttgtttgcaattactaggttttttggtatgtttaaagactgcag   29260
agacaggcattcattccttttcactatgaagaatgtgtgaatgtaaattaagaaccacagctagctgaga    29330
agtacaaataatttgtgaagcctatttaatactcgaaaatttcaatttatgtcagttcattcaatttttc    29400
tacatacagttgactgaacacttttctggttttgtaacccctattagggaaaattctttgcaatggatttt   29470
catgataatctggatagtcttagtgatcttatgttagaattttattttattgctaggatgacttagtccaa   29540
ttcaaaactgatgatcaagaaaaattcctttcatggcattcctgaaaacataattttttaagtcaaggat    29610
gatcaggataattctaggggcctgtaagtttgaacattgagattgttgatactaagttctgaacacatat    29680
tacccaaatgaatcttttattaaacattttgtggtttcaaaggacatagagtagttatgcaaatcaatgt   29750
ggtgcagcaactacagtataaccttcagatgttagggaatcaacgactaaaaaaaaaaaaaggacagtatt   29820
tgaatgttattacaaagacacctgcgattcttgaaggacatttcaaaggcagacaatggggtaaattgtg   29890
attgaaatacacgcgcaatctctatgatatgctccttccacttagaaagtgggatgaaagtcatcaatt     29960
gaagagtaattgctcaaaaaagatttctcctctatctagcttgggagtatttaggagctaatcagagtatt   30030
tcgtcttctcggaaattaaaagagatgaacagagttgtgcagacatggggaaaataaagtttagtttaat   30100
atttagatttaaaattagtacttgatggacattttaaaaagtgtacaattatcaaaacttcaatatcta    30170
atcctttatgtaaactatggtggatacatggaaacaccagggacgggtgctggttcttgttaacttttc    30240
tttctctgtcagccacaagagtgcctgtcccatagcagtaaactaagtatttagctaaattaagaagt    30310
gggaagggcgttgtaggttattgatcaaacgaaaataaatatattttgttgtttattcaaaaattcccc    30380
gacttaattttttttaaaatgtaacttaattttttaaagctcatctgtgtttcttttgttttgtgtcgagtc   30450
aaagattatttatgtcaattaccttttcatgctgaggcaacagtttcagtttcccattctgcaaaact    30520
aatttcctgattcctctctcaccagggaccattcccctccaaaatcctacaaggtgggtccatgacatct   30590
gctagagaaaagagggacatgttggagcgataggattcccatgggcactgacatactggcctctgggga   30660
taggaagattaatgcttagtacaagaaagaaggaaaagaaggccttggcgaggactgttttatctcagca   30730
tttctcagaagctccttcagtgggagacttcgcctgggaccttcgccccaccttcttctaatggcacttcc   30800
tcccctgtggggctccacgcgggacattacgtcggtgatgcgtagggcatcgggtgcggaaatgtgtgcgt   30870
gcctcctggcgtgtgcgtgccttctggcgtgtgcctgtgcgtgtacgtgcgcatgcgtccgcctcccggg   30940
ttcacgccattccctggcctcagcctccggggtagctggggctacgggcgctcgcttttttttttttttt   31010
ttgtattttagtagggacggggtttcaccgtgttagccaggacggtctaggaaattttttaagccactct    31080
gactaaagaaggtggagttggccgggcgcggtggctcaaacctgtaatcccagcacttttgggaggccgag   31150
gcgggcggatcactaggtcaggagatggagaccatcctggctaacgcggtgaaaccccgtctctactaaa   31220
aatacaaaaaattagccgggcgcggtggcgggcgcctgtagtcccagctactcgggaggctgaggcagg   31290
agaatgcgtgaacccgggaggcggagcttgcagtgagctgagatcgtaccactgtactccagcctggtt    31360
agagtttatatttcctttaaatttctagagaaaacagattgtcatgtatttttatagagacaaaatactg   31430
atgaaggtgatatacaggtagcttaattatgattttctaagatttaattagatggtaaatttacagtaa   31500
ttattaatatgttcactgcttttattaaaaaccatcaattctgaatccacaatgacacaaatggtgagta    31570
aggcttatgtcttgtatctgtgttctttcagtgcttaaatgtcaagagaaaaacaaagacttttaacatg    31640
atttttaaggaacgttttcattctatggtggtttctaatgtatgtgtttgtctttagacttcctttatcc   31710
ttttcctttcatctctttctcaaactcataaggtttcctttgtgcagatacttttttgcctgttttcct    31780
ccctagtttatgctgcttttctgtcaagaggctatatttcagaatgggaaaaaaggggcaagcatatatag   31850
ttaaatgaatcattttacactgtttgtaagttattatacataagctaatgtttttgatctctggaggataaa   31920
aatgagctcaagtttgagcaaatgatggtgccgcacacatgccctaccttatggtgagtcaactatggcc    31990
tatggtggtggccaattttgtaaataaaatgttttgcaacccaaccacacacttaaatttacattttc    32060
atatatggttcttttatactacagtgccagagtggaatggttgccccagacactgcatggcctacaaagc  32130
ctaaaatatttatcatgtgatcctttaccagaaaacattggcaatgcatactttggcaattcatggtgat    32200
catcttgggcctatgagttaatgcatccgtcgtgcatacattttaattagaaatatgtaatcattagcatt   32270
aacaacagagacatatgcttttgtattaggaattctatgaatgcatgcactacaactcttaaacacagagc   32340
aagtttaaagcctggcatctgggtgtatggatgagtgggggcctgggaacacccttgaattttacctgta    32410
aaatttatgtgcaccagggaaagattcagtggcgttcaacaacacaagaagctgcagctggttcgtgtgg   32480
gttttcattggtggtctctagctgctcaagtgatggattccagttgctggttgatctctcttagggctaa   32550
ggttcattattgcacagattgatcttggagaaacatcttgactgttttttttcacactccaatccatttgt   32620
tttatgatctagaagaaaggaacgcttaaatgcaaacaattattgtgatttttattccgcttcactgaac    32690
ttttttaatgaagtgcatttttgtacagttaaaaccaggggggttcctggattctatttttttgtgggaattttt  32760
```

FIG. 8A-10

```
tgagagagaagtaattctgactcagtacgcttccttggagtggataattaatattaatgggaatggaat    32830
tgttttgtcttcgctggcatgttgttctctgccacacctggcatgctgtggacctgtagtaaatattaa    32900
ctaaatatattttagacacagatgattaaggatcttttgctgaaaaacattctcttaatcttttatactt    32970
cccttttccacagtgcctgctgaaaacatgaatttcaattgtgtttctaagtcttggtcaatttaagtgtg  33040
acatggggtgatggggaaatagcagttaggactaaaggtagaaggtaacatgatccatgtgaattgtggt    33110
cagtgcaaaggcctggaacagcggtcactcttttcctgtccatgaacctttgtgctattcctctttgtaca    33180
cagtttaaaatataaataagaaaatgtcatgctgccaagtatgtatcacagtgcaggccacgtagaagat    33250
gctttatatgtgttggatgcaggccagtgttctcaactcagcagtttcagaggaagtgaaacaagccctg    33320
gctggaaaccagtagccgtaaggtctaagtcctggctgagcagtccaaatgggttccctaacctattgcc    33390
catccccctcagctaagaagggcaggcagtgcccctgggcaatgctggttttatccaactctcagaaggcg   33460
ccattctttgcctacgctctcccgtgtattggtccaaagcccaccaacttcctgagtggagttccttcac    33530
attctgcagaaaaccttctgtggtgctttaacattggatgggaagatgaagttatcttgggctctgggct    33600
atgttagtcatgttttggtaaacgaagcattctgttttcaccagggggatgagtaggtataattttccttc    33670
ttgagttttgcaaacctgggtggagaagaaaatcagtgcaatgtcttatgaatttttttttaatagaag    33740
atagcaacttggaagcaattgagtgttgagtctaagagattcccacccccccccagcattttgttctgatc    33810
tcatatatatgtacagaaaaatataaattatttagcattgacttatctgtaattaagtcttctaaaagga    33880
ctactgttttagctgctatattttcttctcaattacttggaaaatttaaaccttccttggggaatgttta    33950
gtctttcacttgtcctttaatgctaattgattggattgttcaaattatgctgttctgagaagaagttaa    34020
caaataaaatctggcaaagtaataagcaaatggcatcaggtaaatgaaaagaacagcacactgtgtccag    34090
tgatatgtgtcttcactaatttcttacctttcaaaagttgaagattgataatcaaggtaaactttaaaat    34160
ggaaaatttgccagctacagatttttaaagttcataaaaggtggttttttgatagcttttgttgctactat    34230
ttccatttagcctttttataataattagttaaaaatctcaactaattcttttgataagatatcataggttg    34300
tattttcaatgtttaagccagatacttgcttaaaaatcagttaattaactgagagtgaataattgtcat    34370
ttattatttatatttgaaatattaggttatagtttaaacattttacttaaagtgtaactagaataactgg    34440
acacattttgctaacactcagtgttttcaggtgttttttaaaatcatcaccatttctatggttaagtctta    34510
gaacaacactctgaaatgatgtggcatcaaccatctgagaaagtaattaaaagggataaaatagtaccac    34580
atgagttgggattccttgactatccaaccaaaaaattaccgattttaggaaacattctatttaatctaat    34650
tatccttcaaagtgagtggacctttgacgtcatttttcaacagcagtgccatcttgtttttgtgtagttga    34720
agatcagttcattgatctctatgtctcaggaagaaattgcagtattctttttttgtcttttttttttttga    34790
gacggagtcttgctctctcgtccaggctggagtgcagtggcgcgatctccgctcactgcaaactccgcct    34860
cccgtgttcatgcatatctcctgcctcagcctcccaagtggctgggactacaggcgcccaccaccactcc    34930
tggctaatttttttgtatttttagtagagacagggtttcaccatgttagccaggatggtctcgatctcctg    35000
acctcgtgatctgcccgcctcagcctcccaaagtgctgggattagaggcgtgagccaccgtgcccggcca    35070
gtatttatttttttggtgtttaaaaggttaaactgctttggaaagaaatttcaaaatgattttgggttttc    35140
cgggcttagaaagcagactccagctctaatagtatatgctttttttctacaaatgttttccactagatgg    35210
ttatagagaatcgtttcaattgatttctttctgatgtcttctctatttggaaatgcagtcgttcacatct    35280
aatggacactttctagcagccctgtttcatccctcctgtatacttcttaactaggattccagaaggagca    35350
gtcacatttgttttttccttactttccactccttcttcagcatgttcatgttctcagctgtaacacataat    35420
cacaaacttaatggtttgaagaacactcattggtaaacatggttctggaggccactttctgaaatggacc    35490
tggtggagctacaatcttagtgtcagcagggctccttccttcggaaggctccaaggggagaatcttttctcc    35560
ttgtcgtttttcccccatggaggctacctgcgttcctagctgttgtggcaggtcacatctccctctctga    35630
ctctgaccctcctgcctccctcttgtaagggcccttgtaatgccactgggctcacccagctaacccagga    35700
tcatctctttatctcaaaatcctaacttaatcacatctgcaaagtccctttgccgtgaaaggtcacata    35770
ttcacagactctggggattaagatgtggatagctttggggacagtgcattattcagcctcaggatgctat    35840
aatcgtatgattgatgcatctcaggggtcatcttagttggcctctgcaacatctttctccctcttgatac    35910
ctttcctgggatgcttcctcaacatctttgacaacactcttgttttcccttttttctccctgatgctgc    35980
ttttctctttattttccttcttcccttgtctctttccctcctccttgctccatctccctgggaatccca    36050
ttgtacattgtatactcgatggaaggtatgtttggaatattatcacgtgtgtgaccaaagactgatggcc    36120
agtgaaatggtcttaggtgatttggccctaagttcccttttctatcccatttcatgacatctgtctacat    36190
atcctgtgtctcaggcatgttgaaggacacacaaccttctggtaccagcagtgtttagccacagacctcc    36260
gtgtcactgttattgctaccttcctcccttgcctgactttctctcccctgcagtgggagtcctaatgattcc    36330
acattcacctgaaagtcatttctcaagggagccttccatgacctgctcccctctataatcatgtatcca    36400
aaagagtaccccatgataaccctctttcctctcttgttaatttcaatgccttacttcccctaccagacta    36470
aaaattcccctgaatacaggaaatatcttacgttattgtaatcaccactccgtctaatgcagtgccccac    36540
tgctatggtttgaatatcccctccgaaacttatgttgaaacttaattctcagtgtggcagtattaagagg    36610
tgggcctttaagaggtgattggatcaaggattaatggattaatgtgtaaaaggattaattggttaagaag    36680
aaggagagagacctgaggtagcactgagccctttggctatgtgataacatgggccacctcaggaatcagc    36750
agagagtccctattagcaagaagcttctcatcagatgcagcccctttaaccttggacttctcagcccccag    36820
aactttaagaaataaattccttttgttcataaagttactcagtttcagatgttctcttataagcagcggg    36890
aaacaggactactaagacacacagtcaaaaattatttattaaattaataatattaccataaaatcatagt    36960
agttaaatctgtgtttagagatagtttcactccttttagtctatcacttttaaatctacgtattcatgtt    37030
agttccgtggtatgagcgtctgtgtgcatagctgtaattatagtgtaagtactaaacagtcatga    37100
aacacttgagggttcttttgtaccaccgctcaaatttatttacatccatacacacttgtcaaaagaggtag    37170
agagtttcagatgcccttaactatccttattccccacaggcctaccctcatatttctgatagcagctgat    37240
ataccaggagactgaaaattaagttccatcctaagcacagagacttaagagttgctgtcacttagagag    37310
agagagaagcaaactattggtgcctccgaatgcaatattggttttccccaaagaatgctttatcttcgct    37380
ttacttaaagaaaaaagcagggcagggcagtggaaatgaactgataaccttgtgtctgtggatataactc    37450
tgctccaggaagacattaaagggtaatgctttgaaaataacatcaagaaatgaaagttaacataaaaaa    37520
aaaaaagctgtcagtacttttaggtgttccaaagtcctgtgagagtggcttaactggagtttatagcaac    37590
tctgagacattttttttttagtacagttctgccactacttttctatgtttataaacaatgaacagatgcatt    37660
cagtgctagttacctagaatcaactctcatacccagcattacactcgaacgttgaatgttgtattagtcc    37730
gttcttgcattgctttaagaaaatacctgaggctgggtaatttataaaggaaagaggtttaattggttca    37800
tggttctgcaggatgtacaggaagcatagggggttttttgcttctggagagtcctcagggaacttacaatct    37870
```

FIG. 8A-11

```
tggcggaaggtaaaggggagtgagctttcttacatggccggagcaggaggaagagagagagaggggcaa    37940
ggtgctgcacacttttaaacaaccagatctcatgagaactcactcactatacagtaccaaggggggccgat  38010
gctaaaccattcatgagaactccgcccccatcatccagtctcctcccaccaggccccacctccatcactg   38080
ggaattacagttcgacaggagatttggatagggacacattttcatcttaatttgtattttggtatagttt   38150
cataggaaagatttaggttggtgttctctcgcatggaaattcacttagagcttttacttgcttgttactt   38220
gttttaaagcctttccaattgaaccaatttattaagggcatctatttaattttctatggtaaatgtacta  38290
aaaactagaagagatcttactgccttgatactagtttattgcttgttttattaggtgccctgaaaagataa  38360
ctttagcatccactgcttgctaaccatccttgtcttcagcatcattagaagatacgaaggagtaaggaac   38430
gtgcttatgagaaaacagaagctatggcatccccatcatagccacatgagtcttgaataggccgcctgc    38500
ttctctgtcttcttttgcaagtgggttgcatcctagctttggtggtgtccttgtaactttggaattgcc    38570
tttgagagaagaccagtctgtctctttccagctgctggacctgagagattgggctgcaggtggcaaatgg   38640
tcgctactgagaaaactgaaagcaatgacagccatataatatggtgtgaacaccatatggatcaaactgg   38710
gacatcacagtcagcacacactcatccaattctcagaccaaggcacaccatgaaattctgacatttaggt   38780
ttcctgcctcttaggaattccatcaaaattatataagtagcactattctaaattttaacctactatcatt   38850
ttaaaaaatgacttactcacagccctaacactcatcggagcaggttgatattgtagaaaactctagccct   38920
atgcaactggagtgatcttgatgctaagacaatatgacccaaagccttgtcctttcctcttggctatatg   38990
aatattttctaactttgtgaacaaaatatgcctcttttcctcatgatggtgtttcaaaatgagtcgat     39060
gggtgttttcagttattagtggataggagctcttagtccttcaaaagcttgtgtttgatgtt           39130
gtagctttgtaaattatctcaatgtatgcatacacacatactcccctaccaaaaaaggtcaatagatgct   39200
tagaattccttccttccttccttccttccttcctttttttcagggtcttgctttgtcgctcaggctggag   39270
tgtagtagtacaatcatagctcactgcagctttgagttcctgggctcaagtaatcttcccatctcacacc   39340
tcagcctctcctgggaccacaggcatgcaccaccacacccagctgatttaaaatttgtttttttagagac   39410
acggttttcctatgtgttgttcaggctggtctcgaactcctggacctctagtgatcctcctgtcttgtctcc  39480
ttggattacaggcataagccgccacgcccagccacgtagtatttctatattttacttttagcataagtcc   39550
gtgaaagaactatatttctcatgcttgttcaactgtgcacatcatgatgttgaaggatttgcacgatgg    39620
ctatgatggtggctgtcactgcactacaatacttttttgaaaataagtgaaatattcattgttcactag    39690
aatagtcttacaggcatttgtttctttagaatttggaaacttcttttatattcatggtcgtatttcatt   39760
ctgctagcagtttaggcagattcaatctgtcccactttccagtggtagaaacagtgtgaagaagtgaagt  39830
agttgttggaaaatcactgtggtttgcttcccaggggttgccttgtccactgattacaaaagtatcataa  39900
cacatggcatcttcccacaaggagtttagagtttgaaaagtcaatgtattaatgtacataggggacccac   39970
ttccactcaaagcaaacattgagtcaggtatcagagctcggtgggtgaacacgatggcatttaattatcc  40040
taaattactttatataatcaatatctactaactgcctttgttatgatgctacccatcattttggagtca   40110
caagcttttcaacctttgtctaactaaaagatggatatctgcattttatattaggtggtctggaagccata  40180
gtaatattagagagcacataggaatgttttagtccatttggctactataaggaaataccatagactgt    40250
gtagctttataaaacaacagacatttattgctcaattctggaggctgggagtccaatgcaaggtatgcag  40320
attcagtgtctggtgagcacccacatcctggtttgtagatggtgccttctccctgtatcctcatgtggta  40390
gaagggggtgagggagctgagttcccttttatgagggcactaatcccattcatgaggctccaacctcatga 40460
cctcatcacctcccaaggacctcgcctcctgataccatcatcttgggggtcacaatttcaacataggaat  40530
ttggaggggcacaaacattcagatcatagcagggagagagatgagccttgcccaactccatgaagccatc  40600
tagattttttcagtctcagtcctatttccattttttaatgttgagttttgaactctattaatgtctcctg  40670
gtattttcaaaactttgtagagctttcatcatcaatattaaacctttcacattcaaaggacatgattatt  40740
ttgtgtgagtagcgtgttgttatttgacaaatgagtacaattataaataatcttgaccatcttgataga   40810
ggaaataaatgcacgtgtcaagatatactataatgcttttgtaatcaaaacaatgatggggccaggcgca  40880
gtggctcacgcctgtaatcccagcactttgggattacacccactgaggtgggtggatcacttgaggtcag  40950
gagttcgagaccaccctggccaacatggtgaaaccccatctctactaaaaatacaaaaattagccaggca  41020
tggtggtgcacgcctgtaattccagctactcaggaggctgaaggcaggagaatcgcttgagcccaggaggc 41090
agaggttgcaatgagtcaagatggtgtcactgcattctagcctgggcaacagagtgagactctgtctcaa  41160
aaacaaaacaatcaaacaaaaagcaatgatggatagaacagggtattatttaaatgaaaactgtaaggggg 41230
agttgtatgctctcaaatgtcattatgcacagtctaatattttcccttttactttgtcactctacctgct  41300
aatttgcttccttaattcagagttatgtctttggttattagttataatataggctgacagttatgtagcg  41370
ttctctgtgctaggacctgttccaagtgcttttttatattaactcattggctccaaccactctacctga   41440
tagttaccattagtattagtttcctatctgtgctgcagtaacaagttactacagacttagtggctgctta  41510
cagctctagaggtcagaagtccaaaatgagccttaggaggctaaaatcaaggtatcatcaggacaccgtt   41580
cttttttggaggctctaggagaggacagatttccctgccttttccagattctagagacttcttactctcct  41650
tggctcataagttcctttctgcaccttcaatgccagtagattgagtccttctcattctgtcatctttctg  41720
gttcttcctcttttcttttccctttctacttataaggatccttgtgattatgtggaccccactggataa   41790
cctggaatcatctcccattcgaggtctgctgactgggaacctttaattctacctgcctctttcatttga    41860
atctcttttccatgtaaggtcacacaaagtcacaagttcttgtattaacacatggtcatcccgggggtc   41930
cgttattctgcagaccacacagttgttatcttcattttacagacaagaaagacaaacagtgagagttaaa  42000
tcacttactcagggttgtttgggctgctaaatggtagagccagttaaaattaggagtgtacacagggaagc 42070
taggcagtgttgtggtcaagggccttggcccctgaaggttcaatgaaaaatcatggagacaaagtgatt   42140
tttactgtccactcaactggattgcacagagaggagagaccaggagcctggctggctggtggagaaat    42210
tcttacccctttggccagcagtgtgggttcctgggtctctgcactgtggcttccaaaagagcagagcgtc  42280
tttgttgacccgctcgctgtgtcataactgtaggggcaaggctcttactccctaaaatttttaatgaa    42350
aaatcactgactaggcagactgattaacaggagaaatgacattacaagtgtatttaatgcagatacacag  42420
gagcctttggaatgaagatctaccctccaaatgaggtccagaagcttatacaccatcctgaggttacaga  42490
aagagtgggggcttggatcccagtaaaacaggtgatgggagggggaggtgaggaattctgttgaggagat  42560
tattagaacagagattaacttgtaaagagttctcttttgaaaattaaatgatccttggagacacccttgga 42630
aaactgtctgctcaggtgtggttttatcttgttttttttttttttttttctgtaatagataatgtatataa 42700
cttgaaggggttgaaaaacaactgtaggttgtcaaatgtatcccatatcctagccctcacttctggttcc  42770
atcttacttttctatgtaagttttcacttctagttctatttcttacttagaaattgtgttaatcactggt  42840
ataagtagcatctttgccagataaaaaggaaaaacaaaaacaaatgctttatgacgatatgtgggagaaa  42910
agaatgtaatagtacttgagaaatattggaactggttaaatactagatggtgttgggtagtgttaataa  42980
```

FIG. 8A-12

```
aatgattatatttcatagagaacattttctctacgctgaggcagaaatacagagataattttatactata      43050
ctcatcctttctcctaatcatattattttttaaaattcaagttagaatttgagtgattgtattgctgctg      43120
tgctgtttttctcagaggaaaaatcatagcaaattatttcaaagatagatggagaacatggtgtttctct      43190
atatccaggttggattgaatgttgtattagccaatggaaaccttcctcttcaccctctggagggtcacgg      43260
aaaatcatgtcacaaaaggcagattaatagaaagcaatacatatttattaagttgtagatttgtgtaaca      43330
caggagccttcagaatgaggacacaaagatacaggggagactgtccaatttttttttttatttcaacttat      43400
tttagattcagggggtacatgtgtgtaggtttgctagatgggaatattgcgtgatgctgaggtatagggtac    43470
aattgatcccaatcaatggtggtaagcatagtgaccaccagctagttttcagtcctcaccctactcact      43540
tcccattctagtagtcccctgtgcctattgctcccgtctttatttccgtgttttctcaagctcccactta      43610
taagtgagaacatgcagtatttggttttctgttttatgttgactcacttaggataatggcctccagcag      43680
tatccatgtttctgcaagggacctgattttgttcttttcatggttgcatagtattccacagtgcatatg      43750
tggagaccacatttctttatttattccacccaccactgattggcatctaggttgattccatgtctgtct      43820
ttgctattgtgaatagtactacagtgaacatacaaatgcatgcgtctttttgtagaacgatttattttc      43890
ctttgagtatatacccagtaacgggattgctgggtcaaatggtagttttgtttcatttaagtcctttgag      43960
aaatctccaaactactttccacagtggctgaactaatttacaatctcagcaagaatgtataagtgttccc      44030
tttttctctgcaaactcactggcatctgttatatatttttttttttgactatttaatgatggcctttctg      44100
actggtgtgagatggtttctcattgtggttttgatttacatttccctaatgatcaatgatgtggagcatt      44170
tttcagatgtttattgattgcttatatgccctcttttgagaagtgtgtgttcatgttctaggcacagttt      44240
ttttttgttttttgttttgttttgttttgttttgtttgagacagagtctagctctgttgcccaggctgga      44310
gtgcagtagcaccatctcggctcactgcaacctctacctcctgggttcaaaaaatcctgcctcagcctcc      44380
taagtaggtgggattacaggtgcccaccaccatgcctggctaattattttgtatttttttagtagagaca      44450
gggtttcaccatgttggccaggctagttttgagctcctgacctcaagtgatctgctgcctcggcctcctg      44520
aagtgctaggattacaggcgtgagcgaccactaccagccctttgcacagttttttaatggggttatttgga      44590
aactcagtttttatgctaaggttcaactaactgtggacaacccagtagaaataggggttggacaaaaaggg      44660
cctgatctaaagctaatggactgagtggggaaacccagccaggtctgtctgcctagattcttcttggcct      44730
ctctgagcagcattccttctgggtgtgaggtaggaccctctgtggaatgggggtcttaggacctacagt      44800
caaaaaggcaggtcagaggatttatttatggccagtgtttacagaaaggcaggggaaagttgaggtcatc      44870
tttttttggtttcatgggtgctttgtggggaagggtctggttttgtatgacctgcttttagggaggagga       44940
ttccagttcctatggccagccttcggggagaatggaattgagagacaacaggtcaggggagggtcagaga      45010
aaaacctttgcctctgaggctgctgaagccttcattttgtggtatcattctctgagccccaacaacaca      45080
aatttttttaacttcatgcaaaactcttaggtcagttgagcctagaatacaggtttctacgctgtgtggc      45150
taaagtacggtccttccctcctctccacagggagcagatgaaattttattttggaggaagttaactcagaa      45220
tagaaggacccagagatgtcagagagtggagtgggggcgagagcccagactccgtatctgtcctgagaaa      45290
gttaggacataaggaccccacagacatcagagagtggagtaggggtgagggcccacgctctgtgtctgtaa      45360
gggaattgtctacactctgcatactcacagccatcagcttcttgttcttccttccaagttgaaagtcac      45430
tggactccttcaagtccatcctggaggatccctttcttggtaaactgaactggcagagaaaagtattcca      45500
taactggcatttggaggccatttgggcctattacttatttactgtacaatatgttcacctgctgaggaag      45570
gaccccctggctatccacacagacctgattcttaagtgagaaaagacagtcttacatcctagatattttg      45640
agaagctttcaataagaaattctttttttaaaaattgaaaaaagaatcatctggagggtagcacagacaacac      45710
caaccaagaaaacaagagacaaaatttctaatctgtaacttgtaggagatatgatgaaatagtgactcat      45780
aaaaaacatggaaattctattaaaatgtgacatattaggcaaattaaataatcagattggagaacgatta      45850
tgaggatatctccaatggacaaaactttaatgagagagagatagcaaatggaaaggaacgaatatggag      45920
actctaggaatctgacattcgaagagtattttcaggaaggacaacagaatacaaataagcaaaagtgact      45990
tatgaataattttttaaaataatcccagcattgagggatctacacttccaggcttatgaaacaacactcag      46060
ggctcaccatagtgaatgaattgaaactccaaactacaaaagcacattgcgagatttcagaagaacaaat      46130
atataggggaagatcctaagagcttggaggctgtattaggccgttcttgcattgatataaagaaataccccg      46200
agactgggtaatttacaaagaaaagaggtttaattggctcatggttctgcaggccgtacaggaagcatgg      46270
cggctcctggggaggcctcaggaacgtgtcaatcatgacagaaggtgaagggaaagcaggcacatcttac      46340
atggctggagcacgaggaagagagagaggacgtgctacagccttcaaaccaccaggtctcctgagaa      46410
ctcactcactatacagtccaaggggtgtgtacagtaccattcaagagaactctgctccccatgatgcca      46480
tcacctcccaccaggccccatctccaacactggggattacaattcaatatgagatttgggcagggacaca      46550
gatccaaatcatatcagaggcaaagaaaaaaaacttattaagaatcaagaatttgtaatgtcatagaatg      46620
cttcatgtcttcactgaacgttaaaagatagaaactttcacaattctaagaaaaaacaatttactacgta      46690
gaactcttggagcaaactgtccatgggcaggcagggtcaaggcatttacactgatgtagcatttccgaaa      46760
atttacctttgtgcaccttctcttggaaagctgtgtgattgtcttccttcaaacagcgggaataaatg      46830
acaaatagaaagatggggaatccaaggaacagtggccttcacagaagagctgaaagaatgcaggtctc      46900
agattaatgcccagagcaggctgggacagctggaatcctagagtgagacttcaaggagaaagtacataaa      46970
agaaaaggaaatgagccatttgaccatgtagaaatagtacttgagatgggctttagttcccttggaacat      47040
tcagaaaaattgaacaatagacacacagaaaagcatgaaatgaaaatgtgaagttgttgttgtctccaga      47110
taaaacaggaggcaattcaatgaaggagatttaattgagtagaatgcttcattcaggagtgattattaa      47180
ttgcacagttcaataaagttaaagagagaaggccaggtgtagtggctcacgcctgtaatcccagcactc      47250
tgggaggccaagataggcagatctcttgagtccaacagttcgagaccagcctgggcaatgtggcgaaatc      47320
ccacctctacaaaaaattcaaaaattatctgggcatggtggtgtgtgtggctgtagtcccagttactgcaga      47390
ggctgaggtgggaagattgctggagcctggaaggttgggctgcggtgagttgtgactgtaccattgcac      47460
tccagcctgggcaacagagcaagaccctgtctcgaaaaaacaaaaaggcagaagggggcaaatagagtggt      47530
ggttgcccattgataatttataggtaatatctaaaaataatatatcaagaaaaaaatagcataaactatta      47600
cttagaaaatatcatagagcatatatttggagaggagaagctaagaaatctgaaagcatttgctttctaaa      47670
gcaagtgtggtcatgggatgttgtatgttgggcaagaaagtgctgtttgttgtgcaaataacacttgtag      47740
tagtttgacctttaaaacttcatgcatgcctttctttattgaaacaaaattttttcaaaagaaaatgat      47810
aaggccaagattgaatggtatgtgaatgtgaatatgacagttaaaagcatgatttctcaaatgtacctgc      47880
ccattggaatcacctggagaatgtaataggtattaatgcctgtgctgtggtcctccagagattctgactt      47950
gctcggtctgcaatgcagactgggcagtgaaattttttcaattctccttagggattctaagatgcagcaga      48020
gtttaggaagcatggatctaggtagctcagattcttacttgaatttaaaaatctctagctgggtgcagtg      48090
```

FIG. 8A-13

```
gctcatgcctgcaatcccagcactttgtgctgggctgaggtgggaggattgcttgagcccaagagttcca    48160
gaccagcctgggcaacatagcgtgcctgtgttcccagctattcaggagactgaggtgggaggttcgcttg    48230
agccctggaggtcaaggctgcagtgagctgagattataccgctgcactcaagcctgggcaacagagtgag    48300
accctgtttcaaaaaaaaaaaaatcttgtccagtgttctcttcaccaagatacagtggtttcagtaata    48370
aactactactaacatgatgatttagattgagccaacttcatcactcagtcatttctttgttatctgatat    48440
gttctttatggaaaggctttaattgcttgaaaatgacctaatgcttctcccaagcttcccattttttttt    48510
cccctttcttaactgaagtcacagaatgttctcgtgtgtggaatgctttgtctatcctacgggaagccaat    48580
tgtgcatggctcatggcgccatgctggcttaattgttccaattcctcctgtttctccgaccacacatgag    48650
gttgaattaaatataattcctcagtttgcatttcccaggcagtcgtcctaagtggcttcttggaggagc    48720
tctgtgcattccactggtctaattctgtgatgcccttaactcgagggccaaggacataattaccagctc    48790
tagaaattcgttccgtggtcaaggatgcttgtgcagaggccaaatttcttcattataatttggccttt    48860
gccaagcttcaaagtgaaggggattgagttcctactaaagagtattggcacctaggaagtgaatgctttc    48930
tctatcttttgcagctagtgtgttctacatttcttcaatgtaccttctgcctggtaaatgtcagattatt    49000
tgttgatcatcctcagggtgtagttctttgtgttgttaaataagaacccagtggcttaaaagcattggct    49070
tttgagaagtcattttatcctggatgataactcaaatccatgcagtgctgatatttacagctgggaggt    49140
gacatgatcttatcctttggtctgttgctcaaattattgatttcagtaggacttactggctcccttctgt    49210
cttggggataccttttgatctgtcttgccttggggaccctccctctgacagtagcagccttattcc    49280
acaagaagggaccctctgagagaggacagtcttcataccgcctcttccgattttccttatctttatgg    49350
gttttggctttataaacttactcttagaatgtccttaaagctaatgattttttaatgttctctagtgtat    49420
tactaaaagctcttcatctacttgaaagactggggcaggaagattgcttgagcccaaaaggtcgaggctg    49490
cagtgagttgtgatcctgccactgtattccagcctgggtgacagagcaagaccctgtctcaaaaaaataa    49560
aaaggacaggtgcagtggctcacgcctataatcccagctttgggaggctgaagcaggaggattgcttg    49630
aagccagagttctagaccagcctgcaacatagagaggacccatctcttcaaaaataaaaaaaaaatagct    49700
ggacatgatggcacaccctgtagtcccagcttcttgtggggctgagaccagcaggaggacttctagagc    49770
ctaggaattccaggatgcagtgagcaatatgtatgtgttaatacatagtgaaccagttattggagaatt    49840
agtatatgtcctcccacaaattcagtatgttttcctaattatccaattaattcaaagggcataaacataa    49910
tagatgcaaattattttacgtttttttgttaaaaacctttttgactgaatcagtctatgacgctttagta    49980
tttgaagttgcggacagaacttagtcttaagatagcactcgcttgttgatagattccatggaggaat    50050
ttttgccagatgataaattagcttgaagatgttatagatgtggacagtcacacctctaagttacacagt    50120
ctgggtgggcaattgaaagaacatgcagaaacacaggcttgttaagggataattaacgtgggggaa    50190
atagaacagtcatggcagaggatttaataggtttaattgggttaggaagaataggccggagtgaaagaa    50260
tagctcttaataggaggtctagaaatagccaaggaaagcattaattgcagaaaatctgtgacatctgatt    50330
actgtagtgaaagaaagatccaccttttaaaaaatcctatctataacagaaagaagtgataggagaaggaaa    50400
tcttcccacggacatatttaagaaaaacagtggggaggtttgagatttcaaaggcccatggttcaggtta    50470
taattcaaaagagaggcaaatgatagtcctactcttcttgagtttcaggaagggggaggattttgccact    50540
tgctgtgaaataattttggagcttctataacgttgatcctttcatcctatttttcttggacttgggatg    50610
tggggagtggataagatggggatggagaagaagcagggtttgaaatgcctcttttgattctgttcattcc    50680
cggaattcttctccatgggcccttaaagagtagagactccttcccggtgcatgacatccagtggccaatta    50750
atgaaactttatttcctcagataagttcccttcctccattaatttgtgggaattcagatgaaaacttact    50820
tggactgtggttttctatgtgtttgtgaatggaaggacatgtttgtctttgaccttcctttagtttcacg    50890
tcttagtcttgatatttaagtagctttggttcagacagagaaggaccatgtgtgcagttgctgggactgc    50960
tctctagcttggaggttccctggtcttgggaaagatctccctgccctatgcaggtggcatagatgtttaa    51030
ttttctacatgagagaagcgctagagttttttttattcattacttgtgtgcacagctgtggcctctaggga    51100
agctcagctgaggtggtctcaggttccaccaaaggttaccggggagagatgactaggaagacaggaagac    51170
ctgtctcacttgggagggtatggcaagagctaggcaagaccctcctggtggagatatttgccttttattct    51240
ttctttttttttttttttttttttttgagacagtttcactctgtcacccgggctgaagtgtagtggtgcga    51310
tcatggctcacaccaacctccccgtctcgagctcaagccatcctcccacctcagcctcttgagtagctag    51380
ggctacaggcatgcaacaccatgtccagctaattttttaaattattttttagaaacaaggttttgccatgtt    51450
gcccagactggtcttgaactcttaggctcaagtgatcctcccgcctcagcctccgaaagtgttgggatta    51520
taggcatgagccatgttgcctgacccatttattctcaagtacttatgctcagggcaggtcttccaaggga    51590
agagaacagccagataagactcgtatgagatagctgaggaggtggcatttcatccttccatgcacatgct    51660
ccttatccacaagcagaaagctgtaacctttgctgtccccactaggtcatgataggtagatacgcaggtg    51730
atgaccacagactggcaattagccaaggattctcagctgtgcacgctacatgtgtgagtgtgtgtgacag    51800
atcccttttggcggtttggtggaaaattgatacattttgtaaaaatgatatgtttaagtcatacaataagg    51870
taaataacgcataaaaggaaatcggttttattgaaatagttaccaaggtatattaatattaatatttaaa    51940
gttggtgcagtggctcatgcctgtaaacaccagcatttggggaggctgaggtgagaggattgcttgaggc    52010
caggagttcaagaccagcctggccaacaaagtgagactctgtttctacaatcaataaaataaaaaataaa    52080
aataaaaagatatatttaaactgggctacagtaatacatgtgcatctttattgtgtgctaagtacctgga    52150
tctacttaagaggttcgtaatagtcacaattttcaaagtacaataagcgtaaacagtatttttgggatatct    52220
gtgataacagtgttaagtgtcctacctacacgggtaattggaagcaaatacttaattcagtgcattagtag    52290
tgaaactaaagatgtaattacttttgcccattgcaatttgtagaacccatggaatctatctaaagactcc    52360
tgggtggcaaaggataaatgcttgagggtatgatacccccattcttcatgatgtgattattacatattgca    52430
tgcctgtatcaaaacaactcatgtgccccatatatatatatatgtatatgtatatacacctgctatgtac    52500
tcacaaaaaaataaataaagacacctgggtgggattgggttttttggacttagggtggagaacatctgca    52570
tttagaattgtgtagaggaaaggttttgatttatttattataacctcgtttttcttaaaaaacctgcatg    52640
tgtagtaggaattttgccagaggtggaatgtgagagtcactagtttgcagcatagagcattctatactg    52710
agataattattttatgtcaaaaagaaagtgaagaatctggcagattagaatcttcatgttattttcatt    52780
taaaaagcttggaagtgtcaatatcaattaatattgactgctatttactgacattttttggcaaaaacat    52850
ttcattttaatgaatttgtcttgtttgaatgtttgtaaggctttggaggtagttttaggagatagttgc    52920
ctttgattcctgaggtatattcttgggtctaccctgattctgtctcttgactttgcacctctttccttcc    52990
tgaaccctgtttaaaagagccttccttttacgactcttttcttccatccattcttccttccctccatgctaa    53060
tgtgagacacagaggtttttatgaagcctgttctgtctatatgctggatcttggaagccttggttatttc    53130
ctagagatggaaggtctgatctcagttaagttcctgaccccaggacaagaagcctctctggagtaactgac    53200
```

FIG. 8A-14

| | |
|---|---|
| tcactgggatagagcctgttttcacaaattaatattcctgtctggggagggcagaggaaacattttgggg | 53270 |
| agtgggtggaggtgatgaggttcaagcctgaggatgaagcttgcctttcctgggagcttgtacagtgtca | 53340 |
| tactcaggaaataaactgtgtggaaaggtggtgtttagtaatctagagccgaacaccttgtaaggccct | 53410 |
| caccttgtcattctgcactgtcagaagcacatgagaaagagtgtaggctgccagagcaagcatcacacc | 53480 |
| gaaataggaacttctcagatagagccgtctgcctaaaacaaagtaaccttagcaaataggatctgtgcta | 53550 |
| cagaaaatggagcactctagccagggttgtgagatggagctggtcctgggtcacaggtggtgtcttggg | 53620 |
| aaacgttctgaagacactcagcttttcggatattgcacagttcattaggagaggtatgggcagtggttat | 53690 |
| gaagctcctatgtaagagacatagagatacactcaacagtattactccagagggttctggctcctgtct | 53760 |
| tgcacttgggagtacacacttgttcttgtccacattaacctccaactgtccacatgatcaaccatctgca | 53830 |
| gacccactgccagttgagggtcgtgccaggtcagaagtactaactgcaggttaaactgtgctatttagaa | 53900 |
| attgagtgttttttcttactcaaactgacagttttcctttgtagaagaactcactcagcttccactctg | 53970 |
| gcttaaatatttcctttacatgatcaatattatctctgtccatcagatacagcaatgagaaagcctttta | 54040 |
| aaggaaatgaggttaaaagtgactgggtatctagaattctttattttgtttgctaaattgcaggcaaata | 54110 |
| tattcccagaactagttgtgatacctttcagaaactggcttatttgacattggctgaaagtaatactct | 54180 |
| aacactttactgctgtgtcaatgagtgaaattcctgcaggcaaaaacaatagggactacatcgtgaagcc | 54250 |
| tatgagaattttatggtggaaacatgagtggagcaggtggtggaagtagctcatcttctgtggttgtggt | 54320 |
| acccacaggagatgagctaaggagaatgccctgaaacctaaccttgccaattttctgtcttctgtgtcct | 54390 |
| ggttccttctggtttccttgtgtctcttttcttccttttaatttaatagtgtttactgaagaccttctgt | 54460 |
| cttccaagttcaagtattagtcatctctgggctttgcccttagatacttatcatagtctagcaatgaatg | 54530 |
| taagcattgaggaagtaatggtgacataatgtgaatgttcagtgtggtatcatcttcccactctttgta | 54600 |
| aatcttggtggtcttaattcttgaatgtcaatgcttacccctctgtcctgtcttttacagaagtcctctg | 54670 |
| gcctagctctctctactgtctaaaattgtagaagcatcttctgggcactccattgcaaagtccattctg | 54740 |
| cagaagcccaccatcccacagaaggagcaggtgggaggcagtggaccacaggctggctgcatggtagcaa | 54810 |
| ttgaaagcaatggagcacaggctggcttcatggtaacagttgaaaagcaatggagcacaggctggctta | 54880 |
| attgtagcaattgaaaggcaagcttcatctcatcagctggagtgtttactacttgaggatgggtacttga | 54950 |
| ttggtgtatctttacattttatcaaaatgggtttcaccttggaagcattcagtggtacctcagtgaataa | 55020 |
| ttgtaattagctaggattctcttttggggaatacttattgttctaaatttatatgtgtttacatatatgtac | 55090 |
| tgtattagtctttttttcacactgctgataaagacataccggagactgggtaatttataaagaaaagaga | 55160 |
| tttaatggactcacagttccatgtggttggggaggcttcacaattatggcaaaaggcaaggtaagaacaa | 55230 |
| aggcatgtcttacatggcggaaggcaaaagagagagcttgttcaggggaactcctcattataaaaccat | 55300 |
| cagatctcatgagacttactatcacgagaacagtatggggaaactgccctcttgattcagttatctccc | 55370 |
| acagggtccctctccctatacgtgggaattatgggagctacaattcaagatgagatttgtgtggggacac | 55440 |
| agtcaaaccatatcacatacatatgcatatctttatgtaaggtgtgtgaatataggtgtgtatattcata | 55510 |
| tactcttgtactttctcaaacacaaaccatagcacgtgcaataatatccttgagttacatctgctactct | 55580 |
| gcccatttacacataagagatggaagcattgatggttatattaggtaggttctctagaggaacagaac | 55650 |
| taataggacagatagatatataaaggggagtttatcaagtagtatttgttcacacgatcacaaggtccca | 55720 |
| caacaggccatctgcaagctgaggagcaaggaagccagtccgaatcccaaagctgaaggacttggagtct | 55790 |
| gatgtttgagggcaggaagcatctagcacaggagaaagatgtagacttagaggctaagctgtctagtct | 55860 |
| tttcatgttttttctgtctctgctttatatttgctggcagctgattagatggtgcccacccagattaaggg | 55930 |
| tgggtctgccttccccagccctctgactcaaatattaatctcctttggcaacaccctcagagacacacc | 56000 |
| aggatcaatactttgcattcttcaatccaatgaagttgacactcagcattaaccatcacaatggtgtata | 56070 |
| caccccttctctggttgctgatggagttaaagtgagagccaggatttgaatcatagtcataaaactgcaca | 56140 |
| aaacctctgccccatactacctcccagatacataatacacacatgagtaggtgttttttgtgcctgttata | 56210 |
| gtgcatttgagcctgttgttcttagtttgctcttatgtaggaccatctctctgaaaacagatgatcagca | 56280 |
| tcatatgcaacaggtagtattgattatctgtagcataaaggcatggaacacgggattttcagggaatgga | 56350 |
| gtaggaaaaattcctgaacctaagcagccttaatagtttaatatttcacttggttagttcgaatatatatg | 56420 |
| ttcatatgcacatgcatgaaatgacatggataaaataagttttaatgtattgtatctatataaatctctt | 56490 |
| taaacctcaaaaaatgtatatatccaaactaattatttgtcagtctctccctctctttctccctctctct | 56560 |
| ctttccacgtatttatatataaatatttctgcaaactaaccaactgaaatattaagctcctatctatgtt | 56630 |
| ttatatgtatttctgcaaatagccaaccaaaatattaaagcaattaaactcctaaatataatatttcttt | 56700 |
| tatctattatattatttcttcaaactaaccaattgaaatattaagcttcatgtttatatatataaagt | 56770 |
| atttctccaaataaccaagcaaaatattgagtgtattaagctcctgtgaatgttttatattattctatgta | 56840 |
| tatagaataatatattttatatgtttttttattatattttatattattctatatgtagaataatatattt | 56910 |
| atatcctatattatatagaataatatatttttatatcctatattatatatatat | 56980 |
| cctatattatatatagaataatatatttttatatcctatattatatatagaataatatatttttatatccta | 57050 |
| tataatatatagaataatatatttttatatcctatataatatatagaataatatatttttatatcctatata | 57120 |
| atatatagaataatatatttttatatcctatataatatatagaataatatatttttatatcctataatat | 57190 |
| atagaataatatatttttatatcctatataatatatagaataatatatttttatatcctatattatatatag | 57260 |
| aataatatttttatatcctatatatagaataatatatttttatatcctatattatatatagaata | 57330 |
| atatatttttatatcctatattatatagaataatatatttatttatttttttataatatatttt | 57400 |
| tgtaatatatatgttttttatatatagaataatatatttttatattattctctctctatatatagcaggtt | 57470 |
| agtttgaagatatctacgtataatatattaaaatttattttggccaggcgcgttggctcacgcctgt | 57540 |
| aatcccagcactctgggaggccaaggcgggcggataatgaggtcaggagttcaagactagcctggccaat | 57610 |
| atggtgaaaccctgtctctactaaaaatacaaaaaattagctgggcatgggggcatatgcttgtagtcct | 57680 |
| ggctactcaggaggctgaggcaagataatccggagcagcagagttgtagtgagccgagatctcaccactg | 57750 |
| cactccagcctgggtgacagagtgaaactctgtctcaaaaaaaaaaaaattattttatagatataattt | 57820 |
| catatatgataagttaaagtacaaactcttgaaacaactcctcttatatgaggggaagaagaagatt | 57890 |
| atttgtacagtacaattagtacagtgaattctgggaaaaagtcagtaaatactcatttcaaatcctcatg | 57960 |
| tacaattcaagtaaagaaaaatctggtggcatttttatatcctgctaataaaggttatctggtgttggaa | 58030 |
| aacatattttatttttacatgtacatagtaggtgtatatttgtgggtacatgatgagatattttgatatag | 58100 |
| gcatatgtgtaaaaatcacattagaataaatggagtatacatcacctgaagcatttatcatttctttgtg | 58170 |
| ttacagactttccaattatgcttttagttatttaaaaatatacagtaaattaatgttgactgcagtcacc | 58240 |
| ctgttgtgctatcaaatactagatcttattcattctgtctatattttttgtgcccattaaccatcctcact | 58310 |

FIG. 8A-15

```
tctctctctctctcccattacccttcccagcctctggtagccatcattctactctctgtctccctgactgca        58380
actgaaagaaatatttttaaagaataggctggaaggccacactgactctcactgtttctggcacactaaa         58450
ccttgccatttctgcagtagggattgtctcgcttcagttatgccttgctacttcagtgaaggactttct         58520
gttcccactgggctcctatactgagtctgctttggagataatagtctgagatgtcagagcgtcttagtgg        58590
tgaaagcaacttaagaggtcactggcacaagccctcgttttgcagtggaggagttgatggcgagggcac         58660
ttggctaattagtgaccagggctatagcaggctccaggttccatgactgtggcttaccatggctggcaggat      58730
cccagggcttttctgtgtaatatgtgggtggatggtctattgccttgggcttgtcgcataatcatggaga        58800
aaacagtttatattttcccttcaattttaaatccaagatagtttgatagcacatgggaaaataaagtca         58870
ttgagtaaaacttatacggatgagaatcttttgattaaattttcattgtaaaataatcatagtcataaaa        58940
agtgtatcaaaatgtgtatttggatattcattaaagagtaaaaataatcagatacatagtattgtac          59010
ccactgacagacaaggaaagagaacattcccactgttttatatatcagtgtgagttgcttccctctctc         59080
ctacctttcagtgaaatctaatcccccaagatttggttttcatactgtccttgctgtatatttcaggaca        59150
aacatagctctgagcaatatattgtttagttttactattatgtaaataaaatcacactatttgtagtctt       59220
ctgtgacttgccttttatgtttgagattttcccattttcctccatatatctgtattttattcatttttga       59290
ctgtttgtaaagccttctgttttaatatgccaacatttatttattcattatcctatttatggatatctg        59360
gattgtggcaatattttttgcaattataattggggcttatttatcctcagcaaactaacgcaggaacaga       59430
aaaccaaacaccgcatgttctcactcataagtgggagctgtggagctgaactcctggacacatgggga         59500
gggaaacaacacacagttgggcctgtctggggatgccggaggggagagcatcaggaagactagctaata        59570
gatgctgggcttaatacataggtgatgggttgatttgtgcagcaaaccaccatggcacatgtttacctat       59640
gtcacaaacctgcacatcctgcacatgtaccttggaacttaaaagttgaagaaaaaaaatggggctgca        59710
gtggacatttccgtgcatgtttcctgatgcatgggagttctagttgctccacatcgttgctcagtacttg       59780
gtatcattgttttgtttgtatttttattaatcctattgtgatttcatctgcatttcaccaataatgaatga      59850
cattgagcctcttgtcctatgttgaggctatctgtagattttgaggactccttcctggatgtggatttatg      59920
gtgagaaaccaacaaagatggctttgagtgtaggctgaattactagaaaagtaatgatctagttatcca        59990
aatatgaaacaaaagcatggaagcagtttggggattggagaatgagattttaggagcaccataagatgt         60060
ctatctgactatattcttgaagagaaaatagtcatggcactacaggcatggtggcacataccatgttatc        60130
agctggcactacaggtgtatgcctccatgaccttgaggacatatgactttgagttcggtgagagagatga       60200
acacaaagcctagagagatctgcaaatcatttgatttagatttagaaatttgtgtctgtgaaaacatttaat     60270
ttcacacagaaaatcaagcattaacgcacttttattatttggccagtccttgtgctagctttagatatgca     60340
gaagatgaataagaagaaaaaatgcatcacaggtagggatagatacccttcatgagaatgtaagctcctag      60410
tgggcaggaactccttcttaccccattacgtacccttacctagcatagtgatctttacgggatacttct        60480
gtggtctgaaggcttgtgtcttttccagaatccccatgttgacgttgtaaccccaaagtgatggtgctagg      60550
aggtagggcctttggagctgatgagatcatgagggtggatgccccagaatggtattaatgacatttaaa       60620
agataccccagggagattccttgcccttttccccttttccaaagttataaggaaaatacagccctctagg      60690
aagcaggccctccaccatacactgaatctaccatgccttgatcttggacttccagcctccagagctgtgag     60760
caatgaatatctgtggtttataagcccccccaagctatgatattttgttacagcagcctgaatggactaag     60830
ccaacttctaagtttggtgttgtcttattcttggtcggtgtaggatctttctgtccacatagtttac         60900
tctagaaagatgtatgccctattcctcatggtatatttgtctttcctatctgtggaatatcctcttatcc      60970
aattcgtcttggctgggcaacatataagccattaactctttacccttgggtttagtttgggttctgctga     61040
ggcccctgctgaaaattctggtttctacaattatggctcatgcatgttcctgacccattaaactttcagtg     61110
gaagaacagaaatggtgagggaggtgatggagttgataccttgagctgccatatggtgcaagatcatct       61180
gaagatagaacatttggcatccttttttttttaagagatggggtcttgctaatttgcccaggctaaact       61250
caaactcctgggctcaagtgatgctcctggctcagcctcccaattacctggcaatacaggcatgtgccac     61320
catgcctggccacattttactctccaattgcttaatatatagtaaagataatggttcaaaatggtaaat       61390
tttttttgtgtataccaataacattttttttttaccttaaacatattcaatctttatttgacaatttt        61460
taaaatttcaactttttttttttattcatgggatatatctgcaggattttttacctgtgtgttggatg        61530
gtgctgaggtttgaggtacagttgattctgccacacaggtatggagtatagcacccaacaggtagttttt      61600
ctaccttttccccctccctctccctgctgtagtagtcccaagtttgttattgctttatgtccatgagtac       61670
ccaatgtttagctcccacttctaagtgagaacatgtggtatttgattttctgtttctgcattaattaact      61740
taaaataatggcttccagctgcatccatgttgctgcaaaggacatgatttcatttgtttttttttgtttg      61810
tttgttttgtttttttgagacggagtctcgctctgttgcccaggctggagtgcagtggcgcgatcttggc     61880
tcactgcaagcctccgcctcctgggttcacgctattctcctgcctcagcctcccgagtagctgggactaca    61950
ggtgcccgccaccacgcccagctaatttttttgtatttttagtagagatgggggtttcactgtgttagccag    62020
gatggtctcgatctcctgacctcgtgatccacctgcctcggcctcccaaagtgctgggattacaggcgtg     62090
agccaccgcgccggctgatttgtttttatggctgcatagtattccgtggtatatacgcatcacatttttct    62160
ttattcaatctactgttgatggactcttagattgattccatgtctttgctattgtgaatagtgctgtgat    62230
gagcatacatgtgcatgtgtctttttggtagaacaatttatttttcctttgtatatatacccagtaatgtg    62300
attgctaggtcaaatggtagttcctctctttaagttcttgagaaatctccatactgctttacacaatggc     62370
tgaactaattgacgttctcaccaacggtgtatatagcctctctttttctgcagccgcaacagcatctg       62440
ttgtttttgatgttttatgaatagccattctgactagtgtgagatggtatctcattgtggttttgactt      62510
gcatttctctggtgaaaatggtggattttaaatgggatttcattttagatttaatagaaactgcata        62580
ggtgactgtgcaaagaactcttaagatttgacaaaaggcaaattagattgtaatctcctttatgtaggag     62650
gggaaataaaaaccagaatattaaaatatctacatgtacaaaaatagacaaagtggcagattgctggtgt      62720
tggatggatgttgagcagggatggaggacttgtgtgtgcatgcatgcatggccatgcgtggagagtggtc     62790
attcattttggtaacagcatagagctttgggcttcagaacaaaagataagccacatcccactcaggtacc     62860
ctaaaatgttgtctccactagacacaaaagaaaaggaagccagagatgtctgtagcttatgcagagtttt    62930
gggaatagctattctagactttcttagtgaacagtatagaaggattattgtacaagcccagtaatttggg    63000
caaggatcagattctgttgcttttgttttctggatgctccgtaatgaatgtgagatggaagcggatgtct    63070
caagtgcttcttgttctcagaaacctcctggcagcagacgtccagtgggcccagacgttcagcgtgt       63140
ggaagtaaaacacagggaagggtgctcttttctcagttatcctattttttttaaaagcatctacaaagct     63210
tcctgttttctaatatattcccaggcctttgaaagacaaggccataaacacccaggagatgtgactttat    63280
tcttttaaggtccagataccaaaatgcctgtcatcagggctccacccttaattaaatacgtatcttaaaat    63350
taaaccaatctcaattaaggaatgtatactttggggagaaattttattacaatttttattcagaacactt    63420
```

FIG. 8A-16

```
taaattctgataggcctgaagagtgtgagcctcaccttaattgcaacctgagtcagaataactgccctgc      63490
agagaatcatttaaaatacccaatcaagttataaattagtcaaaatgccattctgagatattattatttt      63560
atgcagtctttgcagagaatacatgctatatagcccttcttcactcccaaagtatatgtatatatttaat      63630
gaagttttcaccttttttattaaaattttaatccattaacaattttagaattcattttgtagcatatcc      63700
tctttatcttagagatattaaatatctacctatttatgaataactatcaataaccacgtttcaccctttg      63770
tgaaatcctttcagttttgaaactcacatgggagatcttgtttttttttttccccacaaggatgtagg       63840
ttggttaaatttacagtggttctttaatgatgataagtgcacatttgattgatatcaataataaatattga     63910
tatcttcaatatcaacatttcttgtaatgctaaaaatttacaagttgccaatttttttgaatatgactata     63980
tttcacacacacacacatacacgacagcactaattatattcactaaatatacctacagatacttaatca      64050
tttacacagccactataattttatacttgatgccttaaaccagtaattctcccttgagggtggttttggc     64120
ccctgggctacctagcactatctagagacattttccatagttaaaactgggtaggaggtgccactatcat     64190
ctagtgagtagaggtcagggatgctgcaaaatactgtacattgtacaggcgacgcccccacaacaaagaa     64260
ttatatggttcacaatgtcatttatactgagatggggaaacgctgggctttaattatagcaattttgtgc     64330
aaattagccaaattcaaaaaacaagggagtgaaaaaagatagctctcaacctgtgaatattgtgaatgc     64400
ccaatctagacctagtaagtgtacagatgcccttgggcgcgtcttcttaggttgctgctgcttcataatc     64470
gctcactgcccatcaggaccttgtgggatgtagatttaggcagaggagggttttgatcatacagctggat     64540
cagtcataaccaataagtgactcatagtctcattcacattgagtttgagaatttaaggtgtgggctgaa      64610
ttccttatggaactaactttatatacccttggaagaagtccaccccactgaattctacatttattgagctct    64680
gtgtttcagggaatgtgcaataccttgaggatacatactatctcatttagtcccaagtagcttttaaata     64750
tttgagagtggttttggccccccaggctgaaagtaacagctacctctggttaaaaatctttcaggaagaa     64820
gcaaccaaacaggacatcacctctttgtttttcttgtctgtctcttaattattcagaaatgggattgctg     64890
tatggcagacatccaaatgttgtctacagtagaattcagagatagaagcaaacacctaaatcagtcattg     64960
gtgagatgctatttgtcactttcaaagttataatccagattttcagtgcgttttcatccaactctggtga     65030
acttttcccaggatgtcatgtactatggaatttccccccattgtattattgttctgtgatagatccagct     65100
ccaatatgttttatttaaaaaaaaaaagccatgtgatgtattctgttcaactgattacttaaatgaaatg     65170
gataattattttctgatgcagatgctctgaataacccacaaaatccttagaaacacatttgtatattttg     65240
agttgaagaacatgctaaaggcaccctccttgcaacacctagtgaaatattttctgttcctaggggatca     65310
tttaacaacataatgtccattcctgcacagcattcttttattgtcacaggagcagcgacttatgtaggga     65380
tagttatattatctatgtaaagacaaattgaggtggtgacccttaaaagttgactccaggctcaatggg      65450
aaagtaactcaaatgcagcctcagcttttaaatgggctgaagggtgaaggagatacccctctaaggcatg     65520
cagtggcttactggaaagtcaggataattgtatcaacacttttaattatgaatgaagtcttcaagaaact     65590
agcactacagcatgtacttgaaatgcaccatcttgtatagtgttttacaaggaaactgagattcagagca     65660
gtgaagtgtgtagcctaaatatatatgcacttgaccagaccaaggagaatttgtgtccaaagtctacact     65730
cttttcatttgatgatgttcccttttgtggcctgataaatatccacatcatgatgccagattgacttggat     65800
gcatgcttccatctttctcctactggaaaaacttttagagctccatgcatgtctccttaggaaaatgtgac     65870
aatttccttaaacatttgagaaacagtgtttttggaagtacccatgtattgataaccagtctggtaaacaa     65940
tagcaaaactgggaggtgttgttactataatctgcataacctgtataactcttgaacatctgtttgatca     66010
ttcaacacagatttgtttagtgttttctaaatgtcaggcattgttcatggtgataggatgtacagaggaa     66080
ttaagacaagtggtggctgctgaggcatggtgactcatgcctgtaagtcccaacactttgaaaggtcgaggg    66150
gtaggatcccttgaggccagcctggacaacataggggtgacccaatgtctacaaaaaaaatccaacgaatta    66220
gccggacatagtggtgcatgcttgtggtcccagctactcgggagggtgaggcgggaggatgggttgagcc     66290
caggagttggaggctgcagtgagctatgacagcaccactgcactgcagcttgggcaatatagcaagacac     66360
catctctaaaaaaaacaaaataaataaagacaggtgatgttcttgctgttgcctactatgtggagatggc     66430
actatacacatttctatacaaatgaataggaatttcatagagagattgtggatttcgtggaagagcca       66500
gccagtgttctaggtggtcgttgtgtggcttcattattcttgtctgcttcttcctctttttaggctgcct     66570
tggagttttcataagaaattgtccctggaggtgttggatgatcacagcttccttggagcattgcagttgc     66640
tggaatccagtttcaggattaagggagggctgcctccttgcaatgggctgccaagaaaacggctgtgctt     66710
gttcttaacctcaggctctgtctgtgatcagtctgagagtctctcccaggtctactgctccctggaaagc     66780
cctatctctctgcaggctcgcctctgggctttgtctccttgggagccacatcactgggacagtcgtggatg     66850
tggatgcagatttgaaccATGTCACGGCCCCAGGGACTGCTATGGCTTCCTTTGTTGTTCACCCCGGTCT     66920
GCGTCATGTTAAACTCCAATGTCCTCCTGTGGTTAACTGCTCTTGCCATCAAGTTCACCCTCATTGACAG     66990
CCAAGCACAGTATCCAGTTGTCAACACAAATTATGGCAAAATCCGGGGCCTAAGAACACCGTTACCCAAT     67060
GAGATCTTGGGTCCAGTGGAGCAGTACTTAGGGGTCCCCTATGCCTCACCCCCCACTGGAGAGAGGCGGT     67130
TTCAGCCCCCAGAACCCCCGTCCTCCTGGACTGGCATCCGAAATACTACTCAGTTTGCTGCTGTGTGCCC     67200
CCAGCACCTGGATGAGAGATCCTTACTGCATGACATGCTGGTTTACCGCCAATTTGGATACT           67270
TTGATGACCTATGTTCAAGATCAAAATGAAGACTGCCTTTACTTAAACATCTACGTGCCACGgaagatg     67340
gtgagtacctcactggaacagaaaacaatacctcttgtgcagtgtgtagagagatttgctaggagggttt     67410
tataatgtctcatgcatgatctcttctataacccgtttatttattttaatttattttttcatattccaaa     67480
tgcaattcttgcagcaacttaccacatgttccacttgtatgtattgggccatctactgactggacaaaac     67550
tataaataataactttaatttatttttcatatattgccttcttaactttttataatgcttatttgcagatga     67620
aaataaatatgagcatataatgttgcatgttatacctgaatcatctgtaaaggaatgaatctatagaaaa     67690
ataatagaattaagtacacactattatgctccagtttgcaaactgaaagatagagaaatggttctttctgc     67760
cttaatgacttaagatattagcaccttttttgagttttcaaagaaaacttgattgttttttaatatacaa     67830
gtaggggatagttcatacaatggttggatttcattgtttagaatcggttttcttaacgtaaatttggatg     67900
ttctttcttccaatattcgctgcaatcaagtggcaaaatgtaatcagatgattctagctacattagaga     67970
tgaatgcgtttgtattttaaaaattccttttttatataaaacaacaatgaaagtctgtagcacaata       68040
acgtttaatatattaacctaatgttagtaaaacatgaatagttttatgtctgtatagatttcaaattcag     68110
atttccttggaagaataaccagactaaagtatgccataatggtatcacatttcccagttagcatttccat     68180
atgccgttttagatgaggagaaagaacaacagagaataaaatatacctggaaagaaggaagttaattt      68250
gtgggaatgatagatgtatctaatgtagaaactagagtgtgtcctttgtataaagttcttcgtggaaagt     68320
gtgataaattctcttttatggagaaatttcttcttcttcttttttttttttttaaacttcaatccctgga     68390
aaacatttttcagtaagatttggctgaaaatagtaaatcaacaacgacgttaatccactgatctccaaaa     68460
ttgttttgcatctatcagattactctttctcccatataaatgccagatagtttaagtagagtgtcatgaaa     68530
```

FIG. 8A-17

```
aaccataccagggttgtgtgtcactgaggttacaaattgtcattgagattacaaagaacagcccagagaa        68600
agaaattaaaggattctgcttcattatattagtggtttctggcatattgcccttgtcgttatggtgacag        68670
acctctcaattatctcataaagtccaggtctgaatgtgattcaaggagttaaactgacatttggacgctg        68740
tacttccatggggtgttctgagctgtctccgtgcctaacagtccctctttgtgtgtgtgtgagatgaa         68810
taagagctctcaaaagcaattagggttctcatttgagcagccacctgggttgagatctttctcataatga       68880
actattcaaacaaaaaccaaaaagaaaggaagacaaaaatggggagaaaaccccccaaacaggacaaagg       68950
gttaaaattgctttcataatactttggatgtgctagagtctggtgattttgtagagctagccttggcaac       69020
aatgaatgcacttcaaatagaaggcctcctcatataggagttggacagaatgagaccacccatgaaaaag       69090
aatcaatagcctccctgactgcagagccctgtatgtacaattgtgtggatggagaccacaaacggtgtgg       69160
ccgtttcattgcaattcggtattgaattaaaatttgaggaatgtaaatatgtgaaaatgctattcagtg        69230
aaaaagtaatccaaacttcataataaacccagttccacttgtttagatcttttaggcttttttgaagcaata     69300
tgtgcatatgatcttgacaaggaatcagaaatctaatagtgactgaaaaggtagaatcgatctccccac        69370
gatgtgtaaactttagaattttgctggtgagagttcaaagctacagccctgcatgtttgtaccatccaca       69440
agtcacagcctattgggttaggagtttttattttggttgcttgcttgttttcttaactctatcaacgaa        69510
gaaccagtgcaggccaggcgcggtggctcacgcctgtaatcccagtactttgggaggccgaggcaggcag       69580
atcacgtggttaggagatcgagaccatcctggccaacatggtgaaaccccatctctactaaaaatacaaa       69650
aattagctgggcatggtggcgcgtgtctgtaatcccagctactcaggaggctgcaggaggaattgctt        69720
gaaccaaggaggtggaggttgcagtgagccacaatcgcgccattgcactccagcctggcaacatagcaag       69790
actccgtctcaaaaaaaaacaaaaacaaaaaaagaaccaatgcagagctttagatgtttaattattaatt       69860
attcactaaatgaatgaactccgcatccacaacatattgaaatgttggcatcatgctgattctctccaaa       69930
ggccttctcttagggagtatctcagttcagatcaatgcttttatttagcaggagagagagcaatattatt       70000
atttggaattcaaaattccactctgaccagtctgacaaagccagaaagacaaatctaaacaataacaaca       70070
gcaaaaatctactttttttgtttagctttgtctttctgccttgatcagattggctcaaatttctatgttt       70140
ctactttcataaaatgtgtaggtatattaaaaatacaaaaatagactattttagatacgtacttatcctt      70210
acatttaagaactaacttgcatgaggaaagtgttggaaattcttcgtagtacaatagtttatgaaaca        70280
tatatttttttttctgtagaaaacaatacttttataattcccttttaaaataaatcaggtcttgctgaagg      70350
tgagtcttttcatttaaactggcatcatgatctactaaacttaggcttgggtctttataactatttccta      70420
ccttacaaattttctttatttaaattttcataggttattaattttctcttgttgttagacaacaggctaat     70490
taattaacttgaattgcatatttaacctttttgataggtgctcaaataaggtcaaagtcagtcaagccagt     70560
cggaagctctagtaggacacgtgggccattgttgacaaggaacagttggagaccgattgaccgaatctgc      70630
atggtgtgtgtgtgtgtgtgtatgtgacagagagagagagagagagagatagcagagagagtgtgactga      70700
gtgactactttgaggaagcaatgcagaatatggcttggtagcttgattaaacataaattgtgaaagtcaa      70770
gccgagaagttccagtctcacatactaagtccacttgagttcatacatgaggggatggcagtacagttcg      70840
tgattcgtcttggtccccaaggagactgaacacagaaagatgagttatggagaacttaaggtttttaat       70910
gagaaccagtgatactgtttagaagtgaggttaaaaagtaaggggaaaaataaaagacacattttgaagga     70980
gttgctcagacaagatatcatattaaatataaagcttggaggagaaagagccacaagtgagtccagattg      71050
ccttgggaaatggacagacccatggaaccacttcctgagtgacctacacctgtgctttttctctggatcc      71120
ttggacatacatcttaaggtcttattcttgaaagatttcaggggcgagaagcccttccattcttcatcat     71190
gggactaaaaatactgggaaatataaaggaaaatataaatgaaagtcattatcgcccaggcacagtggct      71260
catgcctctaatccgagcacttcgggaggtcatggtgggtggatcacttgaggtcaggaattcgtgacca      71330
gcctggccaatatggtgaaaccccgtctttactacaaatacaaaaaattagctgggcatggtggtgtgcg      71400
cctgtaatctcagctacttaggaggctgaggcaggagaatgacctgaactcgagaggtggagggaggttg      71470
cagtgagccgagatcgcaccactgcactccagcctgggcaacagagtgagaatccctctcaaaacaaaac      71540
aaaagcaccactcattatcattgtattttcattgtagcataacagcaaatgccattatgatttctagaaaa    71610
gtgaaatttgggttgttttttttttttgctagcaatacaattgaaaaggaagatattaaaaaagaaca        71680
gattattggatgcaaggtgtccctatcatctttttcccccaagatgacacctgactctttgaatactatg      71750
acttaagtaagcttgctatgattgttgattgaggacctatttggtgaaaacatggagctttatgatgaaa     71820
tataaacagacacgacatggacaatgacctgtaggagtttgcacagttaataaacctagaggtagataat     71890
aagccagagcatcctagttagggaacaaagaaagctctgtgacagctcagggacaggctatttttgagg      71960
aaaaacttgatggaagctgttaagttgttgagctgtgccatagaataatatgggtgatggaaggattc       72030
atctattaaagcatctgatgaatggaacatttgaacacagaaatctatgttaagcagttggtgtcaatc      72100
gttgctgttgttactacttgggtgttaagtgtggcgtggtaacagaagctgtgctttagcatgggctgtt     72170
tctggcagtgccatatcatgaaagttctttttttttttttttccttttagaaacaggatcttgctctgt      72240
catccagggtgaagtacaatggtgcactcatagctccctgcagcctcaacctcctgggctcaagggatcc     72310
ttccatctcagcttcctgagtagctgggactacaggtgcactccaccataccggctaatcttttagtt       72380
tctgtagagatgggggtgtcactatgttgctctggctggtcttgggttcaagtgatcctcccacctcggcc    72450
tcccaaaatgctggcattaccagcataagccattgcactgggcccataaacttttttatgttatccacag     72520
ctgctgaccctatactttctagggtagacaagctacctaagatgaaaggtggcaggagaacaacaggga      72590
aagaagctggaaagtcaaccagctttgctagcgatttttacaaaaaaaaatgtattcgcttcttttatag     72660
ataccactggatctaattcaagatataatttatagcatggttttcatccttgaatagctcccatcttttc    72730
tgagggtcttacaaacttttctggcattctgcattagtcagtcaagagatattgtgttcaaatgtgaaggc    72800
aacctagcctcaatctgactttgagggaaaaaatggaaatttattagaagggctatgggatatccaaact     72870
tactgtaaaagttgagaaatcagattggcagaatggcagggatgcagctagactttagacacacctggaa    72940
gcattgaatccaaggacatcaccaatcttcatatctcgttctttgcttctttctggaaataggcttgctt    73010
taaatggcagtaagagggttctctgcagttttgttagttgcatttttgttttctcagtaccaccagtga     73080
gggacaaagttccataattccatactaaaaatcccagggcgggttttgattggccacttgactcagga      73150
gtaagaagagataaaactgggctgttcttgtgtataccagttggcaggggagaaggacagttctcacca     73220
taaggtgtctggaatgagcaggcactacttcacttcactgtccaaaatattttttgagcatcgattatatg    73290
ccagacatgccttagaggctgagattgtgagagatacaagcattcctaattttttgagagataggtacttgt   73360
aggcagaaaagtcatggtccctgagagatgtgcaagcaccgccctccaccccctaccccccagccaactcg    73430
cccattcctggaacctgggaataggttggaggcatggcacctgacttcttcaatactctgccttaaataa     73500
tgacttcaaatggcaaaggggaattaaggttgccgattgaattaggtttgctaatcagcagaccttccaa     73570
taggagaatctatcctggattctcatatatattaacagagaccctccactgtggatgcagaagactcaa     73640
```

FIG. 8A-18

```
aaggagatcagagttggtgtaaagcaacgtgagaaagagatacctggacattgctggctttgaatatgag      73710
agagccaggagaaaggaacgcaggtggcagtctctagaagccggaagagacagggaaacagattttttcct    73780
tagagcttccagcaaggagcccgacagccctcctgataccttgattctagccccatggaagaaactctga    73850
ccttagaactgtaaaagaataaatgtgtgctgttctaagcttactaagtttgtggagatttgtcttagtg    73920
gtaatagaaaactaaggaagagtttatcaccctgtaatattatttgaaattcataatgaagtattactc    73990
tgaaaacaaaagttcagagtctctgaagttgtttggtttcgggcctctggaccccctctccattctggga  74060
ttctacttccaagaatttctagttgaaaacaccccttgggcacttagagctttctaccttgctcaagcatg   74130
ctaaggagatcatatcaattcttatttlagggcagacattttttcagattttttaaaaatgtatttttaaa   74200
aatttgagagataggtaccctgtctctgaatgggggtcttgcactgtggcccatgctgcagtcagtgtca   74270
cagtcatagctcactgcagcctcgaactcctggccgcaagtgatcccccaacttcagcctcctgagtgtc   74340
tgggactataggctgagactactatattgaggttcagagaagaagcatgtccaggtgtctgcaaattaga   74410
aaatggtggcagatttttaaaaaagaaacgatgaaaaattatccctgattagatttacattacaattt    74480
cagccaccatgactggctagttttttaaattttaaagagttggagccttcctatgttgcccagactggtc   74550
tggaaccctagcctcaagtgatcctttcatctcaaactccagagttctgggattacaggtgtgagccacc   74620
acgcccagtgacatttttgcaaatttgacatttttgcatcatgttaatatagcctcatggccaattgtccta   74690
aatggtatattcaaaagataatactgttttgacacagaaaggtaccaaagggtcatttagaatttttttca   74760
ggaagctataacagatttccagagtagatggcttttgaatgacatataacaaaataccgaaattgttcttt   74830
cctcatctgtctcccagagtttcactcaagatcgcggctgcacctttacatgtcttatttttcctactta    74900
caaacactgctgacaaaatcctctgtgttccccactccttccggctacaccttaagctgtggtctcttct    74970
gggcaaagtgattctctgaccttttcaagctacaccttgtttcctcctccaaccaaaacttgtttgctgg   75040
agttgaaatgccagtttagcccccttagcagatcagtcattatgggcaagtgacccagcttgcttgggcca   75110
cagtgtcctatgtctaaaatagaggcggctgagaggtttaaggttttaatccatataaagtgcttagta    75180
gccagcacgtacaagcaccctgtaatctgatgttagtgcagcatcattaataacagaaaaggggaaccga   75250
aaatttcagcaaaattgcatgtgcatagtgggctctggtatgtatattagtctaggcataataaatgttga   75320
acgtctgtgacataactattgtagtagtagaggggtaagcttaagaagtaagaccaataaatagcccatc    75390
atttctggcagtttctagtatggttttaacaaaagggaattttgggaggaataacattttttaaaagagc   75460
ccactattatcattctgctttattcctaactttagtccttttgagcctgtgttatcaaatggattttgag    75530
catatgtgaattagagaaattaatcactaggaaaggaattaacttttttggaaaagttccttaaa       75600
ccgtgaaaaggcagtaacaccattctttgtgtgtgagattaaagagaaattaattttctttctcttcttg   75670
tctagacacacaaagtccaattgtacgcatacagtcacaaaatataggtgaaaaacgaaaactgtgttaa    75740
cacggtgagacagatgtttaaccaatcaacatcaacatgcaactaggtgaaaataattaaattactcca    75810
gttttcatctgtcagttggatgtttgacattgtgtagacacagcttataagtaaagataattatgaaaga   75880
ttattaaataaagatctccctgacacggattaattgaaaagtatttagtattttttgtaagcacagttaa   75950
actggagtggatttccgatagcatgtgtctctcccccagctcaaaaagcttttcagcaatttgaatactga   76020
gtaataatcttattgagggtttagaaattacatatgtttggaataatactatttagtagtatgaattatg   76090
cctgtttgaataattaagaaatatcttttcctaacaaagaacattttcccttatgtacataatcttccaa   76160
tacatgaattttaattcaattcaatttgcaatttagattcttgtcataatttgaacaaatacagattacc   76230
tagaatatattaaaaatcaaattttcacatagtgcatatcataagaattttttttttagaaattgtcagag  76300
ataaaacttttaggtacaactagtccactggaatatttggccattttaaaacaattagctcattatttatt  76370
tgtggagtcttgcttcctaagatgttgtagtcttatttgttgtcaattaatattgctggtttgaacatgg   76440
ttatttattttccgtactatttttagccaagctattaattttattattttatttttttaattttatttttt   76510
ttatgtttgagacagtcttgctctgtcacccaggctggagtgcagtggtatgatctctgctcactgcagc   76580
ctccacctcccaggttcaagtgattctcctgcctcagcctgccgagtacctgggactataggtgcccacc   76650
accacaccaggtaattttttagtagagatagggtttcaccatgttagccaggctcaaactcc         76720
tgacctcaggtgatcctcctgccttggcctcccaaagtgctgggattacaggtgtgagccaccgtgcctg   76790
gcctagccaagccatttaaccttaaatatttagtgtcctcagctattaaaaataagagtaatatgatta    76860
tacatcctatgaatttgtttataattattgtgatttgggagtaaacaactatataagaaataattataa    76930
aagagataagattagtgcatattaagactttgatgtcaggttaattgaatgttaatcccatgactttatc   77000
tttcattgcaagattctttgcctgagtggggtactggaagccattgttgagagtagatccgatcttacta   77070
gactgtttggctggttctctcctaaaaccaggctgttttcataatgagttagtttaacattttgtctttatgt  77140
ttaagcaccccttttccttggtgcagtcacagccaaactgcaaacagaaatcgagaagttgtgagctccag   77210
atttgagagccacagagagtttgtgagatcaaaaacatccactctcagtaaataaatcagagctacctaa   77280
atcacacagtcagcttaaaggcaagggaaccagagggaaaaactccaaaggagtgatctcttcatgcaat   77350
tgctactggtaaaataaagcaaagatgagacagtgtagtctccacccttattatttcaatctaatattcta   77420
tattgaggttcagagaagcaggtccagatttccacaaattagaaagtggtggcttgctcttgtaatccta   77490
gcacttgggggaggtctaggtgggtggattgcttgagcccaggagttaagaccagcctgggcaacatgaca   77560
aaaccctgtccttaccagaaaaaaaaaaaattagctgggcatggtggtgctggcctgtagtcccagctac   77630
ttgaggggatgaggcgggaggatcacttgtgcttgggagatcaaggctatggtgagctgagatcacagca   77700
gtgcactccagcctgggtgacacagtgagaccctgtatctaaaaaagaaataaaagagaaacattttcctt   77770
gttagactttacgtatctgacgatgactttttgatggtgaaggtaggcattggtatggtgctctggtgtg   77840
tgtgtgtgtgtgtgtgtgtgtgtgtgtgtgtgtgtctgtgtgtgaatgctattgaaggaaacccggta   77910
ggagaaatatccacaattcagttaagatcaaacatgttacaattttctgggaagtgccaagttttacaac    77980
acctaaactatatcctcttcctctctgaaacccaaacatcccaaagtctccttcaagccagacatcctc    78050
ttggtctactgtgcatggtgtctgcacggtcctcaagtttgcctcagggaaagtgcctgttgccatcaga   78120
aagaaagaatgcagcaggtactgatttatctcaggcaaggagctcttgtggtgggtttcaacaagatat    78190
gaaaatttaggttcttgaacactctttttcttcttcctttaaaatggatgtcttttagctacattctactc   78260
tcttctctgtctttttatgacataatcagtcattcactcaacaaggggaacatctaatattcacctaacatc   78330
ccatttgcctgtcacatatggactttagcctccagtcgggccaatgacactattgatctccctaattccaa   78400
tctagactctttgggtatttttttctcttttccattccttattttctttagaggcattttagataactca   78470
tttaaaaaattattagtaaataaatcattatttgcaatcagcatagacaaggccttgggtgagtctaagtg   78540
gatatctggagagatctaaacccgctgctggaaaagtgagtgggaaagccccattgatatgtgacccaac   78610
taaaccaacgtttcatcaaaagcagtgtcttcagggactgctttaggatttcagggaaaagaaatggag   78680
gcaaatctgaaagtggatgttttctatggaggatcctgatagaaaagttttcacccagccttgagtgaa   78750
```

FIG. 8A-19

```
tatgcagagcgtaaacacatgtttgtgcagtgaggaaatgctgtctatgtttcctaaaatggaagttctt      78820
gtttattgcttcttttagctgcacggagacataaaagatgcaaaactggggagaagggagagataaaacta    78890
agacaaaactggaggagggtgcaatgatgttgtaatttaacatgcaaaatactcacttgggtatttttta     78960
aattgttacattgtgacattggagggttcataaatggaattccatccaaactaattctaatgcctatctt    79030
ttcttttttagcagactatagaataaagttaaatcaaagaacatgaggtcccattcttaccaaattcaaat   79100
atacttttttatcacctggtgtttaaatcattaatacaaaagcttttcagtctcctccaaatttctattcta  79170
gtaaagtactttcataatttttatattggaaatgtactaatccagataactagtatgaaatcaagttataa   79240
tactattttgcatgtttctaaaatgtttacatttaaaaatagagaagtaagccttagggagaaaacttca    79310
gctttcccaagaatattaaaatgttaacaaattatttcattttgagctaaaatcagataataatgagaac    79380
aaatttcaccatcgcacattctacagggatctttgcattttatacttttttttttgttttgctttataag    79450
aggggatttggtatattgaatatcatactggaaatttacctggacggaaacgatagagtcaacttagac     79520
tttaatcacagaatgataacatcttccaaggagaaggagcttttgaggtcatttcaccaaaactctttca    79590
ccatacagtattttcccgttcattaaccttttggcactctaagcagagatgaagtatcctcccctgagtt    79660
cctagaagttgaatttaatcaccattttacgagtctgccctcccagtagatggtaaacccttttgaagac    79730
ccagagcattttttgagataaaagaatgaatcatatacttcagtacatggaacaaatgaataaacctgtag    79800
tgcctggccacccagctttttttttgaacctgaccgataaagacgtttacagcttttttaatttcattatc   79870
agagaaagggttggcaatatttacctgagcactctctacaaacagagatgaagaaatttggaatgtttcc    79940
tttctctcctaatacatagctttggaagtcttagaaaacatgttggtatgttccttctaggtagtctttt    80010
gcaagcatcctcttcagtgtcaagcatctattctcatgcatcacattacaggttatgaatatacccagag   80080
tttatgtgagatcttttttttgtcaaatgcattaaaccccttggcttatatatattgagctggaagccacaa  80150
gttttttgtaatattttaaaagtaatatattttataatatgccttagaaattaaaaagaaaatagaatacc   80220
tccacttcctatgacaaaatgtcagcatatacagcaaggcaaagccatttgttgctgaagctcagttttt    80290
cccaccggatgctgaatgcacaacaatcaccagccaggagccaggagctcgttttactgcacgtttccctgaa  80360
atgccaagccccctgaggtgttacaaggagggaaggcagcacatacatgtgtgatagaatggccaataaacta 80430
attggtttatagttttgagaaagcagctggttgcctgtttttaaatgcagtggtctataatttgatagaa    80500
tgcagaaggaatcatttccaagaaattaattaaagttcataggttggaaaataatggagctcatcattag    80570
ggaaagcttattctaagacttaggataaaatgagcttcctcttgcatttcattcaacttaaggttttgta    80640
gttacttgtcatcatcaaaaatatcatcagagtcatcgccatcatcattaaaatttgagtagctatg       80710
agaaggtattgtgaggtcctagcttttagaggaatcaatttcttttgagattttgatattgtttattttaagac 80780
tgcagagcataggttagaatctgtgttttaaaaactttgacaggccacgtcataggtagtaaagttttct    80850
cttggcatgagttttgagttgacttgtgttatggttgaattgtgtctctcaaaaaaaattgtttatgtctt   80920
aactcctggtgcctaggaatttcaccttatttgaaaataggatttctgcaaatgtaatcaaggtaagatg    80990
agttcatactgtgttagggaagatcctaaacccaatataattggtgttcttgtaagaagagacacaacaa    81060
caaagacagaaacagggagaacaccatgtgaggatggaagcaaacgttgaagtgattcatccctaagcca    81130
gggagcactgttggaaaccaccaggaaccaagaacaactcaatccaagacagaagcatgaaatggatttt    81200
ctttaagagcctctagaaggaatcatcttaattttggactctgccccagaacagtgagacaatgcgttct    81270
tgtttcaagtcaccaagtttgtggtaattagttacaaagccccagaaatgaatgcagtctggattaggta    81340
tattctgcgtacatatgctgcctaagaatgccagaagccagaagaggtgatgtctgcatttttggttcct    81410
aaaatcctctctcagtacccactgctctgtccagggcaaagctcccctgacacatttttagcctttaggc    81480
tatgtcctatctcccctgctcaccagagaagtaggtcttggattccagtctctcaggggctggcattttcc  81550
aagtgaaagacactgcctttgtgtaaatccttccccccttgagtgtaggcaggacattggatttgtttgtg   81620
tctcatggaatatggtagagataatggaacaccacttccatgattatgttacataagcatataaattgtg   81690
tcttactagtataccctttttgttgcattcttggtttccatgctttgatgaaagagcagccatattaaac    81760
aggtgcatatggcaagaagctcagagctgcctctgaaacaacagccagcaaggaacagaggctttcagtc    81830
cagcagtccacagggcattgaatcctgccaacaaccacataagtttggaagcgaaccttcctcagttatt    81900
cagctttaaaatgagaccccagctcaggccaacaccttcatcagtgagacttcaaagcagtggaccct      81970
gctaaggttgtgcctggattcctgatatgcagaaactcataaaataaatacattacttgaaactgttaag    82040
ttttggttatttgttacatagcagtcaataactaatgtggcataatatgcaaaacatggatttcagctga   82110
gcacagtaatcccagctccttgagaggctgaggtggggaggattgcttgaggtcaggaggtcgaggctgca   82180
gtgagctatgatagcaccattgcaatcatagctcatggcagctatgagcctgggagacagagcaagacct    82250
tgtttctaaaaaaagacatggatttcaaatttggccagattgtaaccaacttctacatagatattatgt    82320
ctccattggagggatatatattttgagactttgcaatccttaattacttaggaacaattagttagcaagt    82390
gaaagaaattcaggttgaattcacttaagggaaaagaagagattttcgggttccatttactagcggtgca    82460
tttagtttcgaaaatggtgtcctcaggtctaatcattgctgttaggaatctggcacttttggcgccatgtt   82530
tcttctttggctttcttagagaggcttgtccgtgtgtggtggtaggcagtcaacagcatttcctagtatg    82600
tcatccttttctcagagaagcacattggcctagcaactatgcgtactggcctaattttagttgcatgcca    82670
accaatgtctatatccagtggaaagagatacttgaattgatatggactgcttgggttatgtatactcttc    82740
agaaatgagaagagattgggtaagtccagtaggcttaggqtagatgqaaqtaaqattqctccccaqaqqa    82810
aaattgaatgctaggtaagcaaaactcattgatgtccattgttgcttatattacaaatagtaccaaacaa   82880
gaaagaatggcatggctgcttcatggaagaggagatgaacttgggcaaaaccttacctaggatatttcc    82950
ttttttcagctaaaagaggaacttggacattcagaaatgagaaaacttgtatatcagttgctgttgttg    83020
ttggtttgtaaacagctgtagctcttagtgacatagagagataaagtgacaggaacagatggaggatattt   83090
ctattaggatgttatccaggcagttctatgttgggagtcaccctcctgggacactcctgggtctggaagc    83160
tgtcagctggtggcaaatcagagatagtctgagatttaatgccagatgggaaacgtgacctcaaatgaat    83230
gaggctgtttaggagtgggcgcaacatgctgtgcttgccatctcttttaagagttctaactgaaaggtta    83300
ggtttactgaaggataagccaatttggggagctgatctggtgaacatgaatttggccaaacttcagccta    83370
agcgtttagcagggtgaaagtttgggagagtttcgttgtagaacattaggcaaatggctgacaaaagag     83440
cttccagttctctcacaaggaattcttcaaaaagcaaaggaggttcctttctcagtcagcctgctctttctg  83510
ctcagtagacttctttgtgagactatgctgtgagtgagttctcaggctggtgatataacctggtcttcaa    83580
ttcttgtgcagctctgtaagtccacgtaggcaccactaaatatccttacgacattaagtgtcattggatt    83650
gtttgctaacatttgcttccatatgggccccaggcattagcaaacatgtagtttattcatttatttattc    83720
actcagtgaatatttattgaacttattctaattgtcaggccacttttgctaaatgttgttccatcactttc   83790
cttgcagaacatacaggggaaaatgcacaactaactggaatcatcatttagtgtaatccatgcaatgatg    83860
```

FIG. 8A-20

| | |
|---|---|
| caacaagttggggagatgtgagaacatctgggagaagcatgtgtcccagactgagagggtgaaaatgcac | 83930 |
| taaggagaaatttgaagaatcagtaactgaccaaattgctgggaggagagtcatttcagacagacagagg | 84000 |
| agcacgttcaaggctgaagtccacagcctgacattaatatcgattctcttagctaagttttgttaaagaa | 84070 |
| accaaatgacagtgaatttgaagtcctgcactcagccaaccgtatgaagtgtagtcactgtatggtcagt | 84140 |
| taattacagggcagcatccttcagtcatcagtcgagctagagagaatattgacagatgtgctcttatgaa | 84210 |
| agctgagaagctcaaccaggacaagtatttagctaaaggggtctgacctcctttttagagatgggaagc | 84280 |
| aagggtggacagcataacctgtagactaaatctatcacactgctgtttttgtgaagggttaatggaaca | 84350 |
| caaataagccctttatttatgtattgtctatgtctgctttcacactacaaagacgaagttgagtagttg | 84420 |
| caaaagagaccatatggcctgcaaagtctacaatatgtactatcttacccttttattttaaaaagttttct | 84490 |
| gaccccctgatgtaaaggaccaacttcatgaagtcgcatgtggattttctagttaccatatagacatgaat | 84560 |
| ggaagagtacagaagttccatgtcagacagcaattgttttcaaacttgctatgaatttttccaaatgca | 84630 |
| gattcctgggctccatccaggcttccagtgactcaaaatctgggtatagattccaacaatttgccttta | 84700 |
| gtgacccttagaggtgatattgatggcaaaattttatatatgtacatattcatgaaacagaaaattggac | 84770 |
| gtgaaatattttaatccacatataaacagatactcctttctgtcattaaaaaccaattaggaaaaaatg | 84840 |
| ataaaagcctgatttttaaaaccatggtccatatggcttatgcaagataattttctgaagtgaccttcaag | 84910 |
| atgaaatagttgcaaagtatatctgtgttcagttaaattaggaggtgtgtgtgcaacaaggaattattag | 84980 |
| ccgtagatcttaaatcaaatcaatgtaaacaaaacactgtcagcccagtggccaaagaacacaatcaa | 85050 |
| tcaaaatatgaataaatatacacaattatacactactactactagatgatgatgatgatggtgatgatga | 85120 |
| tggttatgatggtgatgatgaggatggtgatggtgatagtgatgatggtgataatgatgatggtggttat | 85190 |
| cgtgatgacgatggtgatgatggtgatggtgatgttgacagtgaatgaagataacaattatt | 85260 |
| gtgatgataatttatggcgataataatgattgtggtgatggtctgtttctatgcgtcaatctcagttgct | 85330 |
| cccccagactccatacaaacagaaccaccttagagatgtttcaaacttaccatgttcgaaactcagctgc | 85400 |
| tgcttttgacacaatgaatgccctcctgtctccatttttaccatcttaggagaactcacaccatcccctc | 85470 |
| atcactcagtgagccaagtgtgctagctgctgatccacatgtctgaatggccgccttgaggaattgacat | 85540 |
| taccttggggacctacaggggagcaatgatgctggactggggcaaggatgaataaaggagggataagtcca | 85610 |
| agttgttgggggaagacaggggcagccaactctatctggagctctcagatgggtttagcggttgtggagat | 85680 |
| atttccaatggcattttgaagacgtggaagaatgttattaggcatagcagagattcttaactaagagcaa | 85750 |
| ttttggccccactgtaagggacatttgacaatgtctagagatattgttggttgtcacagctggggaggtg | 85820 |
| ctactgacatggagtaggtggtgaccagagatgctgctgaacatggtaaaatgcagaagaacgactcaca | 85890 |
| cagcagagaattatctagtccaaaatatcagtagttctgtatattgagaaacttggctctgtattgtgcat | 85960 |
| gtgtaatcgttttttacttactgattctagattcagctgtgcaaggggtgtcagcaatgtctggagattat | 86030 |
| tttggattatcccatctgggcagtgtgtgctcctgacatctagaaggcagaggatgctgctaaacatcct | 86100 |
| acaatgcacagtacagccctcacaacaaacataatcatccagcccccaaatgcccacagtgctgatgttg | 86170 |
| tgaaaccctgctctaagtcaaagcattgtcttactcaattttaattcctagtgtatatcagtggttctc | 86240 |
| aacttttggggaggggacaggtttgcttccagtgtacatttggcaatgtgggaagacatttttgtttgttg | 86310 |
| tgagtatggagtgtgttactgggaatggaggcaagggatgccactagacatcttaacagtgcataggaca | 86380 |
| gcctccacacctcagaatgatctggcccctaatgtgaacagtactgaggtagagaaaacatgaggtagac | 86450 |
| tgtagaagcctatagaagaagagaatctgagaaaattgttgtgcttggggaacactgaagaatgtggagc | 86520 |
| aattgaacaaatgcttgtgcagacagattggcaccaaattgcaatggagcaccaatgggacagtgaaaag | 86590 |
| ggacaagtcctacaatgcacagttcttgaccatccccaaagtgctccaaagctacagaagttggtgtgca | 86660 |
| tgtattatctcattgatcctatttggagttatcatgtttgacagctggagtcccatgaagaacattttt | 86730 |
| aagcagcaaagttgacaagctctgatttgccttttgagattaatgactcagagactgccagttatttgtta | 86800 |
| acttgcttgattcagcctaagcagacatctagagggtgtaatttgatttattctgcagaggggtgattgg | 86870 |
| cccctacattatcttggcacactgcctgaatttctgaacaccaaagacttatttatttagtgtatggcca | 86940 |
| tctcatttccaagagtcaccaaagaagtgagaatggattagatagggaacaagctgaccattggattagt | 87010 |
| ttatcagatgattagcatgccatgctaatttatcaagcacttaaagaaggggagagtaacat | 87080 |
| atacagggaagataggagatctttgtcccaatttatttcttttttttttaatgcatgaatagtcttttggta | 87150 |
| aatatagttatgtttgtttctgctttctaagttaggctgcaaaatattatttatcggtggtattcttg | 87220 |
| aaaattgattggcatggcaagactgtaaaagagtatccataggtgtatttaaaaataaaagatcgtctttt | 87290 |
| catctttgcagaaaaacatgtatttactattgcttggaatagaaagcagaattttgctgtagccattagg | 87360 |
| aagtgacaaacactacgccataattatagtgagaagaaagcatcaaaagaaatgttttggttttttta | 87430 |
| tatacagttggcacaaaaattccacatatatgaataatctcaaagaatgcaaaagaaccttcca | 87500 |
| ccactattaacaggattaatccgtgctcattaccatgggattggggatacatttttacatgttcttgatt | 87570 |
| agattcaagagccaaagaataaggcctaattgatgaaagtgggctcaattttgtgcttttaaaataatg | 87640 |
| gcctctggccaaatatgggcaaaagaaacagcacttgatttgttactttacatttgtttcttgcatcctg | 87710 |
| ctcgaaaatagagatgatttacagttttaatatattttttcatgcacaattaacatcattgttgccagttt | 87780 |
| tatagaagaggcaggaaagtgggccttctatgatttagttgagtgcatgaaacagaagtaagtctacta | 87850 |
| gcaacagagttttagtaggaaaaagttaaagcacacagtcttaaaaaggaaaggttggtgtcaaaattat | 87920 |
| gtttgctttaggtaagctttatacctccatggatggcttttttatagtaacaacaacagtaactgtatt | 87990 |
| tacattgggggccttttctctgtttcagaggctttcatgtggagtgccaaaatggtaaaatatataacatt | 88060 |
| gttatatgaaggagtgagggaaaatccaatcaagattggcattttttaaaaaagaaaaggagcatgggga | 88130 |
| atattttaaagattttgggggccaaagcctcgtggctgcctgatccctgtgttttgagaggctgagga | 88200 |
| aggagaatcacttgatccaggagtttgagaccagcctgggcaacatagcgagacctccacctctataaaa | 88270 |
| aagactaaaagttagctgagtgtgatggcacgtacctgtagtctcagttactaggaaggctgaggtggg | 88340 |
| aggatagcttgagcccaggagggccaggcttcagtgagctgtaatcacatcactgcactccagcctgggc | 88410 |
| aacagagcaagacgctgtgtctcaaagaaaaaaaaaaaaagatttggtatctttctttccccacag | 88480 |
| tttgcatatacattgaaaactgtcatttaagcaaaatagttttttttttaaacattttcactataaaa | 88550 |
| aaggagtctggctttcacatgggtacatgattttgctttggctcttcaatttcccacctgccctgttgtg | 88620 |
| agacccatgaagtaagcaaagcattctttttgccacggaaatgaaactcctaaacatattgtttattgtc | 88690 |
| acataatggaaaggagaaacgtttcaaaaataaggatacatgaagcccttattgaaaagcaatcatacat | 88760 |
| tggtgaatttaatgtttttggagcaaaaactgttatgttggatacctattagtctttttagctagtgaaat | 88830 |
| atgtacaaggcaaaatcaagcatcaatagaagggtctaactaagcttgtttctcatatggttttctctgcc | 88900 |
| agctcacacctcaagggtgcctcctgcctgcaatgtgtactctctggtccacacactgattttccccttt | 88970 |

FIG. 8A-21

```
ctgtttcatggggtgacttgctgaccttctctgtgcatggctagtagtactctattgactggcaagggtt      89040
gtgtcttccacttgggtcttccaagctgctgaagaaagcaacacagaaagtatagctgacaataattatc      89110
tgtcaaatgtatgtgaatcacagtgtggatggtcgacctgttgtttcttttttctctttgaaaggaagat      89180
ttcagtttttctctgcagccatggtactttataaattatttcctcttccatctcttaaaagtcactgttat      89250
ttaccacccccattagctgtggatgggggtgaaatgcccactcatgcagcacaggaggatacacagattgtc    89320
acacatcttttcaggagaccacacagcagtgggtagtgtagtattaaataaatgcctgaaatatgagctg      89390
ggaatgcattgcacttcaaggaatttttatccataggatgtaactgggaaagtgcagaagaatgcatatat    89460
atatagttgttcattgttacatgttttatgatagcaaaaaataaaaaaatattcaactttcatttta        89530
gacacggatttgcaggtttgctacatgggaatactgtgtgatgctgaagtttggggtatagatcccatta      89600
cccaggtagcgaacatggtacccaacaggtagttttcaacccacatcccctgtcttcctccccttcta        89670
gtagtccctagtgtggagtgttcccatatttatgtccatgtgtactcagtgtttagcccccacttataag     89740
cgagaacatgtgatattttgttttgttttctattcctccattaagtaaccaaaattttttaacaatgtaga    89810
atccattacataattagagatacaatacaagcattgaatacacagctgttaaaatgcattacaggataat     89880
atttagtgatatggaggaatattcagagtgtattatacaaacattttcatcatatcgttttttactag       89950
agtggactgtcattttcttgtgggctcccttgtattatttactctattgcatctcagtttttgttgcatat    90020
tatgtaaaatagaagataatgatagcttggcgcattctctgctgagactatttacagtggtgtaaaaaga    90090
tgttgccaggggtgtgtgcctcagtctgtcccagccttcgtagggcccatgtttcaactccctaatgac      90160
ccattgaagacacacgggcacacaggggagaatgctctggtttaaacagtcaaccataagccagacacag    90230
tggtgcaacctgtgttgcaccttgtggtagcctcttgctacccaagaggctgagacagaggatctcttga    90300
ggtcaggagttcaagaccagcctgggcaacatagcaaaactcccattctaaaaaattaaagcaaactcaa    90370
ccattttgagttttacatgttgtaaatatcttctcccactggcacccacccatcattcctggttttgatt    90440
gaaacaaaaccattagttttaatgtagcaaaatgccatcaacatattttctttctaacgtttctccta      90510
cgtagtgcctgttaaagaaatcctgttctaccccaacatcacaaaaacattttcctataagtatcagaat    90580
ttcattgttcatacagacagttttttaatccatgcagagtttattttttatatatgaaatgaggtgggaatc  90650
tcatgttattttttccccaatagggaacattgctttgacacatgaaggaagcaatgtattcttttttt      90720
tcttttgagacagagtcttgctctgtagcccaggctggagtgcaatggtgcagcctcagctcactgcaac    90790
ctctccctctcaggttcaagcgattctcctccctcagcctcccaagtagctgggattacaggcacacgcc    90860
accacgcccagctaattttgtaatttagtagagatggggtttcaccatgttggccaggctggcctcga      90930
actgctgaccttgtgatccaccctcggcctcccaaagtactgggattacaggcatgaaccactgtgccca    91000
gctacaatgtattctttcccaatgatttgtggtgtcagccaggaccttgataggatgatgcatgcaa       91070
cttgagaaatgtaattaagatggggacaggatagtgagtccttatgtgaagttgctgatgcccgctgag    91140
gttgaactggacctacctaccagggagggaactggaggtcatatatacaggccttactcgccttctgccc    91210
tccggattacctgctagtgtcttccttggctgaaacccaggagcagccagaaggcaagagtgaacctgtt    91280
tatttaccttccacaccagagaggagtggagatgaggaaaagtcttgaaggggacagactcctcccccca   91350
caaaatagtacaagctttttaaaattcatcatatatacatcagcaaatcacaagggctttatatttggtctt 91420
gttgatttcctgatccattcctgcaagattaaagtatgactcaaatagtacaaatgcccatatattttc    91490
atcttcaacattctcgttgctttttgtagaattattctttcatatacaatatggaatcaatgtatcaaa    91560
atctgcaacattcttctgtctttgctgggaattgtatttattgaaatgttggtttgaggaaaaataaaca   91630
tcttccaagctcatgttatctcatttgtaaactggcatagttcattacttgttgagatctaatcatagct   91700
ttattaaagactttgagcattatgtgttaattgattattattattattttgcaaatgatatcttcaatta   91770
cattttctactcctggtataaaagaatgtcgatcttttttatacattgattatatgttcagccatctttt   91840
ttgattcccctattatttctagtagctttctgttaaattacatggttcccataaaaatggtgacattatg   91910
tacaaataatgaccattttctctcttttcctttcaatacttgtaattttcattctttataacttgtacc    91980
attgtatggcccactgacgtccagtgcgaggatgaatactgttggtacaaacttttgttcccattcatga    92050
ttttacaggaaatgagtctaacatcttttttgtaaatgcagcgttgaggagagattttaaagcatgcagt    92120
cattatcagataatatgaattacttgcaattcccagttttttctaagtttttaaaaaaatgttttcttttg  92190
ttcataaatgttgattatgaccaaataatcaactggcatttctacagctggttatatgattcttctctta   92260
taattaatgtgctctgaaaattaatatatttttaaatatatattcaatttcgggaataacacattttaa     92330
tcttaaaagaaacattttaaaatggccattattctattatagtggaatatattgtatatgaaaaatagc    92400
tactattctactaagtttggtttgtaaatattccacttaggttgtctacatctaccttcataaatgaatt    92470
tgatttataattttctgatgttatacactctatacttttgatatgaatgttaaactgtccatacaaaagg   92540
atttgggtagcttttaattgtatattttctgaagaaaacttaaataagtagaattactaaaattttt       92610
gtgaaaattatcttgggtggtgagttttttatgtgggagattttagtgattcttcattactacttatag    92680
cttttagtttattcatttctttgcgtaaagttgctttgtttgtttttttcctcaaatatttcaatttctt   92750
tttttaataccagggcttatactattaaaatagtattttgtatttttataactttgtttatttgttatt    92820
ttaaaaatgattttcctctttaaagactatttgttctcattatttgttgtatattatttgttgtatattg   92890
ttgtatattatttgtttcattatttgttgtatatgttactcttccttggtcagtcttgccagaagtttgt   92960
ttatattattaagcttttcgataaactagctttcattttggtaattagctcaactgttttttctctgttt   93030
cgctaatttctgctcttaccttgatcatttcctattttcagatttatttggatttattctgttttctctt   93100
cttcctgtttcttgacttgcctccatggctcgtttatttccaattcttcttgttaccttgtaaagatatt   93170
tgaagttttaattatcccttttaagcacttcttcagtcccatctgacaaattttcacatgtgacatttga   93240
actatcactggactctgactgttttgtgtttatacggtagcataaaggcacatgcacacatatacataca   93310
cacatagatgtgtgtgtatatgtttagtgtttctatcattattttgaatgcttttttactattgatttct   93380
aattctgttgaccgatagaatatagtgctgaatgctgctgtttctttaaagtactctttatgaaggcag    93450
attttgtaaacgttcggtgtgtgcttgaaagctatggacacatttacacatacatagacatattcacaaa   93520
tacaaatacagatatacgtgtatatgtgagaatgtgtgttttgaggagcataggtttccatagatcccca   93590
ccagatcacatgtatgggttacttcagtcttctatatcttatttgttttggtgggtggggctagggacag   93660
agtctcgctctgttgctcaggctggagtgcagtggcgtgatctcggctcactgcaacctcggcattctgg   93730
cttcaagtggttctcctgcctcagccttccaagtagctgggatcacaggtgcacaccaccacgcccagct   93800
aactttgtatttttagtagagacgcggtttcacttgttggccaggctggtctccaactcctggcctca     93870
agtgatccaccagcctcggcctcccaaagtgctgggattacaggcgtgggccactgcaactggcctatat   93940
cctcaattacattttatttcctaagtttatcactccaagaatgttgtgttttattctactgtaacatttt   94010
atcttttcttatctgtcctttatcttatatatttaatgtatatggatatactatgttatatatatgtagt   94080
```

```
atgtatatataaaatgtacttatataccttttacatgttttgaagctgtattattaggatgttacatgaa    94150
agtgtcagttacacctttttaatcttccattccttttctagtatttattatccattttttgacatttacaa    94220
tttttgtttgatactaaatttgcttcctgtgatatttttttcatttatattttgttttatatttaaaattt    94290
ttagtgtcttcattttcaagtttatgtatccatttattttaaatatatcttttcaacaatatgttgctaa    94360
aagtattttaatcaatatttttatcttattctaattttatttctgcagttatcattattatagatttcac    94430
ttctgacattttattttatattttatatttatcaatcatgctttttaaattttacctttttttttttg    94500
ctttacctgacttccattatataattttaaaagtttcttttactgaccttattattatatttttctttct    94570
tctgttttttttccttatagttgggattcatcaaatttccctcttcccatttatgctgcacttatatt    94640
ttaatgaagatgtatctagtcttattagctatcaaacatttcagtatccataatttcctcaaaacaaga    94710
tattgatttagcattttctctactcttcggcatctctctctcaatcacccacactgtgttagattct    94780
aagagaatctgggctctagatcatgttaaaaatttgattttagatcattgtttcttcggaataatttttt    94850
gtcgttacctgtattatgttgctgtgttctgggttcctctccttgcagaaatatattgtgtcaagattc    94920
tgtgatgtaagtggatttggatttaagctatcatttaaatgacagtttcactggacataaaatccaggct    94990
gatttcttcctgtacttgctgggggtgagaagccactgcattttgtatcctacgttgctttgcaat    95060
tagcctggttttcattcctttgcacatcgcctgcttttctccttggaaaaattagacatattttgttta    95130
catttgaggtactcaaaaattggaatttgttttgctttgttctgttttaaatcaacgtattatttactt    95200
tgtgagtactttcacttttaagccttttttttttcattctgggaaattctcagcctttctgtctaat    95270
gtagttcttcctagtctttttctcttgttctctttctgggtcatttttttttataggactggtaacact    95340
tctatttccatcttccatactttagcatttggaggatgttttccaccatttttcatcccagatccattt    95410
tgggaaaatgtatctctgtcttttggctccatgtgcattgtttgtgggtatccttccatttcagtctgt    95480
tctttgtgctctccagttcaacaatttcatttcttctccccggtatctcgtgtgacttcctttgaaaccc    95550
tttgttccaactttatatcgctatcattgtctctctgtccattggagggatctgcttcttttgaatccca    95620
gtttgtttacttgggtcattttattattatttttttaaataggatgttccttttctttttaagtgcttt    95690
gcttttgactggctcttaaaaatttcttgggagttctttattttcttgaggccggtagaggtcttgga    95760
aggtaccaagtgtccaatgggcaatcaaaagcccacctctctgcctggcgcggtggctcacacctgtaat    95830
cccagcactttgggaggccgaggcaggtggatcatctgaagagttcaagaccagcctgaccaatatggtg    95900
aaaccccatctctactaaaaatacaaaaattacctgggcatggaggcatgtgcctgtagtcccagctact    95970
tgggaagctgaggcaggagaatcacttgaacccgggaggcagaggttgcagtgagccagagattgtgccac    96040
tgcactccagcctaggtgacagagtgtgactgcatctcaagaaaaaataaaaaacaaaaaataaaggcc    96110
cacctctcgatttcatgcctctgggtaaattggagggaaaagagggtccctctgtgaagagcccttggaa    96180
ctcgagttctaatttctaaaccaagaactttatattctttcctccctccctatcacttccatccactggc    96250
tggctcttatctgaaaactgtcgtgtgcagttataaatactcaacactttagggaaggagaaggaattctg    96320
agagatttcgccagcctgattcttttcattgccataaaattccactgcttttaccagaaatccttggaatg    96390
tggctttcctagctttgcactgtgaccttcttcattcggaataacgaagatgagaaaagcattgatccgc    96460
ccagacagtgaggagcgaagagcaataccctaggtggaaagctctatctcccctgactgtcctgtgaaatg    96530
cacctgagtctcagaggactccactgccatctgtctgtccaggaatttcccattttgtatggcgacttca    96600
aagtaggtaaatactttgattaaaggaatagagaacagaatttgggtagcttgttcaaaagatggcatgg    96670
aaaattctgtgactggagtagttgtgaagcatcactcttcccgtaagaataaaggaggcattgccagat    96740
gtctgaaaacacacagacacacacacaaaggaattacttctggctgcaagaatattctctctcagcatct    96810
tcctgcatctccatgggcaaacagacccacaacagcctgggatttttaattgccaacagttttcattgc    96880
atgagagcctgacatgtctgttgcatgatagggtgtgttttattttggcttcctattggttcaacat    96950
atccctccttccatgtcataatgacaattacaaagacctgagttgaacctagaacgcttttttttttgtca    97020
gacacaacaatgcagtggatgttagtcataggtaattcaaacagagataattttgtatattctagaata    97090
ttatgttttcaaacgtaggttttgatgtaccataagatttcttctgccattgaggcgatatatatgtgtg    97160
tgtgtgtgtgtgtgtgtgtgtgtatgtatatatatgtgtgtatttttaaatttaaattagatattttttt    97230
agaggccttagcccttaagcagaattccctcctaatttaatgattttggacgaagctcattgtgaatcat    97300
ttaaaaacacattcatgcttcttcaaacagaggtaacaaaggatacagcaccttgacttgttgactaagt    97370
gctgtcatggtagatgttatttagcatagaagatgcctgcagggtcagttctactctctaaagtttcttg    97440
aggctgtgttaaatgaaatcaaacacctgtgatttttttattcttgttcacgcttttttataccctctcctt    97510
tcttctccctgggcaacctgctttcacactagtgcctacctctgtttttccctttcagaatgtgatctatgc    97580
tacacaatctgattaacaagctcaacagagttctactggacatagaataaagaaaccagtatagttttct    97650
ctctagggacaaggcagtgaggaagccagtttgaatacaggttcttgctcttgtaagcattgacattcag    97720
caggttccttacttttctgaacactgcagttatatgatgggcagacagggactaagaataacacctacctc    97790
aacggggctgttgtgaggattactgagataatttatgtaaatccctagcacaatgcctgactcatgcgag    97860
atctttaattcatggtagcagttactaatttcatttatcataatgagctgcctgagctaccaaggagctc    97930
tgccactcccagtactgttctacagttctttaattcaacaaagaattttctttagttccaaataagtg    98000
ccaggcatcaggctaggtgctgggtgtatgatgatgatcaaaacagtgttcgtatggggtagtcatcat    98070
tttgtcgatgggccatttttatgatgtccctcttcattataggtcttgattcttgcctctgttttgtat    98140
acatatgtgttgcggcagggctgtctataaaaatcagaatttgccaggctgagcgcggtggctgcaatca    98210
tggctcattgcagcttcgggcttcagtgatcctcccacctcagcctcttagtagctgggattacaggca    98280
cactccaccacacctgcctctgttttgtgtagctgtgattacgtagcaattttctgaatcagtgacaaga    98350
tgcaatgcatatttttttcagtaggttaattaatttatctaatctacatttggagctatttttggagtg    98420
ttagtcatcataataaatatggtggcactgtcaatagtaatataaatataatggtaccttaattccataa    98490
tacaaagatcacgtcttcatgactgatgggcatttcaaaccataggtacatttgctcgctctgtaaag    98560
tatacaaaagtaagaattctggacatctttaaaagttgtaaatttttacatgaaaacttacattcacacc    98630
atcttttgaatattgaaaagatttgggaacatgggcctatatgtgactgtggatgaggtgtggctgttc    98700
cctttagacacagcactcactttgccatagtcacactcccaccgctcccctattgtgtctccaacccccca    98770
ggctgttgtctgtttctttccaacgttattacccactcatagatggtcaaccttatgatcattgttact    98840
ttctttcctcagaatctttctagtatttgtgatttttcatgtggttatttttgagcttttttgcattaa    98910
gaatttgggatcacatacctaaaagtttagtatttaccagtttgtattattgagcacttcagaaatttat    98980
ttctgttgctgttatcaactcataaaatatctgtttaattatccaactaaagactagataggatagtgat    99050
tcctatttctccaagctcatatctcgtgaactccttgattgcccaacataggcattcaatcattcattca    99120
acaaatacccattgaggacctactatgatctgggcacttttctaggtgctgataattgtagtgaaatagt    99190
```

```
agaccacagtggacagtgtttctttatggaatttaagtgaataaggaagttattttggagtatttcagat      99260
cgtgattcctgctacgaagaaaaataattcagaataaagtagataaggaataataggaatggacccacac      99330
agttattattttttattgctgtggtcatactgatatctgaagcaagtaagagaagagtttcctatgaggat    99400
ggaatagcatgtgcaaagaccctggagttgtagaatccttgatgcgtccaaggaatatggagaagaccag    99470
ttgggctagagttgacaaaatgagggtgaagtgggggtataagaatagagaggtgctggacagtaggccg    99540
ttgagagggctttagcttttccgtgatgaatattggaacccacaatgtaattttgagcatgaaaatgaga    99610
gccttgatttacattttttatcagatcaccctgagttctggttggagaatgagctctaaggatctgtgggt   99680
atatttagggagatacttaggtggcctttgcaataatacgctcaagggaggatgctggcttcaccagaga    99750
gctgatagataagccatggccagattctgggaatattttaaaggaagatccaacaaatcgattattccta    99820
gaatgcagaatgaatgagaaagagacaacttatggccaaccccaattcctttggccgccgtaactggaag    99890
aattgcgttgccatgtgctgacaacagggagattgtgagaggagcactttagggtgagggaattaggaga    99960
ctgcttttgtttaagttaagaacaaccaaggagagatagatgtcttagagacagctgggtacagtagtgt  100030
ggacatgaagagagaggtctacgctggagatacaagtgcaggagacatgagcatgtagatgatatttaca  100100
gttgtgagactgaatcgcatttccaacacaatgaatgtagatagagaggagaagtaagtgtactagaaga  100170
aaaagaaggatgaagaggaggagagagagaagacagtgaggaagaggaaagaagcagcgtgcatgtgtgc  100240
acttgtatgagaaagagagagagagagggagaaagtggaagatatagataagaggagagagagagagact  100310
gggggaagaattacatccacccaaaacccaaattttaatgacttacaatatgaaagcttcattttttttt   100380
tctcttatgttgcacctcactgatggactatcatcagccccacttctcttccaagtctttattccagaat  100450
ccaggctggaggccatgcctgaactgagggaaatggtgttcatgtacaacagttcttttcagcttctgctca 100520
gatgtggcattgcacatccactcatatgcgattgtccaaagcatttttctattctctgggagatacttca  100590
aggggcacaacagtggctggggattgaggggctgtgaatagactttcaggaaaaaggatcagctgtgct    100660
aaatgctgctgatgagtgcagtaacacaaggatgagtaacttgagtagcttgtagagaggtataggccat  100730
ttgtttcatgcccaggaacaaggcaggaccaggaatcctggttgagatgctgcagtttgggctagttgga  100800
ggtggggcaagttttttctctcactgctgggacttactcaggttaacagttgggacgtttgtggaggagct 100870
ggagacggaggagaaagtgtagaagagttaactaggagatggattgagagtgtttgatgtgagaggcagt  100940
agagcatgcattgaacctaggctgtatggttggagggtttttttccagccatgtcctgtctgctcaggtt  101010
cagaggaggtaggaggtagattgaaccagccacaggtgatgctccatgagtaaagaagggttgagagtca  101080
ggaattgaggagtccaaggcattaactgaaaagatggttcatggaatttaacaaagatgcggacaaatat  101150
gaggagaggaggcagtcaagggagagagaagaaggaatgaaagtgagctcctt                     101220
aagatgaatggctaatcccacaaaactggccaattcccataaggtgaacggctaatcccattagtgcatt   101290
gttgacatgaaaatgtcctcaccaaataatgaagaaaaatttgattttcttatgtggaaaaagcaggacc   101360
aaaagcaatcaaccaaaatcgtatctactacctggcagtccattagaacacactaaacacacacataaag  101430
agaaaaatgaagtatgttaattgtgaaacttgtatctccaaaaactggaaagcttcttggcacttaaaag  101500
cacttcttggcacttgggattacttgcctgtaatcccaacttgggaggtctgagacgggcggatcgat    101570
tgaggtcaggagttccagaccagcctggccaacatggtgaaaccctgtctctagtgaaaatataaaaatt  101640
agccgggcatggtggcgcatgcctatagttccagctactcgggaggctgaggcagaagaatcacttgaac  101710
ctgggaggcgggggctgaggtagaagaatcacttgaacctgggaggcggggggctgaggccgaagaatcac 101780
ttgaacctgggaggcgggggctgaggcagaagaatcacttgaacctgggaggcgggggctgcagtgaact  101850
gaaatcgtgccattgcactccagcctgggcgacagagtgagacgctgtctcaaaaaaaaaaaaaaaaaaa  101920
aaaaaaaaaaaaaaaaaaaaagaaagaaaggttcaataccctacttgttgaatgaaagtggacgtgtga   101990
attcaaagtttccgctctcttcacagtgtttttttttttttttttttttttttgacagagtctcggtct   102060
gtcgcccaggctggagtgcagtggcacaatcttggctcactgcaaactctgcctcccgggttcacgccat  102130
tctcctgccttagcctcccgagtagctgggactgcaggcgcccaccaccacgcctggctaatttttttgta 102200
ttttgagtagagacggggtttcaccgtgttagccaggatggtctccatctcctgacctcctgatgcaccc  102270
accttggcctcccaaagtgctgggattacagacatgagccaccgcgcccagcctcattcagttctttatt  102340
acatttgtaaaggtaactctaactccgtgagagcactttctcgctcacctcttaattcttgagcaaacag  102410
agaagctgtgcatgataaagctggagaattgggtggtgtcttcctattaagcttacaggaaagcactggg  102480
catttggaacagatgttgcatcttgagagccacagagtcaggtgtgcacgttaaaacgatgcttctaatt  102550
gttgcatagagacagaagacaatcacaaagattctgccttgacctccttacctctccagttctaaaaaca  102620
tttctcccactacagaagcatccatctatgtgttttttgcctccacgtggtcctattcctgaaatgctc   102690
cttccaagtctgtactttccaagagctactatttctggatcttttgcagttgcttcagcaagaatcagt  102760
tctggcttccttggttctaccatgccaactttaccttctcgtccctcagtgggatgctagggcttgggtt  102830
aattcatctctctccttcaaggcgacatgaagcccctgagaacaggggcatatttttgcccagccattac  102900
ctacaatgatacaggagtcctgtaatatcgttagagaaatgtgtccactgaacatgaatttcctatcct   102970
gttccttctaaaaaggatgcatgagttatcctatattcccaaggcacaacatgacctttctgatatgt   103040
gccaccgtgatcctgtagaatttgttttgtttccagtccctaagaataaatgtctcttaaagtattgtag  103110
tcattcactctacattttatgagttattactggcccacctacaaccatatttcctccgaaattcatcca   103180
tcctcctggaattacctgattctgaattattaagtggttctcttggccatttgctcaaaaaaagagcaca   103250
cttattccaacacacaggcattgtttctaaattattattgttttttcttcctagaaaccatttagagatg  103320
aagatccactttagaacatgaacccatttagtttagactataacaattgaagatatggtgactactgttt  103390
atttctgttagggatatattttttgtagatttcacaaaagacagaaccctgctgtgtgacagcttatctgc 103460
aggacaccgatggtttgtaggacgatggtgaggctttgtgacaaggcagaaatgtggaaggctggcaaga  103530
ttgtttactgagcttcccctaaggatggaataattcaccaatcccacaactcctccaccctcagtcacta  103600
ccaatagctgtgcctcagtgttttctttttaatgattgtatgtattaagaaaaaatcctcatatgtagt   103670
gtttagtttatctgattttcgttactaaaataataaaggagaaaagtaaataattcatataaaagtaaac   103740
tttcttattccaagcaggtgtatgtgtgcatgttttgtgtgtgtgtgtgtgtgtgtgtgtgtgtgtgtg   103810
tgtttgccactttgatggaaagaggctgactttgcagagactattttttgttaagaacttccattaaat   103880
tagagctttaagttataacactgattgcataggccagggaaaatggtaggatgtggccttaaaaggcaatc 103950
tcacaagaagtatgacttttatcttatattataaacaacagcacaaccttggaatttgtcccaataaatt  104020
ccataagtataaaataaactaaataagtaaagtgactaatatcctactaagtctttttccttcacacatgc 104090
tttttgcctaaagccatttaaagtctctgaggatttaaatctatgattctttcatggagtagaagaaac  104160
ccagagaatatagaaatttagaaaaactttaagacttattggtttaacagaagtaggccgggtgcggtgg  104230
ctcatgcctctaatcccagcactttgggatgctgagctggtggatcacttgaggtaggagttcaatacc   104300
```

```
agcttggccaacatggtgaaaccccctctctactaaaaatacaaaaattagccgggcgtagtggtgcaca    104370
cctgtagttacagctacttgggaagctgaggcaagagaatcacttgaacccaggagacagaggctgcagt    104440
gagctgagattgcgccactgcacttccagcctgggtgacagggcaagactccatctcaaaaacaacagca    104510
acaaacaaaacaaaacaaaaaacccagaggtagatctaattctgcagactgcaatcactcagttatggat    104580
ggataagtcagtccttaagtccatctgctatttgtgtatcgtgcatttttttttttttttgaaacaagca    104650
cgttcccacctggattgaatgttaatattcactgaaagccagggcattgcaacgagcccttaggatgtta    104720
taattctgggccatttttacagttcaggatttcagatttattgcaatgttgtaagttttttagtttcttgt    104790
ctttctctaacatctagtaagttccaaaacttaaagaactacaggttttcttgataaatacctgtgtcac    104860
tacttttttattttttagattttttcttttttactacatgatctgagttaaaagttaaatatatatgaattat    104930
tgttttgaaaaatattacctataatagttttttaaaagaaactttaattttagatttgtgctaaattggc    105000
gaagattgtgtagagttttccttataccccaccctcaaattccactactagaaacaccttacatcattat    105070
tgtacatttgacactattaatgagccaatatgtgtgcaatttttttactaaagcccacccattcttctgat    105140
ttcgttggtattttccttctgtctttttttcttcctcaaatcctatccaggatcccacattacatttagc    105210
cgtcatgtctccttgagctcctcttgactgtgacagttttttcttcttttgtctttcatgaccttaacagt    105280
tttgaggagggctggtcacgggattggtaccttgtttggtttgtctgatgtttttctcatggttatactg    105350
gggggctatggattgtgcagaggaagaccagaggtgaagtgccactttcattacattgtatcaagggcac    105420
atactagcaccatgacattgcagttgatactaaccttgatcccatggatgaggtgatgttggccagatat    105490
ctccagtatcacgttcgtcctcctgcacacacacttctatactgtaccctgtggaaagaggtcactacg    105560
tgcagcctacacttaagaaagcaggaggccgggtgtggtggctcacacctgtaatcccagctactccaga    105630
ggctgaggcaggagaatcacttgaacccgggagaaggaaattgcagtgagccgagatcgcgccattgcac    105700
tccagcctgggtgatagagcgagactccatctcaaaaaaacaaaaataattaaaaaaaaaaaaaaaaaga    105770
aagcggggactataatcccctccttgagggcagagtatctacagaaattatttgaagttattttgcatga    105840
gagatgtgcctattctcgcctactcatttatttattccctcatttacatatatcagtatggactcatgga    105910
tatttatttatactttgggttgtaatcaatgtgatgttgtttatctgcatagatttttgtgtttacgta    105980
acttttttttcaaattcctgagggatagcttttttagaaaatccctgttttttactttagatccaaggattac    106050
gtctgcaggtgtgttacaagggtatcttgtgtgttgctgaggttcaggcttccgttgatcccgtcactag    106120
gttattctgtgcccagataatgagcacaggaagttttttagtcctctgtccccctctgcaacagattgta    106190
ggaaataatctgagactgatcattttttaattttcaagcactgaacatgcagttattttatctagaaggta    106260
gaccagcaaaacaaaattatatttgacattttagcatataagtatttctagttaacttgtacatacaag    106330
aagccaggttatgaatgtatttgttcatgactctagcttgtttggttaaaattattctcctgccaaccaa    106400
atgcttttttgctaccctgaatatttaaaaaattttttacaatatttcatctttaagagctataaatgtat    106470
gttttaatatcccagggtaagatataggatattttttagtctgtcgaggctgctataacaaaataccttt    106540
agactgggtaatttataaacaatagacatttattgttattattatcattaagacagggtctctttctgtt    106610
gctcaggctggagtgcagtggcttgatcatggttcactgtagccttgacttcctgggctcaactgatcct    106680
cccacctcagcctcctgagtagctgggaccatacgtgtgtgccaccatccctggctaattttttatttttt    106750
taatttttagtagcgatgaggactcactacgttgaccagggtggttttgaactcctggccttaaacattt    106820
ctcctgccttgacctcctaaagtgttgggattacaggtatgagccactttgcccagctaacaacacacat    106890
ttattctcatgtcctgggaagtccaggatcaaggtgctagcagattcagtgtctagtgaggggccatt    106960
cccccaaatggcatcttcttgatttatcctcacatgttggaagggacaaggtggaagggcctgcagcctc    107030
ttttataaggacactcatcccattcatgagggtagagttatcatgttgtgtattggatttcagcatatga    107100
attttgggaggacactaccattcagactatataacaagatacattaggtttgggggtgttctgcacttgag    107170
tgaatctatgtaagcccttttcacatatttttttactttcactgaaatatttaaactaaataaggaaaccaatgct    107240
atcctatatcttaaaatgagaatggtttgtaacagctcattgccttgcatcatggtctttttagggttagg    107310
gttcgggttagggttaggattagcttcgctttgctgggcagagtaggtatttccgcctcgaaccacctct    107380
aagggcttcagcttttcagtaacgcacctgtcacttctaatgcaaaaccttgagtcctctgtctgtgtgca    107450
gattcaggaacaggtttgaggtctaagaattttcttattattgccttccatttcaatttctagttcctcc    107520
aaagtccttcacaatgatgaccgagaggagacactcaaaaatttgttagccagagtctcaaagtacatag    107590
aagctgttttctcttgggtggtattacaagtgcctctacaggcaactgcatttcttttctcttccaggat    107660
ttttgcttattgtccagatatgctcctcctagtgagagggacacttctgattttttcctgcctccatggaa    107730
cagggcttcagagaagaaactctctacagcccctttcgttccattaataattttataattaaatgcatttc    107800
cagcatgaaggctgcctaggagtagagaagcatattagaagaaccaatctgctgcgtatctgcttatagg    107870
gtttgagcccagtcaaggagggatgcacagaaactcaggattctgacagcccagccccccttgcaattggg    107940
agggtcgccaaatttctttcttgcaaggggtacttactgtcgtgagtgggagcctcttgtggataagga    108010
gtgagggcagaggggaacagcagagccctgaaggttctttccacttgactctgagcgtctagacagca    108080
gcctgccccaccccctagattggctttgtacctgtgagcaaagttttctgactgtgccatacatctctgg    108150
aatacatttagttgctaatggagatattactataattccacatatgttttttagtctctccttggggctgt    108220
gcccttctgtgtggcttggcagaagagaaaggagagaaagattatacatggcagccttgctttggaggga    108290
gtgaaacctgtgattttccttttctgtgtcaggaaagcgttttttctgctgcttgactagccaccctcccag    108360
gcacattaaccagtcaggtgatgctgacatttgtacccccctactctggcttatttctgaaaccctccctt    108430
tgagccctaactgctataattaggagactggatcctaacaggtttggaaaaaggtttgcaatctcaaaat    108500
aaagtagtgattttgaaagagaaatgtatagtagagttagctatgggggtttgcacattctacatttatgt    108570
ttgtttgtttttatttttcgctcagactgctcacagatgcagtgagcacacccaaatgcatgtgatcaa    108640
tgcatgtctgacttctgcagctatggaaggtctgggtttgtaagatcactgctgtagacccttgtttgac    108710
cttttttggattgctggatcagaaagtgagagattgcgaaagttttcttaaaagaacaagtcagtgaatca    108780
attcattaattcttttgttcattaggattagttaatatactacagtaaaaccttttgttattggtcatg    108850
taataataaaagttggattatggcatggctaaccccaatctccatacaatctgctcatagttttgacctc    108920
attctaatataaccctgtatttcacgtgattgaatgttttgcaccatatttataatattacatccaggta    108990
ttacttggttctgaaggtttataaaattgtaaatgcagtacataggtattagagattttgttgttttta    109060
ttttttttagagactgggtcttgctctatcaacccaggctggagtgcagtggtgcaatcatagctcactgt    109130
aaccttgaactcctgggctcaaacgaccctccaccctcagcctctggaggtagcttgttattggtgcat    109200
gccaccatatccggctaatttttttattttgattttttgtagcgatagcatctcagtgtattgcccagattg    109270
gtctcaaaatcctagcctcaagcaatcttcctgcattggccttccaaagtgctgggattacaggtgccag    109340
ccactgtgcttggccattacctagagttttttgttagagataatgaaataagaatgagattaaaatgaggt    109410
```

FIG. 8A-25

```
tagtctcatgctgcttaaaacagtgatatgcttaggagcagctgcaggaacatctgatccaatcttggag      109480
gcagcctggagggcttcccaggggaagcacaatgtagtccaaaacctgagagatgagcagggattgacta      109550
actaaagagcagacctacacaccaaattctgccatcagttccttgcatggcatggaaaattgatttctac      109620
aactacgcagtattttcttcctttttttttgaaacagattctcgctttgtcacccaggctggagtgcag      109690
tagagcgattttggctcactgcagcctcgacctcctgggctcaagtgatcctcccacctgagcttcccta      109760
gtagagtagctggtactacatatgcacaccaccatgcccagccaattttttatttatttatttatttatt      109830
tttgtagaaacagggttttgccatgttggccaggctgctcttgaactcctgagctcaagtgatcagccca      109900
cctcggcctcctaaagtgctgggattacaggcatgagccaccattttatttggtatgtgtgcattcata      109970
gttattctacaaaaataatatttaataataattcacagtatcctgcagattccaaaataaagtaagctt      110040
aagttctgttggaaaatgaatttctgtgagaaggctttggtgctttgacttgaagctgacatcaacatta      110110
gtgttgggcatttggctacacacctgtcacattcaaaagccaattcactttgagtctttattttgttggc      110180
agtaagggctgcacatttcgatccactgtgtattttcctagcccagattccactcaaagcagaggtttag      110250
agaaaaccttgtttattgcaaatattatgccaaaaatagggatgaggaaccagcactgtgttgtgggaa      110320
ggaacgagaaataatcactatttacaatagccgagttgtggaatcaacctaagtgtccatcaacagtgca      110390
ttggataaagaaaatgtagtacatctacaacacagaatactaggcagccataaaatagaatggaatcatg      110460
tcctttgcagcaacatgaatgtggctggaggccattatcctaggtgaaataactcaaaaacataaaatca      110530
aatatagcatgttgtcacttataactgggagctaaacatgggtaccacatggatataaagatggaaacaa      110600
tcaacactggggactcaaacaagggaaaggctgggaggggtgagggttgaaaaattaacctatgggtac      110670
aatgttcactctttgtgtgattggaaccctagaagtccatatgtcaccagtgtgcaatataccatgtaa      110740
gaaacctgcacatgcacccctgaatccaaattaaaatttaaaaacaaacaaaaacacaaaaaagtgtatt      110810
ggccacagaggagtgactgctgcttgacccagtgaggttgtctgaaaacccttatgttatgtgtctccag      110880
accaccttttacccggtgaaaatggaggacccatattcacaccatcttcacctcttattagtttactggg      110950
ggtaacctctccaggctgcttgggagtgctaagtaggttttagtgtgcatccactgtgaggcatcagag      111020
aaacttcaggaaatcaagaaaaaggcaagtttgcaggtatgaagtgaggctgcacctgcgtgaagctggc      111090
tgaagtctaggcagagcagatcaccacaagagcggctggaataagccatgtggccgaatggcatccagca      111160
caacgatcaagtgaaacagagctcctccagctgtggtagaactagggcaaagtatgtgaaagtgttcaa      111230
agattcttcgcattgaattcaagctcatcattgtccacaaatcaatgagaccatgtctatattggtaaag      111300
aaagaataaagcataaattcatattttcaattttttaggttatctgaataaatgaatttcaagagtgcttaa      111370
ggttttttgctagatgtttgcaggttttttgcctggagaggcacaggcagttctttgtcctatcattctagc      111440
cttccacttgtagggattccctggaaagttgacataaccgctgattcctagttctgttttgtgggaagta      111510
tcaagattaagagaccctctgggtgaacaagatgtctttcaatagatgaatgggtaaataaactatggtg      111580
tattcagacaatggaatattattccatgctataaagaaatgagctattaagccatgaaaagacatggagg      111650
aaaattaaatgcatattactaagtgaaagaagctgatgggaaaaggctacatacagtatgattccaacta      111720
taggacattctggaaaaagcagaactgggggacaataaaaaatccatcattgtcagagtttcggttgggg      111790
atggggaaagaaaagataaataggtggatcatagaggattttatggcagggaagatattctgtgttata      111860
ctgtaatggtgatgcaaggaggttcttttgtctaattaactgttcacattcatcataattgattccat      111930
acagtatgcatggattttcagggtccaagtgttaaccaacttcagtggacttaaaccactctgtaaatgg      112000
ggtgctctttagtgtttgttttgtttactgttctaggactggttaatagaaatcagaggacatacagatc      112070
cagagtcccttatctacaatttgaaagtcaaaacagttcaaaactttacagtgatatcaaaactcattt      112140
ggggggcaaaacctgatctgacagatgactatttgtgtctttctttccacctcagggtggacatttaga      112210
tattttcctgcaggaatattaatgagtttgatttgggagtgatgttccatattcctctgagggtgctgca      112280
taaaacagatgtaaaaaaattaaaaagttctgagtccccttcctcttgtccacaaaagcatactcattcc      112350
caagggtttcagatccccattggtggatctgtgatatcaaaggtctcattgataatgttggtggtcagtg      112420
gaaaatagttgtgtggagagagatgtgttagtctggacctcatgcaatgactgcagaaataattttatga      112490
tttccaaagaacaacagcaatctaaccacctccctttaccctttaaagactgacatctgtgttgtgttcat      112560
ggatgattatgcaaatcaagaaaagtggcttccatcaaaataatgtcatttctttttggagaaaagagcc      112630
tgggactgagttgtgttatgtgtgcagtttgccagctaaactcctggcttaatgattgggatgggttttcc      112700
aagggctggttctgagactcagtggcagttagtggtaatttccccattaacattaatgagaaatg      112770
aaataagttacttaagaaaacgtgctagacgatagtctctaagtactgaaaagtaaatgaacccacctac      112840
gtttgttcacataaaatttcttagtatattttaaatttgctaatctaatgtacttttttttttgcttgtg      112910
ctttaactttgttaaattatgtcacgtaaaacattttattccatattctaaattacataaatgtgtcaca      112980
cacaatgtcatgaatcaagtttgtctaaagaggagataggccaaggcaggtggatcacttgaggtcggga      113050
gttcaagaccagcctggccaacatggtgaaaccccatctctactaaaaatacaaaagttagtggggcatg      113120
gtggtgcacacctataatcccagctactcaggaggctgaggcaggagaatggcttgaccctgaaagtgg      113190
aagttgcagtgagtcaaaatcatgccactgcattccagcctgggagacggagtgggactccatctcaaaa      113260
aaaaaaaggagataatacactttcacgtttgtaaaataatgttgattaaatggtctaatgtgattttat      113330
cttgctaatccagttaccgtcccagtatctgaattatgataacagtttacgcagcatagttttctaacag      113400
tttttggttccatctctgctattaaattcaggccactggatctgtttggttcaacttggattagggtgta      113470
ggttctgtttttcctacctctaactccatatacattgtccgtgctcctgaccttccatgcaggaggcttgc      113540
aggtatctccttaatcgtctgtcatctgtttctttctgccatctcagggactcctgatctttccagact      113610
gcccatcctctcctgtcccttcgactcttccttttttgttcactttctgtaactccagtctgatcatcta      113680
aatagtctgagggaagatgaggtactgaaggcactcttgtgagaatatttctcaggttcctaggtccaa      113750
gtttccgttgcatcttggtttctatttcagtctgagcagagagagagagagagagacaaaaaagatctt      113820
caggataaagtgagagagagaagatgagaaataaatataagaacaactgataaatgccttgagc      113890
tataactctgccaaatgaacacagaaactcatgtgcagttagatattatccacctgagaatgtagttgat      113960
aacatatttcatcataaataatatcgtctaaagccccttacttgggaagattatgaagcaagccaaatctt      114030
atgcagtatgtccttctgttctcttgacaagcataagtttctatttctgtattgctagaaattttttagtc      114100
acatgcaattccaacagtgctttaagctggttattactaagtagaaggtaaatgtttgatgatggaagaa      114170
tttgcggttggagggtgaaatttaggataaatattagcaaacttttgaaaagtaaggtgtagatctggcgta      114240
ccagaaaacatttaacagattcagaagttagtttatgtgtacctatatgtgcacacacatacacacacaa      114310
tgcatgcacacttatgcaaatcacacacacatgcctcacgcacaagtgcaacactcaggtgcacccaatt      114380
gcacatacgtattctattactattctttgcaatgctttgaatgctcatcatgtaccacaaagttatggtc      114450
taattcataataccataaggtgcgtgtgctttagagatactgtgtatttccttcaacatcgaactagtg      114520
```

FIG. 8A-26

```
actattaatgttttaaaatcaaatttgataacattctgaaataaaatactgatgtattaagtaccaatgc   114590
gttgacatcaggtttcataggtgttgaactgtagcgaggaaaacagttatcaggtgtcctactgtaactc   114660
tacccagcaggaaagctctatgtaatgatggtagaatatccaaatgatggtgtccacatctgcacaggta   114730
cgatttgagattcactgacttatttaggaggattcagtaaaatttcgcagatgttgttatgtagtaaata   114800
ttggctcattcatattctgcactcctagacattgcagaaagacatgcaactgtgatttccatctcatccc   114870
tttcacccctatttttgaaacatttagttatgtctactagttaccctaagttgtatttttaccctctaaaa   114940
aggaacaagagaagttggaatccatcccagctttccttccagaaaatggaggggaggaacaattggaatg   115010
gagaggaactccaggggagaaaaagacaaaaggcacatgagtgagtttgtctaggctgggagagtgggcga   115080
tcacatgagatttgtgaactaattttgttctccttctgtttccactgataagcactttatgagtgccacc   115150
agtgtaagtaaatattaaacctcatctcaattagtatctactcttttccaaatatatgcttatgtcagaa   115220
aatgagcagtagaaagcaaccacaggataccacctgcacacccacgggctgagcattgcatactttcaag   115290
gagtgctgttgtgttttcaaacttagtaatttcccaaaacagagaattcacagcttccctaatcaccttc   115360
ctcagaaccctgaatcttgttaattgagtcattttctgatgatcatgtactcatacaattgactaaatg   115430
tctcactatgccttcctgataagtagtgtctctacatgtgaagtatctattaatctatctaccctctc    115500
tctctatctaatctgttgatttcttatctatctaatttatatctatcatctctatgtatctatgtatgta   115570
tgtatgcatatatgtatgtatctatatatatatcgatctatcttatctatatgtatctatcatctctatg   115640
catctatgtatctatctgtctatgtatgtatgtatgtatgtatgtatatatctatcaatcctctct       115710
ctctctcttagttcagcaaattacttacaggttttttgttatgtaactgagcaaaattatatacacaca   115780
taagaaggctggaagttcaagatcaaagtgcttacagattcagtgtctggtggggacccacttcctgatt   115850
catagacagcgccttctcactgtgtcctcacatagtggaaaggcaagggagctctgtgggatccctttt   115920
ataagggcactgatcccattcatgaaactccactgtcatgacctcattacctccaaaaggcgcccacctc   115990
ctaatactgtcccgttggggattaagatttatatattttttctttttaattctaattttgtgggtaca    116060
tggtaggtatatatatttatggagtacatgagatattttggtgtagacatgcaatgcataataatcatat   116130
catagaaaatggggtgtccatctcctcaagcatttatcttttgtgttacaaacaatcaaattatattatt   116200
ttagttattttaaaatgtacaattaggccaggcacggtggctcacgcctgtaatcccatcactttgggag   116270
gctgaggcaggcggatcacgaggtcgggagattgagaccagcctggctaacacagtgaaatcccatctct   116340
actaaaaatacaaaaaaattagctaggtgtggtggcgggcacctgtagtcccagctactcaggaggctga   116410
ggcaggagaatggcgtgaacctgggaagcagaggttgcagtgagccgagatcatgccactgcactccagc   116480
ctgggcgacagagcgagactcagtctcaaaaaaaaaaaaagtacaattaaattactattgactatagtat   116550
tgactatagtcaccctgttgtgctagcaaatactaggtcttatttattctttctgactataattttgta   116620
cccattaaccacccccacttccccacatcccaccccactaccctttccagtgcctgataaccccttttg   116690
actctctatgcacatgagttcaatcttttttgattttttagctcccacaaataagtgagaacatatgataac   116760
agtctttctgtccctggcttatttcacttaacataatgatctccagtttttatctatgttgtaaatgacag   116830
gatctgattctttttttatagctgaacaatactccattgtgtatatgtaccactttttccttatccattc   116900
acctgttgatggacagttagtttgcttccaaatcttggctattgtgaacaaagctgcaacaaacatgggg   116970
gtgtggatatctctttgatatactgatttcctttctttgggggtttggatataaacatatgaattttgag   117040
aggacagaactttcagactatagcatactgtaccatctatctatctgtccatccatctgtttatctgtct   117110
cccattcctgaatattgcatggcatattttgttaattatttccaatgtcatattgagttttaaagtaaga   117180
ttacatttctgagaggcctcacgtgggggcatcctgaaaagtacattctctttatagtttaaatgttttg   117250
gttttttttctttatttttttcatatttaattatatattcttttcaagtgactccttttgggagacatgattttt   117320
cctacctcctgggactgccacaattcccctgcctcttggaatgcaatcgatctctagtctgcctcaagta   117390
taaagatgatattcatgttgatgacattgagaaggatgaggagaaaggagttgatcagagatctatattc   117460
atggtatatatgtttatcgtatatatatttatctgcttatcgtcttcagaatataaactccaagactgtg   117530
ggtctttgtttcttcagtactaccttgcagagtctaggcctatttattcaaagcttaatatttgtgaag   117600
tgcatgaatgaataaatgaattctaatgttatcactgccgttggtatgtgatctgttttctctatctgtat   117670
tgtcctctctacttttcattatttgtttaattcccactcattgagacagttgcagaagattcctttgcc   117740
aactactctctgggtagagataaaatttccctccacggagctcccactggactctacctgcagctatatgtt   117810
atcttgtattttccaacactcagctgtaccacataagacttgattgagtgaagaccctgacttagctttg   117880
cataaaaccaaagtaaatgctttccacacatagccattcacagacatttttcacattttatacagcaactg   117950
atgaactaggctagtgttgggaacaggccccctaaaatctggccataaacttgccccccaaactggccaaa   118020
acaaaatctctgcagcactgttgacatgttcatgatggccatgacccccatgctggaaggctgtgggttta   118090
ccagaatgagggcaaggaacacctggcccacccagggcggaaaaccgcttaaaggtgttcttaaaccaca   118160
aacaatagcatgagcgatctgtgccttaaggacatgctcctgctgcagataactagccagagcccatccc   118230
tttatttcagcccatcccttttgtttcccataaagaatactttttagttatctctataatctataaaaacaatg   118300
cttatcactggcttgctgttaacaaatatgtgggtgaactgtttgaggctctcacctctgaaggctgtga   118370
gacccctgatttcccactccacacctctatatttctgtgtgtcttaattcctctagcgctgctgggtta   118440
gggtctcccggaccgagctggtcttggcaggctataaagacattttctactggcttaacagagaagaaa   118510
acaaagcttagggagactgattatgcagaatttaatttgcaacaagcaaagacaagtctattgacttcaa   118580
atggacatcatcacattgtcatctgataattttccagcatcctttgcctcctctgtgttaaattataaa   118650
ttaatgctgatttatacagttcagttcagcttcacaaatatttaatgagcacttgctgtgtaccaggtat   118720
tattatatataagtagttctttatggtgtaagaatggatagtacttttttatccattcaactttaaaa     118790
ggttgatgcctagtcatagataccaggaaacacttaagtgaatgaggcaagttttctgctgtcaaagag   118860
agagatcagacaccaactagagtccaagaaagaacaaagtaattttgatcaacaaaactcatagaagaaa   118930
ataagcattctttgttgttacatatacttcagagccattttagtgctcaaagtttgatagaaattgatac   119000
acaggacttgctgctctgaattggctatcccagaatattctacgagctacaaccagacctgacattaacc   119070
tgtagttacttgtggtttattcatctatccatcaaatgttatgagcatcctctatgtactcttcatgt     119140
actagactttagacattgaataccggagcaaaaaagacatagtttcttatttaatgtggcttatactctga   119210
tgtagcatttcttcaccaggggtaattttgcctcaggggacatttggcgatgtctaaggacagtgtaggt   119280
tgtcatgactgagatttgttgctgatgtctagtgggaagaggccagaccccttcacaataaagaattat   119350
ctgaccaaaaaggtcagcagtgccaaggttgagaaactcttccagcagttgagaaaaataatcatcag   119420
atcacccacaagtataattacaaactgaaatacatgttagatgctggtagagctggtttccaaagtttct   119490
gatccagttgtgaggatacatattgatattgagaacgggcggttgaaggggcagtagtaagttattaggg   119560
taagaaggtcttggtgagcagagggactttcatgcgaagactccagggctcgaaggagcccagtgcagtc   119630
```

```
aggatctgaagtgacaggtgtggcttgagaacagcggcaatgggagttaggcaggaggggaagctggaa    119700
atgcaggcaggggtagacaataaaagtacgcaggccgtttatattatacaatcctgtagacttctttctt    119770
ctttcattcttgatacttttctataataacattcaagcattggatcagcacccttgttgtcttctgtca    119840
tgtagcccaaaggtttaccttggagacacaaaggcaactaagacaatggtttctgcactagggagatcat    119910
attctcactcagaagacatttgcagggtgtgattagtgagtctcacatacatgtcaatttcttcctaaga    119980
ccttgtgcttttctagttttttattttttttattatttttatttatgtattttatttgagagagagcctcg    120050
ctctgccacccacactggagtgcagtggtgtgatcatagatagctcactgcagcctccaactcctgggct    120120
caagcaatcctcttccctcagcctcccaagtagctagaactacaaacatccacaaccacacccagcttat    120190
tttatttttgtagaggcaaggctgtctctacaaattccgttgcccaggctggtctcaaatgcctgggct    120260
caagcgatcctccggcctgggcctaccaaagtgctgggattccaggtgcgagccatcgcgcccaccctc    120330
tagttttttaattggtttatttctttctcatatttcagttgagcattattcatttattgctgttgaggttt    120400
tacttttttttttcttcccaaaggtagattgtagacagctcacctttgttaccaatttgaaatgctagat    120470
gttaattcttaatgttgtagctgtaaagggccatgatttgaggacgtgttattttttaagcctgagttt    120540
ggattggtctgagttgaatgcagttgctaagccatcgaatgagggagtgtccctgaactaatgagtgaca    120610
tggaccttttcttataggtgagagtccatttgtgataaaggcattgttttaggatacataagggtcatgg    120680
tgtatattcttagcaagtgttatgaatacattcgatctatttcttttgaattttagtgtttctctactct    120750
ccatcttactaaaccaggtgtcccagatttcgggttcacatttgtgtcgggttcacatagagggac    120820
taactaggtggagtttagggtaaggggtattcagagtcctgccctcctgcaaccacagcaacaccccca    120890
agtctctctcattagattgtatttgttctcctacttatgttctttggcctctgctataaacattttcaaa    120960
aaagtatccaatgaaaacaatgttgtcaatgactgtctttagtaagtctgtagtcagattcatatcttta    121030
aaatatgtacactgtgtgaatatttcaaagtatgtatcatgaaaacaaataaggaaaaaaaaaaaaagc    121100
caagaaagctgagatggctctattaatatcaggcaaagataccttcaagataaggattattcccaaaata    121170
aaagagagacatttcataatgatacaaggaagaattcacctaagagaactaataatgtttaatttgtgtac    121240
acctaataagagagctgttaattatacaattagcaataaatgcaaagaaagactcatcaataatgacagt    121310
tggagatgttaagatgttaccacaatagatgaaagatgaagatagaaaacacacacacacacacacacac    121380
acacacacgatatgaaaattttcaacagcaccatcaatgtccttggcaacttcgtacttcgagtccaacc    121450
tcccttcacaatctaatacagaaacaaacaacccatgattttttctgcatttcgtggttaggttccctgtg    121520
gctcaaggcctctggcgcaaatgatgttgtcttttagattttcatgctaagaagatactcatgttcgtat    121590
gtgtgtgcttttttcctctatagcatccttaatgttggcctccagatgagagtctctgacaatgggcttt    121660
aacatcaaacagccaaagtctctcagcgagttaacctcttttggcctttaaaattctcacataatgacatac    121730
aacagtccgctcttcttcaagtggcctttgaggagtctagggacacttgtgaattcacttccacaactca    121800
gctgcattgcgaattcaattattgtgctgggagatgttgtaccattatttttttttaaaggtgcatattc    121870
taaaggttaatcttgaggctatcacattaagggttaacattttatcggggggcattatagagtgcattttt    121940
gatgctgtgatttcagataacaagcttgttgtttctatttttcagctctagcttggcctctaatctgta    122010
gggaaggctggttcctaaatgcaggaaatgaggctcaatagaacatgaaaagccagtgttaatacaccat    122080
tcaatctcaagaaagagtgggaggaagaatgacagagctgtttttgacagatgagtggttaggcatccc    122150
cctagctctccaagtcaccactaggatgaactttcaggatgcagtgtcctgtggaatttggctctgaaac    122220
ataacttcttcataaggcagatattgtaacgcatttctggattttgtacctacagacagctctgtgttat    122290
ggtaactgttttctgttggcacaacaaacaattagttagcttcatgctgtagaataattccagatgccct    122360
gatactccaaaccattggtcattgcagcctccatattcagatgtagcggctataaacaggtgatgcatgc    122430
atcctggccagggaccatttgatttttccacctttttctttcccaaattcagggtttgtccacattagc    122500
actattaaaacttttggggcgcttcctgtgcgttgtaagatgtttagcagcactcctggcgtctacccac    122570
tccaagtctttaacacctaacgcccatccttaattgtgacaaccaaaactacctgcaggcattgccaagt    122640
ggctcctgaggggggcagcattgtcttcattgagcaccagttaaatcctagcctaatctattgtgtta    122710
cctattgttccttaacatatatgggtgtagaatcagaattacaggaacgtgaatttctttcaacaattat    122780
ttctttacaattatgtaataaaatcataaaaggtaaaactgtatcttttagaagccaagaagcaacagt    122850
ttatgaaacaaaacctcttttagtatttcatattaatcaatagatattgtggaaaggctagttcttcttt    122920
aaggtaacagttgcttaagagttgaagtgcagcttatgagttttacaagcccctgatttatgcacagcttg    122990
aggcattgttgttttgcaactattgttttccagcagcactgctattttataaaagcatgtatcagcaata    123060
gtatagaattgcatatatgcttcagagtcaatcattaaatagcatgcaatctgagtagagctac    123130
ccaaagctggaattcagagcgcatatttatgcacttagcaacattgccataattacacacacacacacac    123200
acacacacacacacacacacacacacacacgcacgcacgtacttaaagcctttagccatttaaaaatag    123270
aattcaacaactaaggctcgtacacatggaactcttttcatagcaggatttccaatgtgcaaatttgata    123340
aaattactcttttttaaaaaaaaaattgctgcaacgttttttcattaacaccataaacatttacacatgatt    123410
caccccaaattgcaccctagatgtatttaccctgacttggcaattttcatacttcatgtctctacttccct    123480
tcatgcttcaatacagaaacagacaaccgatgacttttctgtatttctgtggctcaagtcctctggccaa    123550
cctgataaatggcttaggctattcgataacctgcagcagatcctctgagatcttcttttagaaatttcctc    123620
caagatcctaactacattcatttgtagaaatatttgagatgcaatgcataccctgtctagtatcccccca    123690
ccccataacagaaatgtgaagtagggtgatctgtcatctttgtgcaggtcattgccagctctagcaccag    123760
aatctcctcacctgggaatatctcagtcccaggccaactgggacttggatactctaattctaggtgtgg    123830
ttgaagcatcggtggttcctataacactggcacaggaaaaacattaacagtgggacagaatagagagt    123900
ccagaagcagaagtgcatatgaatagagaagctggtcccagctgggaccagcttttaaccttgccaaa    123970
tcttgctattgcatctttagctttcttctttccttttataccttcttccttctactttctgtttagtt    124040
tcttctgttttctccactaatttcttaagtgggatgattcactcattacttttgcccttgtgtttgtt    124110
actgatgtcagtatttatggctttaaatttctctactgctaatttcctgcctcctgtaaattctaaaa    124180
cacagtatttcagtatttgtctattaagtgttaagtgagtttgtgtgacgttctaataaacagttaatt    124250
tttaagtgtttgtgtgtatttctaatgatgagatacaaaattatgtaattgtctatcaaatcatccggt    124320
taactgtttatggcatctgttttttcctatttttgatcattaaaattgaaaataggtttctttgtatct    124390
tccattaatgaatgaatttataaattcttcctataatactactgatttggggttttttaaagaacgtatg    124460
tggcataaaatataacaagttatctccttgaagaatgaaatattttactatgtaatattcttgctatc    124530
tcttaaaatgctttctgttttacaatagatatccaatattagtagaaatatgcttgtttcttttttactt    124600
ttgggttggctattgctgagaatatattttttatattttcacctttagtaatttcagatattatggttgt    124670
atcatttcatatgacagatatctataatttcttttttttcaatgtgacagtttcagtctagtaattgcata    124740
```

FIG. 8A-28

```
acttatgctatttatgagtttgaagatatttgatataattcaacgtattttaatctttcggatttcctttt    124810
tttatgcattccttttaataaatgagtttgttctttttctgtattttcttcttaatttgccatttacttg      124880
atttctacttttcaagaaaagcttgcagttgtaaaactcacatttaagtcattaaagtctaaaattaagc     124950
aagaccttagctccattctagaaaataccaatcacctgtctcccctagttacaggctattattatgtatca    125020
tgaatatttgttataaactctttcagttttgtttgattgaataccttttgttccctgctcattcctgaaa     125090
gataattttgcttattatgcaaatccaggtggaccattatttcacatttcactgtcttctggctatacag    125160
atgtcagttggttttgagttaaactttatgcacaggttgtctttggcaagggctaaaatttaagatctcc    125230
tgtttatttttggcattcatcagtttcatgtcaatattgattttttttttgctttatccattcttttctat    125300
ggtttctgtgcctttggattcatatatttaatcattatttgaagatcttagggatcacctttcaaatact    125370
gacacttctccattcttcctgttttctcaaattttgatttgatatatgagattctcattttgcacccat     125440
gtctcctaaattgacttttatattattagtttctgtcttctgttttttgtaagattttcccagacatatc    125510
ttttttttattgtcttttcttctgtgtctaatctctttagctaatccattaatttctatttatttcaacaa    125580
atacagttttatttatttcatttctatgtggtcattttttcaaatcttccttgtccttttccagtaatttc   125650
ctgttttttgttttattgtttcctgtttcaaactttattttttaaatagctattttaataccacaagtttt   125720
gtgtgcagcacctataatacctcagtgttcatgggcttagtgatctttgactgtgaactcatgtttgttt    125790
gatcttaatctgtgggaatttctggcctatgctggcattcttttcccaggcaggtaggttcgctttcct     125860
tctgatagaagctagagtgtaagacttgagccctttcaagggtccaaattctccacttactggaagcca    125930
agcttgggtttctggccccagccccttgtcttacacatctggctgcccttccagctacctgctcccttg     126000
tctgaggtcagtgctactatggggtgtgttacataagggcagacttccctttaggtccagtttttccctttgc  126070
tcaggacacccaaatattcttttgcttacactgttggaggagctttatgtgggaaagcttaattttggat    126140
atttctcttacttccttgtgcccagaagttcactagcaagtgcatcttatcaggaggtaattgttttgtt    126210
cagggaaggtctcccagagtgatgtgttacctgctgatgataggagtggaagcttttcctttgagaaggt    126280
ttcaccaatggaaaaacaggaaggaatgagggagggagggagggaggaagggggaagaaagaaaggaag     126350
aaaggaaggaagagagagaagaaggagtaaaaaagaaagggaaggaggaagggaagagagggaaggagtgaaa  126420
aaagaacaaaggaagaaaggaaggaaggaagtaaagaaggagaggaggaagaagtactgaggaacatctt    126490
actcaatggtgagacccagttcgtacatgttcttatcctatgagctaatttttctcttttgttttttctt    126560
aagagaattggctgtctcttactctgtaatacagatctgtgagaaaatagctttataaaaagagatttt    126630
gtagtattacacacttggcaggaatatagttgtctgttgtaataatgaatactaatctagaataggaggc    126700
tgagaagaaaaatataattaaaatggtaatggctttttttttatgtgaatgaaactcatccagtattggt    126770
tttgaaagatatctaagttctaggagcagactgtagcagaatctcctttaatactctaaggaaaggacgc    126840
ttttagaaagtaggcattgcctcctttatgtgaaaactgcattcctttcatgagggttccatttctgaaa    126910
cacaggatgtaagcaggagacataagaagggatcttgtagcagtgcagatgaatcaagtcactgcactt    126980
tcttatttgatcttatttttaaaaagatgcttccagggaagcaggaccttggaacccacaaagtctggagc   127050
aagtcattgacctcgcaaggtattcacgtcctcacagtaaaatggagaataaaattgctagttttttaagg    127120
atactcttaggaataaataacttgttatagcacatatcagaccatcagtcatgccagcctgttttcctttt   127190
ctctcttactctctccctctgttcattttctccatcttctctccaactattcctccctctctaccactgt   127260
tgctccctccctccctccctccttcctccttccattttttccttccttccttctacatccctccttc      127330
ccctctctttcttttcctttgcttccttttctttttcttcctctctcttttcctacaaaacagtatttg    127400
tcaactttggcactcatgacatgtggagctgatcacccgtctttgttgtaggaggtgtcctatgcattg     127470
taggaggtttagtttagcagcatgcctgggctctgcccagtgatgacagtggcaccactaccacaagtt    127540
atgaaaaccaaaaatatctccagacattgtcaaatattgcctctgaggcgaaaccaccccctggttgtgaa   127610
ccaccactcaaaaatacacttcatatcaataaaaatcctgctttatatatatatgttttttgctcagttc    127680
agggttattaagattgtaagacactagtgttttacaagatttctagggatgttctttgattgagtctta    127750
aaatcttactgttgatgaaaaattgaaattatgttgttattttttatattccttcatatagcagcataaaa    127820
cttggtattttatgggaatgagtatgcatcttgttctgattctattggtctacttttatgtgtctcaaaat   127890
gagattcagatcaaagaaaattaaaacgagagcaaaagtgaatattaaggtaaaggtatagcattctgat    127960
tatctgctgcttgtccatctcaggtatgcaatactgacactgtgccactagtagcttcttgacattctta    128030
agatgaaaatagtttagttttttatctaaatatattaatagagaatatacaatatatatttattcatatat   128100
taatactggaacaatagagtaaggttaaacactcaaaatttagctcaaccctgagattattatgaagtac    128170
ttacaaaaataaaaactaaaaagacattagtagcgtacttcccagcttcatctctgcgagaggtgttacc    128240
ttagctcagggcttggagaataggacatgtgtttacgtgattgactcttgttgggattgttctcagagct    128310
ctcctgaccttggtccacacacttgggagcacatgattcctaatactgataaccacagtctcatgaattt    128380
ttctcattttgcagaggagggaattgaggcactagatggtaatatcttttttcatttcacatagttgctgg    128450
tggctaagggaagctggtgctcagcttgtcccaggccatatctaagacatttgtctggcccttgctttc     128520
cttcctttcatgcatacagcaagcatatccaacttttctgctgctgtcttctagaaggtgttatttg      128590
acatggcatcacctcctttgtagccctctgactatgagaatgataaatgacctctcttttaaacctatc    128660
tccttatccgccccaacacatacccctttggggtggggtcataaggggggtatcccttctccacactaact  128730
ttaccgacttctctcttcattgtctctctgcagcagataatgtaagcaagaaaaagattaagttaattac    128800
atgcacctcaagtttcagtaggaatatcccacaattcctctgtctcttaatttaactgttatttattgaa    128870
cacctgctgtgttcttgggaaaattccaggtgctggatggaattagtttatgatgatagctaagacttgc    128940
agagacattaatgtgctgttcttcttcttcagaaagtatagccatgtacaaactactaaagggcgat      129010
atcaaatgttggggagataaatatcaaatacagagcttccatacctgtagttttggttagtttaatagg    129080
cgttaacatttactcattttcagctacctacatttattgagcagtgcctataccactcattgtaatttaa    129150
ttgcataataaattacactgtatttgctgtttatagaaatttagaaatttagtttaacgatatgtttata    129220
atttctttactactatggataatacatttaatgactataattaaattcttgcaaaattttttgaattgttt   129290
ttagtaatttgccaatgattttcccaggtattaatttatattgaaatttttattctagaaggtgttttag    129360
gtttttttatttcattcatttatttaacaggcatttatcattcatctgctttatgcaaggaaaaaaatggt   129430
caagacaaggatgccaagtctttaacctcagggaacttacagtttatgtacagggacacatacttatcaa    129500
ataaacagagaaaggaatgtatattcatatgaactcggcatcatatatatcttctttatgttatcattaat   129570
aacatccaaatgtcaacaacacatctattgttactttggttaaaaagctacacagacagtagtagatatg   129640
gtacttggatgaagaaagctgaagtttattattttctcttttctagttttaatccctaagggtcattgata    129710
aaagacttacacaaacccccctttagtaacctaataatgtataataatcctgttcttaaaatggtgatag    129780
agatttgcttggtttctactacataacaccataataccatattaagacttgaatctctcttatatcatgga  129850
```

FIG. 8A-29

```
acaactcaggtagtgttacaaactgctgttactgaataaatgcggagaagaacaagctctccagagcagt      129920
gccatgcctgtgtctgatgtttcccaggatagaaaactgcgcagatgttgatggtttgtttcaggtgctt      129990
tgacagcctgatcatgggctctagccgtggaccatgaaaaatggcttctgcaggggcttaagaaagacaa      130060
tgaagagcttcgcatttctcttggcatttcctgctattgtttaaaaggtcacatatgcaatttaaaatg      130130
ttccatgcatggagcatgacaaatgccacgtagaaatgaaactgctttcgttgacatttttggccaatt      130200
tccaaagggtaccattttccgccttttcccttttgtggatttgcaaaatttggcttgtgcaaaatgcgtg      130270
ccccacggtgcactctaggttgggaagtgccacatgttaggtagaaaatcgtgtgtagatgagaatggca      130340
cattcagaataaaagtgagaaattaaatgacatcaaaaaatagagaaaaatagagaaaaacttgtaaat      130410
gagtccatcagaactatcagaagctcaaaaagaaagaaaggcttagaactcatcaataacaatgtccagt      130480
ctcattcatatgtaaagaaagtgaaatcaactttattttagttaattttacttttattttatttattatc      130550
cttttacctagctgaatggcaaaactcagttcagttatctttgggcatggaaaaatgagcactctcacag      130620
tttgctagttggaggaagaattgaagtagagttttagaagacattgggtattatacaacaaaatttagaa      130690
agagaccacttttactcctctggaagcattttttgcttccaggaatctatcttacagatatatacacaaag      130760
atatatgtacataggtgatcattgcaactgaaattttttctcatcaggaagatgagtgaattattttaagc      130830
acttagaatattaaaactatctttcccttgaaattgaagaggcagagcaaaatgtgaggcacacagagtaa      130900
tattcacataaaactccttaaacctatgtatgcacgtatagatacttgtatatatacatagatatgaatgc      130970
acaatagtatccatacacatatgtgtacatatgtgtgcatgtgggtgaatgcttatgtgtagatttgtat      131040
acaaatgtgtgtatgttgctgtattaaaaaaagtcaaaaaataaacaaattattaacaatgtttgcctct      131110
tagaaggtgactatggtacggtgcccttagagagaggctttgattggcagagaaaatgaaaaaccataac      131180
tgcacctatatttaagatttaaaaaattctttgtagtgagtttgagtaacttttaaaagtacattgaca      131250
tttcatttatgcagatcttctaggtgtgtataaaaagccatgagaaaaagatgatttcatgtgatagaga      131320
aaactagcacaggttagaatttggactcagctgatgagacagtatctgcccaaaccaatttaatcaaagc      131390
tttgttgcatgagccgggtgtggtgagtcacacctgtgactgcagcgctttgggagaccgaggagtgagg      131460
atcacttgaggccaggagttcaagaccaggctgggcaacataatgagatcccttctctacaaaaagttta      131530
aaaaatctagccaggcgtggtgactcaggcctgtggtctcagctactcagaagactgaggtgggagggtt      131600
gcatgagcccatgagtttgaggctgcagtgagctatgatcacaccactacactccagcctgggggacaga      131670
acaagaccccgtccttaaaaaaatttgttttaaacacttcattgtgtggaagaaagctgtatatttaaac      131740
aaatataaccaaacccgtaatactggggagaaagattgatggattgttgaaaggattataccccgttaggc      131810
caattttgagatgtaggcaaggaatctcagaagttccaaaaagttctgtggttcagtgttacagggga      131880
aatctactcaagggaataatatatggcttgcaatcattttgctttttgttacatttcctattattcatt      131950
gcttcattgggcttgagagaagccccacagaggaataagaaataccctacatcattcacatcttcttggc      132020
ttttgaaaattaaattttatatacttaaaagcagccatgacacatgaaaacattttctttcttcctcaaa      132090
ccatctttacctagcctcacccaaaccaaactttaatttttacattaattttctttttccaaagctatgc      132160
agctgacactcatctgctcacttggcataattcattggtatccagtagtttaagaaattctgtctggg      132230
cttcatgcaatcataacctacatccaaatagcaacacttataataacagtaataagtatttttttagtg      132300
ttcacatggatttctcccttaattttcatgacatctcaacaaaatagacaaaatacatgggcttctcct      132370
cagccctgagctttgcctatcgttaaccccttgaagaaaaatggcgctgagctatcagtcagtcattccc      132440
tggcagaaagggaacagaatcagtatagatggctttctgaagacattgacttgatttctgtcaccaacaa      132510
tggcatattcaggctgtgctccatgccaggtgccgtgtgggcatggagtccaccacaccaggggaattct      132580
cagaagcagtattgaaaacacataggaaagcattacttaagcctgtataaacataagctctgtccagaca      132650
tggaatacagtggggagttcttcctaggataatcccaaaaactaatacatcagaaagcttacctataacat      132720
gagaattcaaggcaaaggcattttttggtatgtaagtaaaatattaggttgaatccatctcttaatgcgga      132790
tgttgaagaattaatgttatatccatgaagccagtgttgactggaaggactcaaaaaaatctgaagaata      132860
taaattccttgaccttctttattgaagacttcagctccattacacgaccacctcacagtcctcattcggt      132930
tgccttttgcctgtttctgacttactgaaggacaatggtgtggagctacgatttatcacccagaaaatga      133000
ttactaaagtccgtattctactctgaatactgaaaactctgaaactttaacctaacctaaacctcctct      133070
tcttctggctatcacttcttccttcccactttgatcactcttccatgaatcctggcaaacctcctagtac      133140
tgagtatccttccagccaccaaacgtctgacatagatcgctggatctgactttaattctctcactaagac      133210
cctcaatttcctcctctgcttgtggtgggctcaccctgttgtttctcagctaagggtgcatccagatatc      133280
aatttcttgtgtcccatagcactgctagcattaagtgaattactgcatggtttggtctcattagtgtgtg      133350
gtttccagaaacacttgagatcttactgttggcttgtaatctgtcttgctcattttgtgctgctataac      133420
agaatacctgaaactgggttgtaaaacatataaatttatttctcctagttccagaggctggcaagtccaa      133490
gatcaaggcaccatgatctggcaagaccttcttgaacatcatcaaatggcagaagggcaaagagcttaag      133560
agagtgaacccactcctgcaagccctttttataattacactcatctgttcatgagggcagagcctttgtt      133630
acctaaacacctgccattgtccctctcctgcaacactgtcttactagggtttaataatattcatgtcaa      133700
cgcatgaattcggggaacacattcacaccataggacaacccattcaactcctcctcatcggggtcaaa      133770
gggcatcaatttaaggttttttgacctttttgttttcattatatctcattttatactaacagattcat      133840
ttgttcgtataactctcctgtcttccagaatctgggacagttttccacctcccaagtgggatctaggagt      133910
taaccccaccatcaacccaagtactcctcctgtgtccaatggccagtcagcctcaatcctgtcttctct      133980
tgagttatgacatatttttctccttccattaatagtgaccattactgtaataggaatttatagttctttg      134050
tcctccagttctccaaaactggttctctatccttcaatttttatgctaacaaatctcattaaagtatgac      134120
cagtgatttctacattgccaaaaccccagtggttcttttttgatgatcctatatcaatttgatgggca      134190
ctttatcacttgcagaattcttattcctttttcatttttatcactatgttctggttttattctacaattgtg      134260
agaagctcttctgtatttcttctcttattattcttaaatgttgacttttcctaggatttgttcttgact      134330
tcattctgtatattgtatgtctaggtaattcattgcatcttcttatcttcaactatctgcctctatgtgg      134400
atgattctcaagtctttatttccagctcaggccactagcttcagttacagtgtttgtaattttagcccct      134470
attagaaatctctagttgagtgtcacatagacactccaaacacaacacattcaaatattaagagatgctc      134540
ttcctctaaaacctattcctcctctcgtcaccctcctgttagttaaaggtgcccatataccagtgtgtccaa      134610
gatcaaaactctgttggatttttacttctctttttctcagcacttatgtaaatggatgtctacttctcatttt      134680
ctgccctgcagaacattcctagctatgtgctgtcttcctgtggcccactgtgacagcttccttatctcag      134750
tttagattgttatgcagtccattactcttctgcctcctaccttcaagctactattggagtcatcttcctg      134820
attctcacatctgatggctttcagtggctaagtgatgcattccaatctttcttagttcattttatgctgc      134890
tacaacaaaacacctgaaactgggttataaaaaatagaaatgtatttctcatagttctagaggctgggaa      134960
```

FIG. 8A-30

```
gtccaggatcaaggcaccatcatctggcaagaccattttgcacatcatcaaatggcacaggggcaaagag      135030
ctcaagagagtgaacccactcctgcaagccgttaaaaacgcatcatgggccgggcgcggtggctcacgcc      135100
tgtaatcccagcactttgggaggctgaggcaggcggatcatgaggtcaggagatcaagaccatcctggct      135170
aacacggtgaaaccccgtctctactaaaaatacaaaaaattagccgggcgaggtggcgggcacctgtagt      135240
cccagctactcgggaggctgaggcaggagaatggcgtgaacccagggggcggagcctgcagtgagccga      135310
gattgcgccaccgcactccagcctgggcgacagcgagactccgtctcaaaaaaaaaaaaaaaaaaaaaga      135380
aaaaaacgcatcatggcaaaatctcttttttttaccacctgggaaaacctaagaccccttgggacagcacag      135450
aagactccttaatctgcccatgtgtcccttccagtgttagcttcttttacttttcttgtacacctcgt      135520
gcccttgccccttggaacaaacagctcacagttccctcagcacacccacccttctacctgcccgggagct      135590
gccttccgataagttgtatctcgatgacttcctccccactctccatctgggaagatcccagtcattcatt      135660
tgttaaggcccagtgaaaagatttatttattttccttcatataatatttttatgtatacatatatg      135730
catatgtatgctatctatctattagatacatcttgttttggcttatttttattttttatgttttgagaca      135800
gagtctcagtctgtcacccaggctggattgcagtggcagtgatcacagctcactgcaacctcgacctcctg      135870
ggctcaagcaatcctcccacctcagcctcccgagtatctgggactacaggtgcataccaccatgcccagc      135940
taattttttgtattttttttttgtggagacacagtcccactatattgcccaggctgtttttgaattcctg      136010
ggctcaagcaatccacctgcgtcagccttctatagtgctgggattgcatgcctgtgcccctgtgtctgac      136080
gttatccttgttattttaatgcctacctcatttgtctttttcaaataataatcaacaaatgatttctgga      136150
ttgataaatgcatgaatgaaatgatagtttgccaaaatacagaatattaaaaccataggtaaccttgag      136220
acaatttaggtaaaaaataggggattatttatattagaagattattcaatgtattattaaaatgtttgt      136290
ttattgcatgtgttttaagtgttgagaattaaacagagaacgagacatgaatggtctaagtgtttatgca      136360
tcataataaagttgaagaaatgtagggttcccatggtgtttcttttcaaactttgataataacacttctt      136430
tattgatcgcaactgtacattggcagcaccgcctccagactggaaaataagatcgatttctcctttgtgt      136500
ttcttttataaccttgcaattttattcctcttgggcttactgttatgagtttggtttctagtttctagag      136570
catgagttctaagaagtggaaatcaagatggaaggaagttactatagtgagagggtgtcatgcctgcag      136640
gctaggtatcttagagtctgactgcaactcccttgacacaggcagttcttttttcttgcctgcagcccttt      136710
ccaaacaaatatcaccagcctcatattcccctccccttttatagatggagcccccttgtcaagcaggccag      136780
tttactgggaaaaggcccttctcagacatgctttctcatcctgatgctttgcctttaccaggagtgaggc      136850
cagaaccttcagcatgcatttatatcaaaaagagagatgtgctgttttcatttaaattccgcatttcca      136920
ctgggcatagtggctcatgcctgtaatcccaggcaacataatgagacccgtctctacaatttttttttgagaaagggtctc      136990
aggagatcatgaccagcccaggtcagttcttctgagctgttacttggattcttcaactgagggtgattttgcatc      137060
agtctgtcacccaggctggattgcagtggcatgtccacagctccctgcagcctcaacctcctaggctcaa      137130
gcaatcctcccacctcagcctctggagtagcttggaccacaggtgtgcaccaccatgcctggataattttt      137200
tgttttttggtagagacagggttttgccatgttggtcaggttggtcttgaactcctgacctcaggtgatc      137270
tgcctgccttggcctcccaaagtgctgggattacaggtgcgaatcactgcgctcagcctctataattttt      137340
tttttttaattagtgtgctagtagtctcagctacttagaaggctgaagcagaaggattgcctgagcccag      137410
gagtttgaggataacaatgagccatgatcacattccaccctgggtgacatagtgagacgctgtctctatta      137480
aaaaaataaataaacaaattataaattttcacatagtcgtaaacctctgaagatgtggatacttcatttg      137550
tcacatttaggtctttaatacactaataccttctcttgggaaacagtgtttctcagtctctcccgtattg      137620
ataatgtttccactttgcccttgaagattttgtgggttatgggaaacagtttatgggtgtctttcagc      137690
agaaccacaacccttttaggaagaagctaattatggtgtgaaagggacaggtgctcttattaggtagtg      137760
atagtaagagttaaaacccagttctcttgagctgttacttcttcaactgagggtgattttgcatc      137830
tttggcactagatgtcattcaactgacagtcatggactcccagggggaccccccaaactctatgtcacctttt      137900
atgagtaggcgagaatggattttttcttggagaggagtgtctcctcaaagaagtctgtgacctagaagaaa      137970
agatgaaaaatctctgctttggattcggaatgtcaggactgttcacttggaacttaaggagagtttcttc      138040
ctagtatatacgagactgaaccttatggggttgccatttttcttagacccaaagctttcaaatacagtcat      138110
tttcatatgacttctacttagacaataagatcatcatgtattctcttttcctcttcagcatctggcat      138180
tttttctcctcttgggcttgttgttctggttttttttttttttctggtttctagaccataagcattcatgc      138250
attcacattatgttgcctcctaagttgtaagctctccaaagagagggaatatagctgctttatgtcttca      138320
cccaactttgagtagagatgatggcaggaaacagagagcattttcacagagaagatggagtccatttgag      138390
tcaggggatcttgtttgaaatcttacctgtgtgatctggggtgaattaatacagctgtctggaaaatta      138460
gaacagagacctcagaggattgcagtaaggagtcctagaagttaggatctcctcagtaaatataaatact      138530
tattctcttgggtaatgaagctgacccacaggatgactattttcctttggtattataagcacataa      138600
acaatagttcacatttattgagtgcttactatgtgtaagataacaattatgtgctttgggatatgggttca      138670
cacatgaaacaagtgtttatttagtgcctactctgtgcccaacactggagatgcagctgtcatgagcact      138740
aacaccatcccaatatcatggtgctcatgtacccatgtgggaaaagtaaagacaggctcaagcatataa      138810
aatagggaaggtggtcttaggataattcaagctggattgggatcagtagtgattgaagggctagattaaa      138880
tgaggagtttaggacatgcatcctctgcaagatggcattttgacgcaagaaacataggcaagacttatctact      138950
ttaattttcacagtaggggtcatgagattacactgtttattaactctgttacagagatgtggaaactgaga      139020
ttaggatgattgaataacagccagattagtaatagggctggtagtctttaatgcaagtctcatgggctat      139090
gctgcacacagtcttaacaacttgccaccttcgtggtataagagaggaaccaacccaattcccgttgcc      139160
tgcctttcctgctatattagtctattcttacactgctataaaaatacctgagactgggtaatttataaa      139230
ggaagagggtttaattgactcacagttccgcatagctgggaaggcctcaggaaatttacaatcatggcaaa      139300
aggtgaaagggaagggaaagcaccttcttcacagggcagcaaggggaaagtgctgagcaaggaggaa      139370
gaaccccatataaaaccatcagatctcatgagaactcactcgctatcatgaacatcgtgggggaactg      139440
tcctcatgatctaatcaccccccatgaggtccctccccccaacacgtgggggattacaatttggattacaat      139510
tcaagatgagatttgggtggagacacagagccagaccatatcacttgccatctaattaccttgatcaact      139580
accctgcaaccattccttagtgagtaatagggccacactcaggaatggttttaatagaatttaaaagtta      139650
tcagtattgtagtttaattgtaatttttaaaaatggtgaacctcactcagtggctaggatcagcagcatga      139720
tatgctgcatctgggggtcaataattgccgcaagcacattattagttgctgttaatagtcatggaaac      139790
cacccctgtaccttcttcccccagtgcaaccaacctgcagtgattgacctactcggtagcgagttgctag      139860
acatcaggagaagtcagaagtaagtggaagaaggccaggtgtctagaagaccccccccactacccatagca      139930
gtagcaaacacatatgcataggaataggttaaatgagtcttcactccattgatccattcattcatctttcat      140000
ccatgaattaactattcatgacccattgttgttgactctgaagatacgatagcaaacaggatgcacaaat      140070
```

```
tgtcctgctgttacttagttatggggacagaagataaagcagtgatcaaatgcatgaaggacagaattg      140140
ctgatggtgatcatagctttgagggaaatgaagcaacgataacatctaatgtgggttatgaggatctttg      140210
agatggagtggccagggcatgtctttatgagggtgaggaatttaagcatcccagacacaagttctgactc      140280
aaacatcagccttttaattatgtgaaagggtctcgcaaaatttaataaacttagtggtaggagttcaggt      140350
aacactacaagaaaccaagctttctttgtgaatggtgaggttagaagggggtttgttgctgaaaatcccat      140420
ttgcaggttctaaggctggggatgaagtagaaggaacaatctcttgtcatttgccaatcaaagaacaatc      140490
cctgtatctggcaaaagagacataccttctatgaatcctggttttggtcataagccaaacttctatatt      140560
agtttcccttttggttgagttagtgaacaattggatgattagctaaatgttgctgaaataggaggaag       140630
gcagattaaaaatacagaaagtaactcttatttaatgatttgaaaaaatgaggttaatccgacaaaattt      140700
taaggaaaagtgagataattttggtgtataaaactatgaaattttaggctgggcatggtggctgacacct      140770
gtagtcatagcactttgggaagctgaggcaggaggattgcttgacccaggagttcgagaccagcctggg      140840
caacatagtgaaaccccgtctctacaaaaattacagaaattagctaggcatcctggtgtgtgtgcctatggt      140910
cccagctatgagggaggctgaggcaaggagaattgcttgaacctgagagttcaaggcctccggtgcactct      140980
gtcctggcttgtagagtgagaccctgtcacacacacacacaccacacacacacacagacacacacaca       141050
cacacacacacacaaaataaaattttggaatgtaataacattgatgctgaagtgaattgtggaaaaatat      141120
catataaaatatattttaatcacatagtataaatttctctctgtgcattagttaccaaaattgaacata      141190
aacatttcaaatacacacttgtgcaaatgtcaggatagcaggtggtatatcactttttatatttaaaa       141260
tgcatgtaggaatgaaaggaaaaaggtaaaaatatgttaagtgtagaattctaatgaaagaacatattgg      141330
aactatgaaaacattatggaggactttgttcatttatggtctgagcacagatgatgctaaacatggtcct      141400
tcaactttagctggcagccatttgaaatgaacacactaaacaccatgagaagcaactgcatgaaaagcaa      141470
agagagttatccaagtgaacttcatatctcatcatttgcctgtgtttatgtaatagtaaagacccaagga      141540
attggtctaattaattggtattttatttagtgatgaaataatgagtgcggttgagcatgccagatgtat      141610
tcatctgatacattcttccagtcacatggtaggctgcattaggtgataagtgcttcaccctgcattcattt      141680
ataagttagtgaagggaagtccacaactctggtctcagacatttatcccattgttgatcagctaagctg      141750
ttgctcttacttagctgctaaggaatgaagctaattggaccattccagcatgtaaaatatgtaaaatatg     141820
tcctttcatggaactctgaaacaaacaatgagaacaaccagaaaaattgccagagtcatacaaaagctgt     141890
ctatttctaaatgatcattcctcaagctcttgtcatctactgggagccctagatggatgtatagttgtt     141960
gctgttgtggctgatttgataggactaacataggaccagtgtatggagctgtttattaagatgcttttg     142030
ttgctgagtatttacattttgggtgttctcggataacatacgttaattcctactgcagtatttaataaag     142100
tgtaactagtgcctgtctcacctgtctgaagacattcaaatatggagcgtttgtttctttctctagtgca    142170
gatactaaatatcatattgtaattagagctatacagagatttagcatataggactggcaagtcttggagg    142240
ccaattttatgatgtgggaagaggggggcgtgatttagagtggacaaataaagtgtgggaaaattttgt     142310
gtttctggcttgagtgaccagctcttacctctcctcccatattcctttcctgcctcagtgcaaattca     142380
cactgtcttcattttgtatgatcaccctctgtcttagtccattagttttgcaattaaggaatctctgag    142450
actgggtgacatatagaggaaagagatttatttggctatgattctgcaggctgtacatgaatcacggcat    142520
caggatctgcttctggtgagggtgtcaggaagcttccactcatggtgaaggtgaagaagagctggtgta    142590
tgcaaagatcacgtggcaagagaagaagcaagagaatggggggaaggaggtgctaggctcttttaaacag    142660
tcagctcttgggggaatgaacagagcaagaattcagtcattactgcaaggctggcaccaagctgctcatg    142730
agggatccacctccatgactcaaacacctcccactaggcttcatctccaacattgggaatcaaatgtcag    142800
cttgatacttggagaggacaaacatccaaactatagcactctgtctccttaggtgcacctttcttcttca    142870
gtgactaatctagagttctctttggaaaatgcaaatgtagttatgtttctttttttgcttttatgccttac   142940
tggttccctgttctttatagcatcaggttgcatcttcatcaactggggaaccagttgatgaagagaagat    143010
cagcatcctgaagtatcttgtaacttcttgaagtatcttgaagtatcttcaagattcagaatgcatgtta    143080
cctctctgcaaagtgctctttgcaccttgtccagtgtagctgtgttaactccagtgcaccttcctgatg     143150
atcttcctaaggctcttaccttcttgtcattagtcgttctgtgaccatcttgcctataggaatgtgggc     143220
tactgtgggcaagtacaatgcctggcatgcagcaggcttccagaaatgcttgtttggcttctagagttc     143290
tcttctgctgttaccacatccatccctttatcatccttttttccctagtcatctttcctctgtacctttgc    143360
cgttggttctttctccatgaatcaatataaataataacaagctttgtgcatagcagaccttcactcttgtc    143430
tcatgatttcatttcttcctcggcatactgaaaggcaagtacctttctctctctgactctcaattact     143500
catctgtataattttgatggttctttcaattgtctgctattgctgatgatgcacgaactcagatatgca     143570
aagtatcagactttcactcttgtctcatgatttcattgcttcttctgcatacttaaaggccattaccttt    143640
cctctctatgactctcaagttcctcatctgtataattttgatagttgtttctactgcctgccattgctac    143710
gacaatggcacaaactcagatatgcaaagtacctctgggttaaatgtgaacaaaaccttcaacctgctgc    143780
aagataatctgacctctgcttgactgtctagctctgttttcctggcagttggatgagaacatggcaaca    143850
atattcttggccacattgcttacaatacaaacgatcccctatttgtaaatagcatcatgaccaggagaaa    143920
ccataaagacctgaaagaacctagtggtaataccacccacctcaggcttcccggagggcaagttttgga    143990
gtcactttgcagctgctctgttcactctaggaaccatggaaactctgctcatggagtatttacagggaat     144060
attggctgctgtgaaggctgggacttcaatgccaaggaatacccaattcccgtggatatggaccttgtag    144130
ggatctttgcatctcagctgtccttgtggagcagatggttcccatatgcctgctgcaaccttcctgatg    144200
agctgagcttcttgtctgtattgttttgagtcggttggccaccatggtaactttgggggggtcttgtgatt    144270
ctgcatgtttaatggaacctgagaagaccttactgggcattaaagaacaaagacaaatgtccctgtgac    144340
agaatactggctcaacaattggttttctctctgatgcctcttccctgcttggaaagcccttttcttat       144410
ccttcataatcacttcttacatctggcacagccttcagctttgcattattccttcattatcttttctcat     144480
cccacattaaaaaaattctttaaattgtggccaaatgaacatgacataaaatgtaccattttcacatgt      144550
gcagttcaagagtattaagtacattcacattgttgtgcaaacatgctttttttcactctgtgcctcatt     144620
ttgctctttcctggtttccaatgcagtatcttatatatgatctaataaatgtgtcctgggcatctcagtc    144690
ttgtatatttggtcctctgttatatcaggtacaccttaaggatagacattgtgccctactaatcttcct    144760
ccttcatcacatgaaatattgtgcttgcatagtacattttcttcactcccctcctgttatttttatgt      144830
atatcatgacacttatttgccaaggatggctttggccctctatgcaaaatgtcaccaatgggaacaatgc    144900
taaagtctgcataaatcttaagtttaattctaatttaaatatttgaatatagtgctagtgttgtcattc     144970
tataggattcattaattcatcccatcaacaaacacttattgagttccaaatttgttcaaaacatggccgt    145040
atgtgctgctgtagaaaaaatgtaaaaagtcagtttctagtgtaagggaaataaaatatggatatcatta    145110
agtcctggagaaggcaggggtgactgatttcaggcttgtaccatagggattcccaggaggaataagtag     145180
```

FIG. 8A-32

```
gttgcagcatttaagaagggatcatgaaagacatgccactttaactagttccaaatggaatttttggaagc        145250
agagccattggatgttatagctgaagtaataattttaagcaaggtgtcagaacaggattgaggcataattt        145320
cagaagaacatgaagtccttgtttactaatgcagaataatgtttttatgataggctggaaagtgaatctgtg       145390
actagatttgggagtgattcagtgtacaatgaatatggcagtaaagagcttggacttaattcgggctgct        145460
ggtctggtcagcccttgtgtttggagagatgagtaacatttgcaaaggtggagagaaggaattggagatt        145530
ctagttaggtgctttgggcatatgttcagtgagggatgaggcattaatgttcatcaaggcagcattcaca        145600
agggctatggcggcactgaatgggagagcagacagacacaggtgtcatcccagaggtggactccgtatgg        145670
cacagcggcaagggagtgtgaagggttatgacgagtaggtaggtgctgagtaggcaacatatttttttaaaat        145740
agtggcaaaatgtatgtaagatctataatttttgcatgtacagtttagggatattaacaatattcacact       145810
gttgtgcaaacatgcttttttcactctgtcctcatttttactcttttcctcatttacagtgcagtatcttat       145880
atatgatctaataactgtcccctaagcatctcagtcttgtatattttggcccactgttctatcacgtaca        145950
ctttgaggggcattttcagataattccaggtaaaacgtaaacctcacgatggcagctaagaaaacaggg        146020
gcgttctctgcattggttagttgcagggctattagtcaaaattccaaatctcatatgcagaaggccagga        146090
tctgcagtcttaagtagttcagtttgtttcacggaggtaaataaaagaaaaaaggcatgctgaagataca       146160
tatccctggcctctagataatcagacagtaagatctctcccacacaccagagaaatctatttccagcttt        146230
ctgttgcagtccatgaaaatgacagaaaatacatgccctgcttggaccacagcctagctcatgggaaaaa       146300
aaaggaaaataaaaaagaacccgagcttgctgtggatggttcctatggagtgtttttggcactgtcagag       146370
tgcacactctgacaggctgggcatggtggctgacacctgtagtcgtagcactccatggcactgaatttac        146440
ggtggaaggatcacattggcaagtcaaatccttgggctacaggaaagactcccatgtgctgcttttatgc       146510
tccccagcagccaggctgtcgttcacaaagcactcttccaagcatcttcatttaatgttgttgggcacaag       146580
gccctggtgaccccgttaaaattaaatcttgctcatacaaagtgagggcaggttttcagttgacatttg        146650
gaggtttctccagccatgttagaaacaaaatgcatttaagtgatgagcccttgatacataagaaggtgta       146720
gagccagctggatttctccgggaccatgaggggatccatctgattaggcgcttctgaagccgaaggaaact        146790
acagagagatgtaacttggctgactctcagttcattattttctcttggtaagagcacttctcatattgga        146860
caatcttttcttcactgatttagatattatttttagatgcacctttctctttttgttatggaagctttattt        146930
taaaataagttaacctaaaatggcgtattactctccccccgccccaccgctaatgattttagaacatga        147000
aaataatccacaagaccatgggtgctgtcttcagctacaattactacttttcttaattgtcatggaaacat        147070
gatttattattggatggttttttactgtcttatgcaaagatttcatatgagccgcaatacacactgtttc       147140
atatgggtaagtctcaatattatctgacaaagagagcttctctgcccaagtttatgaaaagtacattttt      147210
ttttaagtcactgtcttgcccaggctgcagtgcagtggtaccatcatagctcactgcagcctcaacctcc       147280
tgggctcaagcagtccgctcacctcagcttccttagtagctcaggtgctttggttttggcttttttatcccca       147350
cttgaatatcatcttgaattgtaatccccagatgttgagggaggaatcttggcgggagatgattggatcat       147420
gggggtggtctcccttattctgttctaatgatagtgagtgagttctcacgagatctgatggttttaaaag      147490
tgtctggcaggttcctccttcgcacattcttctctctcttcccaccatgtgaaaaggtccttgcttcca      147560
tcccgccaccttctgccatgcttgtaagtttcctgaggccccccatgccatgcggaggtcaattaaacct       147630
cttttccttcttaaattacccagtctcgggtatttatttatagaagtgtgaaaacaaactaggacactagg       147700
actacaggcacatgccatcacggccagctagtttatgtttatttttttaattttttgtagagatggggtctc       147770
actatgttgctcaggctagtctcaaacttttggccttgagcagtcttttccacctagacctcccaaagtgt       147840
tgggattacaggcatgatccactgcacctggctgaaaagtttctattgaatggaaagaacaatgctgtga       147910
aaatatatttttattaatgttcaggaaattgtggaacttgaaaaactctagcttttttagcagttttaatgg      147980
ctactatgtgcttctaaaaatttgtacctgctttttttgaagtgttatatgcattttttgtttgttgatggtg      148050
gtgatgttttttgccgttgatctcacctgctaacgtggaaacatttcaagaagtggaaaaatgtcttattt      148120
tagtacatacatggtgtcagctgcattaaaaaaaaaaagcctaaagaatgtagcttgaattgagggttg       148190
ctatgacttttttgttgtagtagatttatgaattgtgtatcatcattttccttcagtggaaaattcagtaa       148260
ctagtatgttactggttcctggattccaagggaggagaacatgaaacattgcaatggaattaaactccaa       148330
tgagcttgacccagctacgatgttgaagtgagggaatacataaagacttgggtgtatgtgtgtgatctgt      148400
tggtattaaagtgccaggattacaacattctatgaaaatggctaatcatattcaatatttatttgagacg       148470
cttaagatgcatggtttgggtggaactagggttagggggctgctgtttttgaacagccaaactagaattct       148540
gctcaattatctcacacaggcacacttctgaggcattttttacatgatgcctcaagaaagctttgctcca       148610
ttttgtatttcagcatgaatacaaatttttgaaatttccacagtaaagtgctttagacttaccaaaaggta      148680
ggccttgttataataacaccagtaggaccgatgtagtcatttctaaaatgattcaagcactttatgtttc       148750
tggatgagctattagatcttaccttatgtgtctggataagctattagatcattacatatttttaaagtgaa       148820
ttttttgaaattgttggttcattgtttaaattttcaattttgtttctgttgcattaatctctgagatttga       148890
aaatgaaaaagaaaaaagatggatacacattaagtcttttataccttctggttcttgtaacagcaattgattg      148960
tgcacttgcttttggctgtagttagtcctttttcttaaattagtttctggtatggatgtctactttttattt      149030
aattttttttttttttttgagacggagtcttgctctgtcacccctggctagagtgcagtggcgcgatctcgg       149100
ctcactgcaagctccaccccccgaggttcaagcaattctcctgcctcagccagctgagtagctgggactac       149170
aggcacctgccaccacgccaggctaactttttgtattttttagtaaagacggggttttcactgtgttagccag      149240
gatggtctcaatctcctgacctcttgatccacccgcctcagtctcccaaagtgctgggattacaggcgtg       149310
agccaccgtaccccggccccacttttatttttattcaattttacattttatatgccttgttacttc       149380
atttcttagcaccagaactacaagtttaattcttcagacatcttctctagcacctcataaggtattcttt       149450
gttacttggtgatagagaactatgtaatttgattttcttcttttgcaatggagtgttcaaatacgtcgtt       149520
gcttttaggtgagggatgtgattaattagaaaaatgagtggatcttagctcaatgaaatttaatcagcag       149590
aatggaattttccattcagagcaaatgagttcctaggactggacacacctagatctgctgacccaaaacc       149660
ctttatagattttcatttctgaatgagctattagatcattgtatattttcaggtgaatttttacaattgtt       149730
gattcatcgtttaattttagtttttattttctgttgcattaatctctgtttgacatatagaagaaac       149800
tctcatgccagccccaaacgctttccctatctcctcctcccatgccttcctggagtggagggaacgtcag      149870
gcataagcagagcccaggagacactcatagacattctgagaaagcttttctctgtagaagggaccaacac      149940
atcttgcaccctctccctctcttgcccctgcctgcatgtgggtgcaggtgcttttgtcaggaccccact      150010
gcttatctcaggtcaggagctggcaaacctatgaacaagatgaaacccaactgctgaccagggtggtgt       150080
tctgacaggagaagacttgagcccttcatagacactgttgaatcactaagctgtaaacaattttcttg      150150
gtcttcttgtctggtaaaatcaattctcttcatccttttaaagaccctcagtttgggctttagaatcca      150220
tactggcaaatgcttcctcactaatattgtgagatttaattagagatagcattttatgtgctcacctaaa       150290
```

FIG. 8A-33

```
actatacggtagacacaaaggagtctgggtctcagatcccaacacgtggattatagagaaggcagaatgc    150360
tataatgccttgagggtgagccatccattatttgggatttgaaaaaggacaatttctgttttatgtttc    150430
tgtcctcctaaatggagttgagagacagcttcttttctccttagcatttgggcaagaacagaatccagta    150500
aaaccactgaggaaggtcatcattgcagcgttatttaacatgagtaattctagcatgagctggcatgcc    150570
atttacatccatctgttttaagtgtttgcaagcagaatggtaataagaaactggggtaagtgttaaaaat    150640
aattatatggaatatagattgccccagatgcactatctaatgctgatgggaaaggagagagcaggggta    150710
cctggaacctggacttctccttggaaacatgccatgaccgggtatgttactggattgcataggtgcagaa    150780
catggaacattgcagtggaattgaactccaatgagctcagcccaactacgatattggagtggagaatgca    150850
tgaagacaaaacctttattataagtctgtgtgtgtgtgtgtgatctgttgggattaaagtgccaggat    150920
tacagcattctatgaaaatggtagtggagaaaaggaaaggtagaggaaaagagaaaaaccaaagcaagag    150990
gaaaccactggaagaaaagaagatgggaaggagaaagggcatctctgaagaatgtaaggagtacaagat    151060
cccttacaggcagtgaacacataagaaggcatcattcaccagaaagtcataccagtttatgtattaaaac    151130
tgggaatggcaatgataggcattagttagagattatgctttaaattgtatgcatttgcatattttttat    151200
gttttattaattttgttttgggggggggactgtatctcactctgtttgcccaggctgatgtgcagtggta    151270
caatcctagtttactgcaaccttgaactcctgggcttaagtgaccctctccacctcagcctcccaagtagc    151340
tgggactacaggcatgtgctactatgtccaactaattttgttatttttttgtagagacagggtctcaatg    151410
tattgcccaggctggtctggaactcctgggctcaagtgatcctcctgccttggcctcccaaagtgctggg    151480
attacaggcgtgagccactgtgaccagccccttttgcatatttattgttttgtttgtttgtttgtttttt    151550
gagacagagtctcactctgtcacccaggctggagtgcaagtgcgatcttggctcactgcaaccctctgc    151620
ctgctgcgttcacgcgattctcctgcctcagcctcccaagtagctgggattacaggtgcccaccaccaaa    151690
cccggctaatttttttgtatttttagtagagacaggatttcactatgttgggcagactggtctcgaactcc    151760
tgacctcatgatccgcctgcctcatcctcccaaagggctgggattacaggtgtgagccactgtgaccagc    151830
ccatttgcacatttagtgtttatttttcttaatcagtatcgaaactgtgaaagggaatgttaaaacggtgg    151900
agccaggtgaaaaagaaaatccaagagtcagaagagagcatccaaagaagaaggcagaggcaataacaag    151970
tagactctgagactgaaattaaactgtatggctagaagatgggctagcataggacaagatgaggtaacat    152040
gctaacatggaagattgagaagaattgcaaatgagaaatcacggataaaacactgaccgcctaataggat    152110
aaaagcagaggatgttcataagcagctgtcatcaccaaggaagaggaaaacatgggaaaggttttgccct    152180
ctgagcagaacaatcctgcatgtcaaggggagcctcatataccatgtaacctcatgttaaaccataaat    152250
acttaccaatacctcttacagtgtgacaggacacaaactattaaacctgatgcagataatgccttttaaa    152320
atgagtattatatttgattatttctaaataatgcttataactatctttaaaccatccactttattccct    152390
agatgaaatataattgaattaaatgttaaacatatttgacatgcattctcggggcttttgatttaacat    152460
tttaaaatatgcaatttagctatttaaaaaaacagtcttaaaaaataacatagtatatcaagataggcag    152530
aaggaaaatttaggcaccaaataatagagtacatgtttcctattatgtgttttggtgggagatgatctt    152600
tggaaagtgctgattctgtttttgttccataaaacaaaatttccagagattatatattggattctgctt    152670
gaaagagttcagtagacattgcacttctatcacactgatagcccaggaggaattttaactatgtaattat    152740
ttaaccgcaaaattttccacctttctccccttaaacatttggcggtaaattatgataaaagcagtcatga    152810
tatgcagttcggtttcatagtttcctttctcttccttttgctatatttcctaaagttctattatggaga    152880
gataccagttttaaatgtcaagcaatgttaacatctttgcatctttatcttttcctatccactcttctct    152950
cttttcttttcttttttttttaagggccagagagtgacacttagccaatacttaaccagtactctcttt    153020
ctgtttgtttgtgggaattttatatctattttttcttttcaattttatttaggttcagagggtacat    153090
gtgcaggtttgttacatgggtgtcgctggggtttggtgtacagatgattttgtcacgcagg    153160
tagtgagcatagtacctgataggtagttttttgacccctcagccttttcccaccaccacttgaagtaga    153230
cccttgtgtttattgttccccttttggcccgtgcgtcctcaatgtttagatcccacttgtaagtgaga    153300
atatgcagtacttgcttttctgtttctgcattagttctcttaagataatggcctccagctgcactcttgt    153370
tgcttcaaagaacatgattttgttctttttatggctatatagtattccatgatgtatattacaccacatt    153440
ttctttatccagttcaccgttgatggccatctaggtggttccatgtctttgctgttgtgaatagtgctg    153510
tgctgaacatgcaggtgcatgtgtctgtttggtgaatgatttatattccttgtgatagatatccagtaa    153580
tgagaatgctgggtcgaatggtagcgacttgtctcttaatagttttttactttgcctcgatctcctgattc    153650
tctcccttttttcctggccattcccgctgcacttgcctcatttgctattgatgacatgcttgtcccctg    153720
cttccatagatgtgtccacaaatgcatgtgcacacgtgcttcagctaaagattcctcagctaaagattct    153790
cctctccatcagggttttctctcttttagctcacctgccctctctacatggttttaaagtgagatgattg    153860
taaatgtgttttcacaatggaaattctcccagccggtcggggaggaaaacatcttgaaatatttc    153930
tgagaactataggaccggcagagtttgacatgttttgaggcgataaagtcatgtgtccatctgtgaaa    154000
gacaggcattggctttatccacatccacacagccttccccgctgtgtggcttcattattgatttgctgtc    154070
atgtagagtcgataatgagaaacctaggtagccttgaacccaactttgcaagaaccttttaggactctg    154140
ggacttctaaccctctaggaaggtggagttaaggggatataggcacagaatggggcagaagggaaagaca    154210
ttaagagacgcctttagcagaccagagaatacatgccgttatcaaatttgttagatgtctgtgcaccag    154280
gaatgttgattcaattatggtatctaaaaataggacagaaataaggaggaaataaaaggaaatgaaatag    154350
cagtttacctctggcaaaaacaaagagcccaatcagaaaaactagacaaagccacctgtaggactggaag    154420
aaaccatgtgagttaggtatcactaaccttggaaggacaaggacttcctagtattttttgtattttgtgaa    154490
gcacttctctgcattttcttaatttgtccttaagtgattatctctcaaccaaccccaaaatttgactct    154560
tcaaatcatttattctctaagatttttaagcattcaactgtaatggcttatgtatcagcatagtcttata    154630
taattctaaaacaattcatagcatggtatcttgtaatatttgactttcactattaattcttttcagtta    154700
ttatttgagtgcctgtcacatgccaggtattgttcaagcttcaggggatgcatccatgtacaaaataaat    154770
aaaatttcctcccttgtgccactgatattctataggtggatgaaaacaaacttaagagttaaataaatt    154840
aggttttatttaaagacagggtcttgccctgtcattcaggctgggtgcagtgtttaatcatagctcaccg    154910
tactctccaactcccgggctcaagcagtactctcacatcagcctcccaagtacctaggactacaggtgtt    154980
gccaccatgcccagctatttttctgtattgttttttctttttgtagagattgggtcttgctatgttgcc    155050
caagctggtctggaactcctaggttcaagcaaccctccctcctggcccctaaattactaggatcacag    155120
acatgagccaccatacgtggccaaagttttgtattatttttataaggtgatgagtgctgtgaagaaaacta    155190
gaagaggataagtggaattagaattgctagggaagttgcagtatttttaagtagggtggtcaatgacaacc    155260
tcaatgaaagggggatgtgggagtagagaattgaaatagctaagggaaaaagccatgatgatatatgaga    155330
aggatgttccaggcagagggaacagccagtgccaaggctctggggtaggaacatcccctgttctgttagg    155400
```

FIG. 8A-34

```
gcagagcagtgtattagtctgttctcaagctgccaataaagatatgctcaagacttgggaatttataaag      155470
gaaagagttttagtggactcacagttccacatggttgggaggccttacaatcatagcagagggcaagga      155540
ggagcaaagtcatgtcttacatggatggcagcaggcaagagagagcgtgtgcagtcccttacaaaacca      155610
tcaggttttgtgatacttactcactatcaccagaacagcatgggaaagacacaccccatgattcagtta      155680
cctcccatcaggtccctcccacgattatgagagctacaatttaagatgagatttgggtggggacacagcc      155750
aaaccatatcaagcagtaagatccacatttctagagtatcagagtatgccatcagaatggcaggtatcag      155820
agtagggtggtgctatcgagaactttgtaattctgaaggaaccagggagaacaaatggaaggatttcaacag      155890
ataattcatgtgtcaaggtgtgttttaaaggagcactttgcttagctgaggcttgtctgtaggggcaaag      155960
gtggaatgtgggagaccagttagaaggctgatgtaagagtcaagataagaacctacagctgggaggtgag      156030
aagtggttggagttttttatacatttgaagtaagatttgctagttatatggatgtggagtgtgggagatc      156100
gaaggaagtccagagttttttggcctaaacactggaaaaggtagaggtggtcacaggtgacattggaggat      156170
gggctagtagagacattcttaagttatcatcaaagttttaaatgtttgagtttgaaatgtctatgagacat      156240
caaacggaagatatcccataaggagatggatgtcagagtctgaagttcaaggcagaaatctgtgctgaag      156310
agaaaaaatgtcagcctagatagtgtcgatggtatctaaagctatgaggcggaataaaattatcaagaga      156380
gttctgtggacagagaagagaaaggaccaaggctggagcttgccaacaatttgagattggtaataatacg      156450
aggaacctggaaaggaaatgaacataattgtccagggtgtaaaagaaagtctggtaatgtggaagtgaag      156520
gggggaaaaggcatttcaatgacagagaggtagtcaactgggtgtaattcaaataggtcataaaatgca      156590
catctgctgctatggtttccactacagatgcaaggaaaaagtcctcgtccttttgtctgtctgattgt      156660
ggcagttgagattgaatagaggtagacagagggggaaaaaagaatgaggaaaattgagaacatagcaatgc      156730
aaatgtcattttgacctttagtagaaaagtaataattttggtggagtgttgggggtaaaagccccaatt      156800
ggggcaggtttcagagagaataagagcaataaaattggaatcaatatcaataaatattttcaaggatatt      156870
ttcagaaaaggaacaatatagacacacttttttttttaagatgagaaaattgttttattgcttttaagat      156940
ggaaaatctaaccacatttctgtgtgctgtagggttgatctagaggcgtggtgttatcaatcagtacagt      157010
gtatagtgtgctacattaacaaatatccctaaaatggcagcgacatccacagccactaaagttgatttct      157080
cgctcatgttcaaagttcgctaagggttgactgtggctgttttctgtgtattcttaattctgggacccgg      157150
gctgatgagaagactcatttattcttattattactaattattttgttattttagcaaaggggggaaaat      157220
gggcagaaccacattatagctcttaaggttttcgcttggaagtagccccactaatttctgttcatgtttc      157290
atctgccaaagcaagtcaattagctataactgaagtcatggaagtgagtcagtgaaaattcttttcgagtta      157360
gggacagggaaagtcttgcaagtgtgtatttgtccccttgagaggtgtggacagttttttacacaataat      157430
acaacatacaagaggaagacaattctgaggatatagcaagagcaaggtgttctattgttgggttgtcaag      157500
agttgatggagtttgatgggtgagagtcagcttatattgggttcctatcattattctcttatgaaaga      157570
ggaggcacaaaagatgggggccattattgtcacatgggtaaatgggttagtggtggtttgtgcatgttttc      157640
ttgagatagaatttcttcagtgtagtaagaagccagtcatattctaacagtgaagatggagcacgaggg      157710
attgggggattagaagaggaagaaggtgctatttagcagagcctttaagggaattcatcagagaaatt      157780
tagtatgatatacaggcatctcgattaacctactggagggttttgtgttcatgaatttaatgtgagataagt      157850
cagcatgattaaatatcttctttcatctgtgctgatcagtaaaggtgaggcggatgcatgctgggtgggg      157920
aggtggatttcaccaggggtggagttttgccaaggaagaatcaagaattaaggctggattagaattgagg      157990
gtgtctaaaggatcgtggatctgctatgactccacaactctaagaaaagaagattcggtaccaccatcct      158060
cattatggaaataacaaacgaatgaaacaaaaccatttgtcacttttctacaagattcagagggcttgtat      158130
gtctatgatctcaggcctcaaaaagagtaaatcagttacctttttcccacataactctgtgtgtgtgtta      158200
gtacaattttgtatgtttgccctagaatgtgaaccatgaatttgtgaaatgaaagcagtgaataggaaaa      158270
aaggtaaagatacagttttgtattatctgtagcaaaatattaccacagctatgtaatccacaaaaatgg      158340
aagaaatttattaggtatttaattttatccaagagtagtaaaagaaggcagctatatataattagtagg      158410
tgactgttaaaatattagactttttgttgaaattttttggctcagaaaaacaggttttcatgccatgctgaa      158480
aaattacttagtttgatgaaaagtaaacaagacatgacagtgaaatcatacagtgttgaaacaggaaat      158550
agctaaaatgtatttttctcagtaaataagtggctggcataagttgtcctcattttggggtcaagatctt      158620
attttggtgtctcagctgaagatgacctcttcacaatccattaggtattgtgacactgattaattattat      158690
caagcagaaagtatttttttggaagtactttgcactaggcaggtaaggcagtcgctcaccacaggggcacag      158760
gtttcgaagcagttcaggaggagcaactgtcttgctgagaaaccccaaggcagacagcagcaattagaggataa      158830
gataatgtataattaactgccaccgtgtgtggggtagacaattagagaacaaggcaacacagatgttgta      158900
aggtgctgattatgggttttaacaataatgaaaatggaagacaacatcatcagcgtgggctgacgctgt      158970
caggggtggtgtgttttctcatgtgctgttaccctctaatcagtgttgagttggatagtattcccaggaa      159040
tggctgtttggcttcgcttctcttaccagagaattgctctgcctttataaatgtagagactgacatgtaga      159110
cacacttggatctgaatttccattctactctacaagaagtcaagctgcaaagaaaatcaaatcatgttc      159180
agtacctttctggaattttcccaagtactcagtagtcattctagctcacatcttaactctgctagggttc      159250
aataagtataccaaatgcatatttttttttagctaattccaaaatctaattcactttgatcaatagtcat      159320
ctcctatgaattccttgtgttttcttcactataaaatattttttgtgattcatctttcagtagacgaaagg      159390
tgaggtactttgagattatatttctactaaatcatgaatgattcattatttttactgaaagtaaacacatc      159460
catcatatttaaatccatatcatgtctgttgtcacttaagtgtttttattattttcacttaaacagg      159530
ttgtataattgcatagagcttcaggctatctacatagacaaaatatctgaataaaagtacaacgatcata      159600
ttttatcttgtcagtttaaattatgtttaatgattttaattccagggaaaactctaatgtaccaagttac      159670
caactgaaatgtgcccagtatcaatcctttattttttaaatataacattgtaagttgttaagtaagttgtt      159740
aactcttatccctaaaaagacataatgttccctttcttcatatgctaaaataaaaatttctaacaat      159810
gaatgtgccatttttataagccagcaaactatgcaagtaaggatctcaatagaagatttaaacaaaataa      159880
ttattttgctccatattctgttgcttttgtttttttgatgagataatttaatttcatggaattttaaatga      159950
tcaatttgtagtaaattttgggaaatatgtccattatttaatcacagatttagtatcttaaacacattga      160020
caacgtcaaacttgtctgcagcaaatggttactgttaaaaatttgccataggggtgagaactgcaattta      160090
tactatttctaagctatcaatgcttcaattattacatgtgtttatatatatatgtgtgtatgaacatgtg      160160
tgtgtgtgtgtgcatgtatacacaaatttttaaagtaatggcttactgaaaggccttttttttctcttcata      160230
tgactaagatatctgcccaaaattgctaagattatataccttctgaaaaattgcaatgtgt      160300
ttatgacgtatttttatgatatttcagtaccggatatgttcattaccccatgtatgaagtcttatcttgt      160370
gatgatgagttgatcagaccattacattgagaatatttttaggtataaactttatatagtctctgatgg      160440
tgagtgtgtaggtaaattgctttgggctcacctgattgtattttcattgttgttgactttcattatttca      160510
```

FIG. 8A-35

```
ctaatttgggagcaagggcttcttttttatggtctatttctagatcatcttcccttagattacatcatgt      160580
aatgaactggcagaagatattaagtagatcttattcaaacaagaactttgaacctaaatggagatttatc      160650
aagctaaattagcctaattgtctgtaacaatgaccacagcatattaataaaacctgtgacccttacatat      160720
atacatgtgcattttaatgttcttccactatgaaaggcattttgtgatttaatctgcttgatgaacgatt      160790
aatatgatattcactaattttttactcatcttattcttaattcatctaatttatctaattcttagtaatct      160860
aaatgattcaagcctcttacagatttttatctctacccagttttcatccagctgtccgtggtcatct       160930
ctgccttggtgtgcttgagaattatttctgattctatgacaccaatgcactttgcagtctttgaacttga     161000
attggcagaatcaagcttcctctagacaaatcactgaatctcttttctcacgttaaggtttgtaggaacc     161070
ctattctcaaagctgccaaaacactactgcttagtctatgcaaatcaacaactacaaatgcacgtcactc     161140
aatcaacattatgaaactccttttttggaatgattgatgatcacaaaatgtgatcttgtgacaatatgata    161210
tattcatttaagccacattgaggtttcaaattggcaccattgacaacgtacctctttcatgctaagtgta    161280
ataatttgttgcctctcattttcctatgctgcttcacttcattaaatctgaataattaaaaattttcgta     161350
gcatcgccaaagtcacttcccaggagctagggaatgtgtcgatctgtacactgatccagttcctgctgac    161420
gtttgcttggatgcagaggccatccatcgctttccattgattttttgtcaattgatgcttttcttccttct    161490
ttcctggtgacttaggaaatgttctgaaactgtgcattcaagtcaacacatgttagattcataactagga    161560
ttcaccttcacagtggactggtcccaatttgctgtattttattcagcctgtcaactcacactatctgac     161630
taaaagacgctaatgcagtgttggccagtcccctgtcatctcttttggtctcaaagcaatg      161700
gtgcatgttacacatatccatttaactgtccaattaacgcatgtttctagacaattctgatagaaagggt    161770
ctcttttcttccttcagcccaaacaaagcaaaacaaaacaaaagggcacttacacgatgttgatctatgt    161840
tttatctttttttttttttgagatggaatctccctctatcaccctggctggagtgcagtggcgcgatccc    161910
cgctccctacaacctccgcctcccaggttcaaacagttctcctgcctcagccttccgagtagctgggact    161980
acaggcatgcaccaccacacccggctaagttttgtttttttaatagagatggggtttttgccatgttggcc    162050
aggctggtctcaaactcctgacctcaagtgatccacacacccttggcctcccaaaatgctgggattacagg    162120
tgtgagccaccaccccctggcctgttttgttttatcttaaatctcttaggctgagactcatatggtccca    162190
cttacccatctttttacagcatgaaattgtccagttaaaattacagctctttattaatggccttaagact    162260
cttcatttttgaatggataaaatagtaataggctgtgagcaccaacagtattaatgtatcattcatgcatg    162330
atatagtagtgttgacatctttcttttcctttttctgttttaaatgaagttcaggaaaccaatatgaaag     162400
gtaagaaattgccacatcttggactatcaaatcatggcagacaatgaattaaagaattcaacaaatctt     162470
tggcagcatcagtttcaaaggtatttagatacaaccaccgtgtaattctacacaatttaattaaatcatt    162540
tatcaaatcctctacaacttgaataatttaactgatatcagaataatccatttttcagataattattttt    162610
atatttaatgtgttaaatataaaaatatgacacttctcttgcataatttgcagaatgttatttatttcat    162680
tattttattattattttttaaaatttcaacttttatttgatacatgtacagatttattaaatgaaatatt    162750
gcctgatgctggggtttgcaggaaggatcctgtcacccaggtggcataacatccaataggtagttt       162820
tgtaagccccccacaaccagcaccctatagtagttctcagtgtcttgctcttttgcccaggtgcaatca     162890
aagctcaccacagcctccaactcctggactcaagtgatcctcctgcctcagcttcctgagtaaataggac    162960
tacagatgccaccatggccaactaattttttaattttactttgtagagatggagtattgctatgttgac     163030
taggatgatcatccactcctggcctcaaatgatcctcccggctaggccttccaatgtgccaggattagaa    163100
gtgtgagccacctcgcccagcccaatgcttgatcttttagagcttcaggcagttgaagggttttgtctg     163170
cctgccacagccttccatctttttgagatgtgtttacctgagacagcctaagtaggtgacaacctgaacta    163240
cggttgctggcaattggaaaacagaagattgctctgttgatccattgggagaagtacagtagtctgtaga    163310
ggaacagaatcccagggttttttttctggcatgaatcactctagagagccacattaaaaatttaattcct    163380
gctgagcacagtggcttacgcctgtaatcccagcactttgggaggccgaggagggcggatcatgaggtca    163450
ggagttcgagactagcctgaccaacatggtgaaacgctgtctctactaaaaatacaaaaaattagctgggt    163520
gtggtggcgtgcacctgtaatcccagctactcgggaggctgaggcaggagaattgcttgaacccgggaga    163590
tggaggttgcagtgagccaagtttacaccattgcactccaccttgggcaaaacaagcaaaaaactccatc    163660
tcaaaaaaaaattaattcccctttgactgttgattttatttatttattattattttttagagacagggt     163730
cttgctctgtctttcagattggagtggtatgatcatagctcactgcaaccttgaaatcctgaggtcaagt    163800
gatcctcccacctcagcttcccaagtagcttggttgacaggcatgcaccactacacctagctaatttttc    163870
tattttatttttgtagaaacagggtctcgctctgctgctccacagtctggtcttgaactcctggcctcac    163940
gatcctcccacctagttcttccgaagtgctgggttataggtgtgatagtgccgagccatttggctgctg     164010
ttttttacatttataccattatcttcatcctaaataggaattctgatagtattgttggcagaatagggtca    164080
actggaacacacattttgttctctaggtaaagatgatgaaacttaaaatgtagctaatgttattcctgc     164150
aatgaatatgtcaatttctaatctggggacaaaaataaataaaaaaaagttgcacgtattaaacacctt    164220
cttgactaagtggcagctgtaatgatttcacttggggatgccattgcttcttaactcagctaacagtg     164290
cattaaagctattgattttttagtggctgctgtgctttcgtgattgtagatcatttctctctcttggaaact    164360
ctatttgatgacaaagctggctctgttcagagtaatgataaaagaaaggacctaccagaatttcaagtg     164430
aaatgtataacatatgtgataatgcatggtgactgcaatgattatttcccgatgttgctgtttaatagcc     164500
atgaaagcatcctactgaaatagagtatttctgctttgaatggcttagttagctcaaaaatttgaaagc     164570
tttctcagtaaagcatggtgccaggcactgaaagattcctttttggaggagccagagtcaattggatgat    164640
gtttataaaatgctgctggaaaattgggtggtgttttctaaatgatcttcctagtaatgatttatgctgt    164710
aaatcagaaaggttgccatctctctggatgaaatcatagtcatatgcccgtaaatgcagggatttgac     164780
ctcctataaaaaagctctctcttcccccctcatttatgtgatgattgtataccatctgagcgctgagaaac    164850
ccattggccatcttccacttgtgtgtggctggaggtgcttgctgcagctctgtgatgccctgagcagca    164920
tgctcgtggagttccagtctgctgcatgaacaagtggagaaacatgatcttcctaaactgctcacaagct    164990
gctaaatgagtgatttgtgttcccttt     165017
```

>HNL4 Exon3 (19479-19631)

```
cacctagttccccaaaacggggtccattagctatttatgctagtgctctcccttcccccgcctccctga     70
cagaccctagtgtgtgttgtttccctccctgtgtccatgtgttccaattgttcagctcccacttatacgt    140
gagaacatgtggtgtttggttctctgttcctgcattagtttgctgaggataatggcttccacctccatcc    210
atgtctctgcaaaggacatgatcttgttctgttttatggctgcatagtattccatggtgtatatgtacca   280
```

FIG. 8A-36

```
catttgctttatccagtcaatcattgatgggcatttggggttgattccatgtctttgcgattgtgaatagc     350
gctgcaatgaacatacacttgcatgtccacattgagaaaccatctcacgcaagtcagaatggcgattatt     420
agaaaactcatattcttaataacatctttgaaatgatgattcttcagtcttgaatcatcagtgcttcca     490
ggccataccttccccattcttaacttgaatcctgacttcattcttgagcttgttggagttgccctgagct     560
tgatttcttagagtgaattatcctgtgattttactctatgcctaagttagatggacttctttagcatgc     630
taatctctaaaaataccttttcaaaggagagattgggaaaggttttgtaccaaaacatggtagatcttgt     700
tccattatcaactgcgtctcgtgtcagagagttctaaggtgagtgaaattgtgcgtgtttgtagcgtggt     770
cataaagacatttcacagagtggatcgcaaacaaaccaacagagcacagaggggcttgagagcaatggcag     840
ctggtggaagcacaggacagggcacagcgggaatttcatgggaccacgaaccaagaacagaacccatgac     910
caggctgttttccttccagggggcccaggcttctcagctcagccttcacttgcatgctgctttgagcat     980
gtttggcttctttgagaaaatgagccacccaagaggcctacatccaagtcacctgcactcagatcccagc    1050
caggagtatggagggcccatgtggggtggagtggtgcacgtcctcaccaccttagacacagggaccacct    1120
acctcattttagatggagtgggcagataatctgcacacatacctccaaaggtgtcctctattgtagagac    1190
acctttgttttctccctcaatcctggacattttgtttgttttttctttatttcactaatttttacaataa    1260
actgccaggatatgtctccatgtctagctctttttgtgaattattctggaaataacagcctctgcaaggc    1330
tgctaaagtgacaaaggtattttcaatcgcgtctgattcctttcagatatttccatcttcctactccat    1400
catccatctctttttaaaaattttgttttgttttttgagacaaggccttgctctgtcacccagattggagt    1470
gcagtagcatgatcgtagctcgctgcagccttggtcccgggcttaggtgatcctcccacctcagcgcccc    1540
caagtagctgggactgcaggtgcacacccacgaccagctcaattttttgtgttgttagtagatactgggtt    1610
ttaccatgttgcccaggctggtctcgaactccggggctcaagtgatccgcctgcctcagccttcatgttt    1680
tctttaccagttggttccctctcttttcccacacttgctaagaccactactggttcactgtcacgatgtca    1750
cttacttttttgactaccttcagtgatctttcttttctgatttatgtatatatttcctgagtaatgtcat    1820
tctttattaaaaatgtatatgtatatatgtgtacaaaagtatacatatatgtgtatatatcctaaatg    1890
attctattatttattgaaataaataatgtgtataattatatatttatatataatgtaagcattagtat    1960
ataatgtatattatgggatacattatatatacattttatacacaattaggttctgtgtatactatatatgt    2030
atgtatacagacatgtgtatatatatatgtgtttataatatatacaaatgattgtaacagtgtgtgtata    2100
tatgtgtttatgtgtatatatagtatatatataacattaatgtgataaaagtgtatgtgcatatatgtgt    2170
atttgtgttttttgtacatactcatgaccacatttaaagaataccattgtaaaagctgaccatataatcgt    2240
ctatgcgcatatatatatgcagcaaaaatgccatcatcttcattaataaaatacatataggtctttaataaat    2310
atacattggttcacaatatcaacctcagcattatatacatttcaacaaacatgctcattgttttaagcat    2380
acattattaattcatatttatttgttttaagttgagattgttataactccctcttttttcaaattttta    2450
gctaatggtactttttaaaagaatgacttattgtattcaaattatcactagtgggataaataatgtaa    2520
tgatgggaaaagcttcctttgttccagctataattatctgtagttgttttatttgttttattcaacttaa    2590
cattcatgttttattcaaatcatcaatatataatgattttgttctgttaccaagatcttattgggaatt    2660
ctaaagtaataaattattttgaagaggtatcgatactattacactcttgatttatacctggatcaatgaa    2730
tgtttttaaatatgtaagcgttcttttatgtttcttgttatttatataattttatgtaacatgtgctgta    2800
cacttcttagagttattgctagaacatttatcatgaatgtgcaaagaattttttcaaatatatttatgtg    2870
catatatatgacaaatcattttgtgttaattttatacaattctaaataataagtgactcattctaaatta    2940
tttagctgattctctagattctctttctcttgttggatagtcatatgcaggagtgactttatttttgtctc    3010
cttctttctgatattttcagttctcaatacttttttaataaaaaacatataggcttcgagtctgtagaagta    3080
tcttgaaatatgatggtgatgatgaacatcattgccctgtttatactttttagtgaaaattcacttagtgc    3150
aacatttcttttcctatttgttgataagattaaaaaggatttcctgccaaaataaaatattccatgtactc    3220
tacttttttaaattaaatacattaatagtaccagatactatttgccatctttcaaatagcttttttctcct    3290
ttgatctttccctcagctatcacctgacttctttccttcaactgtgaatgagacaaagcaaaacacccta    3360
cttcttcccattgaaccatcttactgtatttgtagagtcaacctaattccttattaggtcactgcatagt    3430
ttttttttaatttaatattttacgctatttattataatgatcattgtggaggaataatcagaacgtgttaag    3500
attccttacaagtaacttttacatttttagtgttcttggcctttgaactgcgttttggatgaagaacttt    3570
aggattttctgtgcttgggggtgctaaaggtgtttacacctgagtgaatgcccagaatttgatcatatag    3640
atttttctattgacagtctcaccttcttatggttattctcttgtaaattatcttttacctcaagaccaaga    3710
tttgcaaatatattgattttcagtagatgcagtgttcacatagtatctcctgaaacaatcacttttttgca    3780
gtgtcttttgtatatcactggttgcgtccccttttactcagtctaaggtacatctgtttctgtatttttcc    3850
ttatgagtggtctggattttaattctttcaatacactttatatttattggagtatgctttgccaacgca    3920
tccttttttatctcagactgttcttatgtctctgtaataaagaaactgcatcttatttttactccatgaaaa    3990
atcacaaatgattccctaagtgttcctttagagtgttcctgagaggactgtggttgtcttttattctaca    4060
ttgtgtgtctttttttaagacttttattagcgcagttttaggttcacaacaaaatagaggggaacgtacaga    4130
gagttctcatatatccccctgccccccatacatggacggtctttccctattttccacatcacccaccagaggg    4200
gtgtgtttgttacaatccatgaacttacactgacatcttcatcacccaaagtccgtcctttacagtaggc    4270
tacagtcttggtggtggtgtacattctgtgggttcagacaaatccgtaataacataaatccaccattaca    4340
gtatcacacagtatagttctgcaaccctaaaaatcttccataaaaaaacctccacaattttagcagtttg    4410
taacaacaaaggcttatttcctttttctgaagttcatgtcggttgtgggtggacttgcttgttacttagg    4480
tagactgatattgaaggtgggaaaagaataataacctctccaggaaagataggaactattttgaaccaa    4550
taatacagctcactacacaaaatgagtgaacacagtcacactgaaagagagtgagtgacatatgcttaa    4620
gttatgcttatgttgacaaggtctcactcacctaaactggagtgcagtgccacaattatagctcactgca    4690
gcctgcaatccctggactcaagcagtcctcccacctcagcctcctgagcagctgggactacaggcacaca    4760
cctgtgtgattttgtatttatttatttatttatttattttttaatagaaacaggttctcattatgt    4830
tcctagactggtctcaaacttcagcgttcaagcagtcctctgccttggcctctcagagtgctggaatta    4900
caggcatgagccactgcgcccagcctcctttagtgtttaactgaacagaataaagaacctcttcattatg    4970
gtgaattggctaagttcaaaagagtagcaaaagccttcgtgggcagtaataattactctatcttccaaat    5040
acttgagtgaccttatgcttcttaaaatatatattttagggctcttaattgaaatcaattgcctttatag    5110
cctctattacagcatactcagaaattgaagagcgggatgattttgtaaatctagactaattttgtttt    5180
tctggaatgactagaaccatttaccatgtcaggtacacacacaagaaacgctaagggcgagttgtgaatg    5250
atttgactaggaacaatagttgggctgcttttagatgtctccttttgctacatagacagcaaaaggagaa    5320
ttcaccaaaggtgccagcccttcagaatccttgtcccacaccaccaaaaagtcctgtgacagaaattcca    5390
```

FIG. 8A-37

```
cctattaatcagctgctgtgtcctgactacggagaaaagtatgatgcaacagaacgcaaacttttccaca    5460
atctcataacaaggaaaaaatatatgtatgtataatatgtgtacatatataagaaaatgtatattacata    5530
tatagtaaatacatacaaatacacgtatgtgtgtatgtatatatacacacatattttgttttgttaggta    5600
ttttttatgactatttatttaaaaaagtcacattgaaaataaaattgacttttatttgccctaagttacc    5670
tcttgaaatattgtgttaaaaacctaataacttctgacaggtatatatatacctgtagaggttaatatat    5740
atacgtgtgtttgtgtgtgtgtgtgtgtgtgtatgcgcgtgcatagaagttattaggttttgtttg       5810
tttgatggttttgttgttgttttttgagatggaatctcactctgtcgtgcaggctagagtgcagtggcgt    5880
gatcttggctcactgcagcctccgcctcctggattctagtgattcttgtgcctcagtctcccaagtgct    5950
gtgattacaggcatgtgacaccatgtctggctattttttgtatttttagtaaagatgggatttccaccatg   6020
ttggccagacttgtcttgaactcctggcctcaggtgatctgcctgccctggcctcccaaagtgccaggat    6090
tacaggcgtgagccactgcgccaggcattattaggtttctagtacaacatttcaagagttatatgtatag    6160
atatgtgtacgtgtgtgtgtatatatatatatatatatatatatatatatatatatatatataaaacc    6230
tctatgggtatgttaggttttttaatacaacatttcaacaagcatcttaggacaagaaatgaaagtcaattatg  6300
ttctcaacatgacttttcttaataaacatacatttaaaaatacctagcaaaatacattatttagtaccta    6370
tttttaaacacactgtggtttaatctcaagctcatagattcttcgagataatattgtctatcagctgaaa    6440
attctaaaaaaaaatgggaaaggctcatgtaaatataataggatttgtatttcatttctgaggacagaa    6510
acatttcaatagtaaaatttgcaacaaaaagtgcttatggaaagttagacaatgctctaggactctaata    6580
gtaagcacaggaatatgtcagagacccataaaatcttttagattttattttgattcctacctgtaaaagtgt    6650
gaaatcaattattgctaaatccagcaaaacagcaaaggaaaattactattcaccttttctctcagtctg     6720
tcttccaaagctactaagagaaaaacaagaaaaatacagaaaatcctacttccattattacaatgaagca    6790
tttttgagctagtagaaaattagaattagaccttgcttttactggcatcacaaaagcatttcatcctgtt    6860
ttttgaaatgacaaatggcagaattcttatatacaatatgctaaccaaaatcatgttattgccacgtcat    6930
gaattataatttaatttctactctcaaagttaaataagaagatacaatattgcatttccctgcttgaaga    7000
ggagaattagttacacttgttacgtaaaggctgtattcatcactgttgtcatagctgttatgactgtga    7070
ctcttataatagaggtgggcttgcagccaaaaatatatgattcatccaaaagatatttaccatgtaactt    7140
atattatatgtgctgaatatttggtagtcattgcaaattaaggaatatggtgttgaaaaatcacaggta     7210
acacctttttcttgttgctaacaatctaacagggagaccttatttaacaagatatcatattacacattac    7280
aattcatcttgtgaagaaaaatgccaactacagtgaataattgaggaacccaagttcatttacgaatgga    7350
aggttgggatgaacagggaatgccttctgaggaaatggaatttaagctgatcagtaaaaatgaatcttc    7420
caggagcatatgggctttgcagatgggagaaacagcagagaatgccccaaaagttctaaaggaaacctgat   7490
gatgaaatgagttaagccatgttcctggtagtgtatcagttagctttgctacataaggaaccatctcaa    7560
agccgagcatctcaaaccacctttatttagctaagcatctcaaacaacctctatttaggttatgattctt    7630
ggctggacatctgggctgtgctcagctggaggctcttcagtctagagtcagcttccaggtctgttgggt    7700
gctcattggccaagcactatcttaacaggtgcttgacagtgctccatgtggaatatcatcctctaacag    7770
gctagtatagactcttcatggaagcttgtcaggttgcatgtaggtggttcaggtcctccttataatgaa    7840
agctaagaataaggacagtgtgtcacccccacatccgaatgtccaaataagcaaatccagaaagacac     7910
agatgaatgggtagtttccaggggctgagagtgaccactaaatggtaccatattttttggggggggatca   7980
tgaaaatgttctgccattagatattgtcaattattgcacagatccatgaatatattaaaaaccattggat   8050
tgcatactttgacacggtgatgtgtatggtatattaattatatctcaattaagcaattatatctgtctat    8120
catttatctgtaaaccagataaaataagacaggctaggtatatagaaaatagaacagaacaaggtaggc    8190
agaaacagaatctagcagatataaaacttggcatgtaagtaaagagctgtaatacctatgtagctgaaaa   8260
tggaactgttctctaaggaaataattaaaataatctctatgctctagcatccagataaataaattccagg   8330
tgagttatgacccagatgtgaaatataaaaccttaaaactgttaggagaatatgtaagcaaataaaatgtct  8400
ttatgtttctggattaagtaatcctttttttttaaaaaaagcagaaattatagagaaaatagtgataaat    8470
tataatacttatgcattttaaagcattagtttagataattaaaaatcaataaaatggttaaagacaacag    8540
actagatatcaccaatgctcaactgtgtaaacttgggcaactattttaatatctgtatacctaatttttcc   8610
tcagctataaaatgatattagttacacatctcataaggtatttatgaagattgcatattcggagctggac    8680
acagtggctcacacctgtaatacagcactttgggaggctgaggtgggagacttgcttgaggccaagagtt    8750
caagactagcctgcacaacatagtgagactttatctctacaagaaatagaacaaaattaaccaggtgtgg    8820
tggtgcacacctgtagtcccagctactcgggaggctgaggtcgaagaatcactggagcccttgagttgga    8890
ggctgcggtaagctacagttgtgtgactgcactccagcctgtgtgacagacaagactttgtctctcaaaa    8960
aacaaacaaacaaaatgcatattcaacatgcataaagcccttagaaccatacgcagcactgctatgcact    9030
gttaaatgtttgcttttacatgctcaaaaagaggccagcatccatgaatataaagatttcctacaaatca    9100
ataacagacattcagccagtcaaaaattggattgctattcaagatgggaatttagaatgggaatatagaa    9170
atgcatctgtactagttttaaggaacatgcaaattgaaatataaactgttaatattttatactcatcaaa    9240
gtggcaaatgtattgtctgataatgtcaagtgttggcaacagggtaagggccaggaaatttttcttacctg   9310
ctagtgggtgtatagcataatcaacttgtttgaaagaaatattgccgtatctactgaagatataaaatta    9380
gtattacccctatgtatcagttagctactgctgcataacaaaggactctaaaagtcaatgccttaagacaa   9450
taagcgcctattactgcttatgagcctctgcatcttgttagctggaaatttattttggtcttggctgggc    9520
tcattcatgtgtatgcattgttgatttggagtgagttctcttaggtaattggggggttgctggaggtaatt    9590
ttgcctaggttagggccaatgggttcttctctatgagatcttttgttgtgcaacctgctagtctgattt    9660
tcacaggacagtggcagaatttcaagagagtaaggtacaggggatttgagtcccagtcttggaaa       9730
cagcacatcattatatttttcttttgaaaaaatgcaatcttaaagccactcaagattcaaggggtgaaa    9800
gtacagactctctatgtatgaggaatagtaaattcatggggaggattgtagaactgggaaccttttgcct    9870
gtcagtggactacaccctgtaattcaacaattgtctatctagtagttatgtgccctgaactgggtctt    9940
caaactggcagatgtcttttcaaaattttttcaaagtatgactctgctgatgattttaaagaaactaattt   10010
tcaggtactcagcccccagatgttctcctttctaagccttcctggtcaccaaaagcttcttcccacatca    10080
caaaaggatgaccttcagtaggcatgacactttgttaccaacctttctgccaggttttataatacaaga    10150
aatatctttttgaatgctgctttctggaaagccccttgctgaaggctccataaaataagcctcctatct    10220
tatacatatttccattaagagtgaagtttggtcctgttcaggtgttctgatttcagaaaaagaaaaaga    10290
agccataggtcagctatggcagttctttcaaatgcagaaactgaacttttctgttgctaaccaattttc     10360
aaggtgcatatacattgggtgaagcccatcggtaaatgatccaatccgaaaatcatctgaaggtcatctt    10430
tcaaattcattgtggtagtgttattcaagtggaggctcaaatatatttcaagtgtatgcatggaatattt    10500
```

FIG. 8A-38

```
tccccagctagagtctgttctccaggtgtatggaggaaagaggagttgtccaggttgtgtacctgttctt    10570
ctcatctttctggggctattcatgtcctttctgtgccctcagcctccaacccatgcttctgctcagagca    10640
gcctgttttctttgctcccataaatgtattcctggccccagatcttctgtgcatatttagaagccctaac    10710
ccacttcctcaccagccaccccctctatcccagactctcctaccaggaacagcagaggatcctaaattca    10780
tgcatgcatttttcctgccccgttggaatgatctgtgtgcatgtctgtctctgatgttcatctccttcttc    10850
agtgtgggtgtgtcattacctccttttagccaggactgcatggcattacctgtcttagtcgggactgcatg    10920
ttaaaagggtcaacacatatttgtagaaggaattggcttctgagtgaatgaacccatgtgtcatgggcag    10990
tctgtgaggacataccagtcacttccttgctgccgagagctggggatattgcattggattagaagattaa    11060
gcccatattactctatggccaagtgacaaaataatcaatcacatccacatctgtgatagccaggaaaaca    11130
tttcttccgtgcccctcccccacccccgccgtatgcaacttccctgtgtggaaataatgtacttagc    11200
ttaaaaagtctctttctctacttaacaagactaagttgaaaattaaccttgcccacttaaaagaaaacga    11270
atatgcagtaaactatgaactactaatacagttcaatatgatatctcatgcagaacaataatgctgaagg    11340
ttcttttggttctattatttccttatattcttgcttagataagatcacatttgtatctattgactttct    11410
atgatgatttagatacataagtggcaataattaatatatattaaaaatacagatttaaattgtttttctg    11480
acttgtaatgttaacagcagtatatgtgactgtgaggttttcctttgatgttaattttcactttgacaat    11550
agtcttcgttttccaatttttttttaattttttttattttttattttttttttgtgataaggtctggc    11620
tgtttcaccaggctggagtgcagcagggcgatctcagctcactgcaacctccacctcccaggctcaagt    11690
gatcctgccacctcagtctcccgaatagctgggactacaggcatgcaccaccatgtctggctaatttttt    11760
gtaattttcatacagaagaggtttcaccatgttggtcagtctgttccagaactcctgacctccgcccacc    11830
tcgacgtcccaaagtgttgggattacaggcatgagccaccgcgcccatatcattttccaaattctttaca    11900
aagtttttctcttacattcataacataaagtgctatttaaatagactaactttttgaaaataacatagat    11970
aaagcactaaatggggacatcagaggaacaggctaaaaaaaagctggaatattcttcaggattagggaca    12040
ttgagattttatttataaaatgatattttaaatttaatatagaatttgttgtacttttgcttggagtatt    12110
taaatcttctctttaatatttaaagccagttctgcacagaggtttttacggagatgctaattgttgtatga    12180
aaaggaatattattctgaattttgaggaagggtagacatagagaagataaaggaaactcacagccctacc    12250
taggtttatttgggctgtgtgtgtgtgtgtgtgtgtgtgtgtgtgtgcgccagccacaagctgggtt    12320
tattcttgaataaactgtagacaaattgttttttcctgaatcttctaaaacctgcatttacatagtccatg    12390
gttgtgtcaaactagatactcaagagaacttggtttgttttaagcatttaattagttataatttacat    12460
ggacaaatagagcagcagtttattaaaaaagaatgaaaggataaacaaattaaatatacgtagaacagga    12530
aagacagcatctaattatgtttctgggtcaggctctgatatacaagattaattaaaattgggatttggc    12600
aagtaatttctatcgaaatctcagcaggagttttattgcaactaacaagctgatttggaaagtttcatg    12670
gaaaggcaaaggatctagagcaatcaaaaagaccttggaaaaggggaagaaagttggagggcttccattt    12740
ctctatttaaaaggtactataaagatatagtaatcaagatgcaggcaactcacatgggtataaattta    12810
gaccaatgaaatataattaattacagttggcccttgaacaacgtgaaggttagaaccctgcacagtcga    12880
aaattcacttaaaactttttaccccccaacacttaacaaccaatagtctactgttgactggaagcctta    12950
ccaataacataaacagctaattatcacatcttttgtatgttatatatacaatgcactgtattctcacaat    13020
aaactaagttagagaaaagaaaataccattaagaaaatcataaggaagagaacatatatttaccactcat    13090
taaatagaagtggatcttcttaaagatcttcatcctcatcttcaggttgaataggctgaggaggacgagg    13160
gagaggagaggttggtcttgcagtctcaggggtggcagaggcagaagaaaatccacatataagtggatct    13230
gcacagttcagaactgtgttgttcaagcgtcaattataagggtttagaaataaatccttcaatttgtagt    13300
caatagattttttaacaatggtgccaaaacaattaaaggaggcaaggatagtctttttcaataaatggtgct    13370
gagacaattggatattccatatgtaaaaagatcaatttcaactcttacctcttattgtacccaaaaattaa    13440
ctcgaacgacaggtggcaatataagaattaaagctcttaaacttttaggaaacttcagcaacacaggaga    13510
aggtcttcagggccatggattgggaaagatttcataaatatgacctcaaaagtacaatccttaaaagaat    13580
tgatcaagtgaaactcatcaaaattaaaaacttttacacttcaaaaggcactattgagaacataaagtgc    13650
tatttgttgagaaaaccaaaagacaagccataaactgggagaggagatttgccaaccatattcccaataa    13720
aagactttatttagaaaatatgtaaacaaaccacttactattcaataataagaaggaaagaaattatt    13790
tttaatgggcaaaaataaattaatagacatttctgcaaagacagtgtacatgagaagatatttaatatca    13860
ttagttactaaacattagctaaatgcaaatgaaaactacaatgaggccaggtgcagtggctcatgcttgt    13930
aatcccagcacttaggaggccaagatgagtggatcgcttgaggtcaggagttcaagaccaacctggccaa    14000
cagggcaagacccatgtctactaaaaatacaaaaattaaacaggaatagtggtggcatgcctgtagtccca    14070
gccacttgagaggctgaggcacgagaattgcttaaacccaggaggtggaggttgtcgtgagccgagatcg    14140
taccactgcactctagcctgggcaacagagcaagactttgaaaaaaaaaaaaaaaacctatgatgaga    14210
caccatttcacatccattagtatggttataacaaaaaaggatattagcaagtgttggctaggtattagag    14280
aaatagagaccctttataccaccgttggtgagaatgctgcagctgattgggaaaatgtctgt    14350
cagtttattaaaacattaagcataaatttgccttatgaaacagcaatttcaccccctaggtatctatgcaa    14420
tagagatgaaaacatatatccatgcaaaaaatagtacacaaatgttcatagcagctttattaataataat    14490
caacaagtagaaataaaccaaatgtcactcaacaaataaatggattttaaaagatgtggtatacccataca    14560
atggaaaataatttagccataaaaaggaatgaagtattgatgcatgctacagtatgaaaggacattgaaa    14630
acatatgctaagtaaaagaaaccagacacaaaataccgcatattatatgagttcatttatatgaaatgcc    14700
tagagaaggcaaatccttataaagacagaaagtggatcagcaaggctatcacaccccacgcaccaccaggt    14770
ctggttttaaaaggtattaagccccccatgaaatggacattacttgacttttgtttgatatatggaaacag    14840
cattatcaagtcttggtttcaaaatatgtttaagctcttctgagttatgtagaacagaggagtgttttcc    14910
attcacaagtgttggagatgacagtattttcccttttgccttaatccgcttatcctagaaccctataggaa    14980
ggcaaagactgtcttgattgattgacgcagttaaagttattgatagtgggatatgcacatatgggctgca    15050
tctgtctatgagaaggaagcaatggagccaattaattaattgcagcaaaatttaaatgttcacaccttta    15120
aatgtggaaactataaaaaccaaaatggtgctctgtgcactaagagcataagctagttttttgctatcct    15190
taagggcctcttcctgcatttgcctatattaaaattcctatgcagatcttattgaggtgatcaaggtag    15260
atgacttcgatttttatttttcttcaacaaattcacgtaccaataactttcaaatgatatttagtaactat    15330
tttaaacacagaggacatgatcttcaaacgatatttaatagctattttacacacagagggcataactttc    15400
aaatgatatttaataactattttaaacacataggacatggtctataatgtttttgtcctgacttaaatatt    15470
tattgcatgtagtagatttttaatagaagaaaacaagagtgaatagtgggtagtgcttctctaaacacaga    15540
gtagaggtaaatcttagtgatttaaattagtcacaattctgactttttgagattgcatgtttataagttt    15610
```

FIG. 8A-39

```
ttaatgcatgaaattaatgtcaattatataatattttgaataaagtccttccatgtttactgtgttttttg      15680
cttgccttatgaaaatttctaaccataatgtgtcagtaacatttcaaaaatttatttaaattacaacatg      15750
ttaacatcagaggaccattgaatacgccataagcatttctttaaagaatgtgggaaatgtcttttctaat      15820
aatttaatttttctttttttaaaacaactcacgttagcattttttttttgcagtagcatcatttttaac      15890
ccccaactgcatattcacaggatatctaatatttttgcaagtaacattttgaatttgttcttcttgaca      15960
tctttatgtttatatgcattttgcattcctatctcattttttttgaaatccaaatgtaacaaatttcaa      16030
cttttgtgttacattcttttctttttttcttttcgggtagcatctctctcttttctgaatttttga      16100
aaacctgttgttttgaattctctttttcccttattttccttctcaatatgaccccaggagccaacac      16170
aaagaaaaacgcagatgatataacgagtaatgaccgtggtgaagacgaaggtattttttgttttttcaaa      16240
gctcaaccccagtgcatgattttatatctatctatctctctttttttttttcatttcaatctgtttttc      16310
tccccttatttaaaactagtacacttggtgtgcttccttaattattttcttcttgtatagaaaccactg      16380
tcatttttttaatcccagttaccatgtacaggaaacaaatcactgtgagaagtataaacattgtttctaaa      16450
catgaaaagagtaatgaactactgtttacagagaagccctttttttttttttttggcttggtcgcaaga      16520
agagaaaatggaattttaaaacatgcatgtatagtctattttctcccttccaaatgttatttgtaagtt      16590
aatatactactttggagctttggtcttcttaattatttttatgaactacaaaactgtacagcaccttaga      16660
agaatttttttggggggggggggctgaaatatcagttttttttttcttcacaaacatattgattccaa      16730
catagatttctgataatctgctcacagtgaagtacaccaaaaagtgtttttaatgagatgctgttgttaac      16800
gagccctgatgcattcaggactgcctttacagcatttaagggggggtgggggaagataagagtatctcag      16870
aactgaaaaaggacaaaaagctagctatgttcatctttcttttcacaccacggctttttgaaaacgttt      16940
ttctcctaaaatgttttgttgctgtgaagtttcttcttaaggctaccaaattgctcaacacattgtcta      17010
ccagaagtgaaaggattttttttaaagatggtaggtctgaggtactcatgcagacaactcgcatgctg      17080
ttttttctgccctttctgcacaagaaatgatttttttttttttaaagaggagaagcaacaaaaaagtac      17150
tcaagcaagcccttccttcattggtaaggctctataggattagctaaaagcacattttttcccatctgggta      17220
gcaaaatgcatggaactccattaaggtcctggctggaccttttgggtctctgtctgaaaggcaatttaaag      17290
cccaaaagtgagtcctgaattatccttgctggtcaagcccaacgtccatgacagggtcttttgaccaatt      17360
cttgtagttgctccccctccttgcttatcttcataaatcaactgttctccaagaaaagaaatcttgccaac      17430
acccttgctgtgcccagtcttcccttaacattttgagtattgttacttttactgagctcatagagctgtc      17500
actgtctcaagtagctctctgagagatctccattctgatgccatagtctcaaaatctacacctgctt      17570
caggtagcccttctttgataagggcttctgaatgcctgacattttatcagtattgagcaaatacataaa      17640
aatgaaataaacttttgtctcatatcttatactgctctaatttgtatcctgtttggccttctcttttaa      17710
tacatttcctctcgataattagaatctgttttcacagtgttcccagtgaatctttattaccattaaaatg      17780
ccatctaatttttcatttcatattgttaagttatgattttttgactttgcattaatataacagctggttat      17850
tacttccacaagttcaagagagtcttgttctatattttatgaaaggtaagagatgttaatctcacatatt      17920
ttccaagggagcactttaaagcagccccttcaaaatctctacttactcttttttccacaatttactaggca      17990
accgctggtaatggtaaaagaaatgaggccaaaacagcaaattaggaaccagaaagaagcagtggatca      18060
tgagaaaagccatttcttattcatatagcagaagacatttcccgtagtgtatgatgaataaatgattaat      18130
agaagattttactttcatatttgaattttatatgagaaaacaaaagacactttctgccgtggattaaat      18200
atctgcaaataaatacttgggtaacttgacactcttttgtgtgctttactgtgaccaatgggtatgtcgt      18270
gtcttctgtatgcacccagtaaaattgtgatcataattcattcaaattggagccaccatccaaacgatgg      18340
taattcatatcctcagaattcctttgtggtatttcaaaagtgtccctgtggattatgaggaaaaaaaaac      18410
tttattgatgaagaaattgaaaataaatatgcataaatacttgagtttttcttttagttacaaagatattt      18480
aaattgtacacacacacacacacacacacacacacatatctgtatccagaaatatttatacgtgaggtca      18550
gtcttccaaagatttaaatgcagccctaatggctgattaatgttataaaacaggtcttttttcacaaagcag      18620
gcccctacagatggtctccaacttctatcatcacagatcattgtttttacatcattgttaatttaaataa      18690
taaagtaaattaccaagaggaatcattggttgcaagtcacaatgggagtttatattccctgtgaaaatat      18760
aaagcatttaaatagtttggattcttttgccatttttattacatctcttttattttttgtcacctaagta      18830
tgttagtatgttactgtaatcactggaacaaagacatttgcttggacatcttttcttttttttccctatt      18900
tctgttcagttaataatttttaactgttgattttgctttcttgtcattatctgtcccttattgatagttt      18970
atagcttcactactacttttatgttttttattgttaaattgaagatgaatctgtacactcacctgcgaatt      19040
aagatgcaactattaaaattaaattataatttgaagttgatttttatacttaattagaagataaaatat      19110
atttcatcaagggtcccatgtgtttattcaatttaaatcacattttaggggtttgagcaaaatttaggaaa      19180
tgtgtactttacctaaaaccatttcttttagtgcttttagatatatatagaagcttagatgagcagagtac      19250
gctaaatgtctgtatgcttcttaaaataccatttccataaatagaaaacgtaatagcattgatcatttttc      19320
cttagacactcttatcaagggtcatatcatccataaaaataaatgtgcttaattcaagtcaaaataggga      19390
aatcagtgaatctccttttttcttaatttagcattggtgagtcagtgtgattcttttattgtgtttccta      19460
cttggctttttttccagATATTCATGATCAGAACAGTAAGAAGCCCGTCATGGTCTATATCCATGGGGG      19530
ATCTTACATGGAGGGCACCGGCAACATGATTGACGGCAGCATTTTGGCAAGCTACGGAAACGTCATCGTG      19600
ATCACCATTAACTACCGTCTGGGAATACTAGtaagtgatttcatcatgtgaatgactgagcaagaggaa      19670
acatgaaaagtccacttctcgttttgacgggctcgtggatttgaatcctgttattccagttcctggtta      19740
attccacttcacggtattacttttatgtgattggatatgttttattcctttactacctttgtgcaacatg      19810
gtcatgaatcccttctcaaccaatgcagactttaagatctaaagatgaaatgaaattttatttatatgc      19880
atgtttctcccttggagttcaatgaatgtatgtttgtctacatagacctgtacaatgaacacatatttgg      19950
tgatattatagttgggaatggccatagatcttagctttcttttctgattgtgtcattgtatgaatcagta      20020
tattgtgtggaggaaaagattttatccaattctctaactgattatgttgagcctttggaagatctgttgt      20090
tttggttccattgcatttgcatgcagggaaacttagctgttagttgactttgtccattgatgatctacg      20160
attaaaggctaaatacatggaaattcaagtttagttcctccttgttttgcatttctttttcctttc      20230
tttcttttttttttttttctttgagatggaatctcactcgtcgcccaggctggagtgcagtggtgcgat      20300
cttggctcactacaacctctgcctcccgggttcaagtgattcttctgcctcagcctcccaagtagctggg      20370
actacaggcgcatgccaccacactcagctaatttttgtgttttaatagagacagggtttcaccatattg      20440
accaggctggtctcgaactcctgacctcgtgatccgcctgcctcggccttccaaagtgctgggattacag      20510
gtgtgagccactacgcccggccatcattcatcttctctaattgtaggttggaaaattatacatcttcag      20580
agtcagatttcagtaccttctgagatggcctttcctggtgttggttagtttgtgaataatattcctaaga      20650
cctatgtaaaaacatttgtttttccaggcaaaaatgcattaaatggtatagaagataaagttttttaacaa      20720
```

FIG. 8A-40

```
gttagccatgagagagatgtgtatattggttccagtgtgattatgatacaatatgaaatacaaaacaaaa         20790
tgaaggccaggtgtggtggctctcgcctataatcccagcactttgggaggcccaggcaggcagatcactt         20860
gaggtcaggaattagaaaacagcctgaccaaagtggtgaaaccctgtctctactaaaaatacaaaaatta         20930
actgggcctgatggcaggcgcctgtaatcccagctactcaggaggctgaggcgggagaatctctggaacc         21000
cagtaggtcgaggttgcaatgagcagagatagcgccattgcactccagcctgggtgaccgagtgagactt         21070
ttctcaaaaaaaaaaaaataataataatactagtaataaattaattaaaataaaaagcaaaataagatgg         21140
actaaaggaggtctgtcaaacaagaaatatgactgaaaatgttttcttcaaatatggccaagaatatttt         21210
cttttcaatcagatgacttcatttcattttgagtgggttttttttttcctatgtgaaaacattaacctg         21280
taagaagccctaaaaggtggtgaattgctgagaaaccctaagaggtgttgtaagaaaccctaagagaaat         21350
gcatttcttactttgaaatgcaaatcagtcacaggtgttgctaaagttgtatcttttgaaacattgataa         21420
agaactcaaaattccaggttggtttctgcattaaagaaaataaacaccaccaaaaaaccttttagtgtca         21490
aaaaacttattatgtcgttggctttattcctatattttttgtagttttctgtgagccacatcttggcgg         21560
aataatgtctctgaacttttgcatagcagtaattgcacgcttcactgaatagttttcagaggcgctggat         21630
agttgctttggctactagtgttggaaacaggaaattgtgcttcttgatgttttacaaaaggttcattctg         21700
acaaagaggtggaaggaggaaagtatgtgtgagggcattgcacaggccctcttcaaagggagcagtgtgt         21770
gcactgcctgtagcacggccacacggaagaaagcttgggcatgcttttctgagggaagcagtgggcatca         21840
agaaaattcttgctttgctggaaccacacacaatattctgttgcatgcgtgatgaattgatgtgtctgataa         21910
gatagagtttcaaaataaattgatctccttttcccctaaagctcagttgtatcaagcaactctacacta         21980
tgattttttttttatcagttttgtcccttcgtgaatcaattgcacatcttgcaaattagcctggaaagta         22050
tacacactttttttagaggaaaaaaaaactaattgaaaaattgttaagtctacttttgttatggagagt         22120
ttttaaaagtcataagataacagagagctgtaaaattggtggggaagaaataaaagaagcgatttagcat         22190
ctctatgccggtctatttacattcctccaatgagctagtgtggaacagccaagcacactacagaccccct         22260
ttcatttgatggaatgaaatgtgccaagtttgccgatttacaggacgatagagactttaaaatgtgact         22330
gcgttggttttttatcatggatcttgcatttactattgtcctcttgaaaacagctaggcggcatttactt         22400
ttgcttgcaggaaactcctattatcggtcttgaaaaaatgttttttaaacctttggcatccagatatttaa         22470
aaagatgatcaaataaaatacacagcaggcactgcaatgatcatttcagtgagtgcatttcatacaagta         22540
gatacaattttaggcaaaaagttgaaatattctttgagttctttttcttccagtaaaagtcataaatgca         22610
taaatgttatcttcctacctgaggaatggaaaaatattgttttaagattttttttttttaatggagtaac         22680
aaatgctattctctgttacccaaaagagaggattaaaaagatgaaacatgcccataatggaagcggaatg         22750
ctggcattggaaagaatgtagatcgcagccagagacagacaggagctaacaactttcctctacctctgcc         22820
ttgagaaagtcagctagcgtttcctcagactctttccttagatgtagaaggcagtggtctctcccttgca         22890
aggttgttgtacagtataaaagttccatggttcaaaataccacactttacctcattaatatataatcctgc         22960
ttgtcaataaaaaaataacttttttcttttcttttttttttttttgagatggagtctcgcttttattgc         23030
ccaggctggagggcagtggcatgatctcggctcactgcaacctctgcctcccgggtccaagcgcttctcc         23100
tgcctcagcctccgcagtagctgggattacaggcgcctgccaccacgcccgctaatttttgtatttta         23170
gtagagacggggttttgccatttggccaggctggtctcaaactcctgacctcaggagatccacctgcct         23240
tggcctcccaaagtgctgggattatcagcatgagctactgtgcctggccaaaaaataaccttttaaaaaa         23310
gatttaatggactcatgtagatgaagtttcataggctctcagcagcaaccattatacccagtcacactac         23380
aatttctagtgttattaataccattatgcattgtattaatactactgtttatccacagtaagaattgtag         23450
ctgacccaacctgtaatggctaactaatatctatcaaatattggcatccagactgaacatgtcgttaattta         23520
aaataacattcaagacacttgtagacattaaataaatcagaagatcatcatgtttgctatttttaaaa         23590
aataatcagaactgtgctacacaatcttgctagccattggccatataatttatgatccaatccaggacat         23660
gtttgagagttgctcatgtgctatgaataaactgggattgtcccaggcaaattgagatgtatcattatag         23730
ctataaagtaattatttatatctacatgaagtgtcttctgattgaattggtgttcagtttgttttttaaag         23800
aagctgcacttctataaacagatttcctatgtgttctgctatacacccttgtcactaggaaggtgtatat         23870
gttaccagaaagggatcctaatccagaccctaagagagggttcttgattctcgtgcaagaaggaattgga         23940
ggcaaatccgtaaagtgaaagtaagtttattaggaaagtaaaggaataaagaatgactgctccataagca         24010
gagcagcccgagggctgctagttggctattttatgattatttcttgattatatgctaagcaaggggttg         24080
gttattcatgagatttccgggaaaggggtggcaattattggaactaagggttcctcccctttttagacca         24150
tatagggtaacttcctgacattgtcatggcatttgtaagctgtcatggtgcttgtggaaggtctttag         24220
catgctaatgcattgtaattagtgtataattagcgtataatgagtagtgaggatgaccagacatcactct         24290
agttgccatcttggttttggtgggtttcggctgcttttttttactgcatcctttatcagcaaggtcttt         24360
gtggcctgtatcttgtgctgacctcctgtctcatcctgtggctaagaatgcctaacttcttgggaatgca         24430
gcccagtaggtcccagccttacgttacccagcccttattcaagatggaggtgctctggttcaaacgtctc         24500
tgacatatatattcaagaatttggaaaacctcaagttcaccaatgcctctcagattagtcattgccaggg         24570
tgtgtggtgttcctatctgctcagaagccagaagccagcaaaatccttgctgagctgtacgtgccagggc         24640
atttgcctggtctcacctacccacttgagtacctatgccctatcaccttcacctcacaacatccatac         24710
gtatcatttaccctaagaagattagacattaatccaggtaataaacttcagaacatcacctccagac         24780
agaaactgcagaggataatctgataaatctgaatccctgtaaggccattactgaatcaataaatactctt         24850
ttctccatcttagttccttactttagtataacttgagttctccccaatctgttttttttttgttgttgtt         24920
gttcatgatagtccaaagaccttcgatgtaaaagagaatgcatcttgctcatgcttttttgatggaaatac         24990
ctggaacttatttattccttccccttccagttgtctccaagtgcaagtctgtctgtacctgcagtggat         25060
ttcatctacctccatttaaatatgtatttccgttagctcacatggtactatcaccttttggtgatcct         25130
atgacttcatgcttcatgtatgctgaaattaattgttgcttcaaaaagagtccaactatgtaacatcaac         25200
tcattgtgtgcctctatgtggctggcagatattacttcatttaatcttcgtaaactcccttggaagagtt         25270
aaccttatgtcctacctatgaggagatgaatgctttgaggtaatgggatttactcatggcatcacacctt         25340
ctagcagtcagagcagggactgaaacccgggtgtaactgaagccagagctctgacttaccactcagaact         25410
catccacagccttcttaattaatgtcaagtatgaattagtaaaccatggaatgagtgaagaaattgagta         25480
tcactttagcatcagatgtagctttttatcattatgcaaaaaagttcttactgctgatcaagatacacaat         25550
tgtgataagatgcttacagtgtattttttaagttcctcaaagtgggtcttgtggcattaaccacaacaatggcatttgtcacat         25620
tcaatcgatactggtttgctttggttcacggtgatggtggcattaaccacaacaatggcatttgtcacat         25690
caaagctcttcggtgcagtagaactagtgtttcatcaggaaatttggtgtcctaccccagttcccatgt         25760
cattgctggcttgctgtgtcgtgtgcataaattgagtcaaatgatcatttcggtgcatttcttacaatct         25830
```

FIG. 8A-41

```
ttcacatattatagctatcctgaaaattttcatctgagggtagattgcgtcatggtcttctgaagttgtc    25900
tttctctttaagaccattcattgaataaacctattagacgctttggagtcataattgaatataagacaga    25970
aatggtttgatataaaagcaaccaacatgcatagcagaaacagcatttgtagtcataatttgggtgactt    26040
aacccatatgcacgtgctcagcctaataatgtggtcactttccctgttctggtgtcccttgtagggtttt    26110
cctctgaaattgagggagggtgggctgagctctgaagcattcttgcaacatcggccagagtggtctcacc    26180
tttatgcttttgtgatatgtgtgagccatgtaatattccactcaacaaaagaagcctggaaatcattaga    26250
agagaggaccaatacgttcttcccaagagttacagcctcaattccatgggtgtgcatttatgtgacatgc    26320
atctgacattagtgggagttcaatgggtcactataatttccctgaagcacacctgctgaaaaatgtcaag    26390
ctatcttataaatgacctgtatgttcttctcccctttggaagttagaggagttgctctattttggtaca    26460
tttgctattttatttctttttttctaacaatatttcttttcttttaatgctttatgaaggattttatttga    26530
aatgataaatggaacacatcttatgtatcaagtcaaaagttcataagcgtatatattaaaaaagaaagca    26600
tcatttcctttttcgagaatcaacacaccttgatgccagtctcctggtttcattagaatccctctcttct    26670
cttcctctaaccaaaatgtctcagattcccccgatttgatttctgtaaatggcctactttgactggaaga    26740
attgcctctctctgtctaaaacaggacccaggcgttactaaaacaaaacactgcaaaaagttaaatgagg    26810
agaaaggaaagttaagcattgtacttagtgagaaatacataaacaaaagtagagacgtaaaagaagcatg    26880
agagaagggtgagaaagtgaaatcctgagacaagatgaatggtggtgagcactcaaacccaggaagtag    26950
caaaaggtggaaggaagaatgggagccttagaataagattcttgtgggctgggtggcagatgttatcg    27020
gtaaagccagcctggggagttggcaggggtccatgcagtagataacacagcaatagagtgaacacattgc    27090
agaagataggcaacctctaatccagaaattatcagataaagaaaaaccaagacactttgcaaaacaaaa    27160
aaaaaaacaaacaaaaaaacacaacacaatgtcttgttttcatcatcatcttctttataatgaggtttc    27230
catgcattgaatacacacttggaaacactgtaatcccatggttgttgtggctgcagattgataggtgtgg    27300
acaggtctttggtggggcaaacaaaaccaggatcatgttttttgctctcagaatgatcgtttgcttggac    27370
tttcctcttctgcctcctagtggctcaaaatgcccactgtcattcattggatttattcaggatgtgaagaa    27440
ggtcaggggaaattaaggatgagtgctttgtcattaggacctgagaggcaaatggagcagagatggggac    27510
gactgcagtgggataaggactctctcaccaggaaggtgccattgatgtaatagttgatgggaacagcaga    27580
gcaaagaggctccctcgtcctcagctgactcaacaacaagcgagacatcagatggaacggtatttattgg    27650
gcaaggaaaatcaggggaaggctaggtgcagtggctctcacctgtaatcccagcactgtgggaggccaag    27720
gtgggaggattccttgaggccaggagttccagatcagcctggacaacctagtgagaccctgtctcagaaa    27790
gaaagaaaggaaagaagagagggactctggatgaccaaaggacattatgttaagtgatacaagccagaca    27860
cagaaagacgaatatcacatgttcttactatatgtggaatctaaaaaaaagtcaagcttacagaagcag    27930
agagtagaatgttctcttacagaacttgaagctggaggtggagaggaaacgggagatgttggccaaaggt    28000
tacaaagtttcagttggcaggaaaaagtcaaaagatctgttcaatatggcaaacaaagttgaatcacaag    28070
gaattgaatatctgacgtctctaagaaagtagattttaagcgtttgcaccagaaaaataagcatttgaa    28140
ggtatgcacttgtgaatcagctcgagtaagcatttctcaatggagcatatttcaaacatcactttggaca    28210
tgat                                                                    28214

>HNL4 Exon3bis (29948-30058)

cacggagctagttcatcattgctttgtcattaggacctgagaggcaaatgtgagcagagatgtgggacga    70
ctgcagtgaggataaggactctctcaccaggaaggtgccattgatgtaatagttgatgggaacagcagag    140
caaagaggctccctcgtcctcagctgactcaacaacaagcgagacatcagatggaacggtatttattggg    210
caaggaaaatcaggggaaggctaggtgcagtggctctcacctgtaatcccagcactgtgggaggccaagg    280
tgggaggattccttgaggccaggagttccagatcagcctggacaacctagtgagaccctgtctcagaaag    350
aaagaaagagagggagaggggagagagagagagagagagagggagggaggagggaggagggagggaggag    420
ggagagagagagagagagagagagagagagagagagagagaaagaaggaaggaaaaagaaaa          490
attagccagatgtggtgatgtatgcctggtgtctcagctacttggaggtgaggcaggaggattgcttg    560
agcctaggagttcgaggctgcagtgtgctgtgattgcactccagtctcagcaacagagtgaaatcctgtc    630
tcaaattttttaaaaaagactcaaaagaaaatcaaggggagggagtggagacaaggtagaaaagaatttttt    700
ttattttgtgcttttttttccctaatgtattcatttaatcatcaaataaaaattgaatatattgatcatgta    770
caaagtgatgttttgaaatatgtatccattgagaaatggctaaatcgagctaattcacaagtgcattact    840
tcaaatgcttattttctggtgcaaacacttaaaatctactttcttagagatgttcaaatattcaattcc    910
ttgtgattcaacttgtttgccatatttgaacagatcttttgaactttttcctgccaactgaacttttgta    980
acctttggccaacatctcccgttctcctccacctccagcttcaagttctgtaagagaacattctactct    1050
ctgcttctgtaagcttgactttttttttagattccacatataagtaagaacatgtgatatttgtctttctg    1120
tgtctggcttgtatcacttaacataatgtcctctggttcatccatgtagtcccaaatgacacaacttctt    1190
tcctttttttttgaggtagaataatagtcccttgtgtgtataaaccccatttctcttttattcattcatctaa    1260
tgatggacattcaggttgattccatatttcagctgttgtgattctgcaatgaacatggagtgcag    1330
atttctcttcaaagacttctttttttccaatcccaaatacacaaaattatcatctggcatctgtcatgcta    1400
tggagactctccttgatctatttataaacgattcaggatttctttaaagaagctgaaatttttattttac    1470
atgcataaccatatttagaaatcaaaatatttcaaacagaaatcacagaagaatctattccatcaatatat    1540
aattcccagttaattgattatataatgtcatttaagcatgagttagtagtcacagagaatatgccttaaa    1610
aatgttctgtctttgaaagttttacattcaaaacagtctcttaagattattaattctaaaagacaccatc    1680
cctttctctcttcagcctgttttcttcattttgttctcatccagtgatgtgaaaggttgatgattttttag    1750
ttgatgaggttgacgtgccctctttctccttggggacagaaggacataagttgtgctttaaatgaaaata    1820
agagtatgatgagtatcccaagggatgatggaaagttccagggagaagcattgaaattgagagccaaatt    1890
caagtacattggaattaggttctggtgataattctgtcagtatctacatatattcaaggaaattagtcc    1960
tttcgagtaggataatggaaaaatctctaaaaggcaatctgagcgggatgtttaaagactacgtgattat    2030
tatgcagtgcatgcctgtaccaaaacatctcaagtaccccacaaatgtatacacttactatgtacccata    2100
aagtttaaaaaaatgtaagactactacacatattctgcatgatgaatatgcacatatgtacatgtgacagcag    2170
cccgcctgtaatagcacaggcaattctacaagaagcatgatgaatatgcacatatgtacatgtgacagcag    2240
tgatacaaagacagatgtgttgtgttctagtataattgtcttattttgtccattccaacgttaataagt    2310
cattagctttatggaaatgaaccctaggggatgaaacatacaggtgcaaagtaaatttcctagggactaa    2380
```

```
attataaccaaattatggcaggtacaccctgcatttagcgatataaatatatgtttcaaataaaattgta    2450
acatattgattggcacgtccagccatattcttaagatactttatccttggactaaaaataataataatcg    2520
ctttttttgaatgaagtgttttaattttcagtgtaaaaagtcaggaatattttagaatgctcaacgcaacat  2590
tgcttcaatgagctagggcctttatgaagataagtcactagaaagtctgtgttgattcggttaattattt    2660
gagattgtatgcactgattttcactgtgttaagtatagtggcatttattagaggctcagatgttatagag    2730
agaaggctgtgtccagttatagggctgtagtcataaacagatgggtaaaatcaacacatcattgtaaatc    2800
ataaacaggcaggtatgataaacacataatgataagcatttcagcactgggtgcagtgttgcatgcctgt    2870
agtctcagctactcgcgaggctgacgatctttggagcttaggagttcaagagcagcctgggcaacatagt   2940
gagaaccatctttaaacattaaaaagaacaacaaaaaaacatcatttcagtgtagacaggcataacatg    3010
atctcacagagaaacactacgatttgtacacaagaaaactaagctttgcactggtgttgggagaacattt   3080
tggaatgataaactatttcctgtttgttttaagaaatatttggtaaggtttaaagtagtgtctgcctctt    3150
tactaaaatattccagtatctgtttagatgtcccagttggtcttagatacttggtggtaaacatatatat   3220
acacatatatagcgcatatatgtgtatatatgtgggtgtgggtgcatatgggtgtgtataatctatgtgt   3290
gtatacatacatatatgtgtacatacatacatatgtgtgtatacatatacatgtatcagttgtttgccct   3360
tgtgatgcacacacagatctatatgtgtgtatatatatgtgtctatatatgtatacatgctaatgtgtat   3430
gtatacatatataaaatatgttccttgattcacagtgggattataaaaccccgttgtaaatgta         3500
agatgtcattagttgaaaatgcatcaatacatctaacctaccaaacatcatagcttagcttggctgacat   3570
tgaacatacttataacacttacattagcctacagttgggtgacatcatctaacacaaatcctatttata    3640
aataaagtgttgaatgtttcatgtacactgcagagtagcagttgtttgcccttgtgattgtgtggctgac   3710
tgggagctacagaccgctgcctggcatccaaagagactatggtactgcatattgctagcttgggaatata   3780
tcaaaattcaaaatatgatttctactgactgaatatcattttttgtatcatcttaagatcaaaaatcataa  3850
atcaaaccattgtaagtccgggaatgtctgtgtaataattggctatagtcttaaacaggtgggtagaat    3920
aaacacattattataaatccatcctgtgcttttgaacacatggaggctacccaccaaaatgcctgtgtt    3990
caatatattgcgaacctctaggtatctttttccttcattgctgtttaattttccttctaagcatgaact    4060
tacaagattacttaggaatagcattcatcctttcttcattcctctttgtttaaaacatgcttagcatttct  4130
catccttgaaagaaatgagtagctttcttcttttcaatcatatttcatcagaactattctcttgagggcca  4200
cagaaatgtcataagcattttctctggcacttctgatactttttaatggctttttgatacatcttcatgttt  4270
cttaatcttcttgtgatccttaccatgtaagtgacccgttgagcttatctccaactcctatttttcattg   4340
tctccttcctttatttgaaacaacttacatccagcgtgcacgtttgaagtgtgcaattcaatggcccttta  4410
gtatatgcacaacattgtgacaccagcaacaccatctaattttgaacattgacgtcattccaaagagaa    4480
atcccatacctcttctctcccaggtccccaggagataggcttccactaactatctacctgtctatataga   4550
tttgccttttgggggcatttcatgtaaattaaatcatataacatgctttttttgtgtgtctgacttcat    4620
tcccttaatgtttttgaggctcatccatgttgtagcatgcatctctactcttttattttttatggttcgg   4690
taatatttcattttatggatataccacactttgtttatccatccatctgttgctagacattgggatcatt   4760
tccagtttctggctgttctcaataattgtgccatgaacgttcatgtgcaagttttttgtatggacatatat  4830
ttcattttttcttgattggggatataggagccgaatcgataggtcatatcatgaactctgtgtttaaatat  4900
ttgagaatctttcaaattattttccaaaataggtgtacccattttacattttacccatcaatgcacaaaag  4970
tttttaacttctccacatcctcactcacacttgttctcatctgtcttttttaattatagccatcctaatggg 5040
tgtaaagtgatatcatgtttgggggttttattttttgaatatttacatcattccaaaaagaagtcccgtatc 5110
tcttctctcctacatccccaaaaagtaggcaagaggtaatctactcaagaaatgataccagcttaaacca   5180
gggcagtaccagtgagaatgcaaagaaaataaaaaagaagaggttgttctgcgtgtcttacagatgcaac   5250
aggatttgctgatggattggatgcaaggtggcagagaatgagaatgcattttcctgatgactaatgatg    5320
ttgaacacctattcatgtgcttattggacatgtgtgtaaatccttttggaaaaatatctattcagatcctt  5390
tgcctattttaattggattatctttttcattactgaggtttaggaggggtactttttaagtagtataatgtg 5460
gatacatgttccttaccacatgtgggattcacaaacactcccattctgtgtcttccacctccactttctt   5530
gatggcacattcttattactcatgtttctgaaaacataatcttcagcctcattgaccaatgactctgaat   5600
attgactcatatatgtttaagcaggcttgtccacttactatatctccaagtcccatgttttgtaatcgtgaca 5670
gtccactgctatcccgtcccttgtggctgtctcatcattgtatggagacaatataaggatgccgggacag   5740
ataaagggtattaggatagagtgccatcaatgtgtctgtgaagaagggttcgtttcaatcagttcaccat   5810
gactgggatttgattctgtcaattgctgactcaggaatgtaaatgctgagtaaggcaggacttgatcag    5880
tctattgggggaaggcatcattgaccaaagtgcagtgcaaatttattcattgactatgaggcatataact   5950
ctttataactgtcaatagaaaatggacaaggcatccctccgttcctaaaatacacagtagaatatgatctcacaagt 6020
gatttaaaaaaatactagtaataataagagaaagaggggagacagagagagagagagtgagatagagtt   6090
tctagtttaagtgaagttaaaatgtttttttctatatatacaaaactagctttgccaaggaagatgtagta   6160
gtggttttcattcattcattcttctttcattcaagaaacagatattgacaacctgctgtttgacacatgg   6230
tataacaacttccattgaaaatggagtagcaaacaaaacagagaaaaaatccccaatcctacagcatttc   6300
tatccagtaggggaaaaaacaacgacagacaagtatcgtaaaatacacagtagaaatatgatatcacaagt 6370
gctatggagaaatatttagtagagaagggtgctaaattagaaattttgtgccaaaattttgactaaggtg   6440
gttatggaaagtttcacagataaggcaaaactgatgtgagggagtgatccatacagttacctggaggaac   6510
agcatcttggctaaggaaagatccagtgcaaaggccctgtggccacagagtccctgagaatatcagtgc   6580
agctggaaagtagtggtgaaggggatagtagcacctgatttcagagatgtcagcatgagccacatttat    6650
atgcctttaaaggactagtgtattgttcttagtgagaaaggaaattggctaaagggcattag          6720
gttagaaggttgttgcataatccacccaagaaataaaaggcatttcgatcagaatttagctcttctactc   6790
catgaaactacttatcagttccattaatgccttccactctgcactctcagggttcgatttctggaaaat   6860
tttgaattttgattttgattttccagaacatttagagttctcgatgactctctccttcacgaaaaacatt   6930
ccttacttggtatctatatttgtttctttcctattgctgctaaaacaaggtatcacaacttgttataact   7000
ctaatgttaactctagggaattaaaagcaatgcagatttattatctcacagttctgggtgctaaaagtcc   7070
caaatgtgttcacattcaaagagagaatccatttccttggtttgtctgtttgtcttcttttgaagactgg   7140
ctacatatctctagatctcattctctgtttctaaccttccattttaaaaaacaaacaaacaaaaaacatta  7210
tgattaccctagattcatccagatgaaccgggttaagtctcatcttaagatcctcacttttttttttttttt 7280
tctctctctgagatggagtcttgctctgttgccaggctggagtgcaatggcgcgatctcagctcactgca   7350
acctcccctcccggtcaagtgattcccttgcctcagcctcccgagtagctgggactacaggcccgca     7420
ccaccatgcctggctaatttttttgtatttttactagagacgggttttcaccatgttggccaggatggtgt 7490
```

FIG. 8A-43

```
tgatctcctgacctcgtgatccgctctccttggcctcttaaagtgctgggattacaggcgtgagtcaccg    7560
tgcctggccaggatgttcacttttaaaattgatttattcttattttatttagagatgaggttttgctc    7630
tctcagataggttggagtgcagtgtcataatcatagctcactgaagtcccagcctcttgggtcaattgat    7700
cctcctatctcaccctcctgagaagctgggactacagacatgcaccaccacgcccagctaagttttatat    7770
ttgtttacagagggggtttccaccatgttgcccaggctggtcgttaactccaccctaggctcaagtgatccaccg    7840
gcctcagcctcccaaaatgctgggattataggtgtgcttcctgacaccagtttctgaggtccttgacggc    7910
tgtggtcatagctcatactacctctctctcccctagtgtctaccggacaataagcagtttctgaattgatta    7980
gccgttgcagggttttgactccaaattgcaaaatgcaagctaattaaaaaggagtgaatctatttact    8050
cattttttttttttttagtttgagtgaactgattctcaaaatcagtgaatgcccagtttcatgtaaacc    8120
gtgtttatttccactgtttacactcagcagctgtttctttttcacaaacactggagattccatgttcccc    8190
gaaatatctatgtatacctgtatcataattcattacacataggttagctggaatggagatattttatatt    8260
tgtggcatgcatttgatcttgaattgaaacctgtagtttagaaaaatctacatatctttatattttaac    8330
agattttgagaattataaaagcaaaacagtagagctctacggtagaattttttttttcttaggtctttcc    8400
atgggtattttaaatgtctcattatgaaaagaccataaaccatggttttctaagagttctgctgaatttt    8470
gcaattggctggcacattttctaaatgatcctgtaatctccatgtattagttttctagagcggccataac    8540
aaatgaccacaaatgtgatggctttaaaagagagaaatttactctttctcatagtttgggaaaccagatg    8610
ttcaaaataaacgtgttggcagggctgccttttccctgggtggttccagaaaaagatccttccttgcctt    8680
tcagctctggtggcctcggtgttttgtctctatcttcccaaggctgtcttccctctattgtatgtgtcgtc    8750
tccttttcttataaagataccagtcattggatttagggttataccctcaattcaggataatttatatctgc    8820
agatcctaactaattatatctgcaaagaccctattttcaaataggtcacattctgagtttccaggtgg    8890
acatgtatttttggaggatattacgcaacccactccacccaacacatcattattgcaatatatatgtatg    8960
aatataggtgtttcagatatttacactacacatgtgtgtaacaatgtattcaggatgccacctggct    9030
ttctccttactaggccacactctggcaagaagatctaaggacaatctgggattcttcatctcctttcttgc    9100
atcctctttgcttccaaataatgtagtcatgcagtatctgaaagtttatttcctgagcctttaaaacttc    9170
tccatcagtttgacaaggagtaaaagcgttttccccgttggccacaaaacttgtgcttttgctccagca    9240
atacgcaaagctatatttcacacttccttcttaaattacaggctataaatataaagcaaaaccttttacc    9310
ttggatattcttttctgtcttttccctctgtgattaaatctgattacaaatgctcattaatgctctgcctt    9380
ggaattgcaatttgggcatgtgccatgtgaaaatgcaggttcctaaaaattaaaatcaaagattaatgca    9450
ggttttaaaaaagggtcttattcaaatatatctcaagtttttaaaacgactcatggactttttaatgaaatc    9520
aatggccttgtaatgcctcatttttttttttcaaactcaactgtttcatagccttctctttagaacatatc    9590
tgatttaccagaacccaagatttgtgagatggtgttatttttatcttttacttttcctcaccccacggt    9660
accatgaagagatcgtgtaacatcctttcctggttttaaagacaggtgagtaacgattacataacgttca    9730
aacaagtcaggtgttctccagaagatggtgttaatggtgtctgattcagcagatgctgccttgaccctgg    9800
cggtggtaggacctatattctggtgaaagccaatttaggccatggattataggacctagatggagaaaa    9870
acgatacctaaacctcatgagatcttaattcactgatcggtggagagatattttcttcagatggtatc    9940
atcttattgcatctccagcagagtgtttggccggtgaaataaaaatggccattataaagaagttcttta    10010
gactttaaaaattttactaggatcatgccagaaattcctgctgtagaagtagatatgtatgtgtgtata    10080
catatatatatatatatatatttctgaatttgagatgttgggtattggtagagattcattcatttgaa    10150
tggaaatacgcttgctttacttttggccagcatgaatgctctcatttgccacaggttggcaagcttattg    10220
gtttaaatataaaggatcttgtgggtaagactaacagcaggttttcatagtgccaacatttctttcttt    10290
ttattatcatatttaggaaagtctcttgactctgagatactttatattgtgaaataatagttctggtgca    10360
agtatagattaatagattattaaacacttttaagatatggatggaagagtacaactaggatattattaatg    10430
agtcccatttactattcttttaatttgcagtggaattttcatttaacttttgaatataccaatgataggaa    10500
gttagtagtgtttgcctgtaatttatcctgagctcattttttgaagttcaaatttgaaagcttccttt    10570
gttgtttggtaaatagagattattgtgattcaaaatgagtaatccctaaattgatgtagaaaaagatatt    10640
tgaggctgggcacagtgactcacgcctgttatcccagcacgttgggaggctatgggaggtggatcacttg    10710
accaggagtttgagaccagcctggccaacatggcaatacccgtctctactatgaatacaaaaattagct    10780
gggcatggtctcacaaacatgtaatcccagctacttgggaggctgagacccaagaatcgctggagcctgg    10850
gaggcggaggttgtaatgagctgagattgtaccactgcactccaccctgggcgacaggcaagacttcgt    10920
ctaaaataataataataataataataataaaataaaaagaactttgagatattcatattgtcca    10990
aaaagtataattcaaatacttaatgcagaaggcagtaggatcactaaactacagactcattcatcaatta    11060
taacagatggaagggtcttgttagagtcctggaggctgattgagcattttaaatggcaggttcatagggg    11130
gagatccaggaggtctaaaggtgagggtctacaagcaggaagcacccccactcccaccccaaattcatg    11200
acaacaacactaactaggcagcaaagggatatttcctgatgtcagcagtcagcagaatggtactgaaggt    11270
tgctagataaatgcaagtttttgtagtcactcacctgcaagttataggcaagatattatctgtactccta    11340
caggaaattagccctaattgactgctcttaatcagaacaagacattctaacctcttattcatggttagca    11410
gtatatccccacttgcttcactttgtgattctccatcacattggaataactggacgtgggatacatttgga    11480
attgagtctcaaattcaaatcgccatagaacctgaaaagaaaatgtaagaagagacaaaacagaagaaaa    11550
atgcaggatagagagttatgatttagatgtgttcattctgtgaacagagagcagattctcttggatctgg    11620
ctgaaacaggggcccccctgtgttgtgaaagtggtgtatgtcttcatacgtgtttcccacgggcctggacaa    11690
ccaaccacatttgcaaaaatgaagaaatgaaagcttgtggtcagggtcacaaaacttgacgtggcagaag    11760
tggatccaatttccagtcaaatctatgactcgttccatcttggccacaattatactgcaactcaattgct    11830
tttcttccagtcagtacccacccaccgaaatgtcagctcttcaagggcattaattgttgtttgtttcatt    11900
cattgttgagtcttaggagcctgggacagtacattgaaaatctcaattgttgacattctcaataatacac    11970
aagaaatcatgttttcagatcatggaaatcatatccattaggatggctgttaataaagtaaacgtaaaat    12040
aagaagttgtaatggagatgtggagaaactggaactcttttcacattgctggtgggaatgtaagatggtac    12110
agtcattgtggaaaactctttggctgttcctcaaaaaagtaaacatggaactaccatatgtgatccaaca    12180
attctacctccgggtatatactccaattctacctctgggtatatactcaaaagaattgaaagcaggaatt    12250
ccaggagatatttgtatacgcagtccttaaccatgttattcacaatagctaaaaactgaacttttgaact    12320
agccaactatccattgatggatgaatggataaacaagtgatatatatgtatatatttatgcgtgtacaca    12390
cacacacacacactgctgaaatggaatattattcagccccttaaaagaaaggaaattctgatacatgctac    12460
aacataaataaaccttgaggacatcattctaagagaaataagctacatgctagtcacaaaaggacaaaag    12530
ctgtatgattttaccaatatgagtacgtagagttgtcaaattcacagaggcaaaaagttgaatggtgtt    12600
```

FIG. 8A-44

```
tgtgtgcggctgagaggcggagagaatggaaaattatttcctaatggatagagtttcagtttggaaaggt         12670
acaaaatgttctgaagatagatggtggggacagttggacaataatgtgactgttcttaaggccactcaat         12740
tatacaccaaaaaatagtttaaatgatcaatttcatattctctatatcacagtaaaataaaacattatgg         12810
tatctgtgatttaattgactatttgtaatcatcaccatgttagagcatgttcagtatctcatatcctgca         12880
atattggaatggacatggtaattttgagtggtagaaaataaagtaacttttaaaaacccatctctatgt         12950
attcacataatcttacatttcatataagtgaaatcatcacatctatatctcatttctttctcctaataaa         13020
atgtttacaaggtttacaaggttcatccacattgtagcatgtatcaatcagtaccgcatgctggtttatg         13090
gctggatactattccattgtatgatagaccgcattctgttatgtttatctattttttcatttgatggatat         13160
ttggattcaattcatagagacagaaagtagattagtggttgctggtgcttggaagaggactataggaat         13230
tagcgtgtcatggttacagagtttcagtttgcgaacatgaaaaatttctagagatagattcacaaaaatg         13300
caaatatactaaatgacattgaacagaacagtacactttaaaatggttcactttatgttacgtgaatttc         13370
ctcttaaatagaagaaaaataaagtctgaagttgtcatatccttcactgggatgctctctttaaaagtgt         13440
agaaaggtcctgaaaggagcatataaacaaactaaacaacaatcaaacaaaacatgtcatcgtacccccac        13510
agcatcctgacatggaagactaaaaactgtcccagggctctcttcttcctatctgttactttcaggggc         13580
attttagcttaggatttaattttgactattgacaaccccagtgtctccatttgatctcagagcaaacttga        13650
attgataattaaatttccatgcttttgaccagggaaagactttaggaaatgtctttgaaactgtgaactt         13720
gcagaaaggagaaaattttatatgtatctagcttctatccattccatttgtcatatggtcagaacttaca         13790
tgatgcaagcaggccatttacagggccctgggctgacagctacatgctatattttgtatttgcttccact          13860
attttgttagcaaatgtatgtacttactaacaaaatacgtgttttaagaaataaaattattttaagaaca         13930
aaataatacaatgttttaagaaaacctgcttttatttgcttttttattttttatttaaaaatgtttataaa        14000
tttatgggtgttacaaattcagttttgttatatgggtatattcatagtggtgatgtcggggcttttagtg         14070
tactcatcacccgaatagtggaaccttttatccagtaggtagtatttcatccttcatggtcctcctcctc         14140
cttccacctcctgacactttatagtctccagtgtctattattcaccctgtatgttaatgctgcacctgtt         14210
gtttagctcccacttataagtaaaaacatgcagtgttggacttctgagttatttcacttaggataatgg         14280
cctccacccagtttcatacatgttgctgcaaaagacataatttcattcttttttatgactactactgagt         14350
tgtattccatggatatataaaccatggtatatataaacatttatatatccagtcatctgttgatggacac         14420
ttaagttgattctcatgactttgctgttgtgaatagtgtagtgataaacatatgagtggaggtgtcttttt         14490
gatagaaccattctttttcctttgagtagaaacccacaagtgggattgctgggccaaatgatacttctat         14560
cttaagtcatttgggaaatctccatactatttttccatagaggttgtattaatttaccttcccaccaacag         14630
tgtataactgtaccctttctcagcatctttgccaacatgtgctgcttttttgacgttttttcaaaatgtca        14700
ttcattttcattttttattataattacttaaaaatgatgacttttaacagagaagggaaaaataaagttgg        14770
taatcttttgtagtgccatataattctagttacaagaccacagataagtcccatgctgaagagaggtgg         14840
gtaaaatagctcgtttgaaatgaagcacatttgggaagataaaaattgttttaggatggagtaacgatgttt        14910
gatgtctaacttggtctagtttttctaatgttaagtgtattcttaacatctgcccaaattattcactct          14980
ttaaaccacatgccaaaacattacttacatttacttggtttataataaaatttgggactattagtggatg         15050
atatttactgcaagaattgttaatctggcgtttggatctagtatttagattactttatattttcagctgc         15120
atatgcaactattagatatctgcccacactttttccttccccactgtggaaaatacacactgtattaaggt         15190
gacaggtttttcctattttcaccccttagactttgagttatttctcatcattattaactcatagaacctgt         15260
gctttgttcctggcttcagcttgagcactgtgcaaaaatttatctttataagatttggtcaaaactgttgg        15330
ctgtgtaggcacttcccctagtagaaacttccccttccccctctgaggggttcactgaaaaatcaacttaa        15400
aaaggcagattaattgaagaaaaggcatgcaaatttccttttaatgtggatagcttggcaggaaggattag        15470
gagactgattacccaatatcttaatggagtagatatgcttatatactctacttcctagaggaaagggagg         15540
tgaggactcctggatgatacttaggggggataagtaaatgattttttaggggaattaagtgggcttgaagaac       15610
atacagtggcttagaacaaagtctgttgggcttgcagagcagacagtggtttgtcacaaaagtctgtcca         15680
ggtgtgttgacagacttcattctttcttcctgcgatatgagtccagttactagaatctcgggggaagggac         15750
cagaggtcattgttttcttctttgatgggtccagactttaggcagataaaacaacttcagaaaacaacttc         15820
ctcctgtgctttgggggtcacagagggttgagagacaagagggagtgggagaagatgagagagacgttga         15890
ggcttcttcttcagttcagcacatcaaagtgccatattttgctgtatgggtttatgagtcccaacaactg         15960
ggtagtgaagacaacccaggggctgtgtgttgattgttccgctgcagacagtcaaggctcacttctctggg         16030
aggaagctaaatgccactcagagacacatccccatctcagatgtctttgttatattgatgacagttggca         16100
cccagatggcatgtatcccttgtggtttcaaccattggttgacatgaccttaaaggcccaaggtatgtat         16170
tcgttggtccatttttggaggaatgccatttttacttccacaatgcagcatagctgttaaccattcatca         16240
tgccagtaagagaatccccgggatctgcattgggacagaatccccattcactgccttgtctcacttttgt         16310
agtttgttttgttttgttttgaattgttttagttttttaacaaataatctgaaggtaaaatacaattgaaa        16380
gaagcacttatcttatgatatcaggataagtaaactagtgcagtttcagaaacatctaaccaagtgttgt         16450
tttcttgctggattgcaatattgataggcacatgggataatatctcatgtaaattctgaaacatctaatt         16520
gcatcttgatccttcatcttgaccctcttctcagtgggctgcatttatccctaaacagcaacattctgtc         16590
aattcttaggaacgtgaaacgttacagtctgcagagcaaattaccagcaggagaaaatattactgaatat         16660
tcaaaagcatgccttttgtgtgaatgatcttgaagccccaggggaatggggaaacagggttgggagtaca         16730
taagccaagaaccttatttgatccagcagtttccggcttctaaaacctacccatgcagttccaagaaga         16800
aaataacaaattggcatcacttaatgtttagtgatagaagaagaaaagcatgcctttgttcattttctac         16870
tcttctcatttcctgcttcaccattcctatcaaatgaaacatttcgttttcattcctctctataacttg         16940
tactatttctgtgaatagatgatgtgcttaacatattgatgtttgtgagtaaagatactcttgctatcat         17010
caaagaaatagtatccatttgagaagcatctagtatatgaagagaagttttgttttcattttccctta         17080
tgttgtttttttatattttaaatgtagttgtaaaatgacagaacatgggatcaaagaaacacaaaattc         17150
gtaattaataaatgtgattttgtatttatttttaggtatgcaaggggcacgtttgtgtgggagttcaaaag        17220
catttaaatattttaaatctccctttcattcatttaataagtgtcttttgaggtcagatgtaaacagacaa         17290
cttgttacacatgtttcttgtttttagggaacttccaccccaacatgggaaataaacagagaccctacta         17360
gttctttaacagtttcttaatgaaacaggatatttccctgacccctcacaggtgggaactggagtgcac         17430
tggtgctggaactagccggctgcttccaggccagcgggggtgaaccctgctcactcgctgctctaccccct        17500
tgtgggaggggaagcacaggtgagcaggtacaggagccagggcgaacaatttgggcaccagcaagaatg         17570
aactccataccagccccacggcagcatctagtagagggtagcccgcaacccctgaagacccagaggaagt         17640
gttacactgcctgtttggctttgccatccgcagagaccgtaagtgttaacagctcagtggagggtcaatg         17710
```

FIG. 8A-45

```
tgacagccttttgcacccacactcatggcacgcaagttttgtcctgaggtgggaaattaaagaaaaata     17780
aaatcaaaagaaagagaaataagttttcctgtattaggctgacttttcccagaggcagcaacaggcaca     17850
gcccagacccaggaaaagtcttgataatattatctaatgtgctctggagactctcccagcactccctcaa    17920
catagggagaaggaaaacaaattttcgtttgttttatggaatgagtttatagattcctgttctctgtaac    17990
taatgacttcaagtattctgttttatctaaaaagtacaacgaaggtcatgagaagcctgattaggcctga    18060
actacagctgcttgggcaccatagtgaaggttatgaaataaaccagtgcaaggcactttagagcaaaacc   18130
taggtaacagacatctggattgcttggcaatggtcatatgcggtcctgagtttgtcctgcctctgtatcc    18200
ctgctttcacgccactgtaagcttacttcaagctagccacccccttttgttaagtgtgtatgaaagaca    18270
agtgctgtctttgttccgggcccagtcgttggacgttgagtctgctgggtctgagtgcactcaataataa    18340
agatatcctcctgtatacaccccgaggtctctctctggtcctcctgatcccgcaacagactgacgtccag   18410
gagcaatcaggtcacacgaacaaattgaagatggtaaatgcaggggatttttttattgctggttgaaagta   18480
gctctcagcaggaagggggaactgaaaacgggatggagcaggaagataatcttccccaggagtcccgtcat   18550
ccccggccagaatcttctccaaagctatgccatcaagctgtccctctgaagtcaagccacttctctctga    18620
tgtccaactataatttccgatgtccagctgcttctccccttccaagctatgcctggagtttttatgggc    18690
acaggatgtggtcagggcaggccatgggtggttttggaaaaggcagcagtcgagtgggaaaacaggaat    18760
gtaaattctcactttgggccctggttgcttttggcttgagggtgggcacttaccgggaacccgctctc     18830
ttctgcccagaatttccctgccttctgtccctatcggttttgtatttatttaggtatgcaagaggcacg    18900
tttgtgtggaagttcaaaaacgtttaattatttaaaatctccttttattaatttaatgaatgtcttttga    18970
gctcagatgtaaacaggcaagtacagcttatagctgcagtgaatgctgagaatgaagtactcaaacaatt    19040
ccagctgaacggggcggggaacagctcttctgagagagtgctgccccaagatccatccacctgaatattt    19110
attgagagagcttgtttaaactacagttcagatgaacaaaagacatccaccaggtggctctttgcggttg    19180
ggtcatgaggcacatatgaccttgtaaaaaacactcaaaccacattcttaggaggctgtgttcagcactc   19250
cttatcacacatactccctgtcctgttttcagggacaaggagttctagtctcatgcacaaacaacat     19320
gcacacagtgcctcagtatttttccatgcctcgacctcacgtgtcttctacattagcttgaatatgttgc    19390
catgcacccccccacaggaagtcattacacatgtttcctgatttagggggagcttctaccctaacatggga   19460
attaaagagagatcctactagttctttcaagtgtcttaggtaaccaattagatatattctacacccctta    19530
gtggcaagtgctcatgttgtcaaatttgcatttgttttcaaatgagattaaaacacaacaacaacaatgt   19600
ttaaatgtttctactattagaaaataaaatcaatgtattctatcttggattttttcctttatttctttata   19670
gagttctggtttgcaacaaagttttatcagtagcttatttaccttcccaagagctcgggcaggattttgat  19740
ggtgaatgtacattagtggtttccatatttaaaaaaaaaaaaaaaatgactctgaataagctcccaggct   19810
ctcagtttcttctagttctttctgaaatggtccacaacatgattgttttgaaattgaaaaattaaatgct   19880
tttatttcaaaccccaccgatctaaaaccagtaggtgtacctttcatgagcacacttcattctgcaggtg   19950
aaaaattttcttccaacaattgtctatgatagtgatttataagtcagcaatttgctctaaagaatgtgtc   20020
tctttctaagcatcacaagaagtaatttaaattatgctgtttcttagtaagcatgttgattgaacctcac   20090
atatttccactgattctacactaaacacagactctcttttagttgtactccatttgacttggtttataca   20160
gttcacatagtcacttttgtatgtctaaacttgcctgaccattttactagatggcatggtgatatggttt   20230
ggctttgtcctcacccaaatgtcatcttgaactgtagttcccataatccccatgtgtcatgggagggagc   20300
cagtgggaagtaattgaatcctgtggtggttacccctcatgatgttctcatgatagtgagttctcatgaga  20370
tcagaggattgtgtaaggggcttttcctcctttttgctcagcacttctccttgctaccaccatgtgatgaa  20440
ggacatatttgcttccccttccgccatgattgtaagtttcctgaggactccccagccatgctgaactgtg   20510
agtcaaacttttttcctttatacattacccactctcgggtatgtctttaatgcagcatgataatggaaa    20580
ttgctactgagagtggggtgctgctgtgaagatacccaaaaatgtggaagtgactttggaactgggtaac   20650
aggcagaaattggaacagtttgaagggctcagaagacagggagatgtgggaaagtttggaactttctaga   20720
gacttgttgaatggccttgaccaaaatgctgatagtgatatggacaatgaagtccaggctgaggtggtct   20790
cagattgatatgggtaacttgttaggaactagaataaaggtgactcttgctatgttttaccaaagagact   20860
ggaggcattttgcctggcgttgttgttccatgatttttttttttatgttcaacaggacgatggcacaacc   20930
tagctgcaaggcacagaccaactcccagcattgccaggggcttaggtacattaccaggtcagctgctgac   21000
cagcaggggctgcttttctcttttgtgagtaactgagaattaaataaactaagtaacatgcctcaaatcc   21070
tgcagagggttggagataatactggagtctcaacatagactatatgggaaagtctagcccattaatctcc   21140
aggcttttttctaagaaaccaaacgccaatatttatttgttgcagaaaagggacatcctgtggtcaaca    21210
caatcttcagtggagttaattttaatcaggttcttagaattcaggaaagctggaaaaagaggagttg     21280
tgtaactcacatactgggaggcatcttctgtggccagtcagcagataccatctccattggagagatgcag   21350
gcatcttaaggatgggagaattccatttatagcctaggacttttgtccatgggcctggcttggataggga   21420
tggcccatattaatgtctttgactcttggttttattgttacattctgtatggctgattcagatttgtcca   21490
cactgatatatttgttctctgattctgatcattgtggccatctttcctagaacaaagggcttaggttaa    21560
ttttttgcggagtaatgacattttctgtggcagccaaactccgtagaacaatattgctcctacttcttgtt   21630
ttcttccaatggtaattgaacgtgcaagccacattcaggagtgagggtctgaaattccccaagagctagcc   21700
agcgtaataagtgcaaatctaatacatgcccttgaaacaccaagggataaactcatgtgcatttgttctt   21770
ttggggtttgaagaaccagatgacatgcaaaagaaaaatattgacaaaagatatctcatcgtttactttc   21840
aattattgagtttgattttcatgcattcaaccttagttttttaagaggtaagtgattctagtttgtgag    21910
agccagaagcatgcacaaataaaccttatttaacaaattaatctcatattttcttggttctgatgattgc   21980
atactgctattttaaaaaggttgtgagcaagccaaagttatcatacttattttttaaagtgacagcatgg   22050
ctgagcttttcaaaatatgtttaaagattctaagagaaacagtgttagaaaacaagatgattgacagcttt    22120
tgggttattagatacagaaaattatacttagatttatttaggttgaaaattaatcctacagcatttaaac   22190
cagctgggagagcttgtgcatgcacaagagtgttcaagctgcaacttaaggccattgggcaacagtagaa   22260
agaaaaaaatggttatttcttctctttcagaaccaactgtgactgattaaccacaaaagatcagtgggggg  22330
tattcaggcctaggtcgtcttggtggcaactgggggttttagtttgctttcaggctcattgctggaaaagg   22400
ctgttcagaagcttcctctacaacaagggagtgatgacgtgcgtgagtacaaagcagagaggagttg     22470
ttctacagcaccgagtgggcaaattgtgcagattttttcagtagaatctacttaacaccaatccatgcatt   22540
tgcattttattaaaatgaaactgtgatcatttcaactgcacattgcagacatgccctataaaatgtttga   22610
agtcctgttttggacaaaagttttgaaaacatgcaccccgtatcaatttctctacttatattttgtattt   22680
aatttgtctaaagaatgccacattttcaaagcaagcaggccaagagaatgatctttttttcctctttttt    22750
ttccccagtgtttaaaatgcaactgccatggggctgtgccattttagctgttggaaaaaataatctacta   22820
```

FIG. 8A-46

```
tgccttggttgtatgtctgagtcatcagagcttctgggaatgattctttggcacattctaccaacaattt   22890
aacatgacacaaaatcattttcatatcttgtgatagtgtcagccaagtgtttcatacacatggtgctagg   22960
tgctgaaaaaggtgtctgaataaaattgttttcttaaaggaaccataggggacatgataaaaagatgcac   23030
aattatatatcttttttttttttttttttgagaaggagtttccctcttgtcgcctaggttggagtgcaat   23100
ggtgcaatcttggctcactgcaacctctgcctcccaggttcaagtgattctcctgcctcagcctcccgag   23170
tagctgggattacaggagcctgccaccacacccagctaattttttgtatttttagtagagacgaggtttca   23240
ccatgttggcctggctggtcttgaactcctgacttcaggtgatccaccgcctcggcctcccaaagtgtt   23310
gggattacaggtgtgagccactgcgcccggcctaaagatgcacaattacatttcataaattgagagagtt   23380
tcctaaacaagagagagcatacctggaaatatcagagaaaaatacaaagggcttaaagatgttgtattaa   23450
gcaaagttagactaaggcagcttggatgtgcatcctcctccacttatgtttatacctaagtagagattaa   23520
aagcagaggaattcaatttccacatgacttgtatatgagcaacagatgggagttctaactactgaccac   23590
attggcacatcacacaatgttttctttcaggtttctctacctatggcaaaaccagtgctgtattagagcc   23660
tcgtgagctgtgtgttgttgattaattgacttaacctctctgggcctcattttctcaccttaaaataa   23730
atgagtcttatggtgttttgaggatcaaaagagttactgtacaaacagtgctagtaagagtccctgccac   23800
atggaaaggctattatatatatatatatacgtgtgtatatatatatatatgtgtatatatatgt   23870
gtatatatatatacacacacacacacacacatgtaattttatatattaaatgtgtataatttataaat   23940
ttttgtattataaatgtaaatctgtgatatatattaaaactatgaaatacagatcatgtaatatatacta   24010
cctattgttttttttttaatttgtaaccatattttgaaaattttatttgcttataggtcttgaaagtca   24080
ttccccaatcaacctttattaaaatcccttgattcattggagaatatcaatacatatgaggtattaata   24150
tatataacatatgtaactcttctgagtttataaatgtatgtataaaacataaaaattactaactcttcat   24220
atatatgtttgtatctatatataatttatatatatagatatatatacatatttgtattacatatgaataa   24290
tcatcacagtgtgtctgcatttgttaatctaacctcctccaaccccaccccccaaaaaagcagaaactaaa   24360
aatagaggaattttaagttccacatgatttatataggagcaacaaatggaactactaacttccgaccgca   24430
ttagctaatcatacaatttttttctttcgtgcttttgttgtaaatatgattttatttaagagggtatta   24500
ttgattatctacgcaagaattagccatgttctccatacttctacttcagtttttttaaaaaaggatgagga   24570
tagaccgggcataagtggctcatgcctgtaatcccagcactttgggaggccgaggccggcggatcacttg   24640
agggaaggagtacaagtggcctggccaacatggtgaaaccccatctctactaaaagtacaaaagttagct   24710
gggcatggtggcgcatccctgtaatcccagctacttgggaggctgaggcaggagaatcgcttgaacccgg   24780
gaggcagaggttgcagtgagccaagtcacgccactgtgactccagcctgggtgacagagcaagactctgt   24850
ctcaaaaaaaaaaaaaaggtgaaaaggtgaggattgttatttctgtgggcagggcccacacagcatcag   24920
attcctcagaaactgcaccggtaaatgggaagtctttgagtccctctgacagagcttcaaggggctggc   24990
tgttcattatcccacagcctcctttgctctgtgtaagtggaggctctgtgcctctgttatcttgcagtcc   25060
ctaggtgaccccggcagggagaaaatcagtggaatcaaactcggtagcacagaaaaacgccccaaaggc   25130
aaggatgagaggaaagttgtgatcccacatatcaaagtcggactcttatctagatgggcacacctgagcc   25200
acaggctggcaggctgagattctgcaaaggctctggaccccagataagctctgactgattgcattgtgatc   25270
tcttcttttcatcaggggaggcgctgctttgaatgactaagctggatctgacttccagggaatcctttc   25340
agggactgtgaccatccagctatctttggatggctttgatgccctaattattttcacttggttgaggat   25410
actttttaggtatctgttcatgtgtcatcttgtacagaaatgtgtgttctgggcttataaaaaagtttaa   25480
ttgtaagacaaagggctctaggtttcatatttattcacagtctgatgaatgcacttatggatacgtacg   25550
tgtatacagtaagtgctcactgaatttctcttgagtgataaactgggatacaaaatgtcagaaaagaaag   25620
agtgaggatgggcactggatccagatgtcagtgaactctgagggtctcttgctggttaaaagaacagggt   25690
actttatttttcattctaaaccctgcctgaccccttgcccttatatcagtgaatcaccatctcgatggccc   25760
ctcaaacatggcatctttgaagtagagcctcattgagaaggactcctagaagtctgtcatggctactaa   25830
aattcatatctgtgctttgtgcctgagcactagtacatgtgcagctgtttcttaagcctacattgaacc   25900
attaggtaaagcccagtgtgctcccagttcctaaaatctggtcaagtcttgatgttggtcaacatcttgc   25970
ctggccccagtcagatgtctccagctatctgtaacaggactcagtgtcttgtttacaaaatgcattagtc   26040
atatggcttcgttgctggctttgctgtataggtcaggaataagtcagaaataaccaaaatgctccaaatc   26110
aagttctagctgtttgataccaacatcttccatcaacttcgcttctccctgactcatctgtctgtctgt   26180
tcctgtgctcttcgcacacagaggcaattttgtgtataaagctccccaagggaagaagaggacagtgcct   26250
tcatgggaaactcctttctcttaaataggatttgcatacttaaccagagcattttgcttcagttaaccaag   26320
tgagaggtggagaaattcttgcaaaactatagctacattgagagggattattaaaagtattgactcattc   26390
attagaggagctgttacaaagattgtagcaaccaaagcaaaataaaaaatattgccaaagtattctcaa   26460
acgtattttaaaatgtccaaaatattgggcaagactaacatcaaagaaggtatatgttttgacattgatt   26530
tactaactacttatcagtgtaagtaaatacaccttcaagcacttatttaggattaaggtagtcaagttat   26600
atgagttgtatgagtatgtgcaggccacaagggttgcaaaacatagtgaattcaatatccctctgccata   26670
ttgaatatccttctgccgaacttctgcatcacagttgttggcctgcaaacaggtaacagttgtctgccaat   26740
cccttaggggatcactgcattctataggggcttgaccaggaagtaagagagctcttcccaataagcgatatcg   26810
ttatggtccttgtggttctgctaagaatctcagagaagaaatgaaagatacatgaaattgtttgcatgct   26880
actagctctagtgggtaggttggtagcgtagttcttcatggcaaaagacagaatatatccaaaattttca   26950
ccatttttgcccctggtttgagggatgcatattcctttagaccattatgttgaaaagaaagttaaaaataa   27020
cataagaagaccctcctaagttgtttaatccaagccctcaatcttagcaagtgcctggtgtaaaatgtc   27090
tcattaggtaattacccatctcctgtctacccactaagaggttctagtaaagtacatactggctggattc   27160
aataaagcacaaataggcagcaaatgcttcttacatctcaatctaatcggtagccttctttatcctcacc   27230
cttggctgactaacgtgcataaagcataggaattctggccactcaaggatcttaaccatccagttcagtc   27300
tgttgcaatttctcctccattacaaatttttttcactttcctttcctgggaaagccacagacaggacaac   27370
cattcagtgagaaaggagtgttgaagctgacgtctttcctcgactaagaggagggggccatgagaggaaaa   27440
ggcaacttcttgcgtggctggtggtagagtttaaagtctgatgctactgtcttcctgggagcagcagctgta   27510
cacagttgaactttactttggaggcatatatgatttccagggtttctgtggcaagttccacccactgcag   27580
ttcatttgacttgggttgaatctcttttcctccctccatcacttcagctgaacctcttctgtgatcctcac   27650
ctgttctctagaggtgagaccagggcacagtcccttctagatgaccaaagagcacttctttctatgtgg   27720
ttcacatttggctccatcaccatcgtagctgacagggccaaccctccggcatcttcatccttcaccactg   27790
tctttgctgtgccccataaggcctgaacaaggctgatgggccaagtatggtgtggcagcccccacagtct   27860
gttactaggccttgctttggtagacacacttcttgatttagaaccatggctctcagtcatgggcagttgt   27930
```

FIG. 8A-47

```
gccctgcttggcaatgtaaggagacatttccagttgtcagagtgagtttgaagggtgttaatgcacttag        28000
ttggtggagaccacggttactgttcaacatcctacaattcgtaggacactcatccataacaatgatctga        28070
ttccaaatgtcattgatgctgacattaataaaccctgctctaagttaatgttttttcttactcatattt        28140
aaaatgcttcctctagctaaaccattagcccccagtgaggtataagttttcctctccagggacatttga        28210
ctatgcatgtacatacttcgggttgttacagctggagattggtgatgcttctggcatctaatggatataa        28280
gtccaagatgttgctcaatatactgcaatgcagaggacagcccacgagaacaaggaattatcccattcat        28350
aatgccactagtattaaggttgaaaaaccttggtttagaatatggggatacttattggtgctccctaagg        28420
tgctatctgaaagcagctttgaagacaagcagaggctttgaagcatactcacagggtatgatatagttt        28490
ggatatttgtcttctccaaatctcacgttgaaaactgatcccagtgttggaggtgtgacttggtgggag        28560
gcatttgggtcattggccggatccctcatgaatgacttggtgcagtcttccaggtgatgcctgagttctt        28630
gctctattatttctcaggagatcaggttgttaaaaagagcctggcacccttcctctcctctctctcttgct        28700
tcctctctcaccatatgatctgcgcacacagcagctccccttcctcttccaccataagtggaagctccct        28770
gaggcctcaccagaagcagatgctggtaccatgcttcttgtacaccccgaagaactgtgagccaaataaa        28840
cctcttttcttttctttttattttctaattagagacaaggtcttgctctgttagactggagtacagtg        28910
gtgcaatcatagctcactgcagcctcaaactcctaggctcaagccaccctcccacctcaacctcccgagt        28980
agctaggactacaggtgcatgcctccatgcccagttaattaaaaaaattgtagggacagtcttgctgagt        29050
ttcccaggctggtctcaaactcctgacctcaagcggtcctcctgcttcagcctcctaaagtgctgggatt        29120
acagatgtgagccaccatgcctggaccgtcttttcttttataaattgctcagcttcaggtattccgttata        29190
gcaatgcatatggagtaagacattgtacaagtcccactttgggcacgtctagatctgtctgtgatcctag        29260
acaagttatgtaatctctctttgtgtctaaacctgttgtttgtttctgtcttttattcctcattaggtcca        29330
actctaaagatagtaaaattataggtataaatggagttaagaggggtgccttaccaagagtaaaccctcc        29400
aggagtgttattctgtcagtatgacttggtttttagctttgaaactttagcatgaaactaacatggcag        29470
gaaaaggcctaaattagaattcttcacacacaaaatccttctatcaggaggcagcccatctgttgtcaa        29540
ataatcctactcgtagaaatgtattaaattttttctttttccttcccttttcccccttcattaaatggaatt        29610
agattgtgacactatgaggaaattaaagtgaaggtaaaataaaacaaacaggaagaagtctgtcttcaga        29680
ttggatatgcaattatcctgtcttactgctgatttcaattataactcattggtgttaccagcccacgat        29750
agatgtcccctgcctatgtggtgtttaaatcaagtgttggcatcattcacacttgtttactgttattagc        29820
actgatggatgtaatcttcatgtcttcctctgaacactgcatgctgagaaaggggccttatttcctcgtg        29890
gatttctaggcaagagaatgtcaggccctcacctgtcctatttccatctcactcagCAGAAAACACACT        29960
GGCTCATGGAAACTGCAAGCATCGTTGTCAGCTGCACCTGCAGGCACCATGGGGTTGCAAGTCAGCATCC        30030
CCTTTCAGAAATGAGGATGGAATTAGAGgtggaaagaaaattctccacagtcctctcacttctctgggct        30100
tagacagggaggtttctgctatgttttcattgattatgctgtgggggggaagggagaggaggaatcccta        30170
agaagaacaatgtctcattggatattgttcctttgggggaaaaaaaaaaggaaaggaaatatttttcatt        30240
ttttcttactttttctaccctagaatctcaagctcaccttcaaacattgaatctcacagggagaaggcg        30310
gccacatatttcaccccaaatgctaggccatgtcttctcatgtcagaaatgccctattgtgcgtgtgtc        30380
cttgttgcaagccatcttagacttgttgtttcagggataggaaaccattctgcaatccaaataaggttg        30450
catttcttgcaattcaaaataaaaggtgtgcatgcacacacgcatgtgctggtattattgtacagcttgc        30520
gtggtgcaaggctgaaggctaagggactaatggaggctgaaatttagccctagatacactctgcaagctg        30590
agtacctgtggggccgtattacctggctagaggtgtgcctatttctcatgcatccagtatcaggtactt        30660
tctgacttagagggtccctcaaccctctcctcctttcccctccacctatcgtacttagcatactgtatatt        30730
tgcccttagtctgtttcatccaacttgatcacttggtagcctgtctttatccccactgtctaaatcagta        30800
tttggaatgtagtagggacacaaaaaaaattagttgaataaaggaataaatgggtgaaatagtgaatgca        30870
tgaaaaaggaaaaaatgaatattttggctgctgtgtattcttgtattgttgttatatataattcttctgc        30940
ctgtctttcttcatacatacctcattattagtataaactaccagcattcgtgatatgcaggtctttgctt        31010
ttgcagagagcatgggtttctctaaaaggcatcttcgacccttcccgcccagggtgtctctgtgcagcta        31080
acctggttgctaatctctgcaagctcgtactttttctgcagcacgtgattctgttctcatttactcttgt        31150
aatccttctgtttccttctgaccagcttgagcttctgtatctagtgccttgacgttctcttttctttcttg        31220
gtctttttaacattattatgtcagttataatgttttcagttgcttttagtattcagaaaattcttgaag        31290
ccttcttattgcccactggtattttgtcttcgccgcttgttgtttgggtggatttagatatagcagagag        31360
agagagagagagagagagagagagagagagggaaaatagagacagagatatgtaatcccccccaaccaac        31430
cccgttatctgtgatttccattacccatggttaggttagtacagtgatattttgagagagagaa        31500
agagacatcacattcacgtaacgttttattagagtatatattgttacagttgtatttttattttaattgtt        31570
gttaatctcttactgtgcctaattttataaaataaacgttatcatgggcatgcaggtataggaaaaaacat        31640
tgcatatatagagtttggtactgtccacagcttgaggcatccaatgggggtcttggaaagcatccctcac        31710
tgcccctggtaaggaggagctactccagttttgagaggagaaactaaacagatatgaaaaacatacaagt        31780
tgtaacctaataggaaaaattttaaagtgttattaaaaaccatatcttatatatctcatatattaaagga        31850
cttcacaatggacttttaggaaattaagatggaagttgcaatagcaaaagtttagcaatgcgtattcttac        31920
atatgaaaatcaaaattaacctagcagtgttctgagcaacttcactttaagaagtaaaactagtgaaatg        31990
ataaaggtatatgggtgctgactgttacgtaattaggctgatataatttagcaaggatatcagaaatcat        32060
atacccaaaatgagctttattatattcaaattagtcacttcagaggcagtacactaattacaataaggta        32130
agactgctggaaacttctttatttctcctcacttttaaaacgtttcagagcccatagtaatttatttttaa        32200
tatcttgctgaggcaagtcttaatccttaaggaggcattttatatttggatacagcaggttctgttgag        32270
taaggtcagtgaccacattgtataacacaatttttaattcaaagacaaggaacagctataaataaaggtga        32340
gcttgtttcaactaactcttttttatttttttttttttttttttttttttttttttttttgagacaga        32410
gtctcgctctgtcgcccaagctggagtgcagtggcatgatcacggctcactataacctccacctcacagg        32480
ttcaagcgattctcctgcctcaacctcccaagtagccagaaatacaggcacgtgccaccacgcccagctg        32550
attttgtattttttttagtagggacggagtttcaccatgttagccaggctggtctcgaactcttggctt        32620
caagtgttctgcccgccttggcctcccaaagtgctgggattacaggcgggagccaatgcgcccagcctca        32690
actaaaccttaaggcacattgaaaagaaaatcaaaatgcattgagctaaatgccaggcatatgcctttcc        32760
aaatggacttgccatgaaggatgtcattcctgtgcagccaggtgttgtcttctatgtattttagaatgc        32830
ccatcatatagtctcacctttttaaagtctgtttagtggaatgttttctaactttcccatgtacctcccat        32900
gtcattttttgccagttctgccttccctaataaccaatgaaggtacttgcttcatgttaaattctaggta        32970
atctggtttctactgaattagaacattcccacccgccaatgtctttgaataattaaaggttttataatgt        33040
```

FIG. 8A-48

```
ggtttccatacaactaactgaatatttcatgtggctagataaataggtaaattgcagtacagtagcaatt    33110
ggtgtagacacttagagggtcctaataaattattgcacacgccaatgtgcaatcagaaagaataactgta    33180
gtgttaagcctcagacaatgctatagacctgaggatgggcctgtgatggacggatcaatggctcagttcc    33250
tattggagtttcacatctaggaataagtgaattcacgactattcatcagctgctgctactgtacggaagt    33320
gtgtccattgagaagttgcagaagggggctgggagattggataaggcttttgcagtacccctccttttaa    33390
aaaagcagacagggtgtaactctattgcaggctggagtgcagcgttgtgaccatggctcaccgcagcctc    33460
caactcctgggctcaagtgatcctcctgcctcagcctcctgagtagctaggactacaactaggcaccacc    33530
ataccaagctaatttttttaaataaattcactgagacagagtcttactatgttgcccaggtgggtctcaa    33600
actcctggcctgaagcagtcctcccatctcagcctcccagagtgctgggagaacaggcgtgagccacggt    33670
gcccagcctcaataccttttaaattaacaggaagtggaaaacagaaattctgcagcatgttttttctcatt    33740
agcatgaatcactctctggtgatgtgttcatggtttctaatggtattttcaagatggacaatataaagac    33810
aaccattagaaaccacaaataataggggccatatgaaacaatataatagatgcatgaggttaactggtcaa    33880
catttatgctgaacttagatttacactgattaaaaaaaataatccatttgaagtgtaacacacagaaacc    33950
aaagttctgtgtgttctgttatcttatattcaatgctccatgcaatgtgaaagcttaaggcaagtgtt    34020
tctataaccaacacccatgtgaagaaatatagtttccatcttcaaagcagtgcatgctcttttcccattc    34090
tatctccttatcctcctccgtgataaccattattcccttttactactcatttccatgcttttctttatat    34160
tttcccaatgataaaggcatccctgaatcacataattaaattttgcttgtttggagactctaaatgaatg    34230
caactttctattacttctggtgtgtttttttcatgcataatactgttttttataaatttcatatgtgttgc    34300
tgtgtatacatccattccactcattttaattgttgtatagtgttctaaagtctgaacataccacagtccc    34370
tatgtccatttattcctaatagatatggttattattttgagtttgaggttattataaattcgtgttatt    34440
aacattcttttcaggcaccctcctttctcacaagcattggttttctgagacatataccattatggaatt    34510
gctggttcaaatcttcaactgtatagtttatataaggatgaactgttttccagtacagaaatgcctgttt    34580
tcaccaggagtgtgcaatcttcaacatgtggcagtataaagttctattttattttctgatctagcgtg    34650
tgtacatggaaacccattgtgtgttcactgtgtttactctgaggttgagacatttccatatatctcttgg    34720
ccattcatatgtcctgtttggtgaagcgtctgtttttgatctgtttttctactgggttgtgtgtcttatt    34790
gctgtatttcgattagagtgcttcactgattatatatgttgcaaatatcttctgattttccttccatgtt    34860
tttaatgatttatttaaataagctaaagttcttaatgttagtttatagactttacaatattttctttcag    34930
attagtgcttttggaattttttgtttaggatatcttttcctaccaagagatgaagatttccttttattt    35000
atctgaaaaaagcttaatatttttatctttcatattgaaaccacacagggaatatattttattgcattctgt    35070
aagaggtctagtttattttttccttagaatatcacaatacaatttattttaaacagtttgatccatgtcac    35140
taaagttcaagtgatctctttgtctacctctgtgccaatcatcacatttttatcttcatgatttataat    35210
aatccgcaatttatattttatactttgtttatttcttgccaatatgcattgcatccctgagaaaagtgt    35280
ttattttgcgatggttggtgcaatgtgctatatgtctaatatctcaaactgttgaagtatgttgttcaca    35350
tactctatatagttttccaggtggtagtttacatattctttcagtaactaaaataggtctattaaatttt    35420
cccacgatgtttatggatgttttaaaatcttttcgtatattttccaaaatttagtttcttgcatttat    35490
atgcttatgaatttagtggatacagtctagaattttattgcattgtggcaaattaaggttcttctcat    35560
tataaagtgatcctctgtaagtctgtggtgcttcatgccttaatgtctgtttagtttgacgttaacatta    35630
cctttgttttgttagtaatccaattgtgtatagttcccatgtgtttacttcaggcctttctgttgactca    35700
ggttttgagtcttttctacatagcgtctatttgggtctcataatctttgattttcaaccgcagatccact    35770
gatatttactttttattttgatatatttgtgtttaagtcttctatcctaaattgtgctactaatatccca    35840
cttctacatcttgcttgaattgctttttaaaaaatcattcaggccaggcacagtggctcacacctgtaat    35910
cctagcactttgggagaccaaggcaggaggatcactttagaatcctccaggagttcaagaccagcctgag    35980
gaacatagcaagacctcatctctatgaaacataaaaaaaataaataaataaaaaaaataaattagccag    36050
gtggtggtgtgtgcacctgtagtcctaggtagctccagagataagagttgacaggagagtctgatcccatg    36120
agttccaaggctgcagtgacctatgatggcaccactgcactgcaacctggatgacagacaagatcctgtc    36190
tcagaaaataaagaaataaagacaaataacattactccatttccttcactcccacttctccctctacac    36260
tagatgttaaaagactgtactagtttagtaaataaccctagaaattacaacacagatcctaatataat    36330
cactaattttaattaatacattttccacttctctgaaaatacccagtagtcagtgtatttagctccatg    36400
tttatgacctaacctacttgctgttagtaccttcaatgtttgtgtttttttaggaatctttttcagata    36470
tgattgcttatcttattatttcaatattaattttgattttctgatgattacactattttatttatgtttc    36540
attacttttttgtacctcctactttttatctgtgattattgtcttaaaagaatctatccggtcgatctaaaata    36610
tattttcagagctaacaagctgttggaaactctgtttgcatggctaaatgtgtctttatgacatcctctt    36680
cttgaacaatattctcattgaattttaatttgcaattacttctttcagccatctgagaaatcattctcct    36750
attctctggattccattattggtatggagaatttagctgtcagtttaagtgttgctcctttaaaaataat    36820
atattttctgcagatagtttgtctatatccccctgatacctttaagatagttttctttgagtttctgcc    36890
gtttcactgtgataccattaggggtttattaatctgattggaattccttgatgaccttgaaatttgcaat    36960
cgtggtttcttccattctgaaaatagtcattacctcttcaaattttggtgctgtttctcttgttttcact    37030
ctgtttgcacataatttagattttctccctctggctcctttttagtcttttttttttgtattttgtat    37100
taaattttactttcaagcttcattctggattactttttctcaagacctataatctatttcattaattctc    37170
ttttctactgtatctaatgcatggtttaaaccaatgcatcaaatctttatgtttgatatatattttcatta    37240
catttcaaggattaatttttagtttcttcttatagtttccacattttcgaagttctcaattttatattttc    37310
tggaatgcattcttcctagttatttttaaagtctgcatttgtatttctattttttcaatcacccttttg    37380
tttcttctcttttttgcttttggtttcattgactaatatcttcatggtctaagtattataattatgca    37450
tatattagatattctcatattgttttccttatttctaactctctatttatatttttgtatatgacagc    37520
tccctgtgttgcccaggctggagaggttgtgctctgtgcccagtggcacaatcatagctcactgtagctt    37590
cgatctcttgggctcagtgattctcctgcctcagcctcctgagtagctgggactacagtcacatgccac    37660
catgcctagctactattttatactttaaaattttttagagactaggtcttgctttgttgcccaggctct    37730
tctctaattcctggcctcaagcaatccttctaactcagtcttttgaatagttgggattacaggtgtgggc    37800
cactgcacccggtttcccagctttttcagatttccacgatactctctggatcgtttcttctcacctctt    37870
ctcaagtttgtccattttctcttcagctttgtttaatctgcccttaggtggacccattcatttctcat    37940
tttgtttatttctctgatctagaagtttgatttgatttttattttttcatttttaatactttcttattcc    38010
ctgcagatgttttccaacttttttgttttcaagcttttgaacattcttcaaaaaattggttatcatgtat    38080
atattttcatggcatcttaattcctttgggatttctgctggctcttgttggtgacttcttgtttctttct    38150
```

FIG. 8A-49

```
tcatgggcttggtaatcattgtgaattggccattgtatttgcaaatggattagtggcatctttctccaaa        38220
gcagataacccatgggtagcgaaattctaggttctttcatccatggggccatgctcttccctgaattgtt        38290
catagatgttatgaaggtagactgcaagcacttgcaagactgaatttagttttgtttcatgtttgccttg        38360
agggtgaaacccatgaaggtaggaaaatgttaaaggcaagtatattagattgggaccttcaggcgtgact        38430
agggtctgagagttgccccattacatggtgatgctgcaagaactcccacagtttcttccagattggaaca        38500
gtgcactagggcaaaggctgctttgtgtgctgggcatctagctggatcatcatttggtcgtcagtgtgtt        38570
tttgtttgtttctttgtttttttgtttgtttgtattgtgttttgagacagggtcttactgtgtcatccagg        38640
ctggagtgcagtggcacgaacaggggttcactgcagcctcgaactcctgggctgaagacttcctcccacct        38710
caccctcccagtagctgggaccacgggtgtgtgccactacgcctggccacttttaaaaaattttttgt        38780
agagacaaggtttcaccatgttgcccaggctgtgataatcagttttgaagctgtaatcttaaatatgatt        38850
ttagcactaaaatgttttaagagacttaaaaaaatcacacatattacaatccattttcaataagaaggt        38920
tggtttgaataatctactctgttactgctagatgtaggcttctgatttattctaatatattacagaaatg        38990
agtaggtggaacatgagtttataaagataatgcaaatattttattagcactgtattctcttaagagcagt        39060
tcagagttcaaagaattgtgactttatttcacaggcattaaaataaattaaatcagcaatctcattccta        39130
acaactcaaacttcaaagaaatttcagacagttaatcatcacctgacaccacagcctatgcaacttgggt        39200
ttaattaggatttatgttactggtagcattgtggttgaaaagatattttcattaacatttctctctgaag        39270
cactgagtcatactccttgtttattcgcaagtttctttacactttacatatttgagtgttccttgg        39340
gaaatgtatgtttggctattttggtgtttttgagagtgtttgatctttgaaaatgcatgattaaaagcca        39410
ttttagaaataaacatgagtgttttaaatacaaattactaaagccactgttttgtttcaaatttagggat        39480
ttaatttttttaatgaaaatgctcctgtttatatatgcatgaggttatgtaaggtcatcaacttaaagat        39550
tgatgatggatttagtgccagctgttgattagtatgtctgcaatcaatctacaacatagcaataacgcta        39620
gctaccttggagagttactgggagaaataaataagacacataatgtatgtaattggcctagcaaacttcttt        39690
gtatactataattattcagtaaataatacccttgtgattatttatctatcaatcagtcttagagcagta        39760
atttacctttaaaatctagacacattaggaaagaataatggtagatttaagacaaaattaaaatttctt        39830
ggtgtactcaaaaatatatattttctgttaatgcaaattaggcttttatatttattattttaatatttg        39900
actctggaatgttttcaaaatttagttgagtagatcttaatgcaagtctacttttaaaaaatctcattat        39970
ctagtaggcttactagtaattaatttgaatttggtagacatgaacaccaattcttgtgtacacaatc        40040
ataaatcctgtatactatgtatactctgtatgcctgtatcttggtgaagtgggaattaaacttttatcaa        40110
tttccattgaaaaactgaagagcaaactaagatgtaatcagaatgttaataaatattgtagaaatggaaa        40180
agtttcagaatgtttagatttctcaaggaaatctcaaagcatgacacttttcattggtctgtcatggata        40250
attaggtcttttgctatttttatttatttccaatccgtcacaaacgtactttggttgatgcatata        40320
tcaactatagagtagtaaatctgacaaagtctatgcactgaaaactatactctgtcactgagggacactg        40390
atgaaggcttaagcaactgggagacagactgtgttcacaaacacaacacccctcctgagaagatacaatat        40460
tgttaagatatttattttgtacaaattaatctacagactctttgcaatcccaaataaaataacagtagac        40530
ttttagaaaatacataaattaacaagataaatttaaaattttaatgaaaatcaaaagatctacaataac        40600
caaaacatttttgtagcagtagaacatacttggagggctcctgctacctgagctcaagacttagtataga        40670
gctatattaattgaaacagcgtattattgacataaagatgtaaaacctgatcaatatcatagactagaga        40740
caccacatagaactgtacatatatggacaatgaatttttccaagacgcaaaggtaattctatgcagga        40810
atgattttttttcaagaaatggtgttggaaacattaagtatccatatacaaaagaaaagaaaaagtaaa        40880
caaaaagctttgatctctataactcacaatttgtacaaaaaacaactgaaagtgagtcaaatacctagatg        40950
taaagcttaaaattgtaaaacttccaggagaaaaaaaaaaaaagaaaaattttgtgactttagattttg        41020
gcaaatatttcttacttaaaacaagaagcttgattttaaaggaaccaattaatacattggactacatca        41090
aaacttaaaaaaatgcttatgctacatgaaagacattgctaagggaatgtaaagagaattcacaaactgg        41160
gaggtaagataggcaaattaaatatcggatgaaggtattgtaccagtataaatgtatgcatacatacata        41230
tatatgatgcagtttcctataaatatatagtatatatgtattagacatatatgtatagacacgtactgg        41300
tacaattatatactatatatacaatattcatatatagtatatatgatacagtattgtatactatatataa        41370
aatatatcatatatttaccatacagtatactacacatatgtatatatgatatactgagtatcactatt        41440
actaaaaattacagaatgtgaactatgaaaatgtaaaagcctatttaaataaaataaatatttaaaatac        41510
tgtgttttttatatatagcacatgtatctaaattgtatacagtatagtatatagtatagtatcgt        41580
atcatatatattgtcaatatagtatataatttaccctgtgtgtgtatagatgtgtgtatatgtgtgtat        41650
atatacacatatatgtatgtgtgtatatatacacatatatgtatgtgtgtatatatacacatatat        41720
atgtatgtgtgtatatatacacacatatatattctaaaggagaattaaaaagaaccaccccataac        41790
aattggacagaaaattgaacaggcagttccacctaggaaaacatacatatgaccaatagcccaatgaaat        41860
gtgctcagcatcattagtcattggataaatgcacaaatgaaaccgaaatacactacacatctga        41930
gaatggctgaagccacaagactcgctatgccagggcttggtgaggattggaggagctagagtccacccc        42000
aagctgctggtgggaagtgatatgaaaccaggacttttgagaagagtttggcaatttttttgttgttaa        42070
acctacaagtaccatgtggttcagccatttaactcctaggtatttacacaagaaaagaggagcatatgt        42140
ccataccaagaccaagaacctgaatgtattcataggctggaatgcttctgagcagtaaaaatgaatgaac        42210
tgttggtgcatgctacaacctgcatgaataattaaaatgattatgccaagcctaagaggccaagcaatgaa        42280
gagaccgtaattctgttacttcgcttttaatattttggaagctgtaattcataatgcctgtctgtaagca        42350
gataactgtttgcctgagatgaggaggaggagcaagagatatagattataaagggatatgggtaaacttt        42420
gggtgtgatatatatatgtacatgtatatatgtgtgtgtgtatatgtgtataaaatacacatata        42490
tgtatattttaaacagagtctcactctatcacccagggtgaagtgcagtggcacaacctcggctcactac        42560
aacctccacctcctgggttcaagcagttctcctgcctcagcctcccagtagctgggactacaggtgcat        42630
gccaccacgccctgctatgtgtgattttctgtcacctttgctgtggtgatggcttcataactgta        42700
tacataagtcaacatttattatactgtatactttatgtacagtttatacttttacaactataacttcaga        42770
aacccactaccctattttaaaaaagttaataattactctcagccactgtgagacctcactgtttccttat        42840
gctcattttccctttaacaacaatggggaactagtattttatcagataaaaataatgtttgataggatt        42910
ttgtgcaaagtctgttttgcctactaattctgccttatggcatctcagacatgtaaattagacaagagcc        42980
ttcagtatgtctgatctgttgtcacgttatttttccactagtttgtgtgattttagattatttttaaagagc        43050
tgataaaggaaaggaaaggaagagagagatagaagaagaaaagagagaagaaaagagaaagaagagaag        43120
gaagggaaagaaagaaagaaagaaagaaagaaagaaagaaagaaagaaagaaagaaagaaagaaagaaag        43190
aaagaaaaaagagacgcctgtcttttaattccagttggaagcagctttagttataaaatttccactct        43260
```

FIG. 8A-50

| | |
|---|---|
| ctagaatattcttggggaaaaaatgaagtgtcaattaaattgattttttaacttgcatcctatgtctct | 43330 |
| gaacatgattcttttcaatcaggcatgtagttattgaggacccatttatgagctgtgcatacatcccat | 43400 |
| ccaattccatccaattccgtccaatcctgtccacagacatgttgaaagcatgagcttcctgcaagagcaa | 43470 |
| tgcaccagccgttttcctagagatgggtcttcaaagagagggttctttctcggagcacctgctcagggaa | 43540 |
| caagactgactttaaaccagtgttagcaatatgcatggtacactgaaccatctgctggaggacctccttg | 43610 |
| tgtccaacacagtccttctgttgaatgtcatgaaaagactgagggttgaagcaaatcattttatgcagt | 43680 |
| gaggagaagaccgtgctcatctttcagttttgagccacatctacctaatttatagtcaggtttggtagc | 43750 |
| ctcagcactactgatatttgctgcataaatctatgctttgttggggttgtcctgtgcattttaaggtatt | 43820 |
| gaatagcatccccagttcacacccaccagataccagtatataaatatataccgttttgccaattaaaat | 43890 |
| gaataagaaaaaaatcattgttacagattaataataataataataattaataataagtggctggacacag | 43960 |
| tggctcatgcctgtaatcctggcatttgggaaggccaaggcaggaggatcccatgagcctgggaatttga | 44030 |
| ggccagtctgggtaacatagtgagaccccatctctaaaaaaaaaatgaaaaattagccagcatggtgat | 44100 |
| atgtgcctgtagtccaagctactcaggagactgaggcaataggatcacttgagcccaggtgtttgaggct | 44170 |
| ccagtgagctagctattgatggttccactgcactccagcctaggcgacagagcaagacctggtctctaaa | 44240 |
| aaataaaaataagtaaataagctaaatgctcttgaactgaaaaaagaatgtattctatgagagatacct | 44310 |
| gataatcacctactttgaccatgttttatccttcaaggatttcaaactgttacaacaaacttctaaacg | 44380 |
| tgtatctcttagttcagcttccttacatgaatttaatgctccagtatgtgagaccaattattgatttaa | 44450 |
| aaaagggtagatctgtttttaaaattccttaccaatattcctcatgctcatgagaaagatatgaggcagt | 44520 |
| gctgttgactgcatttgtatttagttaataccacgagcaagtgggaaaaattcagaagtgacactgagtt | 44590 |
| ggtcatctctcaattatcatcatgagaagtacgcacaatgtgaacattctgccatagggcttgtctctgt | 44660 |
| aaactgctggtcaaggggcatggacagattctactattttaaaaacatctttctgaacagataacggag | 44730 |
| gcttaattgtagtgtaaacacactgatgtacaaatctcgaaaaacataaaataaagtgtgttgagattgg | 44800 |
| aggtgctctgttcaactttcgagggataaaaatatgcctatcagctgtaaaagcggtgcattttattttc | 44870 |
| attttttgagaccaacactagagcagaaagacacattaacaaaagggtaagagtcttcagagcagattac | 44940 |
| tcccacttgaaaaatgagttaagtgattcacagcgggagagagggatatttgcagcaagaagtttcatt | 45010 |
| agtcactgaatgaggtttctctgacatatatttttcacagaatgagaagcatgatctttagaagcaagagc | 45080 |
| cataaccttctatatttttcttctgttttattcattttgctggaagattcccttccctagccttctggaa | 45150 |
| atttcagccttctagtctgatttggtgacctttgttcactaggaagaacatagtccgtttctctttgcca | 45220 |
| aaaggtagttgcatgcatttgcaatttaaacaaggaacatccaaaaaaattagaatgtgtgtttgttgaa | 45290 |
| aatattgtgattattaaagtcagagaagatagctaaaacagaagatgcccatactttgaaatcagatgat | 45360 |
| tattaatagatgctgctttgtgttgactggagtttaactgccagtccttcttttgccaagatattttcc | 45430 |
| caaaagaaacatttcagttgtaggctcaataaggagactggaatctgctttgtgaattggtggcaaaagg | 45500 |
| aaaaggtggggaaggtaggagaagaaaagagagatggagccttcaggtaggagactacttttttcttcctt | 45570 |
| tggtgtctcatcttaatatttaaaaaattaaattgaagactcagctaaggtatagaaaaattcaggctttt | 45640 |
| ttcttttttgacatataaccaacattatctcttgtcaagcaatttattttttttattttattttttaattt | 45710 |
| tctaataagactaggtttattcagtaccctagtaaaagttttattataagtatccaacagtataaaaag | 45780 |
| tacaaaacagacctgtagatttctaatatattaatacaaagtgcttattttttaaactgctttttttttt | 45850 |
| ttttttttgaaacggagtcttgctttgtcgcccaggctggagtgcagtggcgccatctcagctcactgcaa | 45920 |
| cctccatctcccgggttcaagcaattctcctgcctcagcctcctgagtagctgggattacaggcacccac | 45990 |
| cactatgcctggctaattttttgtattttagtagagatgaggttttcaccaagttggccagcctgctct | 46060 |
| caaaactcctaaactcaagtgatccacccacctctgcctcccaaagtgctaggattacaggtacatgtcac | 46130 |
| cacgcccagctaatttttgtactttagtagagacagggttttaccatgttggccaggttggtctacatg | 46200 |
| atgacttcctaaacaagtgcataacttcgattctacaaaagatgacagaattcattagtactactcgttt | 46270 |
| gtcctcagttatactttctgcagtttcagttatctacggtcaaccatggtctgcagaaaattccagaaat | 46340 |
| aaacaatgcatcagtttttacattgcccttggttgtgagtagcatgatgaagtcttccagcagtcctgctcc | 46410 |
| ctcccaatccatcctgcccaagaggtgaatcctccctctgtctggcattttcatgctgtagagactgcct | 46480 |
| gacccttagtcacttagtagtctgctcagtgaccagatcatctgtcatggtactgcagtgtttgttctca | 46550 |
| agtaacccttatttcagttaacaatggccccaaagtgcaagagtagtgatgctggcatagtgttataatt | 46620 |
| cttctattgtattattagctattattgttaatttcctgtgactaattgataaatttaagctttatcatagg | 46690 |
| catctatgtataagaaaatgcacagcacatataaggttcacagtgctatctggtttcaggtaaccactac | 46760 |
| aggtcttggtacgtgtccccgtgggtaacggaggactcctattgtctgtgtttatttgaagggatttt | 46830 |
| gattcatttgtgatctgtttcacgccctcttcctttttctcctctggcaaatttgagttggcatgccctcc | 46900 |
| acttaatcttttaaatgcttgatccattctattctgcagaagaatgttaaattttttcattatgtcagtca | 46970 |
| atatgcttttggaaaaagggacactcctgtttgtgtttcctctttaaattcatggtttagagttttctcc | 47040 |
| tcttccttgcttgagcctccccaactgcagtgtctcctcagtcctcatccccatgactgtggatgaa | 47110 |
| actccatcttgttttcttcaatgtgctatttctcaagtttacatctacaaatgtgctgcaaatatctgg | 47180 |
| tactgaatgatgtttcatttcagtgaagcgtttgtttttgtttgtttttgaaagttaattgtgcatgtggt | 47250 |
| ttaaaaaatccaatataacaaaaggcatacagggacaccatttgaccatgccattccccaccccttcatt | 47320 |
| cagttgtttcagcgaccacctttctttgttgtggcttgagaatccttccagagacgtgactaaacagcca | 47390 |
| tggaaatgccagtgcaacagagcattcttacatcttgcttttccacttaataacataactttgaggtt | 47460 |
| gtcctattttgacacatagacatccacctcattcttcaggaagcctctgtcacaggcacatatatgacc | 47530 |
| taccataattcattgattggactgccatggttggacacgaagattgtttccaaatacttgctaccataaa | 47600 |
| ccctagtcagtgaaacttccttcacacaccttttttttcttttttgagagggagtctagctatgtcac | 47670 |
| ccaggctggagtgcagtggcacgatctcggctcactgcaagctccgcctcccgggttcacgccattcccc | 47740 |
| tgcctcagcctcccgagtagctgggactacaggtgcccgccaccacacccggctaattttttgtatttt | 47810 |
| tagtagagacggggtttcgccgtggtagccaggatggtctccatctcctgacccttgtgatctgcctgcct | 47880 |
| tggcctcccaaagtgctgggattacaggcatgagccctcacacacctttgagtggggtaggattccat | 47950 |
| atctctatttttaaatgtatatagatgttattgagttttagaggactaaacaattttagcttccaagcataacc | 48020 |
| tataaatgcatcttggccactttcttgccaacagagtgtgttataaagcatgtcattttttgtctgtctca | 48090 |
| ggtcagtgaaactcctgtaaaggaccagatagtaaatgtgagccacatggtttctgtcctgactactcaa | 48160 |
| atctgcccttgcagtgtgagagcagcaatagatgatttgtccatgagtggtgtggctctcttccaataaa | 48230 |
| tctgtatttacaaaaggaggtcctggccaggtttgcttcctggatcatagtttgctgaccctggtctat | 48300 |
| ctaataacaacaataataatctttagtttgttctttttgtatgagttaggctgttcatctgtttaaaaat | 48370 |

FIG. 8A-51

```
ctacttaggtatttttttcctgttaattacatccgttgctcatttttgcataatgcagtttaactttctct         48440
tgttggtttattaaaagcaatctatatatttgaaacttaattacttttatatattctgaaaaataattga         48510
tctgttagctgttgcaacagttggctttctgataaatttctatttgacatagaaccaagtaaaaattatg         48580
ttaccttgggttgtaacagttactcttaaaaacatttagatctgcaaggcacagtgtctcatgcctgtaa         48650
tcccagcactcttgaagctcctggcttcaagagacatccccgcccccaccccgccccgcccccccacctt         48720
gtcttcccaaagtgttgggattatagttgtaaaccagcaggcctgacctgtgtagacatggtaattgac         48790
aagaatcttgtagtcacattttcatagactatgcagtagatgcaatagactaacttctgtatgaatcttt         48860
ttcattttgtattaattataatcatttgccaagtttgcttcattcatttgtttagtaaaagagtatgtgt         48930
aaggaatttggtaggcaatttttagaacttttagtgacaactttgttttttgattgtttcttagtgaaaga         49000
aggattacaataagaacttagccacaaaatacaagtttccatgagtcactgcaaaataacagggatagtt         49070
tggaaaggcaaggagtaaccagaagctttgggcatagttttccttagttaaatcagtataataaatggg         49140
gtacacattgcaaattatttattcatagtttggtagtttgcattggtatgtcttaaacctgaatacttta         49210
gagtgaatgaagtaaataggatgagatgatggggaatgcacacacacccacacacatgcacacacaaaca         49280
cacatgcatgcatgcatacatacatgcacacacacatatacatatgtgtgtgtgcctgtgtgtgcacatg         49350
tgtgtgtatgtatgttacgtttacattatttctgcatattaaacactttccccttttcgttagatattctt         49420
tattgagaaaatgcactcactagattaccattacttaaaagttgctctcgcagcacaaatcaattcatt         49490
atctttaaggataagcccatgtctggaggtagggaaatcattttttaaaaattaaagtttctgtcttgaa         49560
atattgtcatccttcactttttctatgcactaggatgctcttttgctttcaggaaaacacgttatgactca         49630
tttaatactgttgtccctcttatccagaacagaacataccgtggttgcctaacaggaaggctgcatataa         49700
aacccagttttgtctagtatcatttttccccaagtccattatgtgtgttattgtgcagtgcatgtccaaat         49770
gaggatttgagcagtagagaagaaattcattaaagaaatgtgtcatctccttgcaaaaaggaaagtattg         49840
ttgaggaaattgttactgataagacaaaagtggtgaatgaacatctaccatttgaaggcatttctctgaa         49910
gtgaaaattaccttgaattgtcttgggatcagttgtgacttgacttgatccttctattaggagctgtttcaaact         49980
cagagaaggggtgatgattcacactgatgactgaaggtttcttggagctggtgtgaataagaagggaaaa         50050
gtattgcaaatgcatcattgtggctttcactgagactcagtggacagaattcatcatgatcttcctgggc         50120
tccagaaacacaggcttgaaatttagtagccagtctgccaagcatggagttaggcacagatgggatctga         50190
gttagagaactctcctgggactggtacccagggagggtaatgtagggtgaaatgtcattgttcaacatgc         50260
ttattattcacctgaacatgggtgacattccttttcctgagaaactctggtctgacaaatgggttcttaca         50330
attatttctgaaaatagaaaatgtatttccaataattattagttatatctatttattatttctagtcata         50400
ttattcctaataattgagctctatggctattgggtgaggttcctcagggaacagcggattctctgttact         50470
gaaggagtttaaacagtatctataccgagagtagtcaagacatgcagagatgatttccatattataagag         50540
aagttggattgaattaagtctgtgattccctgccattctgagattttaaaagtccaggcctttaatgtac         50610
caattccctgtcatcattagtctaattattggcaactacattgaattatacagtatagtatcagttgatg         50680
aatatagtatcaattgattggtacaacactgtatcaggttgaatttaactgagttaaggtatggccctac         50750
cttctaagagcttaccagttgacaataaaagcacatgggtaggcaagagacacccacattattagatata         50820
actatgttattcatgttacctaaagttggagataagaagaatgaatttcttgaggtagggatgaaagta         50890
tatccccattccaacagtttagatccagagaagaaaaaatgtttcagagaggagatatgattttaaaaat         50960
tgcttcagaggaaaaattcagattggtaatggcagcctagaaagatgctaaatgaggaattctaagtcaa         51030
aggccttgcagaaagctaggaatgaacatgtcactggttctcatggaaaatgcttagagtcctgcaggga         51100
ataaattcctttttttttctttttctttttattatactttaagttctagggtacatgtgcacaacgtg         51170
caggtttgttacatatgtatacatgtgccatgttggtgtgctgcacccattaactcgtcatttacattag         51240
gttatctcctttttttttaaatcattattactattgtatttatttatttatttttattatacttttatgt         51310
tttagggtacatgtgcacaatgtgcaggttagttacatatgtatacatgtgccatttggtgtgctgcac         51380
ccagtaactcgtcaattaacattaggtatatctccaaatgctatccctccccctcccccacccccacaa         51450
caggccccggtgtgtgatgttcccattcctgtgtccatgtgttcactgttcaattcccacctatgagt         51520
gagaacatgcggtgtttggttgtttttccttgtgatagtttgctgagaatgatggtttccagcttcatcc         51590
atgtccctacaaaggacacgaactcatcatttttatggctgcatagtattccatggtgtatatgtgccac         51660
attttcttaatccagtctatcattgttggacatttgggttggttccaagtctttgctattacgaatagtg         51730
acgcaataaacatacgtgtgcatgtgtctttatagcagcatgatttataatcctttgggtatatgatcag         51800
tagtgggatggctgggtcaaatggtatttctagttctagatccctgagaaatgcgccacactgacttccac         51870
aatggttgaactagtttacagtcccgccaacagtgtaaagcattcctatttctccacatcctctccagc         51940
accgttgtttcctgacttttttaatgattgccattctaactggtgtgacatggtatctcattgtggtttt         52010
gatttgcatttctctggtggccagtgatgatgagcatttttttcatgtgtctttggctgcataaatgtct         52080
tcttttgagaagtgtctgttcatatcctttgcccacttttttgatggggttgttttgttttttcttggaaa         52150
tttgttggagttaattgtagattctggatgttagccctttgtcagatgagtagattgcaaaaattttctc         52220
ccatttgtaggttgcctgttcactctgatggtagtttcttttgctgtgcagaagctcttttagtttaatt         52290
agatcccatttgtcaattttggctttttgctgccattgctttttggtgttttagacatgaagtccttgccca         52360
tgcctatgtcctgaatggtattgcctaggttttcttctagggttttttatggttttaggtctaacatttaa         52430
gtctttaatccattttgaattaattttttgtgtaaggtgtaaggaagttgagactggtagaagactaagct         52500
tcttccagactttaatcattgttatctggaaggaattgaaaatagttttttttctgaatcattgtaatca         52570
tgtgaaatcactaaatgtcagtgttgaattgaccacaaggaccaagctaattatgaagaaataggtggg         52640
ggagacattgaacacagcaatccacaggagtttgagtaagtctggagtgttgaactggtgaaagtcctcc         52710
ctgcaacagctccatcggggcaattctgttaagtcaagactcaagcactggacggtgaatggtccagaaa         52780
aactatgtcattaaaaatgcacatttgtttaaaataactaactgctcttcgtggatgattggtactaag         52850
attttataaactgtttagggaccaccatgattcctcacacacattaattaattcatgagagttgattttc         52920
ttttcaaacacattgatacattattagtagatagcaccccaacacacacacacacacacacacacacaca         52990
cacacacacacacacacagagagagagagagagagagggtacttacaatcaaagacagcctatct         53060
agatccaattggtagcaacaaagtgagaaaagtgacagaaccacaggcaaattgaaaatacacaaagcc         53130
acatccacagcatgccctttaatgaggaagtgggaagaaggttccattttccactctgctcattttctt         53200
ccccaccacccattaagagtgtcaattctcattcacattccttttagagaagaacgaaccatcgaaaagg         53270
gagctgagagttgtaataaaaatattgcattacggatttctccagtttcctttcagtatgaagtatttgt         53340
tacttcattgaaaaaagtagaagtattgatcagccgcttagcttgtggcttctgctctcaaggagtcagc         53410
acatagtctgatgtggaggaaaatctataaatggatttctgcaatctgcaggtaagcatgggatgaaatg         53480
```

FIG. 8A-52

```
ttccttgacatccaacccaggttagaaatcagttttcaagactctaaatttgaggacccctaggagctca      53550
aatgataaagagaagaaggtttatagtccatgatgggggagggactgcacactacctgcagggtgagcag      53620
aaaggatgcaggggcttggtatcacaggaccagcattgtaaatattacaggaagtaacctttcctgtgtg      53690
tccttcatgtgcttttctttgtgcatattcttgaggcttaaaggaaagggagccagtctgtgtccatact      53760
tctctcccgtgcacatcatcccggcatggcactgctgatgcaaattaaaaaaataaacctttgactagaag      53830
cattttcccagctaccagtttccttctccccagctgcaagacaatgtgacagcaaaggttcatgcacagaa      53900
gcagaaaggtagtggaatgactcagcttctaactaaattccttccaccttcctagctttgtggtctcag        53970
gattttataagaggtctctcatgtgctgctacagaaccagcaggaaaaatcagacagggccaagacagag      54040
agaaaagagacacctttctcctatattgcccctacctagggctcctatccaaagcatgttctagttccta      54110
gatggttgattccaataaaataacataaaaataaactgtgcaataaaaatttaaagggagttgcgctgac      54180
catcattttgaaatatttaaaaatgagtcctcagtaaattttggtgtgaacattagtatttgtcatgg       54250
atagaggcacaagaaaggagtaaatgtgagacctacattgcatccaatgcctgcatcagtagaatctaat      54320
ctcttccccccatgataaaatggcctcattctgtcaactacaggcctttgctagcttttctcagacaaca    54390
gaccaaatttatccccagcctgataaggatcttattgcatttgctcccaccccacctactgtatttagg      54460
gtaatggtgaaaaatgtacattgatgctgaatttatagaaatagtagaaatggaaatgatcttacagag      54530
ttgtcatctactatctggtgtaggtttggttacaaagctgtatttcctcttccaagttttaagtaatcaa    54600
gtttcaaaacaatctttcctgacatccagtttgtgttaaagccaattccaatgattttcatttgcat       54670
tctggaaatgcagtgaagccttgacattttacaaaatgacctatcttctactcaagtcaatgaaactaca    54740
gtaaacattttatgtgtagttgcaatgcttgtatctccctcaagattaaacacagaaaagcatctttggg      54810
gaggatatttaaatacgatattaaagcataacatgtgtctgtatttttcagttttaagtatacttac        54880
taataataacaggcaaagtggtacgaggtaaaacactactttcattgttcagtttacagtagtcattga     54950
ctattctacatatgcgcttagcataatatttacagactatgtaatacaaatcacactctgtgaattctca     55020
tgtcctgtgagacacaggaacagaagagctttgtaaaaaacagcaaagtaccaacttgaaaagttaagcc      55090
atatgagtaagaaatcaaagtgatgaatttactaagtgtttattaatatttaagctaagtttacacatga      55160
ctcaacatcatattcactcatagtctgttactgtactttgccaaactgtctgtactattttgtgagag      55230
gatattatctttaatattgctctcactgcaatgaagcataaataaagtatatgtcatgttctacctttc      55300
aggagctccaatgaacacatgctatggttttaatgactgtaaagaaaatttcaaagccatatcttatct     55370
gtttctatggagaagttgatcaatgatcaataccatttgcaaggacccccgatgtgtgacttgttttctctt     55440
tatactgtgacatgtttccctgaaggtggaacgtcaatgagacattcattttctactaaatgaaaatgat     55510
gttaaagttgcagtctagtgataaagttaccaagatctgcttcttggatttttatgggtttgggcaac      55580
acataaagaaactttcctctcattcaagttgaacatatccaaccacttatatatatgttgcccagtgagg     55650
tcagtgttacatgaagttgtagaacatttactttgaaatgaggttttctcatttaataaaagtgtcacct    55720
tgtgtcagtggcttagctagttccagcttctatttattctctatccaatgagaatatgcctatcacata     55790
aggagtgtggctgggaagaatggtggtctgtcctttatctcctgggttctccttggtttcagaacctgcacag      55860
cggacagttccaaacactgcattccaccatcatttcatcagcattcctcttggaataaatgtgtcttgac     55930
agtctctcttagaagtgctttctctgaagctactgaggaccatgccatgtgtaggcataactgaagcgtg     56000
cacattctatagagtgcctcgaagatgtgcacattctatagagtgcctccaaggttttcaagaagaatgg     56070
agcccaacttggccacattggttacacacttgtgcatggtccatttattgactatcccaccttccaagta    56140
atttacctgcacccgacttcttgtctcatgtgggcctttagagtaactccaaataagacaggtggatg      56210
tgcagatgaaacgtttgatgcttgcatgtgcttgcctgattatgactgttaatcaccaggtgtgtcaaac     56280
tactctagatgctcattgtgtgtgtatgacaggttttggtgctcttctgcttttgataagccattcaat     56350
ttaatagggtgttctctgaatgccagcttttctttaaacttagcatgtatattcactaccccacgatcc     56420
acctaagacagttgcgtatcatttctttatgcctgttccgtgttctatgtatattagatgatttcatata      56490
gataaggagggaaagctcatattttatacattttaactattatgatgaaaaccttatctagaagggttc       56560
tcttcttttttgaagttgcatagcattagtaaagctataggagctatctcttgtatctgactagaaacgat     56630
acacatttaagataaaaagcatgggccaggtggtggcatatgcctgtaatcccagtacttttggaggcca    56700
aggcaggaggatcatttgaggccaggagttcaagactagcttggaccacatagcaagccctccctcccca    56770
ccctgtctctacaaaaagtgaaaaaattagccagtcatggtggcatgtgcctatagtcacagctgctcga    56840
gaggctaagttgggaggattgctggagtccaggagttcaaagatacgctgagctatgatcatgccactgc      56910
agttcagcctgggtgacagagtgagaccatgtgtttcagaaaaacaagtggtaaaaataaaaagcaat      56980
aacaagattgcattatgctttgagggcattaattttcaaatttaactttacttgcattttttcctgtca     57050
ttcttctctgtgtcggctagttcttatttttagttgtaatctttttttagaatactatgaatagaataaat    57120
accactgtattcacatagtatatttactattatttttgtctccttgcattgtattttaattatctatgtc    57190
agacactttcctcagtcaaatgtactactagccatctaaatggagaatttatcttaggaggagaattctt    57260
ctcatttattttgcataccccagcaaattattcgggagtgagtgcactgtttcatcctgttagtagtctt    57330
ccctgaacatttataacccacccctgactggctccagtctttacaccttcctcaagacctaacttaaata     57400
cactgaactgcctgaagtcgtctttgaattttacatccttctcttaactctcatacactttgcattgtt      57470
ttcccatacagggggcatcaagaaatagaccatattataatgaatgtacaataaagtactaagagtaataa    57540
aagtaaatatattccgaagcaggaaagagcaaatgcttgggtttttatagaaggagagaaacgataatt      57610
tgagaatgtttcatggaaactcttgcatttgagcagaactttacaaattaggcttaggcttcaatagtta    57680
aaaattagtgaagagaacatctctgcaaagttgaatgttcctggtctcctttctgtttgtttagtgagcag     57750
aattgataatcgacatgcaagtggctttaaactttttccaaggaccagtcattgggggaattagtgtggtt    57820
cctctgaaccttctagtaatcccaggatttgagtattaagaacagttagttgtgttagccttaagatga      57890
aattctcctaccttgttgttttgaagatgttacttagagggaaggagatgttttggtctgttcgggctgc     57960
taatacatctttttcttctcaaattttactttaagcagtcaggaggaaccaagccattccttcaacactt    58030
ttcttagaaatagcttcagctaaatctacttttatcactcacaatgcttcatttcacacaaattactaaa     58100
catgaacacagttcagccaagttctttgccactttgtagcaaagatcacctttctttcattgtgcaatgg     58170
catattctcatttgcctctgacagctcataaaaatggagcttcctgtccatatttctagtgtcattctg      58240
ttcaaaattgcatagatttcccctaagatgattgaggctttctgtacagctcttctcttttttttttctga    58310
gccctcccctcactagaatcaccttcaaaggtctattcatggcaacgtaggctgtgtctagcatacactt    58380
caaaacttttctggcttctacttattacccagttccagagctgcttctgcattttaggtatttgttatc    58450
ttaacaccacactctcagtaccaatttctgtcttagtccactcagactgctataacaaaataccatagtc    58520
tggggggtgggggtgggggggggtaataaacaacagacatttatttctcacagttctggaggctggaagcc       58590
```

FIG. 8A-53

```
caagatcaaggcagcagaagattcagtctctgttgacaacccacttcctggtccacagacagtgacttct    58660
ccctgtgtcctcacatggaaaaagggtgagggagctctttgagatctttttcttgaaggacactaacctca   58730
ttcacgagtactccatcctcatgatctaacaacctcttaaagatgccacctcctaataccatctcctggg    58800
ggaagggagtttaggatttcaaggttgaatttttgggagaatgccaacattcagcccataaaaggagatag   58870
tataggaaaactacagaaatcaataaactcttctactgttttgattaaaatatagcaagtgcatttttgg    58940
tgtacatattttactttatctttgttattattcatctagaaaacaaacgtacatagtgatagttaattct    59010
tccatgacttttttgcaaaagtgttggtatgcattggctataagtctcctctctgacttcataagacctt    59080
ggaaagctgccaaatatctcagaacttgttgtcttgagtcttaaagtgactaaaatgaccttagctctac    59150
ctgccttataggatgctctgcccaatgatgcatgcagtatgcatgttctttaacagagtatgttttgaga    59220
ctgcaggtttaggcgttattagaatccatttgactccatagcccttttatggaaacatacatacatact    59290
taatgtcaaatagtttatatctttttactagctaatatggataagtactgtctcttcccatttgactgtg   59360
tgtaactgccttctcttagaactcaacacaaaatgagcttttatgattcacatttacagtaacatggagac   59430
agaaccacctcattcaaaacaggaaaaagcaggtataagatgccatgaagggaaatgagactgaatgtgt    59500
tcaattttctcttgtttggcttatcacatatcgtagagagatgtcctcttcacatgcagtagaaataagaa   59570
catccttgaaaactcggtttgagcagttcaaaatcatatatttttttaatgttgtatgagtttcaggtgat   59640
aaatcctcttcaggatacctcagggggttcgcaaaaatgtaaaaatatgtttaaagtttgaaatgactcac   59710
atttttttagtatccacggcaaagaactgcttttccaaccttaataggatttcaaattgacattgacattt   59780
tagtaaatcagaattagcttttctttttttaagctcctgtgtcttatgtaaatggctgtgctgacttttat  59850
ggaattgaatattccagaaaatgtcatggaacctaatataaaacaagttaacattctcattttagatct    59920
taaagggatatggtgttaaaatatagcttttgatacccatccaacctgtgcaaggttttctgtgtatatg    59990
cgaatttcaaatttgagaacttagcatgtcgatgaaggcaaatctatatacctgttgaaaacaaaattga   60060
aattctgaaggaattattgtaatttacttaaataagaactgtaagaagtcagactgttaatggagtgtca   60130
atagatttcttctgagagcttcaaaatctttttcactgcctttattacaagtctaccaaaatatctgttag   60200
attctgaaagccaatctctcattacaaaaagcattattcacaatttttaacttatttccacaatgaacatt   60270
ctacagaattattgtatctttgtttaaagataaaaaaattctccctcgggaggctgaggcaggagaatggc  60340
gtgaacccgggaaggcggagcttgcagtgagccgagatcgcgccactgcactccagcctgggcgacagag    60410
ggagactccgtctcaaatataataataaataaaataaaataaagtaaataaataagtaaatgaat        60480
aaataaattctcccccgaggtctgaaatttattaattaatgtgaatattttaagcatttttagaagaaaa   60550
taatttttgtaaaaaatattgtaagttatggaaaatatggtggtgaagtataacattcacgaacttgctag  60620
aaccttgccctaaaaatgaactaattattggatcatatggcaaactgattaagaagaataaggaactact   60690
ttatatcatgaaaaaatacatgactatccacctgccttcctaaaacttcttcctctcatgtgccgctatt    60760
ttacttagagttttcttttcgggttaaggaacaatatctttagaaggctattcattaaagtactaattaga  60830
aaaggtagttaattaagcttgtcacacacaatttatatattttcttatgatgtgtaagagaaaacagcat   60900
aaaaaagataaattattttcagtcaaaataggcacttttttttcctgcagctcattatacc            60970
taaattccttttgtgaaagtatttaagtaagttcttttgaaatattgcttttaaaaatatgtttactcttta 61040
agttttaaaaataaggaaatgtataatatagtgaaatttccccatcagtgtgttctgtgtattttctcca   61110
gctctttcttgaattacaaacagcagttctacaactttaccacccacacacacacatttattcatttgca   61180
catatttcttttagtgttttttttttttttgcaaaattggcatcatattaattatactactctgcaactt   61250
gctttattctgttttaatatggaaattgactgaagttaatttttcaagcagttgtgtaatattgattg     61320
aacttaattgatatactataactgattaaactacctcactgttatttggaacacttatcgacaacactgc   61390
agtgtaaaaccctctttctacttttgcagctttatgataattctataaataatcagacaccgattgtgat   61460
gcaatcgtatcacaaattcaaagacacattataatgtcagtggaataagttagacatacagtgccaatta   61530
actcaggggttccagggggtaattcttttcgtattgatgaaacgcaaatgcatcttactcattcagagttgc  61600
cagggccctggtgtagaaatctaaatcataaccaaaacaaaacagcatcaccacgaagaaatcaacaaaaa   61670
caatttcatgagggttttgagtatttgaataatatttcagtaatttaaattttaaagcaagaactgacagg  61740
tttgcccaccccatccatcctgtgatgtcaaatgcacggtatgtatctggctgacagggaaattgaggta   61810
ggaaaatagaatagataatatgctattatgtacctgcgcttcagtttgaggaggataaaaattgttttaac  61880
cttatgtccacattcctggagtggtttgctagacctgcatcagaaaatccacatcttagttcttcagctg   61950
ttcacatctcaatccacacagccttttgtcattagcatgccagaaatgcactacattcatgaaaggaatt   62020
actagttacatcatggtgaatgttagcatgaactctcattggcccataacattaaaatattcaaaacata   62090
caaattggctaaaatcgtttagagaaaatgttcacatggcatgatgaaggtataaaaaatccagaaatgc   62160
ctatgcctttgacctgctccagtgcccataacttgaagtctctttagtcctacgctcagccatggactaa   62230
ggaaaatttctcattacctgatgctgactgagaaagataaaagaacaccacttgttttgtccttaaagac    62300
ttgagaggcaaagagctacatgatagaagttgtacctctcacaagtttatggaaggagacatatgaactg   62370
ttttctgtctgctgtgaagtcagatgaatgactgcctatatgtgtaacatttgggcctgagacacac      62440
atgatgagggggaggaattacaaactatcactggtctcctcttttttctgccgattactgttaccttaccta 62510
acagtaggtaactgtaatctaaaatgaacctaaaaattgtgcatgaacaaattagctcaggtagcttgca   62580
acattgactttacagtttgacctaggggagccccacgggctgaacctaatgaaactcagccaggttatat   62650
taaaactgcgatagcctgtatctctacattttctgcaacctggtttctacataggggaaatgctgcttgtg  62720
tttgctgtaggcaaatcttaaataaaccatgactagcaactctcagcaagaagaagaatgatgtgcagagatatttt 62790
agggaagggataagatggcagttttgaatgggagcccacatgtacaagtactcatattccattaccaac    62860
ttcaggagcttttttactttggaaaaccatttttcaccttatttcagtaatatgtcaagcatttcaggtgg  62930
tctgcaaaagccacatagctcagaggcttagcaaacctcctcagacatcaggcagaaacactttctaaac    63000
ccccttaatgagtgtcaagcaggaaattgtgagtatatagtattaaggagatggacttgctattcttaaat  63070
ttacagaaaaaaattctggattttcttcctcagtctccacttaatgacagatttttttttaacaaaaga    63140
tgcatgacagtacctattttaaacttactctgataaatttgataaattttgataactatcttttttaatccagacatc 63210
tctatgagtttcagaattattacccttgtcaaattcatctatgcttttttttgtggaaatgttcaacttttt 63280
gttctcactgctccctgccttcccccatcaacaaaccctgaatatctgggaatttctcaccagctattat   63350
ttaactccattccacatgtccatcagatgtcctacacaagattggttaaatagaagtttgttcgctggga   63420
gaagatgacaactttttatattaaatgcataaaaattttctcaatactgcagggtgataaagacaaagaa   63490
aaggccaatttaaaggaagtctttagaaaaaatacaataaagcagaaatgcttcactttcctacacaat    63560
agggaaaaaattttaatgcttttgcaaaaatttaaactctaatgatgaacaaagtttattttatactggg   63630
taaattttatgttaggcatgaaactacataaaaatatgtggacaacaaagagtgattcagggctgcttaat  63700
```

FIG. 8A-54

```
cgctgttgctcttggtgtggtttttaggggattgcataattggtgagttccttacacgttgatttctcag    63770
attcaccaggcaatacataccagctgtcttggtaaatgcatgaaatgttgcaatctttgcaagtcctgca    63840
attttacttcaccagtaactttccctggtcaactaacagtatctagagatcaggcagagggtgaccaatg    63910
gctgctctgacgtacacatggagatactgaaagatgtggagttaaggatatttgaataaatatttcatat    63980
aatgacaactgtctttgttagcaagcagaaatatccactgtgatgcaaaggcatatccttatgtcatata    64050
tatttgctgtgaaaggtactgattcgtgcttatgtgaaaacctcttaaatcccgaatctggggtctcctc    64120
tccccgttttttctggaactcagatgctaaagttgatacaggaggagtggactgtcccaaataaagcagt    64190
cggggaaaggaggatccattgcaaataaagggtaaaaaaggtacatatgaatagtatatctatttgcacg    64260
taatgcaggttattctggagggtattaaatatctatcagtaactatccattgttaaaaaccagggattcc    64330
caaggatgttagtggatgtatgagaaagagtttctggagatatatgtttgggtgtccactacgattgttg    64400
catttcttttcttcttgtctctctctgtctctgactgtctctctctctcagtttgcttctctttcccctt    64470
taaacacacacaaacacacacacacacacacacagacaccacacagaatattcccaacttcttaacacac    64540
aacaccaataaaaaatgccaataatcagattgtaaactggcagttcttttctttcaatgtggctttcta    64610
ttctattgtctctcacatatcaaagaaacaagaggacaacagatcaggatacattttgtcatgtttacat    64680
tatgtagtaacctgaaacaaatgcccagtgagtggagggtttcttagcttctgtcagttttcaaatgtt    64750
ttccctcctcctgcctccctggctttgggttggtgatgcacgtgctggtgctcagagatgccgtgcgccc    64820
tgacaagagattttgaactgggcatagatgattgtccccaaagtgatctgctcagttcccataattcta    64890
cacatttcaggcaatggaaacacaatgagagagatagtttgggtggttttggattgcaaacttaggcag    64960
ccacagtttcaaccagcaatactgattttctcagccttttccatttctacccagtgcataacttatataa    65030
attttcttccaaaacttcacaattaaactattccttatttatgaagttatcaatgtgtgtatgtcttag    65100
aatataattggtgtcatacaaaccagttatgcctcttttaactttagtgctatgatcttaaaaattttga    65170
ctcccaggcaaatatagatataaatataaatatacatgcatttttttcttgagagtcaaaattatatatt    65240
tatatatatgtgtgtatattatatatatgtgtgtatatacacacatatagattaaatatatatattcat    65310
attatatattacagattaaatatatattatctatattttaatttcattagtcatattgttttctacagttt    65380
gatttccagttttgcaggacttttgtattcatattcctgatatcaggaaagggtgcatattgacactcag    65450
ctcaggtggaatatttagaagacacatggttgtaattagttacttgcattttttcctgaatgcttttatg    65520
gtgttgactgtttaagaatatcttgcattgcttccaaacaaatatactacacaagcagcatttcttgaa    65590
tctcgttgatctgtgtggtgtgttggtgtggtcttatacaggattttgtcttttttttttttttagtgtg    65660
gttgtttctcctttttccttaactaacaaatatttaagtactttaaaatttttaatactggttttta    65730
tggagaatgagagtttcctatcattttcctggggtaatgtcatacaatgcatttctgaaaaaaaaatact    65800
tcttaaattttgttaatgttctgattattttttctgtcattattttgccactttgtattatgttacattac    65870
tattccataacctcctttgattccagcattgggaattggttttcatttccatggactcattactgaggtc    65940
cttgtttctttcgagatattaaacctgaccctgaattttttttcttccctgtgagagtggaaattataat    66010
tcttttctactggttcaggaaaaaaagaaacttacttttcttaaagaatatatttcttttttatggtcagat    66080
acgtttaaataaaacgaaagctttcaatatctgtctgtaaaagagcagggtttggaattctcattggtg    66150
atggatatgttttattttcttacctgacacgtcagctactgcagctaaagccagtgaactatttctatatc    66220
acttactgatgaagaaataaagggctctctcatgatactaagtgtattgctgttccaccatccggatatt    66290
tttggcttaaaccctgaggtgttaccagatggtaaggattttagaaatgctaaatgataatagtaggga    66360
ctactttcgatattgtgaagtcagatatatcattgcaagttttaaaaaaatggaatattttatatttta    66430
agtatctgatttaccttaataaacacttttcatcaatttcaagagcatctacattctggtcctg    66500
aattttcatggttaaaataaagccccacccagagactagctaataactatggtgatcaacagtggacaga    66570
aattcagagatactagttatggtaacatcctttaatgctggagccttactgtcatagaaacatgtgaatg    66640
tcaaactaaaagtttaaaagccagatatttcaaaagagtggggagtgggagagtataaattacccccaag    66710
gaccctggaagtgctagattctgggcaagatccagatatttgcaatttgtttaactcccagttgaccatc    66780
tgagaaatattgagcaagagagacagagagagagagagagagagagagagagagacagagagagagag    66850
acagagacagagacagagacagagattgccaggaccaaggatgatgctagtgaaccatttagctacaa    66920
agtgtcaatgtatgaggctggcgtggtggctcatccctgtaatcccagcactttgggaggtcgaggcag    66990
gaggattacttgagcccaggactttgagaccagcctgggcaacatagtgagaccctcatctcttaaaaaa    67060
aaaaaaaaaaaaaaaaaagttagccaagcatgctggtgcctgcctgtagtcccagctacttgagaggctg    67130
aggctggaggatcattgagtcctgcagttggaggctgaaatgagctgtgattgcaccactgcactccagc    67200
ctgggtgacagaacaagacctgtctctaaataaataaataagtactatgtatatgctgactctccagcc    67270
ttgcctagtccccagaagccttgcaaccttccaaaacttgattgttttctcctaaatttctcagataat    67340
tgagggaaaatagagctcagaatttgacaacagctgtccacatctcctggaatccctggcagaatgctg    67410
gtgctgtctcttctctgggtttcacagggcgggcataaattataactttattaggttgagcacatatggc    67480
ctttagccccaggagaccctccatggggctagtctgttggcagaggcagcttctgcactttcattcaaat    67550
tcacaatccataaggaaaaagaggccttcaaggctgcagcctgccttgggcttccgtggggcatctccta    67620
tcattgccaataatgctgtggtgaaacccaggccaaatattccaacatcttttttgctgcttgtatgaaca    67690
cgatgcatattgcagttcaaaactaggaaaaagaagagcatattacaggcgaacacgaatgcatcagaa    67760
tatggtacctttaaattaaaagagaaggctcttgattttgaattctcaagtgtttctcttcaaatacaca    67830
caatgatgtctttcactttaattttaactattatggatacataatagatgtatatatgtatggggcacat    67900
gcagtgttttcctacaggcatacaatgtgtaataatcaagttaggtgaattggggcattcatcaccctcaa    67970
gtatttatccccttctctgtgttaagaacattccaaatccactctttagttattttaaaatatacaacaga    68040
ttatttttgactatagtcactctggtgtgctatcaaatagtagatttttttttcgaggcagggtcttgct    68110
ttgttacccaggctggagtgcagttttgtgatgatagctcactgccgcctcaatctcctgggctcaagca    68180
atcctcccacctcagcctcctgagtagctgaggccacaggcacatgctaccacagctggctaattattat    68250
tttttaattttgtagattaggtctgtctgttgcccaggctggtctcaaactcccgagctcaaatg    68320
atcccccctgccttgtcctcccacagtgcaacgattacaggtgtgaacctgtgccggctgataggaattt    68390
ttgatggagtttcccaatatctggcctttcaaagattttggatagtgaacgagatactgcaaagatctct    68460
ctaaatatcaccagcctgaccagggaccttgtgttacctatatgaatacactgaggttgctgtctgtttc    68530
tctgttaatgtataagcagagaaagttacattgatgctcatcagattttcagtttaatatcagagcattg    68600
caaattaaaatataaggtgcgggacatgtacaattttactgcggggcatgcaaaacctgagggccccaa    68670
agcagaagaaggcattcggcctctagtctgcatttcctccctcctgagttgccagccagccagccagcct    68740
gtcttacagattccagacttgccagctcccacattgcatgagccaattccttaaaatagatcaatttaat    68810
```

FIG. 8A-55

```
aaatttaacctatattggtgaacaaatttagcagagaactttgatatacattagtaccacttattatttt    68880
tagaaaaattggaattcgaataactaacactaaagtctaattcgtcatctggtgtgtatgttataaatgc    68950
acacccactcaccgagacctattcacagccacagcctcatataaaaataggcaatagatacaggaaatga    69020
gaagcagccatagagggtcttacgtaagaaaccccatccttctcacacctactcaagaacgttgttccca    69090
acatctacatcttttgtagtttatatccactgggcgcacctaacatcacatccacattcttttgtttatc    69160
ccgtttggaaatacgtgcctgaccttcactttctctgcctgatgtggctgcatgttttgtttctctggc    69230
aaccatctcctcgtcttccaagagtcctcaccgatcacatctcaactcctctccacctatcctttcttaa    69300
attcactccaatcagtatatagcctcaccacttcaccagactcctcttgccaattataccattgcatcct    69370
aggcccacaaaagtggagttgctattcctaatgtttctaaaaaatggccattctgcatttccctcgaa    69440
tctccactgcctctattttggaaaagagtttcatctttgaaaagcatttaagaccaacttttttccca    69510
ctctggagggaaatgaaatattgctgaatgcagaggatatctccaaggcttcatactacttgctctggca    69580
atatttccagatccttatcctgcagcatttgcggtagttgtcccccctagaaatcatagttgaaacctact    69650
cctcaactgtgtaggtatttggaagtgggcttggaaggtatttggagagtggagcctcatgagtggaa    69720
ttcctaccattataaaagggaccccagagggcacctcgtccctttatcatgtgaggacacagcaagaa    69790
ggcgctgtctatgacccagaaagtgggtcctcaccagccactgaatctgccatgccttgatcttggactt    69860
ccggtctccagaactgtgagcaattttttttacaagccgtggggtctgcagtcttttgtttagcagcca    69930
aaagaggtaagataggggcatgttgggaaggaatggagatgtccacaaacaccctgaatcatatactgctc    70000
cccaaccccccgtcctcccagcagagagagcaggaaagagaagagaaggcttacttcctccaggttcgatgctct    70070
tctacacacagttgatgacagacagattgccttatattttattcttttttagttcatctgaccaattgtca    70140
aattgctcaaatgtcagaaaaatggctcaaagggccgctatggatttctgcagtagaaaaagaaaagaca    70210
gaagactagatcccaatgtgttcctggactggaagaaagttcttatttatggagccataaataaatatg    70280
acatttcttgtgcctgagaatttgaggcaggtagtactcctgtgaagtaagataatgtcttctgtaaaag    70350
aataaattcattaaaaaccatgggaatcattgtaagtttcatttgctcaagaaagaaacagacatgattttg    70420
gatgtaggtgaatgttaattattgaagatgattattgttctcagaacaagtttattctgattcgtagcca    70490
cagcagttcaagagaaaagcaataaaggaaccacaaccatatgacccttcttataatcatgttgtggtgg    70560
ggatgtttcttctccgtcctacttcctgagaatgacagaagggttttgcaagagtgaaggcagctgggaa    70630
tatattccagccgcttccatagttcatgctgtggtaaggagtttcaaggtcacagtgaggcaaggagttt    70700
caaggtcacagtgattgaacactagaacttgtgcctctgttctctgctgaacgtcttccatgactgctac    70770
atcagggcttgggtttcccactgacgtggtgttttaagtaacattttagagtccttatggttatacactttc    70840
atctccttgtacagaaagtttctggaaactgcccactattatatgacacatattaacctgttgaatttgg    70910
ttatttatgtgaggaaaccacagaaaaccataacaaatcaaaataccctaagagccacaaatttcctccag    70980
tgcagccacatcccatagacaggtaatgtgcactacatgtgtaatttttaagttttctagtagttgcattc    71050
aagagtgcccgaagaaaccattgataccaattttaaaaatacatttaatgtatcccaatatttataaagt    71120
actaagtcagcagacaatagagacaaaatatagtttgcatattttttactacatattttgtatattcagagt    71190
acatttttacacttacaacacatctcggttttgaacaagccacattttatgtgctcaatagccacatgtggt    71260
tattggctagcattttggaaaacacagtgctagaaatgcattcttcctgccatgatcaaccattgtctc    71330
tcacttactcctgggcaactgtgttctaattgatttccgggcattgattattgcctttcaggagaacaa    71400
ctgatcaccgtattatagtaggtcattcctacacatggccttcaggtcccaaacccgtctgatttgctaa    71470
gccgtttttccctcttgtcatgccatcttccctttcatttgctacattccaggttttctagtctaatgcag    71540
tcactccaggcactctgtacttgtactcagcatttactgggtggtgtatatctgtcgtaggctgttggtt    71610
gtaagtttcatgacagcatacactatgcctcccttttccacatgcaccaatccatcaaacctcattgag    71680
gacataaaacacagcatataaagcactccatcgattgaattgaattaatgtgtgaacaattgcacctgca    71750
agtgtaactgagggctcacgtggttgtcatgtatcattttttaaaatgtttaaataatgcgagttttcatc    71820
tatattcttattacttctgtagaaattaatctataatattttcaacagtaacatggttgaaattgaggcct    71890
tatgtaatgtttgaacacaaatgataacttgattctgaatcaacactgtatgtgcgatttgatgtctgat    71960
gtatgatttgggcagtttgagggtcagtcattttatttgtactgagcctctcaaattccctgtatgtgaa    72030
gggaacagtgagaataagtgtcttcagtggataagacagtcgtctttatccctggaaggcatcaccaac    72100
tgatcacagcagtctgtttttctgagtcaagaggcaacttcccctctatgtaggatactacttttagtgt    72170
agtgtgctcttccatatctattggaatcattacacctgatcaatcaggtttaagataaagggtgtgatag    72240
atagaaatggatgcagatgctcttgcaaattgagttgaacccttgtcttgctcttgctggcctca    72310
gtgactgtcttcttgaatagaatgttctgggagtaaaacactgggacttccagggctggatcataagaag    72380
ctattaagcttccatttagggcacttggagtactgaccctcagggcattctctcttggaaaccacatctc    72450
atgttgcaaagtgttcaagccccatggagaggctatgcatggtgctccagtcagtagctttagcttcact    72520
cccggttgacaaccattagtaccgccatgtgagtcacccattgtggacatcccagctgattgaggactcc    72590
tgtctcttcctatccctttagctgactaaggagatctcaagagagaacttctcagctaagccagtcagct    72660
cacagaatcatgggagatcctcataaaggttgtttgaagcccccacattatgggcatgtttgttacacaa    72730
cattagctaaccagagcaggcactgaaactggaagtgaggttctgtttcaacagaaacctaaagtacatg    72800
gtgttggtgttggaccctccatagggcaagactaaaggcttgaagaacaagggaagaaattggaggctg    72870
gggaaatggaatggacaaagagaactctttgaatgactcactcacagccttacaggacgagaagtaactt    72940
ttagcactgtgcaactgcaagcaaactggattttgtccttaaaatagaaagatggcatctcaaagaaca    73010
catttgtcatgtagttcctaataagcataatacttaacataaagttcactggcgtatgttattattataa    73080
tcttactatagtataatttccattggatagcaaaaggtcaaggatataattacagaaatatattcttta    73150
aaattcttttggttacacttaaatgtaaattgtgaacaccattttattttctattgtatcccatgactt    73220
ttctattgtttgggtcatattaaatctattttttacagtataaattttgcagcatatattcccacaggaaa    73290
gaacaaattataaaacacacagtttgtatatgtcttttcctttaaaagtgaaattttaactagttttctt    73360
tttttttctgttatttcccattctttggttcaatacattcccaactcactcttgaacgtttttgg    73430
aaagttggcaatgacccctttaaattcttttcagtctctatctgcctaacatatatattaggttccgtatat    73500
atttatatcatttcctacttaaatacacatatttccattttttgtgctcatgctattctgcaaatgcctgc    73570
attttaaggatgagacatacatttaaaaaggggcatctatgccttctttcagaattttttttctaaatatc    73640
tattactttgatatttgaaattttgtacccacaaacatacacataccccatgtgtgcataatatacatc    73710
tcacagaaatgccagccatgtcgggaaaatgacagctccatcagaaatgtcttttacatccacgtaatata    73780
tcttatttccttgtataaggcacagatcctctgttaccaatatcaactatcccaggctctaaatcact    73850
tgaagctacttttgattctctggagaatttcagaatatattttttttcctcaaaatttttcatgaacttgtat    73920
```

```
gcattttgtgcctcagactttgaacgccttggacaaattcctttatccctgtgaattttaacgaattct      73990
aaacaaaatacctgactccacttttcccccaaatttcctgaccttgcgtgcatttttgaactgcagacttg    74060
aaaacacttgtgcaaacgttccttcatccctatgaatctttaatcctaaacaaaatgcctgtatcaatgc     74130
tggcaaggttgtggagaaaagggaatccttatacactattggtggaagtgtaaattggttcagccattgt    74200
ggaaagcagtgtggccattccgtaaaaagctaaagcagaactaccattagacccagcaatcccatccat     74270
tactgggtatatactcaaaggattataagttgttccatcataaagacacatgcgcacatatgttcattgt    74340
agcactattcacaatagcaaagacacagagtcaacttaaatgtccctcagtggtagactggataaagaaa    74410
atgtggtacatatacagaatggaaaactatgcagccataaaaaagagcaagatcatgtcttttgcaggaa    74480
catgaatagagctggaggccattatgcttaaccaactatgtcggtaacagagaatcaaatactgcatgtt    74550
ctcacttataagtgggagctaaagatgagaacacatgatcacatagtagggaacaacagacactggggcc    74620
tgctggagggtggagggtaggagagggagaggatcaggaaaaataactattgagtacttggcttagtacc    74690
tgggtcatgaaataatctgtacaacaaacccccatgacactagtttacctgcataacaaacctgcacatg    74760
caccccctgaacctaaaataaaagttttaaagaatgccagtatccactacatttatgggcggtcttctga    74830
gtttcacctcagagaaacactcctaaaattcaagttatgactatttagactatttgttaatgatagctct    74900
gtgtgtgtgtcttagcccccctctctgtttcctatgtgttctacttgattttaaataaactataggagct    74970
ccacatactaatttgattctctacataaaatggtgccatattctcttattttccctttaggatttgtaca    75040
gagactgtacaaaatattttttgagttgtgtaatggtatccaatatggacaataaatgataagtaaattt    75110
tggaaaaatcagttaaaagaagtgtaatagatacataggtgtcttaattgttttccgtcctcaagtatgg    75180
acgttttttgcaaagacacgagcttttttacttcaggagacatttgtcgacgtctggaaaaaattttggttg    75250
ccacagctagatcatggggtgggtatcacttgcatctagaggacagaggccagggatgcttttaaggga    75320
cccacaaggcacagaacagccccccatgacaaagagtctttcatctacatgtgtcaatatcgatgagatt    75390
gagcaacccaggtatagagtaatactgatgagcacaaagtatagcttgaagcctcttttttccatatggct    75460
gtgatagattgttttaaatgatcattggaagaaataacctttggttctatggaagtcatgaggaatatt    75530
ctgcccatgtgcttgtgaaacctcagcttggagcaaagaggcgaatatcatgcaagtggcttcctagaat    75600
catgggggttttgtacagattatttcatcatccaggtattgagccaagtacgcattagttatttttttgat    75670
cctctccctaccccaccccttcaccctcaagtaggccccagtgtgtgttgttcccctctatgtgtgcatg    75740
tgttctcatactttagcttccgtttataagagaggacacgcagtatttggttttctgagctggaggccat    75810
tatccttagaatccttctatgtttaaaaacaacagacaacctcctggcttcctgggaatccttgttttcctg    75880
attccagacaagcgccatggctgtgaaatcatgtatttatgtgtatgctgttggattttaatgtgaaata    75950
ccttttcactgcgccaagttcgcttcaaatgtgatcccgccaggctgaccaacaaggcattcagtcagc     76020
ctacttttcttatgccgggacctttcacaaaatgaatcatatgtcacttttcttttcagaagcatatgcca    76090
tttttatttttattctgggagtttgaatcacaccatgcatctgttttagtgttgtttttagtaagttcacta    76160
tcagtgcttcctgagcatgtttctcgtatggggtactcactgacctgtcccatccatcttttcttccta     76230
taaagcctttactgctatacttgtctacttgcagaaccctccacacttttttatgagctcccatttttctct    76300
cttcttggtatttatcattacttattgtgactcttgcatattggatggtcaaaagagatccccagtggtt    76370
acactacaacaagataaatgtaggtatactttttcttaattgttattagtgttacttattattttgtttta    76440
ttagacactacttttcaaaggctttacagcactgggtatgtgttctacctttttctttcattttatcctcc    76510
acaacagttctgtgatgaaagtactattattaacttcatagtttacacgacaaagcatggtttcataact    76580
tgtcaggatttcttagccattatttgataaaattaggatctaaattctagctccaaacagat           76650
ggttcttttccatgctatttgctattatcttgtcaaaagtaatgacaaaatagaactcaaatagtattttt    76720
cttttggctgatttcttcttcagaccagagaggtttccaaggttaaagtagttcattaatttcaatttc     76790
ttcttcttttttttttttttttttttttgagacagagtcttctggttcttttgcccaggttgaagcaca     76860
gtgacaccatcatagcacactgcagccttggcctcctaggctcaagcagtcctcctctcttggcctccca    76930
aagtgctggaatacaggggtatgccaccatgtcaggctacttttttatttttatttttttaagagacagtc    77000
ttgatctgttgcccatgctggtctcgaactcctgggcttgaacattcctccctccttgacttcccaaagt    77070
gctgagattacagacatgggccaccatgcctggcctaatttgggtatcttctaattgatgtggactctt     77140
atgccctattcatttgtgtttgaagtgaactgactctgaatgtcagtgatagggcactgcttagtgttg     77210
ggggtggttaggaagatatgcaagtttcttagagaataaagcagcttgctgttcacagcagaggggtgt    77280
aactgtttcaaggaattttagaatactactgtcgtgagttctgcaagaagttagggaagcctcccactcc    77350
tggttagactggcagcaacttttttgcattataacacaacagacatttcatgtccaagccaggtaatctga    77420
gctaccttgttcattccagatccaggggttggtgaggcaaaaagggtgtccccaaaatagatgggtctct    77490
ttattgaacttctgggttatctccatcatgtacagagatacagaatcatgcatttataaacttatggtt     77560
gaagatggcacccacagttacagtttcctcccaaacctccctggcctatctcagttcttaaagatgtctg    77630
gggattcccagttaggcatagagtaacaaggcagctctatccttaaatgacatgccaagctgccaatg     77700
gctggtattcatcctcagttaatgtggatattctagtaggagggcacagtgacataggaagaaatggtca    77770
ctctgtgttcaaattattcctttaacttagaaggcaagtttaccaccctgtgggtactgagcattgcaga    77840
cttcatgtaagcatatttttgagcattttctacaaaccctcatttctccaaatcccatcctttgcaacct    77910
caagtttatccaggggattcacactgcctgcatgtccttgtatgcgtttcttattgttcctgtaacaaat    77980
tatccaacctgtagtggcttaaaacacacgcatttgttatctcaccattctgaagctctgaagtgtgagt    78050
agctcggatggttctcttcatcatcacccaaggggtgattctgtgtggcagaaaggctgtgttttct      78120
tcctccagactccaggggatgcatccacttccaggaacatttgggttgatggctacatccagttccatggg    78190
gttgaggttcctgcttccttgcaggctattggctgagggcaaattttggcttcttgagaaccgtagcatt    78260
ccttgactcctggcctccttcctcccccttcaaagccagcagtggcagcttctaatgcactgaatctctc    78330
cgacttcctttctacctcttgtctcctttcccaagttgcatggcttgtctggactgattgttccattac    78400
cattttcctgcttctcagtatcatgaccccacttggatataatcagcttatcttgacatcag            78470
ctgcctagtaaccttaattatatctgcaaagacaattcacaacagtacctagattcatgtttgatttaat    78540
aaccaggggaacgagaatcttgggtggatgactttataattctgcttaccacattcctgtctataaacta    78610
atcttaaggttggtggacaggccccttacaactgactttgagtacccagaacactggcttcctatccttta    78680
ctcaaccagtgggctcctccaggaaaagcccaatcaaggaagataacgccattattctcatgcttttcct    78750
ttccccttcctcccttctctcccctccccttccttctccccttcctttctcttccttttcattttgagac    78820
agagtctttctctgtctcccaggcaggagtgcagtgcatgatctcggcccaatgcaacctctgcctcag    78890
cttcccgagtagctgagactacaggaccatgccaccacaccacctaattttttctatttttagtagacg    78960
aggtttcgccatgttggccaggctggtctaaccctcaggtgatccacctgcctcagcctcccaaagtgctg    79030
```

FIG. 8A-57

```
ggattccaggcatgaatcaccatgcccagcatgtcatgcccttcgaagtctgggtaataatcctcagat    79100
ggtagtgcacatagttatggagaattagtgaaccactcctccctgatgtggctcgcccccactgcaaata   79170
atttgtctatttttattttttttttttatttatttattcttttttgagacagggtcttactctgtcgccca  79240
gtcttgaatgcagtggtgcaatcatagcccactgcagcctctacctcccaggctcacgtgatcctcccac   79310
ctcagcctcccgagtagctgggactacaggtgcatgtcacctcgcatgactaattttttaaatttttgtt   79380
gacgcaggatgttgttatgctgcccaggctggtcttaaacttttaggctcaagcagttctcccacctaag   79450
cctcccaaagtgctgaaattaacaggtgtgagccaccagccctatttgtccttttttaattttaaaa     79520
gactcaacatgtagaaaccattttacccccttcacctgtgcattaagagcttcctttttcttaacatcct   79590
gctccttgaaatcaacccactctacttgtatggcagttgttattttaatattctaattaagatacagtt   79660
ttcattttaccttacagagacagtgagcgggtgctcttgaattccagtctggctttctccattcctttgg   79730
gtaatcacaggttaaccttttttccttcatcagttttcagcagtcagtgaaaggtgcattcattttcataa  79800
atcagccatttggcaacatttgaatgtttaatcagtttgcgatcacatcaaagaacaagggaagttcttg   79870
ggagatttattacctccttttggaatctgtgttcttagctacaaaggtgcaatgacttttttctagttctct 79940
gccccagatgtctgaactgttaatatttacagtgctcctttcctgaaattcagagtcagcacctcattt   80010
atcctatttgtatcccaacttactttattcaaagagattttacaacctgagatagctccgtaggaagagt   80080
tcagttgtcagaagcaatctgatccatggaaatttctggtgtttgttttcttgaattaatttgcagg     80150
tttaaattcttgcttaggccactctaggacttttaattgctatttcttaggaaatattccttagaacatg   80220
aagcagtctgtctttcaacacacacacacacacacacacacacacacacacacacacacacc            80290
ccctagcatacgatccagaacaacgttttatctttttttttttttttgtaggagggagtgtctcactct    80360
gtcacccacgctggagtgcagtggtgccctcatagctcactgcagcctcgacctcctgaacccaagtgat   80430
cctccagcctcagcttcccaagtagctgggactagaggcacacaccatcacacccagctaatttaatttt   80500
gaaaaaacttttttttttgtggagacaaggtctccatgttgctttggttggtcttgaattcctgggctca   80570
agtgattcttctgcttcagcctcccaaagtgctgagattttctggcgtgagccaccacacccagccctaac  80640
atttttattcttttactgactgtgagattttcattgacttacgctatgtcaggcagacttttcaagccata  80710
acctggctttggtgatttattatttttagctcttcatgttttaacagcttctctgctaccatgataggtta  80780
taataagtgatagaagaaaggcattttaaagtaatttatgaatgtggatctcatttgcttagctaaaaa    80850
aaaaaaagttttttttttttctagagaatagaaccaaacagtgttcactgtatcacatattccttttagt   80920
gtattgagcattaatgggtatttttgcagcatcagatcttcacaaggctggggttcatcagcagcacag   80990
tagctattaggtgatttactcaaggcagcaaaattcgttcttattaacacagtctctattgaagacaca    81060
ctcaaggcagtttgcctcatctatttagctttccaaaattctctcttaaattgcagtttaatgaataga   81130
ctaaaacacaaattttaagaaaaatgtagttataagatatgaagtgtcttttaaatctgccagtggttta   81200
agggatagtatacatttaaaataaagttataggcactgatttagtcctggaaaataatggctttatttca   81270
ataagccagtatcagaaattagttttttgttttctttttttttttccgtgatgaaatgtggtttctagtac  81340
tggataagaaatgcatgagaaataatgtatcccagcatatttaatatgcaacagtgtgatctcagtagcc   81410
ttgcagatggctgagctgaggcactaaaagtgatgagatgacatttttgtattttttccacacgttcttgc  81480
cattctcaggtgagtctgggctctcatcagtatttaaatgctgttttaccttggcaagacatttaggtcc   81550
agaaaatagtttaaaaaattaacatctacgcagaaagaacctccaggtagttaaaaatagggcaatttgc   81620
ggatacaccacatcctgaagactagtgttgctaagtaaaccacattattttaggtgtttcttcctgaca   81690
tttttattttttttcttgtgttatttttaattctggaacataactgggaactgagaatactacatgggaccc  81760
ttatctcttttcttttgttatgactgaaaatcataatttgaaagatgcttggaaaagggaaagcttaatat   81830
cttacacatatttttataagacaaaaatatggaaagatatgaaccataaaatcagtttagaatgggaagg   81900
gttagtaaaacattttttttgagcagaaaaggaatcatggaatggacactttataatatagtaattcagc   81970
caatttatttgatggaattcaaatgtcatgtcctcttttgtagctaagagtgcacattagcattaacccta  82040
aaccagaccacttggagccaaagagatgtgtatgtgtgtgtgtgcatctgcttctgtgtgtgtgtgtttg   82110
ccccatctgagtgatttgattttttcaccatctctctatttttcaccttccaaaattttaagcatttagaca 82180
tttattatatttaaatatgtttgcattctccctccctccacatgcagtgttttacaaatttcctatcagac  82250
tgttcccatcctgcaaaccccccagagctctatggctgaggtactcctctttctgttccctttctccatgca  82320
gatggaatgtctgctgggaactatcttcaatctatatgtttcccattcgtagaggtggctaaatctgtga   82390
catgcatccatcctcatccaatagtgtctccacatgagtgagctggataatgcaaaaccaagcttcgaca   82460
tcagtggtatgaagtacacacacacacacacacacacacgcacacacacaaatacaaacacacata       82530
atctctgtagctcagattgggattgtctagggttaatatctttttgtgctaaaaatatccctgtgccacat  82600
tgaagcttattataataattattaattactgatatatttcaactgttatgtctcctaaaaatatgcatag   82670
attattaagttttcccttctccttgtgttttctgattatgattttctatcataaaggtgaaagtgataa    82740
gggtcccatgtagtgttctaactctaaacctaatactgaccctaaacagaattgaacgctttaaactaac   82810
ccatggcctttgaccattgcttcttgaccgttgagttaacccataaccctgaacagagaatgagaaattg   82880
aacccaaatttgaacccaaaccctaactagtgactggatgaaacctaatcctaaccccaacttttgaaaaa   82950
gaactcaattctaaactcaaaagcaaagccaaccgaacacctaatctaacttttaatgtaaacctttgaac  83020
ttaccccttaacttttgccagtagcccttgactcttgaccccctgatctgaacactgaaggcatccccaaa  83090
ttctccgacccatggcctttgatcctaatcttgacttttgatcactgtccctaataatgaatataatccc   83160
ttgatcataacattgaactttgctcctaccctgacattcaattagtgatctaaccataccacaacctgaa   83230
cttgaacccaaatcctaacatgaaccttcctccataccctgaaagctatcctaaccctttgaccttttgatct 83300
ttattttctccttgactcctgactgtgagatcccagcctggactaaaatgtatacacactcaaaatc     83370
ttttttgttctgaatcgttacccaaacctgaacttgaacccaaaccctgaccctacccaattacaaatct   83440
gaatacaaaacctatccctattctaaagttggggatttgagtctcttagtcccgtagggtagatgtggtg   83510
tttgcagccctgcagccactatggacaccacagacttggacaaaatctccaacgtattttgggaaaaa    83580
ggatgcaaccattagagaacaagatgttgaaactttcatccataatctctgtttgtacagacttcagggt   83650
gaaatacatgtggttggaattgtgatattccagccacaaaattgtattatgttgagataatgtgggttt    83720
ccctatccctgaaaatgtgttcatccaaccaatagttacttgtaccagcagtgtgcaccagggaccatttg  83790
ggttcctggaggcagccgtaagcaaaagcatcccagatccctgcttctggaatccctgactatgaattg    83860
gcatcctcataatgaatgtaataaagaaataaggtaaataaagaaataatctagactcaaatgtgaactt   83930
tagtcgctctggaagtccaaaccctgtccaaacatgtccgccgattactttcagaggatgggtgatgact   84000
caggttaatatggttattttttggagcccgtcttaccttattgtcctttatagatgatgtgttttccacctc 84070
agatatcaacatgaaagactgggtcacttctcaattcagaaatccactcaaggttaggcacttttgggagg  84140
```

FIG. 8A-58

```
tcgaagtgggaggatcgcttgagcccaggtgttcaagaccagcctggccaaatggttaaatcctgtctct    84210
acaaaaaatagaaaaaaattagctgggtgtggtaccacctgcctgtagtcctggctgcttgggaggctga    84280
ggctggaggatacctgatcccaggagtttgaggctgcagtgagctgtgatcatgccactacactccagcc    84350
tgggcaacagagtgagaccctgcttaaaaaaaaaattcattcaactatgtgtaagagagagagagaggtg    84420
tttattagatttaactgaggatttggggagaaacttgggggcattttatcctatgggataagagggaaaa    84490
ataaaccttttaaattaaacatctcgcccttttgctgactacctttggctatcctaacatgaaatattc    84560
ttctggatgctacaactctcagctccactgatcggctagagcagattcaccatcacttcttgttttttgga    84630
tttcaccctctgccactcgtgatttaacaaataattctctgaaaggcagttctcttttgaaaaagagttt    84700
tgcttctctgtgttaaaataatgtgtgctgctgttaaaatagtttttgtatacacgagggaactcctttag    84770
aagctttatcacgtctcttagctgtgcgtgcaatttgagtaattactatgtaccaattccagtaacatag    84840
ccaatacatcagaactctcaggggacgtagctgggaacttttcttgcaaaacaactcccacgtgttcattc    84910
ctgtctggaaaccaccagtaaaatttataatcagtaataatttctccaggcacagcaactgagaatggta    84980
gaacattagttttaaaaaccatttaataaaatgcctttataaatattgagacttaattatttagattaa    85050
tttgttccagttaatgaaagatctcttagcacaagactgggaaaaattagaacacgtataatttcttca    85120
ttccagataaacaattattttaatgtttatctggtatttgaccacaaacttaaattcctgggtttcgtag    85190
gattagaaaattttaaggttagtaatcactcccgttgttaaactgctggattttacctaaaattactgcaa    85260
ggatgtatcattttttatacctcaagctgtttttgtgcagtttcctccaacttccatagacaatttta     85330
atcatttattttgttttttcttatcagataatgtttcataacatggatgtgaagaattaaatgaacatc    85400
cttctgtgcacaaattaagattagaacacgaagattttgggattccctcagttcctttataaattgta    85470
tttctttggacctgtcctaaggataaccacttttgtgaatctgattcattatttccttcttttattaagt    85540
tttatttctgcaaaattgtcatgaccagcataacccaaagaatatattgttcgctctgttttgatcttt    85610
tataaataggatcatcctatgttcttcttcattgacctggcatttccctttcattgaatagtatgtttttgat    85680
tttaaccatgaagatgcttggagctgtagtttatttgtgttcactgatatatggaacctcacccgatggt    85750
tataccacaagatatttaactctttcagaagctggaaatttgaattggccttatgtaaagagttcagcta    85820
ttaggattctgtgcgtgtctcttgttgaaaaaaaatgcagaagtttctccaactagaaatgtatttactg    85890
gaccatattttatgtgcatatttggatatacactctcaggttaaaaactgtttaagtggttggacagttt    85960
tattcacccaagaacagtatcagagttccctgtcctctctgcattcactgcactgaatccaaaattgaat    86030
agaaatgaaattagctgtctcttttgatttgttctctcctttagacaaaaggcttccaatgttgtatcattatg    86100
tataatgtttgaagtaagatataaataaaactaccatttttcagataaagaaatgttttatttctttccttaa    86170
tttgataacatacaatcataaaattggttcaaggcattttttcttttatcttgtaagattatccttgctttgc    86240
atttaattttttcatgtagcaaattaaataacttaactttcaaatgttaaacttagcttgatattcagta    86310
tcttcttaacatgttttttgtatttgttgttagatattaatcattttttctctatctctgtacaaaacaa    86380
gatagactataattttttctttgttgagcttccctggttttagcatcgactaatagtagctgtgtagaaag    86450
agtaagagaacatttgtttatgctttctgggagagttcatataaaacacaaattattcattcattaata    86520
ggtggtagacttgccattcagtccaccttggacagattatttctttgttgtacttaaaaccatcatttat    86590
ttcctccttgatttgtggactacattacatattgacttcttgtatatatgaagaaaacatgtttgtatg    86660
tctgcacatgtctgttatcactctattatgttcccttttctgcatttgtctgtctgctatatacattttgc    86730
taaactgtcataacaaattatgagaaatttagcagcagaaatagcatttattcatacatcagggatct      86800
gtaggtcagaaatcctggtgcagtggagcctagcttggtcctcttcttagggtctcccatggctgaaatc    86870
aagagattgcagggctgcattcctttctgggtgctgtagggatgaatatatcacaacatatagattttt    86940
aaaatctaattatttgcactaacttctgattttaccacattagattcataggtgaattcctgtcatatt    87010
gatcattcgagtcttctatggaagctttcttttctatcttacaacatcgtcagattgttacaggttttcatat    87080
gtatttattcttatgcttttaaacaaggggttttctctgttttatgtaaagtttgacctaatattttcatc    87150
atatctgtgttatacttgagatgtatattgtgaatatataagcacacacaatgaactattcttcagcctt    87220
aaaaaagaaggaaataagaaggaattcatgtaatttgtgacaagatggatgtacctggaggacattatgt    87290
taagtgaaataagccaggcacagaaaggtaaacactgcatgatctcaattatatgtggaatctaaagaag    87360
tcaaactcagagaaacagagagtagactcatggttgtcagggactggaagttgggtcatgggggaatttt    87430
tggtcaagaggcatagacatctttcttcttctataatattatgttcctatgttctagttttttgagctat    87500
taggatttccatatcagcatttttaggtcttatttatgcttgcattttttatattcttgataatttttagtc    87570
tttctatatcttttgggttaaatttgtctcttgagttggatgcattcttcatcttaggttttgttacaa    87640
acatgagattgtctggaaatttttttaaattcatgagtttaaaccatttatgtttgttgaacgttaatttt    87710
taccgatgcttatttctgccatcttgttttatatgttcaatttagttacttcaggataagctgtaactgta    87780
cattttgttttgaaaacataagtttctacctgtcatttaatagatatttaaacatagttatttaaaa       87850
ctctgtatctattttttatccttactatggttaaccataactgatcacagggaatgctgtttattttc     87920
ccagttgttttataaatttaacaacataatattggtttataccaattttgttcaatttctatatgaaaa    87990
tcaaaaatatatagaatacatcaaggaattcattgacagatctgggaatttctaacaagataaacttttt    88060
tcaaacatgcatcttttttagtcccaccccctagtgctatttaagtagatatttccaagaatttaagttct    88130
gggctattatccatatatgattttttgtcttcctttttctacccattttagcagaaattatagtta       88200
ttggttgtgcttgcatttcatatattttttcagaattcttaccaaattagttatattcttttgataagtatt    88270
ttctcaaagataattttcagtctttaaatctttgcttagcaaaatgattgaatctcttttttgatcttttt    88340
ttttaacttggcctatagtattaaattttttaaattcagagttattttcttcaaactttcaaatatga     88410
ctcctgtgtctgctaatgtcttgtgctatgactgggaagtttgatgtcaatctgattcctattcattcat    88480
agctcacccattttctctctgaaggctattagaattttctgtttgtctttgatgtcttaaatttctta    88550
gtaatatatctattcagggcacttttgagcccattcaaaataaggttttttcttttttgtttgttttca    88620
agtgtattttcattctttcatcaacttagttcttcctctgtatttttttttctctttctgttacctgatc    88690
ctggtatctctaacaaagtcatccattttccaaggatgcctttctctcctttattctttcctgatgctt    88760
tctgggaatttcttccatctgatcttccaatttggtaattcattctatgatttatcttaactattaggtt    88830
cttgttcatctttactattatttattctataccctactatatttaccaagttctcttttacttcttattat    88900
aatctcctatttgaaatatattccctaggtgatcgaatatattttatttttgtctattgtaattttcttcat    88970
tgatctgttccaatcattatatttaacgtagaagaattttttttttctgttgagagagagcgtttggtacc    89040
tttgtaaatgttcaggtatatagctctttgttaaacatttagcctgtgttctccttaggtgagtggaaac    89110
tcatccatcactctggtttgtaattacgcatgtgatgggacctaagggcagacccaagtctatgtttctt    89180
ctatgagattaacattcaacaaacacttttagatcactctggcgcactgaagaagtttgaaatttgagat    89250
```

FIG. 8A-59

```
ttggctttaaactctctaaaggagccagcattaggaagaaacagcctctttagcttcattcctgggggtg      89320
tggaggggaagggggtgaaacaggaaaagcccatagtggccataagtgactggtggccctgaaagttttt      89390
aaccagctcctcaacgcagctgagttttccgtgggcttgccagagtcccactacctgatggctgccctcg      89460
agttctaagttgtatggagaagagacgatgggagggagattagacaatgattaactcaaggcattcttta      89530
taagagacaagagtgaacttaatactttgtttttaaaccagcatctttctattaccacttccaccctctg      89600
ccagaaggtgcagccactcccattcaccatatatacatgattcatcagcttgtaatctcctcgggatggc      89670
ttatagcttactgatttcatgttctattattgctctttccgcagattgatgcctcgtcttatcctctgta      89740
gtttttcaaaagtagatttctgtggaggaaggggcattatgttctattcaccatctcaaaagaagcataa      89810
ctctctttcttggatatattactattttccccacgttgtgtatgcttctcattaaaggtaggattctaaa      89880
ccatccaaatgaatctgtgccaccacctgccctggactttggactgaagaggattgagaaatggtgaaa       89950
tacttaactatttgatagcttccttcattcccacagaccacatcagatgtagttagctaatataccaatt      90020
aacaaaattacccaggaaatgcaacatatatacttatttcattacttgtcaaaactttctaaatggcttt      90090
catctatttctaaaaagaatcccaaatgttccaggaacaatttcctaatgttctggttttgaatatcaca      90160
gctcatttatcagcgtatatcatagctatgactatagacgccaaaatattaagtaattcataatgacaat      90230
ttggacaatgaagggtatattagaacttctttgagtattttttattgcaatatgaattttaaccaaaga       90300
cttgtatgagctccagagagcaaatccactacatttccccactctgcctccaacccatcactatataga      90370
tccattgtggagctttttttacttctttgtgtattaaaacaaaggatataatatccccctgattatgga      90440
tgaaagtgatggaacatttactgccatgagagtccccttatgataagtggtagctgaactggaagtttaaa     90510
gaactgtggcagacaggatgggtaaatcaataggatccaggacctaggaatgcatcaggaaagacagca      90580
acagggaaggatgagctagagcaattgaaagggtgatacatatatttggagccaattcttttatgctat       90650
catcaagataaaaccagtattcctcacctggtagatatttctctttgcaaaggtggatattccacagttc      90720
acttccacagacctcatgcaaatgtcagattcagcggggagggagccaccccagtttctttggcagcac      90790
agaatataatgcatcatgtttatttgcaagcctggagatattcttgcatacatattttatctagcagatg      90860
acactggatccaattaattggtggctttgaaatatatttattggaattcattattttgggttatagttgt      90930
ttctgtgatccatgcaatctaccaggatacttcatgcttttgcatttaaaagaatgacaccaagggct       91000
tgtgaaaggcacattctggggtccatcccccacaatttgtgttctgttgctttaggggagggtgtgagga     91070
tttgtgcatctacctgctttccacaaagtagggtccctgctggtataagggcacaccgtttaagtgctac      91140
tgcacagaagcatcagatgtcattaagattgtgttatctacattttcttattgttgctcaactgccagt      91210
tactcttttcataaaatatgtatctgtcctatatagggctaaggaattaatttatcccagtctataactac     91280
agagagaagcctacttaatgtgagcattcttgatggggcataccaccccataaatatggcaccttagcatttg    91350
aaaaaacagaagaagcaggaaagttctctctgaccttctccccatccttctcccctaaagccaggtcata      91420
agaccctcctatgagaggtgactctctataccaagaggaatagaacattcttatctctgaggacaaaagg     91490
acacagaggagaatctgaacacacaggcctttgctaagttctcccagttttttcccattagataataaac       91560
attttttacttcaatcatactttccaatgactgtccactctttatcaaacctaagtatctaagcacaaaaa     91630
tccacaggtttccctgtttcttttgggtcttcattgcccttatgaaggctcctgtgtcatataaaactgtt     91700
attaaatgaagtgcactctttgcttaatctgtcttttgtcataggggcctcagccatgaaactaagatag     91770
gaagaaaagatatttctttttcccttatattattcaacaatattctagttatacatgtaagcttaaccaaa     91840
agcttctagaatatcaaagtaataagtgtgaaatatgtgtgtgcacaatatgttgctgcatgcatatatat     91910
acacacactacattgtaggtgtgtatatatatgtatatacatatacacatatatattttataagatgcgt      91980
atacacatatacattttgtatgtgtgtgtgtgacagagtcttgctctgttgtccaggctggactgca      92050
gtggcgctcactgcaacctccacctcctgggttcaagtgattctcctgtctcagcctctggagtagctga      92120
gattacagccatgtgccaccatgcccggctaattttgtatttcttttagtagagatgggtttcacca       92190
tgttggccaggctggtctcgaactcctgacctcaggtgatctcccacctcggcctcccaaagtgctgg       92260
attacagaggtgagccaccacgccaagccggcacataatacatcttgtaaaatatatttagcaaagtcta     92330
tttaaaaataattaatagtttattaaatcttatgtagattttttttttcaaaatgaacaagcttctgtctt     92400
tccaacaaagctttggaaataataatcattgcattttcctctaacaggttaatcagcagatcaactaaaa     92470
ccaaaatgagtctttctctgggcacggtggtgcatgtctatagtcccagctactcaggagactgaggcag      92540
gaggatcacttgagcccaggagttcaaggaccagcttgggcaacatgacaagatacccatcctctaaaaaaa    92610
aactaaaaattaaaaaaaaaaataagtcttttctataactgtatgacagggctaaggtgattttatttgac     92680
agaggaattaaatttcaatgtaccaagttctatccgtatgatatcttttctgatggttggaagggcacca      92750
aggggcttccatgaagctcagtgacagcattttcacatggaagtcactgcagcggaaagtagggtacaca     92820
ttcttggtaaataatatatgattgcactattgatgaatagcatttcaaaagctctgctatttattgtcta     92890
ttgaaagataaatgaatccagcaagtaaactgccacactgttataaaatgtaaacacc            92960
tctatcatactataaatctccctcccctccgctggaaaagacttcaagctgagatcatcctcgtcctcat      93030
cacatgattgcttggaatagagttgtccctgaggccacctgtcacctaagagggacttgtattcatttatt     93100
cagtgtccatgtaatgaaagaataagacagacatactgtgaatataagaacacagagttcaaaagactat      93170
tctgattgagcagaaggaagatactaaacaaatattagatgaacaaagcttgtgtgtatggctttggaag     93240
ataagcctaggatcttaatcttgtttatataacacaactattaaaccttcctgcgtaaaatacatttttaa    93310
ttgagacttagcatgaagatagaacaccaagtctgggcattctgaaaagtttagacgcagaggaataact       93380
ggcaggcagtgatttaaagtggatacagattttttgccctggagttgcagatgcgtgtaggaatgaaaagg      93450
aagtaatgggtgtgataaccgatttaaacactaatcagtgagccccaaatattaaccatatactgggatt      93520
ctacaaagagatgccatggtaaaaatgaattcaagtgtttttaacctgtatagctggatacattcttgt      93590
gatattaacacgggaaataagaaaagagacgagtttgaatgagaaaaagatgtttagctcaatatagcac     93660
acactgagcttaggctcgaataagacatctgagtggtcagcatgggagaagttaga                93730
gctgaaacccaggtaaaatccttcaagttacaggcagaaatcattaccagatgtgtggtggagtcacacg       93800
ggggatgtgagtcctaatgcctttgcagatgcatggggaaggcagtgtctttttgaaggactggttttag      93870
cgctgcaagaagtaaagtaaattctcttttacttgcattcttgttccctcatggtgcttttatgaggact      93940
aggcaagaatagtattgaaccacttataccatccatctgttagaagaacctataatacagaaatatttgc     94010
tttgggctgaactccaaacgtaatacttaatgattcttcaagttttgttgacacattctactcatctcca     94080
cataatttgctcccagtcgtttctgagatatgctacagaaagtacaattgatcaaacgttggctgtag      94150
ggattcaagaacagtcctgtgactgcattttcgttccttcctgaaactattccaaggccataaaacacct      94220
ttttttgtgtgaactgtctttctgtatcccatttcagatgatatcttcttttcctttaaatacagtcttttta     94290
tattttctaattgtctgattgccaaaacaatatatctgcattgctataaatttacagtatcaaagatca     94360
```

FIG. 8A-60

```
tacagaagaaaaatctttttttaacaaaagaaaaccattgttgataatttagtttacatacatacatatgt    94430
acatacatgtatcctcttagcactctggggcccggagtagagagcaaacctgtgaaacagatagatagat    94500
agatagatagatagatagatagatagatagatagaagatatagagatatgttagagctatagagatatag    94570
tctctagatagatagataagaatatctgtattctctctctctagacaaatgattaggaaacagtctataa    94640
gaacgtgtgtgtgtgtgtgtgtgtgtgtgtgtgtgtatgctctctagaggtagaatatatctctct       94710
gtagggagagagacttatgcatgtgtatgtgtataaaacaaagaaacaataaaaacacaaaggcccaa      94780
atatcaaccagaagaaactgaccagctgtaatgggacaattagaacatctgtaagaatatttgtactgga    94850
tttaaaatgataaagacataaaagttcatgtattcatcatgacacccagaataaaactcactggttatat    94920
tactaggccacgatcgcatttcctgaatcttgatcaataaaagaatcatgatttttttcccactttcct    94990
atatatattgaatttcagagtaactaaaaaattggtgattacaagtaaaatttcagataatatatgcaga    95060
aagaacaatactatctgaaaatcattattttgtgaaactccaaattaagtaagtatattaatctgtcctc    95130
acactgatctaaagaactgctggacactaggtaatttattaaggaaagaggtttacttgacttgcagttc    95200
cacatggctggggaggcctcaggaagcttacaattgtggcagaaagggcagcaaacgtgtctttcttcac    95270
atggtggtggcaggagagagaaatgagtgccccattgaaaggggaaatcccttataaaaccatcagatctt   95340
gtgaaaactgactcactaccacgagaacaccatgggggaaactgccccatgattcaattatctccacct     95410
ggttcctcccacaacatgtggccatggaactacaattcaagatgggatttgggtgggacacagccaaacc   95480
atatcaataagagatctaggaaattatctctgattatttgtgacaggtttatatatatatatat          95550
atatatatatatatatatatatatatatatatatatgtgtgtatgtatatatatatatatatatgtgt      95620
atgtatatatatatatatatggtgggattcattaccaactgaatgtaattatcaaccactcttaagat     95690
aattaaaagtaacactagcaggtatcatgtaagtccttattaaattcagtataaagtacagagcagttcc   95760
tgggtgcgttgtttcctacaaagggcaccataacccctaaggaagaaaaacaagatgtgattaggaaacat  95830
tctgttaattctagaacatggggtgttcttcagcagtaatgttcaaaatgtggttcacaaagcagcaact   95900
tgttagaaatgcaaaatttaagatcctataccgtgggaggaggcttcctgaatctaaaattgagggtgtgg  95970
gttgcaaactattatttcttttcccaaacccatctgtgatgtttatgcttgataaaatttgatgggacggt  96040
tcattgatttccataaggaattaacgatgtaagaaaatgagaagaagaattgtattatgggaaagagggt    96110
gtcaatattttcacttgctttctctttaaatgtgtggatcacaagatttgcttttcattaaaagtattca   96180
gatatatacgtatttgaaatacatgtgcctatacactaaccccaaaacagctcattaagaatctcttc     96250
cactgggacataggcatcagtatttgttaaaatatcactaagtgtttagtgtggttgatgagtgtagaaa   96320
gaatatattttcaccaagcttatgagatgggcagtttggggccaggagaagaaggcagtgaaagaacttg    96390
ggtgataagcagctgtctacttgcaaaacaacttattattaatgaattgggactttaaatttttttttt     96460
attttcataggttttaggggaacaagtggtatttgcttacatgagtcacttctttagtggtgatttgtga   96530
gattttggtgcacccattacccaagcagtatacactgaacccatttgtagtattttatccccaacccc     96600
ctcccacccttccctctgagtccccagagtccattgtgtcattcttatgcctttgcatcctcatagctc    96670
agctcccacttatgaatgagaacataagatgttttggttttccattcctgagttacttcacttccaataat  96740
agtctccagtcccatccaggtagctgtgaatgccattaattcatttctttgtatggctgagtagcattcc   96810
atctatatttatgtaccacagtttctttatccgctcgttgattgatgggcattgggttggttccacatt   96880
gtgacccaatgcttttaaaataatgtgtgtgtttggccacgaacataagccagaacactagaaaattgt    96950
ttactgaaagccatcttagtttcaggaacacaaaggaaatgaggtaatgtgtgaaaagaacttaaaaat    97020
tgtaaggcatttgcataaagatgttaggtgctttttggaagtttctatttaaatgtggtcaattagagag   97090
gtttttttttttttcatttatgtttgccttgaaagcatttagaagtatgagaatatataatttcattttg   97160
taaaacacaatatgttgaacctaataggatctttcttggaaactgaacattgtcctgggttttggaggca   97230
tcccattgaaatttagccatgattccatattcagcaaattgctgtggacccagatacatcttcgctgacc   97300
agaagtctttccagagtggaagattttagtaaatgtacaagtcaatcttgtagaattagataaaatgcat   97370
tctgtttccatcacttgccgatatcccccccactgctaattaaaggaaacacaatccacaattgatttac   97440
ttatgtaaatgtagattacaaaccaacaacatgattttaagactcttaagggattgagggctattttgaa   97510
tgtttactcttggagacatgtatatttaggtgtcctggtcaacaagatcaattgtaggaatggttggtgc   97580
aatcacattggtcattaaatacagacatcacacataatcaagcagatttagctcagggtatgggtaactc   97650
aacatatgaacaccattcaaagtattccccaaaaggctggcatggtggctgacatggtttggttgtgtc   97720
cccacccaaatctcgtcttgaattcttgtgagagggacccagcgggaggcaagtgaatcatggggcagg    97790
cccttcctgtgctgttctcatgatagtgaataagtctcatgagatctgatggttttaaaaagggagttt    97860
ccctgcataagctctcttctgttgtctgccatgtgagacatgcttttaccttccaccatgattgtg       97930
aggcctcccaggcacgtggaactgttaagtccattaaacctgtttcttttgtaaattgcccagtctcag    98000
gcatgtctctatgagcagtgtgaaaatggactgatatagtggcttacgcctgtaatcctagcactttggg   98070
agggcaaggcaggcagatcgcttgagctttgcagtttgagaccagcctgggcaacatggtgaaaccctgt   98140
ctctataaaaaaatacaaaaattagctgggtgcagtggcacaagtgtgtattcccagctacttggggacac 98210
tgggtcaggaggattgcttgagcacaggattgcttgagctagagatgcccaatgcatctcaagggtgcag   98280
tgagccgagatggcgccacttcagcctgggtgacaaagtgagatcctgtctcaaaaaataaaaaaatatt   98350
tccccaatggggacatatggcttaatagttagggttattgtttgtagtgatgaataggtttggaaatagg   98420
tcagtggtgataattataccacattgtgaatgtaatgaaacaacaagaattgtacattttaaaatgatca   98490
aaatggcagggtgatcccacacacaaaggggggggatagatatacatagatatcttcatatggttttc    98560
ttgttttttaattttttattttttattttatgtattttttatttgagacagagtctcgctctgtcgcc     98630
caagctggagtgcagtggcatgatcacggctcactgcaaactccaccttcaagcgattctcct          98700
gcctcaacctcccaagtagccagaaatacaggcacgtgccaccacgcccagctgattttttgtatttttt   98770
tagtagggacggagtttcaccatgttagccaggctggtctcgaactcttggcttccactaagaggttcta   98840
gtaaagtacatactggctggattcaataaagcacaaataggcagcaaatgcttcttacatctcaatctaa  98910
tcggtagccttctttatcctcaccccttggctgactaacgtgcataaagcataggaattctggccactcaa  98980
ggatcttaaccatccagttcagtctgttgcaatttctcgtcacattacaaattttttttcacttttcctttc 99050
cggagaaagccatgatgaactactgcagtcgaactcgatctc                                99092
```

>HNL4 Exon4 (3437-3622) Exon5 (8810-9599)

FIG. 8A-61

```
aaacagtcttattatttcaaatgctaacttcatggctcatagattctgtatcagtaagcccacatgcttt      70
taagtctgatttatagaaaacatgatttgccctcaaacaatgtaacctcccaacagattcatctttacca      140
ctacacagatagagctgattagtcaagacagaagaattgcaatagataaagggtttaattcctgcagagc      210
tggctaaatgggagactggagttttattgttactcaaatcagccttcccaaaaatttggaggcttgggtt      280
tttccagaatactttggcagacaggggctagggaatgagtgctgctgattggttgaggatgcaatgatag      350
gggtgtggaaaacagccctggtgcacccagtcggcctctatgtggggacacagaggagtcactggtccta      420
gtaggaccaatcagttgtcagaaatgcaaaagcctgaaaagcacatcttaaaaggccaatctgtactatgc      490
ttattacctgggtaatgagataacctgtacatcaaacctgtgacatgcagttcacctacataataaac        560
ctacaggtataccccctgaacctaaaataaaagtttaaaaaggcaaattttagcttctagtgattgggga      630
agttgcaaatcttgtgacctctggaataatggctggtaatcattcaactaagcttacatcttagcagaat      700
tcaggcctctctcattcttaacctggtggcctttcattacttttacaaaggtggtttagttttaagagg       770
ggctattatcatttaaactacaagttcaatttctcccaaagttagcttggcccgtgcccaggaatgatca      840
agaacagtatgggaggttaaaggcaagatggagttggttaggtcagatctcttttcactgtcataattgtct     910
gactattgtaagttttgcaaaggtggtttcaaggtgaaaggactatactcttaaagagcataaaattatt      980
gcattcattgtgtacctgaaacaggcactccccccttgttgatagtttaaaaagaaaaaaataataatccc     1050
tggatgttgcaataaatgaaaatgccatggcagaaactgtggaaacaccagcctcaaaacaccacattga     1120
tttgttaaacttcagagatccatggattgtcgtttccctcagccagcctgtaggatatttggaagaattt     1190
cagaacctcaaagatcaaaccatccaataggatgctgttagaagaactaagattttttgaaggcaggggat    1260
attcattagcctgcttttggaaaggttaaaacactctgattttgctaggggaggaagagttttatgg tggaa    1330
gaaaggccaatgatttcctgcgtgttgaaaatcttcatactcctccacagaaacaaaataagtcaacaag     1400
tcattctgcagaattgagaaagagagaacagtgagtgaagaaaagacgtgctgaagacagaatcgttctg     1470
ttagaaaattgctcgtgccttaggaattaatcacctctttctttaataggggaagaaagcattgccctgt     1540
ggtattatagggcacctaaactgacatgattcgtcattgtcatataaggatcttcgatcttttctcccaa     1610
gcaaagcctgatgccttttatgaacgatcgtgtcaaagatatagtgatggagacaggtgttgcagaacat     1680
tttt ggcatgaagcactaattagtaattgctaattaaatggggaggaggcttgggtaatgtctgatcgc     1750
accc actaatcgtagctaatctcccgtcacatccctctgaacttaaagaagatcacattggtaggatgt     1820
gtcttaagtatccaacctcgcagttgcgacgctgcctctctttgaagctgcaggagatagtgactcccga     1890
ttcaggcttggagtttttattgtcattgttgaacgaaaatcgtcctgtgactttctttggagccaggcca     1960
tttcctccttttccagctcagagcatttttccacaggtgctcaggaaagctcatggaagaaatgctggttg     2030
actcaattggtatgcagcctcatcctctactcttttttgttttaaaagtagaagccggcactcagtcactc    2100
cttggaatgccgtcaactttggttagggacgtgcttt gagggaattggtttgatgttattttagggctta    2170
aagcagcctgtcttcatacaaacatgactgcaggtggccataataatgtgctgagcatcccttgaaatga     2240
gtgaatgacatggctcttggaaaaaagaaattgtatagaaggggcaaatatcatagttgggtagttgggg     2310
aaggctcaaataaggacgtgaaaatggttaaaaaaaaaaactttttaaaaattctttgtcttttggaagg    2380
catatccagtacagatttggacataaagttggattaaagtttatgcaatgaactaaacttgcaggaggcc      2450
ttagaaaatattcctagttttgaatctgagtaggagagtgtatgtcttcccaaacttgacttcaaaacat     2520
cagaagaaagcagttttttccaggtcaagctcattttcaatacagaaggaacaaaaaataaaatagattaa    2590
ctcataactttgctatcattaataccaaaattgccattttt caactactaaggagaaattaagaatcgta     2660
tgccttgagtaaaatctagatcctcaactcacagaatccttctttttaaaataaggaaggccagttcctg     2730
atattttgggaacagttggggagatgtgaatattcattagcttttgggtgaggttcaataattacatttt      2800
tttgtatgtgactaatattttcgctatgtaggaaaatagaggtgtatactatttacgagtcggatctagt     2870
ggagtctgtaacttacgttgtttcttaagcattgaaaggagttaaaacaaaatgttaataactaattcag     2940
tgagaaagacaggcgcacactgcctttgtatacatgcacatattcttagacacagacacacatgtgcact     3010
tacgcccctccccccccacacacgtactgttttccctgaaaaatttcttgtaggagtctgttgcatttt     3080
ttcaaaaagaaaatgaaaatgtgcacagaaatgataccttgaacctagtaaaatttacgacgtcttctg     3150
ggattgcttcatgttattaatatttta gattcattttgccttctctattagccacatatatacacaaga    3220
tgccatggtatcataacatcaacctaaaataaccattatttatataattatttctgccacaaaattttt      3290
ctcctgttcttcctctaattggtggggggtgagagttgaggagagagaataagaagacaagctatgag         3360
atatcttttcaaatagcagagacacgtatgcacttttttctatttggccaccaaaaatatcttgtgttctt   3430
ttgtagGGTTTTTAAGTACCGGTGACCAGGCAGCAAAAGGCAACTATGGGCTCCTGGATCAGATTCAAGC       3500
ACTGCGGTGGATTGAGGAGAATGTGGGAGCCTTTGGCGGGGACCCCAAGAGAGTGACCATCTTTGGCTCG       3570
GGGGCTGGGGCCTCCTGTGTCAGCCTGTTGACCCTGTCCCACTACTCAGAAGtaataatggcaccccca       3640
gggtgggcgggcaaatacccctgaaccaagaaatgaatggtcagagttcatatctcagatgcatgtcctgg     3710
ttaccagaagtcactctggcaacagaaaatgcccaaaagatcaaatccatcttcatgtcttttaac          3780
tcagcttttgttccatttgctctgtcacccaggctggagtgcagtggtatgatcatagctcattgtagct     3850
tccaactcctgggcttaaggcttctcccatctcagtctcctgaatacctgggactactggctgccttttta    3920
aaatttttatagagaagtggtcttgctatgtttgcctgggctggtctcaaactccaggactcaagcgat      3990
cctcctgccttggcctctcaaagtgctgggatgacagatgtgagccaccatgcttgatcagtaatatttt    4060
tctcctaatttaaatgtgtgacaattaggtgttggttacaatgattggaacaaaataactactttagaag     4130
tcctgacacttttgtttttttttgccattctgactgtattttgaaatttttattaacttctagc           4200
tacaacttagtaaaagtagtatgtgaagagagacagtatgtcgataaggatgcgggtgtatagattttgt    4270
aaccatcagggcttttagccacatgttttttaagaagtcgctcctctctcctaattcatattaattcttta    4340
aatcttctggaaatattgaaacacgtctggtgcattcatttagaagtagattctgggtagaagtagattc     4410
tacccagaggaatagtgtctctctccctgatggtctccctccctcccttgctcttcccctcccattcttc     4480
tctttccctctctcgtcctctctgtctctctccctctctatgtcctcctccctctacctctctcctgctc     4550
cctctctcttttgtctctgtctctcaccctctctccccctcccaccctgtctctctctccctccctccctc    4620
tctctctccccctcacactgtccccccactctccctgttttctccctctctctcttcctctctctcc         4690
ttttctctgtctcccactctcttactcactatctcctttcctctctctctttccccccttttccctctgt     4760
ccctctctctttgtttcttctctctctcccctccctttcttcttctcctgcaaatatgactttcac         4830
caaaggacctccttcctggtcaggtcagcatgcagcactagggagtgtccagagtttgctttcccctctc     4900
ccttcctctctctctcctgcaaatatgactttcacgaaggacctccttgctgggccagtcagcacgag       4970
gtcctctgcttgtcccgtgggagctccaaaccctccctggggcccgctattaacctggaaaaagctga      5040
```

```
tgttggcaaagtggagaaagaggaaaccacaaaaacacatgtgcatcatgttacctcaaccagatgtgca     5110
cttgaacgtgtagtcagcataggcacccgtacccaaccagatgtgcacttggacgcctaagcagtagatg     5180
gttatgctgcctaagtaatggtcagcataggcagccacacccctgagccctgctggagtgcctgaggctt     5250
tccccggaggctcactcagtggattcccagctgtccctttgtgaaggaggctccctgcagtatccgatga     5320
gagacttcaaagaggagtccacaggaatttgaggcaattggttctggaagcaggatcacaaattcctggc     5390
tgtggcctaaaaggaagaggcaggaaaaatctgcagtgcagatccagccctgggttgcctggccacacga     5460
agtgaatattcctaatagccgtctcagtcatcaagacagctttgtaatttgttctgtgttgtcagtggtc     5530
ttcagaatggcaccacactgactgaacctgaagttctcaaaaccttcatggaatttttttttttttcag     5600
ggagtctcactctgtctcccaggcaggagtgcagtggcacaatcttggcttaccgcaacatccaccttct     5670
ggattcaaagcgattctcctgcctcagcctcccgagttgctgggattacaggcgcccaccactgtgcccg     5740
gctaattttttgtattttagtagagatgggctttcaccgtgttggccaggctagtctcgaacttcctgac     5810
ctcaagtggcccaccacctcgacctcccgaatgattattttttaaagttatcagctggatatggtggctc     5880
atggctgttatcccagcactttgggaggctgagcggggaggatggcttgagcccaggagtttgagaccag     5950
cctggtcaacatagcgagaccccgtttgtacaaaaatgaaaataaaaaccagctgggcctggtggcgcat     6020
gcttgtggtcccagttacttgggggctgaggtggaggatcgcttgagccagggatgtcgaggctgcag     6090
tgagctgtgaggttccactccagcctgggtgacagagtgagacctgtctcaacatacatacatacatac     6160
ataaaattaaaagtatctttcttagagtaactgcaggactttcttcacttcggcaccgtctggacaag     6230
tttctggatcgctgtgctcctcagtgtcttcattggcaagataggacagatgagggtttcctgaaatcct     6300
ccaaactctgaattccttgagttttagttcataatgttttgcccatgagaccaaatggcctttgatttc     6370
ttactagtgctaatgagaggaaaggctcatatttgtattaactttatttcaaaaacacgataagtgaaga     6440
atctgatgaaccatttggtagagagatttctatggcatttttgaaaatacctcgattttcacttttctca     6510
attgatataatcacaattgtagatttagaaagcagtcagaaccaacttcaggagtaatcaaacacatgta     6580
agccacattaattggagggaggtgttaattatttaagtcaataggttggaaattattatactttgcatc     6650
ggtcatttctgcaaggcatgcttctaaacagcccatcaatataatcacgaattatgaaaaatacaagcca     6720
ggcactgaggctcctgcctgtctatcatcccagcaatttgggaggccaaggtgggcagattgcttgagtc     6790
caggagttcaagacaagcctgaacaacatggcgaaaccccgtctctacaaaaaagagacgcatctgttgt     6860
cccagctacttgggaggctgaggtggaaggatcatttgagcctggaaggcagaggctccagcgagccaag     6930
atcccgccactgcactccagcctgggtagcagagtgataccttgtctaaaataaaaataaaatagccag     7000
actgtttgccttaggaattccttgcctggttatatggtctaatgaagacaaagtacacgtggaaagtgat     7070
agtttatgaagatgttcaccacagtattagtatcgtagcaaagaatgaaatgaaaagctacaagatcaa     7140
aaggagaggaaaattataatgaaccatatgtatttactcaataataatttaagaatttacctaagatata     7210
catcagctggaaaaacagtttagacagctatataaatatttgggctcagctatgcaaaacagacatttgaa     7280
tggaggggaaagagctaagaattatgtgaactcctagcatactcattacgctaaggtgagttgtgtttaaa     7350
gtatgaattctgggtgattttttcattatccaactattttagtcttatcaggagttctgttacttccct     7420
aacatacaaataaatgtttttatgtatgttactttatatacactactgcctaaattattgccagtacttat     7490
gagaagggcgggaaaggaacttctcacagcatttttttccaattctgaatgttttaactaatgaaagtatc     7560
caatagaatacatattgactttctcttttggtttttttttttttggacattttaaaataatcttcagagc     7630
caagcactcaagtcaatacttgcacatttctgacagaaacgttcccaggatggctttgatgacatactgg     7700
tcaaagccatattggtttcaagttgcggtcctgtgtgtcatctttgggcaatcctccagtctttaaaatc     7770
acgtcttcctgatgacagttatatttttcctcatatttgattgcttctgttgaccttaaaaatcgacagggc     7840
atgaacttctggactcacaactgaatgccttattctttagtgcccgactcgggctgggattcacgggaat     7910
ggcaggaagcaagtgtaaatggaatgctgatttttacagcgcacctctcttgtcctatcgtagttaaaaa     7980
tacagatttttatacttctggacatccgtgtagtagactgaactcatggagaatttttaagctacacagaat     8050
tttactcctaaaattgcccatgcttttttcaagttttctcagcaagtggagcatttttatatgtggcaaaat     8120
aaaatatacacatctctgagtttccaatggatgtagttttgaaagaagtgacctaaaaaaatactccttac     8190
ttgggcacccagttgaggatttctttaagcatagctagctgaatgtatttattttaattggcaaatcttta     8260
atatcttcattagactcaaggtagaagtagaaatgcgctcctgaattagcactctgaagttgattcaagt     8330
ggattcttttttttcccataatgaagagatacctagttttgcttgtgagacaagagggcctttgaactgg     8400
tactagcttaaagcatttttttttcttggaaatggggaatgcagttgctcttggagttttatatatggca     8470
tctggaggcaaggaagcaaaaacgacactaaattgtggaaggaaaaaaaatcacatgtatttaccagt     8540
gcaggagaagtgtcaatgtggtttcatttccttaaactcgtgtgtgtgtgtgtgtgtgtagaataacatt     8610
ccctaaaatgaatgttcaggaggaggggtgaaggggaatggaaatgaaaatgggtaaaagggcccctga     8680
cagagctgaatgctactacatccagaaactcacatgcctgagagacaatcacagccttcattgctcagta     8750
aaagctgcatttctgtcctgtgggttttcatttgcatgtccacaatttttgcacctgcagGTCTCTTCCAG     8820
AAGGCCATCATTCAGAGCGGCACCGCCCTGTCCAGCTGGGCAGTGAACTACCAGCCGGCCAAGTACACTC     8890
GGATATTGGCAGACAAGGTCGGCTGCAACATGCTGGACACCACGGACATGGTAGAATGCCTGCGGAACAA     8960
GAACTACAAGGAGCTCATCCAGCAGACCATCACCCCGGCCACCTACCACATAGCCTTCGGGCCGGTGATC     9030
GACGGCGACGTCATCCCAGACGACCCCCAGATCCTGATGGAGCAAGGCGAGTTCCTCAACTACGACATCA     9100
TGCTGGGCGTCAACCAAGGGGAAGGCCTGAAGTTCGTGGACGGCATCGTGGATAACGAGGACGGTGTGAC     9170
GCCCAACGACTTTGACTTCTCCGTGTCCAACTTCGTGGACAACCTTTACGGCTACCCTGAAGGGAAAGAC     9240
ACTTTGCGGGAGACTATCAAGTTCATGTACACAGACTGGGCCGATAAGGAAAACCCGGAGACGCGGCGGA     9310
AAACCCTGGTGGCCTCTCTTTACTGACCACCAGTGGGTGGCCCCGCCGTGGCCACCGCCGACCTGCACGC     9380
GCAGTACGGCTCCCCCACCTACTTCTATGCCTTCTATCATCACTGCCAAAGCGAAATGAAGCCCAGCTGG     9450
GCAGATTCGGCCCATGGTGATGAGGTCCCCTATGTCTTCGGCATCCCCATGATCGGTCCCACCGAGCTCT     9520
TCAGTTGTAACTTTTCCAAGAACGACGTCATGCTCAGCGCCGTGGTCATGACCTACTGGACGAACTTCGC     9590
CAAAACTGGgtacgttcatcttcgtgttggggtatcactatccttgccacttgtttgtgtcctcaatata     9660
ggtgttgcttctactgccacgtgcaggagcacacgcatacacacacacacatgcatgcaacatcat     9730
acacacagacacacgcttacacacacagcagtaacaggcagcttctcccccaacatctatggcaactcat     9800
tttttttctttactcctaaagtgttataggagtaaaacacttaactgtcaaaccagatttttactagagtt     9870
ctaattgcccattgggaattccagagttcctacctgcaggtgcaggactcatacatatgatggttctg     9940
ttaacagctgattaaacggttttgttttgtccttgttgtttagagacacagtctcactctgttgccca     10010
cactggagtgcagtggtgcaacagtagctcactacagcctccttgaactcctaggctcaagccatcctcc     10080
tgcctcagcctcctgagtagctgggactacaggtgcctgccaccatgcctggctaatttttaatttttt     10150
```

```
tttttggtagaaagagggtctcactctgttgcctaggctggagtatagtggcgcaatcatagctcactga    10220
agcctcgagctcatgggttcatgtgatcctcccatctcagcctcttgagtagctgggactacaggcgtgc    10290
accaccatgcccttacatggatttttgtagacacagggtttgctatgttgcccaggcttctctcaaactc    10360
ctgggctcaagggatcctcccacatcagccttctgaatagctgggactacaggtgcacaccaccttactc    10430
agctaattttatttgttagagacaggggttttgctgtgtcacccgagctggtctcaaactcttgggctca    10500
agtgatcttcccacctcagcctccaaaagtgctgagattacaggtgtgagccatcacaccagccctcatt    10570
acagagttttaagtctaatttcaaccatatctcttttgttaatttgcaaggatatcacagcacatgtacc    10640
acttggggaactgtgttgattgcctggccataggaatgaaaacaaatatcataataattataaagaaata    10710
taaatatatattcctatatatatttaatgtctatataaaaatatagatattcctatttgtataatatagt    10780
acatttatatttgtatttgtatatatatacacacaaatatatttgtatatacaaatacaaatatatatac    10850
aaatactatatatatacaatatatatacaaatacaaatatatatatacacaaatacgtttgtattttctc    10920
tgctatataaataactagagagagaaaatgaaaatatatgatatttgtatcatattgctatatgtcatgc    10990
atacataaacacacacacacaaacacacatacatgtgtatctcacaggaaagctcatttattggcctaaa    11060
tatagtagaaaatataaaatatacaaaaagcatatatacaacagagtctgccaatattctgctgagcgga    11130
ttctctgcaaaccatgggagaaaagaacccaaaacaacctaaatagctccaaacattgtggcatttttc    11200
attttctcttgtctaataatgtaactgtggaaatggatggggtgtcattctgttctaccagtgtgtgcct    11270
ccatcatcaccctgagcctctttacactgaatgagagagaaagatgtgcctgtcgcccagggagggtaaa    11340
tcttcccgtgcggaatgaggctctgagactgcagtggccctgccacacatgagttatgcacagtaatcct    11410
tagaagatctggggatgctggtggtttcaatgcctacgtgtttagcagctggcatactgtacaaagattc    11480
caaagtggtttgggtagggagtggtttgagaatgtttttgtgcccttggcgaaagtacagcatgttttttgg    11550
agtggaaaaggtatcacctggataccacctttcaataatcagactttgtagatttggtctgagaaaggct    11620
acccagaggagaagagagggaggggaccccacatttgatgcaaatgcttgtctatccactcaacggttctttttt    11690
tgtgtgaagaaatgattgaaatcaaattaatactttttttaaagtaaaccttgtttattagtttgttggg    11760
actgctgttatcagagtatccaaaactgtatggctatgctgggcgcagtggctcatgcctgtaaccccag    11830
cactttgggaggccgaggcaggaggatcacctgaggaggccaagagtttaagaccagcctaggcaacata    11900
gtgagagtccgtctctacaaaacaaatgaaaaaatttagctgtgcatggtagcatatgccgagagtctca    11970
gcttctcaggaggctgaggcagagggatcacttgagctcaggaggtcaaggctgcagtgggccatgtttg    12040
caccactgcactccaacctgggtgacagaccgaaaccttatctttaaaaaaaaaaaaaaatataaaaaaa    12110
aaaaagcaccaaaacggtgtgtcttataacaacagaaatgtatcggttcacgctttctaaggccagaag    12180
ttgcaaatgaaggtgcttgcagggccaagttccctccaaatctgtaggggagggtatttccttgctcct    12250
tcttagttactggtgtttgggtgcagtcttggcattcctaccttgcaggtgcaccatcccactctgtgt    12320
ctttgtcatcttacggcctccctgtgtgtctctgtctccacatggccgtcttcatataagagcatctgcc    12390
aaggtgcattagaagctcaccctactctagtatgacctcaacttaacataaatagtcatatctgcagtta    12460
ccctatttccaaataagctcacatactgagatactgggggttatgacttcagcgtatcttaatttatgtgggg    12530
agacagtattcaatctctaatacccctgtgaaatcagggccaggccctcttttgtgacagcactgagatag    12600
gcggtgtctgcccttgcagagaatttcatcctcttgaagcctaaagacttccatgagagtttcccaacat    12670
ggctatactcattcaatcttcgctacattggcatccaaacgtattaccgacttggtctgcaaacactctc    12740
tttacttactctcattaaaaacatatgcttttctttcctccttacatgatttgaaaataaacttttata    12810
tgattatcttaagtggaaagctagaatcattcctcatacatttatggaaccattaaaacaatagtgaaa    12880
tctaaataatgctgttaaattctcattagctcttcctgacttccaaaggctatgagactgaggctggctc    12950
tctcattattaaaaaaaaataccccaaaaaaaaaagaaaaaagacagaaaagataaaggaagttaatt    13020
agttccatgaggtgatcgttatcactgctgacaccaaatggacgcttttaccaagacatcacgaaggtct    13090
gagagagccgtgagaagagaataccacaatgatctctctgttattgagtgcttttaatgccatgaatctg    13160
tttcttaaaatcacttggcttagagcctgtgattttccaccctgcatttagggaatacattcacgttgcca    13230
ttcatggtctgtgttgagggtgcttctagcttcatgaaggccctgacatggctggaagagatgaggaag    13300
gaataactgctagaacttggagagacgctctgatgctactgaaatcaaaagctgcaggtagagagagttc    13370
attgaggtacccagagctcgaatgtcagtccgtctgaagcctctatttttgtttcttccgcccatgggaa    13440
acatccctgaaataacactgagtgtattaatgcagtgagctcttttaattcattggaaaggtattagaat    13510
gactcaaatgattcctcaaggaagttactcagaacttacatctcatgtgaaatgcaacgtgtggattcaa    13580
atacaaatagtttaagtgatcacctccatgcgccccataaaagaaggaaatggggaatttcactgt    13650
cgggcacagtctggtgagctaggtattcgtcagtggatgacaaggacttcagttgcagttggtagttatt    13720
tgtttattgtaaattgggtggtggcccgatcactccagggcagagaaggattccctggtcaccaggtgca    13790
gagaatgaaccaaactgatgcccgcaaggagaaagtatgggatgcacccttatctgctgtcatggtgtgag    13860
ctgccaagtttaacgccatttgcagagcacacactcagatgatgactcacagaacaggagggcatattt    13930
ctgcataccatcactgttccccttccagcactggaggtgacaggaggaaacaagaatagctcccagcgtgt    14000
ctgtcactacacgctgccgtggagaaaggatcgcattgtgccaggacatacttcaccactctcagtgggc    14070
gttaagtcaagcgttctaaacctgcaggcacagccagtctctcgatggcgcatgtgtttgccaagatgaa    14140
gtggatggggtctggatgcttctatatagacatctcaaagtagatggttctgacctttagtctaggttg    14210
aaggcacatatacctggtatacataaaccctttggttttgggatgagcacagaaaaatgatgttgggatgt    14280
gcatggcggagaaaaggaaggaaggagggagggaatggaggaaagagagttcagacaaaggaacgaaggg    14350
agggaaggagggagggagggaggaatttattaggagggcggagaagagcataaaaggtaaaggaagg    14420
gaggaagggaggaaagaaagagggtaaggggggaggagaggaaggaacgaataccgtcccgccccccgc    14490
gccgcacgagcccaacacccgtcactattcactaccttcctctctccccgcctcctactatacacaccaa    14560
acgcacgtagaacccaaaactctcacagacgagtcaggaccatccattcatggtaatcgatcaaataaag    14630
tcgccacgcccatatccttataatcccatccttaccaacctcacccttctctgtccctccaactcatt    14700
ctgcctctctcacgtatctctgctcttcttccgataaacccgccgcttcgaaatgcgttcgcgtctcat    14769
```

>HNL4 Exon6 (2746-6134)

```
acctcactgtctggagggtttgtaagggcagaatgacttggctatcataatctccacaaagtttatctg       70
gctttaagaattctggctgtgcatctccgagatctttaatagacagacggtatcaggtggcagctcattt      140
atatggatttcccaaatcctctgctttattcttcaagaacaaaatataatgtgttttcttttacctgtcaa     210
```

```
atatacccctgagttccttcgaaaatagccttgtacccaacatgaacagaatactccttttcctagatgct        280
cactgcttaatagatgaggtagccacacatctaatagatccaattcagtaaaattggatccatggaaaaa        350
aaggtagaatcttcacttccatttgtttctttagaatattaaaaatcaataactaatattagtggatttt        420
tttcctaaaatattcattcacttatttttctttcagtacacgttaaataactgaaaatttaaaattatt        490
tcagaggacttaaagagcaaaagaaacatgagttgctgcattgaatccaacatttttttcaaaaccatgta        560
agaatacatgcataataaataaaaaaagcagaagacttttcaaatatattgtttatcagtaaataagaaa        630
actcatggtattagaacctatgagattatatatattttgttctcaccctattagtaaagtgaaaacacagc        700
agttagtgtgcattcaactaaagggtagaggtcaactttcttttttctcctgtattatgttatacatctaa        770
tatctatatctatagatagatatacacatacacatatacacatgacatacatatatatactgcatata        840
gtatatagttagtatgcagtataaactgtggtatgcagtatacttgtatatagtatgtaatatacaatat        910
actttttatgcactctacaatgtatacaatatagaaattcagtatgtactctgatatacagtatatcactc        980
cctacttctccctccccttgcaatattataggtgttctattttttatattggaagagaggggggtaatattt        1050
cctgaattcttaccatatgccagacatcttgtcattatctttcaaccttcatcacttacctccaaccctg        1120
atattttcatcagccatgtagaggagtaagttaaggccaatactggctggaaaacttgcttaagatttca        1190
cagctcttaactagccagagctgcagaaagttgaatacagggaaatgatttatttttatcaccaccacaga        1260
ctcagactgagggataaaatcttccttcagcaagtgtggcgcctctggctcaagtatattgtttgaatc        1330
ctgcacagtgtctggtaatggctacagatacatgatcttccttggtcctgcagccttctgccatgcaggc        1400
catgcaatgactggaggcagtttcacagaagtcccgccaaggagaagttacctggaagatagccctagc        1470
tcacacctggaggccattgatcaggatgttgcaactccctgcttgcctggttctgcacatcacatctcaat        1540
gctcagtgctaactagtacataacatttttgccatgcataatctcaaatcgttttttataacaaataaacct        1610
taagacgtaattgttttttagcttactttacaagccataaaaaaaatgtgaagaaatgagcatttggtaat        1680
ttatttttttgaaggggaagtgttatcctaaaagagtcagttgcaaagatgtttattaaaggccctatgtt        1750
ttatgaattatctccaaattttttatgattctccttctaccgtgaccacttgtgcaaataataagaagat        1820
aattcttggctcatagtttccaagcacaacttagcatctgtaacagcccttgacttgtttctgggtgtc        1890
tttttttatcttaaacatgttaacctcatcataactatatgtaccattttagcaaacttcttacagctaac        1960
atagcgtgctttcatctttttaccttcaaatagagagcaaacacatggtgcatatgtctatttacaaaca        2030
ctttgtaattataaagcctatttttatttctactgttaatatcaattttcattgctaaaactgcaacatt        2100
tattcatttacttcaaaagcaattcttgagcaagaaagagaatacccattttcttggacaatagcttctta        2170
atcagaatttctcaacctcagtactgttaacatttgggtccagataacttcttttgctgtgggggtctctc        2240
ctgtgcaccagagggtatttagtagcatccctcacctccacccttcatagaacaacccttcgtctacgga        2310
aaccaaaagtgtctccagatactgccaaatatcccttcgagcaaatcagtcctggatgagttttacagt        2380
tcgacaagagtgaaacttgaaatactgaaattttcctagagacacttagttttccttcttttcccttat        2450
ttttgaagatcatttgatgccttaaaaaatagtaaacatgttataaaaattgcataatgctgctatcagg        2520
atttatatttaaaagaaaaataagagcaatttttaaaggaaaacaatggtagacaggtctaggatt        2590
aaagcagaatgtaccttgctgcttgggtattttgtgctcattgataaatatatgaagagcagattgt        2660
aacttcctgatttattggtttaagataaattcacgtcacatgtggaagagtatgacctttctttttttct        2730
tccttctatcctcagTGATCCAAATCAACCAGTTCCTCAGGATACCAAGTTCATTCACACAAAACCCAAC        2800
CGCTTTGAAGAAGTGGCCTGGTCCAAGTATAATCCCAAAGACCAGCTCTATCTGCATATTGGCTTGAAAC        2870
CCAGAGTGAGAGATCACTACCGGGCAACGAAAGTGGCTTTCTGGTTGGAACTCGTTCCTCATTTGCACAA        2940
CTTGAACGAGATATTCCAGTATGTTTCAACAACCACAAAGGTTCCTCCACCAGACATGACATCATTTCCC        3010
TATGGCACCCGGCGATCTCCCGCCAAGATATGGCCAACCACCAAACGCCCAGCAATCACTCCTGCCAACA        3080
ATCCCAAACACTCTAAGGACCCTCACAAAACAGGGCCTGAGGACACAACTGTCCTCATTGAAACCAAACG        3150
AGATTATTCCACCGAATTAAGTGTCACCATTGCCGTCGGGGCGTCGCTCCTCTTCCTCAACATCTTAGCT        3220
TTTGCGGCGCTGTACTACAAAAAGGACAAGAGGCGCCATGAGACTCACAGGCGCCCCAGTCCCCAGAGAA        3290
ACACCACAAATGATATCGCTCACATCCAGAACGAAGAGATCATGTCTCTGCAGATGAAGCAGTGGAACA        3360
CGATCACGAGTGTGAGTCGCTGCAGGCACACGACACACTGAGGCTCACCTGCCCGCCAGACTACACCCTC        3430
ACGCTGCGCCGGTCGCCAGATGACATCCCACTTATGACGCCAAACACCATCACCATGATTCCAAACACAC        3500
TGACGGGGATGCAGCCTTTGCACACTTTTAACACCTTCAGTGGAGGACAAAACAGTACAAATTTACCCCA        3570
CGGACATTCCACCACTAGAGTATAGctttgccctatttcccttcctatccctctgccctacccgctcagc        3640
aacatagaagaggggaaggaaagagagaaggaaagagagagaaagaaagtcctccagaccaggaatgttt        3710
ttgtcccactgacttaagacaaaaatgcaaaaaggcagtcatcccatcccggcagacccttatcgttggt        3780
gttttccagtattacaagatcaacttctgaccctgtgaaatgtgagaagtacacatttctgttaaaataa        3850
ctgctttaagatctctaccactccaatcgatgtttagtgtgataggacatcaccatttcaaggccccggg        3920
tgtttccaacgtcatggaagcagctgacacttctgaaactcagccaaggacacttgatatttttaatta        3990
caatggaagtttaaacatttctttctgtgccacacaatggatggctctcttaagtgaagaaagagtcaa        4060
tgagattttgcccagcacatggagctgtaactcagagagaagggaaacgtagaaatttattattaaaagaa        4130
tggactgtgcagcgaaatctgtacggttctgtgcaaagaggtgttttgccagcctgaactatatttaaga        4200
gactttgtaaaaagaaaatgtatatagctgtgagtttaaacaaaaaccacaaacagacaaacaagaaa        4270
aaaagctttttattggtgttttcactttgaaagagcttttagcaaggttgtgcttttcattgtgctctgta        4340
cgtatataaatatatatatatacacacacacacacacattagtcatatccacctctgtttcctcccccaa        4410
caaaagaggcttttccttcttaattacttgtggtaaacatggcagttttctacatggaatgttctca        4480
tttgtaggaggatgtgatgtcccacagaagacccagacggtctgtgtggccctattcccccgtcaggttg        4550
cacaggtgcatgcaagagcattcttaggagaccactgttttgaaaaacttttgacttgtacgtgttagcc        4620
ttcatgaaattgcagtacagagatgggtcccccaaagtggagtgtatttacagcttgttaaattagagaca        4690
tgcacacacaaagaatcagtagggagaaacaaaaatacaagtcccgttctgtagctctggcccttgaat        4760
atgtttaggaagagttgcttcccatttcagggccctgccaaaaaagaagaaagcttgcctttggtgggg        4830
ctatgcccccttggagtgaaatacggctctgtgttccctagcagctgcgggagggtttggccgatgaagtac        4900
ctgctcagcttagctaatcagattgaaggaagacatgtgtctttccttttttgtttaagcactcggtccct        4970
tatttatcagtaagcaggttttttaaaaatctttttatatcatttatgggatcaaacatatgattgtctgaa        5040
aacatcacttttttgtggatttgtgtatccggtcaccaaacggtgaatattatagaagaatgggggaagaa        5110
aggatagaatattaaaactgctttgcatgggttttctgggaaattaggataacttcactgagaagacatt        5180
gaatgaaattattcacccattttaaattggtgacctagggatcagagatttgtcttttccaacagcttgt        5250
cattttttcatttctcttctcatttttcaggaaagttttgagtgttataaggtggaaggaaacatagtag        5320
```

FIG. 8A-65

```
caatggatacttttttgaaaaattattgcattaccaagaaacagtagccaaagatatttgaagatcatgt        5390
tcctcggctccattgtgggttattctagaaatccagtcttaaatctctccgctaaagtggacattcccca        5460
taaaaattgtccagctgcctggctcttttgcaataacaacctttgattactgaatccctacactcaaact        5530
atagtgatatatcagtgtttgagagtgacctctagaaaaaagaaaagtgttttttagaaatgcgtacaagt       5600
cacccccaaatcctattgcttatcttgggtttaaatttgagagtgattctctgtatataaatatgtgaaat       5670
attattatctcaacttagcacacgtgaagcaacatttctttcctacagagaggtgtcatggtaagatttc        5740
attccgaattcattgtttcatagagctatgatcaggccatttctgcaagcaatgtatgaccccacctgag        5810
caaccacaaataggctctctgtgaaactacaaaggaagtatgtgtggcatccatgttggtttcgtctgt        5880
ctgtaatgtgaattccagtatttgtttagtatttccagttgtctcctgctagcaatatgtacagtaacgc        5950
gtcaggcttgtgacatttgaataaggaaaaacagagttcctgttaagtgaataactttagcttttacagg       6020
ggattatgatcaaaagtgattttagtacatcttaaatgatatcttatttctacatggaaagaagttatag       6090
aatcttcatagagttctatgagaaaaaatatacttgctatctataaaaaagagaaaaaagaaaaaaatg        6160
agaaaaaagtaagaaaaaaaaaatcctgtcctaggcttttactcttgatcttcaaaggcacgcagggtt        6230
taatggttccttgggttattattttgcagtttgtttttttatttgccttaagtaatgatagaagatata        6300
tatggccggacacatatgtataaacttttcagcagcatttttaataataaaatatcacagtatttctaa        6370
tgcttgtgtcaaataattatgcgtccattcttcttggtaggtggcgtgtttatttacttttgttgttc        6440
tttgaatgtcttttctttgtaaaaactaagtgatgcgcctgacataggctacaaatagataaatacatt       6510
tggtaatgggatagttctcttttagctttggccagctgcacagttgaggaggctctgctggcctgatttgg       6580
aaaaccaagccctgtttggtgaagctcctcaggtgacactgtctgaaacggagtgtttggatttgttatt       6650
tctaccactgtgccttcttgcgtcactgtgttttgatttgtggtcaacaaaacactttcaaatagcctta       6720
ggtgagtaagcctgcaagtgacagcaagaaattctaccgaatgaaactcaagaggcagaaaatcactatc       6790
ataccaatgggagctcatttgtcaattccttcctgtgcaaccatcacgatcttatttgacattcgc         6860
agtagccctaaggggcacgcacctgcattgctcccctttcataatggaatatgttcagaggaaactagcc       6930
cctattcgacaggagaacttgatggataacaggatagtatatcctcatagccaaatcttttcaccaaga       7000
agttatatggcaaacacttgtaagccaaggccctgcatgttgtgataatcctagctaagtatcagataaa       7070
gaaagatagcaaggacttggactctctgacatatgtgaactcctaaattcttcagatgttgtttgtctca       7140
atcgtgttgtgaaggcacacaggagaaatacatagacacacatacatatatgtacatttatgtgtaca       7210
ttatatatgtatatacatgtacatatcctatatatgcattatgtatagagtcatgcacagcataataaca       7280
ttttggacaaatgcaaataacatgatgacaatctcaagagattataataacatttttcttgtgccttttc       7350
tatgtttagatatgtttagatacacaaatgctcatcattgtgttacagttgcctagggtcttctctccag        7420
tcacacgctgtagaggtttgtagtctggaagcactaggctataccatagagcctaggggtactgtaggct       7490
gcacctcgaggtttgtgtaagtacactacatgatgtttgcacaatgatgaaatcacctaacgatacattt        7560
ctcagaattgatccctattgttaagcgatgcgtgactgtgcatgtcatgtatcattacatacactgtatatgca    7630
cacatgcatatatgcatatatatgttacacatgtaaatatatacatagatatcacatacttaaattcctg       7700
aagatgccaattccgttaaacataaatatacacacactcatatatatgtgcacacacactcgtatatcca      7770
cacacaacatatttaatgtgctcatatatatattcctgggtgtgtgtgtgtgtgtgtgtgtgtgtgtgta      7840
tatatacatagaaaatacattagttctctttatctgtgcaatcacattctgcagtttcaggtactgtgga      7910
caactgtggtgtaaaaatatgtgagtacagttcaatgtagaaagaggccacactcacgtaact         7980
tttatgacagtatattgttataaatgttctcttttattagttattgttcatctctctactgcctctaattt      8050
atgaactttatcaaagtgtgtacatataataaaacatagtatataaagggtttggtactatctgtgg         8120
tttcaggtatccactgagttttgaacacatccccttggaaaagggccattactgaatatacacacct        8190
agacacacatacatatatacagatacataatgtacatagatatattcatagatatgcatgcacttaaatc      8260
tctaagaatggcatttgcattaaacacacatataaacacatgtatatacacacatacatatacttata       8330
cttattgtcatcttcaggcattcaaagtcgaattttttagcaaattttcagctgcagggagaatcactcttg     8400
ttttgactattttatgcattcttgttcattgtgaataacccaaggaatgctaaaaaatatatgcattcat      8470
taattcattcaacaaacctttactgaatatctccactgtcccaggccctgtgctgggctggtgttaaaat     8540
tgaagaaaaaacttctcacaccataaaactcaaggggaaggcagagaaacacagaagcaaggagaggcag      8610
ggggtgctggagatggagatggcacccatgctaatacgtggtgctaagaaatgtctggacactgctctta      8680
acctagtctgggaaggtttgggaacgtattcgtgtctgaagaaacctaagccagatcttttccaactccgtag    8750
aaaaaatgacagtgggtggtgtgttgtggggaagatagaattccacacccttttgaagtgagaagacagagg     8820
aagttgggaaaccatgctcctgcatcatgggtaaaaaatacaaggtattttttagaaaggtgcgaaata       8890
cgaggcagaaagaaactggctgataaaaaacctccagaggcaaggcagggagtttgggctttgtcccaaa      8960
gtcagggagacgccaaatgattgcaccaaattggtgtatgagtgtagctgggacatttagcagtaattct      9030
caaaaattcacgttcttaggaacatgtaggacatcttgcttaaagtgcagatccttattcaattgtggttt     9100
ggtgaacctgtgtctgcatttccaacgagctctcaaagtggtgcacatgttgctggtcctcaactaaccc     9170
caactcttttaggttgcaaaggatggagaactgtccactttagaagtaaccgtgagcatagtttgtatca       9240
gagtgagagggctctggatgcaaggaaagcattaaggaggcagagcaatctgtttgagaaattaatgact      9310
gtcctcttttcaagggtgatggcgatagtgataataagaaagcaaaaaaaaaaaaaaaaaacaataaaaa      9380
cattgcatcattttatagctgcatgtaccagaactgattaggcgcagtcatcaaataccacctggaaccg     9450
catctgaagttaagcttgggtttaggaacttgttcaacagagggagggcataccaaggagaatgatgagc     9520
taccttggagaggggttcagacgggctggtcaagggtttgggcttagactggttgttttagaagtgcta      9590
agaggggcaagaacttgttcctggattagttgctatcaggataatggggatgtcaataacctttagccag     9660
aaagtgacaggaccagagcatgactagcattgtcttcagtaaaaataagcagtggaagagaagggattt      9730
ggggtcgttattagtggttacaaattgttcatgtttctgtctcatcccgtgctggctgtgggctgccttc     9800
ttctgatgtgaagttctttcaattattttttatgtgcagccggatgcaccttgacttagccattaattag      9870
caggctagttccagcagccagatatgagggctgtttctttttgttcttttctcagaacttccagaatatgta    9940
ctcatatgtcccatctctcaggccacctggttcaaaaaaaatctaggttatgctaaggaagtgaaagtga      10010
cacttcctctgcaaattctcattattatattgaaagaaatgggatacaggaaaaagtccacggaaactc      10080
taccttctctaaaatgaccatccgtgtaaatacttagaacacccacaaataatcctgtttcctctagag       10150
gcaagagaatttagggaaatgagataaattagccaggga                                     10190
```

FIG. 8A-66

```
gcaaaccacttaacaatgacccaccacaaccctgctatttctgaatttaccttatctttttttttcctttcacaggcaga
ctataattatgatttcaacttcctcatcggatccccagtcatgaatctatctaacatattcagctgaaggctgtcaagga
tctactgattccacaatgcagtggtactctcccatcgcccttcactcctaaaatctctgaagaccatgacacagttgact
cctgcctactccttgtggaggttaaagtccttccttgaattccataccacactttctcttaccaaagatcttctgcagat
gggagaatgaccctatttaggttgttatcaagaccctacccagtgtcactttctccaaagatttgccttttctcttaag
ggaacactttctctatttacaccaaaatgttaagtatcatatccatagggtttgtgcttggatccgtagatcctacctt
aagatccctattcaggtcaaatctcctgtcccaaagatctcaggtctgtgggtcattggtatttctatgatccaccagca
cctcattttctttccacacaagtgactctggctgagtgcactctcattcatcttagccttcccatctcaccacatgaag
gctatctctagtatcttctcattttagggctccatcccattttgctcaacttctgcaactatgcatatagtcaaatgcc
actcatagtgaaataaattcatcataactgtgttattttcactaatactgccctaatttatgaatgcagcagcctcgctg
tactcttttgttctagaatgtcccagcccttaaatccccctcagagtaagctctctgaaaggtaatctctgctaccatccc
cgactaacacccataaggattccagccaatgaatattcatcaacctctgtagtccagcctgaccaattcttcttattct
cctctatgaatcataagaacctatcatcagctcaccaccactcctgttttcagggtttaatttgaggattatctaaaaaa
gcaacctcatgtagcagggtggccccccaaatgcaggttccaagaactcactcaagacctgctaggtttgaatcctggtg
tttagctctagaggcatggattttgtaaccatcttcctgggtcatccttgtgcaccttgaacttccaaagcctttgctca
cactatatctgtttctcgtctccagatattgttaacttggaataatgtcccaccctgctctccaattccccagggaaac
cttgttcatctgtgaaccattttctcagcatcccaataggaagcctgttacgccttctgtatgctttggagatggcatat
gtcacacattgagttgcattttaataattaaagagcttaatttatcctcttattagattttaagcaccttctatactata
catatttctctctctaataatgattagtaattaataacatagtatatattactattgcacgaacaattattatcctactg
aaaatatttctgtttcacttggaccattgtattaggagagtcagtatgaatcagtagtgccccactggcttcaccagtat
tgcattcagagttctacgtattgatctcacaggagcttgaacataataccagaatgtggttgatggagacactgagatgg
aaaatcagagagaacaagtagtgtggtatagattatttctcatgttccctccagttcttgtaccaaactcagcttatata
tctttcttggaacctacagttttatttcattttatgactccccagctcccacatttcaccatactccacaattagatt
taaaatggaagcatgaagaatgatactcttatctcttccaggaattgtggatctaaacctctgtagctcctctgtctgtg
ttgcaatctggtggcccagttgttaaaaattggtgttttgggtcctatcctggtctcctgtaagggattttggattaggg
aaaatgataatttcataacatcttatattcacttttcttacaatcatgattccacctgtctaagatgctttctgactt
tttcttttttgagggagggtctcattctgcaacccaggctggagtacagtggcacgatcatggctcactgcagcctcga
cctctctggctcaagtgaccttccccccttcagcctcctgcactaccactcccagctagttttaatttttttatagaaac
agggtctcactatgttgccctatttttcaaattattttaaaaaactctcaatggagtcattcagatagaagtgaaaatgt
gcttgcctgctctcttccaggtcacatatctcagggaagagatctggtacccaaccaatccacccacaagctaagccaag
cattcagattttgcccaaactctccttcccaatcttacttttatcatgctgccttatttagaagtgatgtctcccacatc
aacttctcttcccttcactaccttcccttcctttttcctcccttcccttctcctttctctttctctctctgtgtctc
tcattcaggacttcatttgttgcatccattcttgcaacaatcttacaaatattttcttttctttccacgttggccctctt
caacttgttctccatattgccatcacagtgattgtcctaaaatataaatctgatcatttcttcccctctccctgcagaaa
atatgttactggctttcccactgcctactggataaattccaccttttcagtatggcactcaaaattcttcacaattaggt
ctttaatcctttccttaccaccttcttttcatactcaatgtcatggcattccaaaccctccctatttctagatctccaca
catacagtattgctatgatgtctttatccatggcttctttctcaacttcttgacccaatcagtgtctgtgtaccatttct
tccctactcagaaagttcttcctttgcaaacccttctttaatcattttcacctccatgggtccctatgaattcatatgta
ttccttgtgcacaccttcttgtaatcatatttttctcatgcttttggctatctttgtccactagactgtatgctttctca
aaaataaatggatgagtttcactcacagatgcatgtcagtgcttaggactgcaccagtgctaaaaaaaaaaacaaccctga
atttatgaataagtcaatgaattaatacattcttggcaaaacccatgactttctggcctactataaattactgtgttcaa
ggtgagattctgctttagtttaggatatagatatctatatatgtccatatatctgcagctatatatccatatccatgt
atatcactgatttgggggaataagctatacttattaacaatattactatgttaatgggtcttcaatatctatacaataacg
gaaaaagtacatgcatatttctaaatatctatccaataattggaacacacacgtatgtatggatggatatatttttttt
attattgggtatagatatctattaatagataagtgtatatttatgtacctatcttgttggtaaaaggtgcttttatacat
attatttcatttagtctccacaagaaatccacaggaaaggtaattttaatctcagtttaacagattcacagaacataact
gactttacaacaaggcaaagtttgtgaggatagagtcttaacatgaaaccaggtccccaaattggtgtctatcaccttcc
ccattattggtcaggctgcccaaatatccttcacatcaccatggcaggcttcatgctttggttactgcctaaagccgaa
gcaattaggaggatatcctatgtgttgcggacactatctttttccttcataaatgaattaatgggccatgaaataattt
taagaaaagctaacttttctggccaagcagaagaataaaagtaatcaccatgtaatattgttgtgaagactacctggccc
```

FIG. 8B-1

```
cacacattaactcagctaatcattacagtattacacggtgattatctgttccatttracagatacagaaatggaggcaaa
cgattaaaatacacacctaaggtcacatgcatcttgaacccaagcaatctcatttraaaatccgtgttcattgtcacaac
actctattatgccctctgatctttgcattgccaatttaaatccaactttctccaactcaactttaagtacagggggtcata
cccccgtcctcgcccccgcaacttgaaactccctgggaaagataacctcctggaccctggaaatgaagaggcgtattta
aaaacaaatgcctcatcctgggcacaattccaacattttatcaaaatcatgaaagtataagaatagaagtaaacaaaaag
ctttcatcgatcccctctcaaccatacctgagcataaaacaggtcctgtactttacagaactgtattccaaattttgct
gctcttaaaaattttttttatatcattgcttcccaaatgaattacaataacgcagacatagagactgctggagatcgtga
ccttaaacagttaaagatgtttgcatatactgcagcatgtttggtgtggagggtatctagagagtcctaaaaaagcaaag
aggaagaaggtttgctgtacgcgtctggtgcggtggcaccgtttgccatgcccacctgctctatctcccgagtacccggg
atctctccgttacagctggtttgcattggattagcagctctttgcatgaggttgtagctgtggatgtggtttctgtagt
gatggggccgactccggagatctattggctgctggctttgtaaatttcattcagtttggtccaatggcagagggagagcc
ccggagacagcaggacctctctcctcaatctctcttttcttgcagaaccgtctctctcccttctctgtctcttagcaca
gagctcttattcagccactagcttggcccttcctgcttcaattgtaatgcttgttctgcccgtccacagactattggcgg
cagaaacaacgaatttcctccaaactaggcggtgttggtggctcttgcattcctctggatgaggaaatctagttgggggg
ttccAGAAGGGGAAGGCTCCTGGGCTTTCAATACATCCTCCTGAATCATACCTCGTTTCGGGTTCCCTAGAAAAATCTGG
ACGTGTAAAAGAACTCTTAACGGCCGATGCAGCTCTTCCAAAGCTAAGgtaggtgcagttttaagacctgtctctggga
cattattctcatttaaaaagccgtttaaacattttgacttgcagcaaaggatggaaagcctcactgcagatacttgagc
ttcacttcatctgatctttattttttccttttatgattattaatattatttttggaaaatttggacaggactttctccca
tctgtctcgctgcatttcttaggtgtgggtgggagtgtagaccttcatacggttttacatgcaacctctccacagaaat
atttggttttattttcacttaaagagaaaaatccagaccaccgttgtttggaagcgttttgctgcaatcagctatttgaa
cggctctggggccgtgtgtgatgtgtttacaaagtagcgctgccttccacacaaataaacagaagactgtggcggggaga
ggaggaaaaaaatatatatgtatctgcagtacagggagaagaaggagagaagcggccagggctggagatggtgaaggcag
gaagacttctgcaaactgtgaggcatgggaggcttttcttttcttttctctccccccccacccccccccccttattcttt
aagaaaactgtcagctaccaccgcctggggtgcttttttgagggggttggggggggtgctgttaaccagaaagaaaaggga
aaaccggcttggttggggtcgcATTTAAGCGATTTTTTTTCCCTCCTTCATCTCCGGGCCTCGGATAAGATGACGGCTTG
GGTGATGCACGAAATAACGCACGTGATTGATTAGACCTGGCTTGGCTTGGCTAGGGAACGATCCAGGCGCGCTGGAGACC
CCGCGTGAAGATGAAATGACGgtagctccgggctgcttctgtaaaccggggagcgggctccatgcaccctttcccgtgt
gtgtgggtttcgaggcgggtgggaagggtgaggcaagccgcagaaggagggtagagctggtggtttgcttcctttcggag
cctttgagtgtagtctgaacctttgagggggggcgcgggggggcttgcagctgccgccctgggaaccatctctgaactgcc
cgcttttccgaaggagcggaaaagttggaagctgcgaggacagactaccggagccctggtctgggtctcggggggatctgg
agccctagtcggtgcccactgagaacacccccttctcggagcgagggtgtcggggggagtgttaagcctgcggggcgcacg
gtccgccagtccccgaggtggggacggggggaggaggctgaggagtcggttccaataggcgcaccacctctacagccctgg
aaaacgcaaccgccaccccctcttcccttccatcccatcccaagcctctctgctgtcccgggccgatttcatctcgtctc
ttccccccgcctccccgcttcccccgcctcccaattcccgcgcggctcggctcagcccctttcccactccagtgggcagaact
gatggagaagatccgccaagcgcgcagccggcgcggcggaggagacagtgcggggtgggcgagggggcttcgagaccacgcag
agagagagtgaacttcagtcctgaccctccccaaggccgcgcctgggggcgcccacagcccgcctggcacccgcgtggc
ctgacctgcggaagcgcgagcggggatgaggtagggagaggggagggtaggtgccgctcggctgcagatgatgcgtgggtgg
ggggcttgctgtgggaggagaggcccaggtcccggcctgc
```

FIG. 8B-2

>HNL4X cDNA (SEQ ID NO:2)

Exon 1 (1-159)
Exon 2 (160-936)

Exon 3 (937-1089)
Exon 3bis (1090-1200)
Exon 4 (1201-1386)
Exon 5 (1387-2176)
Exon 6 (2177-5565)

ORF (465-3023)

```
atttaagcgatttttttttccctccttcatcgccgggcctcggataagatgacggcttgggtgatgcacgaaataacgcac
gtgattgattagacctggcttggcttggctagggaacgatccaggcgcgctggagaccccgcgtgaagatgaaatgacgg
ctgccttggagttttcataagaaattgtccctggaggtgttggatgatcacagcttccttggagcattgcagttgctgga
atccagtttcaggattaagggagggctgcctccttgcaatgggctgccaagaaaacggctgtgcttgttcttaacctcag
gctctgtctgtgatcagtctgagagtctctcccaggtctactgctccctggaaagccctatctctctgcaggctcgcctc
tgggctttgtctccttggagccacatcactgggacagctgtggatgtggatgcagatttgaaccATGTCACGGCCCCAGG
GACTGCTATGGCTTCCTTTGTTGTTCACCCCGGTCTGCGTCATGTTAAACTCCAATGTCCTCCTGTGGTTAACTGCTCTT
GCCATCAAGTTCACCCTCATTGACAGCCAAGCACAGTATCCAGTTGTCAACACAAATTATGGCAAAATCCGGGGCCTAAG
AACACCGTTACCCAATGAGATCTTGGGTCCAGTGGAGCAGTACTTAGGGGTCCCCTATGCCTCACCCCCCACTGGAGAGA
GGCGGTTTCAGCCCCCAGAACCCCCGTCCTCCTGGACTGGCATCCGAAATACTACTCAGTTTGCTGCTGTGTGCCCCCAG
CACCTGGATGAGAGATCCTTACTGCATGACATGCTGCCCATCTGGTTTACCGCCAATTTGGATACTTTGATGACCTATGT
TCAAGATCAAAATGAAGACTGCCTTTACTTAAACATCTACGTGCCCACGGAAGATGATATTCATGATCAGAACAGTAAGA
AGCCCGTCATGGTCTATATCCATGGGGGATCTTACATGGAGGGCACCGGCAACATGATTGACGGCAGCATTTTGGCAAGC
TACGGAAACGTCATCGTGATCACCATTAACTACCGTCTGGGAATACTAGCAGAAAACACACTGGCTCATGGAAACTGCAA
GCATCGTTGTCAGCTGCACCTGCAGGCACCATGGGGTTGCAAGTCAGCATCCCCTTTCAGAAATGAGGATGGAATTAGAG
GGTTTTTAAGTACCGGTGACCAGGCAGCAAAAGGCAACTATGGGCTCCTGGATCAGATTCAAGCACTGCGGTGGATTGAG
GAGAATGTGGGAGCCTTTGGCGGGGACCCCAAGAGAGTGACCATCTTTGGCTCGGGGGCTGGGGCCTCCTGTGTCAGCCT
GTTGACCCTGTCCCACTACTCAGAAGGTCTCTTCCAGAAGGCCATCATTCAGAGCGGCACCGCCCTGTCCAGCTGGGCAG
TGAACTACCAGCCGGCCAAGTACACTCGGATATTGGCAGACAAGGTCGGCTGCAACATGCTGGACACCACGGACATGGTA
GAATGCCTGCGGAACAAGAACTACAAGGAGCTCATCCAGCAGACCATCACCCCGGCCACCTACCACATAGCCTTCGGGCC
GGTGATCGACGGCGACGTCATCCCAGACGACCCCCAGATCCTGATGGAGCAAGGCGAGTTCCTCAACTACGACATCATGC
TGGGCGTCAACCAAGGGGAAGGCCTGAAGTTCGTGGACGGCATCGTGGATAACGAGGACGGTGTGACGCCCAACGACTTT
GACTTCTCCGTGTCCAACTTCGTGGACAACCTTTACGGCTACCCTGAAGGGAAAGACACTTTGCGGGAGACTATCAAGTT
CATGTACACAGACTGGGCCGATAAGGAAAACCCGGAGACGCGGCGGAAAACCCTGGTGGCTCTCTTTACTGACCACCAGT
GGGGTGGCCCCCGCCGTGGCCACCGCCGACCTGCACGCGCAGTACGGCTCCCCCACCTACTTCTATGCCTTCTATCATCAC
TGCCAAAGCGAAATGAAGCCCAGCTGGGCAGATTCGGCCCATGGTGATGAGGTCCCCTATGTCTTCGGCATCCCCATGAT
CGGTCCCACCGAGCTCTTCAGTTGTAACTTTTCCAAGAACGACGTCATGTCAGCGCCGTGGTCATGACCTACTGGACGA
ACTTCGCCAAAACTGGTGATCCAAATCAACCAGTTCCTCAGGATACCAAGTTCATTCACACAAAACCCAACCGCTTTGAA
GAAGTGGCCCTGGTCCAAGTATAATCCCAAAGACCAGCTCTATCTGCATATTGGCTTGAAACCCAGAGTGAGAGATCACTA
CCGGGCAACGAAAGTGGCTTTCTGGTTGGAACTCGTTCCTCATTTGCACAACTTGAACGAGATATTCCAGTATGTTTCAA
CAACCACAAAGGTTCCTCCACCAGACATGACATCATTTCCCTATGGCACCCGGCGATCTCCCGCCAAGATATGGCCAACC
ACCAAACGCCCAGCAATCACTCCTGCCAACAATCCCAAACACTCTAAGGACCCTCACAAAACAGGGCCTGAGGACACAAC
TGTCCTCATTGAAACCAAACGAGATTATTCCACCGAATTAAGTGTCACCATTGCCGTCGGGGCGTCGCTCCTCTTCCTCA
ACATCTTAGCTTTTGCGGCGCTGTACTACAAAAAGGACAAGAGGCGCCATGAGACTCACAGGCGCCCCAGTCCCCAGAGA
AACACCACAAATGATATCGCTCACATCCAGAACGAAGAGATCATGTCTCTGCAGATGAAGCAGCTGGAACACGATCACGA
GTGTGAGTCGCTGCAGGCACGACGACACTGAGGCTCACCTGCCCGCCAGACTACACCCTCACGCTGCGCCGGTCGCCAG
ATGACATCCCACTTATGACGCCAAACACCATCACCATGATTCCAAACACACTGACGGGGATGCAGCCTTTGCACACTTTT
AACACCTTCAGTGGAGGACAAAACAGTACAAATTTACCCCACGGACATTCCACCACTAGAGTATAGctttgccctatttc
ccttcctatccctctgccctacccgctcagcaacatagaagagggaaggaaagagagaaggaaagagagagaaagaaa
gtctccagaccaggaatgttttgtcccactgacttaagacaaaaatgcaaaaaggcagtcatcccatcccggcagaccc
ttatcgttggtgttttccagtattacaagatcaacttctgaccctgtgaaatgtgagaagtacacatttctgttaaaata
actgctttaagatctctaccactccaatcaatgtttagtgtgataggacatcaccatttcaaggccccgggtgtttccaa
cgtcatggaagcagctgacacttctgaaactcagccaaggacacttgatattttttaattacaatggaagtttaaacatt
tcttttctgtgccacacaatggatggctctcaagtgaagaaagagtcaatgagattttgcccagcacgtgagctgta
atccagagagaaggaaacgtagaaattattattaaaagaatggactgtgcagcgaaatctgtacggttctgtgcaaaga
ggtgttttgccagcctgaactatatttaagagactttgtaaaaaagaaaaatgtatatagctgtgagtttaaacaaaaac
cacaaacagacaaacaagaaaaaaagcttttattggtgttttcactttgaaagagcttttagcaaggttgtgcttttcat
tgtgctctgtacgtatataaatatatatatatacacacacacacacacacattagtcatatcacctctgtttcctcccca
acaaaagaggcttttcttcttaattacttgtggtaaacaaagacatgggattttcttacatgagattctcatttgtagga
```

FIG. 9-1

```
ggatgtgatgtcccacagaagacccagacggtctgtgtggcctatttcccccgtcaggttgcacaggtgcatgcaagagc
attcttaggagaccactgttttgaaaaacttttgacttgtacgtgttagccttcatgaaattgcagtacagagatgggtc
cccaaagtggagtgtatttacagcttgttaaattagagacatgcacacacaaagaatcagtagggagaaacaaaaataca
agtcccgttctgtagctctggccctttgaatatgtttaggaagagttgcttcccatttcagggccctgccaaaaaaagaa
gaaagcttgcctttggtggggctatgccccttggagtaaatacggctctgtgttccctagcagctgcgggagggtttggc
cgatgaagtacctgctcagcttagctaatcagattgaaggaagacatgtgtcttttcttttttgtttaagcactcggtccc
ttatttatcagtaagcaggttttttaaaaatcttttatatcatttatgggatcaaacatatgattgtctgaaaacatcact
ttttgtggatttgtgtatccggtcaccaaacggtgaatattatagaagaatgggggaagaaaggatagaatattaaaact
gctttgcatgggttttctgggaaattaggataacttcactgagaagacattgaatggaaattattcacccatttttaaatt
ggtgacctagggatcagagatttgtctttccaacagcttgtcattttttcatttctcttctcattttttcaggaaagtttt
gagtgttataaggtggaaggaaacatagtagcaatggatactttttttgaaaaattattgcattaccaagaaacagtagcc
aaagatatttgaagatcatgttcctcggctccattgtgggttattctagaaatccagtcttaaatctctccgctaaagtg
gacattccccataaaaattgtccagctgcctggctcttttgcaataacaacctttgattactgaatccctacactcaaac
tatagtgatatatcagtgtttgagagtgacctctagaaaaaagaaaagtgtttttagaaatgtgtacaagtcaccccccaa
atcctattgcttatcttgggttaaatttgagagtgattctctgtatataaatatgtgaaatattattatctcaacttagc
acacgtgaagcaacatttctttcctacagagaggtgtcatggtaagatttcattccgaattcattgtttcatagagctat
gatcaggccatttctgcaagcaatgtatgaccccacctgagcaaccacaaataggctctctgtgaaactacaaaggaagt
tatgtgtggcatccatgttggtttcgtctgtctgtaatgtgaattccagtatttgtttagtatttccagttgtctcctgc
tagcaatatgtacagtaacgcgtcaggcttgtgacatttgaataaggaaaaacagagttcctgttaagtgaataacttta
gcttttacaggggattatgatcaaaagtgattttagtacatcttaaatgatatcttatttctacatggaaagaagttata
gaatcttcatagagttctatgagaaaaaatatacttgctatctat
```

FIG. 9-2

>HNL4X : protéine (SEQ ID NO:3)

Signal peptide (1-43)
Esterase domain (44-634)
Transmembrane domain (712-733)
Required for binding to PDZ domains (851-853)
Extracytoplasmique domain (1-711)
Intracytoplasmique domain (734-853)

MSRPQGLLWLPLLFTPVCVMLNSNVLLWLTALAIKFTLIDSQAQYPVVNTNYGKIRGLRTPLPNEILGPVEQYLGVPYAS
PPTGERRFQPPEPPSSWTGIRNTTQFAAVCPQHLDERSLLHDMLPIWFTANLDTLMTYVQDQNEDCLYLNIYVPTEDDIH
DQNSKKPVMVYIHGGSYMEGTGNMIDGSILASYGNVIVITINYRLGILAENTLAHGNCKHRCQLHLQAPWGCKSASPFRN
EDGIRGFLSTGDQAAKGNYGLLDQIQALRWIEENVGAFGGDPKRVTIFGSGAGASCVSLLTLSHYSEGLFQKAIIQSGTA
LSSWAVNYQPAKYTRILADKVGCNMLDTTDMVECLRNKNYKELIQQTITPATYHIAFGPVIDGDVIPDDPQILMEQGEFL
NYDIMLGVNQGEGLKFVDGIVDNEDGVTPNDFDFSVSNFVDNLGYPEGKDTLRETIKFMYTDWADKENPETRRKTLVAL
FTDHQWVAPAVATADLHAQYGSPTYFYAFYHHCQSEMKPSWADSAHGDEVPYVFGIPMIGPTELFSCNFSKNDVMLSAVV
MTYWTNFAKTGDPNQPVPQDTKFIHTKPNRFEEVAWSKYNPKDQLYLHIGLKPRVRDHYRATKVAFWLELVPHLHNLEI
FQYVSTTTKVPPPDMTSFPYGTRRSPAKIWPTTKRPAITPANNPKHSKDPHKTGPEDTTVLIETKRDYSTELSVTIAVGA
SLLFLNILAFAALYYKKDKRRHETHRRPSPQRNTTNDIAHIQNEEIMSLQMKQLEHDHECESLQAHDTLRLTCPPDYTLT
LRRSPDDIPLMTPNTITMIPNTLTGMQPLHTFNTFSGGQNSTNLPHGHSTTRV

FIGURE 10

>gène HNL4Y, séquence complète (Homo sapiens BAC clone RP11-224C16)
(SEQ ID NO:4)

Contig joins AC010726 (153001-176524); AC010979 (201-109394); AC010879 (201-181721); AC011903 (63481-42522)

Simple repeat (9811-9852)
Simple repeat (9865-9918)
C/EBPalp (10104-10114)
Sp1 (10151-10161)

Exon 1b (10156-10298)
Exon 2 (108500-109001)
Exon 2bis (205869-205928)
Exon 3 (209526-209679)
Exon 3bis (235028-235139)
Exon 3ter (238090-238212)
Exon 4 (310597-310783)
Exon 5 (316139-316929)
Exon 6 (326822-330136)

```
aggatgtgggtggggccagataacagaataaaagcaggctgcacgagccagcagtggcaacccgctcggg          70
tcccttctacactgtggaagctttgttcttttgctccttgcaaaaaatcttgctattgctcactctttg         140
ggtccacactgcttttatgagctgtaaacctcaccgcgaaggtctgcagcttcactcctgaagccagcga         210
gaccaccgggaggaatgaacaactccggacacaccgcctttaagaactgtaacactcaccgcgagggtcc         280
acggcttcattcttgaagtcagggagaccaagaacccaccaattctggacacacctgtgaggtcagagt         350
ttgggaccagcctgggcaatctagtgggaccctgtcttaatattacattgttcctaaataattgtggttt         420
ttgccattaaaagtaattgtgaaaaccaaaactactttgcacgaacttaataaaaattatgaaatagct         490
gggcgtggtggcacatgcctgtagtccccagctaccgaggaagctgaggcagaaggatcacttgaaccca         560
ggaatttgaggttgcagtgagctataataatgcctcaacagagcagactgtctctaaaaaaaaaaaaga         630
aagaaatgaaaacaaaacaaaacaaaacaaaatatgatgaagatccagaaggatgtgcagcccatctct         700
ttgccattcattacacttctgtcttcatatctacttcctccattttccaccggacaaggtgaaaaagcat         770
gaccagttaggcctctaaatttacctgttgcccatctactcctctagagccactgtttgctgtgtacatg         840
gctgtgtccatggattgcggtgtcacagttgtgagacagatttccagggaatgcatatccatagtccagc         910
ttagcttacatgctcaatcttgtaccaagcaacgtggccagaagatgcaaatctctttggatagacccgg         980
aaactcctattttaactctgagcctgtatgaccagatgccttgaaggccatgcaaatctgtcctgcaggc        1050
aagagcttctccaatttcagcatttggttcagcatttggtgcaaatcaccagagaacatgtttgacacag        1120
ttgacctggggtggagacccaaagttatgcattttttaacaggcttccaggtattaataacacccatgata        1190
ttagatccaggactataatctgtttagcaaagtaccaaaacttttagatcttttttgtatatttggaggaaa        1260
agaacaagtattgcatgggtgttctttacataatttttagtcatgacaattccaggagaatatattaccaggc       1330
tcctaatatgccagtgctttataacagatcgatcctcactcaaaacaatcccatttgtatttatacatat        1400
gttccatctgctctgtttccacttgtatacatacacaggtgtgtgtacttgtaacatgcaatacagtttt        1470
tgcaatacattccctctcttctcaatgaatcatacctgaaagaaaaacaaaaggggtgtttttaaaatga        1540
ttccaatacaggctttgagtttgaaagaataaaagagagccattgtcttagaaattttttgtcaacctca        1610
ttttatttcaactaaaatttgtaaaccatactgcattcaccagagaaggtgtatatggctatatgcctat        1680
gtctgacactggtaattaaaaagagagaagcctgtttgcttgagctttgataaataaaacatattgatgc        1750
tacctcttattatgtcttcccccctatgttaaatgttttctttttgaaaatatagattatttgaagtacaaa        1820
gcaagaaagcaggaagagagtgtatgtgcacacacagaagagagatacaatcaggcataaatccaccatc        1890
ctgggaatataaaccctctgtatcatatacatatatatatacatataaaatatagatatagataaa        1960
tctctacatatcaatatatagatataactatacatatagacagatacatccatatctctatagatatcta        2030
tagaagctacagatatacatatatatttctacagatatctacagataacatctcatatagagatagaggt        2100
acagatatgtattgaaatacacatagcaatctttataaacacctattatagagaggtagatgtatggatc        2170
tatatagatctatctatctatatacctatttctaaatctctctctctctgtgtatgtatatatata         2240
tatatatatatgtgtatatatatatatatatatgtatatatgtacatcaacaattccaaggtcc         2310
caattaacttggagaaagatttatgtatatttgcatacttttaaagggtagggcatgtgccattcatcaa        2380
agagacatatacattgtaaaagattttcatttaaaagtcttaggcaagaacattggtgcagtcactgtat        2450
aatgtcatttaaaaatgaactctatttagggcctcttatttgaaattcaatatcctttgttttcttacaa        2520
aagcaatagttaatggatttctcaccatcaatgaatgttacacaatgaatgatgtgttatgggtttgaaa        2590
taacaggtttcagaagactaaatccttcaagaaaactgaaatatcttgcccacaaagaaatctttattcc        2660
catttatcagatgcaaaacttgaattaaggggcctgtacaaccttcttactgtgaaaacgtgaacttaaagt        2730
atttccgtcaaggtttattaatcttataaaatactttccctacaaaaccaaggggaatataaacaagatcat        2800
ctctttatctcttccaactgtatttctgtaactatgtttatgtgtaaaaaaagtacctccatcaactat        2870
ttcaagaaaatctcatttaagtgactgaaattaattttaaattatgataacccaacttaaactggtctg        2940
gagtttacttgatatcattgaaagaaaaaggtttatttagcaacagaatgaaatttgctaaaccttaagg        3010
gtgcaaacatttctaaggtatatgtcatattactcttattgaatccatgttgttaattatcttactctgt        3080
aatctagactttaaatcctgtttgggaataacactccttaaatgttttctaaaaaattgagtatgttgtt        3150
tacctagtttatgatttatatatagataatatataacttaacattatatattttaaatatataatatct        3220
```

FIG. 11A-1

```
atattcatatgtggatatagatagatataggtatcaaaacagatattatacaaatgttacttttttgtcct      3290
atgatttctgatgtatattaaaacttatgctctgaactggcctcatataattgtgaaacctgtggcattt      3360
atcatcaatatgttgcagagactttttttctaaaccatgcctaaaatagcaataaaagtaagaaacacca      3430
taaataaactaacagatacataaaaataaaatgaggaaattgtttggattagaaggggcatggggtaaag      3500
aattaggtatgtgagagcaaaaactatgtcttatttatccatcttttgtattttgcagagtttgtggaaa      3570
agcaacagttctcacattcatgcttagtgaataagtgaataaaaacaacaattagcaaaccacttaaaaa      3640
tgacccactgtgaatcacaaggtcaggagatcgagaccatcctggccaacatggtgaaatctcccctcta      3710
ctaaaaattagctgtgtgtggtggcgtgcacctgtagttccagctactcgggaggctgactcaggagaat      3780
tgcttgaatctgggaggtggaggttgcagtgacctgagatcccaccactgcactccagcttggcaaaact      3850
ataagactccatctcaaaaaaaaaaaaaaaaaagatccaccacaagcctgctatttctgaatttacctt       3920
atctttttttttcttcacattaagactataattatgatttcaacttcctcatctgattcccagtcatga      3990
atctatctaacatattcagctgaaggctgtcaatgttgtactgattccaaaatgcaatgatactctccca      4060
tttccttcactcctaaaatctctgaagactgtgacacaattgactcctgcctactccttgagaaggtta      4130
caatccttccttgaattccatgccatgttttctcttgccagagatctttgcagatgggacaatgaccta      4200
tttcaggttgctatcaagaccctacccagtgtcacttcctccaaagatttgcctttccttttaagtgaac      4270
gctttctctatttacaccaaaatgttaagtatcatatccacagggtttgtgctcagatctacagatcct      4340
actttaagatccctattcagatcaaatctcctctcccaaagatctcaggtctgtgggtcattggtatttc      4410
tatgatccacaagcatctcatttttctttccatacaagtgacttttgggtgaatgcactatcactcatcat      4480
atccttcccatagcaccacatcaaagctatctttagtcttttctcatttttagggctccatcccgtttta      4550
ctcaactttttgcaactatgcatatagtcaaatgccatccatagtgaaaaaaatttactactactctgaaa     4620
tttccctattactgggtattttcactactaatatcctaatttatgaatgctgcagtatcactgtcctctt      4690
ttgttctagaatgtcccggatcttaaattccctcagagtaaattcctgaaaggtaatctctgccaccat      4760
cccccactaacaccaataaggattccagtcaatgaatattcataatcctctgtagtccagccttcttatt     4830
ctcctctttgaatcacaagaacctacaagtagctcaccaccattcctgttctcagagtttaacttgagta     4900
ttatctaataaaacaacctcatgtagcagggtggccccacatattcaggttcccagaactcactcgagac     4970
ctgtgaagtttgaatcctggtgtttagctctagaggcatggatttttgtaaccatcttcctgggtcatcct     5040
tgttgaccttgaagttccaaagcctctgctcactccatatctatttctcttctctagatattattaactt     5110
ggaataattttcccatatctactctccaattccccagaaaaaacttgttctgtgaacctttttctcatcat     5180
cccaataggatgcttgttatgcctctgtatgctttggagatggcatatatcacacattgagttgcattt      5250
taataattgaagagtttaatttattcccttattagattttaagcatctttatgctatacatatttatct      5320
ttccaataatgattaataacatagtatatattattattgcactaacaattatcctactgaaaatatttgt      5390
ttcaatttgaccattgtattaggagagtcaataggaatcagtagtgccctatagtgtatctggcttcacc      5460
agtattgtatttcgagttccacatattgatcccataggagcattaacataatagtatgtatgaatgtatg      5530
tatgttcataatagtatgaacataacagtatgtagaatgtagttgatgaagacactgagatggaaaatca      5600
gagagaacaagtaatgtggtatagattatgtctcatgtttcatccagttctttgtaccaaacccagctta      5670
tatatccttctaggaaccctactgttttatttcattttatgaatcctcctagctcccacatctcaccata      5740
ctccacaattagatttcaagtggaaacatgaagaatgatatcctttatctcttccaggaattcagaattta     5810
aacctccgaagctcttctgtctgtatcgtaatcctgtggctcagttgttcaagaacttggtgttttaggttc     5880
tatcctggtcacttatgagggattttggattagggaaaattataaaactcataatatcttatattcacttt      5950
ttcttataagcatgattccatttgtctaagatgctttcttaatttttttttttttttgagggagggtttca     6020
ttctgcaacacaggctgggtacagtggcatgatcatggctcactgcagcctcaacctctctggctcaag      6090
tggccaaccttcagcctcttgaatagctggtaccacaagcatgcactaccacttcatttttaattttttt      6160
ggtagaaacaggatctcactacattgcccagggtgatatcgaactcctgggctctagtgttcccccctgcc     6230
tcagcctcccaaagtgcagagattccaggcatgatccactgctcctggcctttttttttttttttaagaaa     6300
ttaattaattaatttttaaaaagtcttagtgaagtaattcagacagaagtgacttgtctgctctctcccag     6370
gtcacatgtctcagggaagagatctgctacccaaccaatgcacccacaaactaagccaagcattcagatt      6440
ttgcccaaaatctccctcccaatctcactttatcatgctgcctttaaagtatttagagttgatgtctcccc     6510
acagcaatctccactccctttcccttccccctctcccctcccctcatctccctgccctccactcccctcca      6580
cttcttttctgtcccttcttttttctccttttctcttctctctgtctctctcattcaggacttgattt      6650
gtcacagccattcttgcaacaaccttacaaacatttttctttgcttttccacattggccctcttcaactagt     6720
tctccatgttgccatcacagtgattgtcctaaaacataaatctgattatttcttcttccctcactgcaga     6790
aaatgtgttattggctttcccactgcctactggataaatttcaccttttcagcatgacattttaaaactct     6860
tcacaattaggtctctaatcctttcctcactaccttcttttcaaattcaatgtcctgccatgccaaaccc     6930
tccctatttctagatctccacacatacagtattgctgcgatgtctttagccatggcttctttttcaactt     7000
cttcaaccaatcagtgtcgatgtaccattccttccctactctgaatgttcttcctttgcaaacccttggt     7070
taattattttaacctctatgggtccctattaatttatatgtattccttgtacacaccttcctgtaatcac     7140
attttttctcatgcttttcattatcttgtctactataatgtatgcttttctcaaaaataaatggataagt     7210
ctcactcacagttacatgtctgtgcttaggactgtgtcagtgctaaaaaaaaaaaaacctgaacttatga     7280
ataagtcaatgaattaacattcttggcaaagtccatgactttgtggcctattataaattagtgtgttc     7350
aagttgaggttctggtttagtttaggacatagatatctatatatagtccatatatctacatatatgtc      7420
tacatccatgtatatcactgatttgggggataagctgtatttataaacaatactatcatgttaatgggtc     7490
ttcaatatctacacaataatggaaaaaagtatatgtatatttctaaatatctaatgggaacacacacaca     7560
tatatgtatgtatatatacattttctattattggctatagatatcttttaatagataagtgtatatc      7630
tatgtaccaatcttgttggcaaaggatgctttcatgcatattatctcatttagtccccacaaggaaaagc     7700
aacccacaggaaaggtaataataatgtcagctcaacagagtcacagaacataactgactttatgacaagg     7770
caaaatttgtgaggatagagtcttaacatgaaaccaggtccccagattcatgtccatcatcttccccatt     7840
attgctcatgttgtccaaaatccttcgcatcatcatggaaggcttcatgcttaggtttacttcctaaagc     7910
agaagcaattaggagaatgtcctatgtgttgtggacattatcttttttccttccataaatgaattaatgg     7980
gcaatgaaataattttaagaaaagctaactttttatagccaggtagaataaaagtaatcaccatgaaatat     8050
tgtgaagataagcaggccccacacactagctcagctaatcaatatgacaatattacatggagattatctg     8120
ttccatttttacagatgcagaaatgggaggcgaatattaaaaattcattcctaaggtcacatgcaacttaaac     8190
ccaagcaatctcattttagaatctgtgttcattgccacaacattctatgatgtactctgatctttgcatt     8260
gccaatttaaatccaactttcttgaagccaactttaaatactgggaactttaagcattgtcaatttcaag     8330
```

FIG. 11A-2

```
ccaactttctccaacccaattttaaatacaggggtcacaccctcctcctcgcccctgcaacttgaaact      8400
ccctgggaaagataacctcctggacctgggaaatgaggagtatttagaaacaactgcctcttggtaagca      8470
cacctcctatattttatccaaatcatgaaattataacaatagaagtaaacaaaaagccttcattcatcct      8540
ctttcaaccataacctcggcataaaaagctcctgtactttacagagctgtattccaattttcgctgctct      8610
taaaattttttttaatatcattgcttcccaattgactcacaataacgcagacataggqactgctggagac      8680
tgtgaccttaaacagttaaagatgtctgcatatacgacatcatgtgtttggtgtgggagagtacctagagatt    8750
cctaaaaaagcaaagaggaagaaggtttgctgtgcgcatctgggtaccctgctctatctccagggttccc      8820
aggatctctctgttacagctggtttgcactgggattagttgctcttgcatgaggttgtagctgtggacg      8890
tgggttttgtagcgattgggacgactctggagatctattggctgctgggtttgtaaatttcattcattt      8960
ggtccaatggcagaaggagagcgccggaagcagaaggacctctctccctagctctcttttcttgcaga      9030
gacatctttctcccatctctgtctgttagtacagagctcttattcagccactagctcggcctttcctgct      9100
tcaattgtaatgcttgttctgcccggggacacactattgacagcagaaacaatgaatttcctccaaaccc      9170
ggcaatgttggtggctcttgcattcctctggatgagcgaatctagttgggggttcccgaaggggaaggc      9240
gcctgggctttcaatacatcctcctgaatcatactgcgtttcaggttccttagaaaaatttggatgtgta      9310
aaaagaactcttaacggcgatgcaggtcttccacagctaaggtaggtgcagtttaagacgtgtctttcg      9380
catattattatccttattttaaaaagcgtttaaacaatttgacttgcagtggctctccagcaaaggagg      9450
gaaagcctcactggcgatatttgagcttcatttcatctaatatttatttatttttttcctttattattat      9520
tattattggacaatttgggctggactctctcccatctgtctcgctccatttctttggtgtggatgggaat      9590
gtggacatcgatgtatggcttttacatgcaatctctccacaggaacatttggttttattttcacttaaaa      9660
ataaaaatgcagaccaccaatgttgtttggaagcattttgctgcaatcagctgtttgaacagctctgggg      9730
ccatgtgcggtgtgtttaaaaagtagcgctgccttccatacaaattaaaggaagactgtggcgggaaag      9800
gaggggaaaaatatatatatatatacacagacatatgcgtatgtgtgagtttgtgagtgtacac      9870
atacacacacatatatgtacacacacacacatacatgcagtacagggggaaaaggagggaaaagg      9940
ccagggctggagatggcgaaagcaggaggacttctgcaaactgtgagcatggaaggcttttcttctcttt      10010
tctcccactccaaagccctcgtcttctttaagaaaaccaccactgcctggggtgcttcttttgggaggc      10080
tggggttggggttggtgccattaaccagagagaaaaggggaaataaagcttggttggggttgcattatg      10150
agatttttttttccctcctcatcctcctggcctcggataagtaaggcttggggatgcacgaaataat      10220
ccaagtgattgattagacctggcatggcttggttgggctggagaaagatcggggcgcgctggaaaccccg      10290
cgtgaagatgaaatgactgtagctccgtgctgctcctccaaactcgggagcggtatccatgcaccctt      10360
cccgtgtgtgtgggttacgacgtgggtgggagtggtgaggcaagccgcaaagtggggtagagctggtgg      10430
ttttgcttcttcggaagcctttgagtgtgtgcctagatggggtgcagggcggtttccggcctgcgcctgc      10500
caccctcggcaccatctctgaactgcccgcttttccggaggagcggaaaagttggaagccgaaaagacag      10570
gcgcccggagcccctggtctaggtatcaggtgatccggagccctagtcggtgcccactaagaacaccccctt      10640
ctcccatcgggggttcggaggagtgttaagcctgcgggtctgccagtccctaaggtagggatgggggagg      10710
ggtctgaggaatccgttccaataggcacaccatccccacagccctagaaaaggcaaccaccaccccgctcc      10780
ttcctcccgcaccatcccatctcaaggctctctgctgacccgggccgatttcatctggtctctctcccc      10850
cgcttcccacctcccaatcccgcgcagctcggctccgttccctcccactccctaggcggaactgaaag      10920
cgaagatcagccaagagcacagtcggaggcggcagagacggtggcgggtgagctaggggctgtgagacga      10990
agcaggagagagtgaacttcagccccgtcccctccccactgccacggctggggcaacccaacccgcgcc      11060
tgaagcggcttggcttgacctgcggaagcgcgggccgggatggcgtggggagagggaggtaggtgccact      11130
gggctgcagatgacgagtgggttggggggcttgctgtgggacaagaggttcaggttccggcctgcgccttc      11200
cactccgcggtggcgctctctgcctgcggttttccaggaggccgatctaccccagggacactctcatcct      11270
tcaggcggtctcctggacgccctttcctcccctgcctcccagcctgacctggctcttcgccctcgga      11340
gaaccggtaggttggggtccctcggcggggtctagtgagccgagtcgcgagctttgcgccccggtatc      11410
taggccccgtgccgcgcgcaaatccgggcccaggcgtacagttctggagcctagtcgccgccagacacag      11480
ggcccttgtaccggaggagcgggagcgggagccaggcaggagcaccccttgcaccccagaggcct      11550
gcctaggaccaccctgggaacaaatgtctcgctcggaaaacgaggtgaacccggaggatgtcctacgcat      11620
catacccctccccttcttgagaaggcttttctcttttttctttttttttcccggttccttttctctggc      11690
ttcttccacaccttaccgcaggtgtgggcctcttttcatgtatgtgcggctgctatctcggggatgcagg      11760
ggaaggcggtgtaggaggcagcgtggadggtactaggaggtggcggcgggatttgggcctggtgatgt      11830
gcccgagctgcagctagctggggcactgggccccccaagtcagccaattcagccagggcttgggcgagac      11900
tgcccggagcaaggacggaggatccagatttaccatttggacccaaattaagaaatttggggtgggggtt      11970
gggtaggggttttgaaactaagcaggtgacgtccttgcgagctgaatccacaaggtggtagtatggctta      12040
tattatttttattttattattttattttattttctattgttcattttttttgtgtgtggggagtgggg      12110
atgttttttctctgtgtactccaatcttatgcttttgaaggcatccattgcccgtagggtttacataa      12180
gaccgcgttgcattatattttcttaaaagtgggggtgggtgcataagcttccattcagaatcagtcgct      12250
cctgtgatgtgagggaggcaaaagcaaagaaaaggaaaaataaacaaaataagaagtttagggagacttc      12320
attatccccacgaagccggaattgccagtttgtgtggtcgttctgcgggcaacatagaagtgcgtgtttc      12390
agaaatccttggatagcttctttcttctccaactagaaattaaatggccagggtgcaaacacctgacttt      12460
gatgaaaacaaagtggcagaaactacaagagacctgattgctttcaatgaacgcactgagccttttccta      12530
gaggatggcagagctgggagaaatcagatctcaaagaaatctacagttttgtgagggcagattttggagag      12600
tggagaattatttcataccttagttggccctggtgaagatgttagcagtaatccatcaaatcctagca      12670
tagatttcctgtggaaatgagcaaaatgttaaggggttgggggatggctatataggaattcatggaga      12740
cctctgcaaggatgtattttctcagattagaaatccggtattttattacacaatgcaatgaatgcattct      12810
acacacacatgcattccatatttctgtatgtgtgtctgtgtgtgtgtgtgtgtgtgtatgtagtct      12880
ttttaaagagtatctttgacatgtaaaaacataatcagggccattgtaggaagtggaaaattacttcatc      12950
agttttaaatcagtggattaaaatcggaggcttgattttgtgtgtgtgtgtgtgtaacactagaatga      13020
taattgcatattcataataatgtttgtgcttggataccattttaaagttgctttgatgttttctgctctg      13090
gtgaaagaattttttcttttctttgtgttttatttaaataactaatgcttcatatacagtaggccctaaa      13160
accagtaacctagctgattttacccaaacctaagaatataacagatacttggtaagggactagtggctg      13230
cataaggtagatattatgttatcttgatgctgtaaaatttacaagcagacttgaaggaatttgaaagtt      13300
cacagttttgggcctggaatgtagactaatggtaagcatacagatttgttttttaatttgtgaatttggct      13370
ttttcattttgtgtgtgtgtagtaatttgtggaaagcttatagtctctccacaaagacaggagcttttgac      13440
```

FIG. 11A-3

```
tgactcgccatcagagaattgctttcacaagtgcagggtctcttaaaatctctttggaatactgtgct      13510
tttatttctacaccacaaaaaaggatctcacaaaagtaaacattcaagtgcatgaccgaatgacctttt      13580
taaacattctttcatttttaattggtactccacacttcaaacctttcctaaaactttgaatattgtcaata   13650
atgcaagttgctgagcgaatattgtgaatattgcattcaaatgaagtagcaatataaaaatattttaagt    13720
catttaatgtcctccttctgaagacaggcgtatgtggttaaaatatacttaaattccaaatatggtgaga    13790
gccggtcttaggatgtgaatgtcaagtttaagcaacacaattttagtttgtaaaccagaatgtattcttt    13860
ctatactactttctgattttaacaatatgtattctattcctaaatgggaaaaatatgttcagttgagtt     13930
caaatccattgctgttttttgtttttgtctgagtactacactttttcagaggagagtcttcatctcctac    14000
ttaattatgtgaatggattttcagacagactgtgccttctgtatagccacctttatttcttaaacccct    14070
gagctacaagttttaaatcaaagatacagcttttgcccagtcatttagagaaagtgagaatggaaattga    14140
agcccaggccattgaggcaattaggtcatctgctgtgccctctgctaccattcagtcaatgaatatttta    14210
cagtttcatcattttaatctaaacaacctacatttggactttgaaaggctccactgttttttgttaagtg    14280
aatggcagtgtaggaaaccccttcctcatttttcttgggcagagtggcacacatgaatgagaaaaaaga    14350
aggcgatacctcctagcagtttgtcattgtgacattcataggctttgaataaatgtgtagatgaaaaggc    14420
cttctctctgcaggtgattacatgaaataaaaaataagtaaataaaaggctcataaaaacactacaggag    14490
tggaaggttgatggtggaaaacagcctatctaccttgggttgagatttcaaactttagacatttttgtgtt   14560
gagttcacatgtccctgatgtatggggaacacctccatatacacatcttcccaaggcatgctcatcttc     14630
ccagaaatggtacctgaaggagagcaggcctaaccccaacaatattttaaaaactctctctatatatgt    14700
aactatatatatagagtaaaatctgtatcttactgtatattatatatatagtaatatatattttaata      14770
aggtttgtatttataaaggaaagaagtttaaatgactcgcagttcagcatggctggagaggcctcaagaa    14840
acttacaattatgggaaacgggaagcaaacacatccttcacaggatggcaggaaggagatgaatgagaac    14910
caagtgattcatggaaagcccccttataaaacgatcagatcttgtgagaacttactatcatgagaatggca   14980
tggaggaaactgcccctgtgattcaattatctcccaccacgtccctcccatgacacatgggggattgtgga  15050
gccgcaattcaagatgaggtttgggtggggacacagtcaaatcatatcatgaggttttattatttaagac   15120
aggaaaagagtaatcgtccatactttagacgggagatgaagtacagtgaacattcatagtcccattggtt   15190
gaagaatacatttcgaagagagaaatgttaatttcattatattgctaatgaaatgatctaggctttcact   15260
gctctctgaaatgtggagaagtggcccaagatcttgtttgggttgtctatttaaaatgtacattacat     15330
aaagaaatcatgatttgtcaaagtaacagagtggtatttttggcttacaatgggactttcttagctccac   15400
ctgttaatatcgatgatcatttggttttaagaggccagtatctgattggatgatgaaaacctggatctc    15470
aaagccatcaccccagacatgtgattttattaacatctgtgggcatgtctcctggctcccacatcaaccc   15540
ttcatccaggctcatttctctgtttttgtttggttgtttgtatgctttgggtggggaaaggggacacat    15610
attttgctaagggcacctttttcagtcatgaaaacgtagcctgtcaataagctgaaaaggaacttggttg   15680
tttcaagttgcattaggtagtaagttttttggatccttaaaaaaaaaaaggactgaggttactaaaagtg    15750
ttattggcactgataaaagagccatggtgacttgtggttttgttttcacaaggtgtggaaaaggcctcctt  15820
ggttctttgatgatggctgtagtgaagttgcatgcggtgccattttccatgtttagtatttcaacaacac   15890
caatatgtggctctggagtatgggacgggcaattccaagaactcagtgaggcatgccatgtgactccaat   15960
ggtcagtcagagctgttcagcatggaactatggtcccaaaagcatgggggatgggggcagaagaaactca   16030
ttgcaactgagtgtctttaacttgttccagtcctcactactctctgtgaatataactctgtgagtgggt    16100
aggtgaggaaactcacaaaagtaaatgcgtgttttcacaaacaaatttttatcattgttaactgtttcct   16170
aagtgagacaatatgccctcatgcctgaagctacactgtaagaatggcagtatgtatgagcaggtgtat    16240
acacatacatgtgcacatatgccaacacactaactaggaactagtccttgcagaaaatgtttttctcagc   16310
cattctaacacactagataaaagcaagtatgtgtgtgtgtgtatatatatacacacatatgtacatac     16380
atgtataaacacatatatatatatatatatatatctgaaggaaaaaatatcattttca               16450
ttagttactttcctttttttattcccatcattcaccaaacctatgttatattaaacaatccataacacct   16520
ggcctggacaatagagtgagaccctaactccacaaagaaacaaaaattaaaaacaaagtagctggcacta   16590
ggcaagtacctgtggttccaactgaggtgggaggatcacttgaacataggagttcatggctgcagtgagc   16660
tataattacaccactgtactccagcctgagagacagagcaagacccctatctctaaaaaatatatataaat  16730
aaaacataaaaataaaaatagaaaattttacaatgaaaggtgtaaagttacctatgatgggcctgggtgt   16800
aatcttcatttaggagtgaatatattcattaaagtgagacctaagtagtataaagtatgtgtttagggac   16870
aggtgcccattttctctaggtctcctggaatattttttttctaaattgagttctgattccaaaaaagtg    16940
ttattgcctatgcttatggtgaaactatatgtgtgacaaaatgctactctgtcttgtccatcaatattgt   17010
gcaatgtggtattctttcatggagcaattgacaacttttacagtgatcaaactgggcactcttttactaag  17080
gctaaattcataacctttatctgactttgtagaagattctcacctttatttctctcggtgcccaaggc     17150
ctggcctgagagactgttcccattgaagccttacagaaagcttgtagagcattgtaacagcccagcttca   17220
gaaacccagcattgactttcaataaatatgaaggagtttgaagtcacaaatgttgagaacctcattatag   17290
tctctttatgaacttgagtccctctcttcctgcagacttcctttgaactcaaatttaatgtgcactactt   17360
attcacccttgtacttatgaaaagcattgacaatcccaggtaataactagagaagaagtgagtgaatgc    17430
tagagggtttctcatttaggttgttcactcaccactgtgcacaggctctttagaaatctacttacacatg  17500
atgagactgtaagcagacttatgtttctgaagcatcagtatacaggtgtgcagaaagaaatgggctaggt   17570
cacttaacagctacgagtataactaagatggacaaaatagttttatttgcagttatatctatagagcct    17640
tcatcatctatatctatatctatatataaaatagggtgcatataaacatacacagatcatagattattca  17710
tttcagtttctacatacaatatgtaattatatacaattgcatttatgtgcatttatataatagtatttg    17780
tatacaacttctatactttgaataaaactgtcatcttcaatagctgttaatatatattttatttctagata 17850
gttgtatttatgtacatttacataattgtatttatatacagtttatattactgatgaaagcctttatcac   17920
ttgcaaacttacttatacaaaatacaatttatctaaacataaaatgtattatataaatataagttatata   17990
ttaatatatagcatatacaataagtcataaatatataataaaaatgtgttttgtatacttatttattata   18060
tattgagtataactcatttaaatacaattttatattatataatgtattatatattgtgtaataaatata    18130
atttatatattgctattatatataccctattgtatataagatataataaaatccatctaaatctataataa   18200
aatatgtatatatttatgttctgtatatgtatttttcttgcttttatgtattaaaaatacatacaaact    18270
atatatgtagtatactgcaaactatatatatagacatgcattttccaaaagaaactgtgttataggtggt   18340
gagtgaacttctaggctgattcacaggagctatggttactatgcgtagtggtccatggaaactacaactt   18410
tactttcaagtggagcataagagctataaatgactgtaatatgatagcaagcacatcatggcactctgtg   18480
aatcctgagaaatcgacctttcgtgtgttttgtgaaccagtcaggaaagctcatttgagtgggaggatgt   18550
```

FIG. 11A-4

```
gtcaagccatgtgtctctcccaccgagatggatagacaacatctgcttatagactgagaaactacctgag       18620
gttgtgtggaagtcatgacaaattggcaatgtcctcagtgtgttcggggtgggaggtggtgatgtccctg       18690
gacctatgcttagcttttatccctctgtgggaccaattctgttggcaaaatcacttctgtggtcttgctc       18760
cagatgaaaaatcaacatggaaggcttaggggtttagtgctctagttaatggcaagaaagaaaatcagtg       18830
actaagatcaatttatcctttttgtgtgcaaaacagcttttttattggaggagctaggtcttatatagagcta     18900
gctcttatatagagcaggagctagctcttatatagagccaccctagtatgttctttcatttgtcatttta       18970
ttgatcatctactatatgccagatacaggccagaaagcaaattctgagctggtaatggagaggcaaaata       19040
ggccatccctgtactctaaaaaatcctgcctatgtgtggatgttcacaagaacgttgttaagattttag       19110
ttcaggtatggattactttcttttcattttgttgtatacattacattttttttctttcatcctcatacct       19180
ctctcctccttcctccttccttcccttacttccctccctcctccttcttttttctctattttccttcc       19250
ttttttctctccctccttccctccctccatccttccttccttccttcctccttctttccttccttcct       19320
tcttccctctttcctttatgctatttggatgagtgataaaatctcaagggtccttaaaatattaaaggga     19390
aaatgaagataattctattgaagaacagatcaaataggaaagagtaatgaaaagaaagcttcctggaatg       19460
agaaattagcatgttctttacaatttaatagaattttttcatatactatatttgtatagctggttagattt     19530
taaaactttgtcaaacccctacatttataaaaccttagttttcattttagtaagttatatggatgaatgca   19600
cacataaagcagattaccttgattcaacaaaaacattcaaatattagtgatccttttttttttaacatatg   19670
gtagtggaaacagcttgattaatttatggctatttcctacatactttttaaaatcaataagcaacagtca       19740
gatatttcagcatttttaaggcatgaacagtaccttgaattgtaatatattttagtctaaaacatctggt     19810
aacatcacaggtaattgcttcaaactctactgccgctcatataatttacttttttcatcaatttaaggtc       19880
ttttagagtcatgagaggaccttttaaaatagataacatcactcatactattgagctaggattgcttaaag   19950
atggagcatagattacattgtctcagaggaaaatattttatggaagattcttttttttgtgtgtgttct       20020
tggatacatgtgcagaatgtgcaggtttgtgatagagttatacatggccatggtggtttgctggaccta       20090
tcaaccagccatctaggttttaagccccacatgcattatgtatttgtcctagagctttgcctcccccttt     20160
ctcccaccctgcaccaggccccagtgtgtgaaattcacctccctgtgtccctgtattcccattgttcaga       20230
ttggacttatatgagaacatgtggtgctggttttcggttcctctgttagtttgctgagaatgatggtttc     20300
cagcttcatcacgttcatggaaaggacatgaactcattcttttccggctgcttagtattctatcttgaagag     20370
atttgtgccacatttttttctatccagtctatcactgatggtcatttagtttggttccaagtcttgtgcta     20440
ttgtaaacagtgctgcagtaaccatacatgtgtatgcgtctttatagtagaatgatttataatcctttag   20510
gtatatacgcagtaatgggatggctgagtcatatggtatttatggttctagatccctgaggaatctccac   20580
acactcttctgcaatggttgaactgattcatagccaacaaacatgtgaaaaaaagctcatcatcactggt   20650
cattagagaaatgcaaatgattctttaaaaagtataagaactcccgaatcaggtcttctatcttgaagag   20720
gctccctggtccaatatttctggaaaaacctcatgtatcatttgcctctcttgaatttttaccctgaagaca     20790
gacacattatgcccttaaagcctcctatactaatggatttagcaggcataccaaataacttaaggttggt       20860
tctttgtaatgaattttaatcaaattaactaccaacagtattcagaatacttccattgacacagagcag       20930
aaagaagtgccaacaggatatgaagtatctttaaattaccaaaataatttggagaaatgaacttgttgat       21000
tttttctttattttatttacttattacaaaacttgttgatgccaagaagtgggataaaaatacaatgaaa     21070
ttgtttattttttcctatattaacgataggctaatattattttgcacctctggtcttactggtcttatgtt    21140
tgagaacaaataagttttatctgaatatttttatctctcgtgtgtgtgtgtgtgtgtgtgtgtgtgtgt       21210
gtgtgtttaatctctcatgtcctgtcaaaaattaagaaaaagaacagtttgattcagtcttcacacatct       21280
ttcttaaacagttaaaggcaaaatcatcagagctacatggcccaaatattagcaggtaggttcatgtttg       21350
aattctcagagggtgattatgtagttcaattttaactccttcaacagacagactactatcgttgatgagc       21420
aaggagacaaaagtatttgataaacattatgtagttaatattatccttgagggaggggagaaggctgcct     21490
gtcttaggtaatgcttttcgatggcaggtttgtcctaggcttgaggtagcaggcttgctcttttggctgaa     21560
gaagccctaacatgcataccagtattgcaaatttacccacatgccaattgtatgctgtggaaagaaatga       21630
ataatgtagatcccattacagagaatgatgtggaacagatagacttaatgcatcagaaccagtgagcagt     21700
agacaagacatttagaaaataacaacagcagtgaaaacaaatataaacaaaccacaaaacaaaaccattac       21770
atttgggtttctggttgcctgttacctcagaggtttctggttacaagctaaaatgtcttgaccattagga   21840
aggtcaagacaaggccccttaatgctgtgtaaaacagtaacaaacagtaagggtgacccagggagaaggg       21910
taacaagttacattgaagttaaataccagggagaaagtgtagcagttacatggaaatttaaataccagtta       21980
cctgtgcagagactgaaaatacaaagcagacacaggaacggtagtagtagaaggcctagggcaagggatt       22050
ggcgggcgggggttgggggatgggcgggaatctgaatttgatctgaatttgttgcagcttgaaattg         22120
cagcttgaaactagccagccaactctaatgagggcattgatatgggaaaacactacctcagaaaaaaaa       22190
tctgacaacctaggtagagatcaaatggtaccatattctgaggatggaataataattcacacatggcttc       22260
acataaaatttgtgtgacaatggttatttactatgattcagtctgccatgacaattttaccagtaaaata       22330
actttctaggatttatttgatatcagttaataagcctaccttaaatgaataaccagaatatgacaattga       22400
aaattaatgtaaaattacacaaatagttatgtgtctagatatttcacaatcaaatgtatgtgggcattta       22470
atctagtcagatccaaataataaaaaattctttctttctagacacattatcttgatattatacatac         22540
atatgtaaattacaaccacatatttgcatatgtaaattacacagcaatttacacatagatacatacatag       22610
ctcacttttttgttggtgaacacatttttcctgaaggttttttttttttttttttttttttttttgagatg   22680
gagtctcgctctttcaccgaggctggagtgcagtggtgctatctcggctcactgcaagctccgcctcccg       22750
ggttcatgccattctcctgcctcagcctcctgagtagctgggactacaggcgcccaccaccgcgcccggc       22820
taattttttgtatttttagcagagacgggtttcaccacgttagccaggatggtctcgatctcctgacc       22890
tcgtgatccgcctgcctcggcctcccaaagtgctgggattacaggcgtgagccaccgcacccagccgaag     22960
gtttttaaaataataattattctacctgtaatgccatagcagtattggtaaaagttcaaatgtggctgg       23030
gtggagtgcctcattcctgtaattctagcattttggaaggccaacacaggagcattacttgagtccagca       23100
ctttgagagcagcctggaaaaccctatatgtacagaaaataaaaaaaaataaaaaatagagtaagccag       23170
gtgtgggtggtgcatgtctgtatccctgctactcaggaggctgggtgataaggatcgcacttgaggagttta     23240
tcagtagtttgaggctgcagtaggcctatgacctcaccactgcattgcaacctgggcaacagctgacacc       23310
ctgtctttaaaaagaattcaattgcatcatttatgtgtgacagatttgactggtgtcattctgttgctga       23380
atcattccaaggtatgcacttaccttttctctcttgaaacagcttatgcaaaaacaaacaactaaataga       23450
gaagcagtttgcaaaactatatttaaaggtaaaccatactccctcacccccaactccacaaaaatagttt       23520
tatgtagagaaaccacagatggtgcagcccccaaatctggagcatcctcaggtaccttgggggtattctgg       23590
agtgaaagactaaatctcagaggctttttggtcacacttgggtaggcatcctgattggctagtgaagaaac       23660
```

FIG. 11A-5

```
agctgtccctgctgtggtcagtttcagcctttcctggaagggaattttccagcattgggtgttcctgtag      23730
atgcttatagcaagttatgttcaatgaagccaactgcatcctgatttatctgttattcaatctgtgctgc      23800
ataataaaaaaggtctgctttgaaaatgaaatcatgcactttgctttattttgcccatttgatatttctt      23870
ctaatgttgtaagcttctcatgaattggcataagcagatatgttacaaattgatccatccaggacatcct      23940
tgctagtcttagctcaccatagcaagtcagaatggaagacagttgcttctcctccttcctctcccccatc      24010
ccacctcacatctgacatccttctccctctgaggaaaaataatcctctgttcaaatttaaaagcatggcct      24080
ggtatgatggctcatgtctgtaatctcagcactttgagaagccaaggcgagcagatcactggaggtcagg      24150
tattcagtcagtgatacactctctatactaaaaatatgcaaattagccaggtgtggtgtcatgcacctgt      24220
agtcccatctacttgggaggctgaggcaggagacttgcttgcacctgggaggtagaggttacagtgggct      24290
aatatcatgccactggactccagcctaggcaacagagtgagtctctgaaaaaaagaaaaaaatatagaaa      24360
aatgttcaagtatttactgtccacatctttcagctatttaacacttcactgggattgtgaagtgaaatgg      24430
agtgccattattaccttgttagccactttcaatttggaaaggtaaaaatgtccttcaatggctattgaac      24500
tgcctgcactgaatttaaagtacagtttgttggaatattcgtgatgaagttgaaaaatagaattacagat      24570
tattaggacttgaatgtacttgaggaatcattttgtattccctcatgtacacaaggaaatggagtcacaga      24640
aagtttcagggatttatccccatactttaaacactgaaatgttcccaaaatgaaatgaaatacttccaa      24710
ttgttaacatatccgcttatgtcaattcatgacaagcttacaaaattagaagaaacatcaaatgggcaaa      24780
ataatgtgaagtgcatgatttcattttcaaaacagacttttttattatgcagcagagatcgaataagaga      24850
taaatcattttgatgaaaggaacaatgagagaaagcaaagaaagacatgtcctgcattaaaagctgcatt      24920
tgatggtaactcattttgttttatgagttatgatgaatgcatcttagctgtttctaacctccctccccatt      24990
ccctattttatttgtcagttaaagcacagcatttttccctttttttttgaagtgttaattaattgcatt      25060
tgtttaatgcatcttgctgtgtctcaagcatggttaacaagggataatgccttttttcagggatgattcc      25130
ttcctttccttacgggctttgtctgtgatgggaactttgtgttttatttatttatttttctttttaagag      25200
acagggtctaatcaggttgcacaggctggtctcaaactcctgggctcaagggatccttctgactgacctc      25270
ttgaaacattgggattacaggcgtgagccaccgcacttggctctatctttctgcaaaaacctagcaattc      25340
taattctctctccatctatgtctagaccagggagatataatcaagagaaaagaaacaactaccttcatta      25410
gattaagagtcaaaagggcctacaggcaaaaagactccaggaccctcttgagtgagcctgtgcattgaaa      25480
tcttcagcttcatagagacacagaagtccaaataggaagttggatttgccctatttcttagcctcttct      25550
agtctgtgaccgtttcttagtctttccttgttttttcatgaccttaatagttttttggtattaatattatg      25620
gagaatgtccaccacctgggggtctgtctgatgttttagacaggatatgtgttttggggaggaaatctgc      25690
agagatgaatcaatcatttatatcactatgggcacatggatgttttggatatgctttaggttttaattca      25760
acactacactactgtgacttgctctactttatattcttgtggccatgatgagacactaaaacatctatt      25830
cacttgaatagcaagtaaatgagaggactcaatggcaaatgactgttatgctttaacatatccagttctt      25900
tgtatattttttgacatttaggttatttaatgcctttgctcctcaaggtatttccttcttcttttttt      25970
ttttttttgctccacaccctccctcctctaacttgtttccaaattcttccttgtaaattgtgcattcc      26040
tcattctaggggcattacttattttcttttgcttgcttcaaaaaacactctgcattggtctgtacacatt      26110
ttccctcttatatccttctgtaagcatttgtattcagttgaaatcttatggaatactttaccacagaaa      26180
atttctggtgtataccaaaaaaggggaatgaaaatagaataatggatcccatttgcccatcatttgcttca      26250
gcaattataaatgcatagcataatctttagtatttaacctcatttatgtttccattcttattatggcatg      26320
atgcaatttatttaaagatagtttggtgagaaccattcactccctgaaagggaggctgaagcccaaaag      26390
tcaaagtggtgtggctcggtgggtcccatcccactgagtccggccaagccaagatccactggcttgaaat      26460
ctcgctgccagcacagcagtcttaggtcaacctgggacactccagcttggtgtgtgtgtgtgtgtgtgtg      26530
tgtggtggggggggcggggggggcacatccaccattgccaaggcttgagttggcagttttaccccacagt      26600
tgtaaagaaagccgcctggcagttcaaactggtcagagctctccacagctcatcaaggccactgtggcaa      26670
gactgcccctctagattcttcttctctggtcagggcatctctaaaaaaaaaggcagcagctcagtcaggca      26740
catatagttaaaaccccctatctccctgggacagagcaactgggggaaagggcagctgtgggtgcagcttc      26810
agcagacttaaacgtccctccctgatggctctgaagagagcaaaggatctcccagcacagtgttcaagct      26880
ctgctaagggtcagactgcctcctcaaatgggtctctgaaacttgtgtatcctgactgggacacaccacc      26950
cagcggggcaacggacacctcatacaggagagctcttgctggcatctggctggtgcccctctgggaca      27020
aaacttttagaggaaggagcaggcagcaatctttgctgctctgcagcctcactggtgataccaaggcaa      27090
acagggtgtgggatgaacctggagcaatctccagcagaactgcagcagaggggcctgttagaatgagaac      27160
taacaaacagaaaggaatagcacatccactcagaggccccatctgaaggtcaccaacatcaaaaaacaaa      27230
ggtagatgaatccatgaagatggagagaaaccagtgtaaaggctgaaaattccaaaaaccagaatgcct      27300
ctcctcctccaaaggatcacaactcctcacaagcaagggaacaaaactggatggagaatgagtttgatga      27370
attgacagaagtgggcttcagaacgtgggtaataagcaaattcctctgactcaaagaagcagtgttctaac      27440
caatgccaggaagctaagaaccttgaagaaaggttagatgaatttctaactagaataaccagattagaga      27510
agaacataaatgacctgatggagctgaaaaacacagcatgagaacttcatgaagcttacacaaatatcaa      27580
tagctgaattgatcaagtggaagaaagggatatcagagactgaagatcaactcaatgaaataaagcaagaa      27650
gataagattagagaaaaagaatgaaaagcaacgaacaaagcctccaagaaatgtgggactttgtgaaaa      27720
gaccaaatttaagttgaagtggtgtacctgaaagtgacggggagaatggaaccaagttgaaaaacactct      27790
tcaggatgttatcaaggagaacttccccaacctagcaaggcaagccaacattaaaattcaggatatacag      27860
acaacaccacaaagatacttctccagaagagcaacaccaagatacataatcatcagattcacaaaggttg      27930
aaatgaaggaaaaatgttatgggcagccagagagaaaggtcatgttacccacaaagggaagcctgtaag      28000
gctaatagcacatctctcttcagaaacactgcaagccagaagagagtgggggccagtattcaacattctt      28070
aaagaaaagaattttcaacccagaatttcatatctagccaaactaagctctaagggaaggagaaatac      28140
aatcctttacagacaagcaaatgctgagagatttttgtcactatcaggcctgcgttactggtgctcctgaa      28210
ggaatcagtaaatatggaaagaacaactggtaccagtcactgcaaaaacatatcaaattgtaaagaccat      28280
tgacactatgaagaaactgcatcaaataatgtgcaaaataaccagctagcatcataataacaggatcaaa      28350
ttcatacataacaatattaaccttaaatgtaaatgggctaaaagctccaatcaaaaggcacagactggca      28420
aataggctaaagcgttaacactcattggtgagctctattcaggagactcatctcatgcaaagacatacat      28490
aggcccaaagtaaagggatggaggaatatttaccaagcaaatggaaagcaaaataaaaaagcaggggttg      28560
caatcctagtctctgataaaactcactttaaatcaacaaagatctagagactaggacattacataatggt      28630
aaagggatcaatgcaagaagaagagctaactatcctaaatacatatgccccagtacaggagcacacaga      28700
ttcataaaacaagttcttagagacctacaatgagacttagaatgccacacagtaatagtgggagacttta      28770
```

FIG. 11A-6

```
acaccccactgtcaatattagactgaacaatgagacagaaaattagcaaggatattcaggacttgaactc    28840
cgctctggatcaagttagatcaagtggacctaacagacatctatagaagtctacatctcaaatcaacaga    28910
atatacattcctctcagcacttcatctcaattcttctaaaattgaccacataattggaagcaaagcactc    28980
ctcagcaaatgcaaatgaatggaagtcataacaaacagtctctcagactgcagtgcaatcaaattagaac    29050
tcaggattataaatcattctactataaagacacatgcacacatatatgtattgcggcactattcacaata    29120
gcacaggcttggaaccaacccaaatgcccatcagtgatagactagataaagaaaatgtggcacatgtaca    29190
ccatagaatactacacagccataaaaaggatgagttcatgtcctttgcagggacttgggtgaagccggaa    29260
gccatcattcttagcaaactaacaaagggacagaaaaccaaacaccacatgttcccactcataagtgcaa    29330
gttgaacaatgagaacacatggacacaggggagggggaacatcacataccagggcctgtggtgggggtgggg    29400
ggcaaggatactattaagagaaatacctcatctagatgactagatgacgagctaatggatgcagcaaacc    29470
actatgtcatgtatatacctatgtaacaaacctgcacgtctgcatatgtacccccagaatgtagagtata    29540
cataaaaaagatcttctcagtacattgctgtaaaatataggaaccattttattttatttagctgcagaatc    29610
ttttccatgcctaaaattatcaacaataattcctctatgtcaccaactatcaaattataaatgtcaaat    29680
aatattttcatagtttgctaactcacacaaggtctatgcactacaatcagttgatttgtcttttacattt    29750
cttttaactgatatagatttcttatccttttatgcacattcttgttggaaaaaactgctctttttactct    29820
acatgaaaatgggttttagagtcggaaaatttagctgtcaagttattttagaaggaacgtgagtattttc    29890
cataatgctcagtcttaggttaccaactccttaggagcaaatgctgtgacttggtagtgatctaccca    29960
gaaggaatgctgctgggtaaatttggccagcttgtgtgacagctctttggactcactatgtctcagtttc    30030
atctacttttaacagtgttttattttgaagatagtttctgactctgtcacccatgctggagtgcagtgat    30100
gcaatcatagctcgatgcagccttgaacttctgggctctagaagtcttcccacatcagcctcatattatc    30170
tagtacctggcagagatacagatctgatgagaaacaaagataaaggggtgtcagaaggtagctttgctg    30240
catcatcagacacgcacacatgcgcacacacgtgcatgcatacacacatgtgtacgcacacacaatca    30310
actgcaattttttcctcttttaccaacccacagttagctgaaattatcattgaggtatttctaggttatat    30380
gtgcacacacaacctacttaagttctgagctcaatattctgttttattcttcctgttcagaagccagca    30450
tccatagctctgggtctcattatttgcttttgtcgtccagttgtgctctactgatttaaaagttatctt    30520
tacattttcagtttcccagtcaattcaagccaaagcatatttattgggcatctaccatgtgctatggact    30590
gtgagagacttaaagattaataacaacaaccataaaaacttcattgatatgctgggcattatttctctccc    30660
catggcctccaaatgcttggcccataattcaaaacactacagcaacttgaaggcagcagattgtttctca    30730
tttcagggatccacaggtttatgccttctcaaacaaaggtctggtaattccaggctgcatgcagctattc    30800
ttcctttaaagactgagaaaccatgcatacaacatcttttcttccttcttcgtttatacaattgataatt    30870
acatattgacatcttactttgagaaagtcgtcatactggataccgtcagtcatagaaacagagataagat    30940
tcaacctctgatcccaaggaaggcagactcttagtaaggaagtcaaaacaataaatgaaaatgcccatac    31010
tgcaaggcatgcacatcatacattccataagtgggtaaaaacatgccttggcagcacacagaatcttgcttt    31080
ccatttgtgtcattgaggacagtgcattagttatctattgctgcataaaaaattcctctaaactttaggt    31150
taaaaccgcaaacattttttttttcctcgtgcaatttcttttttttttttttttattatactttaagttta    31220
gggtacatttgcacattgtgcaggttagttacatatgtatacatgtgccatgctggtgcactgcacccac    31290
taactcctcatctagcattaggtatatctcccgatgctatccctcccccttcccccccaccaacagt    31360
ccccagagtgtgatattcccccttcctgtgtacatgtgatctcactgttcaatccccacctatgagtgaga    31430
atatgcggtgtttggtttttttgttcttgcgatagtttactgagaatgatgatttccaatttcatccatgt    31500
cgctacaaaggacatgaactcatcgttttttatgcctgcatagtattccatggtgtatatgtgccacagt    31570
ttcttaatccagtctatcattgttggacatttgggttggttccaagtctttgctattgtgaataatgcca    31640
caataaacatacctgtgcatgtgtctttatagcagcatgatttatgtccttgggtatatacccagtaa    31710
tgagatggctgggtcgaatggtatattccagttctagatccctgaggaatcaccacactgacttccacaat    31780
ggttgaactagtttacagtcccaccaacagtgtaaaagtgttcctattctccacatcctctccagcacc    31850
tgttgtttcctgactttttaatgattgccattctatctggtgtgagatgttatctcattgtggttttgat    31920
ttgcatttctctgatggccagtgatgatgagcattttttcatgtgttttttggctgcataaatgtcttct    31990
tttgagaagtgtctgttcgtgtccttcgcccacttttttgatggggttgtttgttttttttcttgtcaattt    32060
gtttgagttcattgtagattcggatattagccctttgtcagatgagtaggttgcaaaaattttctcccat    32130
tttgtaggttgcctgttcactctgatggtagtttcttggctgtgtcagaagttcttttcgtttaattagat    32200
cccatttgtcaatttggcttttgttcccattgttttcagtgttttagacatgaagtccttgagcctatg    32270
tactgaatggtatggcctaggattcttctagggtttttatggtttaggtctaacattagggtctttaa    32340
tccatcttgaattaatttttgtataaggtataaggaagggatctaatttcagcttttctacatatggctag    32410
ccagtttttcccagcaccatttattaaataggggaatcctttccccttttcttgtgtttgtcaggtttgtca    32480
aagatcagatagttgtatatatgcgccattatttctgacggctctgttctgttccattggtttatatctc    32550
tgtttttggtaccagtaccatgctgtttttggttactgtagccttgtagtatagtttgaagtcaggtagcat    32620
gatgtctgcagctttgttctttttggcttaggattgactaggcaatgcagggtctttttttggttccatatg    32690
aactttaaagtagttttttccaactctgtgaagaaagtcattggtagcttgatggggatggcattgaatc    32760
tataaaattaccttggacagtatggccattttcacgatattgattctttcctacccatgagcatggaatgtt    32830
cttccatttgtttatatcctctttatttcattgagcagtggttgtagttcttccttgaagaggtcattc    32900
acatcccttgtaagttggattcctaggtattttattctcttttgaagctattgtgaatgggagttcattca    32970
tgatttggctctctgtttgtctgttattggtataagaatgcttttgattttttgcacagtgatttgtatc    33040
ctgagacattgctgaagttgcctatgagtttaaggagattttgggctgaggatgatggcgttttctagat    33110
atacaatcatgtcatctgcaaacaggaacaatttgcttcctctttttccataatcggataccttttattttc    33180
cttctcctgcctaattgccctggccaggacttccaacactatgtcagtaggagtgatgagagagggcat    33250
cccagtcttgtgccagtttccaaagggaatgcttccagttttttgcccattcagtatgatatttggctgtgg    33320
gtttgtcatagatatctcttattattttgagataggtcccatcaacacctaattattgagagtttttag    33390
cgtgaagagttgttgaattttgtcaaaggcttttttctgcatctattgagataatcgtgtggttttgtct    33460
ttggcttttaaaactgcaaacatttattatctcatacatttctgttcttcagggattcaggagcaatgtag    33530
ctggccagttctagctcaggatctctcatcattttgtaatgaaattgtagacagggcttgcagttttatg    33600
atggtgtgagagaatctcacttatgtgtgctgggcaggaggcttcagttcttggccacattggcttctcc    33670
ctagggctatacatgagaccttaacagctggcttttctgaaagtgaggagagaaagaaggaggctaaaag    33740
ggagtctaatatgaaagccacacactcttagaacttgatcttggaggtgacaccttgtcgcttttgcact    33810
agatttggaggtgaaaccttgtaaccccagaaggtgttaattgtaggtgtcaattggccatcttggaagc    33880
```

```
tagactatcacagaagctcttccaaaggaggtagcttaggagctgcatagaattttgtcataaggacaaa      33950
ggagaaactgtgaacaaacacataggtacagcaagtgttgaggatgggctgtgttgtgttcagtgttatc      34020
ttaagggttgagcttctgtgatgaaattgaaatcagatcatttcaggtggtgcaacttgctggtaagcca      34090
tggatgttattctgtaggcaatggatgaatcatagcaggactttgcagaattattaaagaatatcagttt      34160
catgatagtagaggttgggatagaatacagaagattagtggtgcgagttgagatctacttatagattcaa      34230
ctggggtagagattgaggaaatggggaaggaatgaggctctgcagaggcattggaaggatgatactgata      34300
gaaatttgcaaaccgttagaggccaagacaagaaataaccatccaaagttgcagttataggtaaaactgt      34370
ccaattaagaaaagagaaagagttcagaggtgggtgaaggtcaagattatagatgcttttggagatcctt      34440
gggactgacggatatgttatttattattttcttggtgattataaggtaattaatagaaatttagagatta      34510
ttgtttttccatattttcttgtttggaggcatttttttttaacctgaaattggcatttccttttttacctg      34580
aaacatatccattatccagacagtttcagtgaggcacggtggccaaagtaggaggatgacttgagttcag      34650
gagttggagaccagcctgggcaacatggcaaaatgcatctctacaaaaaatataaaaattacccaggcat      34720
gacagtgtacacctgtagttccagctgtgtggtggctgagattggaggatcagttgagcctggaatgca      34790
gaggctgcagtgatcccagatcatgctattacactccagcttgggtgacagagcaagaccctgtgtcaaa      34860
acagaacaaaacaaacaacacacaaaacaaaacacaaaacacaaaacaaaaacaataaaactttcttaa      34930
ccattctaacctaattataattctaagacctatctgtgtcctgacctcaagagcaggtacaattattgaa      35000
aaacatttctttaattattcccagttctcttacacctttttttttctcacaataggcagcatcccctcag      35070
ttgtccagcttgaccactggaagggctgataccctcaggaaacacataccctgctaggagattctccatagg      35140
ccctgacttgtttattgccctgctttaggtagcttctccttcctcacattctgttctcctaattttctt      35210
ccactgcctaataattgaactgacttttctgactgtctgttcctcctgcctttgcagttattgtaactcc      35280
ataaatgccacccttgagtcacttctcttccttccttcctactgtctctcttactggcctatgtagccttt      35350
gcatctactcatggtttgatgataatttcctttggagagaccccaggggcctatacgttctgccctcact      35420
tccccctccaagtttcttcctgcccttatagctcccctttgaacaacattgcctatatgttctgcccaaaa      35490
ctcaattcagtgttcccaaaattgtctcgtcatcttcccaagcttacccggctccctgctcatagcatct      35560
cctctcagtcccttatcttgggtttgaatcccctctcttcccatcccaatgtaaatcactttcagaaa      35630
taacagttacttccatttcttcttctgtgatacatctctaatttccttggtcatatgctccctttttctg      35700
ttactattttaatcatatcctgtctatgacttgtacactctctaatctatttttaaagctattcttcatc      35770
ttcctatataattgattgtgtaagactatctcattcaaaattcatcaacaagtgtccactgtgctacacg      35840
acctgccccatctccatcgtcacaacgacagtcatcatttctttcctctggatggtatacttcatcttcc      35910
atccaacctgagtttacctaggaatcactgcatttcaccctttggtttcttgcttttttctcattctttca      35980
ggctctcttcaacttggaatactgctactattccatctccacacaatttattcattactgagggctaaaa      36050
tgctgtttcttgcacttctctcccagtttcctcgttctgcagaactaatttactgattcctctctcatca      36120
gggacagttccttccaaaatcctacaacgtgggtccatgaaatcagctagagaaaaagagggacaggat      36190
ggaggctaggattatcatgggcactgacatactggcctctgggggtaggaagactaatactccctaggaa      36260
ggaaggaaaagaaccttggagaggactgttttatctcagtatttcccagaagctccaacagtggagactt      36330
ccctgggaccttcaccccatctgctcctaatgagcttcctgcctgtggggctccactcagaacgttacat      36400
ccggtgatgcataggacaccatttgcagaaatgtgtgcatgcgtcctggcgtgtgcgtgcttcctggcgt      36470
gtgcgtgcttcctggcgtgtgcgtgcttcctggcatgtaagtgcatgtgcacatgtggcatttactgagc      36540
atgcatgcattgatgtgagaatgtatttcttcctttccacgatgaactgccacagaatggttaaagttt      36610
ttcagggctgaaaaggttgttttagcttgaatatgcacaaatatgtttttattgcagcaactatttaaaa      36680
tagctctgaaagccattattttccccattcttcttccccccaaaatttgactctttatccaattttcca      36750
ttctgtgtcttttaattggggcatttagcctgtttacatttaaggttattattgttatgtgtgatttgat      36820
cctgtcattattatgttagctggttattttgcacattagttgatacagtttcttcatgcaaccttggtc      36890
tttaccatttggtatgttttggcagtggctggtgccggttgttccttccgtatttagtccttccttcagg      36960
agctcctgtaaggcaggcctatgttgacaaaatccctcagcctttgcttgtccataaaggattttatttc      37030
tcctttgcatatgaagcttagctttgctggatatgaaattctgggttgaaaatccttttctctaaaaatg      37100
ttgaatattggcctccactctcttttgattgtagggtttctgcagaaagatccactgttagtctgatgg      37170
gcttctctttatgggtaacccgagctttctctctggctgcccttaacatcttttccttcatttcaacctttt      37240
gtgatgactattatgtatcttggggttgcttttctcgaggagtatctttgtggttcctttatatttcc      37310
tgaatgtgaatgttgacctgttttgctaggttggggagttctcctggataatatcctgaagagtgtttt      37380
ccagcttggttccattcttcctataactttcagatataccagtcaaacataggtttgctctttttacata      37450
gtcctgtctcacgtgcagaaatacacatacactcaaaataaagggatggaggactatttagcaagcaaat      37520
ggaaagaaaagaaaggagggcttttcaatcctagtctctgataaaacagactttaaccaacaaagatcaaa      37590
gaagacaaagaagggcattacataatggtaaaggatcaatgcaacaagaatagctaactgtcttaaata      37660
tatatgcgcccaacataggagcatctagattcataaagcaagttcttacacctacaaagagacctagact      37730
cccacacaataatagtgggagattttaacatcccactgtcaatattagacagatcaatgagacagaaaac      37800
aaggatatcaggacttgaactcaactctggatgaagtggacataatagacctctacagaactttccaccc      37870
taaatcaacaaaatatacattcttctcagccaccacattcacacttattctaaaatggaccatataattgga      37940
agtaaaaaactcctcagaaaatacaaaagaatgtaaatcataacaaacagcctgtcagacacacgtgtga      38010
tcaaattagactcaagattaagaaacttactcaaaactgcacaactacgtggaaactgaacaacctgctc      38080
ctgattgactactgggtaaataatgaatgaagtcagaaataaagaagttctttgaaatcactgagaaca      38150
aacacacaacatattagatctctgggacccagccaaagcagtgtttaggtggaaatttataacactaaat      38220
gcccacaggagaaaatgggagaagatctaaaaccgacacactaacatcacagttgaaagaactggaaaaa      38290
caagacaaaaattgcaaagctagcagtaaacaagaaacaactaagattgtagcagagcagaaggaaa      38360
gagatacagaaaaaccctcaaaaaatcagtgaatccaggagctggttttctgaagattaataaaatagg      38430
tggaccactagcaagactactaaagaagaaattcagaagaataaaatagacacaacaaaaaattatacat      38500
ggcgtatcaccactgatcccacagaaacacaggtaccatcagagaatactataaacatctctatggaaat      38570
aaacaaggaaatctagaagaaatggataaattcctggacacatacatcttcccaggactaaaccaggaag      38640
aagtcaaatctctgaatagaccaataacaagttctgaatttgatgctgtaattaatagcctatcaactaa      38710
aaaaagcacaggaccagaaggattcacagctgaattccaccagaggtacaaagaatagctggtaccattc      38780
cttttgaaactattcacaacaacagaaaaagagggaaccctccctaactcattttatgaggctggcatca      38850
tcctgataccacaacctggcagagacacaacagaaaaataaaatttcagacaaatatccctgatgaacat      38920
tggtgtgaaatttttcaataaaatactggcaaagagaatccagcagcacatcaaaagtttatataccac      38990
```

FIG. 11A-8

```
gattgagtcgacttcatcaatgggatggaagtctgaatcaatatatgaaaatcaataaatgctgtccatc    39060
acataaacagaaccaatgacaaaaccacacatgattatctcaatgcagaaaaggcctttgaaaaaattca    39130
atactccttcaagctaaaaatcctcaatataactaggtattaatggaacgtatctctaataagagctattt    39200
atgacaaagccatagtcaatatcatactcagtgggcaaaagctggaagcattccctttgaaaactggcac    39270
aagacaaggatgccctctgtcaccactcctattcaacatagtattggaagttctggccaggggcaatcagg    39340
caagagaaagaaatagagtatattgaagtaggaagagaggaagtcaaattgtctctgtttgcagatgaca    39410
tgaatgtatatttagtaagctccattgtctcagccccaaaattcccttaagctgataagcaactttagca    39480
aagtctcaggattcaaaatcaagctagaaaaatcacatgcattcctatacccagtaatagacaaacaga    39550
gagccatatcatgagtgaacttccattcacaattgctacaaagagaataaaatgcctaggaatacaactt    39620
aaaagggatgtgaaggacctctccaaggagagctacaaaccactgttcaaggaaataagagaggacacaa    39690
acaaatggaagaacattccatactcatggatttgaagaatcaatattgtgaaaatggcaataatgcccca    39760
agtaatttatagaatcaatgctatccccatcaagctaccatgacttcttcacagaattagaaaaaacta    39830
ccttaaatttcatatggaaccaaaaagagcttgtgtagccaagaccatcctaagcaaaaataacaaagt    39900
tggaggcatcaagctacctgacttcaaactatgctacaaggccccagtaaccaaagcatggtactggtac    39970
caaaactgtgtgtgtgtgtgtgtgtgtgtgtgtgtgtgtaaaaaatataaaatttcaatatgtaaa       40040
tatataaatacataaatatattatattatattaatgtgtaaatatataattcatatataaaaatatataaa    40110
tatataaatttgtagatatataaattctgacatttaggtttccttcttcttaggaattccaccaaaatta    40180
cacgagtaacactatactaaattttttacctactatcattaaaaaataatgacttactcaaagctctgaca    40250
ctcattagagcaggttgatatggtagaaaattctagccctatgcaactggagtgatcttgatgctaagac    40320
aaatgaccccaaaacccttgtccctttccttttggctatatgaatatttctaactttttgtgaacaaaatat    40390
gtctcatttttcctcatgatggtgttttcaaaatgaattgatgggtgttttttcagttattagtggataggag    40460
ctctcttagctcagcccttcaaaaacttgtgtttgatgttgtaattttgtaaattatctcaatgtatgcc    40530
tatatgcttacacacataatcccctacctaaaagatcaacccttagcttagaatttcttccttttatttt    40600
tttcctctatttttttttttttttttttttttttgagacagggtcttgttctgttgctcaggttggggtg    40670
taggagtacaatcatagctcactgcagctttttgagctcctgggctcaggcgatcttcccacctcacactt    40740
cagcctcccctgagagcacaggcatgtaccaccacccagttgatttaaaatctatttttttttgtacaga    40810
tgcagttcctatgttattcaggctggtctcgaacttctggcctctagtagtcctcctgcttcaacctcct    40880
cagagtacaggcatgaaccatcattcctgggccccttactattttctatatttactttttagtataagtctg    40950
tgaaagaagtatatttctcatagtttgttgaactgcgcagatgatgatgttgaaggatctgcacgatggt    41020
tatgatggttgctgtcattgcactacagtgcttttttaaaaaactgaaaatattcatttctcactagaata    41090
gtcatacaggcatttattttgttgcttttagaatttggaaactcttttttatattcatagttgtattcatt    41160
ctgccagcagattaggcagattcatcctctcccacttttccagtggtagaaacaggtgtcctgaggcagtg    41230
aagtagttgttggaaaatcactgtggtttgctttccagggatttcttgtcctctgagtgcgaaagtatc    41300
ataatacatggcacattcccacaggaagtttagggtgtgaaaagtcaatgtattaatatacatatgggat    41370
ccacttccactcaaagcaaaacacattgagtcaagtatcagagctcagtgggtgtacatgatggcattta    41440
attttcctaaattacttcatataattaatatacactaagctttgttattgatgctacacatcatttttgg    41510
agtcacaagctttcaaccttcatctaactaaaagatggatatcttcattttatattaggtggtctgggaag    41580
ccatagtagtgttaaagagcacatagggaatgttttagtccattcggattgctgtaaggaaatacaatag    41650
actgtgtggcttataaataacagacatttattgctgagttctggaggctgggaattcaagatcaaggtgt    41720
ggcagattcagtgtctggtgaggacacacatctttgtttgttgatagtgccttttccttgtatcctcatg    41790
tggtggaagggataagggagttctctgagttccctttttgtaaggggcaccagtcccattcataaggctcca    41860
acctcatgacttcatcacctcccaagggcctcacctcctgatactatcatctttgggggtcatgatttcaa    41930
catgggaatttggagtgacacaaccattcagatcatgcagagagagtgagatgagacttgccgaactcc    42000
ataaagccatatgaatattttcagttccagtcctatttccattttcaaatgttgagttatgaacttgatt    42070
gatgcctcctggtatttttcaaatgttctagagctctcatgatcaatattaaaccttttcccattcaaag    42140
gacatgattattttatgtgagtaatgtgttgctatttgacaaaggagtacaactataaataaatcttgac    42210
tatcttgatgtaggaaataaaatacacctgtcaagatatactataatgcttttgtagtcaaaacaatgatg    42280
gggctagcattgtgactcatgcttgtaatcccagcacttgggaggccgaggagggtggatgacttgagg    42350
tcaggagttcgagactagcctgtcctacatggttaaaccgcatctctactaaaaatacaaaaatcagcca    42420
ggcatgatggtgcatgcctgtaatccctgatactctggaggctgaggaaagagaatcacttcactccagg    42490
atgcagggggttacagtgagccaagacggtgtcactgcactctagctaggcaccagagtgagactcgatct    42560
caaaaacaaacaaagaaaaaatggtggataagataggatatattttaaatgaaaactgtaagggggagttg    42630
tatgctctcaaatgtcattatgcacagtctaatatgtccctttccactctgccactctacctgctaatttg    42700
cttccttaattcagacttacctattaggttattagttataatataggttgacaattatgcagcttttctt    42770
cttttaccaagacctgttccaagtgctttttatattaactcattggtgtcaaccactctaccccatagtaa    42840
ccattagtattagtttcctatctgtgctgtggtaacaagttactacagacctagtggcttcatacagttc.    42910
taccactcagaagtccaaaatgaacttaggaggctaaaatcaaggtatcatcaggacttcattattttt    42980
ggaagctctgcgagaggatacatctccctaccttttcaagattctagaaacttcctacttctcgttggctc    43050
ataggctccttctctccaccttcaatgccagtagactgagtcctgttctgtcatcttttttgtttgtccct    43120
ctttttcccttttctatgggcacagtggataacctggaatgatctcccaatttcaaggtctgctgactgg    43190
gaatcttaattccacctgcctctttcattcaaatcccttttccatgtaagaccacacaaccgcgcatatt    43260
aacacatgggcatctcaggggaccattattatgcagaccacacagttgttatcttcattttatagccaa    43330
gaaagacaaacagagttaaatcacttactcagattgttggtctgctaaatggtagagctagttaaaatta    43400
ggagcatacgcagggaagctaggcagtgttgtgatcaaggccccttggcccccctaaagtttcaatgaaaaa    43470
tcatggagataatcagtgactattactgtccactcaaccgggttgcacagagggagagagagaccaggag    43540
cctggctggctgatgataatgtcttaccctattgctagcagtgttggttcctgggttctctgcactgtgg    43610
ctttcaaaagaacagagcagctttggtgaccccacttgttgtgccataactgtagaggccaaggcttttt    43680
atcccctaaagttttactgaaaaattactgactaggcagaccaatttacaggtgaaatgacatacaaaca    43750
tgcttaatgcagatacaaaggagccttcagaatgaagacgcaacctccctgtgagatcctgaagcttata    43820
taccaacctgagtttacagaaagagtgggggcttggatcccagtaatacagatgatgggagggggagaag    43890
aggaattctgtcgaggagattactagaacggagattaacttgtaaataactctttttgaaaattaaataa    43960
tccttgaggacaaccttggaaaactgtctgttgaggtgtggtgtcatcttggtttttttctgcagtcgat    44030
aaggatataacaggaaggggttaaaaacaattattatccttgtgggagtctgtgtcttaggcaaataaag    44100
```

FIG. 11A-9

```
aaacttcagctactttgggagaggtagtgggagaggggaggttggacttcttcaactcagcctgtcaaa      44170
atgccatattttggggtattgtttctgagcctcagcaggactcatacagtattgtgggatttggggctg      44240
agccatggtgggacagattttcccctgagatccttatgcatccaaatcagtaggtgcctgttcacgttca    44310
acatgaaaaaactgacacaaagcaatgagtaggaaattgggggtaaatgtaatgaaacaaacgtgtgtt     44380
aaacaacatttctccataatattaaactaatgtgaagaatttagagtcaggaattttttctggaaagtgta  44450
ggctccaacttcctcagagtatgatttgtaggatgctcttccccattcactactccacccaacatttctg   44520
acagttatcagaagaaagagacctggtataattaatcaaactcaagacatttaggtcattgtttgcttga   44590
gattcatcaggaggtcttctaaccatgctgcaaacactttaactcatcagggcttcacagatgaatttac   44660
tgattccacaaacttgtaaattgtatttccagagccaatgtgaactctctcagttatggttttttgtcttg  44730
aagactgtgactttcatttaaaatgttgtttcaatgatgcattttctgaactcaatgaaattatgaaggg   44800
acagattttaaagtccataacgattttgttttattaaagctgccaaatattttaatatggtgtgaagag    44870
gcacaagaaaatgtaaaccctagttaccactgagacgtcccattgtttagtcatttcagcaccactgcat   44940
agacttccgtaatatgagaaagagacttaatatcctagtcatgaggagcacagggtttagggaaaaatac   45010
atacacagatatatctatatgttgatatacacacacacatatacatgcacacacactcacacatacacaa   45080
tcagtgacttcttatgatggttcaactaatgattttcaaccttatgatggtgtgaaggcaatacacattg   45150
tagatgtccacaaaatatttaaaaagctttattctgagccaaataccagtgacctaggcctgtgacacag   45220
ccccaagagatccggagaacatgtgcctaagggggttgagcactgtttatacattttgtagggagaga     45290
agttacaggcagatattcatcaattcaaggtatacatttgtttcttccaggaaggtggcacaacttgaag   45360
cagaggattcccggttatagacagattcagaggttttcaaattggctattggttgaaggagttaagttac   45430
ctaaagacctggaatcaatagaaaggagtgtctgggttaagaaaaggtgttgtggagaccaaggtcttat   45500
gcagataaagtctcatagttggccatccttagaagcaatagatgacaaaagtttcccattcagacccttg   45570
aaagatgctagatgctcatctaatcacatcaagatgagcaaaagaccagtcaagggaagtaaacctgaaa   45640
aacttgttcacacacactttatccctccttggattagatagtgtttgcctcatggttagaagatctcctga  45710
tgaatcttgagcaaacaatgccctaaatgtcttgagtttgattaattatcccaggtctctttcttctgac   45780
aattcaggtaaagagtagaatgcagctcttccttataaaaggcagctttgtgaggccatttcaaaatata   45850
tgaaagaagtatattttggggtaaaatgctttgatttcttttagggcctggtatctatcatgtgatgtta   45920
caccagagggttgaaatttggtatcttttgttatcaagtgtctgtttggtcttatgatttctgt         45990
tttaatgttaattctggtcagttgtgcccgagttccaaagagagaagtgtatagtgaggcatgtccaatc   46060
cccatatccccctcatcgccagaagaagttttcaggattagtttggaatgcccttggcagagagggttta  46130
tattcagttaactggggacttagaattttaattttggtttacagaattcactagagactctacatccagt  46200
acccatataatcattctaatttgcacttttggtacaggattcaataaattacatgagatgctcaacactt   46270
tattataaaatagactttctgttagatgcttttacccaactgtaggctaaagtaagttgtactgcacatat  46340
ttgaaatagactaggctatgttgcatgatatatttggtctatgtgataaattttttgtcttatgatatttt  46410
gaacatatcatgggttttcagatgtaatcgccattgcagttccaggaacatctgtatgtatttatgtg     46480
tgtgtgtgtatgtctgtgtgtgtttgtgtgtgtatgtgtgttcttcaactccttggacagatctcaac     46550
ctttcagaggcttcgttttcttctttgtaaaatgggaacagtggtatttctcttatggaatgtcattgtg   46620
gagtaatttagaaaagcgtagcattcaaccggaaacttcatagcatttattgcctggaaaatgatgttg    46690
atttctaggggagataagtactttcttatttatcacatttcataaaaggaaggaacctacttttcttgaa   46760
ttctaaaacacatatgtgcattgggaatgggaatgagaatacacttagcaaaatgatccctctgaagaca   46830
atggcaatgtgtttgccaaggggattaattagacgtattttgcaatactgtttatagaatggaaaacaag   46900
aaattgagaggaggtagttggaagtgtgcacttctctgcagatcagccaactggcctcagtactttaggt   46970
aagggattttaatttgtcctttggtttacaggacaacgcagacttactgctgtttatattcatcaaacac   47040
acatacctgagtagcagatctctactctcccttttaaataaggtaattctatggaacattttttgaaagcct 47110
agaaaaatgtaatacagaggtgatgtgaaagaaaattacatctattgtcctgttatcccttgactttctc   47180
tggatataaatgttttccacatttttgcaaccttttctctgcctaagctttcattttgggaaaacataac   47250
agtgtatgatttctgtgtgtttaattctaaaattgcaaagttaatcccacaccattgtggagatataact   47320
tttgagtttctgttttgaaaattgggatatggaaatttgtcaaatactgctgatatatatgttaagaga    47390
cccaggggcatgaaaacatctggatttttaaatatattgtctggtaatcatataatacatcgtcctacat   47460
tgagaggtaactgtttattaatcatagtttctcttctatattttattattatactttaggttctgggtta   47530
catgtgcagaacgtgcactttgtaataagtatacatgtgccctggtggttgctgcacccatcagtccat   47600
tacctacattaagtatttctcctaatgttatccctccctttaggccctacccattgacaggccccagtatg  47670
tgatgttccccttccctgtctccatgtattctcattgttcagctcccactaatgagtaagaacatgtgttg  47740
tttggttttctgttcttgtgatagtttgctgagaatgatggttttccagcttcatccatgtccttgcaaag  47810
gacataaactcatcctttttatgtattccatggtgtatatgtgccatattttcttaattcagtctatca    47880
ttgatggacatttgggttgtttccaagtatttgctattgtgaatagtgcctcaataaacatacgtatgca   47950
tgtgtctttattgtagaatgatttataatctttggatatatgcccagtaatgggatttctgggtcaaatg   48020
gtatttccagttctagatacttgaggaatcaccaccctcttccgcaatggttgaactaatttatactt     48090
ccaccaacagtgtaaaagtgttcttattttttccgtaatgtctccggcatctattgtttcctgactttta   48160
atgactgccattctaactggcgtgagatggtatcttatttggttttgatttgcatttctctaatgacca    48230
gtgatgatgactattatttcatatgtctgttggctacataaatgtcatcctttgataactctctgttcat   48300
atactttgaccatttttttgatggggtttctttattcttatcaatttgtttaagtgctttgtagattct    48370
ggatattagccctttgtcagatggatagatttcaaaaattctctccattctctaggttggctgttcact    48440
ttgatgatagtttcttttgctgtgcagaagctctttagtttatttacatcccatttgtcaatttgactttt  48510
tgttgccattgcttgtggggttttggacatgaagtctttgcccatgcctatgtcctgaatggtattgccc   48580
aggttttcttcaggaattttatggtcctaggtcttacatttaaatctttgatccattttgatttgattt    48650
ttgtaaagatgtaagaaagggtccagtttcagttttctgcatagctggccagtttcccaacaccatt      48720
tattaaataggagtctttccccaccacttgtgtgtgacagctttgtcaaagatcagatggttgtacct     48790
gaggcctccattcttttccattggtctatatatctgttttggtacccatacatgctgatttgtttactg    48860
tagccttgtagtatagtttgaagtcagttagcatgatgcctctatctttgttcttcttgctcaggattgt   48930
ctggacaatctgccccttttttggttccatatgaagtttaaagtacctttttccaagtctgtgaaaaag    49000
acagtggtagcttgatggggatagcatttaagaaattactttgggcagtttgaccattttcaatatattg   49070
attcttcctatccttttagcatggaatgcttttccattttgtttctgtcctctcttatttccttgaacagtg 49140
gtttatagttatcttgaagaggtccttcacatcccctggaagttgtattcctaggtattttattctctt    49210
```

FIG. 11A-10

```
tttcacaattgtgaatgggagttcactcatgatttggctctctgtttttctgttatcggtgtataggaat    49280
agttgtgattttttgcacaggatttttgtatcctgagactttgctgaagttgcttattagcttagggaggtt  49350
ttgagctgagacgatgtggttttctaaataaacaatcatgtctgtgcaaacagagacaatctgactccct   49420
cttttcaaagttgaatactcttttattctcttctcttgcctgattgccctggccagaatttccaatactat  49490
gttgaacagaagtggtgagagagggcatccttctcttgtgacggttttcaaagggaatgcttccagcttt   49560
tgcccttcagtatgatattggctgcaggttttttcataagtagctttaattatttagagatatgtttcatc  49630
tttacttagtttattgagagttttttagcatgaagtatgttgacttttttgaagcctttttctgcatctat  49700
tgagataatctcatggtttttgtcattggctctgtttatgtgatggattatgttattgatttccatatgt   49770
tgaattagccttgcatcccagggatgaaaccatctcaatcgtattggataagcttttttgatgtgctgctg  49840
gattctgtttaccagtatttttattgaggagtttcacattgatgttcatcagggatattggtctgaaagtt  49910
tatttgtctgaagtgtctgtgccaggttttggtatcaagatgatgctggcctcataaaatgagttaggga   49980
ggattccttcttttttctgctgtttggaatagtttccaaaggaatggcaccagctctctttgtacctctg   50050
gtagaactgggctgtgaatatgcctggtcctttttttatttgttggtaggctatttattactgcctcagtt  50120
tcagaacttgttattggtctattcagggattcaacttcttcctggcttagactttggagggtatatgtgt   50190
ccaggaatttattcatttcttatagaattactagtttatttgcatagaggtgcttataatattctctgat   50260
ggtagtttgtatttctgtgggattactggtgatatccctatgtcatattttattgagtctgtttgattc    50330
ttctctcttttcttcttattaatctctggctattggtctatctattttgttgatcttttcaaaaaaaccag  50400
ctactggattcattaatctttttgaaggattttttcatgtctcgatctccttcagttctgctctcatagcag 50470
ttatttcatgtcttctgctagctttggaatttgtttgctcttgcttctctagttgttttaattttgatga   50540
tagggtgtcagttttatatcttttctgctttctcttctggacattaagtgctataaatttccctgtgaac   50610
actgctttaaatgtaccccaaacattctggtacgttatgtcttgtttctcattggttttccaagaacatct  50680
ttatttctgccttcatttctcgagagggggggccgaagccagggagctaagtggtctggatcggtgggtcc  50750
caacctgatagagcccaggaaactaagattcactagcttgaaattcttgctgccagaacagcagcaatct   50820
gagatccacctgggacagtggagcttagttggggagaggagtccaccattgcttgagtaggtggttttat   50890
ggccacagtataaacaaagctgccaggaagttcaaacttggtgaaccactgcaactcagcaagttggc    50960
tgtgcccagacttccagatttctctgctctggacagggcatctctgtaaaaaggcagtagccccagtcag   51030
gggctatagccaacttaaatgtccctgtctgaaggctctgaagacagcagccaacctcccagcatggtg   51100
ttcaagctgtgctagggtcagtctgcttcctcaagtgggtatactgactgaaagacacctcccagttggg   51170
gccaagagacacctcatacaggagagctctgcagcgcatctggcaggttccctgctgggtcaaagcttcc  51240
agaggaaagaacaagcagcaatctttgctgctttgcaggctctgctgatgacacccaggcaatcagggtc  51310
aggagtggacctccagcaaactctagcatactgacagcagagcagcctgactgttagaaggaaaagaaac  51380
aagcagaaaggattagcatatccactcaaagacccatccaaaggtcaccaacgtcaaagaccaatggta   51450
gataaatccacaaagatggggaaaaaccagcacaaaaaggctgaaaattccaaaaaccaggatgcctctc  51520
ctcctccagaggatcacaactcctcaccagcaagggaacaaaactggatggataatgagtttgatgaact  51590
gacagaagtagggttcagaaggcgggtaataacaaacaactctaagctaaaggagcatattctagtccaa  51660
tgccaggaagctaagaaccttgaaaaaaggtgagtctaattgttaactagaataaccagcttgagaagaa  51730
cataaacgacatgatggagctgaaaaacacagcacgagacatttcgtgaagcatacacaaaatatcaattgc 51800
tgaattgatcaagcagaagaaagaatatcagtgattgaagatcatcttaatgaaataaagagagaagaca  51870
agattagagaaaaaaggataaaaaggaatgaccaaagccttccagaaatatgggactttgtgaaaagacc  51940
aaatctatgcttgattggtgtacctgataatgacagggagaatagaaccaagctggaaaacacccttcaa  52010
atattatccagtagaacttccccaatctagcaagatagtccaagattcctattcaggaaatacagagaac  52080
accacaaagatactccttgagaagagcaaccccaagacacatttgtcatcagattcaccaaggttgaaatg  52150
aaggaaaaaatgttaagggcagccagagagaaaggtcgggttacttataaagggaagcccatcagactaa  52220
cagcagatctctctgcagaaaaccctacaagccagaagagagtggggggggtaaatattcaacattcttaaa 52290
ggaaagaattttcaacccagaatttcatatccagccaaattaatcttcttaagcaaaggagaaataaat   52360
ccttttacagacaagcataggctgagggattttgtgactaccagacctgccttacaagagtgcctgaagga 52430
aggacaaataaggaaagcagcaaccagtaccagcctactgcaaaaacatgccaaattctaaagaccattga 52500
cactataaagaaactgcatcaattaatgggcataataaccagctaaaatcataatgataggatcaaattc  52570
acacataacaatattaaccttaaatgtaaatgggctaaatgtcctaattaaaagacacagactggcaaat  52640
tggataaagagtcaggacccatcagtgtgctatattcaggaaacccatctcacgtgcaaagacacacata  52710
ggctcaaaatgaagggatggaggaagatctaccaagcaaatggaaaacaaaaaaaggcaggggttgctat  52780
cctagtctctgataaaacagactttaaaccaacaaagatcaaaagagacaaaggaaggcattacataatg  52850
gtaaagggatctatgcagcaagaagcactgactatcctacatagatatgcatccaatacaggagcatcca  52920
gattcataaagtaagttcttagagaccgacaaagagacttgcactcccacacaataatagtgggagactt  52990
taacagcccagtgtcaatattagacagatcaatgagacagaaattaacaaggatattcaggacttaact   53060
cagctctggaccaagtggatctaatagacatctacagagctctccaccccaaatcaacagaatatacatt  53130
cttctcagcaccacatcacacttattctataatgaccacagcgcaagtaaaacactccttagcaaa      53200
tgctctccatcccaaatcaacagaatatacattcttctcagcaccacatcacacttattctataatggac  53270
tacagaactgcaagtaaaacactcctcagcaaatgcagaagaacagaaattagagcaaacagtctaccag  53340
accactgtgcaatcaaattagaactcaggattaagaaactcactcaaaaccacacaaatacctggaaact  53410
gaacaacccgctcctgaatgtcttctataattttgaaagccagcttcatatttcctgccctagggggatg  53480
aagtaaagtaagcagtagatctagttagatatatgttgttatttttgtttgcaagggtttaatttgaatttt 53550
gccattttataacaactgattgtggctgggaacatgctaatggttatggtgactgtattcactctttctt  53620
tgctttgaattttttttttttttttttttttttgggagatggagtttgctcttgctgcccaggctgga    53690
gtgcaatggcacaatcttggcttactgcaaccactgcctccgggttcaagcaattcttctgcctcagcct  53760
cccccagtagctgggattataggcatgtaccaccacgcctggcaaattttttgtatttttagtagagag   53830
gtttctccatgttgagcctggtctcgaactcctgacctcaggtgatccacccttgcctcccccaaagt   53900
gctcggattacaagtgtgagccaccacgcccagattttttttttttttttttattgtaacagggtctcat  53970
tctgtcacccagactgaagtgcagttgtgccatctcagctcactgcagctttgaccttctgtgctcaagc  54040
aatcctcccacctcagcctcctgagtagctggaactacaggtatacaagtgtgtgccaccatgcttggct  54110
aatttttttattttttttgtagagatggggttttgccatgttactcagcctagtctggaaatcctgggctt 54180
gagcaatctgcccaccttagccttcccaagtgctggaaatacaagtgtgagccactgtgctcagcttga   54250
tttgaatttgagggatagtatagttctgtgttactacacctagtagaatattagcatattcagtgacttt  54320
```

FIG. 11A-11

```
aattagaccttagtgtaatccccagtaacaatctgttgccttggatgttctgttttctttcttttttttt     54390
ttaaattatactttaagttttagggtacatgtgcactacgtgcaggtttgttacatacgtatacatgc        54460
catgctggtgtgctacacccgttaactcgtcacttaacattagctatatctcctaatgctatccctcccc      54530
actccctccaccccacaacaggtcccagtgagtgatgttccccttcatgtgtccatgttctcattgtt       54600
caattcccacctatgagtgagaggatgttctgttttctaaaggtatatacgagattcttgtattcttttc     54670
atattagagacccctggccagagtaggagctgtagaggccacagtgagcccttcaggagaatgagataca     54740
gcagagtcactgcttgtgttcttgagatgattggatgacaaagagggaaatgataatgttaactgaggaa     54810
agtctagaactgcaggttaccatatgtatcccatattttaaccctcacctgttgttccattgtattttc     54880
tatgtaagttttttacttgcagtcctatttctttcttatttaaaaatcatgttaatcattggtattagtag    54950
catctttgccagataaaaaggaaaaactaaagtgaatgctttatgacgatatgtgggaggaaagaatgta    55020
atagcacttgaggaatattggaactgattatatattacatggcagtgggtagtgtttaataaaatgatta     55090
tattcatagaaagcattacatcttctttgagtgagaaacatagagataatttcatgctaccctcaccct      55160
ttcttttaaacatatatatattttttttaaatttaagttagaatttgagtaattgtattaccatatatat     55230
atttttttaaatttaagttagaatttgagtaattgtattacatgtggtgctgttttctcagaggaaaaat    55300
cagcaaattatttcaaagatatggaggatatgtgtgtttctctatatccaggtgggactgaacaatgtatt   55370
agccaaggaaaaccttcccttttcacccactgtggaggctcactgaaaatcatgtcacaaaaagcagattaat 55440
agtagaaaagcgatacatatttattaagtcatagatctgtgtaacacaagagccttcagaacgaagacgc    55510
aaagataagatggagaccattttttttttcttaatttcaactttttattttaaattcagaggatacagcctt 55580
gctacatgagaatatttcatggtgctgatgtataaggtactgttgatcccaatcaatagtggtaagcata     55650
gtggccactagctagcttttcaacccatacctgcttctccccagtctagtagtccctgtgcctattgt      55720
tcccatctttctttccagatttactcaagctcccacttgtaactgagaacatacagtatttaatttcctg   55790
tatcctgtgttaattcatttagtatggtggcctccagcagtattcatgtttctgcaaaggacctgatttt   55860
gttcgtttttcatggttgcatagtattccacagtgcatgtataccacatttttcttttattccaccactgata 55930
agcatccaggttgactcatgcctgttttgtcattgtgaatattactgcagtgaacatacaactgcatgt     56000
gtcttttttgtagaaaaatttattttcctctaggtatacacccagtaatgggattgctgggccaaatggt    56070
agttttgttctaagtcctttgagaaatctccaaactactctccatagtagcgtaaatatttacgttctc    56140
accaggagtatataagcattcctttttctctgcaacctcactagcttttgttgggttttttttttttg     56210
tttttgacttttttaatagtagccattctgactggtgtgagatgtatctcattgtggttttgatttacat    56280
ttccctaatgaacagtaatgtggagcatttttcatatgtttattgatacttatatgttgagaagtatatg    56350
tccatgttcttggcacacccttttaatgtggttattcggaaactcaattttatgccaagattcaggaaac    56420
tgcacagccagtagaaataagattggacaaaaaggccctgatctaaagctaatgggctgagtggggaaac    56490
ccagccaggcctgtctgcctagattcttcttggccttctgaacagcacttccttcctctcggatgtggg    56560
ataggaccctctctggaatagggtcttaggacctacaattcacactgttaggacagaagatttctttat    56630
ggccagtgtttaagaaagtcagggggaaagttaaggtcatcttttatggctgctttgatagaagcggt     56700
ctggtttgtatgacctgcctttaggaggagaggtctagtttctttggccagcctctagggagaatggaa    56770
ttgagagacagcaggtcaggaaagggtcagagataaaccttctgcctctgaggctgttgaagtcttcatt   56840
ttgtggtatcattctctgaaccccaacaacacacattgttttaacttcataacaaaacacttagatcagtt 56910
gggtccaaacatgggtttatacactgtgtggcaaaagtatggtccttccctctactccaaagggaacaaa   56980
tgaaatttattatttatttatttatttattttttattatactttaagttttagggtacatgtgcaca       57050
acgtgcaggtttggtacatatgcatacatgtgctatgttagtgtactgcacccatttactcttcatttaa    57120
cattaggtatatctcctagtgctattcctatcccctcccccacccccacaacaggcccccagtgtgtgatg  57190
ttccccttcctgtgtccatgtgttctcattgttcagttcccacctgtgagtgagaacatgcggtggttttgg 57260
ttttttgtccttgagatagtttgctgagaatctaacggttctgccagcttcatccatgtctctacaaaggac 57330
atgaactcatcatttttttatggctgcatagtattcagggggtgtatatgcgccacattttcttaatccagt 57400
ctatcattgttggacatttgggttggttccaagtcttttgctattgtgaatagtgcagcaataaacacacg   57470
tgttcatgtgtctttatagcagcatgttttataatcctctgggtttatacccagtaatgggatggctggg   57540
tcaaatgttatttctagttctagatccctgaggaatcaccacactgacttccacaatggttgaactagtt   57610
tatagtaccaccaacagtgcaaaagtgttcctatttctgcacatcctctccagcatctgttgtttctgac    57680
ttttttaatattcgccattctaattgttgtgagatggtatctcattgtggttttgatttgcatttctctga  57750
tggccagtgatgatgagcatttttttcacgtttctgttggtggcataaatatcttcttttgagaagtgtct  57820
gttcatattctttgcctactttctgatgggggtgtttgttttcttcttgtaaatttgtttgagttcattg    57890
tagtatctggatattagcccctttgttagatgaggtagattgcaaaaattttctccccattttgtaggttgcc 57960
tgttcactctgatggtaatttctttggctgtgcagaagttctttagtttaattagatcccatttgtcaat    58030
tttggctattgttccattgttttcagtgttttagacatgaagtccttgctcttgcctatgtactgaatg     58100
gtatggcctaggatttcttctagggttttttatggttttaggtctaacatttaggtcttaatccatcttg .  58170
aattaattttttgtataaggtataaggaagggatctaatttcagctttctacatatggctagccagttttc .  58240
ccagcaccatttattaaataggggaatccttttccctttttctttgtgtttttgtcaggttttgtcaaagatcaga 58310
tagttgctatatatgcgacatttatttctgacggtctctgttctgttccattggttttatatctctgttttggt  58380
accagtaccatgctgttttggttactgtagccttgtagtatagtttgaagtcaggtagcatgatgtctgc     58450
agctttgttcttttggcttaggattgactaggcaatgcagggtctttttggttccacatgaactttaaa     58520
gtagttttttccaactctgtgaagaaagtcattgatagcttgatggggatggcattgaatctataaatta    58590
ccctggacagtatggccattttcacgatatgtgattcttccttgcccatgagcatggaacatgttcttccattt 58660
gtttatatcctctttttatttcattgagcagtggtttgtagttctccttgaagaggtcattcacatcccctt  58730
gtaagttggattcctaggtatttttattctctttgaagctattgtgaatgggagttcattcatgatttggc   58800
tctctgtttgtctgttattggtataagaatgcttttgattttgcagtgattttgtatcctgagacat      58870
tgctgaagttgcctatgagtttaaggagattttgggctgaggatgatggcgttttctagatatacaatca    58940
tgtcaatctgcaaacaggaacaattaacttcctcttttcctaataccctttatttccttctcctg         59010
cctgattgccctggccagaacttccaacactatgtttgaataggagtggtgagagagggcatctttgtctt   59080
gtgccagttttcaaagggaatgcttccagttttttgcccattcagtatgatattggctgtgggtttgtcat   59150
agatagctcttatcattttgagatatgtcccaccaataccgaatttattgagagtttttagcatgaaagt    59220
tgttgagttttgtcaaaggcctttttctgcatctattgagataatcatatgatttttgtcattggttctct   59290
ttatatgctgtattaggttttttttgatttgtgcatgttgaatcagccttgcatcccagggatgaagcccac  59360
ttgatcatggtggataaattttttgatgtgctgctagattcagtttgccagtattttattgaggattttttg  59430
```

FIG. 11A-12

```
cctaggtgttcatcaaggatgttggtctaaaattctcttttttgttgtgactctgccaggctttgttgt      59500
caggatgatgctggcctcataaaatgagttagggaggatttcctcttttctattgattgcattagtttc      59570
agaagcaatggtaacaggtcctccttgtacctgtggtagaattcggctgtgaatccatctggtcctggac     59640
ttttttttgcttggtaagctattaataattgccgcaattgcagagcctgttattggtctattcagagattc    59710
aacttctttctggtttagtcttgggaggttgtatgtgtctaggaatttatccatttcttctagattttct     59780
aatttatttgcgtagagttgtttatggtattctctgatggtagtttgtatttctgtgggatcggtggtga     59850
tatccccttttatcattttcattgcaactattttgattcttctctcttttcttctttattagtcttgctaa    59920
cggtctgtcagttttgttgatcttttcaaaaaacgagctcctggattcattgatttttttgaagggttttt    59990
tgtgtctctatttccttcagttctgctctgatcttagttattcttgccttctgccagcttttgaatgtg     60060
tttgctcttgcttttgtagttcttttaattgtgatgttagggtgtcaattttagattttttcctgctttct    60130
cttgtgggcatttagtgctataaatttccctctacacactgctttgaatgtgtcccagagattctggtag     60200
gtagtgtctttgttctcattggtttcaaagaacatctttatttctgccttcatttccttatgtacccagt     60270
agccattcaggggcaggttgttcagtttccatggagttgagcagctttgagtgagtttcttaatcctgag     60340
ttatattttgattgcactgtggtctgagagacagtttgttatgatttctattctttcacatttttttgagg    60410
agtgctttacttccaactatgtggtcaattttggaataggtgtggtgtggtgctgaaaataatgtatatt     60480
ctgttgatttgggttggagagttctgtagatatctattaggtccacttggtacagaggtgtgttcagttc    60550
ctggatatcctgtttagtttctgtgtggctgatctgtgtaatgttgacagtgggtgttaaactctctca     60620
ttattattgtgtgggagtgtaagtctctgtaggtctctaaggacttgcttatgaatctgggtgccctg      60690
tattgggtgcatatgtatttaggatagttagctctcttcttgttgaattgaccccctttaccattatgtaatg 60760
gccttcttcgtctcttttgattgtgttggtttaaagtctgtttatcagagactaggattgcaaccctg      60830
gctttttttgttttccatttgcttggtagatcttcctccttcctttgttttgagcctatctgtgtctgt    60900
gcacatgagctgggttcctgaatacagcacactgataggtcttgactgtttatctaatttgccagtctg     60970
tgtcttttaattggagcatttggcccatttacatttaagattagccttgttatgtatgaatttgatcctg    61040
tcattatgttagctggttattttgctcattagttgatgcagtttcttcgtatccttgacggtcttacaa     61110
tttggcatgttttttgcagtggctggtaccagttgttcctttccatgtttagtgcttccttcaaaagctct   61180
tgtagggcaggcctggtggtgacaaaatctctcagcatttgcttgtctataaaggttttatttcccttc     61250
acttgtgaagcttagtttggctggatatgaaattctgagttgaaaattcttttctttaaggatgttgaat    61320
attggcccccactctctcctggcttgtagggttttctgtcaagagatcagctgttagtctgatgggcttcc   61390
ctttgtgggtaacccaacctttctctctgggctgccctttaacatttttctttcatttcaaccttggtgaat  61460
ctgaaaattatgtgtcttggagttgctcttcttggggagtatctttgtggcgttctctgtatttcctgaa    61530
tttgaatattggcctgccttgctagattggggaacttctcctggataatatcctgcagagtgttttccca    61600
cttggttccattctccccgtcacttccaagtacatcaatcagatgtagatttggtcttttcacatagttc    61670
catatttcttggaggcttttctctttttctttattctttttctctaaacttctctcttctgacttcattg    61740
cattcatttgatcttccatcactgatacccctttcttccagttgatcacatcggctactgagcttatgca    61810
tttgtcatgtagttcttgtactgtggttttcagctccatcagctcctttaaggacttctctgcattggtt    61880
attcttgtatccattcgtctatttttttttcaaggttttaacttctttgccatgggttcaaactttctc     61950
ctttagctcagagtagtttgattgtctgtagccttcttctctcaatttgtcaaagtcattctccatccag    62020
ctttgttccattgctggtgatgtgctgcattccttcagaggaggagaggcactctgatttttagagtttc    62090
ctgttttttctgttcggtttttttccccatcttgtggtttttatctaccttcggtcttttgatgatggtgac  62160
atacagatgggttttggtgtggatgtcctttctgtttgttagttttccttctaacaatcaggaccctca    62230
gtagcaggcctgttggaatttgctggaggtccactccagaccctgtttgcctgagtatcagcagtggagg    62300
ctgcacaacagtggatattggtgaacagcaaatgttgctgcctgattgttcccctggaagttttgtctca    62370
gaagagtacccagctatgtgaggtgtcagtctgcccctactagggtgtcctcccagataggctactcgg     62440
gggtcagggacctacttaagaaggcagtctatccattctcagatgttccagctgggtgctgggagaaccac   62510
tactctcttccaagctgtcagacagggatatttaagtctgcagagttttgtgctgccttttgtttggcta    62580
tgcccttcccccaggggtggagtctgcagagacaggcaggcctcttgaagtgtggtgggcccacccag      62650
ttcgagcttttggctgctttgtttacctactcaagcctgagaaagcgtgggtacccctcccccagcctc     62720
actgccaccttgtagtttgatctcagactgctgtgctagcaatgagtgaggactttgtgggtgtaggacc    62790
ctccgagccaggcgcaggatataatcttctggtgtgctgtttgctaagaccattggaaatgcacagtatt    62860
agggtgggagtgacctgattttccaggtgcggtctgtcatccctttctttgactaggaagggagttccc     62930
tgaccccttgcacttccaggtgaggcgatgcctcaccctgctttggctcatgctcggtgtgctgcaccc     63000
actttctgacactcccagtgagatgaaccccgtacctcagttggaaatgcagtaatcacccatgttctg     63070
catcgctatgctggaagctgtggactggactgtgttccattcggccatcttgctctgccaccccccatgaa   63140
gtttattttggagaaagttaactcagaacagaaggacctaggggatatcagagagttgagatggggcaagg   63210
gcctgggctccctgtctgtcctgacaaagttagaacagaaggacccagagacatcagagagtggagtgag    63280
ggtgagggcctaggctccttgtttgtaagggaattgtctacactgtgcatactaatgatcatcagctttc    63350
ttgtcctcccttcaaagttgaaagtcaccgtactccttcaagtccatcctggaggatcccctttcttcata   63420
aactgaactggccaagaaaagtattccataattggtatttaaaggccatttgggcctattacttatgtac    63490
tgtacaatatgttcacctgctgaggagggaaccctggctatccacacagacctgattcttaagtgagaaa    63560
agacagtcttaaatcctagatattcttgagaaggcttcaataagaaactcattttaaaaattgaaaaaat    63630
aatcatctgcgaggtagcacacacaccaaccaaggaaacagggacaaaattaatcctgtaacctgtaggaaa   63700
tacactgaagtagtgactcataaaaaaatggggaattctattaaaatgtaacatattacacaaattaaagt   63770
atcctattggagagagaatgtgaggagatctccaatggataaaacttcagttagagagtgatagcaaa     63840
gggaaaggaacaaatatggagactctaggaatctgacattcaaagagtattttcaggaaggatgacagag    63910
aatacaaataagcaaaagtgacttacattcaaatagtgtttaaaaagtaatcccagcgttattgtgtaac    63980
agtgctgaaataaatgtatctgtacatgtgtcttcatagttgaatgatttataatccttttttgtatatac   64050
ccagtaatgggattgctggatcaaatggtatgtctcattctaggtccttgaggaatcaccacgttgtgtt    64120
ccacaacagttgaactaatttatactcccaccagcagtgtaaaagcattcccatttctccacatcctctc    64190
tagcatctgttgtttcctgacattttaatgatcgccattctaactggcatgagattgtatctcattgtgg   64260
ttttgatttgcatttatctaatacaccatgaaatatatgcagccatgaaaaaggatgagttcgtgtcctt    64330
tgcagggacatagatgaagctggaaaccatcattctcagcaaactaatacaagaacagaaaccaaacac     64400
cacatgttcttactcatgagtaggagttgaacaatgagaacacatggacacagggaggggaacatcacac    64470
accagggcctgtcatgtggtgggagtagggggagatagtattaggagaaatacctagtgttgatgac      64540
```

```
gcgttgatgggtgcagcaagccaccataccatatgtatacatatgtaacaatcctgcacattctgcccat      64610
gtacccagaacttaaaatgataataataattgccatcatcatcatcatcatcccagcatt              64680
gagggatctacacttccaggcttaggaaacaacatcaggggttcatcacagtgaaagaattgaaactccaa   64750
actccaaaagcacattgtgagatttcagaagagcaaatatgtgggaaagaccataagagcttgaaggctg   64820
tattagtccattcttgtactgacacaaatacccgagattggataatttataaagaaaagaggtttaattg   64890
gctcatggttttttaaactgcacaggaagcatgatagcgtctgtggtggcctcaggaatgtttcaatcat   64960
ggcagaaagtgaaagcaaagcaggttcatcttatgtggctagagcaagaagaggagagagacagaacatg   65030
ctacaaaattttatacaaccagatctcctgagaattcacttactatacagtaccaaggggatatacagt   65100
atcattctagagaactctgccctccatgatgccatcacctcccgccaggcaccatctccaacactgggga   65170
ttagaattcaatatgagatttgggtgaggatacagatgcaaaccgtctcaagaatttgtaatttcataga   65240
atgcttcatgttttcaccaaatgttaaaaatatagaaacttctcattattctaagaaaaaataattttacc   65310
acatagaactcttatcttggagcagctctttgtgggcaggcagagtcaaagcatttacgctgatgttatca   65380
tttcaaaaaatttacctttcatgcttcccttcttggaaagatgtgtgatcgtgtgttccttcaaacagtg   65450
gaataaatgatgaatacaaagatggagaatctaagaaacagtggccttcacagaagcagctgaagtaat    65520
taagacatcagattattgcctggagcaggctgggacatctgacatcctagagttaaactttgaggagaat   65590
gaacataaaagaaaaggaagtaagccattttgaccaggtagaaatagtactcgagatgggctttagtccag   65660
aaaaattgaacaatatacacacagacaagcatgaaatgaaaacctgaagcagttattgtctccagataaa   65730
acaggaggtgattcaatgaaggagatttaattggggtagaaggcttagttcaggagtgattagttcagga   65800
gtaattgcacagttacagtaaagttgaagagagaaggctgggtacagtggatcatacctgtagtcccagc   65870
actttgggcggccaagacaggcagatctcttagcccaagacttggagaccagcccgggcaatatggcaa    65940
aaccccatctctacagaaaaaaaaaatgaaaaaattagccagtatggtgcacttgcctgttgtcctagtt   66010
atggcagagtctgaggtgggaggatgttttgaacctgggaagtcggggttgcagtgagttgtgattgtac   66080
cattgcactgcagcctgggcaacagagcaagaccctgtctctaaaaacaacaacaaacaaacaaacaaac   66150
acggggcaaatagagtgggggttgcccataggtaattaataggtaatatctaaaaacaatatatcaagaa   66220
aaaatagcatgaactatttcttagtaatatcaagaagatatttgaaggagagaagctaagaaatctgaaa   66290
gcatttgccttctagcaagtgtggtcctgggatgtcgtatgctgtcaagaaagtgctgttgtgcaaata    66360
acacctgtagtagttcgacttttaaaaattcatgcatgcgggaccatcctggctaacacggtgaaaccca   66430
tctctactaaaaatacaaaaaattagctgggcatggtggcaggagtctgtagtccctgctactcaggagg   66500
ctgaggcaggagaatggcgtgaacctgggaggtggagcttacagtaagcagagatcgcgccactgccctc   66570
cagcctgggtgacagagggagactccatcacaaaaaaaaacaaaaaacaaaaaacaaaaaaacaaagaaa   66640
aaaaccaaaaaaaaaaaaaaaaaaaaaaaaaaacacctcacgcatgcctttctttgtttccaaagaaa    66710
caagtagttttatactacttacatattatggtagaatgatttataatcttttggctatatactcagtaat   66780
gggattacttggtcaaatggtatttctactattcttttgtttccaaagaaaggcatggtatggaaatggtt   66850
tccaacagttggagaaacaaatttttttttccaaaagaaaatgataaggccaagattgaatggtatgtga   66920
atgtgaatatgatagttaaaagcattatttctcaaatgtaccttcccattggaatcagctggagaatgta   66990
ataagtattaatgcctgtgctatggtcctccagagatactgacttgcttggtctgcaatgcagaccgggc   67060
agtgagattttttcagttcttcttagggattgtgagatacagcaggttttaggaagcatggatctaggt    67130
ttgctcagattcttactttcatttaaaaatctgtatctgggcacaatgggtcataccctgcaatcccagaa   67200
cattgtactgggtggaggtggcaggatcatttgtatccaagagctccagacaagcctgggcaacatagtg   67270
aaacccatctgtatggaaaaaaaaaaaaaaaaaaaaaaaaaagaaaagaaaaaaattagccaagtgt     67340
aatagttcatgcctatgttctcagctattcaggaggctaaggtaggaggatcacttgagccttggaggtc   67410
atggctgcagtcagctgagatcacaccaccacactctagcctgtacaacagagtgacccctgtctcaa    67480
caaacaaacaaaaattacgcagtgtactcttcaacaagataaagtggtttcagtaataaactactaataa   67550
tatgatgatttagattgagcaaacttcacttagtcatttcttttttattatctgatatgttctttataaa   67620
aagttttaattgcttaaaaatgacctaatgcttctcccaagcttcctttttttttttctctctctcttaac   67690
tgaagtcacagaatgttctccttgtgtggagtgctaaacaacattaagaaattattagctttaaggacatt   67760
ctaagagtaaggttataaacctaaaaccccctaaaaggtaaaagaaaattgaagaggcagtacaaagactg   67830
tcctctctctcaaagggtcccttctcatgggaaataggctgctattccaggtcagtggaggtgatcctatgg   67900
gaagcccattgtgtatggcccatggcaccattccagctaattgttccaattcctcctgtttctctgact    67970
gcacatgaggttaaattaaatataattttctcagtttgcatttcccaggcagtcatcctaagtggcttct   68040
tgaaggcggtctgtgcattccgctatctaattctgtgatgtcctttaactcgagggccagtgacatgatt   68110
atcagctctagaagttcattctgtggtcagagatgcttgtgcagtggccattttcttttcattatgatctg   68180
gcctttcccaagcttcagaagtgaagagaattgacttcctactaatgagcattggcacttaggaagtga   68250
atactttatctttgcagctagtgtgttctacattcttcagtgtacctcctgcctggtaaatatcagat    68320
tatttgttgaccatctctcagggtatagttctttgtgttattaaatgagaacctagtggcttacaaagca   68390
ttggcttttgaggagccacttttatcctagatgataactcaaatccatacagtgctgatatttacagctg   68460
ggagatgacattgtcttatctttgggtctattgctcaaatttctgatttcagcaggacttactcactggc   68530
tgccttctgtcttggggatgccttttgatctgtcttgccttgggggaccctccctctgacctggattagca   68600
gcctatttccacaagaatggaccctctgagagaggacagtcttcgtactggctcttccgatttcctttta   68670
tctgttatgggttttgggtttataaatttactcttagaatgtccttaaagctaataattttttaacgttc   68740
tttagcatattactaaaagctattcatctgcttgagagactgaggaaggagtgttgcttgagcctgaaag   68810
attgaggctgcagtgagctgtgatcctgccactgcactccagtctgggtgacagagaaagaccttgtctc   68880
aaaaaaataaaaggacaggtacaataggtcatgcagtgactttgaggggctgaggcagga             68950
ggattgctttaggccagagttctagaccagcctgcaacataggggagatccatctcttcaaaacataaaaa   69020
attaattagacatgatggcacatgcctgtagtcccagcttcttgaggggttgagaccagcaggaggatttc   69090
ctagggcctaggagttccaggatgcaatgagcaatacttatgtggttaatacatattgaaaccagttgtt   69160
ggagaattagtatgtgttctcccacaaattcagtatgtttttgtaatggtccaactaattcaaatggtat   69230
aaacataatataaacaaattatttttatgttgtttttaaaaaacctttttgactgaatcagtctatgacg   69300
ctttagtatttgaagttgtgggcagaacttagtcttaagatagcactcacccttggtgatagatttccatg   69370
gagggaattttgccagatgttaatttagcctgaagatgttatagatgtggacagtcacgccctctaagt    69440
ctggggtgggctaattgaaaagaacatgcaggaaccaggcttgttaagggataaacataggggaaatgga   69510
acaattatggcagagattgaattgggtttaattgggttaggaagagtgaaagaatagattttaataagag   69580
gtctggaaatagccaagaaacccacttattgtagaaaatgtgtgacatctgattaccgtagtgaaagaaa   69650
```

FIG. 11A-14

```
gatcccccttcaaaaatcctatctatacagaaagaagtggtaggtaaaaggaaatcttcccatggatgta      69720
tttaagaaaaacagtggggaggtctgagatttcaaagggccatggttcagattataattcaaaagagagg      69790
caagtgatagttcccctcttcttgggtttcaggaaggggggaagatttggccacttgtgaaataatttttgg    69860
agcttctataaccttgagcctttcttcttattttttcctggacttgagacataaggggattgataagatg     69930
ggaccagagaaaaagcaggttttgaaatgcctttttgattctgttcatttctggaattcttcatcatgg      70000
tccttaaagagtacatatttgttcctgatacacaacatgcagtggtctattaatgaagcttttatttcctc    70070
agctaggttgcctcctccattaatttgtgggattttagatgaaaacttacttgaactgtggttttctctg     70140
tgtttgtgaatggaaggacatgtttgtctttgaccttcctttagtttcacatcttagtcttaatatttaa     70210
gtagctttgtttcagacagagaaggaccatgcgttcagttgctggactgctctctaggttagaggcttt      70280
ctggtcttggggaagattccccacaaactaagcaagtggcatagatgcttaatattctaagtgagagaag     70350
cactagagtttttttattcattacttgtgagcgcagatgtggcctctggggaagctcagctgaggtggtct    70420
catgttccaccaaaggtcaccagagagagatggccagggagagaactgtctcacctggagggt           70490
atggcaacagctatgcaagacctcttgttggagatatgtgacattcattcatttatttattttttgaaac     70560
atagtttcattcttcacccaggctgaagtacagtggcacgatcagggctcactgcaacttccctgtctc     70630
gagctcaagccattctcccacctcagcctcctgagtagctaggacagcaggcaggtaccactctgtccag     70700
gtaatttttaaaatcttttttagaaacaaggtattgccatgttgcccaggctggtctggaactcctaggct    70770
ccactcccgcattggcctccaaaagtgctggtattgcagggatgagccttggtgcctggcccatttattc     70840
ttaagtacttatgctcagggcaggtcttccaaggaagaaaagaacagccagataagactcgtatgagat     70910
agctgaggaggcggcatttcatccttctatgcatatcctccttatccacaagcagaatgctgtcctacaa     70980
ccattgctgtccccattaggtcatgataggtagacatgcaggtgatgaccacagactggcagttagccaa     71050
ggattctcagtgttgcacgttgcatgggtgagtgtgtgtgacggatgcctctggcagtttggtggaaaat    71120
tggtacgttttgtaaaaatgatatgtttaagtcttctaataaggtaaatactcataagaggaagtcagtt     71190
ttattgaaatagttagcacacatatttaatattaatatttaaggcacaggtgcattgactcattcttgtaaa   71260
tcccagcatttggggatgctgaggtgagaagatctcttgaggccaggagttcaagttgccagcctggaca     71330
acaaagggagactatttctacaaacaataaaataaaaaaaaataaagatatatttaaactgggctgtag      71400
taatacatgtgtatctttattgtatattaagtagctggatctacttatgaggttcatactagtcacaatt    71470
tcttagtacaattgagtttaaacaatatttggggtatttgtcctaccaacattgataatggaagaaaat     71540
actaaatttcagtgcacggtaatgaaactaaacatgtaattcctctttcccattgcagttagtagaaccc    71610
atagaatgtatctaaagacacctaggtggcaaaaggtaaatgcttgagggtatgatacccccattctccat   71680
gatgtgattgcatacctgtatcaaaatatctcatgtacctcataaatatatatacatgctgtgtacccac    71750
aaaaataaataaagaggaaacttggatgggattgggattttttgatgttagggtggagaacgtctgcattg    71820
aggattgtgtagagggaagagttttgatttattataccgttctcttaaaaaaacaaaacaaaaccaaaa     71890
aaaacctgcatgtgatgtgaggaatttttgccagaggtggggaacgtgaaactcactagttgaaaacattc    71960
tatactgaggtaattttttttatgtcaaaaagaaagtgaagagtgtggcagattaaaatcttcatgttatt    72030
tgcattttacaagcttggaagtctcaatatcaattattattgactgctatttactgcaattttttgacaca    72100
aaacatacttcattttaatgaactttgccttgtttgaatgttcgtaagactttggagggagttttagaaa    72170
gagatagttgcctttgatcccctgaagtatattatttggtctatcctgattctgtctcttgacttgcact    72240
tgtctttcctgaactctgtttaaaagaagctttttttagtgctcctcttttcctcctattctaatatg      72310
agatacagaggtttttatgggtaacatcttgtctatatgccagattgtggaagccttggttgttacccag    72380
ggatggaaggtctgatctcagttaagttctgaccctaggataagaagcccctctggagtaactgactcag    72450
tggggtagagcctattttcacaaattaatattcctgtctggggatggcagtgaaaacattttgggcagtg    72520
ggtggaaatgataatgttcaagcctgaagatgaagtttgccttttctcggagcttgtacagtgtcatact    72590
ccggaaataaactgtgtgggaaaggtggtgtttagtaaactagagctgtacaccttgcaaggccctcatc    72660
ttgtcattctgcactgtaagaagcacatgaagaaagagtgtaggctgtcagagagagcgtcacactgaag    72730
taggcacttcttacatacagctgtctgcctaaaatagagtaactttagcaaataggatctgtgatataga    72800
aattggaaactctagccagggttgtgaaaaatggagctggggtcacaggtggtggactggaaaacgttct    72870
gaagaaactcagctttttggatattgtacagttcattaggggagctatgagaagcagttatgaagctcct    72940
tatgaacgaaacgtagaggccgggtgcattggctcacacctgtaatcccagcgcttcgggaggctgaggc    73010
gggcagatcatgaggtcaggtgattgagaccatcctggccaacatggtgaagccccggctctactaaaaa    73080
cacaaaaattagctgggagtggtgttgcatgcctgtaatcacagctacacagaaggctgaggcaggagaa    73150
tcgcttgaaccaggaggttagtagttgcagtgaaccgagatcacaccactgcattccagcctagcaacag    73220
aggaaatctctgtcttaaaaaaagaaacaaagaaacaaaaacaaagaaagagacatagaaacatacccat    73290
cagtgttactcaggaggggttctggttcctgttttgcacttggcagtgaacttctttgttcctgtccacatta  73360
tcctccatctgtccacatgatcaaccatctgcagtcccaccaccagccaagggtcgtgccaggtcagaag    73430
tactactccaggtcaaactgtgttattttgaaatggagttatttgttattgttgttcttactcaaactag    73500
cagttttcctttgtagaagaactcggtttccactctggggttaaatatttcgtttatgtgatcaagattat    73570
ctctgtccatcagatacagcagtgagaaacccttttataggaaatggggttaaaagtgacaggatatcta    73640
taattgtttattttgtttgctaaattgcaggtaaatatattcgcagaactagttttgtaaccttttaa      73710
aaatggcttatttgacgttggctgaaactaagactctagaacttttactgctacatcaatgaatgacaag    73780
tctctctattcagcatgaaatccctgcagacaaaaaccacagggactacatcatgaaggctatgagaatt    73850
ttatggtggaaacctgagtgaagcaggtggtagaagaatctaatgtagtaccatgcccacaggagatgat    73920
ctaagaatgccctcacacctaaccttgcaagttttctaccttctgtgtcttggtttcctctaatttcttt    73990
gtctcttttctccctttaatttaatagggtttgctgaagactttctctcttccaaggtcaagtgttagt     74060
catctctgggcttgccgttagatactcatcatatgtctaacaatgaatgtaagcactgaggaagtaagta    74130
atggtgacaatgtggatgttcctttttggtatcattttttctcatgctctgtaaatcttggtggtctcatat   74200
tcatattattgaataccaatgcttaacccctctctgccgtctttacagaagtcccctggtctacctctct    74270
ctacgtgtctcaaaattgtagaattgtcttctagacactctattgcaaatttccttctgcacaagcccaac    74340
atttcacagaaggagcaggtggggggcaatgaaagagagcatggctcaattgtagcaattgaaaggcaag    74410
ctttgtctcatcagctgcagtgtttactacttgaggatgggaattttgattggtgtatctttacattttat    74480
caaagtgggtttcaccatggaagcattcagtggtacctcagtgaataattataattagctaggatttctt    74550
tggaggatatttattgttctaaatttgtatatatttatatgtacatactgtattagttcattttcatgct    74620
gctgataaagacataactgagactgggtaatttataaagtaaaagaggtttaataaaactcatagttctt    74690
gtggttgggaggcctcacagtcctggcaaaaggcaagggaagaacaaaggcacatcttacatggcaacag    74760
```

FIG. 11A-15

```
gcaaaaagagagagcttgtgcagggggaactcctctctttaaaaaaccatcagatcttgtgacctcatagttc      74830
acatgagaacatgacaatgaataagtcatgggtggaaactgccccccatgtttcaattatctcccactggg      74900
tccctcccccttacatgtgggaattatgagagctacaattctagatgagatttgtgtggagacacagccaa      74970
accatgtcacatacatatgcatatctttatgtaggggatctttatgtaaggtatgtgaatacaggtgtgt      75040
atattcatatactcttgtactttctcaaacacataccatagaatgtgtaataatgtgtctggaattggtg      75110
ggttcttggtctcactgacttcaagaatgaagctgcggaccctcgcggtgagtgttatagctcttaaggt      75180
ggcgcgtctggagtctgtccccttctgatgttcagatgtgttcagagtttcttccttctggtgggttcgtg      75250
gtctcgctggctcaggagtgaagctgcagaccttcgcggtgagtgttacagctcttaagatagtgcatct      75320
ggagttgttcattactcctggtgggctcgtggtcttgctgggctcaggagtgaagctgcagatcttcaca      75390
gtgagtgttacagctcataaaagcagcgtggacccaaagagtgagcagtagcaagatttattgcaaagag      75460
caaaagagcaaagcttccacagtgtggaaggggacccgagtgggttgccaatgctggctcaggcagcctg      75530
cttttattctcttatctggccccacccacatcctgctaattgtagagccgagtggcctgttttgtcaggg      75600
cgctgattggtgcatttacagtgcctgagctagatacaaaggttctccatgtccccatcagattagttag      75670
atacagagtttcgacacacaggttctccaaggccccaccagagcagctagatacagagtgtcgattggtt      75740
cattcacaaaccttgagctaaacacagggtgctgattggtgtatttacaatcctcgagctagatacagag      75810
tgccgattggtgtatttacaatccctgagctagacataaaggttctccacgtcctcaccagagcagctag      75880
atacagagtgtcgactggtgcactcacaaaccttgagctaaacacagggtgctgattggtgtatttacaa      75950
tccctgagctagatataaagactctccacgtcctcacaagagcagctagatacagtgtcgattggtgcac      76020
tcacaaaccttgagctaaacacagggtgctgactgatgtatttacaatccctgagctacatataaagatt      76090
ctccacgtccccaccagactcaggaacccagctggcttcacctagtggatcccacaccgaggctgcaggt      76160
ggagctccctgccagtcctgcaccatgcgctcacattcctcagcccttgggtggtcgatgggactaggcg      76230
ctgtggagcatggggtggtgctccttggggaggccgcacagggagcccatggagtgggtgggagg         76300
ctcagacatggtgggctgcaggtcctgagccctgccgcatgggaaggcagctgaggcccagctagaaatt      76370
gagtgcagcgccagtgggccagcactgctggggactcagtacaccctctgctgccactggcccgagtgc      76440
taagtcccccattgcccggggccagcagcgctggccggctgctccgagtgcggggcccgccaagcccacg      76510
cccacccggaactccagctggcccacaagtgctgcacgcagcccagttcctgctcactcctctccctcc      76580
acacctccctgcaagctgaaggagtgggctccagccttggccagcagccagagtatattgtcctcacagtgcag      76650
tggaggggctgaagggcccctcaaatgccaccaaagtgggagcccaggcaggggaggtgacgagagccag      76720
cgagggctctgaggactgccagcatgctgtcacctctcaatccccctctaaacaggacaccccaactgc      76790
tgttgggaatttggccaatgaccgctttggctacttcctgctgcatagggggtgaagaaggggccctgaag      76860
ttgtggtatccttcagagggaactctctaggccaggggaagtgccagcaagtcggtccaggggtcctcg      76930
gtagaagttgttagttgaactcatttggggttccatttgtcagagctgtagcttgatggcctcaatt       77000
ctagaggaaacaaacttgacaagaaggttaaaaatacagggcccaaagcgagtaacagcaagatggctg      77070
ccacaggacctagaaagggggagaagccatgttgcccaactccagaggttggtataagaatttgaaaggcg      77140
ttgtctgatttcagaagccttttccagtaaacgccgggcagcatctcgtactatccctgattagttagtg      77210
taaaaacaacactcttcccctaagaaggtgcagagtcctcctttctcagcagtgaggcagtctagacctc      77280
ggcggttttggagagtcactgctgccaaagagtctatttgggattgtaagataagaagattttttattt      77350
cttgcaaactatctgacaaatcgtttgagagtgtgtggtaggataatgaagttgatagaccagctat       77420
tctggttcctgtagcagtagccattcctaacactataagtaggggtattagttgtacggctctgcgctga      77490
cggacttgagcttgaggggtactgataaggtctgatttcctgggacaatgttaatgttaggacttagaa      77560
agactaaggtgcatgtgcctgtccagttagtggggaggcagatataggttgacattccacataagaagaa      77630
tatgccttggctgggtagacagaactggttatgtattgttaaaaaaggtgtgagttttgttgttttcatt      77700
ttcccatactcctagagtacttgccaaggtacctccagtgagcagctggaaaggggtgttgggagaaaac      77770
tgagtggctccctgtgttctatttccccatcggagaaaaaatgtttttgtatccactaggaaccatctga      77840
tagagtgattgaaagaggggatgagaaggcattcactagtggtaggggcgctgttgcagggagtccaggg      77910
gtgattggtcatgcagggagtatgtttgccattgcaaaacctggactgtttgttcaccagggaggaggtg      77980
atgattttgggggggcactgagaagcagaaggcatcagaatggagctgtttgggtgactcaaaagttac      78050
tatgatcatttggagcttgaagttgtaaggtgtaattacactgatgcgttggtaggtgccgcagaggcag      78120
gcctgataacaggttgcattggatgcataaagggggcttggaaagttaagatagtgttcgtggttacaagg      78190
cttttcattgcttgtgtaataggtgaggttggaaatgtaagaacataaaatttgggttgcacgtcctgtt      78260
agggtacttttggtcccatcagatattgggaagtcagccaatgattgcatatttagaagttggaaagggt      78330
cttttccttcgtaacgagggtggaaggtcaagttggtaaagacccagtttttttgcaggaatgggagtggg      78400
aacgtaggcagaggttgatagagagatacacagccaacagtcatttgccagggaagtattggactggttt      78470
aacagagtgtgagttaagttgagagtcttgtagaggtaattaggagctagtgaaaggggaggggtgattg      78540
tatgaggtttccaaggaagcaggagggatacacaggcaaagagcaaataggaaggtaaagagggtgctcc      78610
agaaaatgagatcattttatctagtctgagttagaggtaggagtaaattactgtcaaaaggaaggaagat      78680
agaaaggaggttgatgtgattaggattttcattctggcaggagctgagtatattgtcctatcacaaaga      78750
gtatggttagtgtgctgttttcacttatctttttttaaggaggaagaggtctttcctcaggatcagttgg      78820
ggagcctttttagtctgggatgtttccttctgaaataagaggtgcaagtcctccaacggttcgcaggtgt      78890
atcgaagctggtctggctgatcttgggactcctgagctgatgatccagcaggttcctcaggagatgtcca      78960
aagtttaactcgggtgtggtgaatccaagtttccactcctgccatgttaactgcaatgggagtagagagg      79030
attatagagtatggtccttcccacacaaagagtccatagatgggaggtagagggaagagattgaccaaca      79100
ctagatctcctggttgaaacaactctgttccctgttctctgtgacatccttcaggtagattttaaggtt      79170
ttgttgatattttgccaaagttatatctttgacaaagttggccatttcctgattgagtaggaggtcattt      79240
gtgagaaaaggtcgcccatacagcatttcatatggactgagccctatttgtggggagaatttcgaattc      79310
tcaacaaggccatgggcaaaagagtaggccatgggaggtgagtttcttgtgttagtttccttaagtgcct      79380
cttgagtgtttgatttgccttctcaaccttcccagaggattgtggcctccaggagcaatgaaggcgatat      79450
tgtatccctagtgcttgggagattccctgagttatcgtggctttaaaagctggaacattctcactcgtta      79520
agctttggggaagcctgaatctaggaattattaggactttaatcacttcctgagccttctctgtcttgta      79590
agagaaagcttctatccaatttgtaaaggtatcaacacagaccaacaagtattgaaatccctttgactta      79660
ggcatatgggagaagtctaactgccagtcctctccgggatagtgacctattctttgttccccacagggg      79730
ccttatgatataccaagggataattcttttggcacacctcacaggcttttgactacctgtcagatggtctg      79800
gaggagatttggccctgtaaatagggatttggccatttgattagtgttttcaatacccatatgaaaagtt      79870
```

FIG. 11A-16

```
tggtggagggtcttaagtattttccactggctgccttccggtataagtacctttccttcttctgtcacca         79940
accaccctgaagggagaaaactatgcccccatgaaagtccccattctgtttcagtccgggaatactgggg         80010
cttcatctcctggaggggggttgttccataccaagggtccttccataggcatttctaatgggacattcctc         80080
ctggcagcagctttgacctcagcatctgcctgatggtttccttctgccttttctccttcacctttctgat         80150
ggctttgtcagtgtaagattcccacctctttgtgttttttcactgtgtgactgggcgggcattttttttgc       80220
cctttcagattgtccttccaatgcccagacttcagggttgattccctcctcaagtaggggacaacaaatg        80290
ggtaaattgttccccatattcatgtagataatagctccagccttggctaatatatccctccctaataagg        80360
gtgtgggactttcaggcataacaagaaaggcatgtgaaaagagcagagtcctcccaattacaactgaggag       80430
atgggagaaataccctgattacaggctgccccaggattcctcagatggtaactgaccttgaggacagtcgt       80500
ccaggacaggagattaacactgagaaggctgtgccagtatccaggaggaagtcaatttcctggtcatcaa        80570
tagttaaacatacctggggctcagtgagggtgatgacatgagctggtgctagccctggcaccctcattc         80640
cttctgttggatcatctggttgggggcttctgacccagggaaacttcatcctctggggcagtgcaccttc        80710
cagtgattgcctcggcatagtggacacggacgaggggcagcttgtttcttattggacaatcttttttaa         80780
aatgtcgtagtaaaccgcactgataacaagccctaccaggtgattggcctgctccattttctgacctctc       80850
tgaaccaccaaagtttgtttgtctgagggccatgactaaggctgtggcctttctctgatctcgcttttcc       80920
ttttgggcctgttcttcttggtccctattatagaacactgaggttgccaggtttaataatgtctctagat      80990
tttgttcagggcccagggcttgcttttggagctttctcctgatatctgcagctgatggattgggtaataa      81060
acatatcttttagaatcaattgaccctcaagtgattcaggtgacagggagtatattttcttaaggcctc        81130
tcgtagccgctcgaggaaggcagaaggttttcttccttccctgggttatggtagatatcattgaataa         81200
ttcatgggctttttctaattctccttagtccttccagaacacaggtcaatagatgtttacaactccagt         81270
ccccatgatctgagtcaaggtcccagtggggatccgtactggggatggcttgctgaccagtagggaattt       81340
gtcccctttcttcagctgtcattctatcatttacttgactaagacaccaggtatctccaaactcctaggct      81410
gcagctaaagccgcattcttttcattaaaggccagggttgaactatcagtagcatgcatgacatctctccaag    81480
tgaggtcaaaggtttgccctagatgctgtaggacatctatgtacctatcaggatcatctgaaaacttccc       81550
caggtctgccttgatctgctttaaatcagagagggagaaggggacatataccgggttgggccaaattcc        81620
cctcctgctacagattgaaggggacataaccgacagcccgggggttttgtggtcctttggagatttctt       81690
tgcttgtttccttccgggcagggagattagaggaggagtatcaataataggaaggggagctatagggag       81760
gctaggatataggggtaagctgaggggtcctcctctgggatgtaaattgcaagctttgcatagttgtgta      81830
ttctccctcaatgaaaagaaagctcggacataaggcatttcactccatttgccttccctcttacagaaaa      81900
gatcaagctgcaggatagtattgtaatttgtacttccctcaggtggccattttttcccccatcagaaagaga    81970
atattggggccaggccgcagtgcagaaaaaaaatgagctgcctcttttttcagggtttgtgggtcaaattg     82040
gtcccaatggcttaggatgcatttcaagggtgagcctgttgatgcctgagtgtttcccatctgaaagaca      82110
aaattacccgcagttttggtttgtttttgttctctccctgtccaagaacccgcaacggtccctggaccct      82180
gctgatcggaatagttgcactcactgacgcagcaacagaaacactagttttcctcccagaccacatggag      82250
gaccgaggaaggtcggatttagtggtccttactgacgcaatgttgaaaacctgcacccttgcttgtcctc      82320
ctagaccacaaggaggaccgactgagaaaaatcggatttagtggccccttaccaacgcatcctcaaaaacc     82390
tgttagagtcctaagcgttctcctgttagtattaggactttaccccctgtcctataaagatgttatgcccc    82460
aaaaatgaaatggagggccataccctgagggagggaagggatcttcatggttggaagagtgacacctttt     82530
gtcctcacttataggaaggatacaatttctgaggattcccccataatcctagcttcaggaataacttttgtta  82600
ggcctgttagtctgaggagggatcctaaaattccaggtagtccccactatgatggggccttgggcaaaaa      82670
ctgtatcttctgattggtgagcccgggtgcctaaagaagataacagagtcctggagtttatactagaag       82740
tcattcttataggagaaacaagaaaagcaccagaggcaggtagcaatttttagaagcgggtctagactca      82810
gaagagaggcgagaggaagtttgtctggcaggcattgggacccagagggcaagggtcagtatagatagga     82880
tagatagcgagtctcgcttgggcgacatgcttgagagttccgctcatggctgcagggtcaaccaacatg      82950
ttgttgggaccccggagatgcatgcttttcctctctgtcgaccctcggctcagcccagaagtacagaaaa     83020
agcagaagctggttctaggtaaaacaacggtcccaactccaaagagttgggggttgttagagagcccttt      83090
cccagaaagcctgacacccgcgtctttagtctggcagccacactagttgcctttaactggctgacaggtg     83160
cctggtatttagccccccgaattctaaggaaagataggacaatatagcaagcgaaaggggtccaatggtac    83230
tcactgcttggcgataggtgatggtctcaccgcttggcgattgtctcaccgcttggcgcaataggcgatggt   83300
ctcactgcttggcgataggcaaaagtcccttcgtggtcaccaaaatgtgtctggaattgctgggttcttg     83370
gtctcactgacttcaagaatgaagctgcggaccctcatggtgagtgttacagctcttaaggtggcacgtc     83440
tggagtctgtcccttctgatgttcagatgtgttcagagtttcttcctctggtgggttcgtggtctcgct      83510
ggctcaggagtgaagctgcagaccttcgcagtgaatgttacagctcttaaggtagcgcgtctggagttgt     83580
tcgttttccccggtgggctcggtctcgctgggctcaggagtgaagctgcagatctttctcacggtgag       83650
tgttacagctcacaaaagcagcgtggacccaaagagtgagcagtagcaagatttattgcaaagagcgaaa     83720
aaactaacctccacagtgtggaagaggaccggagcgagttgccaatgctggctcgggcagcctgctttt      83790
attctcttatctggcccatccacatcctgctgattggtagagccgagtggcctgttttgtcagggtgct      83860
gcttggcgcgtttacaatccctgagctagatacaaatgttctccacgtccccatcagattagttagatac    83930
agagtttcgacacacatgttctccaaggccccaccagagcagctagatacagagtcgattgcttcatt      84000
cacaaaccttgagctaaacagagggtgctgattggtgtatttacaatccttgagctagatagagagtgcc     84070
gattggtgtatttacaatccctgagctagatacagagtgccgattggtgtatttacaatccctgagctag    84140
acataaaggttctccacgtcctcaccagagcagctagatacagagtgttgattggtgaactcacaaacct    84210
tgagctaaacacagggtgctgattggtgtatttacaatccctgagctagatataaagactctccacgtcc    84280
tcaccggagcagctagatacagagtttcgattggtgcactcaaatcttgagctaaacacagggtgctgac    84350
tggtgtatttacaatccctgagctagatataaagactctccacgtcctcacaagagcagctagatacagt    84420
gtcgattggtgcactcacaaaccttgagctaaacacagggtgctgactgatgtatttacaatccctgatc    84490
tagatatacagattctccacgtccccaccagactcaggagcccagctggcttcacctagtggatcccgca   84560
ctggggctacacgtggagctgactgccagtcctgcgccatgcgctggcattcctcagccctgggtggtc     84630
aatgggactgggtgccgtggagcagggttggtgctcgtcggggaggctcgggccacacaggagcccatgg    84700
agtgggtgggaggctcagacatggcgggctgcaggtcccgagccctgccccgtgggaagcagctgaggc     84770
ctggctagaaatccagcgcagcgcggcggtggcagcgctgcgggtactcagtatacccctccacagcca    84840
ctggcccagatgctaagtcccccattgcctggggccagcagggctggccgctgcctgagtgcgggcc      84910
agccaagcccacgcccacccagaactccagctggcctgcaagcacagcaggcagcccggttcccgctca    84980
```

FIG. 11A-17

```
cgcctctccctccacacctccctacaagctgaaggagtgggctccagccttgtccagcccagaaaagggc      85050
tcccacagtgcagtgggggtactgaagggctcctcaaatgccaccaaagtgggagcccaggcaggggagg      85120
tgccaagagcaagcaacggctctaaggactgccagcaatgctgtcacctctcaataatatccctgaatta      85190
catctgctactccgctgctctacccatctaacaagtaagtgatggagacattgatggttctattagtcag      85260
ggttctctggagggacagaactaataggagatgtatatatatatatatatatatatatcgctaacc         85330
cttaccataacatatatatgtgtgtgtgtgtctgtgtgtgtaaaggatatacaaatatacatacaact        85400
aataggatatatgtatgtgtgttatatagataatatctatgttttatataaatatatataaattatgt       85470
atatgtaatataacaaaatatatatttatatatagtatatataaacacacacacagatatatatcctatta    85540
gtgataagtgataaagagtagtgtttatatatatacatatataataaattcttctttatatatatataca     85610
catctatatttgtgtgtgtgtgtgtccatatatatatataagtttattaagcagtatgaactcacgggat     85680
ctcaaggtcccacacagtagacgatctgcaagctgaggagcgaggaagccagttagagttccaaagctga     85750
agaatttggagtctgatgttccagggcaggaagaatcaagcacaggacagatgtagacttggagggtaag     85820
gcagtcttgtctctttcacgttttttctgcctgcttttataatttctggcagctgatgagatggtgcctaccc  85890
gcttgagtgtgggtctgccttccccagcccactgactcaaatgttaatttcctttgacaacaccctcaca     85960
gagacacctgggatcagtactgtgcatccatcaatccaatcaagttgacactcagcattaaccatcacaa     86030
tggtgtacaactgactggagttaaagtgagagtcaggcttttgaatcatagtcgtaaaactgcacaaattc    86100
tctgccccatactacctcccagacacataatacatgcaggagtaggtgttttttgtgcctgttatagtgca    86170
tttgagcctgttgttctttactttgctccttgtgtcagaccatctctccaaaaacagatgatcagcatcat    86240
acacaactggtagtattgattatctgcagcataaagcatggaacatgggattttcagggaatggagtagg     86310
aaaaattcctgaacctaagcagcttaataccttaatattcactggttagtttgaatacatatactct        86380
acacacacacacatgaaattacatggataatataagctttaatgtattgtatatataatatataatctctc    86450
taacctccaaaaatgtatatatccaaactatttgtcaattctctctctctttccccccctcttgctctttt   86520
ccacatatttatgtataaaacagttttttcaaactaaccaactgaaatattaagctcctatgttatatata   86590
taatatatatttctgcaaataaccaaaatatcaaagcaattaagctcctgtttcatgtatctattgtata    86660
tagatatatgtgtgtgtgtacatgtatacagtatttctccaaactaagcaactgaaaaatattaagct      86730
cctatgtcttacatatataaaatatttattcaaataagcaagcaaaatattaggctattaagctcctatg    86800
aataatgtttatttttattctatataaatagaataatatgaatatgtttcatattattctgtatattata    86870
tatatatacacagcaggttagtttgaagacatgtatgcatatattaaaatctactttataatttgatata    86940
taataagttaagtacaaacttttcatgaaatatgtatgaagaaggaagactattttttatagtacgatta    87010
gtacagtgaattctgggggaaaaagtaaatactcatttcaaatcctcatgtacaattcaaataaacaaaaa    87080
tctggtggcatgtttacagcctgctaatatagattatgtggtgttggaaaacattttatttttacaagta    87150
cctagtaggtgtatatatttgtgggttatatgagctatttcaatataggcatacaatgataaaaatcaca    87220
ttaaaataaatggggtacacatcacctcaagcatttatcgtttatttgttttacaggctttcatttatac    87290
ttttagttatttaaaaatatgcagtaaattagtgttgactgcagataccctattgtgctatgaaatacta    87360
gatcttcttcattctgtctcactatatttttgtgcctattaaccatcccccacttctctatccctcccatt    87430
actctcccccagcctatggtaaccatcattctattctctgtctccctgaaggcaactggaaggctattttt    87500
cttttttttcttttctttttttttttgagacagagtctccctctgtcacccagaatgatgtcgcccagtg     87570
atgcagtctaggttccctgcaacctgcccttgtgggttcaagtgttttccagtctcagcctcccaagc       87640
agctgggattacaggtgcacaccacctcgcccacctaatttttggtggtttttttttgtagacacaggggt   87710
ttcaccatgttggccaggctggtctcgaactccttacctcgtgatccacccacctaggcctcccaaagtg    87780
ctggaattacaggcgtgagccaccacacctggcctgaaagacatattttttaaaggataggctggaaggtt   87850
gcattgacttttcgctgtttctggctcactaaatcctgctatttttctgcagtagggattgctacacttacg   87920
ttatgctttcctactgcagagaaggacattctgttcccactgggctcctatactgcctctacagtcggct    87990
ttggagataacagcctgaggcgtcagagcgtcttggtggtgaaagcatcttaagatgtcactggcacggc    88060
tgggtgctggtggctcacgcctgtaatgctagcattttgaaggctgaggcgggatcacgaagtcaag       88130
agattgagaccatcctggccaacatggtgaaaccccatctctaccaaaaatacaaaaattagctcggcag   88200
tgcctgtagtcccagctactcgggaggctgaggcaggagaattgctttaacctgggagcagaggttgcag    88270
taagccgagatcgagcaactgcacttcagtctggcgactgagctagactcggtctcaaataaggggggtta    88340
aaaaaaaagaggtcactggtacaagcccttgttttgcagtggaaggagatgaagtccaggccactatat    .88410
gatgggcagagagcacgtggcttattagtgaccacggctatagtggctcaagttccctggctgctggcc    88480
atggctggcaggatcccggggcttttctgcctaatacgtgggtctgttgcctgggtgtgttgcattggg     88550
cttgtcgcataatcatggagaaatagattttctcttcaattttttaaatccaagatattttggcagcacat   88620
gggaaaataaagtcattgagtaagaaaacctatacagatgagcatctttttgattaaattttcattataaa   88690
ataatcacagtcacaaaacctgaatcaaaacgtatacacagataatcatcttaaagagtaaaaaataatc    88760
aggtacatagtattgtactcactgacagaccaggaaaagacattcccactgtttttttgtatatcagtgtga  88830
gtttgcttcctgtctcctacctcgcagagaaatgtacttcctcaggattcggttttcagaatgcccttgc    88900
tatgttatttcaggacaaacatagttctgagcaatatattgtttagttttacccttatgtaaatgaaat     88970
cacactatttgtagtgttttatggcttggctttatgtttgaggttttcccatttttggtccatatatctg    89040
tatttttattcatttttactgttgtgtaaagctttctgctttaatatgccaacatttatttattcattgt    89110
cctatttatggatatctggattgtcgtaactttttttgcaattacaatttgggttgcattgtccccagca   89180
aactaatgcagggacagaaaaccaaacactgcatgttctcacttataagtggcagctcaacgatgataac    89250
atgtgaacacatgtgggtggagaacaacacataatgtggcctgtctggggattgggaggagggagaaca    89320
tcaggaagaataactaatggatgctgggattaatacctaggtgatgggttgattcgtgcagcaaataaac    89390
atggcacatgtttacctgtgtaacaaacctacaaatcctgcacatttaccatgaaaattaaaataaaagt    89460
tgaagaaaaatattggggctgcaatggacatttctgtacatattttctgatgcaaatattttagaaacc     89530
ctatagaggatgatgtgtgtgtgtgtgcgtggtgtgtgtgtgtgtgtctactttccacatagg           89600
attctgtatcttctactttctaatgtgatttaaaattgttttgtttgcagtgggggttgcacagaggctcagcat  89670
cattgcatgggagttctagttgctccagatctttcttcagtagttgatatcattgtatcaaattttatt     89740
aatactattctgatttcatctgcatttcaccaataatgaatggcattgagcctcttgtcctatgttgagg    89810
ctatctgtagatgtgaggacttcttccttgatacggatttatggtggaggaatcaatcaccaaagatggc    89880
tctgagtgtaggctgaatgactaaaaatataatgatctagttatctaaatataaaacaaaattgtttaag    .89950
caatttgggggattggagaatgagagttttaggagaaccataagatatctatctgactatattcttcaag    90020
acaagatagtcatggcagtacaggcatggtggcacataacattttgtcacctggcactacacgagtgtgc    90090
```

FIG. 11A-18

```
ttccatgaccttgaggatatatatgactttgagtttggtgagacagatgaacacaaagcccagagaatct       90160
gcaaattatttgacttagatttagatattgtgtttggaaaacatttgacacagaaaatcaagcattagca       90230
agcatttattatttgcttgtgttagctttagttatgcagatgatgaataataagaaaaaaagcatcacag       90300
gtagggatagatactgtcatgaaaatttaagcttctcatgggcaggaactcattcttaacccactatgt       90370
gcccttactaagcgcagtgatctttatgggatacttctatgatctgaagacttgtgtccttccagaatcc       90440
acatgttgacattgtaaacccaaagtgatggtgctaggaggtagggctttggagctgccgagatgttga       90510
gagtggatgccacgtgaatggcattaatgacattttaaaagataccccagggacattacttgctcctccc       90580
ctcttttccaaagtcataaggaaaagtcagccctctaggcattgggccctcaccatacactgaatctacc       90650
atatcttgatttcggatttccagtctccagaactgtgagcaatgaatctctatggtgtataagccccacc       90720
accaccgccccaacgacactcacccaggctatgatattttgttacagcagcctgaatggactaaccca       90790
acttctgtgctttgctgttgtcttatttctttggtcagtgtaggatcttgctgtccgcatagtttgctct       90860
agaaagatggatgctctattcctaatggtgtatttggcctccatctctatggaatattctcctatccaat       90930
cagtcttggtaacatataaatgattaactctacccttgggtatagttttggttctgctaagtcccctgct       91000
gaaaattctggtttctaccattatggctcatgcatgttcctgacccattaaacttcagtggaagaataga       91070
aatggagagggaggtgatggagttgatatcttaaactgcaatatggtgcaagcccatcttgcagataata       91140
tatttggtgtcttccttatcttttaagagcggccttgctatgttgcctagcctaaaatcaaactcctgg       91210
gcaagtgatgcttgtggctcagcctcccaattacctggcattacagacatgtaccaccatgcctggccac       91280
gttttactctccaattacttaatatataagtaatggttcacagtggttcatttttttgtgtgta       91350
ttccaataacatttatttatttattaccttgaacatattcaatatttatttgacaagtttttataattt       91420
taacattttttttttaattcatgtggtatgagtgtaagttttttttctctgggtgtattggatggtgctgag       91490
gtttgaggtgcagatgattctgtcatacacctatggagcatggtacacaataggtagttttccaacttta       91560
ccctctctgtcaccctatttagtagtcctgagtttctgttattgctttatgttcatgagtatccaatgt       91630
ttagttcccacttataagtgagaacatgtggtatttaacttctgtttctgcattaatttacttaggata       91700
atggcttccagctgcatccatgttcctgcagaggacatgattttgtttgtttttatggctgaatagtatt       91770
ccatggtatgtatgtatcacatattctttattcaaaccaccattgatgggcacttaggttgattccatgt       91840
ctgctattgtgaatagtgctgtaattagcatacgtgtgcatttgtctttttgttagaatgatttatttt       91910
catttatatatatatataaaacaattaatgggattgctaggtctgtggtagttcctccttaagttccttga       91980
gaaatctccatactgttttacacaatggctaattcacattctcaccaacagtatatgtagccttctcttc       92050
tctgcagcctcaaagacacctgttgttttttgatgttttatgaacagcctttctgactggtgtgagttttt       92120
gatttgcatttctctggtacaaaatggtggattttgaaatgagatttgatttctaaattttatagaaact       92190
gcatagatgactgcaaagaactctttaagatatgacaaaagacaaattagattgtaatctcctttataca       92260
ggacaagaaataaagaggagaatattaaaaatatgtacacatacaaaagtagatgaattggcgattgttgg       92330
tgttggatgcatgttaagcagggtgaaggaggtgtgtggcagtgcattcgtggccatgtgttgagagtgg       92400
gcatccatgtaggtaacagcagagagctttggggttcagaaaaaaagataagtcacatccccactcaggta       92470
ccctaaaatgttgtcttctctagaaatgaaagaagagggaagccagagatgtctgtagccttgcatagttt       92540
tgggaatagctattctagactttgtcagtgaacagcatagaaggattgttgttcaagcccagttatttgg       92610
gcaaggatcagattctgttgcttttgttttctggatgctccataatgaatgtgagatagaagcagatgtc       92680
tcaagtgcttcttgttctcagaaacctcctgacagcagacattcagtgggcccagaccttcagtgtgtc       92750
tgtaagtaaaacacagggaggtgctctttctgattttatcttactatttttaatgcaattacaaagcttc       92820
ctatttctaatatattccaagcctttgaaagacaaggccataaacacccaggatatctgattttattca       92890
tgataagacccaaataccaaaatacctatgatcagggctcaccttaattaagtatgtatcttaaaattaa       92960
accaatctcagtttgaggaattcatactttggaagaaatttattacagttttgttctgaacattatat       93030
tatgataggcttgaatagtgtgagccttgctataattacaacctgagtcacaataacttccctgcagagg       93100
atgatttaaaataccccaatcaatttatgaactggtcaaaaatgccattctgaggtattttttttttatgca       93170
gtctttgcagagaagacatgccatatagtcctctcttcattcccaaagcatatatatatatacgtatatac       93240
acacacacatatacatatacatataaatatacagtgaagttagttttttacctttgttatcaatatttttt       93310
atccatcaaaaattttataaatgatttgtggcatcccctttttatcttaggaaaattaaaaatctctcta       93380
tcaacttatctatgaataaccacattttcatccctttgtgaaatccattttagtttgtgaaactcacatgg       93450
agatcttttatttttgcccgcaaggatgtaggctggttaaatttacagagattctttaatgatgataat       93520
gtacatttgactgatatcaataagaaatattgatattattaatatcaacatttttttgcaatgctaaaaat       93590
ttacaagttgtcgaattatttaattatttattttattatacattaagttctgggatacatgtgcagaat       93660
atgcaggtttgttacataggtatacatgtaccgtggtagtttactgcacctttcaacccatcatctaggt       93730
tttaagcctttaaaaccttttaagcatttggtacttgtcccagtgctatctttaccttgcaccccatcccc       93800
caagaagccccggtgtgtgatgttccacttctccatgttcatgtgttctcattgttcaactcccatttat       93870
gagtgagaacatgtggttttttgcttttctgatcctctgtttgctgagaataatcatttccagcttcatcc       93940
atgtccctgcaaaggacattaactcattcttatttatggctgcatagtattccatggtgtatgtgtgcca       94010
catttctgtatccagtctatcattgatgggcatttggtttggttccatgactttgctattgtaaatagg       94080
aatgcaataaatgtgcatgtacatgtgtctttataatagaatgatcaataatccttttgggtatgtaccca       94150
gtaatgggattgctcagttaaatgtatttccagttctagatccttgaggaatcgcgacactgtcttcta       94220
caacggttgaattaatcgacactaccaccaacagtgtaaaacattctatttctccacatcctctccaaca       94290
tctgttgtttcctgactttgaatgattgccattctaactggggtgagatggtatctccattgtggttttga       94360
tttgcatttctctaatgaccagtgatgataagctttttttcgtatgtttgttgactgcacaaatgtcctc       94430
ttttgagaagtatctgttcataaaccttacacttttttgatggggttgtttgttttcttcttgtaaatttg       94500
ttaaagtttcttgtagattctggatattagccctttgtcatgtagattgcagaaaactttctcccat       94570
tgcctgttaactctgatgatagttcctttgctgtgcagaggctcttaattagatctcatttgtcaatt       94640
tttgctttgtttcaattgttttggtgttttagtcatgaagtctttgcccatgcctatgtcctgaatggt       94710
attgcctacattttcttctagttttatgatttttttctcttatggttaggtctttaatccatcttgagtta       94780
attttgtataaggtgttaagaaagggttcagttttagttttctgcatatggctagccagttttcccaat       94850
accatttattaaataggacatccctttcttcattgcttgttttttttcagattttgttgaagttcagtggt       94920
tgtagatgtgggtgttatttctgaggcctctgttctgttccattggtctatatatttgttttcttaccag       94990
taccgtgctgtttttggttactgtacccttgtagtgcagtttgaagtcaggtagcatgatgcctctagctt       95060
tgttcttttttgcttaggacttttcttggccatataagctctttttttagttccacccgaaatttatggtgtt       95130
tttctcccttttttttttaatactgtgaagaaagtcactgttcgcttgatgagaatagcgttgaatttaaaa       95200
```

FIG. 11A-19

```
actactttgggcagtttggccattttcacaatattgattcctcctatccatgagcatgtaatgtttttcc      95270
atttgtgggtgtcctttcttatttcttgagcagtggtttgtagttctctttgaagaggtccttcacttc      95340
ccttgtaagttgttttcctgggtacttattctctttgtagcaactgtgaatgggagttcactcatgatt      95410
tgtctctctgattgtccattattggtgtataggaatgcttgtgattttttgcacattgattttgtatcctg     95480
agattttgctgaagttgcttaccagcttaaggggatttgggcgtgagacaatgcaattttctaaatattc     95550
aatcatgttatctggaaacagagataatttgacttcctctcctgctatttggatatcctttattttttct     95620
cttgcctgactgccctggccagaacttcaatactatgttgaataagagtggtgagagagggcatccttg      95690
tttgtgctgattttccaagggaatgcttccagcttttaccaattcagtatgatgttggctatgggtttgt     95760
cataaatagcactcattatttgatatatgttccatcaataccagtttattgagtgttttagcatgac       95830
gttgtgttgaaatttattgaaggccttttctgcatctattgggataatcacatgttttttttgtcattgtt    95900
tctgtttatgtgatggattatgttgattgatttgcttatgttgaaccagccttgtatcccaagggatgaa     95970
cccgacttgatcatggtggataaaccttttgatgtgctgctggatttggtttgccagcatttttattgagg    96040
attttttgcactgatgttcatcaggaatatttgcatgaaatttcattttctgttgtatctttgtcagttc     96110
atggtattaggatgatgctggcctcataaaatgagttagggaggagtccctgttttttctattgtttgaa     96180
tcatttcagaagaaatggtaccagctcctgtttgtattgttggtagaattcagctgtgaatctgtctggt    96250
cctgggcttttccacttggtagtctattaattaccgccttaatttcagaacttgttattggtctattca     96320
gggattcagcttcttcctggtttattcttgggagagtgtatgtgtccaggaatttatccatttctttgg     96390
tatttccgtagaggtgtttatagtattctgtgcttgtagtttgcatttctgtgcgatcagtagtgatatc    96460
cccctttaatgttttttattgtgtctatttgatactttttctctttatttttttattagtctggctagcaata  96530
catctattttgttaatttttttccaaaaatcagcttttttgattcactgattttcttgaaggattttttttta 96600
tgtctttatcttcttcagttctgctccagtcttagttctttcttgtcttccactaggttttaaatttgtt     96670
tactcttgcttgaatagttctttttaattgcaatgttaggggggttgatttacatctttcttgctttctct    96740
tgtggtcatttagtgctctaaatttccattttgaacactgtcttttaaagtgtcttagagattctggtacat   96810
tgtatctttgttcttatcagttttcaaagaacttatttatttctgctttaatttccttatttacccggtag    96880
tcattcaggagcaagttgttcagtttccatgtagttgtgtgggtttgagtaagtatcttaatcctgggtt     96950
cgaatttgattacactgttgtctgagagatggttcgttatggttttcattctcttgcatttgcgaggagt     97020
gttttacttccaatttgtagtccactttagaataagtgtgatgtggtgctgagaagaatgtatattctg      97090
ttgattgggtgaagagttacataggtgtctcttaggtctgcttggtccggagctgagttcaagtcctga     97160
atatatttgttaatttttttgtctcattgatctgtctaatattgacagtgttgtggtaaaatctcccacta    97230
ttattgtgttggagtatacttaaacacaatattattgtgtttgtaggtctctaagaacttgttttatgaa     97300
tctgggtgctcctgtattgggtgcatatatatttatgatagttagctcttcttgttgcattgatccattt     97370
accattatttgatgcccttctttgtctcttttgatctctgttgtcttaaagtctgttttatcagaggcta     97440
ggattactaccccctgcttttcttttgcttccgtttgcttggtaaatattccttcattctgttattctgag    97510
cctatgttttactttgcctgtcagattggtctcctaaatacaatacaccaaagggtcttgacccattatt    97580
caatttgccagtctgtgtcttttaattggggcatttagcccatttacatgtaattttaatcttgttatgt    97650
gtgaatttgatcctgtcattatgatgatagctgattatcttgcatattagttgatgctgtttctttatag    97720
tgtcattagtctttacattttgggagttttttgcagtggtatttttggtagtttttgcagtagctgatatct   97790
tttttttttttttttttttttttgccccatatttagtacatccttcaggagctcttcaggagtccttaaaggcagtcctg 97860
gtggtcagaaaatccctcaacatttgcttttctgtaaaggattttatttctccctcaattatgaaactta     97930
gtttgtctggatgtgaaattctgtttgtttgtttgtttatttatttatttatttatttatttatttatttt    98000
atttaagaatggtgaatattggcctgcactctcttcggcttgtagggtttctgcagtgatatctgctg      98070
ttagtttgataggctctcttttgtaggtagcctgctctttctctcggatgctgttaacatttttttcctt    98140
tgtttcaacctttggtgaatctgactattatttgtcttggagttgctcttctcaaggagtatctttgtggt   98210
gttttctttatttcctgaatttcaatgttggacttcttgctaggctggacaagttctcctggataatatc    98280
ctgaagtgtgttttctaactggttccattctcctactcactttcaagtacaccagtcaaacataggtttg    98350
atgttttcacatagtcccgtatttcttggaggcttttgttaattccttttcattcattttttctgtaatct    98420
tgtcttcacatttttattttattaagttgatcatcaatctctgatatactttctttcccttgatcgattca    98490
gctattggtacttgtgtatgcctcaggaagttctcgtgctttgttttttgcactgggtgtcttctgcatttata  98560
ttcttctctctaaactggttattctagctagaagttcttgtaacctttttatgaagattcttagcttccttac   98630
atgggggttagaacatgctcccttagctcagaggagtttgttatttcacaccatctgaagcctacttcagt    98700
cagtttgtcaaactcattctctgttcggttttgttctcttgctggtgaggagtgatgatcctttggaaga    98770
gaagagggattctggttttttggaattttcagaatttttgaactgttttattttttcatcttcatgaattta   98840
tctaactttgatctttgatgttggtgaccctcagatgggattttgcatgggtgtctttgttgttgatgt     98910
tgatgttattgcttctgttcgtttgttttcttctaacagtcaggccgctctgctgcaggtcagctgga      98980
gtttattgaaggtccactccagaccctgttttcctggctatcaccagcagaagctgcagaacagcaaaga    99050
ttgctgtcttctccttcctctggaagcttcttcccagaggggtagccacctgatgtcaaccagagctctc    99120
ctatatgaggtgtccattgaacccagctggggaggtgtctctcagtcaggaagcacctgggttagggaccc    99190
acttgagcaggcagtctgtcccttagtagagcacaagttctgtgctgggagatcttctgctctctttcaa    99260
gccataggtaggcacatttaagtttgctgaagctgcacccatagccatccttactccaggtgctgtgtc     99330
ccaggggagatgggaatttatctataagcccctaactggtgctgctgcctttctttcagagatgccctgc    99400
ccagagaagaggagtatagagagccagtctggctacagcagctttgctgagctgtggtgggttccacccg    99470
gtttgaacttctcggaggcttatttacactatgaggggaatactgcctactgaagcctcagtgatgccag    99540
acaccctccctgccaccacattcaagtgtcccaggtcaacttcagactgctgtgtgctagcagtgagaattt    99610
caagccattggatcttagcttactgggctccgagggggtgagtcagctgagcaagacaacttggctccc    99680
tgacctcagccccctttttagggggagagaacagttctgtctcactgcggttccaggcagaactgggcat    99750
ggaagaaacaaaaacaaaaacaaaaacaaaaaaaactcctgctgctagctcagtgtctgcccaaatggct   99820
gcccagtttgtttgtttgtttgtttgtttatttatttatttatttttacttttaagttctaggggtacatgtg   99890
cacaacatgcaggtttgatacatgggtatatatgtgccacattggcttgctgcacccatcaattcatcct     99960
ttacattaggtatttcctaatgctatccctccccaagcccctcagtgcctgacaggcctccatgtgtg       100030
acgttccccaccctgtgcccaaatgatctcattgcttcagtttccacctatgaatgagaacatgtggtgtt   100100
tggtgttctgttcttgtgacagttactgaggatgatggtttccagcttcatctacgtccctgcaagga     100170
catgatctcatccttttttatggctgcatagtattccatggtgtataagtcccacatttttcttaatccgt   100240
ctatcattgatggacatttgggttggttccaagtctttgctattgtgaattctgctgcaataaacatatg    100310
```

FIG. 11A-20

| | |
|---|---|
| tgttcatgtgtctttataggagcatgatttataatcctttgggtatatacctagtaatgggattgctggg | 100380 |
| tcaaatggtaaatctagttcttgatctttgaggaatcatcacactgtcttccacaatggttgaaataatt | 100450 |
| tacgctcccaccaacagtgtaaaatgttactattactccacatcctctccagcatctgttgttcactgac | 100520 |
| gttttaatgactgccattctaactggtgtgaatggtatctcattgtggttttgatttgtgtttctctaat | 100590 |
| gaccagtgaagatgagcattttttcatgtgcctgttgctatataatgattcttttgagaagtgtctgt | 100660 |
| tcatatcctttgcccactttttgttggggttgtttgcttttcttgtaaatttgactttgagttgttttgt | 100730 |
| agattctggatattaaccctttgtcagatgggtagattgcaacaattttctcccattctgtaggttgcct | 100800 |
| gttctctgtggtggtagtttcttttgccatgcagaagctctttagtttaattagatcccatttgtctatt | 100870 |
| ttgggttttgttgccattgcttttggtattttagtcgtgaagtccttgcccatgcctttgtcctcaatgg | 100940 |
| cattgtctaggattcttctaggatttttatggttttaggttaacatttaagtctttaatccatttgaat | 101010 |
| taattttttgtgtaaggtgtaaggaagggatccagtttcagctttctacatatggctagccagttttccta | 101080 |
| ccactgtttgttaaataggaatctttttcccatttcttgttttttgtcaggtttgtcaaacattagatgt | 101150 |
| ttgtagatgtgtgtgttatttctgaggcctctgttctgttccattggtctatatatctgttttgtaccag | 101220 |
| taccatgccatttttggttactgtaggattgtagtatagtttgaagtcaggtagtgtgatgcctccacctt | 101290 |
| cattcttttttgcttaggattgtcttggcaatgcaggctcttttttggtttcatatgtactttaaagcagt | 101360 |
| tttttttgtttccaattctgtgaagaaagtcattggcagcttgatgggggatggcattgaatctataaatta | 101430 |
| ctttcggcaatatggccattttcatgatatattattcttcctatccatgagcatggaatattcttccattt | 101500 |
| gtctttgtcctctctttatttcattgagcagtggtttgtagttctccttgaacaggtccttcacatccctt | 101570 |
| ttaagttgtattcctaggtattttattcttttttgtggcaattgtgaatgggagttcacgcatgatttggc | 101640 |
| tctctgtttgtctgtgaatggtgtatgtaattgattttgtatcctgagactttgctgaaattgcttatca | 101710 |
| gcttaaggagacttggctttgagataatgggggttttctaaatatatgatcatgtcatctccaaacaggta | 101780 |
| caatttgacttcctcatttcctaattgaatatccttatttctctctcttgcctgattgccctggccaga | 101850 |
| acttccaacactatattgaataggagtggtgagagagggcatccttgtttgtgctggttttcaaaggaat | 101920 |
| gcttccagttttgcccattcagtatgatattgattgtgggtttgtaaaaaaatagctcttatatccttg | 101990 |
| agatatgtttcatcaatacctcgttattattttgagatatgtttcatcaatatctagcttattgagaatt | 102060 |
| tttagcttgaaggctgttgaattttgtcaaaggcctttatgcatctattgagataatcatgtgcttttg | 102130 |
| acatcggttcgttttatgtgatggatgacagttccatgtataatgcttgaaccagccttacatcccagggatg | 102200 |
| aagccaactagattgtggtggataagcttttttgatgtgctgctgggattcagtttgccagtattttactga | 102270 |
| ggatattcacattaaagttcatcagggatattggtctaaaattctcttttttttgttgttgtgcctctgcca | 102340 |
| ggctttgctatcaggaagttcttggcctcataaaataagatagggagaattccctcttttttctattgatt | 102410 |
| ggaatagtttcagaaggaattgtaccagcttctctttgtacctctggtagaattcagtctgtgaatctgtc | 102480 |
| tggtcctggactttttttggttgtaggctattaattgttgcctcaatttcagagcctgttattggtcta | 102550 |
| ttcagattccattctcttcctggtttagtcttgggagggtgtatgtgtccaggaatttatctatttcttct | 102620 |
| agatttttctaacttatttgtgtggaggtgtttacagtattctctgatggtagtttgtatttctgtgggat | 102690 |
| cagtggtgacgtcctttttatctttttttattgcatctatttgattcttctctcttttttttctttattag | 102760 |
| tcttgctatcagtctatcaattttgttgatcttttcaaaaaaccagttcctggattcattcatttttga | 102830 |
| aggatttttgtgtctttatctctttcaattctgcttggatcttagttatttcttgccttctgctagctt | 102900 |
| ttgaatttgttcttgcttctctagttctttttaattctgatgttgaggtgtcgattttagatctttcctgc | 102970 |
| tttcccttgtgggcattgtagtgctataaatttccctctacacaccattttaaatgtttcccacagattct | 103040 |
| ggtacattgtgtctttgttctcactagtttcaaataacatcctttattctgccttcatttcattatttac | 103110 |
| ccagtagtcattcaggagcaagttgttcaattcccaaatagttgtgcagtttcaagtgagtttcttaatc | 103180 |
| ctgagttctaatttgattgcaatgtggtatgagaaacagtttattgtgatttctgttgttctgcatttgc | 103250 |
| tgaggagtgctgtacttccaattatgtggtgaattttagaataagtatgatgtggtgctgagaagaataag | 103320 |
| acatttttgttgatttggagtgtagagttctgtagatgtctattaggtctggttttttgcagagctgagttc | 103390 |
| ggttcctggatatccttgttaacctcctgtttcattgatcgtctaatattgacagtggggtgttaaagt | 103460 |
| ctcccattaacattgtgtgggagtctaagtctctttgtaggtctctaaggacttgctttacgaatctggg | 103530 |
| tgctcttgtatttgggtgtatatatatttacgatagttagctcttcttgttgaattgatcccttaccatt | 103600 |
| atataatggccttctttgtctcttttgatcttttggttttcaagtctttatcatagactaggattg | 103670 |
| caaccctgctttttttcttcttcttctttacgttttttttttttttttttttttttgctttctatttgcttg | 103740 |
| gtagatcttcctccatctttttattttgagtctatttgagtctttgcacgtgagatgggtctcctggatc | 103810 |
| cactccagacgctgtgtgcctgagtatcactaggagaggctgcagaacagcaaataattctgcctgattc | 103880 |
| ttcctctggaagctttgtttcagaggggcacaagccagatgccagttggagctcttctgtataaagtgtc | 103950 |
| tgtcgacccatcctgggaggtgtctcccagtcaggaggcaagggggtcagggacccacttgagaaggcag | 104020 |
| tctcttccttagcatagctcaaatgctgtgcctgagatccactgctctcctcagagcagttttaattctg | 104090 |
| ctgaagctatgcccaaagctgtcccttcctaggtgctctgtttcagagagatggatgttttttttctat | 104160 |
| aagtccctgactggtgctgctgcctttctttcagagttgccctgccagtgaggaacaatctagagaggca | 104230 |
| gtctggccacagatgctttgctgcactctggtgggttctgatgaaatttcgggctgcttttttttaatct | 104300 |
| gtgaggggaaaacctcctactggagcctcagtaatggcagacaacccctcccctaccaagcttgagtgtc | 104370 |
| tcaggtggacttcagagtagtgtgctgccagggagaattcaagacattggattctgctgggctc | 104440 |
| catgagggtggaatctgctgaacaagaccacttggcttcctggcttcagccccattccagggggaatgaa | 104510 |
| aggttctgtctcactggattatgaaaaaaaaaaaaaaaacctcctgcagctagctcagtgttggcccaaa | 104580 |
| tgatcgcccagtttcgtgcttgaaaacaagggccttggtggtataggcacctagggaatccccggtct | 104650 |
| acaggttgtaaaaactgtgggaaaaacatagtatctgggctatgtcacagtccctcatggtttccatttg | 104720 |
| ctaggggaggaaggtacctgtcgccgtgcacttcccaggtgagtcagtgccccatcctacttctgctcac | 104790 |
| cctccatgggacacatcctctaaccagtccaatgagatgagtgagtacctcagttggaaatgca | 104860 |
| gaaatcacctgccttctgatttgtctcactagaagctgcagaatagagctgttcatatgtggccatcctg | 104930 |
| ccagatcctccctaatttatatgttagtatattttcacacacactcacacacatacacacatggca | 105000 |
| gcactaaattatattctctaaatgtacctacagatacttaatcatttgcacagccactatcattttatgc | 105070 |
| ttgatggcttagacaagtaactctcacttgtgggtggttttggccaccagggtcattcagcactgtctg | 105140 |
| gagacattttccacagttaaaactgggtaggaggtgccaccatcatctagtagttgagttgaaactgggaatgc | 105210 |
| tgcaaaataccatacagtttagaggcggcatctctacaacaaagaatcatatggttcacaaatcattatc | 105280 |
| attgtgctgagatgcggcaatgctgagcttcagactatagcaatttttgtcaaatttgctaaatttcaaa | 105350 |
| aaatgaaggaataaaaaaagatagctctcaacctgtgggtattgtgaatgcctaacttagacttaggaag | 105420 |

FIG. 11A-21

```
cgtacaggtgccettgggcttgtcttctttgtctgctgctagtttataattgttcactgcccatcaggac         105490
cttgtggggtatagatttagatagaggaaggatttgatcatacaggtgggtcagtcataaccatatgtg          105560
agtcacagtctcactcacattgagtttgagaatttaaggcatgggctggaattcctcatggaactgacat         105630
tataaacctgggaagaaatctacccactgaattccacttgagctgtctgtttcagcaactgttcaatact         105700
ttgaggttacatactatctcatttaatcccaacctgggatagtgtgtaataccaaattctttacagctac         105770
atgggattaaattaggtagtatgtgaaattccaaatagtaattggtaaagtgatgcctaatgaatttga          105840
atgagctgctgccagcctacttagtactaacagtgagctaatagcaccttgtgtccctgtacccagaagt         105910
cttcttgcaggactgtagcgaacatgtcagcatgttgtctacgttgactggacatcttctgttctcttc         105980
agcctttgcctgtgtatgctcctgtcctgctctgcacaatttaatgaagcaggtgggacacactagttta         106050
ccctttagtagtctgcatagattgacttgcttccctcagttcacagagatagcttcccaggatacagat         106120
ttatctgaattacaagttgatggcttcattgttcacaatagcaaagacatggaatcaacctaaatgccca         106190
tcagcggcagactggataaagaaaatgtggttcatatgtaccatgaatagtatgtagtcataataaaag         106260
aatgagattatgtcctttgaaggaatatggatggaactcgaggctattatccttagcaaattaatgcaga         106330
aacagtaaaccacatacttcatattctctcttataagttggagctagaaatgagaacttacgaacacaaa         106400
gaaggaaacaatagaaaaggagcatattggagggtgggcagtggtaggaggtagaagattaggaaaaat         106470
atttattgggaatgaggccttgtatctgggtgatgaaataatcagtacaactaatgcctgtgacataagt         106540
ttacctgtatggcaaacttgcacacctacccctgaagccaaaataaaagttataaaaaaggtgatggtct         106610
cacctattctcttggggaaggctccaaaagtaacagctacctctagttaaaaatcttctggttaaaaaaa         106680
gaagcaaccaaacacgacatcactcttgttttcttgtctgtctcttaattattcagaaatgggattgc         106750
tgcatggcagacatccgaatgttgtctacagtacaattcagagttagtagcaaacacctaaatcagccat         106820
ttgatgagatgctatttgtcactttcaaagttacaatccagattttcagtgcattttcatccaactctgt         106890
tgaactttccaggatgtcatgtactatggaatttcccccagtaggtattattgttctgtgatagatc         106960
cagttccaatatgttttattaaaaagaaaaagccatgtgatgtattttgttcaattgattacttaaatga         107030
aatggataactatttctgatgcaaatgctctgagtaaccacaaattcctcagaaacacatttgcatac         107100
tttgagatgaagaacactctaaatgcaccctcctgtgacacctagtgaaacgttttctgtccctagagg         107170
atcatttgacatactgtccattgctgcacaacattcttttattgtcacaggagcagcgatttccctaggg         107240
atagtcatattatccttgtagggaccaattgaggtggtgaccctttaaaagttgactccagtcttaatgg         107310
gaaagtaactcaaatgtagccttagattttaaatgagatacaggggtgaagaggataccctctcaggcat         107380
gcagcagcttactgcaaagtcaggataattgcatcaacactttagttatgaaagaagtcttcaagagac         107450
cagcactgaagcatgtacttgaaatgcaccatcttgtacagttttttttttttttttacaagaaactgagat         107520
tcagaacagtgaagtatgtagcctaaatatatatgtgcacttgagtagaacaaggaaaattcgtgtccaa         107590
agtctacactcttttcatttgatgattttccccttgtggcctgataaatatccacatcacaatgacagga         107660
tggcctggatgcatgcttctattttgctcctcatggaaaacttttagatctgcatgcatatccccttagg         107730
aaagagtgaaaattgccttaaacatttgagaaaaagttcttttgataaccctctggtaaacaatagtga         107800
aattggtaggtgtcattattatcacttgcataacctgtacaattcttgaacgtcggtttgttcattcaac         107870
atagatgtgatgagtgttttctaaatgtcaggcattgtttctggtgataggatatacagccaggattaag         107940
aaaagtgatggacactaggcatggtgactgacgcgtgttatcccaacactttgaaagtttgattgaggag         108010
gatctctttaggccagcctggataacatagagacaccatgtctacaaaaattccaatgaattgcccgga         108080
catactggtgcatgcttgtagtcccagctactcggaggctgaggtgggaggttggctttagcccaggag         108150
ttggaggctgcagtgagctgtgatagcaccactgccctgcagctttggcaatatggcaagacaccatctg         108220
taaaaaaaaataataataataaagacaagttatgtttttgctattgtcgactatgtgagatggcactat         108290
acacattcatatacaaatgaataggaatttcatagagagatgttgtggatttcatggaagagccagccag         108360
tgttctaggtgatcattgtgtggcttcattattcttgtctggtttctcccctccttaggttgcatttggag         108430
ttttcgaaagacttatctttctgcaggctcgcctctgagctttgtctccttggagccacctcacttagac         108500
agcttcggatgtggatgcagatttgaaccATGTTGCGTCCCCAGGGACTGCTATGGCTCCCTTTGTTGTT         108570
CACCTCTGTCTGTGTCATGTTAAACTCCAATGTTCTTCTGTGGATAACTGCTCTTGCCATCAAGTTCACC         108640
CTCATTGACAGCCAAGCACAGTATCCAGTTGTCAACACAAATTATGGTAAAATCCAGGGCCTAAGAACAC         108710
CATTACCCAGTCGAGATCTTGGGTCCAGTGGAGCAGTACTTAGGGGTCCCCTATGCCTCACCCCCAACTGG         108780
AGAGAGGCGGTTCAGCCACCCAGAATCCCCATCCTCCTGGACTGGCATCCCGAAATGCTACTCAGTTTTCT         108850
GCTGTGTGCCCCCAGCACCTGGATGAAAGATTCTTATTGCATGACATGCTGCCCATCTGGTTTACCACCA         108920
GTTTGGATACTTTGATGACCTATGTTCAAGATCAAAATGAAGACTGCCTTTACTTAAACATCTATGTGCC         108990
CATGGAAGATGgtgagtacctcactggaacagaaaacaatacttcttgtgcagtgtgtggagagatttac         109060
caggagggttttataatgtctctgcatgatcttttctataacctgttttattttatttaattttattttt         109130
catattccaaatgcaattcttgcagcagcttaccacatgttccacttgtatatattgggacatctactgg         109200
atggacaaaactataaataatgactttattttcatatattacctaattaatgttttataattttatttgc         109270
agatgaaaattaacatgagcatatagtgttgcatgttatacctgaatcatctgtaaaggaatgaatccat         109340
agaaaaaataatagaattaagtacactaccatgctccagtttacaaactgaaagatagagaaaatggttc         109410
tttctgccataatgacttgagatattagcacctttttgagttttgaaagaaaaactttattttttttaa         109480
tatacaagcatgaggtagttcatacaatgataggatttcattgtttagaatccattttcttaatgtaaat         109550
ttggactttgttttcttccaagatccactacgatcaaatgacaaaatatagtcagatgattctagctaca         109620
ttagacgtgatgtgtttatattttaaaaattcctctcttttttctataaaacaccaatgaaagtctgtaa         109690
acacaaaaacatttaatatattaacctaatgttagtaaaacatgaatagttttatgtctgtatagatttc         109760
aaattcagatttcctcgaagaataaccaaagttatgccacagtggtatcatatttcccggttagcatttc         109830
catatgccattttagatgaggagaaaggacaacagagaacaaaatataccctggaaagaaaggaaataat         109900
ttgtgagaataatagacatatctaatgtagaaactagagcttgtcttttgcataaagctcttcgtggaga         109970
atgtgataaatttctttatggagaattttttcttctcattgttctttacactttaatacctggaaaat         110040
attttttcagtaaaatttggctgaaagtattaaataaacaattacattaattcattgatctccaaaattat         110110
attgcatctgtcagattactctctctccaggtaattgctagttagtctaagtagagcgtcattaaaaact         110180
agaccagggttgtgtgccattgagattacaaattgccattgagattacaaggacagttcagagtaaaaa         110250
agtaaaggaccctgcttcatcatattagtggtttctagaatattgccttgtcattagggtgacagatct         110320
cccaatcatctcataaaatccaggtctgaatgtgactgaaggagtcaaactgacgtttggatgctgtact         110390
tccatggggtgttctgtgctgtctctgtgcctaatagtccccttgtgcatgtgtgtgatgagaaagagc         110460
tgtcaaaatctattagggttctcatttgagcagccacctgggttgagatctttctcataaaggaactatt         110530
```

FIG. 11A-22

```
caaaccaaaagtaaaaagaatggaatacaaaaattcagagaaaaacccaaacaggacaaagtattacaa    110600
ttgcttttataatacattggatatgctagagtctaggacctggtgattttatagagctagccttggcaac    110670
aatgaatgcacttcaaataggatgcctcctcatataggatgttggatggaatgagaccacccatgaaaaa    110740
aatcaatagcttccatgacagcagagccctgtaggtacaattgtgtggatggagaccacaaacagggtgg    110810
acgtttcattgtgattcagtattgaattgtaatttggggagtataactctgtgaaaaatgctattcagtg    110880
aaaaagtaatccaaatttcataataaacccagttccacttctattctttagtcttttttgaagcaatatgc    110950
gcatacgatcttgaaaagggaatcagaaatttaatagtgactgaaaaggtagaataaatctccccacaat    111020
gtgtaaactttaaaattttgcttgtgagagttcaaagctacagccctgcatgtttacacaaaccacaagt    111090
cacagactatcgagttaggagggttttttgtttgtttcctcggttgttttttgtatctctatcaactcgat    111160
aggcaatacaaagacttagatatttaattattgttcattcactaagtgaatgaactctgcattcataaca    111230
acctactgaaatgttggcatcacgctgattctctccaaaggccttctcttaggcagtatctgaattcata    111300
tcagtgcttttgtttagcaggatagaaatattattatctggaattcagaattctactctgaccacttaga    111370
atctctactttttttgtttagctttgtctttctgccttgatcatatttgctaaaacttttcacattcttaa    111440
tttcataaaatgtgtacatttattaaaaatgcaaaaacagactttatttcagttaagtacttattcttaa    111510
atttaagaaataacttggatgagaagtgttggacatttctttgtagtacaatagtttcatgaaacataaa    111580
ttgttttttcggtagaaagcagtattttttataattcccttcaaataaatcacatcttgctgaagttgagt    111650
cttttcgttcaaattgtcatcatgatctactaagcttagtcttgagtctttataccaattacaaatttc    111720
tatatttgtaattagctatgccatacaaatttatttagattttatatattataaattttctttattgtcta    111790
gatgacaggttaattaacttaaattgcatatttaacattttgataggtgctcaagtaaggtcaaaatcaa    111860
agccagtcagaagctctagtaggacacatgggatattgctcacaaggaagagttggagaccgcatccgca    111930
tggtgtgtgtgtatgtgtgtgtgtgtttgagagtttgtgtctacatgtgtcagagagaaagagccagagg    112000
aaaagagggggtaactgagtgactattttgaagaagcagtgcagaaatatggcttggtagcttgattaaac    112070
aaaactgatgaaagtcaagctgagaagttccaatctcacatactaagttcatgtcagttcatacatgaga    112140
gcatggcactacaatttgagacttctcttggtcaccaaggagactgaacacagaaagcaagctatggaa    112210
acgcttcaggttttaatgagaacccttggtattgaagtgaggttaaaaagtaacggaaaaataaaagac    112280
acatttgaagtagttgctcacacaagatattgtattaaatataaagcttggaagagaaaaagccgtaag    112350
ttgagtccaggggtgtcttggggaatggacagagccaaggaaccacttccggagtgatttacaccctgtgct    112420
ttctctctgtatccttggacatacatcttaaggtcttattcttgaatgatttcagggcaaaaagcccttc    112490
cattcttcataaaggtgtgtccggaattggtgggttcttggtctcactgacttcacgaatgaagctgccg    112560
accctcgcggtgagtgttacaactcttaaagatggtgtgtccagagtttgttccttcagatactcagatg    112630
tgtctggaatttcttccttctggtgggttcgtggtcttgctgacttcaggaatgaagctgcagaccttcg    112700
tggtgagtgttacagctcttagaggcagcgcgtctggagttgttggttccttccggagtagttcatccct    112770
cccggtgggttcctggtctcactggcttcagcagtgaagctgcagaccttcccagtgagtgtcacaactc    112840
ttaaaggcagcgcgtctgcagttcttcattccttcctgtgagttcgtggtctcgctgacctcggtgagtg    112910
agctgcagacctttgtgaaggtgagtgttacatctcataaagctgcgggacccacaaaaagtgagcagca    112980
gcaagatttattgcaaacagcaaaacgaccttccaccgtgtggaaaaggacaccagcagattggcgctgt    113050
gtgctttgggcagcctgcttccattcccttatctggcccacccacattctgctgattggtccattttac    113120
agagagctgattggtccattttgacagagtggtgcatgtacaatccctgagctgactagacacagagtcgat    113190
tggtgcatttacaatcctctagctaggcataaaagttctccaagtccccaccagattagcagatataga    113260
gtgccgattgctgcacatacaatcctccagctagacgtaaaagttctccaattcccagtcagcctggtgt    113330
ctcagcctgtgatcccagcactttgggaagcgaggtgggcggatcacgaggtcaggagaggagaccatcc    113400
tggccaacacattgaaaccccgtttctactaaaaatacaaaaaaattagccgggtatggtggcacgcgcc    113470
tgtagtcccagctactcgggaggctgaggcaggagaatggtgttaacctaggaggctgagtttgcagtaa    113540
gccgagatctcgccacacgcactccagcctgggtgatagagagcaaggctcaatcttaagaaaaaaaaaa    113610
aaaaaagttctgcaattccccagccgactcaggagcccagctggcttttacctagtggatcccgcgctggg    113680
gcctgccagtcccgtgcccgcgcctgcactcctcagcccttgggctgtcaatgggagtgggccctgcag    113750
agcagggggcggtgcccgttggggaggctggggctgcgcaggagcccaccgttgggggggctagggcatg    113820
gcgggctgcagatcctgagccctgtcccacaggcccgtgaggccctaggggataattggagctccaag    113890
cggggcgggccgcagtgctggggacccagcgcaacctccgctgctcctggcccgagtgctaagccccctt    113960
tctgccctggcctgccactccgagtgctgcccgcgagtgggggcccgccgagcccgggcccacccagaa    114030
ctcgcgctggcccgcaagcgccgcgcacagcccagttcctgcccacacctcttgacctctccttccacgc    114100
ctcaccgcaagcagagtgagcgggctcccgcctgggccagtccagagaggggctttcatagtgtggtgtg    114170
ggctgaagggctcctcaagcgcagctggaatggacgccgaggatccgaggggcgaggggaggctgctag    114240
cacgttgtcacctctcaatgggactgaaaacccctgggaaataaagaaaaaaatataaatggaagtcatt    114310
attgcccaggtgcggtggctcatacctctaatctttagtaggcggaggtgagtggatcacttaaggtcag    114380
gagtttctgatcagcctggcctcaggaggctgagacagcggaattgcttgaacctgagaggcagaggag    114450
gttgcagtgacccaagattacaccactgcactccagccttcgtgacatagtgagacactgtctcaaaaaa    114520
agaaaacagaaaagaaagtcactatcattgtcttttcattgtaggataacagcaaatgccattgtg    114590
atttctagagaagtgaaattctgtttttgtttgtttgtttgttttgctagcaataacaatcgaaaaaggaa    114660
gctatttaaaaaagagcagataattgaatgcaaggtgtccctatcatctttttcccaagatgaaacct    114730
gcgactttgaattctattacttaagtaaacatgccacgattagtgattgaagaccattcggtgaagctt    114800
ggagctttatgatgaaatataaacagacgtgacatggacattgacctgtagaaatttggacagttagtaa    114870
acgtagaggtagatgataagccacagcatcctagtgaaggaacaaagaaagttctgtgacagctcaggga    114940
caagttatgttttgaggaaatcttgatggaatctaaaatggttgagctgtgtcctgaagaatatttggg    115010
ctatagaagggattcatctattaagcatctgttgactggaacttttgaacacacaaatctatgttaagca    115080
gcttggcgccaatcgttgctgttgttactacttgggtgttaagtgtggcatggtaacagaagctctgctt    115150
taccacgtgctctttctgtcagtgccatataataaaagttattttattttttattcttattttttttttatt    115220
tagagacagggtcttgctctgtcacccaggctgaagtgcagtggtgcaatgctagctcactgcagcctcg    115290
actttctgggttcaaagaattcttcatctcagatttctgagtagctgggactacaggtgcactccacca    115360
cacctggctaatattttgatttttattttgtataaataaaaaatttatacaaattgttgctctggctgg    115430
tcttgggctcaagtgctctcccacctcggcctgccaaaatgctggaactactggcataagccattggact    115500
gggaccataaatgttttatgttatccatagctgctcaccatggcactttgtggggtagacaagctacct    115570
aagatgaaagggtggcagatgaacgacagggaaagaagctagaaagtcaactggctttgctagtgtttttt    115640
```

FIG. 11A-23

```
acaaaaaaatgcattcgcttcccttgtagacagcactggatgtaattcaagatataatttatagcacggt      115710
tttcatccttgaatatctcccatcttttcaggaagtcgtacaaacttttctggcattctgcgttagtgaa      115780
agggtgttggactatgtccagctggtagaaaataacctagcctcaatctggcattgagggaaaaattgaa      115850
atttattagaagggtggtgagatatccaaatttactgcaaaagtcgagaaatcagattgggagaagggca      115920
gatatgcagctagactttagaggcacctggaagaaatgagttaaaggacatcaccaatcttatgtctggt      115990
tctttgcttcttctggaaatagacttgctttacgtggtggtgagtgagagggttctctgcagttttcactac      116060
atgcattttgttttctcagtaccaccagtgaaggacaaagttccataattccatactaaaaatccctgg      116130
gcagagtttaattggctcagttgacgcaatagtaagaagtgataaaactgggctgctcctgggtataac      116200
agttggcaggggagaaggacagttcttaccacaaggtgtctggaatgagcaggcactgcttcacttcac      116270
tgtccaaaatatttttgaggagcagttatatgccaggcaagctttagaggctgagatttcaagtttacaa      116340
gcatttctaattttgagtgataggtacttgtaggcagaagaatcatggtccttgagagatgtgcatggcc      116410
ttcctcctcccttcacctgtcattgctggaacctcggaataggttgctaggcatggcacctgacttcttc      116480
aatactctgcctaagtattgacttcaaatggcaaaggggaattaaggttgtagacggaattatgtttgc      116550
taaccagcagaccttccaatagagagaattatcctcagttacataactgagcacggtatattaacagaag      116620
ccctccaatgtggatgcagaaggctcaagaggagatcagagttggagtaaagcagcatgtaaaagagata      116690
cctggacattgctggctttgagtatgagagagccaggagaaaggaatgtaggcagcagcgtttggaagct      116760
agagaggcagggaaactgattcttccttagcgcttccagaaaggagcccaacagccctgctgacacctca      116830
attctatccccatggaagaaactgtctcttggaagaaactttacctctggaagaaaccctagccccatag      116900
aagaaactctgaagaaactgtaaaagaataaatgtttgttgttccaagcttactaaatttgtggagattt      116970
gtgatagtggtaatagaaaactaaggaagagttttatcacccttttaatatgatttgaaattcataatgaa      117040
gtattactctgaaaacgaagttcagagtcactgaagtcattaggttttgagccttctgaccccaagtccg      117110
ttctgggattctacttccaataatttctagttgaaaacactccttgggcacttggagctttctgtcttcct      117180
caagaatgtcgaggagacaatacagatgactcttttagggcagatattttttcagattttttaaaaaatttc      117250
tcttctaaactttgagtgagagttaccctgtccctgagcgggatcttgcactgttacccaggctctagtg      117320
cagtggcacagaagctcactgcatcctcaaattcctgggcacaagtgattctaccacctcagcctcatga      117390
gtgtctgggactacaggctgatactgtattaagcttcagagaagaagcatgtccaggttcctgcaaatta      117460
gaaaatggtagcagatatatatttttttttcaagaaggagttttgctcttattgcccaggttgggggta      117530
cagtggtgtgatctccactcacagcaacctctgcctcccaggttgaagtgattcctgcctcagcctcc      117600
tgagttgctgggattacaggcatgtgccaccatgcccagctaattttttgtagagatgaggtttcaccatg      117670
ttagtcaggctggtctcaaactgctgacctcaagtgatccacaaagaaacaatgaaaaaaaaatcccta      117740
ttagatttacattacaatttttcagccaccatgactggctagtttttaaatttttttaaagagttgtagcc      117810
ttccaggctggtctggaactcctagcctcaagtgatcctccatctccaggctccagaattctgggattac      117880
agacataagccaccatgctcagggacattctgcaaatttgacattttgcattaggttaatatagccccaa      117950
ggcaaattgtcctaaacagcatattccacagatacactattttgacacaggaaagtaataaagggtcatt      118020
taaatttttttcagacagctatgacagatttccagagatgatggctttgaatgacttataacaaaatac      118090
ccaaatggttctttcatcatctgcctccatagagtttcacttgtgatggtggctgcacctttacatttct      118160
tattttcctacttacaaacactgctgacaaaatcttctgagctctccattccttccagctacaacttaac      118230
ctgtggtctctgctgggcaaagtgactcacctttttgaatgtacgccttgtttactcctccagccaaaact      118300
tgtttgctggagttggaatgccagtttatcccccttagcagatcattatgggcaagtgactcagcttttcat      118370
gggacacagtgcccttatgtctaaaatagaggtagctgagaggtttaaggttataatccatataaaatgc      118440
ttagtatccagcacatacaagcaccctgtaatctgatgttagtgcaatatcagtaataatagaaaacaga      118510
acttgacaatttcagcaaaattgcatgtgcatagtgggtctggtatgtgtattaatccaggcataataaa      118580
tgctgatcatctgtgacatagctgtttactgttgtagtggaggggtaagctgaagaggtaagaccaacag      118650
cccattatttctggtggtttctagtatggttttaacaaatgggaatttcaggaaaagtaacactttttaa      118720
aagagctgactgttatcattctgctttattcctgattttagtcttttttgagctcctgttgtcaaatggat      118790
tttgagcatatgtgaattagataaattattcaccatgaaaggattagaataacattttggaaaatgccct      118860
taaactatcaagtggcaataacactactctttgtgtgtgatattaaagagaaaattaattctcattttctt      118930
gttgtctagacacacaaagtccaattgtatgcatgtaatcacaaaatctaggtgaaaattgaaaactatg      119000
ttaacagagtgagaccgatgtttaaccaatcaacatcgacatgcaactaggtgacaattattaaaattac      119070
tccagttttcatctgtcagtttgatgtttgacattgtgtagacatagcttgccagtaaagataattatga      119140
aagattattaaataaagatctccctgacatggattaattgaaagtatttagtatttttttttaagcacag      119210
ttaaactggggtggatttctgatagcatgttttctctcccagcacaaaaagcttcagcaattgaatatt      119280
gagtaataatcttattgagggtttggaaattatgtgtgttttgaataatattattggtagtatttggtag      119350
tatgaattatgcctgtttgaataattaagaagtagcttttcctaatgaagaacattttccattacataca      119420
taatcttccagtacatgaattttaattcaatttacaatttagattcttgtcataatttgaacatagatt      119490
acctagaatataataaaaatcaaattttcatatagtacatatcataattttttatcttagaaattgtcaga      119560
gatagaaactttaggtacatctagtcattggaatattttggccatttaaaacaatagcttttattˈtat      119630
ttgtggagtcttgcttcctaagatgttgtagtctaatttttgtcaattaatattgctgatttgaatactg      119700
ttatttattttggatactactttagccaagctatttactattattcattttttattttggagacatagt      119770
cttgctctgttgcccaagttggagtgcagtgtggtgcagtatccacaacctctgtctcccaggttcaaga      119840
gattctcctgcctcagcctcccacgtagctgggactacaggtatctgccaccacgtccagcaaatttttg      119910
tattttagtagagatgggtttcaccgtgttggccaggcttgttttgaacttctgacctcaggtaatcag      119980
cccaccttggcctcccagagtgctgggattacaggtatgagccaccatgccttgcctagccaagccattt      120050
aaactttaaatatttagtgtcatcacttattaaaaataagactaatatgattataggtcctctgattttt      120120
ttttttagaattatagtgatatgggagtaaataaatatatacgaaataattataaaatagaaagattagt      120190
gcattcttagaactttaatgtcatgttaattgaatgttaatccaatgactttatctttcatttcaagatt      120260
ccttgcctgaatgaagtagtggaagccctttgttgacaatagqtcctatcttcctattccqtttttqqtt      120330
ttcctaaaccaggttgtttacataatgactaagtttaacattttctctttatgtttaagcatctcttttcc      120400
ttggtgcaatcacagccaaactgcagtgaaaacaaacagaaattgagaggttgtgagctccagatttcag      120470
agccacagagagtttgtgagatcaaaaatataatttattgtgaggtcaataaataaattagcctaccta      120540
aatcacacagtcagtttaaggcaatggaaccagagggaaagactccaaaagagtgacctatctatggaat      120610
agctactggtaaaatgaagcaacaatgagacagtgtagtctccaccttattatttcaatcaatgttctg      120680
tattgaggttcagagaagcaggtccaggttccacaaattaaaaagtggaggattgctcctgtaatccca      120750
```

FIG. 11A-24

```
gtactttgggagcctaggttgggcttcgcttgagcccaggagtttaggccagcctgggcaacatgacta    120820
aaccctgtccctaccagaaaaatgaaaagagttgggcatggtggcactggcctgtagtcctagctactta    120890
cagggctgaggtgggaggatcacttgaggctaggagatcaaggctgcagtgagccaagaccacagcaggg    120960
cactccagcctgggtgacacagtaagaccctgtatctaaaaagaaataaaggaaaaatatttccctgtt    121030
agattttacatacctgatgatgactttaatggtgaaggtaagcattggtgtgtgtgtttgtttgtgtttg   121100
tgtgtgtgtgaatggtgttgaaggaagcccataggaaaagtacccataatttattcaagatcaagtatgt    121170
tacagttttcttggcaaatgccaagttataaaacacataaaccactctacaacctcttcttccctaaaac    121240
cccaaacatcttgaagtctccttcaagccagatatcctcttggtcctctgtgcaagttgtctgcacagtc    121310
ctcaggtttgtctttgggtaagtccctgttgccatcacaaagaaagaacacagcaggtattgatttgtct    121380
cagacaaaggagctcttctggtgggtttcaacaagatatgaaaattctaggttcatgaacactcccttt    121450
tcttccttaaaaataatattttttagctacattctactccactctgtcttttatgacataatcattcactc    121520
aaccagggaacacccactatttgcctaacatcctatctgcctatcacatatggactttagcctccagtta    121590
gaccaatgatgctattgatctcctaatcccaatgtatactcttttggatattttcatctctttttccattgc    121660
ttattatctttagagacattttaggtagctcatttaaaaattattaataaataaatcattatttgcaatt    121730
agcatagacaaggacttaggtgagtgttaagtgggtatgcagagagatctaaccccactgctggaaaaag    121800
tgagtgggaaagtcccattgatatgtgacccaactaaaccaacattctataaaaagcacaaagccttcag    121870
cgactgctttaggatttcaggggaaggaaaatggaggcaaatgtgaaagttgagttgatgtcttcatttc    121940
ttttctttctttttctttttctttttttttttttgtttttattttatttatttatttatttatttatttatt    122010
tattttttgagacagagtctcactcttgataaccaggctggagtgcaatgggatgatctcagctcactga    122080
aacctccacctcctgggttcaagcgattctgctgcctcagcctcctgagtaaccgggactacaagcctct    122150
gccaccatgccctgctaatttttgtatttttagtagagatgggggtttcaccatgttggcccagctggtct    122220
cgaactcctgacctcaggcaatccacccacctcagcctcccaaagtgctgggattacaggcgtgaactac    122290
cacacctggccgaaagtggatgtttttctgtggcggttccttgatagaaaggttttcatccagtcttgaga    122360
tgaatatacagagtgtaaacacatggttgtgcagtgagggaaatgctgtctatgtttcctaaaactgaggt    122430
tcttgtttattgcttctttagctgcacaaagacataacacatgcaaaattggggagaaaggagagataaa    122500
actatgacaaagctggaggcaatgtgcaatgatgttgtaatttaacatgcaaagtactccactttagtatt    122570
ttttacattgttacactgtgacattgcaggattcataagtggaatttcatccaaatttattctaatgcat    122640
attttttctacttagcagactatacaatatggttaaatcaaagaacatgaggttttgttcttaccaaat    122710
tcaaaaatacttttatcacctgttgtttaaatcattaacacaaaagattcagtctcccacaaatttct    122780
aatgtagtaaaatccttcataatttatattcaaaatatattaattcagatgactagtatgaaatcaat    122850
gaaatcaagttataaatttgcatgtttctaaaatgtttaaatttaaaaatgaaaagtaagccctaaaaaa    122920
ctgcaggtttctcaagaatattaaaatgttaacaaattatttaattttgagctaaaatcagataataatg    122990
ggaacagatttcaccactgcacattctacagggatgttttgcattttatacttgttttgttttgttttata    123060
ggaggagattttggtatattaaatataactagacatttacctggacataaatggtagaatcaacttag     123130
actctaatcacagaatgataacatcttccaagtagaaggagcttttggggtcatttaaccaaaactcttt    123200
caccttacactatttccatgttcatgttaacctttggtactctaagaagagatgaactatcatttctta    123270
agttctagaagttgaatttaattatgattttacaaatctgccatctccagtagatggtaaatgctttgaa    123340
gacccagagcatttttgagatatataaataatgagttatatatttttattgcatgaaacaaatgaatgaacctg    123410
taatgcctggccaccaccctattttttttttgaacctgaacaatgaagatgtttgcggctttttctcttcatt    123480
atgggttgagagggtaggggagggatataattaggagaaatacctaatgtaggtgaaggattcatgggtg    123550
cagcaaaccaccagggcacatatatacctatgcagcaaaactgcacgttctgcacatgtaacccagaatt    123620
aaaagtataattgaaaaaaggcattaaagaaagggaaaggttggtgatgtttacctgagcactctcacaa    123690
acagagatgaagcagttttgaatgttaccttcctccttctaacatatagttctgaaagtcttagaaaacat    123760
gttatttattccttccaggtagtcttttgcaagcatcctcctcagtgtcaagcatttattctcatgcat    123830
cccattatgtgttatgaatacacccagagtttatgtgaaattttttatttttttattttttggcaaatgt    123900
attaaactcttggtttgtatattttgaactggaagccacattttttgtaatactttaaaagcaaaatattt    123970
tataatatgctttagaaattaaaagaaaataggatacctccattcctatgacaaactctcagcatacag    124040
caaggcaaagctatttgctgctgaagctcaatttttccctgcagatgctgaatgtacaagaattaacagc    124110
caagccaggaccctgtttacctatgtttccctgaaatgccaagcccatgaggtgttacaaggagggaag    124180
acagcatacaaacatgatagaatgactaattaagctaattggttttatagtttttgagaaagcagttggttgc    124250
ctatgtttttttttttttttttgtgtgtgtgtgtgtgtgtgtggtgaagaaatatttgtatttcattta    124320
agtgcaactaatttctatttaaatttaagctgccatatgtatctactggctatagcattagagtgtttag    124390
ccttagcaacctcttattactatatactttttctttttctttctaacactttttaaaatatactttaag    124460
ttatgggatccatgtacagaacataggtttgttacaaggccataagccgccatgggtttgctgca       124530
cccatcaacacgtcatctacattaggtatttcttctgatgctatccctcccgtagccccccatacaccaa    124600
caggcctcagtgtgggatgttcctctccctgtgtccatgtgttctcattgttcagttcctacttatgagt    124670
gagaacatgcagtgtttggttttctgttcttgtgttagtttgctgagaatgatggtttccagcttcatcc    124740
atgtccctgcaaaggacatgaaattatcctttttatggctgcacagtattccatggtgtatatgtgtca    124810
cattttctttatctaatctatcattgatggacatttggattgcctattttaaatgcagtgagctataat    124880
ttgattgaatgcagaaggaatcatttccaagaaattaaagttcgaaggttggaaaataaccgagttcatc    124950
gttagggaaagcttattctaaaacttcggataaaatgagcttcctcttacattttattcaacttaagatc    125020
ttgtagttacttataatcatcattatcatcatcaaaaacatcatcagaatcatcaccatcatcattatct    125090
aaatttgagtagccatcagaagatattgtgagttcctgacttgagaaggattaatttctttgagatttta    125160
tactgttatttttaagactgtggagcatgggttagatctgtgttttaaaaactttgacagaccacattatt    125230
ggtaatagttttctcttagcatgggttttgatttgtgttacagttgaattgtgcgtctcaaaaaa        125300
aagttatgttgatatcttaacatctggttcctaggaaattcaccttatttggaaatatggtttctgcaaa    125370
tgcagtcaagttcagatgagttcatactgtgttagggaagattctaaacccaatatgattagcgtccttg    125440
taagaagagacagacacaggaaaggcagagccacgcgcgggcccagcccctgcaaatctctagaaggtgac    125510
gatattcttaaaacacttcgaaatcattggaagaaaattacaactgggctctgcctcctggcctgggga    125580
tgtaattagctgtatagaaaacactgtgataacctactaaggagagtagcctatcaagaagctcaggtgt    125650
ttggcaatcaactcatttctccaaatgcacaagtgaagaggcaactgttttttctcaatcctgcagcttg    125720
caaaggcaaagccagaacttgatttgaaaaaaatgctgccctgatttttacatatatccaggatggatatg    125790
tctattattagggcaggttatgagggataagtcaaggaactcctggaactgatgttaaacacagttgtga    125860
```

FIG. 11A-25

```
tcattgttgtaagaggagatgggacactgaaggaggatgttactggagttcttcaaagaacagatgaggc      125930
taccttcagtaagattcccattggatttatcccactgggacggaccagtagtttgagtcatacctctct       126000
gctgaacgtggaaacaaagtccaacatataactgatgccacatttgccattgtgaaaggaaagacagttc      126070
cacttgatgtcttgcagatgcaaggtgaaaaggaatagcctgtgtttgcagtgactggccttcgatgggg      126140
acccttcagagatgttggcatcaaagttagcaagtactggtatcttgcgcctctaaaaatcaaagcagct      126210
cactttttcagcactctcaaagagtggcctcagactcaccaagcctatattttacacacggcacctacag      126280
agagatctcccagtgaaccagaatagaccctgtgcaaaggccttcttttacagaagaatattacaaag       126350
tcttacatcctactgggcacaaccggagcatgcccttcccaagatgtgagcccagagatctggaaagat      126420
gtgcagctgtccaccattgaactatccatcacaacacagaaaaatcagcttgacctgccaagcgaagaag     126490
atttatgaacatctgaattgaacgaacaccatcagcaaggagactttataactacaggaactcgaaag       126560
gtttgaaaccgcaagctgcacatcgaaggcacagtgtctccaagccagccagtgcactttgcttgttgcc     126630
aatggagctgggggctctttggcatagacagtgaagagtgtgatgtgaagcctgtggaggtgaaactgc      126700
tcccccaggaagctgcagcttttctatgatcccaggaagagagaatagatgctggcaagccccacccagaa    126770
agcaggcagaagacaagtgctctgagaccatactttaggccaccagcaggaccaaaagggaacagatgcc     126840
tcaaccatcccaacagtgttgtcagagtgtcccaagggcttttcatggcaagtagcctctggccttctc     126910
cagcagtgcttcccaaagtatactctgtcacctgttttgcaatcaggttttgttagggcatattttattt    126980
tggtgtgatggttgaccctcctaaacacggactttcctcagactggttcaagatggaaaaggacttttctt   127050
ctgtttctcccaaagtgcaaccacagtgcagagcccacagtgggcttaggctgcctgggcctttccatt     127120
ctggttctgtcttttgaccatgctcagaattctggggaaaatgccttccttccctggtgaccttttcctg   127190
tttctaggcttctccacaagtgctgctattttgtgagctctggctcctgtttagcttttatatcagttct    127260
atcctcagtccagaaatgtatatgaggttgtgtccccttcagccatggcaacaatattgtaaaatgcta    127330
gtttttattttttaggtagtgctttctaaatggtttgcatgaagctacctgggtacatgttgaaaat      127400
tgatttatttggagtccacaccaaatctaataactcatttgggataaggcccaggaatctgcattttt     127470
taaaagttggccaccctttccaggtggattctgtaagttgtccctcaatgcacttggagaaatagtgtttt   127540
aaaagcagtggtccacaaagtattctgcttgtgtgccccagaagtattttgaaaaatcatgtattcccttt   127610
acccatctaagttgatatctaagattgttcatgggacattaaatagttgacataatttgtatttgctgct    127680
ttcacgtaaatattggtatttaaaataaaactgttatatcaaaaaaaagaagaagaatatgcaacgac      127750
aaagacaaaaacaaggagaacaccatgtgaggatgaagtaaagattgaagtgattcatccctaaactag      127820
ggagcactgttgaaaactatgaggaactaagaacagaagcatgaagcatgaagcacaatccaagacagaa    127890
gcatgaaatggattttccttcagagcctctgaaaggaagcatcttaattttggactctgctccagaacag    127960
tgagagactataagttttgttgtttcaagtcagcaagtttgtggtaattagttacaaagtcccagaaat    128030
gaatgcagtctggattaggtatattctgtatatataagctgcctaagaatgccagaagccagaagaggtg    128100
gtgtctgcatttctggttcctaaaatcctctctcagtacccactgtctgtccgtggcaaagctctcctg    128170
acacattttagcctttaggctatgtcctatttccccctgtccactagggaagtagttcttgaattcccgc    128240
ctcccaaggctggcattttaccaagtgaaagacactgcctttgtgcaactccctcccctttgagtgtagg    128310
gaggaaataggattttcctcctgtctcatggaatatgatagaggtaatggaacaccacttccatgattacg   128380
ttatataagcatataaatgtgtcttcctagcatacccttctgttgcattcttggtttccatgctttgat    128450
gaaatgagcaaccatgttgaacaggtgcaaatgtcaagaagctgacagctgcctctgaacaacagcctgc    128520
aaggaacagaggcattcagtccagcagtcccacagcattgaacattgtcaaacaagcgtgtatgtttgga    128590
agtgaatcttcctatgtcagctttaaaatgagaccccagctcaggccaacaccttcatcagtaagagact    128660
tcaaagcagtgggtccagctgagctagtgcctagattcccaataagcaaaaactgtgataaagtaaatac    128730
attaatttgaagctgtttaagcctactggccccacccagtctcttcccaaccctggagagtacatttcaa    128800
tctaggtgtctctttccactggatatagacattggttggcatgcagctaaaatcaggccaatatgcatag    128870
ttgcatattaatttaaatttgtggttatttgttagaaagtagtcaataactgtggcataataagcaaaaag   128940
tggatttcagctgagtacagtagctgtcacctgtaatctcagctacttgggaggctcaggtgggagaatt    129010
gcttgaggccaggaggttgaggctgcagtgagctatggtagcgccaatgcaatcatagttcactgaagct    129080
atgagcctgggagacaaagcaagaccttctatttaaaaaaatacatggatttcaaaagttggacagattg    129150
taacccaaattctacatagataccatgtctccaatggagggatatatattttaggttttgcaatcttag    129220
gaatagttggcaagtgaaagaaattctggttaaattgacttaagggaaaagaagagattttcagcctccc    129290
tttactagcagtacatttaatttagaaaatagtgtcctcaggtttaatcattgccgttaggaacctggca    129360
ctttggtgccatgtttcttcttttggctttctcagagacgctgtctttgtgtggtggtaggcagtcaaca    129430
gcatttccttgtatgccattgttccctcagaaagcaaattggcccagtaactgtgcatattggcctaatt    129500
ttagttgcatgccaaccaatgtctatatccaatggaaagagacacttagattgaaatggcctctccaggg    129570
ttgggaagagaccgggtgggtccagtaggcttaagctggatgcaagtaagattgctccccagaggaaat    129640
tgaatgctaggtaagcaaaactcattgatgtccattgtcatttgctcaaactgcaaatagtcccaaggaag   129710
aaagaatggcatgggtgcttcatggacgagactaacttgggggaaaaatcttacctaggatgtttctttt    129780
ttttttagctgaaaagaagcacttggacattcagaaatgagaaaacttgtttattagctgctgttgttggt    129850
ttgtaaacagctgtagcttttagtgacatatagaaataacatgacaggaacagatgaggatatttctatt    129920
atgatgttatacaggcagttctatgttgggagtcatcctcctgggggcaatcctggatctggaagctgtca    129990
gctggtggcaaattagagatagcttgagatttaatgccagatgggaaacatgacctcaaatgaattaggg    130060
tctttagtcctgggtgtaatatgctgtgcctgacatctcttttaagagttctaactgaaagtttaggttt   130130
actgtagaataagccaattgggagctcatcttgtgaacatgaaaatgaatttggacaaatttcaacct     130200
aagcctttagcacagtaaagtttggaaagagtttcattgtagagcgttaggcaattggctgacaaaaga    130270
gcatccagttttttctcaaggaattctgcaaaaagcaaaggaggtcctactcagccatcctccttttca    130340
gcttagtggacttgtttgtgagattgtgctgtgaatgggttctcaggctggtgataaaacctcatcttca    130410
attcttgtgcagctttgtataagtccaaagaggcaccacttatcacctactacatgaagtgtcattgggt    130480
tgtttgttaatgtttgtttccatatgggccccaggcattagcaaacatgtagtttattcatttatttatt    130550
cactcagtgaatatttattgaacctaatctaatttcaggccattttgctaaatgacatcctatcactttt    130620
tattgaaagccatagaggggaaattgcacaactaactggaaccatttagtataatcattgcaattatgca    130690
gcaagctggggaggtatgagaacatctgggaggagtatgtatccgagactgagagagtgaaaatgcagta    130760
aggagaaatttgacgaatgagtcactgaccaaattgctggaggaaggtcatttcaggcaaagagaagag    130830
tgtgttcaaagctgaagtctagagcctgacattaatatcgattctcttagctaagttgtttatgaaactg    130900
aagtttgtgaatttgaagcctgaaatgtctgaagtgtagtcaatgtatggtcagttaatctcagagcaca    130970
```

```
tccttcagtcatcagtggaactagagataatatattgacatatgtgctctaatgaaagctgagaagctca      131040
accgggacaagtgtttatctaaaaggggggtctgacctcctttttagaaatgggaagcaagtgtggacagca    131110
taacccatagaccaaatcattcacactttctgtcggttttttaccaaagggtttaatggaacacaaataca    131180
cccatttatttacgtagtgtctgtgactgttttcacactacaaaggcaaagtttgagttgttgcaagagac    131250
catgtggcctgcaaagtctacaatacatacaatcttaccctttattttaaaagtgttctgacacctgat     131320
gtaaaggactggcttcatgaagtcaagtggagatcttctaagttaccatatagacatgaaggaagagta     131390
cagaagttccatgatgtacagcagtggtttacaaattggctatgaatgttttccaaatgcagattcctgg    131460
gctctatccaggcttccagtgaatcacaaaatctgaggatagggcccaacaatttgcattgtagtggcct    131530
tgtaggtgatattgatggcaaaaatttgaaaattggacctgaattttttttttttttttttttttt       131600
gtgacggagtctcactctgttgtccaggctggaggacagtggcgcaaatttggctcagtgcaagctctgc    131670
ctcccatgttcacaccattctcctgcttcagcatcctgagtagctgggaactacaggcacccaccacccc    131740
cggctaattttttatattttttagtagagacggggtttctccatgttagccaggatggtctcgatctcc    131810
tgacctcatgatccacccacctcggcctcccaaagtgttggtattacaggtgtgagccaccgcacctggc    131880
ctgaaatatttttaatccaaatataaacagatactcctttctgccattaataaacaattagggaaaaaa    131950
aaagataaaagcctgtttttaagaccattgtccatatggcttacacaagataacttcctgaagtgacctc    132020
taagacgaaatagttgcaaagtatttctgtgttcaattaaattaaagcgtgggcaaaagaaattattag    132090
ttgtagatatttaaaatcaaatcagtttaaacaaaacactgtcaacacagcagccaaagaacataatcaa    132160
tcaaaagatgaataaatatacacagttatacagcactactactacataatgatgattatgatggtgatga    132230
tgaggatggtgatgaggaggatggtgatgatggtgatgatgatgatggttatgatggtgatggtgat      132300
aatatggttgatgaggatggtaaaagtgttggtgattttgatgatgttggtgtagaggatggtgaagcca    132370
tgctaatatgttgatgctgatggtgatgatggtgttggtgatgaggatgctgaaggttacggtgatgatg    132440
accagatgacgatggtgctgctgatgacagtgatgatgtgatggtcatgatgatgacagcaatgaagat    132510
aacaaatactgtgatgattgttttggtgataatagtaataactgtagtgatggcctgtttctacattgca    132580
atctctatttctcccccagtctccatacaaacagaaccacctttagagacatttcaaacttaccatattca    132650
aaatgcagctgctgcttttgatacaatgaatgccctctgtcgcattttttactatcttaggagaattcac    132720
accatctcctcatcatttaatgagccaaatgtgctagctgctgatccatgtgtctgaatggctgccttga    132790
ggaattggggtcctacagtgagcagcaatgctggactagggcaaggatgaataaagaagggatgagttca    132860
agttgttgggggaaaacagggcagccaactctatctggagctctcagatgggcttagtgttggtgaagat    132930
atttccaaagacattttgaagacttggaggtatgttatcaggcagaacagagcttctaactaagagcaat    133000
tttggacctgctgtacaggacagcctccaacccacacaatgatctggcccctaatgtgaacattactgag    133070
gtagagataacatgaggtagactatagaagtctatagaaaagagaatctgagcaaattgtgctagggga    133140
acactgaagaatgtggagcaattgaacaaatgcctgtgcagacatattggtacaaaattgcaatggagca    133210
ccaatgggacaggaaaagggacaagtcctacaatatacagttcttgaccatcctgaagtgcaccaaag     133280
ctacagaagttggtgtgcgtgaattgtctcattgatccctgtttggtaattaccatgttgactgctggagt    133350
cccatgaaggaacattttaagcagcaaagtgacaagctctgatttgcattttgagattaatgactcaga    133420
caaccagttatttgttaacttgctggattcagcctaggaagacatctagagggtgtaatttgatttattt    133490
tgcagagggatgattggcctctacattatcttggtacactgcctgaatttctgaacaccacagaattatg    133560
tatttggcatatggccatctcatttctaagacccatcaaagatgtgagaatggattagatgtggaacaag    133630
ttgaagattagattagtttatcagatgattagcatgccatgctaatttatcaagacatgggatatttaaa    133700
gaaggggagagtaacatatgtatgtaacatatagaggggaagatgaagaggagaccttgtctccaatttcttttt    133770
tcataatgaatcagtaaaccattggtagataaagtttagtttttaattctgctttctaagttaggctgca    133840
aaatatttttttatcagtactctctgaaactgactgtcatgtcaagactctaaaagagtatccatagttat    133910
atttaaaaataaaatatcatcttttcatcttatgtagaacaacgtctgtttactactgcttggaatacaa    133980
agaggaatttagctgtgggccattagaaagtgacaaacagtgtttcttccactatgccataattatagtga    134050
gaggaaagcatcaaaaagaaagttcttttatatcagttggcacaaaatattcacatatgtaaataata    134120
taaataatgcaccataaaaagaaaaccttccattactattaacaaaattaatcagttgtcattaccatgg    134190
gatttaggatacatcttacatgttcttggttagattcatgagtcaaagaataatgcccaattgatgaaag    134260
tgggctgtaattttgtgcttttaaaacaatggcctctggccaaatatgggcaaaataaacaacatttgat    134330
ttattactttacactgatttcttgcatcctgctgaaaagagagatgacttacaattataacatattttt    134400
cctgcaagattaacatcattgttgccagttttatagaagaagcaggaaagtgggcttgcaatgattttatt    134470
atgaatgcatgaaacaattaatgctactagcaacagagtttttaataggaaaaagttaaagcacacagtat    134540
taaaaataaaaggggctgggtgcagtggctcatgcctgtaatcctagcagtttgggaggcccaggcgggc    134610
agatcaagaccagcgtgactaaaatggttaaacccatctccactaaaaatacaaaaattagctgggcatg    134680
gtggtacatgcccgtaatcccagctactcaggaggcttgaggcaggagaaaattgcttgaacttgggaggta    134750
gaagttgcagtaagccgagatgacaccactgcattttagcctgggcaacagagcagagcttcatctcaat    134820
aaataaataaacaaataaacaaacagagcaagacttcatctcaagaaataaaaaaataaaataaaaggga    134890
aaagttggtatcaaaattgtgtctgatttaggcaaggtttatacctccatggatggcttttcataacaa    134960
taattgtattgacattggggcttttccgtgtttcagagattttcatgtggatttccaatatggtaaaat    135030
atataatattgttatatgagggagtgatggaaaatcccatcaacgttggcattttttagaaagaaaagaa    135100
gcttagggaatattttaatgatttgggctaggtctggggggttcatgcctgtaattccagtgtttga      135170
gaggctaaggagggagaatgatttgagctctgcatgtttgagacatcataggcaacatagcaaagcctca    135240
tctctacaaaaaacaaaaagtgagctgagtgtgatggcaagcatgtgctggcaatctcacctactagggg    135310
aggctgaggtgagagaatcacttgagcccaggaatgccaggcttcagtaaactgtaatcacatcactgca    135380
ctctggactgagcaacagagcaagaacctgtctcaaaaaaaaaaaaaaattgatattttcttttccccca    135450
cagttgtcatatacaatgaaaactgtatatttaagccaaaataggttttgtaaacatttaactattaaaa    135520
aagagtcaggcttgcacatagatacatgatattgcttttgatttcttcagttttcacctgccctggtatga    135590
gacccatgaagtaagcattcttctgggcacagaaattatactcctaaacgtattatttattaatatataa    135660
tggaaagagaaacatttcaaaaataaagacaaattaagctttaatgaaaagcaatcatacactgatgaat    135730
ttaaagttttggagcaaatactattgtgtttgatatctattagtctatttaactagtgaaatatgagcaa    135800
cgcaaaatcaaacatcaatagaaagttccaactaagctgtttctcatatggtttctctgccagttcaga    135870
cctcaagagtacctcctgtctacaaagtagactctctgccccacacactgatttccagcctttctgttt    135940
catgggtgacttgctgaccttctatgcatgggtaatagtactctgttgacaggcaagagttgtgtcttc    136010
cacttgggtcttctaatctgctaaagaaagcaacacacaaaatatagcttacaataattatctgtcaaat    136080
```

FIG. 11A-27

```
ttacgtcaatcacaatgtggatggtagatcagtggtttctcttatgtcttgaaaggaagacttcaatttt   136150
ctctgcagccgtggtactttataaattatttcctcttccgtcttttaaaagtcactcttatttaccaccc   136220
cattagccacggattcagtgaaatgcccacgcatgcagtgttggagtcacacattatttcagaagaccac   136290
acagcagtaggtagtattaaataaatgtctgaaatgtgagccaggaatgtgtttttactggactgtcatt   136360
ttcttgcaggctcatttgtataattcactccagtgcatctcagtttatttcctattatgcaaaatagaa   136430
gataatgataggttagcacattctctgctgatactatttacattcgtgtaaatagatattgctaggggtg   136500
tgtgcctcagactatcccatccttcataggccccatgtttcaattttctaataacccatctaagacacc   136570
taggcacacaggggagaatactctgatttaaacagtccaccataagccatacacagtggtgcaccatgt   136640
gtcccagctactcaagaggctgaggccaagatcagatgagctcaggagttcaacaccagcctgggcagta   136710
tagcaaaagcctatctctaaaaaataaaaataaactcaccactctgagtttttacatgttgtaaaaatctc   136780
ccactggctcccgtctattatgcctggtttagtttgaaacaaaatcattagttttaatgtagcaaaattc   136850
catcgacatattttcttttataagagcttctcctaagtagcacctgttagagaaatcctgttctacccca   136920
acatctaaaaaacattttcctgcacattttctataagcatcagaatttcattgttcatgcagacatttt   136990
taatctatgcagagcatattttttatatatggagttaggtagggatctcatttttttttcctgcagtaagg   137060
aagcattgcttttgacacatgaaagaaacaaggtatttttccccagtatttgttgtgtcagccagggtcc   137130
tgataggaaaagatggaatgcaacttgagaaatataaataaagatggggacagtatataggggcaccgacac   137200
agggtagtggagcccttatgtgaagttgctgatacccactgaggttgaactggacctacctacgagggag   137270
ggaactggatttcatatacataggccttactcgccttctgtcctccagattacctactagtatcttcctt   137340
ggctgaaaccaagggacagccagaaggcaagagtgaactcacttatttaccttccacagtacagaatagt   137410
ggagatgagaaagagtaaatctggaaggggccagatcccgccccacccccacaaaaatacaagttttaa   137480
aattaatcatatatacatcagccaatcctagggctttatatttggccctgttcatttgctgatctgtttc   137550
tgcaagatgaagaatgactcaaatattacaaatgacatatgttttccatcttcaacattcccccttgcttt   137620
tggtagaatttattcttttcatgtacattatggaatcgatgtgtcaaagtgtgcaacattcttctgtcttt   137690
gctgggaattgtatttatttaaaagttggttgaggaaaaataaacatcttctaagcttatgttatctca   137760
cttgtaaactggcatagttattacttgttgagatctgatcatagctttattaaatactttaagcattat   137830
gtattaattaattattattagtagtattttgcaattgataccttcaattacatttttgtactcctggtata   137900
aaataatgttgttttttttacattgatgaaatgttcaaccatcctttttggattttctattatttgtagcag   137970
cttttctgttaaattacataattttccacaaaaatggtgacattatctgcaaataatgaccattttctctc   138040
tttcctttaatacttgtaaattttaaatcctttctaacttctaccattgtatgacccattgacatctgg   138110
tgtgaggatgaatgctattggtacaaaattttattcccattcatgattttacaggaaatgggtctaacat   138180
cttttttgtaaatacaatgtcaaggagagattttttgacatacagtcattttcaaataatatgaatttctt   138250
gtaattaccatttattttctaagttttttaaaatgctttcttttgatcatacatattgattattgccaaat   138320
aagcagttggcatttctacagccgcttatacagctgcttatatcataaaagaattataattattcttcat   138390
aattagtgtgcttttataattaatagatttataaggtatctattcaatttagaaaaaacaaatttttcat   138460
cataatagggaacaaaatggcctctcgtgttatagtggaatatattgtatattctaaaaatagccactatt   138530
ctactaagttagtttgtaaatattcacttaggatgtctacatctacattcataagtgaatttgatttat   138600
aattttatgatgttaaacactctatactttgatatgaatgttaaactatccatacaaaaggattttgat   138670
agctttatttaattttatattttctgcagaaaacttcaatacataggattattaaaaattttctgaaaat   138740
tatcttgggtgacaagttttttgtgtgggagatttttagttacccttttcaatactactaatagttttagt   138810
ttaagtttatttcttcgtgtaatgttgcttttttcttgacgatttcaatttagcttttttaatatcaggtt   138880
ttatactgttaaaatattattttgtattttttatattttgatttacttggtgtttttaaaagtgattttcc   138950
tcttttccttaaagactatttgttttcttaattgtctcccttcctggtcagtcttggcagaagtttg   139020
tttatattataaagcttttcaataaactagttttcattttggtaattatatcaactcttttttttctctatt   139090
tcactaatttctgctcctatcttgattatatcctattttcagatttattttgtatttattctgtttttctct   139160
tcttcctgccctcttcttgacttgtctccatggcttcttttatttccaattattcttgttgccttgtaaag   139230
gtatttgaagtttttaattgtcccttttaagcacatcttcaatctcatctgacaaattttcacatgtgacat   139300
ttgaatgatccttggtttccaactattttttgtttatattgtatcataaaagcatgtgcacacacccacac   139370
acaaacaaatacatatatgcaacctaatgacagaatactaaacatatatatgtttatatgtgtgtaaaca   139440
tagatatgtgtatatatatatatgtttagtgttctgtgtcccatagcctttcaagcacacacaaaatgttta   139510
caaaatctaccttttcaaaaagatacagcagcatacagcattgtattctatgaccataattcaatagaatt   139580
agaaatcaatagtaaaaagcgttcaaataatgatagaacactaaacatatatgtacatttacatgtaca   139650
tacatgtttacgtgtgtgtgtgtgtatatatatatatctgtgttctgtgtgtgtgtgagagtgtgtgatt   139720
tgaggtgcatatatttccatagatagccaccggatcacacatgtcagttatttcagtcttctatatctta   139790
tttattttttggggtggcaggtgggggactctgtctcgctcgctggaatgcagtcactcagtctcgg   139860
ctaactgcaatctctgcctcctgggtcaagttattctcatgcctcagccttccaagtagctaggattac   139930
aggtgcacaccaccatacctggctaaactttttttattattattttttgagacagagtcttgctctgttgc   140000
ccaggctggagtgcaatggcgcgatctcagatcactacaacctctaccttccggattcaagtcattatcc   140070
ttcctcagcctcccagatagctaggacaacaggcgcccgccaccgtgcctggctaattttttgtattttta   140140
gtagaggtggggtttcaccacgttggccagcctggtcttgaactccttacctccaggtgatcttccatct   140210
catcctcccaaagtgctgggattacaggcatgagccactgtgcccagccaactttttgtattttagtaga   140280
gacggtttcactgtgttggccaggctggcctgaactcctgacctcaagggatccacctgccttgtcctcc   140350
caaagtgctggaattataggtatgagtcacgatttgtggcctgtatcttcaattagattttgtcttataa   140420
gttcatcacaccaagaatgttgagttttattctcttgtaacatttcatcttatcgttcctttgtctggta   140490
tatttaatgcatatggatatactatgtttatatatatgtatgtataaacatgtacttaccttttac   140560
atgtttcaagcttattaggaagttatatgaaagtgtcagttgtaccttttaatcttccattcctttc   140630
tactatttattatctattattgatatttatgattttggtttgatactaaattgcttactatgatttttt   140700
ctttacatatttcttacatttaaaattttagtctcttcctgttcgtgtatctgtttgttttaaatatat   140770
ctgttttcaacaatatgttgctaaatgtattttaatcacatttttatctgtttatcctaattatatttctg   140840
cagttatcattttattatagatttcatttctgccactttgttttatttttatatgtatcaatcatgctttt   140910
taaactttaactttttttttttcctgacttccagtgtataattttaaaagtttctcttactgacctcatt   140980
attatactcctttttgctgacctcattattatactctttttttatgatttttttttcctcctatagttt   141050
ggattcatcaaatttcctgttttatgttgcacttatattctaatgaagatacatcgattcttcttattgg   141120
ctatcaaacttttcagtatccacaattttcctcagaataagctatagatttaagattttctcaactctctt   141190
```

FIG. 11A-28

```
ggcatctctctctctcaatcaccccacactgtgttagattctaagggaatttgggctgtagatcatgtta      141260
aaatttgattttagaatattgtgtctttggagtaatgtcttgtcattacttgtattatactgctgtattc      141330
tgggtttatttctctccttccttgcagaaatacgttgtttcaagatttctaagaattaaatagatttgga      141400
tttaagctatcatttaaataatagtttggctggacataaaacctaggcagatctttttccctgcactt       141470
gctggggatgagaagccactgcttttgtatcctacactgctttgttgttaccccgatttcaatccatt       141540
gcacatcacctgctttttctcattggaagaattagacttactttgttatatttgagatactcaaaaatc      141610
agaatttagttttgctttttctgttttaaatcaacctgttccttactttatgagaactttccattttaa      141680
gccttttttttttttttttccctctcatcctgggaacttctcagcctttctgcctaatgtagttcttgc      141750
taaccttttctctttgttctctttctgggtctttttttataggactggcaacacttctacttccatct       141820
tccatacttcagcatttggaggatgttttcctccattttcatcccggatccattttgggaaagtgtct       141890
ctctgtcttttgccaccaatatgcattgtttgtaggtatctttccatttcagcctgttctttgtgctctc     141960
cactcaacaatttcatttctcctccccagtttctcatgtgacttcctttgacaccctttgttccaactt      142030
tatatctctataattgtctctctgtccattggacggatatttaatctcttatttttgagtcccatgttgt     142100
ttgcttgggtcatttgatagttgttgttatttcatatatgatgttacatttgtttaagtgttttgcttt      142170
tgactggctctgaagtatttcttgggagttttttgttgtcgttgaggacagtagatatcttggaagataa     142240
tgagtatccaatggccagtcaaaagcccaccctcagctgggcatggtggctcatgcctgtaatcctggta     142310
ctttgggaggctgaggcgggcagatcacctcgagggtcaagagtttgaggccagcctgatcaacatatcatt    142380
aaattagagcttttaagttatatcactgatttcatatgccagggaaaattgtaggatgtggcttacaaggc    142450
aatctcacaagaagtatgacttttgtcttataaacaacaacccaaccttggagtttgttccagtaaattt     142520
cataaatataaaataaactatataaataaagtaactaatatcctactaagtcttttccctcacacatgct     142590
tttttgcctaaagccatttaaagtctctgaggatttaaatctataattctgtcatggagtggtagaaac      142660
ccagagaatatacaaacgttgaaaaacttttaagagtcactggtttaacagaagttggctgggcttactgg    142730
ctcacgcttctaaacccagcacttttgagatgcgtagctgggcagattacttgagggcaagagtttgatac    142800
cagcctggccaacatgatgaaacctgtctctactaaaaatacaaaaattagctcggtgtggggtgcagg      142870
cctgtagtcctagctactttggaggttgaggcaggagaattgcttgaatctaggggtctgagtttgcagt     142940
gccccgagatcacagcaatgcacttccagcctggtgcaacagagtgagactccatcacaaaaaaacaaa      143010
aaacaaaatgacaacaacaacaaaaaaaaaaaaaacagtaaaacagaaatagatctaattttcagacta      143080
gagtcactcagatatggatggataagtccatccactatttgtgtattaagctttttttttttttttttga    143150
aacaagtgtattcacacttggattgactgttaatattcactccaaactaggacattgcaaagaaccctta    143220
ggatgttataattctaggcatttttatagtctcagaatttcagatgtattgcaatgttgtaatttttat     143290
agtttcttgtctttctgtaacacctagtaagttcaaaaactcgaactataggttttcttgataaatacca    143360
gcgtcactgctttctatgtttatattttcttttaatacatgaactgagttaaaaattaaatatacatat     143430
gtaaattattcttttgaaaaaatattacttataatagttttttaaaatacatgttttatttaattttagatt   143500
tctgctaaatttgtgaagattgtggaaaggattttccttataccccacccttgaatttccttctataaa     143570
tatcttaaacatcattattatacatttgacactattaatgagccaatatgtacaatttttttttgactaa    143640
agcccactcattcttcagatttctttggtattttcattctgtcttttttccttctcaaaccccaccccca    143710
gatcccacattacatttagcggtcatgtctccttgggctcctcttgattgtgatgatttctccttctcat    143780
tttgtctttcatggccttaagagcttaaggaggactaatcagggggattggtagactgtcctttttgtttgg   143850
gtttgtctgatgttcttctcatggttattctggggcatggattgtgcagaggaagaccagaggtgaagt     143920
gccactttccttactttgtatcaagggcacatactagcaccatgacattgcagttgatactgaccttgat    143990
cccatggatgaggtgatgttggccagatttccctactatcaagttactcctcttgcacacacactttcca    144060
tattgtactctgtgaaaagatgtcactttgtgcagcccacgcttaagaaatggggacctgctattcccc      144130
cggagggcagagtatctacagaaattacttgaaattattttacataagagatgtctctattctgagccac    144200
tcatttactccctcatttacatatatcagtatggtcttattgatatttattttatacttcaggttgaaat    144270
ctaatatgatgttgtttatctgcatagattttgtgtttgttttttagtagatatgaggtctcactgctttg   144340
cccagggtgttcttgaactcctggccttaaactttaaaactttaaaaaagagggatagcttttaaaaat      144410
cctcatttttactttagatccaagtgttaaatatgcagatatgttacaagggtatattgtgtaatgctga    144480
ggtttgggcttctgttaggttattctgtgtccaaataataagcacaggaagttttttagtccttgtcccc    144550
cctcagtaacagctgtaggaaataaatttgagactgatcattttaatttttaagcgctgaacatgcagt     144620
tattttatctggaaggtagactagaaaacaaaattatatttgacattttaggacataagtgttttctca     144690
ttaatcttgatgtacacaaagccagattatcaatgtatttgttcataactctagcttgtttcattaaaat    144760
tatttcctgcaaagaaaacgccttttttgctaccctgaatatttaacaattttttagaatattttatctt    144830
aagagctataaacatgttttaatatcccaaggtaagatatggagattttttgtagtctgtccagcctgctg    144900
tagcagaataccttagactgggtaatttataaacaataagacatttattattattttttcattgagacag    144970
ggtctctctctgttgcccagactagagtgcagtggcttgatcatggctcactgcagtcttgactttgtgg    145040
gctcaagtgatcctcccaccttagcttcccaagtagctgggaccataagtgtgtgccagcacacatggct    145110
aaaatttttattttttatttaacttttagtaaatatgaggtctcactactttgcccagggtgttcttgaactc  145180
ctggccttaaacagttctcctgccatgacctcccaaaatgttgggattacaggtatgagccacttaaccc     145250
agttaaaaaccgacatttatttcacacagtcctaggaagtccaaagatcaaggtgttagctgattcttttg    145320
tctggcgagggccccattaccccacatgtgcaccttcttggttttgtcctcaaatgatggaaggaaaagca   145390
gcttcctgcaatctcttttatatggacactaatcctattcatgagagtggacttatcacaatgtatattg    145460
gatttcagcatatgaatttgggaggttaccaccgttcagacaatagcaagatacattaggtgtgggtg       145530
ttctggacttgagtgaatctgtgtaagtccttcacatgtgctttgctttactgcttggggtagctatttc    145600
tgcctcaaaccacctcagagggcttcagatttcagtgacacacctgtcactttttaacgcacatccttga    145670
cctccgtctgtgtgcagattaagcaacaggtgattttaaggttcaggcctaaggtttttttattattgcc    145740
tttcatttccatttctagttcttccaaaatccttcaaaatgacacctgagaggagacactcataaacttg    145810
ttagccaggattccaaggtacatagaagctgttctcctgggtgaatattacaaatgcctccaagggcaa      145880
ttgaatttctttctgtctttcatggattttacttattgtccagatatgctcctcctagtgagagggtca     145950
cttctgattttcctgcctccacagaacaagggcttcagagaggagacactctacagctcctttgttatt     146020
aaattattaaatgcatttctagtatgaaggcagctattagaaaaatccagtctgctgcatatctgttta      146090
taggggtttgagcccagtcaagtgaggatgcacagaattccaccattctgacagcccagcccccttgcaat    146160
tggaagggtctccaaattccttccttgcagctagggttactggctatgagtgacagcctcttgtgcatag    146230
ggagtgagggcggagagggaccagcagagccctggaatgtcctttccactggacattgagcatctagaca    146300
```

FIG. 11A-29

```
gctcagactctggaatagcttgtactataggtgcatgctaccatgtatggctaatttttattttgatttt    146370
tgtagacataggtgtcagtattttgcccagattggtctcaaaaatcctaacgtcaagcgatcttcctgc    146440
cttggccttccaaagcactgggattacaagtgtgaaccactgtgcttggccataacctatagtttttgtt   146510
agagattattaaataaggatgagattaaaatgaggttagtctcatgctgcttaaaacagtgatatgctta   146580
ggagcagctgcaggaacatctgatccaatcttggaggcagcctgaagggcttcccagggaaagcacaatt   146650
taagccaaaacctgagagatgagcagggattgaccaactaatgagcagacccacacaccaaattctgcag   146720
tcagttccttgcatgacatggaaaattgatttctacaactatgcattacttttctcccaccaatccccg    146790
ccctgctttattttttatctttatttctactggtgtctctgtcactcaggctgtagtgcagtagagtgatc   146860
ttggctcactgcagcctcgatctcctggctcaagtaatccttccacctaagcctccctagttagaatag    146930
ctgagactgcctacgcacaacaccatgtcggtccattttttttttttttttcttttgtagagatggga     147000
ttttgccatgttggccaggctggtcttgaaatccttggctcaagtgatcagcccaccttggggttacagg   147070
caggagacaccatttttatttgcatgtgtgcggtcagtcattctacaactaataatatttaataataat    147140
tgaaaatatcctgtaaattccaaaaaggtaagcttaagttctcttgaaaaatgaatttctgtgagaaggc   147210
tttggtggtttgacttgaagctgataacaacattagtgttgggcatttggctacacacctgtcacattca   147280
aaatccaatctatttcaatctttatttcggtggcagtaagtgctgaagattttaatccactatgtattt    147350
tcctaacccagattctactcaaagcagaggtttagagaaatcccttgttattgcaaatatcatgccaag    147420
aataaggatgaggaaccagcacagtgatgaagggagaaatgtaatcactatttacaatagccaagttgtg   147490
gagtcaacctatgtatccatcaaccatgcattggataaagaaaatgtggtacatatacaccaaagaatac   147560
taggcagccataaaaaagaatggaatcatgtcctttgcagcaacgtgcatgtggctggaggccattatcc   147630
taagtgaaataactgagaaacataaaatcaaatatcacatgttctcacttataactaggagctaaacaat   147700
gggtacgcgtggttgtaaagatggaaacaaccaacaatgagactcaaacagggggaaaggatgggaggg    147770
gtgaggtttgaaaaatcacctatgggtacagtgtttactcttgtgtgattggtaccctagaagcccatat   147840
gtaaccagtgtacaatatacccgtgtaagaaacctgtacatgcaccccctgaacctaaactaaaattaaaa   147910
aacaaacaaaaaccacacaaaaaaattgtattggccacagaggagagatgcctgcttgacccagtgaggt   147980
tgtgtgaaaacccttatgatatatgtccccataccactttcccaggtgaaaatggaggacccacattctc   148050
ctcatctttcaccttaataatgtactggtgttgacatctccaggctacttggggagtgctaagtaggtt    148120
ttagtgtgcatcccctgtaaggcattgaagaaaattcaggaaatcaagaaaaagtcaagtttccaggtat   148190
gaagagaggctgcaccttcatgaagctggttgaagtctggacagagcagataccacaaagagtgactgga   148260
ataagccatgtggccaagaggcatccagtgcagccatcaagtgaaacagagctcttccagccgtggtaga   148330
actagggtcaaactatgtgaaagtgttcaaagattctttgcattgaattcaagctcatcattcacttgcg   148400
ctcaaatctgtgagaccatgtttatattgtaaagaaaggataaaacataaattcatatttcaattttag    148470
gttatctgaatgaatggattttcaagagtgcttaagttttttctagatgttcacagcttttcaaatcatc   148540
ttcctcagaacactgaatcctgctaattgagtgatttttctgattgtcatgtactcacacaattgactaaa   148610
tgtcttactatgctttcttgataagtagtgtctacatgtgaagaacctatctatttaatctatctacctg   148680
cctatatatctctatttctccatctagtctatcaatctatcttatctatataatctctatgtatcatcta   148750
tctgttatctatctatctatctatctatgtctatcttctctctttctctctcctctctctgagttgagca   148820
aattacttacaagtttttgtcatgtaagtgagcaagactatatacacacatataagaaggcttgaact    148890
acaacattaaagtggctgcagattcagtgtctggtggggaccccacttcgttgtccatagacagggccttc   148960
tcactgtgtcctcacatggtagaaggggcaaaggaggggctctctgggtcccttttataaaagcactc    149030
atctcattcatgaagctccatagttatgatcttatcacctccaaagtgctcgcctcctaatagtgtccc    149100
ctcgggattaagatttatatcttttgttttaaattttaatttctatatgagtacatagtaggtgtata    149170
tatttatggggtacctgagatattctggtgcagacatgcaatgcgtaatgatcgtatcacagcaaatggg   149240
gttgtctatctcctcaaggacttgtctttttttgttacaaaaatccaattgtatttttcagttaaatg    149310
tacaatcagtttactattgactaaagtcaccctgtcatgccagcaaatactaggtcttatttattctttc   149380
tgactataattttttgtacccattaaccatccctactttccccatcctactcccactatcgtttccaatgt   149450
ctgataaccatcttttgattctctatatttatgaattcaattgtttcaatttttagctcccacaaataag   149520
tgagaacatggtataacggtctttctgtgcctcgcttattctcttaacataataaccaccagttttatc    149590
catgttgttgtaaatgacaggatctaattctcttgctatggcttaatagtactctattgtgtatgtgtagc   149660
ccattttctttatccattcacccgttgatggatggttaggttacatccaaatcttggctattgtgaacag   149730
aattgcaacaaacatgggggtgcagatatctctttgatatactgatttcctttctttgggggtttggatg   149800
taaacatatgagttttgagaggacaacattcagactgtagcttactgtactatctatccattcatccacc   149870
tgtttatctattccatttctaaatattgcatggcatattttcttaattcttttccaatgtctttattggtt   149940
ttaatataagtttacgtttctgataggccacatatgggggcatcctgaaaagtacatctgaggcaggtca   150010
ggagtttgagacgagcttgactaacatggtgaaacctcgtctccactaaaaatcaaaaattagccaggt    150080
gtagtgggggttgcctgtaatcccagctactcaagaagctgaagcaggagaatcacttgaacccgggagg   150150
cagaggttgcaatgagcctgtgattgtgtcattgtactccagcctagggtgcagagtgagactatgtctca   150220
aaaaaaaagtacattatctttatatttaaatgttttgggtttttttcttatttttttcatattttaatt    150290
acatttcttccaaatgacttcttttgggagacatgatttttgtacctcctgggactgccacaattctcctg   150360
cctcctgggatgtgatcgatctctagtctgcctcaagtataaagatgatattcatgttgatgacattgag   150430
aaggatgaggagaaaggagttgatcagagatctatattcatggtatacttgtttgccatgtctgcttttc   150500
ctcttcagaatgtaaactccaagactgtgggtcttttgttttttctggtgtactaccttgcagagtctaggtc   150570
ctattcaaagcttaatatttgtgaagtgcatgaatgaataagtggattataatattatcaccaccattgg   150640
tatgctttgtttctctatctgtattgtcctctctactttttccttaattgtttaattcccacacagatt   150710
gccgaagattgctttgccaactgtccctgggtagagataaattccctccatggtgctttcactggactc    150780
tacctgcagctatatattatcttgcattttctaacacccagcccccaccacataataagacttgattgatt   150850
gaagaccctgagttagctttgcataaaaccaaggtgcttttccaacagacattcacagacattttcacat   150920
ttcatacagcaactgatgaactaggctggaaatacactttttactgcttaacagagaagaaaacaaagc    150990
ttagggagactgattatgcaggatttaatttgtaacaagcaaagagaacactattgacttcaagtggaca   151060
tcaacacattatcatctgataattttttccagcatccttttgcctcatctgttaaattataaactaatgctg   151130
atgtgtacaattcagttcagcttcacaaatatttaatgaacactcgctctataacaggtattattatata   151200
aatagttctttatgatgtaagaatgtttaatagatactttttatctatctcaactttgaaaggctaatgcc   151270
tattcatagataccaggaaacacttgaatgaatgaagacatgttttctgctgtcaaagagagatcagaca   151340
ccaacaagtggccaagaaagaacaaagtaattttgatcaacaaaacttatagaagaaaataagcattctt   151410
```

FIG. 11A-30

```
tgttgttacatatacttcagagccattttagtgctcaaagtttgatagaaattgatacacaggacttgcg    151480
cctctgaattggctatcccggaatattctatgagctacaaccagatttaacattaacctgtagttacttg    151550
tggtttattcatctatccacctaaacactatgagcaacttcaatgtgctcttcatggtactcgactttag    151620
gcattgtatatggagcaaaatagacatattttcttatttattgtggcttatactcagatgcagcatttct    151690
tcaccagtggtaatttgctcctggggacatttggcaatgtgtggagacagtgaaggttgtcatgactgg    151760
gtcttgcttctggtgtctaatgggtagaggccagaactccttcacaataaagaactatctgaccaaagaa    151830
tatcagcagtgccaaggttgagaaactcttctaacggttggagaaaaatgatcaatggatcacctacaat    151900
tataattacaaactgagctatgtgttagatgctagtagagctgatttccaaggttactgatctagtcatg    151970
aggatacatattgatactaaggacatgtggttgaaggggcaggagtgatttattagggtaagaagttcat    152040
ggtgagcagagggactgtcatgcaaagactctagggcttgaaggagcccagtgcaatcaggatctgaagt    152110
gacaggtgtggcttgagaacagaggcaacagggagttaggcagaaggggaagctggaaatgcaggcaggg    152180
gtagaaaataaaaatatgccagccatttatattacacaattctgtagacttctttcttctttcattcttg    152250
atacttttctataataacattcaagcattggatcagcacccttttgttgtcttctgtagcccaaaggttga    152320
ccttggagacacaaaggcaactatgacaatggtttctgcaatagggagatcacattctcactcagaagac    152390
atttgcagggtgtgattagtgattctcacatacatgtcaatttcttcctaagaccttgtgctttttttagt    152460
ttttattttaatattattattgttatttatatagtttatttgagagaattttgctctgtcacacagactg    152530
gagaccagtgttgtgatcatagctcattgcagcctccaactcctgtgtcaagcaatcctcttgcctcag    152600
cctcccaaatagctgggactacaagcatccaccaccacatccagcttattgtttattttttgtagagaa    152670
ggccacctctacaacttatgttgcccagactggtgtcaaatgcctgggctcaagcattccttctgcctga    152740
gtctaccaaagtgctgggattctagatgtgagccatgaaaccctaccttctggttttaattggcttatt    152810
ttcttcgcacatttcagtgaagcattattcatttatcgttactgaggttttactttttttttctttccc    152880
agagttagatttcagacaactcaccttttgttaccaattctaggtgtcaattcttaatatagtt         152950
gtaaagggccatgacttgaggatatgttattttttgggcttgagttttggattggtttgagttgaatgca    153020
attgctaagccattgaataagggaacattgctgaactagagtgacatggattatttcttataggtgagag    153090
tgcatttgtgataaagtcattgttttaggatacataagggtcatggtgtatttcttggctagtgctatg    153160
aattcatttgtgctatttcttttgaattttgtatttctctactctccatcttattaaaccaggtgtttc    153230
aggtttgaggttctgcacattttctctggggttacacagagggactaaataggtggagtttagggtaag    153300
gggatattcacagtcctgccctcctgcaaccacagcaacacccccaaagtctctcataagactgtatttgt    153370
tctcctacttacattctttgaccactattatgaacgttttcaatagtctatccaatgaaaacaatgttgt    153440
caatgactgtctttagtaagtctgtagtcagattcatatctttaaaatatgtacactgtgtgaatatttc    153510
aaagtatatatcatgaaaataaataagaaaaaaaaacaagaaagctgagatagctctattaatattaga    153580
caaagatacccttcaagaaaaaggagtattccatgatacaagagagtagtcataatgatacaaggaagaa    153650
tccacctgacataactaataattttaatttgtgtacacctaataagagagctgtaaattacacaattaga    153720
cagcaataaatgcaaagaaagaccccatcaataatgatagttggagatgttaagatgttaccaaaatagat    153790
gaaagatgaagttggaaaacacacacacacacaccccacacacacagatacatacacacataaatac      153860
agggaggatacacacacacatacatgcagggaggatatgaaaattttcaacaacactttcaatgccct     153930
tggcaagtttgtactttgagtccaacctccctttcacaattcaacaaagagacaaacaacccacaattta    154000
ctgcatttcatgcttaggttcccggttgtctcaaggcctcttggccagccatgtgtgtacaggaacacacac    154070
acatcaaataaacagaaaatgaatgtataatcgcagactgtgattaacaccatagatgaaaatcagaga    154140
gggtgtgcagtcattaacaggcaagctgacctcacctttgatacaaagacacaatggtgttcaggcgaaa    154210
agcaatgaataggtgttacccagttggggagataagaatggtgttgtaagagtaaggtaaatttgtgcat    154280
aggattccagttggcacagattttttagtgcagaaacaggaagtggaagagggacagggttgaggatgta    154350
taattcaacagatcattcaggtccctgttggagaacttaagcagggctctgtcaaagtcagtttggtca    154420
ttttgatagatgactctgggtggggagtgatggcagaatgagatggacacatattaggcagtcacttca    154490
tctagcagagacactgacagcctggaccataatgacgaagatggagaaaagttatatgaacctatttgag    154560
agatatttcagaaggaaaccaaagatgtgatactgagttacctggaatgtgggaaaggaatggaaagttg    154630
gatgaccctttccatctagtttctgtgtagattctgtgcatgatcccttggcttaagacataagcactgtg    154700
agattacagataatctatgtataggttcatgtaaagagttttccctttttcttagattcctcaaattg     154770
agattattgtctttcactgcatgtaatctcattactacctgatttggaatgctatttccttatacaagca    154840
tgttgtgagaataatgcttggtgccaaatgttacgcaaatagtattgatttaaatgtggtaacatagata    154910
actgttaacatatgtacaatagataacacaagtataacatataaatatcatataataaatgctaatta    154980
atataaatgaaatatactgggaggaaaatctgaaaggtgttaatgacttagggacccttatcaatatata    155050
tcaatcattctcacactgttatgaagaactaccataagctttttatgaagaaaagaggcttaatt        155120
gacatgcagttcttcatgctgtataggaagcatggctgggaggcctcaggaaacttacagtaatgattaa    155190
aggtgaagggtaataagcacatcttaccatggcagagcaggagagagaccgagccaaggggaagtgct     155260
acacactttaaacaaccagattttgtaagaactcatgaccaccgggaacagccaagaggaaatccaccc    155330
tattatccggacacctgccaccaggtcattcccccaacattgggagctacaattcgatatgagatttgtg    155400
tggtgatatacagccaaatgacaacataacctctcataatgctattttccttcatgataaatatcctttga    155470
ggacaaaatgtcattcaaaatgtgataataatgttgataataattaatgcaagcctaataaacattctct    155540
gtatacattttgtaatacattataatatgaattatattcagtaataatttcacttaaagaataatttaaa    155610
atataacaggcagataactataggtaatagtttaaaacataacactaaaacttgcatggttttggtattt    155680
caaattttacgtggattctactatatttcaaggacacaacgaacataactgaaggcaaaccttgaaatt    155750
ttactttcttaaatctgattactttcttaaatttttacttttctttaaatgtgatgagttgtgttaatttatt    155820
tggaataattaaactcggcattatatattcttttttatgatgtcattaataatgtttaaaagtcaataac    155890
acatctattgctactttggttaaaagctacatagatagtagtagctatggtacttggatgaagaaagctg    155960
aagtttattattttttcttctaatttaatccctaaggggtctttgataaagacttacacaaaccccc      156030
tttagtaacctaatcttgtaaaataatcctgttcttaaaatggtgatagagatttgcttggtttatgcta    156100
cgtaacaccataataacacattaagacttgattctctttatatcatggagcattcaggtagtgttacaa    156170
agtgctgttactcaataaatgtggtgaagagcaagctctccagagcagtgccatgcctgtgtctgatgct    156240
ttccagtatggaaaactgctcagatactaatggtttgtttcaggcgcattgacagcctgatcataggctc    156310
tagccatgtaccatgaaaaatggcttctccaggggcttaagaaagacgatgaagagctttgcattttctc    156380
ttggcatttcctgctattgttaaaaaggtcacatatgcaatttaaaaatgttccatgcatggagcatgac    156450
aaatgccatgtagaagataaaaactgctttcattgacattttgtggccaatttccaaacggtaccatttttcc   156520
```

FIG. 11A-31

```
acattttccccttttgtggatttgcaaaatttggcttgtgcaaaatgcctgcccacaatacagtctaagtt      156590
gagaaatgctacatgttaaaaagcaaactgtgtatagatgaaaatggcacattcagaataaaagtaagaa      156660
attaaatgccaccaaaaaatagggaaaaacttgtaaatgagtctatcaaaactattaaggaatctcaaaa      156730
tgaaagaaaggcttagaactcatcaataacaatgtccaattgcattcatatgtaaagaaagtaaaatcaa      156800
ctttatgttattttagttcactttattttattcttattatcctttttacctagttgaatggcaaaactaaa      156870
tttagttatcttttgggcattgaaaaatgagtactctcacagtttgatagatgaggaagaattaaggtag      156940
agttttagaatttgagtattatacaataaaatttaaaaagagacccactttactcctctggaagcacttt      157010
tgcttccaggaacctatcccacagatatatgcagaaagatgtatgtacatagatgatcattgcaactgaa      157080
atttatctcatcaggaaaacgtgtaaatgaattttttgagcacttagaatactaaaactatctttccct      157150
tgaaattgtagaggcaaagcaaaatggggaaggcagagaataatacataaatttatgtaagcatgtataca      157220
tactggtatatacacatagatatgaatgcacaattgtatgcatagacatatgtatacatacatgtgtgtg      157290
taggtgtatgcttttgtgtagatttgtatacaaatatgtatattttactgcacagaaaaatgtcaagaaa      157360
taaattattagcaatgtttagaatgggactatgttactgtgcccttacagagaggccttgattggcagag      157430
aaaatgaaaactataactgctcctatacttaagaattttttaaaatcctttgtaatgagtttgaataattt      157500
atttatattacaattatgcaaatcttctatgtgtgtataagaagccattagaaaaagatggtttcatgtg      157570
ataggggaaactagcataagttagaattttgactcagctgatgagaaagtatttgcccaaagcaatctaa      157640
tcaaagctctgttgcatgagcctggtgtggtgagtcacacctgtgactgcttttgggagaccaagga       157710
gtgaggatcacgtgagaccaagagttcaagaccaggctggtcaacatagtgagatcctttctctacaaaa      157780
agtttaaaaaattagctggccatggtagctcatgccttgggtctcagctatgcagaacgctgaggtggga      157850
gtattgcttgagtccaggagtttgagggtgcagtgagctatgatcaaaccactgcactccagcctgggca      157920
acagaacaagaccccatccttttaaaaaaaaaaaagaaaaagaaaagaaaaaacgctgggcatggtggg       157990
tcacacctataatcccagcacattgagaggcaaggtgcgtggatcacttgagggtgggagtttgagacc      158060
aatctgaccaacatggagaaaccccatctctactaaaaatacaaaattagccaggtatggtggccggtgc      158130
ctgtaatcccggctacacaggaggctgaggcaggagaatctcttgaacccagaaggtggaggttgcagtg      158200
agccaagattgtgccattgcactccagcctgggtaacaacagtgaaactccatctcaaaaaaaaataaaa      158270
ataaaaataaaataaaattaaacactttgttgtgtgaaaaaagacatatagttaaacaaatataacca      158340
gccccttatttctgaggagaaagactgatgcattgtagaaaggataatacaattttgagatttaggtaag      158410
gactatcagaatttccaggaagctctgctgtggttcattgttacagggaaattactcaagggaatatatg      158480
acttggaatcatttttgcttttttgttacatttcctattattcattgcttctttggactggtgagaagcct      158550
ctcagagaaataaggaatactgcacatcctccatatttctcagcttttgaaaattaagttttatacact      158620
taagggcagccacaacacatgaaaacattttatgctgggcgcggtggctcatgcctgtaatcccagcact      158690
ttgggaggccgaggtgggaggattacgagatcaggagataaagaccattctggctaacatggagaaaccc      158760
tgtctctactaaaaatacaaaaaaattagccaggcgtggtggcgggcacctgtagtcccagctactctgg      158830
aggctgatgcaggagaatggcatgaacccaggaggggggagcttgaagtgagcagagattgtgccactgca      158900
cgccagcctgggtgacagagcgagacacagtctcaaaaaaaaaaaaaaaaagaaaagaaaaaaaaagc       158970
tcatggtaggaagaatcaataacatgaaaatggccatactgcccaaggtaatttacagattcaatgcca      159040
tccccataaagctaccaatgactttcttcacagaattggaaaaagctactttaaagttcatatgaacca      159110
aaaaagagcccgcatcgccaaggcaatcctaagacaaaagaacaaagctggaggcatcacactacctgac      159180
ttcaaactatactacaaggctacagtaaccaaaacagaatggtactggtaccaaaacagagatatagatc      159250
aatggaacaacagagcccttagaaataatgccgcatatctacaactatctgatctttgacaaacctgaga      159320
aaaataagcaatggggaaaggattccctattttaataaatggtgctgggaaaactggctagccatatgtag      159390
aaagctgaaactggatccttccttacaccttatacaaaaatcaattcaagatggattaaagacttaaac      159460
gttagacctaaaaccataaaaaccctagaagaaaacctaggcattaccattcaggacataggcgtgggca      159530
aggacttcctgtccaaaacaccaaaagcaatggcaacaaaagccaaaattgacaaatgggatctaattaa      159600
actaaagagcttctgcacagcaaaagaaactaccatcagagtgaacaggcaacctacaaaatgggagaaa      159670
attttgcaacctactcatctgacaaagggctaatatccagaatctacaatgaactcaaacaaatttaca      159740
agaaaaaaacaaacaaacccatcaaaaagtgggtgaaggacatgaacagacacttctcccaagaagatat      159810
ttatgcagccaaaaaacacatgaaaaaatgctcatcatcactggccatcagagaaatgcaaatcaaaacc      159880
acaatgagataccatctcacaccagttagaatggcagtcattaaaacgtcaggaaataacaggtgctgga      159950
gaggatgtggagaaataggaacacttttacactgctggtgggactgtaaactagttcaaccattgtggaa      160020
gtcagtgtggctattcctcagggatctagaactagaaataccatttgacccagccatcccattactgggt      160090
atatactcaaaggattataaatcatgctgctataaagacacatgcacacgtatgttattgcggcattat      160160
tcacaatagcaagacttggaaccaaaccagatgtccaacaatggtagactggattaagaaaatgtgtca      160230
catatacaccatggaatactatgcagccataaaaaatgatgagttcatgtcctttgtagggacatggatg      160300
aaaattggaaatcatcattctcagtaaactatcacaagaacaaaaaccaaacaccgcatatgcatattct      160370
cactcatagttgggaattgaacaatgagatcacatggacacaggggaatatcacactcactgcctggggact      160440
gtggtgggtggggggagagggggagggatgacattgggagatatacctaatgctagatgaggagttagtg      160510
ggtgcagcgcaccagcatggcacatgaatacatatgtaactaacctgcacaatgtgcacatgtaccctaa      160580
aacttaaactataataaaaaaaatggcataaacctttaaagccacaaaataaaataaaataaaataaaa      160650
taataaaattccctcaaaaaaaaaaaagaaaagtttatttcttcctcaaaccttctttacctagcctcac      160720
tcaaaccaactcttaattttttccttttttttttttttttttccccaaagctatgcagctgacacgc      160790
atctgctcacttggcataattcagttggcatccagtaagttaagaaattctatctgggattcatgcaat      160860
cacaacccacatccaaaaaataatagcagcacttataataaataatagtgttttttgtttgtttgtt      160930
tttttagtattcacataggttttctccctggattttcacaacattgaaacaaaatagacaaaataaatgg      161000
gcttctcttcagccctgagttttgcctactcttaaccctttggagaaaaaatggcactgagctgtcagtc      161070
agtcgccctgtgggagaagacaccagttgtagatgcttctgaatatattgacttgatttctatcaccaa      161140
caatggcatattcaggctgtgctccatgccaggtgccatgtggtcatggagtctaccacaccagaggtat      161210
tctcagaagtagtattgaaaacacataggcaagcattgcttaagactgtataaacataagctctgtccag      161280
acatggaatacagtcggagtttgctaggataatcccaaataccaatacataccagaaaacttactatagc      161350
atgagtattgaaggcaaagatgcttttggtatgtaactaaaataatagcatgaacccatcttttagtgtg      161420
aatattgaataattaatgttacatacatgaagcatgtactggaaggactcaaagtaactgaaaact       161490
atacattcttcacgccatttatttaagacttcagctccttttacacaaccatactcagttacccttttgcc      161560
tgttcctgacttactaagggaagatggtgtggagctacaatttataatccagataatgattactagagtc      161630
```

```
catactctaccctgaatactgaaaactgcaataatgtccctaacttaaacttcctcttctgtttatcact      161700
tcttccttccctctttgattgttcttccatgaatccttgcaagtctccaagcactgagtatccttccatc      161770
caccaaatgtctgatatagatggctgggtgtaactttaagtctctcactaagatgatcgattttctcctc      161840
tgcttgtgctgggctcaccctctcatttctcagccaagatatcgattattgtgtcccatagcactgcta      161910
gcattaatggaattattgcatggtttggcctcattttagtgtgtggttttagaaatatctgagatctt       161980
agtgttggtttgcaatctgtcttagtccctctgtgctgctatgaaagaatacctgaaactggtttataa      162050
aacagaaatttatttctcatagttccagaggctggcaagtccaagatcaaggcaccatcatctggcaaga      162120
ccttctgcacatcatcaaatggcacaggggtaaagagctgaagagagaagaacccactcctgcaagccct      162190
ttttgataatgatattcatctattcatgaatttaattaaattcaaactattcatgttcattacctaaaca      162260
tctcccattacccactaacccacaaaacactgtcttattagggttaataatattcatgacaatgcatga      162330
attctagggacacattcacaccatagcaaaatccatttacactctctcctcatcaaggtttatgtgtttt      162400
ccaaagtgagtcagttcaagttttttttgacctttcctcttttgttttcattagatctcatttttagacta     162470
acagattactttgttcctataactcatgtgtctttcagaatctgggccagtttccactacccaagtggga     162540
tctaggagttaaccccaccgtcaacccaagtactcctcctgtgtccaatggccagtcagcctcaatcctg     162610
tcttctcttgagttatgacatatttttcaccttccattaatagtgagtctgttgaaataggaatttatac     162680
ttccttctttgtcctccatttccccaaaatccgttctctatccttacaatttatgctaataaatctcat      162750
taaggtatgaccagtgatttctacattgccaaacccagtggcgtcttttagtgatgatcctatatcaat      162820
atgataggcacttatcacttgcagaattcttattccttttcattgtatcactatgctctggttttattct     162890
acaactctgagaagttctttgtattttcttctcttactattcttaaatgttgacttttctcaaggtttg       162960
ttcttgacttcattctgtatattgtatgtctgggtaattcattgcatcttcttatcttccaactatctgc     163030
ctctatgtggatgattcttgagtctttattttcagcccaggccactagcttcattcagttacagtgtttg     163100
taattttagctcctgttagaaatctctagttgagtgtcacatatacacttcaaacacaacacattcaaat     163170
actgagaaatactcttcctctaaaacctattcctgcacccctcctgttggctcaaaggtgccccac        163240
atcccagagtgtccaagataaaaactgattttacttctcttttctcaccacttatgtaaatagatatctg     163310
cctctcatcatttctgccctgcaaaacatcccctagctatgtgctttctgcctgtggcccactgtgacagc    163380
ttccttctctcagtttagattgttatgcagtccattactcttctgcctcctaccatcaggctactattgg     163450
agtcatcttcctgattcttacattcgatgacttcaatggttaagtgatgcattgcaatctttcttatatg     163520
atttttctgctgctacaacagaataacctgaaactgttataaaaaatagaaaatgtatttctaatagttccag   163590
aggctgacaagtccaacatcaaagcaccatcatctggctagtccttcttgcaccatcatctggcaagacc     163660
ttcttgcacaaaggcaaacaactcaagagagtgaacccactcctgcaaggtcttaaaaatgtatcatggc     163730
aaaatttcttgagtggccccttttttaccacctgagaaaacctaaaaccttgggacagcatagaagact     163800
ccttaatctgctcatgtctcccttttccagtgttagctcctttttgctttctttttgtataccttgtgccct    163870
tgcccattgaaacaaacagctcacagttccccgagcataacctgccttcctacctgcctgggagctgcctt     163940
ctaataggctgtatataggctgtatcttgatgacttcctctcaactctccctctggaaaggtcccagtca     164010
ttcatttgttaaggcccagtgaaaatttatttcccttcacaaaatatttttaggtatacatatatatgca     164080
tatgtatgctatctgtctattagatatatcttcttttttggcctttatttttttatttttttttatttttt      164150
gcaatagagtttcagtctgacacccaggctggagtgcagtgtcatgatcactgcaatcatgcagccttga     164220
cttcctgggctcaagcaatcctcccacctagcttccgagtatctgggaataccaggtgcataccaccat      164290
gcccagctaatttttatatttttttgtggagacagagtcccattgtattacacagtatggtatcaaattt     164360
ctgggctcaagcaatcctcctgcatcatcctcctaaagtgctgggattacatgcctgtggccactgtgtc     164430
tggcattatccttgttaattataatgcctacctcacttgtcttttttcaaataatacttaatgaatgatttc    164500
tggattgatacatccatgaatgaaatgatagtttgccaaaatacagaatattagagccttggtgtcacct     164570
tgagattatttagatcagaaaaggggattttttttatattagaaggttattcactgtattattttttaaaaa    164640
gtttatttatctcaggtgtgttaatttgttgagaatgtaacagaaaataagatatgaatggtctaagtgtt     164710
taggcattataaataaagttgaagaaatgagaagaaatcccatggtgtttcttctcatgcattgataataa    164780
aacttctttattgattgcaactgtacattggcagcaccgccccaaaactggaaaataagatcaaattctc     164850
cttttgttcttctttcatcaccttgcatttttattttcttgggcttattgttatgagtttggtttctagct     164920
tttacagcataagaaagaagtggaaatcaagacggaaagaagtttactatagtgagaaggtgtcatgtcct    164990
gcaggccagtcatctcagagtctgactgcaacacccatgacataggccattcttttttcttgcccacgacc    165060
ctttccaaactaatatcaccagacttatattcctgtcctcttttataaatgggggctgttgtctagcaggc    165130
tagcttaccggaaaaaggactttctcagacgtgctttctcatcctgatggtttcctttaccagaagtgag    165200
gctgcaagcttcagcatgcgtttataacaaaaaagagagattgacttttttcatttaaattccatgtttc    165270
tgcttggcatagtggcttatgcctgtaatcccagcacttttgggaagtctggtgggagaatcgcttgaga    165340
acaggaggagttcatgaccagcctgggcaacataatgaaactactgtctctacaatatagttttttttctg    165410
agacaagatctcactctgttgcccagtatggagtccagtggcacaatctcagctcacttcagccttagcc    165480
tcccaggttccagtgatcctcttgcctcagcctctggagtatctgagaccacaggtgtgcaccaccatgc    165550
ccagatatatatttttttattttggtagagataattttttatcttttttgtaattgttgcattttttgcca     165620
tgttggccaggctggtcttgaactccagacctcaggttgtctacctgtcttggcctctcaaaatgctgat    165690
attacagtgtaaaccactgcgtctggcctctgaatttttttttccaattagtgtgcttgtagtctcagct      165760
acttaggatggtgagtcagaaggattgcttgagcctaggagtttgaggatacagtgagctgtaatcaccc    165830
caccctgggtgacataatgagatgctgtctctataaaaaaataaacaagttataaattttcacataatca     165900
taaacatgtgatgatgtggatacttcattttcacatttaggtctttaatacagtgataccttctctttgg    165970
gcaacagtcatcttcactctctactgtgttgataaagtttccactttgcccttgaagattttgtggctta     166040
ggaggaaacaattaaagggatgtccttcagcagaacagccaccctgttaggaagaaactaattattgtg     166110
tgaaagggacagggtgatgttattgggtaatgatagtaagagataaaaccagttctcttgagctgttact    166180
tagattccataactgaggctgattttgcatccttggcactagatgttattcagctgacagccatggattc    166250
ccaggggttccaagaaaccccccaaactatctgtcacctttatgagtaggtaagaatgtatttttcttgga    166320
gaggagtatctcctcaaagaagtctgtgatgtagaagaaaagatgaaaaatctctgcttttggattcggaa   166390
tgtcaggactactcactttgaacttaaggagaatttcttcttagtatgtacgagattaaaccatattgggg    166460
ttgccattttcttagacccatatagtcattttcatatggcttttatttggacaataagcattgtgtag      166530
tcctttttctttttttcatctctcaaacttttttctcctcttgggcatattgttccaggtttcctttgtg    166600
gtttctagatcataagcattcatgcagtcacattacattccctcctaaattgtaagctctccaaagagag    166670
gggatatagctgctttatgttctcacccaactttgagtagggacaatagcaggaaacagaaagcatttc    166740
```

```
acagaaaggatggagtccatttgtgtcatatggatcttgtttgaaactttacctgtgtggcctgggtga        166810
attaatacagctgtcttttaaaatctagaactgaaacctcagcggattgccataaggattcccagaagtta      166880
ggagctcctcagtaaatataagtatcctattctcttgtgtaatgaagctgacccacaggatgatgccaat       166950
tatatccttggtattataagcatatgaacaacagttcatatttattgaggcctcactatgtgtaagacac       167020
aattgtgtgctttgggatatttgctcatacatgaaacaaatgtttaaataaaacagcgtgccccacactg       167090
gagatgcagctgtcattagcattgacaccttcccagtatcatggtgcccatgtctccatgtgggttaatc       167160
taaagataggctcaggcatattaaattgggaaggttgtcttaggataattcaagcaggattaagtcaata       167230
gtgaatgaagagctagattaaatgggagtttgggacatgcatctctgctaagtgaatttgagcaggaaa       167300
cataggcaagacttatctgctttagttttcacagtaggaccatgagattacactactgtttattaactct       167370
attacagagatgtggaaactgagattaggatgattgaataactcagccagattaggaatagggctggtag       167440
tctttaatgcaagtctcatgggctatgctgcacatactcttaacaacttgctaccttcatggtaaaagcg       167510
aagaaccaacccaattcccttttgccattccattcttgctatattagcctatttttcacactttttataaaga    167580
aatacctaagactgggtaatttacaaaggaagaaggtttaactgatttacagttccgcatggcttgggag       167650
gcctcaggaaacttacaatcatggcagaaggtgaaagggaagaaaggcaccttcttcacaaggcagcagg       167720
aaggagagaagtgctgaggaaaggaggaagaacccgtatacaaccatcagctctcatgagaactcactc       167790
actatcatgagaacattaggggggaactgcccccatgatctaaacacccccccacagggaccctcccccaa     167860
cacatggggattacaatttggattacaattctagatgacatttgggacaggacatagagccagaccacat      167930
cacctaccatttaattagcttactcaactatcctgcaaacattccttagggaggcaaaagggacacactca     168000
taaatggttttaacgtattttaaaagttatcaatattgtagtttaatcataattttttaaaatggtgcatc     168070
tcatgtcattggctaggatcagcagattacatgctgtatcttgggtcaataattgctgcaagcacttta      168140
ttggagttgctgttagtagtcatgctgtctactttgtcctttcttctcccatttcaaccaacctggcagg      168210
gattgacctcagtagtgagttgctagacatcaggagaagtcagaagtaagtggaagagggcctgctgtct      168280
agaagaacctcccccacccgcctggcccattgcagtgacaacacagatgcatgggagtaggttaaataa       168350
ttcttctctcattgatccattcattcatctttcatccatgaattaactattcatgactgattgttgttga     168420
ctctgagcataccacaacaaagaggatgcacaaactgtcctgctgttactttagttatggggacagaaga      168490
taaagcagtgatcaaatgcatgaaggacagaatttctgattgtgatcatagtttttgagggaaatgaagca    168560
gtgataacatctaacgtgggttatgaggatctctgagatggagtgtccagggcatgtctttttgagggtg     168630
aggaatttaagcatcccagacacaagttctgacccaaacattagccttttcattgtgagaaagggcctca     168700
ggaaatttaataaatgtaatggtaggaattcacgataacactacaagaaaccaagctttgtttgtgaatg     168770
gtgggggttagaaggggtttgttgctagaaatcccatttgcaggttctcaggctgggggttgaagtagaagc   168840
aacaatctcttgtcttttgccaagcaaagaacagtccctggtatctggcaaaagagaagtatcttcctct    168910
gaatcctggtgttggccataagccaaagttctatattaattttccttttttggttgagttgggaagcagtt   168980
ggatgattagctaattttgctgaaatagaaggaaggcagattaaaaatatagaaaataactcctattta     169050
atgattaaaaaatgagattaatcagacaaagttgtaatgaacaaagttgaaaggtgaaataatttgtttttataaaactg  169120
taaaattttaggctgggcatggtggctgacacctgtaatcactttgggaagctgagggtgggaggattgct   169190
ttagcccaggagttcaaggccagcctggtcaatatagggaaactacatctctacaaaaattatagaaatt    169260
agccaagcatcatggtatgtgcctatggtcccagctactagtagtctgtggcaagtagaattgcttgac     169330
cctgagagatcaagggtacagtgtactctgtcctggttgatagagtgagaccctgtcacacatacacaaa    169400
aaaactataaaattttcatatgtaataatatattgaagctaaagtggaaatgtcataaaatatatttttaat  169470
cctatggtataaaattctctctctgttcattagttacaaaaaatttgagcataaacacttttcaaatacaaacc 169540
tgtgcaaatgtcatagatggcaggtggtatatcactttatatatttaagctgtatgtgggaataaaagga    169610
taaaaataaaagttaaatttaaaattctaatgaaggaacatattagaactacattatggaggactttgtt    169680
catttatggtctgagcacagatgatgctaaacatgggttgtcaacttcagttggcatccatttaaaatga    169750
acacactaaacaccttgagaagaaaactgcatgaaaagtaaagagcattatccaagtgaacttcatatctc    169820
atcatttgcctgtttatatattaataaatacctacgtaattggtttaattaatcagtattttattttg      169890
gtgttgaaataatgagtggctgagcatgccagatgtattcatctgatacattcttccagtcacagggtag     169960
gctgcattaggtggtaatgctttacccctgaattcatctgtaagttatgaagggaagtccataactctgat    170030
ctcagagcatttattccattgttgataagccaagctgttgctctcatttagttgttaaggaacaaggcta   170100
actgaccttgatatgtaaagtatgtaaaatgtgtccttcacgaaactctgaaacaaacaatgagaaca       170170
accagaaaaaaatgctagagtcatacaaaagctgtctctatttttttagtgatcattcctcaagctcttgt    170240
cagccactgagtgaccatagatggatttgcagttgttgccagtgtggctgattttgataggactaacata     170310
ggaccagtgtagggagctatttattaagatgttttttgttagtcagtgtttacatttgggtgttctctga     170380
taacatacattaattcctattgcagtatttaataaagtgtaactgtgcctgttccacatgtctaaacata    170450
ttcaaatatggagactttgtttttggtctcattgcagatactaaatatcatattgtaattagagctatac    170520
agagatttagcatgtaagactgcaagtcttagaggctagcttttgtgattcagtcaagaaggtggtgatt    170590
ggagtgaacaaatcacgtggggcacaattttgtgtttctggcttgagtgaccagtactttcctcttccct     170660
gcctcagtgcaatttcacattgtcttcattttgtgagatcaccctgtgtcttagcccatttagttttgca    170730
attaaggaatctctgagactgggcaacatacagagaaaagaggtttatttggcttatggttctgcaggct    170800
gtacatcaatcatggcatcaggatctgcttcaagggtacagatcctagtgagggcatcagaaagcttgca    170870
ctcacggtggaaggtgaagaggagctggtgtatgcagagattacatcaagagaagaagcaagagaatg      170940
gggggaagtatgtgctaggctcttttaaacaatcagctttgggggaatgaaaagagcaataattcagt      171010
aattcagcaattacctcaaggagagcatcaaggtgctcatgaggcatccacctctgtgacccaaacacct     171080
accaaccaggcttcacctacaacattaggaatcaaatgtcaacctgacacttggagaggacaaacatcca    171150
aactctagcactctgtctccttaggtacatcttaatcttcagtgacttaccttcagtgactaagttctc     171220
tttgaaaatgcaaatgtagtcatgtttctttttgcttgtaatgtcttactgatttcctgttctttata      171290
gcttcatgttgcatcttcatcagttggtgaaccagttgatgaagacaagatcagcatcctgaagtatctt     171360
ctacactttacttcaagattctcagaatgcatgttaactttactgcacagtgctgtttgccctggtctgg    171430
tgtatctctgttaacccagtgcacttttctctgatcttcctaaggctcttaccttcttagttcctacgg     171500
cagtatttaataaagtgtaactagtgcctgttccacctgtcattagtcgtttctgggactatcttgcct     171570
atatgagtatggctactgtgggcaagtacaatgcctggcatgcagcaagctctctattaatgattgttt     171640
ggctgctagagttctctttgctgtttcacatccattctttgtcatcctctttcctagtcgtctttc       171710
cctgtaccttgcccttgttctccatgaatcaatataaatagtataagctttgtgcaaaacagaccttc      171780
acgcttgtcttatgtcttcattgctttcttctgcatactaaaaggccattaccttcctctctctgactct     171850
```

FIG. 11A-34

```
caatttcctaatctgtataattttgatagttatctcccctgtctgctatttctgacgttggcgtgaacac    171920
gaatatgcgaagtaccagactttcactcctgtctcatgattgcattgccttcttctgcatactaaaaggc    171990
cattaccttccctctatgagtctcaatttcctcatctgtatacttttgatagttgtttctactgtctgcc    172060
attgctgtgacaatggcacaactcagatatgcaaagtacctttgggctaaatgtgaacaaaaccttcaac    172130
ctgctgcatgataatctcaccttttgcttgactggctagctctgttttcttggtagttggatgaagaacat    172200
gccaacaatgttatggacaatattgcttacaatatagatgatccccctattggtaaatagcatcatggcca    172270
ggaaaaaccataaagacttgaaagaacctagtgggaataccaccccacctcaggcttcctggagggcaag    172340
ttttggagtcactttgcagctgctatgttcactctagggacaatggaaactctgctcatggagtatttac    172410
agggaatattggctgctgtgaaggctgggacttcaatgccaaggaataccccaactcctgtggatatggac    172480
cttatagagatctttgcatctcagctaacctttgtggagtagatggttcccacatgccagctgcagcctt    172550
cctgatgagctgagggtcttgtctatattgttttgagttggttggcaccatgttgactttgaggagtctt    172620
gttattctgcatgttttagtgtaacctaagaagatccttactgaatattaaagagcaaagacaagtgtccc    172690
tctaacagaatactggctaaacaattggtattctctctgatgcttcttacctgcttgaaagctcttttct    172760
ttcatccttcatagtcacttcttacatctgacacaaccttcagctttgcattattccttcattatctttg    172830
tttgccccacatttcttaaaaacatagttttttaaattgtgaccaaatgtacatgacataaaatgtaccat    172900
ttttatatgtacagttgaggggtattaagtgcattcacatggttttgcaaatgtaccttttttggtcat    172970
cctgtgtccttattgtactcttcctggtttatgatgcagtgtcttatatatgttgtaataaatgtcccc    173040
tgggtatctcagccttgtatactctggtcttctgttatatcatgtacaccttgagggtagagattgtgcc    173110
-ctactaatcttcctccttcatcacatgaaatattgtctctgcacagtaaatattcttcagtctcctttct    173180
gtcatgttttctgtataccatgacacttatttgccaaggatcactttgaccctctaggcaaaatttcac    173250
cattggtaacaatgctaaagttcacataaatcttaagttgaatctgaattttaaatatttgaatatgttt    173320
tgagtcccaaatttgtccaaagcatagccacagtgcccagctatttattttctgaattttttttttggtag    173390
agattgggtcttgctatgttcccaaggctggtctggaactcctaggttcaagcaaccctccctccttgac    173460
ctctcaaagtattaggatcacagatatgagccaccatacatggccaaagtttcatattattttagaaggt    173530
gatgagtgttctgaagtgaactagagaaggatacgtgttatcagagttgctgaggaagttgcagtacttt    173600
aagtagggtgatcagtgacaacatcaatgaaaacagaatgtggcagtcgagaatttaaagagttaaggga    173670
agaaagccacgatgatatatgagaaggatgttccaggcagagggaagagccagtgccaaggcctggggtg    173740
ggaacatccctgttctctcttagcacagagcagtgtaattgctctctcatgctgccagtaaaggtatac    173810
ccaagactgtgtcacttataaaggagaggtttaatagtctcactgctctacatggctagggaagcctcac    173880
aatcatagtgtgaaggcaaggagaagcaaagtcatgtcttacatggatggcggcaggcaagagagagcatg    173950
tgcaggggaacttcctctataaaaccatcagatcttatgagacttactcactgtcatgagaacagtata    174020
ggaaatatccatcccccatgattctgttacctcccattacttccttcccacaattatgggagctacaattc    174090
aatatgagatttgggtggggacacagccaaaccatatcaagcagtaagatacctgttgccagaaaagagt    174160
gaatagtaggtatcagagtagagtagagcaacactattgatatttgtaattctgagaaccaggaagaacaaat    174230
ggaaagatttcacctgataaatcatgtgtcagagtgtgttttaaagcaggactttgcttagctgaggctt    174300
acctgtcagggcaaggatgggatgagggaaaccagttagaatactgatgcaagagtcaagatgaaaacct    174370
acaactggaaactgaggagaagtggctcggttttttaacacatttgaaataaaatttgctcatgatttgg    174440
atgtggagtgtgggagatggaaggaagtccagagttttggcctaaacactggagaaggtagaggtgatc    174510
acaggtgacattggaggatggagctggcagagatattcttcagacattattagatttgaatgtttgagttt    174580
gaaaagtctatgagacatcaaacataatatatcgcataaggacatgtatgacaaagtctgaagttcaaga    174650
gagaaatctgtgctgaagagaaaaaatatcagcctagatagtgtcgatggtatctaaagttatgaggctg    174720
aatgaaattatcaagagagttctgtggacagagaaggcaaagggcaaaagaccaaggctggagtgactgg    174790
tagtcataggaggacctggaatggaaatgaaaataattgtatacagtgtaaaagaatatctggtaacatt    174860
gaagtcaatggttgaaaaaggcatttcagtgagacagaggtagtcaactaggtgtaattcaaataagtct    174930
caaatgagcatctattgctaagatttccactacagaggcaaccaaaaagtgtcatcatgcttttgtctgt    175000
ctgattgtggcagctgagattgaatagaggtaggaagaggtgaaaaaagaatgaggaaaatagaagacat    175070
agcaatgcaaatgtcattgttgacccttactggaaaagtaataattttagtggagtttggggtaaaagc    175140
acaattggagcagctttcagagagaataaggtcaataaaattgggatcaatatggataaatattttcaag    175210
gatattttcagaaaaggaggcatatatattaaatataatattatcatatataataatatatatgataggag    175280
gtaactgaatcatggggatggagttttcccatgctgttctttgtgatagtaagtctcagatagtattgtat    175350
tatatattatatattaatatcaattagttaataattaacattaatatattattataataattatatataa    175420
tgtttgtgtatttcagatgagaaaattgttttatcgcttttaaggtggggaatctaaccacatgtctgtg    175490
tgctgtaggggttgtaaagtttatttctcactcatgttcaaggttcactaagggttgactgtggctgtttc    175560
tgtgtcttcttaattctgggactcaggctgatatagaagactcatttcttattattatttggcaaaggg    175630
caaaaatgtgcataaccgcatttttatctcttaaggtcctccacttgcaagtagcccttttaatttctgtt    175700
catcttttcactagccaaagcaagtcaaatagctataactgaagttcaagttagtgtaattcttt    175770
ccagttaggggcagggcaatattgaaagagtgtatttgtccctgtgagaggggaggaaatttctttatac    175840
aataatacaacatacaagaggaaagcaattctgatgatgtagcaagagaggagtatttgttgttggatt    175910
gtggggagtcgatagaatttgaagagtaagagtcagctttagatatgattttatttcattcctctcttatg    175980
aaaagagggggcacagaagatgggaatgttattgtcacatgggtaaatgggttggtggtggtttgtgtat    176050
gttttcttcagattgttagaattttttcggtgtagtaagaagccaggtcatacgctaacagggaagacgg    176120
agcaggaaggattggggattagacgagggagaagaaggtgccaactatttagcagagccttgagagaat    176190
tcatcagagaagtttattattccaggcatctccatgagcctactggaggtttgtggtcctgagtttaaca    176260
tgagacaagtcagcatgattgaatatctttttcacctggctaattggcaaggcgtagccactgcatgc    176330
tggggtggagaggtagatttcaccaggtttggtgttgtgccaaggaagagtcaaaaattaagactggatta    176400
gaactgaaggtgtctgaaggatggtggatctgatatgactccacaactctaagaaatgaagatccagtgc    176470
caccatcccccatcatggaaatgacaaatgaatcaaacaaaatcatttcactttgtacaagattcggag    176540
ggcttgtgtgtctatgatctcaggcctcagaaagagtaaattggttatttttttctcacataactctgtg    176610
tgtgtgcattagtacaattttttattttttgccctagaatgtaaacataaatttgtcaaattaaagcagta    176680
aattggaaaaaaaatatacagttttgtattatctgtagaaaaaatgttaccacagctatgtagactatga    176750
aaatggaaaatttattatgtatttaattttttacccaagagcagtaaaatgaagacacctatataattag    176820
gcaggtgactgttaaaatatttgattttttgttgaaattccttggctcagaaaacaggtttcatgccatg    176890
ctgaaaaattacttagtttgatgaaaaagtgaacaagacatgacagtgaaatcatataatgttcagacag    176960
```

FIG. 11A-35

```
gaaatagcaaaagtctatttttcaataactggctggagtaagttgtcctcattttgggtcaagatctta      177030
ttttggtgtctcagctgaagatacctcttcacaacctattaggtattgtgacattgattaagtattatc      177100
aagcagaaagtatttgtaggaaattctttgtactgggtaggtaaggcaatcgctaccacaggggcataga      177170
ttttgaaacatttcaggaggatccaaagtcttactgagaaacctaaggcagtcagcaattagaggataag      177240
ataatggatgattaactactactgtgtgtggggtagacaattagagaacaatgcaacacacatgttttaa      177310
ggtgctgatcatgagtttgaacaatggtgaaaaatggaagaaaacatcactggcatgggctgacgctgtc      177380
agggggtggtgtgtttctcatgtgctgttatcctctcatcagtgttgagttggatagtattcccaggaat      177450
ggctgcttggcttcacttctcttaacagagaattgctctaccccataaatctgcagacacacctggatct      177520
tgaatttccatttactctggaagatgtacagctgcaaacaaaatcaaatcacatttagcgcctttctgg      177590
aacttccccaagtactcagtagtcattctagctcacatcttaagtccccctaggggttcaataagtatacta      177660
aatgcatatttgaaccattttccaaaatctaattcacttttgatcaacagttgtttcctatgaatttgctgt      177730
gttttcttcaatatagaatactttctgtgattaatcttcagtagaccaaaggtgaggtagattacatta      177800
aattctaaatcatgaatgattcattcttttactgaaagtaaacacatctatcatattgactccatatcat      177870
attctgttgtatatcctcacttagatgtctttattatttttagacagcttatatgattgtttagagctt      177940
caggcagtttacatagacaaaatatctgaataaaagtacaatgatcatattttatttttgtcagtttaaaa      178010
tgatgtttaatgattttaatgccagagaaaacgtgtgtgtgtgcatgtatgtgcaaacatattttaaagt      178080
aatggtttactgagaggatttttttttctctttgtatgactaagatatctgaattctgccaaaagttgtt      178150
gaaatacgcccttcttaaaatgtcaatatgtctataacatatttttatgatatttcagtattagatatgt      178220
tcattaccccatgtactaattaggtcttatcttgtgatgatgagtcattagacctattatattgaaaata      178290
ttttttaggtagaaatttatatagtctctgagtaaaatcttatgttgagtatgtgggtaagttgccttggg      178360
atcacctgattgtattttattgttgctgacttttcatcatttttattaattttgggaataaggacttctttt      178430
tttatggtgtagttctgtatcaccttccttagattatattgtacaatgaacaggcagaagatactaaga      178500
tcttattaaaactagaactttgaacctaaatgggggatttatgaagctaaattagcctaattgcatattac      178570
aatgaccacagcatattaatcaaacatgtgaccccttacatttgcaatttaatgatctttaatatgaaaag      178640
cattttgtaatataatctgcttgatgaacatttgctattttactaattttttacttatctaattgttaat      178710
tcatgcaatttatctaattcttagtaatctatatgattcaagcctcttatagattttattctctacccag      178780
tttttcatccagctgtctttctggttatctctgccttggtgtgcttgagtattattttatctctgtgac      178850
tccaatgtactttgaagtgtctgaacttgaggtggcagaatcaaggtacttctatagaggccactgaatt      178920
ccttttctcatgatgaggtacaggaaccatttctcaaagctgccaaaacactgcccccttagtctatgcaa      178990
atcagccagtacaaatgcatgtgactcaatcaacatcatgaaaccacttttttggaatgcctgatgttgac      179060
aaaatgtgatcttgtgacaatgtgatacatttatttaagccaccttgtggtatcaaattggcaccattga      179130
caacatacttcttagacgctaagtgcaataattgttgcctctcattttcctacactgctttacttcatt      179200
aaatctgcatcattaaaaatatttatagcattgctgaagtcacttcccaggagctaaggaatgtctccat      179270
ctgtatgctgatccagttcctgctggcatttgcttggatgcagaggccatccatctcttgccattgatat      179340
ttgtcaattgatgctttttttccttcttcctggtgacttaggaaaggttctgatgctatatctgctaca      179410
gatgccaccatggccagctaatttttttaattttttgttttttgtagagacggagtattgctgtgttgcccag      179480
gatagtcatccactcctggcctcaagtgatcctcctggctagtcctcccaaagtgccaggattggaagtg      179550
tgagacacctctcccagccccagtgcttgatattttaagagcttcaggcatggaaagattttgtctgcctg      179620
ccacagccttccatcattttgggatgtatttgcttgagacagctgaatatgtgacaacctgaactgtggt      179690
tgctggcaattggaaaatagtagattgttctgttgatctgctgggagaagtacagcagcctgcagaggaa      179760
tagaagcccaggggttttatctggcacagaattactctagagagccatgtaaaaaattttaatttctgttt      179830
ttataaatttattgttattattttttagagacagggtcttgctctgtctctcagattggagtaggataatca      179900
tagctcactgcaaccttgaaatcctcaggttgagtgatcctcccacctcatccttctcaagtagttgggat      179970
gacaggcgtgcaccactatacctagctaatttctctatttttcttttttgtagaaacagtatctctctctg      180040
ctgcccagtctgttcttgaactcttggcctcacgtaatcctcccatctagttctcctgaagtcctgggt      180110
tatgggtgtgatcgtgcctatccatttggttgctgttttaaatttgtaccttattgtcatgctaaata      180180
ggaattctgatggtactgttggctgaataggtcaactggaacacacattttttgttttacaggtaaatac      180250
gatgaaacttaaaatgtagctaatgttattcctgaaacgaatatgtgaagttctaatttagggacaaaaa      180320
ttaaaaaaaaaaaaacatgttgcatgtattaaacacctttgttggctatgttttcatctgtaatttcattt      180390
ggaggtagccattgcttcttaactcatgctaaccgtgctttagagtcgtattgattttttagcagctactatg      180460
cttttcatgcttgcagatcatttatctctttggaaactctatttgatgacaaagctggctctgttacagag      180530
taatggtaaaagaaatgacttaccagaatttcaagtgaaatgtgcaacatacatgatgatgcatggtgac      180600
tgctataactatttcctaatgttgttatttaacagccatgaaagcatccaactgaaataggattgaatgg      180670
cttagttagctcaatgttttttgaaagctttctcagtaaagcatggtgccaggcaccaagtggttccttat      180740
agaggagccagagttaattttgatgatgttttaaaaacgctgctagaaattgggtggtgttttccaaatg      180810
atcttcctagtaattatttatgctatgaatcagaaaggttaccatctctctggatggaaatggatagtca      180880
tatgtgcacaaattcagggatttggcctcctatgataaagccctgtcttcccccctcatttatgtgatgat      180950
tgtgcactatctgaatgatgagaaacccattggccagttttcacttgtgcatggctggaggtgcttgctg      181020
cagctctgtgatgtcctgagccagcatgcttgtggagttccagtctgctgcatgaacaattgaagaaaca      181090
tgatcttcctaaattttcacaagctgctaaatgagtgattttgtgtttcttttgaagaaacagtatctctgcaact      181160
ggaaatgcttgctccttcccaggttattgctcaatctacatgccatttgaggatgcagataattactgaa      181230
tctttatgaagcatcccatcttagtccagatttcccttttcacagaccaaaaggtcaaagtcagacttg      181300
gcagacaacacagcttcagtctcatgggggggatttctttgtcttatcaacctcagtcatgggctttccag      181370
ccattataaatttcacatgtaatatggagggtattgttccaagaaagtgtggtgcctcagtagggttggag      181440
gaggcacatgcagctgatatagctaaagaagagtgtgttaaaatgggaaggaggcaaattaaaagcacta      181510
aggaaagtttctttacacaccacagaaaggtttacaaaacatcgaggaagcttcagacccaatccaggt      181580
actgcttttacttctgaactatgtcataatttgtgatatcagaatattctatggaatctatggatacctg      181650
cagaaatagtttgctgttgttcccattctgcattacatttataagcagttgctgtatcatgggataca      181720
taatgttctttaatcctaataggggcatcagttctaaatataaccaaaacaattgtgaaaggcacacatg      181790
cacaggttggcatatagagatggagatggccgatacgttgtgttttgtacagatgggaatgctttctgtg      181860
tcctgccccacactgcaggacagctgacaggtagtccaaatgcccatgtagacagctggactccagaca      181930
gcttgctggtactgtctggcacgccttcaagtcctgactttcttgggtcccctaatggaatttacattacc      182000
tgaaatttccgggagtttgtgaggctggctaaacagattccctaaataactggagatgtgcagtcagaga      182070
```

FIG. 11A-36

```
gcgaatagacaaagaaggatgcggtggctgtcagtgtattcattttcttttgctgcatatttgattactg     182140
caaatttagtggcttaaaatgacacacttttgtcatctcacaattcttgtgggtcaggtttctgggcatg     182210
tctgaactggatttagtgctcagtgccacacggggatgaaatcaaggtgtcggctgggtagcatgattct     182280
ctgaaggttcatagtcctcttccaagctcactcaggaattggcagaattagtttatttctgttgtaggat     182350
cgaagtcccctttcctttctctctgtcagcaggagctgattctagctcataggagtcccccaagcagctt     182420
gttgccatgcagccttctcagggaccatcttccaatatgttcatgcatgcatgcctgcatcttcatgtcc     182490
agcaggggaatctcttgctccagtctgctaagaaaaggaaaaatcttagataacataaccaaggcaatag     182560
catcgcattccatttcctaggtaacataacatactcacaggatgacttctaacaacttcataagtccagc     182630
tcatattcaccttcctgggattaaaggagggcatggcttatcgggtccttccaacttataaatactccaa     182700
tatataaatttcccagggcttctataacatattaccacaaacagggtagcttaaaacaacagaaatgtat     182770
tccctccagttctggaggccagaaaaccaaaatccaggtgttgtcagggttggtttcttctgcaccttct     182840
gagggagaatctgttcctgcctctcctacttttatggggctgccagtaattttggcttttcttggcagt      182910
gtcacttcaatactgtcttcatctttccaaggccttcttctctgcatatgtttctggatgctctcttctt     182980
ctaaagacacagtcattggatcgagggaccattgcaaatacatgatcattttatctctaaggagattaca     183050
tagtcacatctgcaaagaccctgcagtagtacctccttatccattgttttgttctccgtggtttcagttc     183120
ccggtgatcatttaatctcttggcttaatcagttaactcttgagagattaagagttaatctcttactgag     183190
cataatttataaattaaactttattatgggcatgtacataggagaaaacatagtatctatagaatttg      183260
gtactagctgcagcttcacatcttggagcctatcctcacgcataacaatcggggtgttatgtatttcca     183330
aatagggtcacattctgagaatctggtagatgtgggtttctgcaacattattcaacacaatacaccctgt     183400
catgctttgcctgtgacctgacactgcccaattctctggtataatcttgcagcagactctccttttaccttt   183470
ttctggaatatttccttacaactctctttctgactccttgactcccaattcagatcatctaaaactaaga    183540
gtaatatttagggattatcttgctgaccattagagaagatggggtcactaacagatagatagataggtag   183610
gtaggcagatagatagatagatagatagatagatagatagatagatagatagattgatagataatagatgtgaa 183680
tcgatagatgggaaatggatggatagtaagatgatagctaggtgatatatgtatatatagacagatagata    183750
gaaagatagatagatagatagatagatgatagagatggatagatatagatacagatagataaatgatagctc   183820
ataatggatagatataggtagatagatgagagataagacagaaagtaagacatatagatagatatagat      183890
aagcagataggtgatagatagatagatagatagatagatagatagatagatagatagataagtagagatag    183960
aaacaggtagacaggtatatagatgatgggtatatagatgagagagatagatagatagatagatagatag     184030
atagatagatagataggcaggcaggcagacagagagacagatacataggcaggtaggtaggtagaggaca     184100
gagggatagataggtagacagagaaatagattgtagattggagagacggatagatagacatcttaattcc     184170
tgtgcgccaatccttctctctctatagctaattataatcatacatgtatatgttacattctattagtagc     184240
atttcacagtgggaattcagtgatttagtgattactgaattaattgttgtatgaggctccctgacagcaa     184310
acactgagtctttttgttcactatcctcagtgctatcatttacagtaaatggtggaggaaacgtaactt     184380
cctaccaaaagcattttgtggcgctgaaataggagaaagtgagattctttactccatttccaaaatcatg    184450
gatactggctccaacatcagaatttacatggtgcctaaagaattcatcctattgcattgaatacattcat    184520
gcacatgagtattttctgagcaattttggttttccaatgagatactcatctccagacagcactggaccta    184590
ctaagatgactaattattagttgacatgtgaatactatgtgctaggtgaatgtgtgaaaaatgtcattgg    184660
ctggaagggctttttctcaaattgtccaacttttgcagccgtggactaataaccatttttcatgaaccaact 184730
ctgtctcttacatatttgttttaggttgggttaaagtttatttcaattgaacgtgtacatagagttgttgt   184800
atttaggagactttctgaaataattctcaggcaatcccttgaggtagaaaaacatctccttgctttactg   184870
taaatccatttccatgcttttttctattcatagaggccacctgtattccttggcttatgactttagagac    184940
tgacacttgttgcctacaagtggctaaatgcaggaaggacagtacccctttgaacttaatttgtttccca    185010
ttggatctatggaaccattccctatgtgctaaggccataaaataatccctgagggatggattactgttc     185080
agcttattgaaagagttagcataaatctacccagatctctccttagattttggctgttctgggttggca     185150
atcatgttcacatcttttcctttcttttttttcattattttaaatttaagcatatttatgcagtagtt      185220
agcaatgttttgatacatataaggcatgctgatcagatcaaggtattcggcatatccatcatctcaaaca    185290
ttgatcatttatttgtataagaacttccaatagcctcttttctagccattggatacgatacatccttgtta   185360
actacagggttatagaatactagaaacttattcttgatatctggctggaattttgtattctttcacaaatc   185430
tttctctatcccttttcctttcctttcttttccttcccagccccctaatatcctacgttctattcttcctcct 185500
atgagattaacgttttagatgagaaattcataacaggggatactacctaaatactatgttgggaagttac    185570
ctgttagaggactgggtcctctcttaagaagtgacttcccagtatagtatctaggtagcatccctcagcc   185640
tgcagactccatgaggccaagaatgcttttagtgtgccacaaaatttgcaaccttttctaaaacat        185710
tgtgagtttttttgtgtgattttaaaattagctcatcagcaattgttggtgtattttacgtgtggccc     185780
aagacaattcttcttcttccagtatgacctaaagaagccaaaagattggacaccccggcagagggaggag    185850
gtttatctaaatcatgaaaactggttggaatattggccagcagatgccgccatggcagggaattgggat    185920
ttcttgttaaaggtgttaccatttgagcatattgtaacattatttattactttcttatttactcttttc     185990
atgctgttaagtattttggggtgaattcagtaatttcccatccctgcaattgaatgtagtagtaatagta    186060
ataacaataacaattctaaacctggagagatttttataaatacctaaaattgcatgtaattgatgaaagaaa  186130
tgaaatcattaagctaggaatcactctttttagtgaatctcaaaataacatgctttttttaatgaaaaaaa   186200
agctaattatttaaggtaaatctgtaaacacctagaggtacattaagcttacatgttggcccaaagtgat    186270
ggtttatgaatttgtgaaagagtgaaaggattggcttagagtcattactgtatgggattaaatacttgcg    186340
ttcaacaaaaatctcatcatataatcaccacacagtattattttctgaagaaacataatgctaatgcaaa   186410
cataaatggatattaaaatggagacaaattagaaatcatcaggatgtgtttttaaaagctaggtagtatt   186480
ttttgattatagaattaggtaaaggctctgaatccttgagagcaacaacttggaatactaaaattatct    186550
gtattattaacaatggaggactgtgttcaaaacacaagatatcttaagaagaatttgcatcaagtttggc    186620
atcagaatcttgccaggtgaattggctgtattttaaagtaatattgtgatgtttatgggaccacctgc     186690
agtgaaataggtctcttttcattccacacctggatacagcaatctctttgcattgctcttcttcttctctt   186760
ctgaaatgccatcctctttgtgaactacaattctaacacttagtccgtgccttctaaacaaaagtgtc     186830
agttctctgaatgccatttattcttcgtcgaataacatgtttagttataattcttattttctttactgca    186900
tcaaagatcttaagacataatcaatgatgtattcctctctctgttttatatttcattttgtgtgagtaaa   186970
acaaaacttccttgccagagattaacttaagaccgtgttctgactatttgtttaaaagatgatgttatgc    187040
catgaagtgtttgacttctaggttttgaacccccaaaaccccaatagcttgatctcattgactaagttattt  187110
aaggattctgtgctgcagttgcctcatctataaagttaggacaaaaaatactaccttaccacttttaagaa   187180
```

FIG. 11A-37

```
ggctacaaagtatttggaatagtgccttgaatgcattaatcaaatactgcagttcaatacttaatattgt         187250
cattattaaatatctgttgccataggaagaccactggaataggagtaaaaagggaaggtgcaaattttca         187320
ctccagcaccagtagcatgtattataaacacaatgatacagcatagtccttactatataaaaaccaggtg         187390
ggtcactaactagtgctagaatgttctagggaagtcattcttatttttctcttcttcaggctcttaaccta         187460
taaaatgcagataccaagtaaaaggaactagggcttcttggagaaatggctgatttgagaactggggcag         187530
gaaatataaaaggtaagcttgtagtgtgtgttgtagtgccagaaaggaggacaatgctaagcccgcatgc         187600
acacgcacacacacacacacacacacacacacacacacacacgcacaatgacatggtcatgacactgcatacaagg    187670
gccaacttagagagcattccatggccctctttgggacaactggagtaacaaaataaataacgtagttttg         187740
agttataaactcaaagtgtagaatacatatccacaatccaatatttgatgtagatgactgaataaattagc         187810
atgatatagtaatttcctaatgctactatagaaaattacattatttttggcataaaacagcacaaaggta         187880
tctcaccattttgttttgttagacatcttcattttaaaggttagaagtcccacatgggtctccctaggct         187950
gaaatcaaactgtccatagaattgattgcttttgagacctgttgggggaaattcattccttgttttcca         188020
ttcatagaaggcacctgcatttcttggctcattcttttgcttgatgtgcaaagccagcagtgcagtgtc         188090
ttcagttgcttctctgactgcactcctgcttccttcttgttcttgaaggaactgttatgattatattggg         188160
gccacctggataattcacaataatcttattttaaaatcaggcaatgcacaactttaattccatctgcgaa         188230
ctcataacatattggcagattgaggaaattaggatgtcgatatcctgggggaagtatcattttccctt         188300
accactggagagatgagaagaatttctcatgaagaggcatttaaaataatttatataggtatttatccct         188370
taagaagttggagtataaattttatttatttatttatttatttatttttactctttgaattcattttt         188440
acattttggagatgaagtcactcaatattgcccagactgttctcaaactcctggcctctggcaatccttc         188510
tgcttcagcctcccagtgtttgggattataggtataaggcactgcacctggccataaatctccttttt         188580
tattattatactttaagttttagggtacatgtgcacaacgtgcaggttagttacatatgtatacatgtgc         188650
catgttggtgtgctgcacccattaactcttcatttaatgttaggtatatctcctaatgctattcctaccc         188720
cctaccccccaccccacaacaggccccagtgtgtgatgttcccccttcctgtgtccatgtgttctcattgtt         188790
cagttcccacctgtgagtgagaacatgtggtgtttggttttttgtccttgcgatagtttgctgagaatga         188860
tggtttccagcttcatccatgtccctacaaaggacatgaactcatcatttttatggctgcatagtattcc         188930
atggtgtatatgtgccacattttcttaatccaggctatcattgttggacatttgggttggttccaagtct         189000
ttgctattgtgaataatgccgcaataaacgtacgtgtcacgtgtctttatagcagcatgatttataatc         189070
ctttgggtatatacccagtaatgggattgctgggtcaattggtatttctagttctagatccctgagaaat         189140
cgccacactgacttccacaatggttgaactagtctacaatcccaccaacactgtaaaagtgttcctattt         189210
ctccacatcctctccagcacctgttgtttcctgacttttaatgatcaccattctaactggtgtgagatg         189280
gtatctcattgtggttttgatttgcattgctctgatggctattgatgatgagcatttttcatgtgtctg         189350
ttggctgcataaatgtcttcttttgagaagtgtctgtccatatccttcgccccacttttttgatgggtttt        189420
ttgttttctcttgtaaacttgttttaagttacttgtagattcggatatcagcccttgtcagatgggtcg         189490
attgcaaaaattttctcccattctgtaggttgcctgttcactctgatggtagtttgttttgctgtgcaga        189560
agctctttagtttaattagatcccatttgtcaatttgctttttgttgccattgctcttggtgttttaga         189630
catgaagtccttgcccatgcctatgtcctgaatgatattgcctaggttttcttctagggttttatggtt         189700
ttaggtctaacatttaagtctttaatccatcttgaattaatttttgtataaggtgtaaggaagggatcca         189770
gtttcagctttcacatacggctaaccagtttttcccagcatcatttattaaatagggaatccttttccccat       189840
tgctggtttttctcaggtttgacaaagatcagatggttgtagatatcggcattatttctgagggctctg         189910
ttctgttccattaatctatatctctgttttggtaccagtaccgtactgttttggttactgtagccttgta         189980
gtatagtttgaagtcaggtagcgtgatgcctccagctttgttcttttggcttaggattgttttggcaatg         190050
caggctcttttttggttccatatgaactttaaagtagttttttttccaattctgtgaagaaagtcattgg         190120
tagcttgatgggggatggcactgaatctataaattaccttgggcagtatggccattttcacaatattgatt         190190
cttcctacccatgagcatggaatgttcttccatttgtttgtatcctcttttatttcattgaggagtggtc         190260
tgtagttctccttgaagaggtccttcacatcccttgtaagtggaggattcctaggtattttattctctttga        190330
agcaattgtgaatgggagttcactcatgatttggctctctgtctcttattggtatataagaatgcttgtg         190400
acttttgcacattgattttgtatcctgagactttgctgaagttgcctatcagcttaaagagatttccagc         190470
tgagacaatgggttttttctaaagatacaatcatgtcttgacccaaacaaggacaattttgacttcctctttt        190540
cctaattgaataccatttatttccttcttctgcctgattgccctggccagaacttccaacactgtgttga         190610
attggagtggtgagagagggcaaccctgtcttgtgccagttttcaaagggaatgcttccagtttttgccc         190680
attctgtatgatattggctgtaggtttgtcatagatagctcttattattttgatatacatcccatcaata         190750
cctgatttattgagagttttagcattaaaggttgttgaagtttgtcaaaggccttttctgcatttattg         190820
agataatcatatggttttttattgttggttctgttttatatgtcggattacatttattgatttgcatatata       190890
gaaccaggcttgcatcccaggggatgaagcccacttaatcatggtggataagcttttttgatgtgctgctgg        190960
gtttggtttgccagtattttattgaggatgtttgcatcgatgttcctcagggatattggtctaaaattct         191030
ctttttttgttgtgtctctgccaggctttggtagcaggatgatgctggcctcataaaacgagttaggga         191100
ggattccctcttttctattgattggaatagtttcagaaggaatggtaccagctcctccttgtacctctg         191170
gtagaattcggctgtgaatccatcaggtcctggactttttttggttggtaagctattaattattgcctga         191240
atttcagagcctgttattggtctgttcagagattcaacttcttcatggtttagacttgggcgggtgtatg        191310
tgtcgaggaatttatccatttcttgtagattttctagtttgtttgtgtagaggtgtttatagtattctct         191380
gatggcagtttgtatttctttgggatcggtggtgatatcccctttatcattttttattgcgtttatttgt         191450
ttcttctctcttttttaggtttaactgtgcatgatatcttccttccaaagagtgtacagtattgaaagg         191520
gtagacaaacggtatctttatagtggaggaacctgacaaacaataactcagacagatcagactcaatatc         191590
cacagcgataaactatttttactgtatgcattcttgataggctgtgagaagaagcagcattttctttctcc        191660
cttcccaaaaattcataattagatctcagcttaatcacggtagacatgaaagacatcccagttgtgcaat         191730
actctataaaatgcctgacaaaaattcctcaaaaccatcaaggttatcagaagcaaggaaaacatgagaa         191800
acagttatagccaagaggcacctaagaagacaagatgactaaaatgtcacatgggattctagattgaatc         191870
ctggtacagaaaaaggacatgagctacaaactatgagaatctgaacaaaatgcaggctttactgaattat         191940
agtgtttccatcttggttcattaattataagaaatattgtcacactgatgtcaatgttattgtaatagggga        192010
actgactgtcaggcatatggcagttctctttactgtcttcacaatttttctgcaaatctaaaactttccaa        192080
aattacaagttaatttaaaacaaatggacaaatggaaatgaaggtattataccttttttttctctaattct        192150
tggagaggctttgcagatgctactgtgtaatatccataaagttgccttgaaaattcttaaattttaagt         192220
ttaaatgagattttgcttaaaaataaaacacgcacaatgtctagtcattttttgtttaataataatgcaag        192290
```

FIG. 11A-38

```
tgattaccttggtgtgtcttcctgggtaagatctttctgtgataagtggttggagtcatagagtaaatagtc    192360
aacacactcttgttttcttgagtagcatgattatatggccaaataattgacatgcaaatcatagtgtcat      192430
cagggatacgtacaaatgttcatgcaacacagacttcttctaatgagtacggtattaaacagttcagtat      192500
agcattgagctgaggaacatgtcatagagattctggcacttgtacttggtgctcaaaggttttacaaagt      192570
tagagaggaaattctggaggggaagcttagagacatcacattctctgaatcaaggaagagaatacttca      192640
tgagaaaaatctgagtggaagaaaaatgtttgagaaatcatgaaaaataccactgccagctatgatatga     192710
gctaacatttatggatcaccagttgtatgcaagaaaacatttacatgttaccagggaatcagaaggattg     192780
aaagagagtaataagcaatatttatgtatatgttattttttgtttgtttgcttgtttgttttgagatggaa    192850
tcttgttctgtcacccaggctagactgcagtgatgtaatcttggctcactgcaatttctgcctccctggt     192920
tcaagcagttcttctgccttggcctcctatgtcttgggattacaggcatgtggcatcacacctagcaaat     192990
tttcctgttttagtagagatagggtttcaccaatatgattctttcaaagtgctcattacatcagaaagt      193060
ccctcgtggaaatagttcctcatagaaaggaaacagtctcgtgtttcttggccttagttcttttaggatg     193130
taatgaggataatattttgcttaccctaactacataggtatttcacaatctaggttgataatctcattta     193200
aaaaaaaatatatatatatatatatatatatgtatgattgtgtgtagtgtgtatatatacacttatat       193270
tgattgcgtgtgatgtgtatatatatacatatgtgtatgtgtatatatacacaatcagatatatgtgtat     193340
atgtatgcacatatatatacatacacacatatgtgtatatatatacacacatatatacatatacacatat     193410
gtgtatatatatacctgttcaaagttattcggttttgaatacaacatttgagaggtatcttaggtca       193480
attaaaagtcaattttatgtgtatatatatatatatatatatatatatatatatatatatctgtag        193550
cggtctatatatgcgtgtgtgtgtagaagttattaggttttgtttgtttgtttcattgttgtttttga       193620
gatggagtctcgctctgtaatccaggctatagtatagtgtcataaccttgcctctctgcaatatccgcca     193690
cctaggtgctagggattcttgagcctagtctcccaattagctgtgattacaggcatatgccaccatgcct     193760
gtataattttgtattttagtagagatagggtttcaccgtgttggccaggcaggccaacagatagatgt      193830
gtgtgtgtcgcgtgtgagtaatacatataaacatctttggtgttcatgagattttaatacaacatttca     193900
agaaacatcttagggcaaataaatgtcaattttcttttcaaaatgacttttcttaataaaatgtatttaa    193970
aatacctagcaaaatataatattaagttagttctcattttaaatacactgtgatttaatcacaagctca    194040
cagatccttagagatgatattgtctatcagctgaaaattcaaaaaaaatgggagatgctcatgtaaatat    194110
actaagatttgtatttcattcctgaaaacagaaacacttcagtggtaaaatttgcaacaaaaaaaaatgc    194180
ttatggaagctagacaatgctctaggactctaatagtaagcaggaatatgtcaggaagccatacagt       194250
ctttagattcattttgattcctacctgaaaaagtgtcaattcttgctaaatgtagcaaagcaacaaagaa    194320
aaattattattcacctgtttctctcagtgttttttcctaaccttaaccctatttcctaacccctatttaag   194390
ttatttcctaacccttttcctatttccattattataataaagcatttttgatctggtagaaaattagaatt   194460
agaccttgctttactgtcatcacaatagcattttatcaagttttttttaaaaaaatagcaaatggcagaa    194530
ttattatatgtatgttaatcgaaattattttttaccatgttgaattataattttatatctatctc         194600
aaaactaaagaagatgcaacattgcatttgcacacttgagaggagaattagttccacatgctacatagag   194670
agctgtatttatcattgttttcacagctggtatgactgtgactattataatagaggtgagcttgcaagc    194740
caaaaatatgtgattcatccaacagttatttaccatgtaacttatatgttctggatgtttaggtagttat    194810
tacaaattaggaaatatggtgttgaaaatcacaggaaacacctttgttttcttttcctagccatttagc      194880
aaagagacctaattcaacaaggtatcatgttaaatattataattcatttggtgatgaaaaatgccaacta    194950
cagtgaataattgaggaactcaagtttatttaggaatataatgctgggatgaacaggaatgcctttctt     195020
aggaaatataatttaggctgaccaataaaaatttgtcttacaggagaaaatgtgccttgcaagtaggggg    195090
aacagcagaattcccaaaagtcctaaaggcaacctgatgatgaaatgagttaagccatgttcacagtggt    195160
gtattagttgacttttgctacataaggaaccatctcaaagctaagcatctcaaacaacttttatttagca    195230
aagcatctcaaacaacctctatgtaggttatgattcttggttgggaatctgggctgtgctcatctgggag    195300
gctcttcagcctagagtcaacatccaggtcagttgggtgctcactggccaagcactatctcaacatggtg    195370
cttgtcagtgctcatgtggaatatcatcctcaacaggctagtgaggactcttcatgaaacttgtcaga      195440
gttgcatgtagatatgttcaagttctcttacagtgaaagctacatagtgtcagtgtcacctccctgatcc    195510
agaatgtccaaataagtaaatccagaaagatacaaatgaatgggcagtttccaggggctgggggaaagag    195580
gaaatggagagtgaccactaactggtacagtatatttgggggcatggggaatcatgaaaacgttctgcca    195650
ttcgatattgttttattattgcacagatccatgaatacattaaaaaccactggattgcatactttgacata   195720
gtgatatgtatgatacagtaattatatctcagttaagctatttatcaacctatctctatctaatcaatct    195790
atcaaccaaataaattaagacagcctatgtatagagacaaatagaccaggagccagtcactgtggctcac   195860
acctgtaaacctagcactttgggaggccaaggtgggtgtatcacttaggtcctgagtttgagaacagcc    195930
tggccaatgcggtgaaacctcacctctattaaaaaatacaaaaattagccgggaatggtggcgcaggcctg   196000
taatcccagatatttggggaagctgaggcagcagaatcacttgaatcagaaggcagagctttcagtgagc    196070
caaaactgcaccatttcactccagcctgggtgacagagcaagactccatcttcaaaaaaaaaaaagacaga   196140
acagaacagaggaaggtaggcagaaacagactctggtagatgtaaaacttggcatgtaagtgaagagcca    196210
taatacctatgtagctgaaaatgggagtgttatctaaggaaataattcaaataacctgtatactatacca    196280
cccagataaataaattccaaatgattttatgatccacatgacaaataaaacttttgaactgttagaagaag    196350
agtaatcaaataaaatgtctttatgttttttggattacataaaataatccttttttaaaaaagcagacatta   196420
tggagaaaatagtgataaattataataaatatgcatcttaatgaattacttttatataattaaaaatcaat   196490
aaaatagttaaaggcaacagaacagatatctccagtgctcaactgtgtaagcttgggcaaattatttaat    196560
ctccacatatctaattttcctcactgtgagatgatattagttacacatctcagaaggtagttatgaaaaa    196630
tatatattcagagctgggcatagtggctttcacctgtaatgcagcacctttgggaggccgaggtggcagaa    196700
tcacttgaggccaagagttcaagactagcctgagaaaaatagtgagatcctctctccacaagaaattaaa    196770
aacaaaaattaactgggtgcagtggcacacacctgtaggggtcccagctactcgggaggctgaggttgga    196840
aggatcactggagcccaggagctggaagctgcagtgagctaaaaatgctcttcaccctgtgtgacagagt    196910
aagagttcatctctaaaaaacaaacaaatgaaatgcaaattcattatgcataaagcccttagaacagtat    196980
gcagcactgatttgcactgttaaatgttttgcctttacatcctcaaaaagagaccatcatccatgaatgta   197050
aagatttcctgcaaaccaataacagatgttcagccaatcaaaaattggcttgctattcaagaaggaatt    197120
tagaatgatcaagacaacaaatacagaaatgcacatctgcactattttcaaggaacttgcaaattgaaat    197190
ataaactgtcaatatattatactcatcaaagtgacaaatatattgtctgataataacaagtgtttgggaat   197260
aggataaggggtgcagaattttcttacctgctagtgagtgtatagcataatacaacttgtttggaaagaa    197330
atacaccaggatatactgaagataaaattagtactaccctatgtatcagttagctactgctgcataacaa    197400
```

FIG. 11A-39

```
agcactctaaaattcattcccttaaaacaataagcacttactactgcttatcagcctatgaatgttgtta    197470
attgtaaatttattttggtcttggctgtgctcattgatgtgtatttattgttgttttggggtgaactctc    197540
tcaggtagttggggatttgcggaggtaattttgcctaggttggggccaatgggttcttctttatggcat    197610
ctattgtattccaatccactagtctgcatttttcagagagcagtggtagagtttcaagagattaagaata    197680
tgtacaggggatttcagttctagtcttggaaatagcatatcattatatttttttttcttttgaaaaaaca    197750
caatcataaaccagtcaagattcaaggggtgaaaatacagactttatctctatgtatgaggaatagcaaa    197820
ttcatgggacagattgtagaactgggaccccttttgcctgtcaatcgactacaccctgtaattcaacat    197890
tatctatctagtagttatgtgccctagagctgaggtcttcaacctggcagaggccttttaaaactttt    197960
caaagtatgactcagctgattatttaaagaaaccaactttcaggtactcaacctccatatgttgtcttt    198030
tctaagccttcctggtcaccaaaatctcttcccatatcacaaaaggatgaccttcagtacacaagatgcg    198100
ttggtactgacctgccagggcttgtaataaaagaagtaaccatctgaatgctgctttctgggaagctact    198170
ttactgaaagctccataaattaagcctcccagggaggtgtggtggctcatgcctgtaatccaagcactct    198240
ggaggctgccagaggtggatcgcctgaggtttggagtttagagaccagcctggccaacatggcgagacc    198310
ccttctctactataaatacaaaaattaatttggcatgctggtgcattcctggaatcccagctactcggga    198380
agctgaggcaggagaatcacttggacccaggaagtggagcttgcagtgagccgaaatcactcactgcact    198450
ctagcctgggtgacaagagccgaactccatctaaaaaaaaaaaaaaaagcctgccatcttatacgtatt    198520
tctattggtcctgtaccaatgttcttatttcagaacatgaaaaaagaaagaagccataagttatctaag    198590
gcaattcttccaaatccagaaatcgaactttcctgtcaaaaaccagttttcaaagtgcacatacattgg    198660
gtgaagcccatcggtaaatgatccaatctgaaaatcttctgaaagtcatctttcaatttcttggtggtag    198730
tactattcaagtggaggttcagatagatttcaaaatgtctgcatggaatattttccccagctagagtctt    198800
ttctctcagtgtatggaggaaagaggaagtatccagattgagtacctgctcttctcatctttcttgggct    198870
actcttgtcccttctgtgccctcccccttccaacctatgcttccctcagagcagcctgtttttctttgctc    198940
ccataaatgtattactggtccttgctcttctgtgcatatttagcagcccctaaccctcttcctcaccagcc    199010
accccttctatcccagactggcctaccagaaacagcagagtatcctcaattcgtgcatgcattttcctgc    199080
cacgttggaatgatctgtatgcatgtctgtctctgatgttcatttcctttttcagcgtggctatgtattt    199150
acctcttttagccaggactgcatggccattacctctctaagccagtcaaaaggttcaatacatacttatag    199220
aaggaatgggcttatgagcaaataaaactcatgtgtcatgtcagtctgtgaagacagatcagtcacctcc    199290
tagctgcagagaactgggggattgtaaattctcccccagttgcctttctgcgttggattacaagattaagc    199360
ctgtattcctctgtggccaagtgataaaataatcaatcacacccacatctatcatggccaagaaaacatt    199430
tatttcctcacctcctcccataggcaaattgccccgggaggagcaatatggaaaataatgtagttcacta    199500
aaaaagcctcttctctactaagataacagtatcaagttgaaaattaaccttgacctcttaaaagaaag    199570
gaatatacagtaaaatatgaactactaaatacattttaatataatatctcatgaagagcaataatgctaa    199640
ggttcttttggctatttccttatattcttgcttagataacaagatcacatttgtatctgatgactttct    199710
ctgatgatttagatatgtaagtggcaataaaattaatatatatataaacagatttaaattatttcctga    199780
tgcataatgttaacagcagtagatgtgactgtgaggtttttccttgagtgttaattttgcttttacaata    199850
gtcctcattttccacattttttaaattttcttttttgttataaggtctagctgtgtcacccaggctggagtg    199920
taatcacacaatctcagttcactgcaatgaggttcaaatgattctcccatctcaatctcttgaatagctg    199990
ggactacaggatgtaccaccatgtctggctaatttttttgtaattttgtagagacgagctttccccatgt    200060
tggccagtcttgtctgaattactgagctccacctacctcaacttcccaaagtgttgggattaaggcatg    200130
agccaccatgtgcatatcattttccaaattatttacaaagtgttctttactattaataacataaagtac    200200
tattttagaaagactgactttgaaaataacatagataaagcactaaatgtgaacatcagaagaacaggtt    200270
aaaaaatgctggaatattcttcaggattagggaaattgagatttttttaataaaatgatatttaaatctt    200340
aataatagaatggctgtacttttgtttggagtatttaaatcttctcatttaaaaccagttctgcacagaa    200410
gttttacagagatgctaattgttgtatgaaatgaatattattctggcattttgaggaagggtagacata    200480
gagaagagaaaggaaactcgcagtccacctaggttttatttttgggcttctttgtgtgtgtgtgtccaag    200550
ccacaagctgggtttattcttgaataaacattagccaaattgtttttcctgaaccgtctattacctgcat    200620
gtacatagaccatggttgtgttcaaactagataatcaagatgacttgttttgttttagagacatttagtt    200690
agttgtaattacatggacaaataaagcagcagtttatcaaaaagaagaaaggattaaaaaattatgca    200760
taggaaaggcagtatgtaatttctgcctttctgtttctgggtgaggctgtgctaaataagattaattta    200830
aaattgggatttggcaagtaatttctatcaaaatctcagcggaggtttgttgcaactaacaagctgat    200900
gtggaaatttgcatggaaagtcaaaggaccctagaacaagcaaaaagaccttggaataggggaagaaagtt    200970
ggagggctttcatttaccatatgcagaaacctgaaaccggaccctttccttcaccttacacaaaaatta    201040
actcaagatggattaaacacttaagacctaaaaccataaaaaccctagaagaaaacctaagcaataccat    201110
ttaggacataggcatgggcaaacgcttcatgactagaacaccaaaagcattggcaacaaaagccaaaca    201180
gacaaatgggatcctattaaactaaagatcttctgcacagcaaaagaaactagcatcagagtgaacaggc    201250
aatctacagaatggaagaaaaagtttgcaacttatctaactgacaaaggactaataaccagaatctacaa    201320
agaacttaaacagatttacaagaaaaaaacaagctcatcaaaaagtgggtgaagtatatgaacagacact    201390
tctcaaaagaagacatttatgcagccaacaagcatatgaaataaagctcatcatcagtggtcattacaga    201460
aatgcaaatcaaaaccataatgagataccatcttatgccccgttagaatgacaatcattaaaaactcaga    201530
aaacaacagatgctggagaggatgtggagaaataggaatgcttttacactgttggtgggagtgtaaatta    201600
gttctaccattgtgaagacagtgtggcaattcctcaaggatctggaactagaaataccatttgacctag    201670
aaatcccattgggtatttacccaagtctcttttgggtatatactcaaatgattataaattattgtactata    201740
agacatgactatgtatgtttattgtagcactattcacaatagcaacaactcgtaagcaacccaaatgcc    201810
catcaatgatgaactggataacaaaatgtggtacatatctaccgcggaatactatgcagccataaaaag    201880
gacgtcctttgcaggcacatggatgaagttggaaaccatcattctcagcaaactaacacaagaacagaaa    201950
accaaacaccacatgttttcactcataagtgggagttgaacaggagaaaacatggacacaggagggaa    202020
agtcacacacccgggcctgtcatggagtggaagggtaggagacggatggcattaggagaaattcctaatg    202090
tagatgccgggctgatgagtgcaggaaaccacaatggcacatgtataccctatgtaacaaacctgcacgtt    202160
ctgcacatgcacctcagaactgaaagtataattttttttaaataaagtactataaagctatagtaatt    202230
gagatagtaggcaactcatttgggtataagtttggattaatgatatataattaattacagttggcccttg    202300
aacaacacaaggtttagaaccctgcacagtcgaatattcacttttaactttttactccctcaatactta    202370
acaactaatagcctactgttgactggaatacttaccaataacataaacagctaattaacacatcttttgt    202440
atgttatatatacaatatgctgtattctccaaataaactaagttagagaaaagaaaatgatattaagaaa    202510
```

FIG. 11A-40

```
atcataaataagagaaaatgcatttaccactcattaaatagaagtggatcttttttgaaagtcctcatcct         202580
catcttcatatttagtaagctaaggaggaggaaggagagaagaggttggtctttctgtttcagggatggg          202650
tggtagagatggaagaaaaaggtagatctgcacagcacagttcagacctatgtagttcaacagtcaatta          202720
taaacagtttagaaatcaatccttcaatttatagtcaacaagttttttttaaatgctgcgaaaacaattaa         202790
aggaggcaaggatagtcttctcaataaatggcactgagacaattggttattcatatgtaaaaagatggat          202860
ttcaacccttaacacttattatacccaaaaatttactcaaaatgaatgacagatgaaaatgtaagaatta          202930
aaattcttaaacttttaggaaacatcaacaacacaggacaatgtcttcagggccatggattgggaaagat          203000
ttcataaatgtgacttcaaaaatacagtagttaaaagaattgatcagttgaacctcaaaaggacaatcct          203070
ttaatgaaagtattgatcagtttaaagtcatcaaaatgaaaaacttttgcatttttgaaagttatcactg          203140
agaaaaccaaaagacaagccataaactgggagaggagattggctaactatattcctgataaaagatttt          203210
atctccaaaatgtgtaaaacaaaacaaaacactattcagtaataagacacaaattattttttaattggca          203280
aaaatatattattagacgtttcaccaaagagagtatacatgagaagatacttaatatcattagttattag         203350
acattagctacattaaaactacaatgaggtcaggtgtggtggcttatgcctgtaattccagcacattggg          203420
acgccaaaatgagtggattgtttgaggccaggagtttcacaccatcccggacaatagggaaagatcccat         203490
gtctaccaaaatacaaaaattaaccaggggcggccgggcgctgtggctcacgcctgtaatcccagcactt         203560
tgggaggccgaggcgggcggatcacgaggtcaggagatagagaccatcctggctaatacggtgaaacccc         203630
gtctctactaaaaatacaaaaaaattagccggtcatggtggagggcacctgtagtcccagctactctgga         203700
ggctgaggcaggagaatggcgtgaactcaggaggcggagctggcagtgagtagagatctcgccactgcac         203770
tccagactgggcgacagagcgagactccctatggaaaaaaaaattagccagaagtagtggtgaaggcct          203840
ggagtcccagctacttgagaggctgaggcacgagaattgcttaaacccatgaggtggatgaggttgtag          203910
tgagccgagatcacaccactgcccaccagtctggctaacaaagtgagactctatctcaaaaataaaaac          203980
aaacaaacaaaaaaaccctacagtgagacacaattttacaccccattagtatggctataacaacaacaa          204050
aaaaagatattagcaagtgttgtctaggtaatagaaaaaatagagacccttttatatcaccattggtgaga         204120
atgccaactattacagctaatttggaaaataatcggccaatttcttaaaacaaaaacattaaacataaat         204190
ttgccttatgaaacagcaatttcagccctagatatgtatgcaaagagatgaaaatatatgtccatgcaaa         204260
aaatggtacacaggtacacaaataattgttcatagcagcattattaataataatcaacaagtagaaatag         204330
accaaatgtcactaaaaaataaatggatttaaaagatgtggtatacccatacaatggaaaataattagc          204400
cctaaaaaagtattgatgcatggtacaatatgacggacattgaaaatattatgtaaagtaaaagaagcc          204470
agacacaaaagactacatatattatatgagttcatttatatgaaatgcctagaaaaagacaaatcttacaaa        204540
gacagaaagtggatcagcaaggctgtcactcccacgcactcagccaggtctgattttaaggatattaag          204610
ccccattaaatggaaattaagtttgtttgatgtatggaaacagcaatatcaagtcttggtttcaaaata         204680
tgtttaacctcttttgagttatgtagaactggaaaatgttttcactcgcaagtattggacataacagta          204750
tttccctctgccttaatccacttatccctagaaccctataggaaggcaaagactgtttttaattgagcgac         204820
acagttaaagttattgatagtggggtatgcacacatgggctacatctgtctatgaaaaggaaacaatgga         204890
gccaattttttaagtaattcaagcaaaattaaatgttcacacctttaaatctggaagctataaaaagca         204960
aaatggtgctctgtacacaaagagcatagcctagttttgctatccttaagcctcttcctgcattttgcc          205030
tatattaaatttcctatgcagatattattgaggtgatcaggtaggtgacttcaattttttattttctataa         205100
caaattcaaattcaataacttttcaagtaatatttaataactatttttaaacacagaagacatagtctataa        205170
tatttttgtcctgacttaaatactattgcaagtagtagatgttaatacaagaaaacaatactgaataatg         205240
ggtagttgttctttaaacatggagtagaggtaaatcttagtgatttagggacatttctaatttttagaga         205310
ttgtgcaattttaagtttctaatgcatgcaattaatgtcaatttttctgatattttgattaaagtcctccc        205380
atgtttgctgtatgtgcttttgcttgccttatgaaaatttctaaccatagtgtatcagtaacatttcaaa        205450
aatgtatttaaattataatatgttcaaatcaaagtactgtcaaatatgccatatgcatttctttttaagaa         205520
tgtgggaaatacccttttaataattttattttctcttttttttaaaactcacattagcatttttttgcagtag      205590
catcattttaaccccccaactgcatatccacagtatagctaatatttttttacaagtaacattttgaattttg      205660
ttcttcttgacatctttatgtttatatgcattttgcatttccctatctcatttttttgaaaccaaatgta         205730
accaatttcaagttttttgtgttacattcatttttttctttttactaggtagcatctttctctttttctgaa       205800
ttttttgcaaacatattgttttctgaattctctttcatccctttattttccttttcaatatcaccccagGA        205870
ACCAACATAAAGAAATGCAGACGATATAACCAGTAATGACCATGGTGAAGATAAAGtgtattttttgtt          205940
ttttcaaagctcaaccctgatgcatgattttatgtctatctatctctctcttttttttttatttcaacctgt       206010
ttttcctcccttatttaactcttgtacacttttgtgtgcttcttattttcttcttgtatagaaaccac           206080
tgttattttaaccccagttaccatgtactggaaacaaatcactgtgtgaagtataaacattgtttctgt          206150
acatgaaaatagtaatgaaatactacttacagagaagcccacctttttttttttcttttttttttggctttg       206220
tcacaagaagaaaaaatagaattttaaagaatgcatgtatatgtctctttttatccctttccaaatgttattt      206290
tgtaagttaatatactactttgcagcttcagtcttcctaattagttttgcaaactgcaaaactttgcagc         206360
accttagaataatttttttcataggactgaagtttcaattttgttttctttggtttggcattcttttacaaac      206430
atattgattccaacatagtcatccaataatctgcttacagtgaagtacatcaaaaagcatttttaacaaga       206500
tgctgttgttaacaagccctgattctttcagtactgccttttcaacattttaagaaaaaaaataagaagt        206570
agctcagaactgaaaaaggacaaaaagctagctatgtgcatctttgttttcacaccaccgttcttttgaaa        206640
atatgtttctcctttaaatgttttattgctgtgaagtttctttttaaggtgacaaaattgctcaatagat        206710
tatctaccagtagtggaaatattttttcataaagtggaaggtctgagcagtcatgcagaaaacatagaca        206780
ctatttttatccccttttgtgtagaagaaatttgttttttgttttttgttcttgttttttttaaaagaggagaa    206850
acaacaagaaaagtactcaagccattcctcattggtaaggctcatatgattagctaactgcactttttt          206920
cccatctgggtagcaaaatgtatggaattctatttattttttcataaacaataaggccctggctggaccctt       206990
tgggtctctgtctgaaaggccaagcccaaaagtgagtgttgcattatccttgctggtcaagccccattt          207060
cttgaaagtgtcttttgaccagttcttgtagttgctccctccttgcttatcttcataaatcaactgttc          207130
tccaagaaaagaagtcttgccaacactctttttcatgcctggtcttcccttaacattttgattattactga         207200
gcacataggttgtcatgcctcaagtagctctctaagaggtcttgattctgatggtggtagaagttcag           207270
gtaccctcttcttgataagggcttctaaatgcctcacatttgtcagtattgagcaaatacataaaaatg          207340
aaataaactttttgttctctcatacccttatactgctctaatttgtatcctcttttggtgtcctctcacatac      207410
ttcctttgataattaagatctgttttcacattattcccagtgaatgtttattaccatgaaaatgccatc          207480
taatttttctcttaatattaataagctgtgattttttgaatttgctttaatgtaacaactggtatcactcc        207550
acaagttcaagagaatcttgttgtatgtttatgaaaggtaagaaatgttaatttcccatattttcaaag          207620
```

```
ggagcactttaaagcagcccttcaaaatctctacttactcttttaccacaatttactagccaacagctg      207690
gtagtggtaaaagaaatgaagccaaaaacaggaaattaggaaccgggaagaagaagtggaacatgagaaa      207760
agccatttcttattcatatagcagaggacatttcccatagagtatgatgaataagtgatgaatgaagatt      207830
tttactttatatttgaattttatatgagaaaataaaagcacttttctgccgtggattaaatatctgcaa      207900
ataaatactcgggtaacttgacattcttttgtgtgctttactgtgaccattgggtatgtcatgtcatctg      207970
tatgcaccctgtaaaattgtgatcataattcattcaaattggagccaccatccaaacgatggtaattcat      208040
atcctcagaattcctttctcatattcaagtgtccctgtgaattatgagggaaaaaaaatctttattaaa       208110
gaaaaagtgaaaataaatatgcatggatacttggattttttctttagtaacaaagatatttaaattatt      208180
tgtatacacacacacacacacacacacacacacacacacgtatctgtacctagaaatgtttataggggag      208250
gtcagttttctgaagattaaatgcagccctaatgtcagattaatgttataaacacatcgtttaatcacaa      208320
gttttcagagagcaggctccacagatagtctctaactttctatcattacaaatcgctattttatatcat       208390
tgctaatttaaataataaagtaaattatgaagaggaatcattggttgcaagtcaccatgggagtttagtc      208460
cctgtgaaaataaaagcatttaaataatttgtattcttttaccattttttattacatctctcttaatttt      208530
tgtcacttgaatatattaggatgatgatgatactataatcactggaacaaagacatttgcttggacatct      208600
tttctttttcccccattttgttctgttaataattttaactatagcttttcctttcttgtccttatct       208670
gtcccttatcgatcatagatagtttcactactatttttaagtttttattgttaaattgaagatgaatctg      208740
tacagttacttgtgaattaagatgcagctaagttaaaatcaagtataattttgaagctgattttacattt      208810
aactagatgattaaatatattttttcaggtgcttcttcaatttaaatcaagttttatggtttcagcaaaa      208880
tttagaaaatatgtactttacctaaaaacttttctttagtgctttggatatatacagaagcttaaatga      208950
gtagagtatcccaaacatccagatgcttctcaaaatagcatttccggccgggcgcggtggctcacgcctg      209020
taatcccagcactttgggaggccgaggcgggcggatcacgaggtcaggagatcgagaccatcccggctaa      209090
aacggtgaaaccccgtctctactaaaaatacaaaaaattagccgggcgtagtggcgggcgcctgtagtcc      209160
cagctacttgggaggctgaggcaggagaatagcgtgaacccgggaggcggagcttgcagtgagccgagat      209230
cccgccactgcactccagcctgggcgacagagcgagactccgtctcaaaaaaaaaaaaaaaaaaaaaaaa      209300
aaaaaaaaaaaaaaaaaaaatagcatttccagaaacagaaatgtaatagcattagtcaagttacttag      209370
aaactcttatcaagtgtcatatcatccataaaaattaatttgcttacttcaagtcaaaataaggaaatca      209440
gggaatctcctttgttcttaatttagcatcagtgagtgagccagtaagattctttactgcgtttccttac      209510
ttggcttttttttccagATATTCATGAACAGAACAGTAAGAAGCCTGTATGGTCTATATCCATGGGGGAT      209580
CTTACATGGAGGGAACCGGTAACATGATTGATGGCAGCATTTTGGCCAGCTATGGGAACGTCATCGTTAT      209650
CACCATTAACTACCGTCTGGGAATACTAGgtaagtgatttcatcatgtgaatgactaagcaagaggaaac      209720
atgaaagttccacttcttattttgatgggactcatggatttgaatcccgttattacagttcctggttaat      209790
tccacttttacggtatttactttatgttatcaggtatgtttttccttttattaccttcatgcaacatgac      209860
catcttattgttttattatcattcttttcctttcgcttctgatccaaaaattttttttcttgtggaagttg      209930
aatcccttctcaaacaaatggccacttcaagttcatcaggattaaatgaatttttatttaaagcatgttt      210000
cttcattggaattaaatgaatgtgtatttatctacataagtgtgtataatgagcacatatttggtgatat      210070
gataattagtaatggccatagatcttagctttctagtctgattgtgttactatatgaattagtatattgt      210140
atggaggaaaagattttatccagttccctaactgattatgttgaggctttggaagatctgctgtttaggt      210210
tctgttagttgacttttttttttcatttgataatctacaattaaaggccaagtacatggaaattcaagtt      210280
tagctcctccttgtttagatgtttcattcattgtcttctaatttgtgggttggaaaattaagttacaactt      210350
cagggtaaaggttttaataccttcttagatgacctttcctgcttttggttagttcgtgaataatattcct      210420
agatctctgtaaaaacatttgtttttttgggtaaaaatccattaaaatgatgtagaaaataaaattttaa      210490
caaattattcaattcactacatgtaggttagcttgaatgaagttatatttgttgcatgcatttgatcttg      210560
aattgaaacctacagtttaagaaaatctgcatgtctttatattttaacagactgtcagagttataaaag      210630
caaaacattagagctttacagtataatatttttcttagatctttcatgggcatttaaaatcactcatt       210700
atgaagagaccataaaccatgggtttctaagaggtgtgctgaattttgcaactggctggtgtgttttcta      210770
aataatcctgtaatcttcatgtattagtttttttttttcataacaaatcatgacaaatgttctctttaaa      210840
caagaggaatttactttctcataatttgggaaaccagatgttcaaaacaaaggtgttggcagggctgtct      210910
ttccctaggtagctccagaacaagattctttcttgccttttcagcttctggtggccctggtgtttgttc      210980
tatcttcacaacactgtcttccctgtattttatgtgtcatctcctttttttccttttcctttctttttct      211050
cttttttttgggggaggtaggggggacagaatctctgtcacccaggctggagtgcagtgacatgatcttgg      211120
ctcactgcaacctctgcctcccaggttcaagcaattctctggcctcagccttctaagtagctgggattac      211190
aggcacccacgaccatgcccagctaacttttatatttttttagtagtcatggggtttcaccatggtggcc      211260
aggctggtttcgaattcctgacctcaggtaatccacccctgtcggccacccaaagtactaggattacagg      211330
tgttggcgaccttgccaggcctccttttccttgtaaggataccagtcattgatttaggggtttatcctaaa      211400
ttcaggataattatatctgaagaccccttaactaattacatctgcaaagaccctgtcttcaaatagatcac      211470
attccatagtttccaggtagaaatatatttttggaggatatgctcaacccactccacccaatcgatgatt      211540
attgcaatatgtatgtgtgaatataggtgctttcagatgcttccattccatatgtgtgcacaaccactgt      211610
gttcagaattccaccttgctttctacttactaggccacactctggtaagatgatctgaggacagtctgga      211680
attcttcttcccttgtattcaaataatatagtcatgcagtatctaaaagtttattccctgagcctttaa       211750
aacttctccatcagtttgacaaggagtaaaagtgtttttcccattgtcacaaaacttgtgcaaaaagc       211820
acctttcccatgggccaatacacagagctatatttcacatttcttcttaaattacagggttataaatat      211890
aaaacaaaacctttaccttgctgtattatttccaacttttccctctattattaattccgattacaaatgc      211960
tcattaatgttctaccttggaattgcaatttgggcatgtgccatctgaaaatggaggttcctaaaaatta      212030
atatcaaagattaatgcaagtttaaaaaagggacttattcaaacataactcccattttaacgtgactcg       212100
tggacttttaatgaaatgaatggccttgtaaatgcctaatttttttcctttaaactaactgtgtcatagcc      212170
ttctctcttagaacatatctgatttgccagaaacccaagatttgtgagatggtgttattttttattttact      212240
cttttccccacccccatagtaccatgaagagattatgtaacatcctttctggttttaaagacaggtgaata      212310
atgattatgtaacatgcaaacaagttgggtgttttagagaaggtggtgttaatggtgtctgattcacaga      212380
tgctggcttgaaccttactggtgttaggacctatattctggtaagatccaactttaggccatggattaca      212450
ggacctaggtgtataaaaacgataccctaaaacccataagatcttagttcactgatcagcaggagagatag      212520
ttttctttcaaatgataccatcagatgcatctccagcagactgttaagtcagtgaaaagaaaaatgccat      212590
catgagaagttcttcgagactttaaaaatttcctaggattatgccagtgattcctactacagagacaaa      212660
gatatatgtatttctgaatttgagatgttggatattggtagagattcatcttttgaatgcaaataaatat      212730
```

FIG. 11A-42

```
gctttacttttagccagcatgaatgctctcatttgccacaggttggccagcttaagtatgaagggtgttg      212800
tgggtaaccttaacagaaggttttttatagtaccaaaatttcttttcttttttttattatcctatttcagaaa     212870
gtttcttaactctgagatactttatattggggataatagttctggtgcaagtatagattaatagattatt       212940
aaacacttcaacatatagatggaagagtacaaatagtatattattactgattcccatttactcttttcttt     213010
aatttacactggaattttttgttttatgctaacttttgaagataccaatgataggaagttaatagtgcttgc   213080
ctttttataattttttccagagcttattcatttgaagttcaaattttggaaacttttcctttttgttctttggga 213150
aacagatatattgctattcaaaatgggtaatctctaaattgatatagaaaaagatatttgaggctggat       213220
gcagtggctcatatctgttatcttagcacattggaaagtaaggcaggaggacaacttgaagccaggagt       213290
ttgagaccagcctagacaatatgacaaaactccatctctgctaagaatacaaaaattagctgggcatggt     213360
gtcacacacctgtaatcccagctacctgggaggctgagatgcacgaatcagtggagcctgggagttggag     213430
tgtgcagtgaccacctcactccaccctgggctacagagcaagactgtgtttccaaaaaaagaaaagaaag     213500
aaagaaagaaagaaaaagaaatttgagatattagtattgtccaaaaagtataattcaaatacttaatgca     213570
gaaggtagtagcatcattaacttactgacccattcatcaattataacagagggaaggttctatgttagtg     213640
tcttggaggctgattgagctaggggatacaattttaagtatgagtttcatagaacagattcaggaggtct     213710
aaatagaggggtctacaattaggaagcaccccttaatcccaccccctgaattactgacagcaacactaacta   213780
ggcagcagagatatttcctgatctcagcagtcaagacaatggtactaaaggttgctagataaatgtga      213850
tttttgtagtcactcacctgcaagttataggcaagataatatttacctgcactcccaccagaaattagac    213920
ctaattgactgctcttaatcagaacaagacattccaacctcttattcatggttagcaatatatcccactt    213990
gcttcactttgtgattcatcattgcatgggtataactggacatggaatgcatttgaaactgagcctcaag     214060
ttcaaatcaccatagaacctaaaagaaaatgtaggagagacaaaacagaagaaaaatgccaaacagaga     214130
gttattatttagatgtgttcattctgtgaacagagagcagtttctattggatctggctgaaataggggcc     214200
cctggtgtcgtgaaagtggtgtatgtcttcatacatgtttcccatgggccttatacaaccaatctcatttga   214270
caaatgaagaaatgaaggcttgtggtcagggtcacaaaacttgacagtggcagaagttggatccaatttcc   214340
agtcaaatctatgactcaatccatcttcgccacaatcatagtgcaaatcagttgctctgtttccgatcag    214410
tacccacacaccagaaggtcagctcttttaagggcatgaattgttgttgtttggttcattgttgagtgttt   214480
ggagcttggaccagtacatcgaaagtcttaattgttgacattctcagtaatgcaaaataaattgtattct    214550
tggatcattggcatcatatccattaggatggctgttaataaagtaaatgtaaaataagaagttgtgatgg    214620
agatgtggaggaactggaactctttcacattgctggtgggaatgtaaaatggtacagtcattgtggaaaa    214690
ctctttgtctgttcctcaaaaaagtaaacatggaactaccatatgtgatccaacaattctacctccgggt     214760
atatactcaaaagagttgaaagcaggtattccaagagatatttgtatgcccaaattcttagccatgtttt    214830
ctcaatagctaacaggtgaacttttgaaatagccactgcccagtgatggatgaatggataaaaattgatg    214900
tatatgtatatatgtatgtgtgtgtgcacaaatacaataacataccactacttgttttgcaaatatggaatgttattcat 214970
ctgtaaaaggaaggaaattctgatacatgctacaatataaataaaccttgaatacatcattctaagaga     215040
aataagctataagctagtcacaaaaggacaaatgctgtattattttaccaatatgggttccacctagag     215110
ttgtcaaattcatagagacaaaaagttgtatggtgtttgtgtggggctgggagacaaaatggaaaattat    215180
tttctaatggatagaatttcaattttgaaaggtataaaatcatttggagatggatggtggggacagttgg    215250
acaataatgtgactattcttaaggccactcaattatacaccaaaaaaatagctaaaatgataaaatttcat    215320
attatcctatattgtatcacaacaaaagaaatcattatgatatctgtgatttaattgactcattgtaatca    215390
ttaccatgttaggtcatgttcagtatctcatatccagcaatattgcaatggacatggtaattttttgagtg   215460
gtagaaactcacgtaacttttaaaaacacatctgtgtgtattcacatattcttatatttcttggaattga     215530
aatcatactctctatatctcatttatttctcgtagcaaaatgtttacaaggttttcaagattcatccaca     215600
ttgtagcatgtatcagtcagtaccgcatactgtttctggatactgttccattttatgatagacca         215670
cattctattatatatctgttttttcatttgatggacatttgggttcaattcatacagaaagaaagtagact     215740
agtggttactggttctgggatgagaaccataggggaattagcatgtcatggttacagagtttccatttgtg   215810
aagaagaaagagttctagagatagattcataaaaatgtgaattactgaatggcgtcaaacagaacagtac    215880
actttaaaatggttcacattatgttatgtgaatttcatcttaaatagaagaagaatacagtctgaagttg    215950
tcatgtacttcactaggatgatctcttaaaagggtaggaagaaattatgtgttcatccatgtcctcaaa     216020
agagcatataaacaaactaaacaaccatcaaatataaaacatgtcaatgtatacctcacagcatcccaaaaggg 216090
aagactaaactaaactgttctcagggctccttcttccttatgtgttactttcagaggcactttagcttag    216160
gacttaatttgactattcacaaccccagggtgtccatttgatctcacagcaaacttgagttgactttgac     216230
cagggaaacactttactttaagaaactgtagaaaggagaaaattttatacgtatccagtttctatccatt    216300
tcattgcacatattggtgagaacttaagtgttgtaagcatgccacttgcagggccctagggccacagctac    216370
aagctatattttgtatttgcatccactgtttttgttagcagatgtatatacttgctgacaaaatacatgtt   216440
ttaagaaataaaattatttttaagaacaaaataataatatgtttttaagaaaacatgcttgtatttaccttt  216510
tattttttcataaaaaaaatgtttatgggcagggcacggtggcttatgcctgtaatcccagcactttgga    216580
agccctaggcaggtggatcaggatgtcaagagtttgagaccagcctggccaatatggtaaaacccatgt    216650
ctactaaaattacaaaaattagccaagcatgtggcgcacacctgtagtcccagcatcctgggaggctga     216720
ggcaggagaatcacttgaagccagaaggcaaaggttgcagtgagccaagatcacgctactacactctgac    216790
ctaggtgtcagaataagactccatctaaaaaaaagtttatgaatttatggatgttagaaactcagtttt     216860
gttacatgggtttattcatagtggtgatctctgggcttatattgcacccgtcacctgaatagtggaacct    216930
gtatccagtaggtattatttcatcattcattctccttccatgtcctcatattttgtagcctccagtgtct    217000
attccactctgtattccactattccactctgtatgttaatgtgtacctgttgtttagctcccacttataa    217070
gtgagaatatgcagtattgaacttctgagttatttcactcatgatactgagttccaccccagtttcaccc    217140
atgtccctgcaaaacacataaatttcattcttttttatgactgactactgagttgtattccatggatatat     217210
aaactacggtatatataatttatgtatccagttatctagtcatttgttatggacacttaagttgatttca    217280
tgactttactattgtgaatagtgcagtgataaacatatcagtacaggtctcttttttaatagaacaatttc   217350
tttttcctttgggcagaaacccactactgggattgctgaacaaattatgtgtgtgtgtgtgtgtgtgt     217420
gtgtgtgtgtgtgtgtgtgtatagttcttgtttgttttttgagacagagtctgactctgtcaccagg      217490
ctggagtgcagtggcatgatattgactcagtataaatttcatctcccaggttcaagtgattcttctgcct    217560
cagcctcctgagtagctgggattacagacctgcaccaccaccccagataatttttgtatttttagtagg    217630
aacagggtttcaccatgttggccaggattgtctcgatctcttgaccttgtgatctgcttgccttggcctc    217700
ccaaagtgctgggattacaggcgtgagccactacgcctggccccaaatggtagttctatcttaagttatt    217770
tggaaaatctcccatactgcattccatagaggttgtattaatttaccttctccaccaacagtgtataactgt    217840
```

```
accctttttctcaccattcttgccaacgtatgttgcttttcgacgtttttcaaaatgtcattcatttccac      217910
attttattataattccttaaaattatgactttaacaaagagaagggaaacatacagttggtaattttt         217980
taagtgctgtataatttctagttagaaagccacagataagccccgtgctgaagcgaggtggtaaaatagc       218050
acaagtttgaaataaagtaaatttgggaagataaagttgtttttaggatgataaagatgttagatgtta        218120
aacttggtccaatttttctaacttttactgtattcttcacacttacccaaaccacaaacaacaaaagtga      218190
gataaggcagtgattggggatcctgttccaatgcagataccagagattctcttactggaatgatgaatgg      218260
ttaacagctatgctgcatgtggaagtaaaatgctttcccccccaaaaaaaatggaccaataaacacatag      218330
cttgggccttaaggtcatatcaaccaatggttgacccaaagtctgtccaggtgtgttgacagacttcag       218400
tctttcttcctgtgatatgagttcaggtagtagaaactcagggaagggcccttttgctttctttttttgatg    218470
ggtccagactttagcagataagcaacattagagaaaaacttcctcctgtgctttggggtcacagagggtt     218540
gaaagacaagaggagtgagagaagatgagagacattgaggcttcttcttcagttcaacacatcaaagca      218610
ccatatgttggagcatggatttctgagtcccaacaactgggtagtgaagaccacccagggctgtgtgttg     218680
aggattctgatgcagacagtcaaggctcacttctctgagagggaagctaaatgcgactcaggaacacatcc    218750
ccatctcaaatgtgtttgttatattgatgacagttggcactcagatagcatgcatcccttgtggtttcaa     218820
cggttggttgacatgaccttaaaggccaaagctatgtattcattggtccattttttgaggaatgcattt      218890
tatttccacaatgcagcaaagctgctaaccattcatcatgccagtaagagaatcccgggatctgcactg      218960
gaacaggatccccaatcactgctttatctcacttttgttgtttgttttgttttaatttgttttatgtttt     219030
acaaataatctgaagttaaaatataattgataaaagcagttatcttgtgatgtcaggataagtaaactag     219100
tgcacttcaagcaacatctaaccaagtgtcattttcttgctggattgcaatattgataggcacatgggat     219170
aatatatcacgtagatcctgattgtagatcaatgcatcttgatcctgcatcttgaccctcttctcagtgg     219240
gctacatttatgcctaaagaaaaatattctctcaatcctcaagaacatgaaacattacaatctgcagagc    219310
aaaattgccagcaggagaaaatgttaccaaatattcaaaagcatgcttttgtgtaaatgatcttgaaact     219380
ccaggtaatgggggaaacagggtgaggagtgcataagcagaaaccttatttgacccagcagcttccggt      219450
ttctaaaaccctactcatgcagtgccaggaggaaaataaccaattggcatcacttaatgtttagtgatag     219520
aaaaagaaaagcatgcctttgttcatttttctactcttctcatttcctgcctcaccattcatcaaatgaaa   219590
cagtacattttcattttctctatatgacttgtagcatttttgggaatagatgatgcgcttaacatattgc    219660
tgttcatttatgtgaaaagatatttctgctattgtccaaagagagtgtccatttgcaaaatatctagtgt    219730
atgaagacaagttttattttcattttttcccttgtcttatattttaaatgtagttataaaatgagagaac    219800
atgggttcacaaagaaacatgaaattcataattaataaatgtgattttctatttgtttttaggtatgcaag   219870
aggcacgtttgtgtgggagctcaaaaatgtttaattattttaaatctcctttcactaatttaataaattt   219940
ttttgagttcagatgcaatctattacacatgtttcttgattttagggcgattctaccccaacatgcaaa     220010
ataaacaagagatccttctagttctttacaagtttcttagtgaaacacggcacttccctgatgctttcat   220080
gggtgggaactggagtgcacaggtgctggaacttgctggccacttcggggcaggcagtggcaatctccat   220150
tgactcactgctccacccctcacaggaggagaagcaagttgcaggagcccaagatgcagcaat           220220
tttggatgccagcaattttaggtgtaaggaagaaggaactccatatcaccccccacagcagcatctcatag   220290
agggtgtttgctaccctggaagcccagaggaagtactacagtgtccctttatctttgccatctgcagac    220360
agcatgttaacagctcagtggtgggtggtgtgacagccttttacacccacactcatggcacctaagttc   220430
ttgtccagcctccaggaacaatgaagtcacacaaacaaatttgaaatggtaaatgtgggggatttttattgc  220500
cagtagaattgctctcaggggggaagggaagctgggatagagcagaaagttaaccttccctagaaatccag  220570
tcattcatggtcaaaatcctctccaaagctgcaccatcacgatgtacttctgaagtcaagccacttctct   220640
ctgatgtccaaccattgtctctaatgtccagttggtatttccctctgctgtttatgcctagagtttttat   220710
gggcaccaaatgaggggcagggaggggccatgggtggttttggaaaaggcaacattcaagtaagaagacag   220780
gaatgtaagttctcactttgggctgtggttgcatgcttttggcttgaggtggagccctctccaggtac     220850
ccactctcttctgcccataatttccctgcctctgtccctatcaattttatattatttaggtatgcaag     220920
aggcacatttttgtgggaagtttgaaaatgtttaatttattttaaatctcctttgttcatttaaggaatgt   220990
ctttggagctcagatgtcattacacatgtttcctgactttggggagcttccttgctaacatgggaaataa    221060
acagagtccctagtaattatttccaagtttcttaggtaaccaattatatgtattctacaccccttagcag    221130
tgagtgttcatgttgtcaaatttccacttgttcttaaatgagattaaaacacaacaacaacgatgtttaa    221200
aagtttcaactataagaatataaaatcaatgtatactccttttgggttttttctaatttttttcacagaat   221270
tctggtttgcaaaaagccagtagctgatttatcttctgaagatctctgtctaaaattaataggtatactt    221340
tcataagcacacttcattttgcaggtgaaaaatttctcccaacaattgtatatgatagtgatttacaag     221410
tcagtattttgctgtaaagagcgtgcctctaagtatcatgtgaagtaatttaaattatgccatttttta     221480
gtaagcatgttgactgaatctcatgtatttccactgattccacactaaacaaactatgtttatttttac    221550
tgcatttgacttggtttatatagtttacatagacactttgtatgtctaagcatgcctgagcattatact     221620
acatggcatggtaatgtggtttggctgtgtcgctactcagatctcatcttgaattgcacttcccataatc    221690
cccacatgtcatgggacagacacaatgggaggtaatcgagtcttgtgggtggctatcttcatgctgtct    221760
caaaatagtgagttcttatgatatctgatagttgtataaggggctttttccccttttgctcaacatttttt   221830
gttgctaccaccatttgaaaaacacgtttgcttcccctctttccatgattgcaagttccctgaggactcc   221900
ccagccatgctgaactgtgagtcaattaaaccttttactttacttccaatttggctggcccccacaggattta 221970
tattagcagtgtgagaacggactaaatacagtaaattagttctgagagtggggtgctgctgtaaagatac    222040
ctgaaaatgtggaagtgactttgaactgggttaaacaggcagaggttgtaacagtttggaaggctcaga     222110
aaggaagatatgggaaagtttggaacttcctagacacttgttgaatgacgttgaccaaaatgctaatagt    222180
gatacggaccatgaagtccaagctaaggtggtctctgatggagaagagaagcttgttgggaactggaata   222250
aaagtgactcttgctatgtttaaggaaagagctggcagcattttgcccctgccctagaaatctgtggaa    222320
ttttgaacttgagagagatgatttatagtatctggtggaaggggaatttgggttagaacccacatacag    222390
agtctccactgggacactgcctagtggagctgtgaaaagaggggcatactccagacaccagagtggaaga   222460
ttgcaccaagcacctgaaaagccacagagggtcaatgccagctattgaaagcagctggtgttgaaggt     222530
gtatgcagcaaagccacaggtgtggagcttcctaaagccatgggagcccaacttttgcattattgtaact  222600
tggatgtgagacatggagtcaaagaagattattttagagcttttacaatttggctgccccacaggattta   222670
gacctggatgggacctgtagcccccttcatttttgtgaatttctcacatttggaacaagtgttttttagcc   222740
aatgcctctactcccattgtgtttggaagtaactaacttgcttttgattttacaggctcataggcagaaa   222810
gcacttgtcttgccacaggtgagactttggacttggacttttgagttaatgctgaatgagttaagactttt  222880
gggggactgttggtatgatatgatttgtgttttgaagtgtgaggacatgagatttgggagggtctaggga   222950
```

FIG. 11A-44

```
ccgaaagatatggtttggctgtgtctgcatccaaatctcatcttgaattatagtttccctaatctcctta    223020
tgttgcgggagggacccagtgggaggtaattggatcttgggggcagataccctcattctgttctcatcat    223090
agtgagttttcatgagatctgatggtttcagaagggctttctcccatttgctctgcccttctccacgc     223160
tgctgccatgtgaagaaggacattttttgcttcaccttctgccacaattaagtttccagaggcctctccag  223230
ccctgtggaactgtgggttaattaaatgttttttctctataaattacccagtcttgggtatgtctttatt   223300
agcaacatgagaatggactaatatccatgtgcacacagaaatcttttctggggagaaaatcatggtctacaa 223370
tatttttcttactcagaaataaggggattctttgggaaatcatcttccagataaaatcatagcaagctgtg  223440
gcaggagatttctgaagatcaaacatccttgtatgtgtctataaatattatctgagtcagcactcacaat   223510
ctgataaatgccctatgtgttccagttttcaaatggtaggttttgagacagaattcacatgtcagatgag   223580
tcacataaatttgcagaatgtctgtgaaggggcatggatatctttggttagtaactacccaaccatttttc  223650
caaagtggacttgatctttggtattagaattgagaagtccacctgacctaaagagaataaggtatcatca   223720
ggaagaaacaatataaaacaaatttttttactgttccattagccaaaggcagatgatgtcttagagatgt   223790
ttggttacatagaggagaatcaaattaaaacacacaaaacaaagctatcctcctattaatatgatttact   223860
gtataggacacactaatttacttggtgagaaaagaaaatggtttaggggtacaaaatgcagttagataga   223930
aggaataaattatatgattggataatgtggtaggaaaatgtatatttcaaaatagctggaagagaagaat   224000
tggaatattcctaacccaaagaaaaaataaatatttgagatgatgaatatcccagttactctgattggat   224070
cattacacattgtttacaggggtgaacatattacatttgcctctaaaatatgttcaaatgtattatattg   224140
ataataaataagtaaataaatgggcaaaaaacagcatttccaaaagagtatatttctattaataacttttt  224210
aaagggaaagagtccgatgaattgcaataaggttaaaagacagaaagatcctgtctctaaaaaaaaataa   224280
taaaaataaaaatacataaatacattgccaaaaggttaaagaagtaaaaaccttctacacatccataact   224350
atagcaccattcttgctgtggtaactatggttttctctaggcttaaatattttaattatattttatattg   224420
atacttgctaataataataatgtattgtatagatgacagactggccttttctgtgatggcttttgcttgc   224490
ttggcgtatggtaaaattatttatgaaacttttaggaaaaaggttttttatattttcttttttcttttagtat 224560
tgtggagtacagttcaaactaactaggaaaattaaagacctaagatattttataattatattaatatcat   224630
gagtaattacaaaaataacaataatgactttcactctgttttccagtcctgttcaagatatttacatgca   224700
atgtccaattcaattcacaaaagcaataaaaagagacgctattttttttttccatttgtcaaacagtaaag  224770
ctaaggttacagtctctttcttattgataacctggtggtgatctttttgggatatcattacagcctccaactcctggt 224840
tttctctccagaggtacctgccattaagacttgttgcctcagtcggttgatattggccaagacttcttaagt 224910
aaaaaattatttaatgttaggacttctgcctcacttttctaattagtggagcattttgcctctctacaga   224980
agagaatcccggaaaatgcaagagctgtctggtgttgcttagtgttcctgataatctagtattttcagta   225050
acgttaactcatatccgcagggctatgagggggtcacatatttttattcaattaaatgtcaacacttga    225120
gaaaaactttgactgtcagaaaaaaactgagtgagtactcagcaaattgtttaacagttgggggagtttg   225190
caatagtctatgaaaactgttttactttatagagccagagaaattttcattgaccctagcacagtgttg    225260
gtttcactcagggatgctaactttgctaatatatttatccatatactgatataataattataatatcatg   225330
cttgtcactcactttgtaacaaccaaccacattgtcagaataacatttgttatcccatctccctcctac    225400
aaaaatcctatgagatcctaatattatcttgattttcttaaacaaataccaccagaggcccctcttct     225470
tgaattaagttgggtttattgactcttatgtatttctattagtattattattcattacagataggat      225540
cttgctgcgttgcccactctggtgtgcagctgtgatcataactcattacagcctccaactcctgggt      225610
caaacaatcctcccacctcagcctcttgaatagctgggactacagttgcctgccaccacgtttggctggt   225680
ttttatttattttttttacaggtgtgatctcattatgttgtccaggctggtcttgaattcatgaccccca   225750
gatgttcttcccacttctattgactctttacaacaagaaagaatatgtacataggggatgtctcagtaca   225820
agggtaggaaagagttagagaattgggggcttgttttaaatgatttacagagggttctggaaaactgtgct  225890
tgaatttggaattgatactttcaggacgtgttggcagttctatgactggttatcttaatctttatgtaaga  225960
ggaggaaaaatgaagcataggttaaagcaatggttgacaaagaaacaacagtcactgatgataccaagga   226030
caggtggacacttgatcatgtttgagtgtttgaataaccacttttttgtgtaagtgtccagacatgatta   226100
caatgtggtcttcattttgtcttgttctttcatgatcacacagtggttttttccttctgtcactgttccat   226170
tattattattattactattatttatattcaatagaacaatggcacaacctagctgcaagggacagga    226240
aaacacccaggattgccagggtttaggtgacattgccaggtcagctgctgatcagcagggattgcttttc   226310
tcttttgtgagtaactgaatattaaataaaccgagtaacatatcccaaatcctaccgagagttggaggta   226380
atactggagtctcaacaaagactatagaggagagtctagcccattcatctccaggcttttctctaggaaa   226450
ccaaagaccaatattatatttgttgcagaaaagagacaccctatagtcaacataatgtccagtgagagtt  226520
aattttaatgaggttctttttcagaattcaagaaagctggagaaaagaggcgttgtgtaactcacatacc   226590
aggaggcatcttctgtagctagtcagcagatgcctcttccactggagggatgcgatcttaaggataggag   226660
aattccatttataaccaagaccgcttcattcatgggcctggattggatagggatggcccataccaaggtc   226730
tttgattctcgcttttattgttacattctgtatgactgattcagatttgtccgcactaatatattttctc   226800
tggttctgatcattgtggccatgtcttcctagaacaaaggccttgggttaatttttgcagagtaatgacg   226870
ttctcagcagcagctgaactctgtagatcaatattcctctcttcttgttttcttccaatggcaactaaaca  226940
tgcaagacacatcaggagaagggtatgagattcccccaatagctaaccagcaataataatgcaacatgtaa  227010
ggctaatgcatgccccttgaaatgccaaggggataaattcatatgcatttttttcatttgggggtttgaagagc 227080
cagatgacatgcaaaagaaaaatattgacaaaagatatcttatcatttattttcaattattaagcttgat   227150
tttcatacattcaaacttagtttttttaacaggtacatgactctagtttttgaaagccagaagaatgcaca   227220
tataaaatcttttttgtctaacaaattaatcccatgtttcttggttctgatgcttgcatactgcttatgt   227290
taaaacaattgtgagcaagcccaaactatactttttttttttgagatggagtctcactgtgttgtccaggc  227360
tggagtgcagtggcgcgatctcagctccattgcaagctctgcctcccagttccacactattctcctacctc 227430
agcctctggagtagctatattatacttattttttaaaatgacagtacggctgaggtattcaaaatatgttt  227500
aaaggttctaacagaaacatgttagaaaaaaagaagcttgacagcttttaagtttattagatacagaaat   227570
ttatacttagatttatttagattgaaaattaatcctaaggcatttaaccagctgggagagcttatgcatg   227640
catacgagtttcaagctgcaactaaggcagttgggcagcagtagaaacaaaaagttgatatttattttct   227710
ttcagaaccaactgtgactgattaaccacaaaagatcagcaggggtatttgggcctaggtcatgttgatg   227780
gccttttgggttttagtttgttctttagggttcattgctgcaaaaggaagcctcctctacaaatgagatgag 227850
actgcatgagtacaaagcagagagatgcagtgcttctctacagcactgagtaggcaaattgtgcagatttt  227920
tcagtagaatctacttaacaccaatccatgcatttgcattttattaaaatgaaactatgataatttaaac   227990
tgcacattgcagatatgacctataaaatgtttgatgtcctatttttaacaaaagttttgaaaatttgcac   228060
```

FIG. 11A-45

```
tccatatcaatttctctacttatgtgtttttagttatttttgtaaagaatgccagattttcaaagcaagt       228130
aggccaagaggatgatctttttttcctccttttttttccccgatgtttaaaatgcaactgccatgggggc       228200
tgtgcccttttagctgttggaaaaaataatctactatgccttggttgtatgtgtgagtcaccagaccttc       228270
tgggaatgattcttggcacattctaccaacaatttaacatgatacaaaatcattttcatatcttgtgat       228340
agtgtcagccaagtgtttcatacacatggagataagtgctgaaaaggtgtttgaataaaattgttttct       228410
taaagcaactatagaggatgagataaaaggatgcacaattacatttcataaattgagagagtttcctaaa       228480
caagagagcattcctggaaatgcagagaaaaataaaaagatcttaaagatgttgtattaagataagttag       228550
actaaggcagcttggacatgtgtctcctttacttcatgtttatatataagtaaacattaaaagtagagga       228620
atttcagtttccacataacttatataggagcaacaaatgggggctttcaactactgaccacattggcatat       228690
cacccaatgttttctttcagacttctctacctacgacaaaaccattgtggtattagagcttcatgaactg       228760
tgtatctttgattagttgatttaacctgtctggccctcatttttctcatctgtaaaataattgagtctta       228830
tgtgatttgaagatcaaaagaattactacacaaacagtgctagtaagagtccctgccacatagaaagct       228900
agtacacacacacacatacatatatacacacaccccctcatacttttatatattaaaggtgtatgattta       228970
tgaattattgcattagaaatgtaaatctgttatatatatcatatatatgataagtgaaatacagattatg       229040
taatttacaccacctatttattttgtaacttcgtaaacagattttgaaaattttattttgtgtgtatgt       229110
cttccaagtcattccctaaacttcattaaaatcccctttgatttatgggaaaatatctgtatatatcaggt       229180
attcatatatatataacacatataactcttctgaggttataaacacacatatatttataacatagaaaatta       229250
ctaactcatatatgtgcctatctatatataattttcatatataacattgtatattacatataaatattta       229320
tattacatacgaataatcatcacgttctgacagaatttgttaatctaacctccctcaaccccacccccaaa       229390
aaaagtagaaactaaaaatagaggaattttaagttccacatgatttatgtataagcaaaaaatgggacta       229460
ctgactacagatcacgttagctaattgtacagttttctcttctgtgctttgttgtaaatatgatttttat       229530
ttaagaggatattattaattatctatacaagaattggctatctctccaaacttctacttcggtttcatg       229600
ttttttaaaagggggtgaggataggctgagcacagtgactcacacctgtaatctcagcacttcaggaggcca       229670
aggcaggtggatcacttgagggaaagagtttgagtggcctcgccaatgtagcaaagtctgatctctgcta       229740
aaaatacaaaaattagccaggaattgtggtgcatgcctgcagtcccagctacctgcgaggctgacacagg       229810
agaatcacttgaacccactaggtggaggttttagtgagatgagatcatcccactgcattccagcctgggt       229880
cacagagcaagatactgtctttaaaaaaaaaaaaaaaaagtgaaaagggtgaggattgttatttctatgg       229950
gcaggcccacacagcattggattcctcagaaactgcacagtaaacgggagtctcttagcacatctgacag       230020
aacttcaaggggctgactgttcattatcccacagcccactctgctctgtgtaagtggagactccatgtct       230090
ttgttgtcttgcagtccctagatgataagggcacagagaaaaatcacagaaatcaaacatggtagcacag       230160
aaaaacaccccaaagtcaaggataagatgaaagttgtgatcgtacacatcaaagtcggactcttatctag       230230
atgggcacacctaagccacaggctgacaggctgagattctacaaaggctctggaccccagataagtttaa       230300
gtgattgcatcgtgatctcttttcattggtggaggcagtgctttgaatgactaagctggatatcact       230370
ttccagggaatccttttaggggaatgtgaccatccagctatctctggatgtctttggtgccataaatactt       230440
ttcacttggttgaggatactttttagttttatattcatgcgtcaacttgtacagaaatgtgtgtttgggc       230510
ttgtaaaaaagtttaatcataagacaaagggctacaggtttcatgtttattcacagtttgatgaacggca       230580
cttatggacacatatgtgtatacggtaagtgctcactgaattcctcttgagtgataagctaggatacaaa       230650
atgtcagaagataaagagtgaggatgggcactgatccaaatgtcagtgaactctgagggtctcttgctg       230720
gttgaaacaacagagtacttttattttcattctaaaccctccatgacccatgtccttataccaatgaatc       230790
acctcctcaataaccccctcaaacatggcatctttgaagtagagcctcattgacaagcactaattaaatgt       230860
ctgtcatggatactaaaatgtatatacggcctttgtgcctggacaacagtacatgtgtcagctgtttctt       230930
aagcctacatccaaccattaagtaaagcccagtgcgctcttagttcctcaaatctgttcaagtcttgatg       231000
tttgttcaacattttgactggctccagtcatatgtctccagctatctgtaatggactcaatatcctgctt       231070
ataaaatgctttagtcatgtgggttcattttggttagctgtataggtcaggaataagttagaaataac       231140
caaaatactccaaatcaagttctagctgttttgatacaaacatttccatcaaccttacttctccctaac       231210
tcatctgtctgtttctgtgcccttcccatggggtaaaacctttttatagtatccagatgccttctacaca       231280
cagaagcaattttgtgcaaaaggctcccaggggaagaagaggacaatgccttcatgggaagctcctttc       231350
tgttaaatcggatttgcatacctaaccaaagcatttgcttcaagtaaccagtgagggtgggatagtggtct       231420
tgcaaaactatagctacattgagagggattattaaaattattcagtcattcattagaggagctttgacaa       231490
agattgcagaaacagatatataaaacaggaaatattaacaaaaacattctcaaaaatatttataatgtcca       231560
gaacaactggcatgactaacatcaaagaagggatatgttttgacattgatttactaaccacttatcattg       231630
atactaaatcctcctttgaatacttatttacgattaagacagtcaagttatatgagtatgttcaaccaac       231700
aaaggttgcaaacatagtgaatttaatattcctctgccatatggccatcctacacttctgacgtcacacagt       231770
catggctctgcaaatagatcagactttttggccagtcccttggggggtcactgcattctaaggtgcttgac       231840
caggaagtaagatgctcttctcactaagtgatatacgtgtggtccttgtggatctgctaagaatctcaga       231910
aaaggaataaaagatacatgaaattgtttgcatgctactagctctagtgggtagattggtggcatattc       231980
ttcttggcaaaagacagaaagtatccaaaagttcaccatttttctcctggttggggaatggtgtcttta       232050
gaccattttgttcaaaagaaaggtaaaaatagcatgaaaagagaacccctaaattgccttactcaagcct       232120
tctactctaagtgacttgtataaaatgtcttgttcagtagttacccaactccaatctacccctaagaggt       232190
tctagtaaagtacagattagctggatttaataaagcacaaataggtagcagatgcattcttacatctcaa       232260
tctaatcggtaaccttcttatcctcacccatggctgactactatgcataaagaataggaattctgacca       232330
ctcaagaatcttaaccatacattcagtctgttgcagtttctcctccattacacatttttttttttcgctt       232400
ttctatccttggacagccacagacaggacaactagtcaataagaaatgagtgtgaaggtgacaacttttcc       232470
tcactaagaggatagggggccatgagagggaaaaggtgtacttcttgtgtggcgtggtggtgagttaaaattt       232540
gatgctacagtcttctgggagcagcagctgtatgtgcttgaactttacttttggaggcatcctctaattcc       232610
aggggttctgtgccagtaccatccactgcagttcacttaacttgggctgagtctgtttcttccctccat       232680
cacttcagctggacctattctttgaccctcacatggtttccagtggtgaaaccagggaagagtctctttg       232750
tagaggaccaaggagcacttttttctatgtagtgcacatttggctccatcaccatcatagctaacatgtc       232820
caaccctccagcatcttcaacctcgcactgtcttgcactgcccctaaggcctgaataaggctgatg       232890
ggtcatgtatggcagggccaccccaacagtctagtaataggtcttgcattgttggacacacttcttgatt       232960
tagaactatgctttcagtcatggtaggtgtgcccagttggcaaggtaaggagacatttccagttgtt       233030
acagtgagtttgaagggtgttaatgcatttagttcatggagaccagggttgctgttcaatatcctacaat       233100
gcacaggacacttgcccatagcaatgatctgattccaaatgtcaacggtgctgacatcagtaaaccctgc       233170
```

FIG. 11A-46

```
tctaagtcaatgcttttttttgtatgcatattttaaaagtctcctccagctaaaccattagcttttaatgg      233240
ggtatacattttctcttccaagggatgtttggttatgcctggagacactttcagttttgcagccagagt       233310
ttggtgatgtttctggtatctaattgatactaatcctagatgctgctcaacatactactatgcagagtat      233380
ggctcaccagaacaaagaattatcccattcataatgcctctagaattaagattgagaaaccttggtttag     233450
aatacagggagagctagtggtatcctctaagatgctgtctggaagcagctttgaagacaagcagagacca     233520
gagactttgaagccatactcacagggtttgatatagtttggatattggtcttctccaaatcttgtgttga     233590
aatttgatccccactcttagaggtgggacttggtgggaggcatttctgtcttgggccagatctctctcat     233660
gaatgacttgatgcagtcctccagatgatgcatgagttcttgctctgttatttcccgggagatctggttg     233730
ttataaataacctggcaccttcctctcctctctctcttgtttcctctctcgccatgtgatctgtgcacac     233800
agcagctctccttcccctttccaccatgaatggaagttcccttagtccctcatcagaagcagatgctagta    233870
ccatgcttcttgtacaccctgcagaactgtgagccaaataaacttcttttcttttcttttattcttcta      233940
attagagacaggatcttgccttgttagaaaggagtacagtggtgcaatcattgctcactggagcatcaaa     234010
ctcctaggctcaagccatcctctgacttcaacttcctgagtagctagaactacatatggcatgcctccat     234080
gtccagttaatgtttattaaaaatagttgtagggacagagtcttgctgtgttgcctaagttgttctcaaa     234150
ctcctgacctcaaaggatcatcctccttcatcctactaaagtgctaagattacagatgtgagctgccatg     234220
cctcgactgtcttctctttataaattactcagccacaggtattcttttatagcaatgcaaatggagtaag     234290
acattgtacaaatcccacattaggcacttatagatctgtctgtgattctggacaagttatttaaccactc    234360
tttgtgtctaaacctgttgtttgtttctttcttttattcctatcaggtccagctccaatgatgataaaaa    234430
tatagatgtaaatggagctaagagggtgcctgaccaagagtaaacagtccagaagtgttattctgtcaa     234500
tatgacttggattttgcttcgaaacttcagctgaaactgacatgacaggaaaaggcccaaattagaatt    234570
cttcttatgcaaaattccttctgtgaggaggtagcccatctgttgtcaaataatccgagttgtagaaatt    234640
tattaaatttctcctttcttgcccttgcctccttcattaaatgaaatcagatggtgacagtataaggaa     234710
gttaaagtgaaggtaaaataaaacagacaggaagaagtctgtcttcagattagacatgcaattattcctg    234780
tctttgctgctgatttcaattataactcattggaattatcagtccacaatagatgttccctgcctatgt     234850
gtgttttaattaaacgttgacatcattctcacatgttcactgttattagcactgatggatgtaatcttc     234920
atgttttcctctgaacactgcatgccaagaaaggggccctctatcctcacggattttctaggcaagagaa    234990
tatcaggccctcatctgtcatatttccatctcattcagCACAAAACACCCTGGCTCATGGAAACTGCAAG    235060
CATCGTGTCAGCTGCACCTGCAGGCACCACGGGATTGCAAGTCAGCATACCCTTTCAGAAATGAGGATG     235130
AAATTAGAGgtagagagaaaattctccactgtcctctcacttgtctctgttatggtttctgctatgtttt    235200
cattgattatgctataggagaaaggaggaaaagaatcccctaagaagaacagtgtctcactggacattg     235270
tttctttgcaaaaaaaaaaaaaaaaaaaagaaaaaaaaagaaagaaagaaagaaagaaagaa            235340
agaaagaaaaagaaaaagaaaagaaacatttttggtattttcactttttccaccctagaatctagat       235410
accacctttaaacagatttgaatcccacagggagaatgtggtcatatattttcactacaaatgctagaca   235480
tgtcttctggcgtcagaaatgctgtattgtgcatgtgttcttgctgcaagccatcttcaacttggttttt     235550
cagggataggcaaaacattaggcaatctgaataaaaattgcatttcttgcaactgaaaattttttgcatgca  235620
cccacatacgtgtattggtattactgtacagcttgcatggtgcaaagctgaaggctaagggattaaagga    235690
ggctgaaatttagccctggacacactgtgcagcctgggtacctgtagggctgcaattcctggctagagt     235760
gtgtctatttctcatgcatccagtagaaggcacccttttgaaggtctctcaaccctctcctcattcccct    235830
ccacctatcatatttagcatattgtgtatttgtcctagtctgtttaatccaacttgatcacttttgtagc   235900
ctttctttattcccagtgtgtaaatcagtatttgaatgcattgagctaagtttcagacatatgcctttc    235970
caaatagactatcatgaaggatgctattctggcgcagctatgcattctcttctgtgtaagaatgctcatt   236040
gtgtagtctctccttttaaagtctgtttagtgtaatgttcgctgacttttccatgcacctcttatgtaat   236110
cttttgccagttctaccatttccaataaccaatgaagatacttgcttcatgttaaattctaagtaatcta   236180
cttttctattgaactaaatcatttctccacaaaatgtcttttgaataattaaagatcttataatgtggtttc  236250
catagactgaactgaatatttcatgtggctagataggtaaagtacagtatagtagcaattggtgta       236320
cacacttagaatgtcctaataaaattattgcagatactgatatgcaatgagaaagaataactgtagtgtta  236390
agccccagatggtattatagacctgagggtgggtgaagatgggcctgggattaatggattgatagctcag   236460
ttcatattggagtttcatatctgagattcagtgaattcgaggctattcttcacctgctgcaattctaggg   236530
aagtgtgtccattgaggagtcgctgaaggggctgggagtttggatgggggttctttcaataccacctttt    236600
aaaaaaaatagtgtggctctgtcatgcaggtttggagtgcagtggtataatcatgcctcactgcagcctc   236670
aaactcctgggctcaaacgatcctcctgtctcaacctcccaagtagctaggactacagctgggcaccacc   236740
ataactaggcaattgttttaaaaactttgcagagacagtcttgctatgttagttagggtggtctcaaact   236810
cctggcctgaagcagaccaccaatgttagccttccagggtgctgggagtaagacatgagccaccgtgctg   236880
aactgcaatatcttttttaattagcgggaagtagaaaacagaaattctgcagcatgttttttcttgttaaca   236950
tgaatcagtcttgggtgaagtgtccatagtttttaatgatattttcaaaatgaacaatttagagacaggc    237020
atcagaaaccacaaataataaggccatgtgaaggaacacaatagatgcataaggttaattggtcagcatt    237090
tatgctgcacttagtttcccgttgattttttttaatgagtttgaagtataacacacagaaaccaaagtt    237160
ctgtgttttgtattatgttatattatcaatgttcagtgcaatttgaaagcctaaagcaagtatttctgta   237230
acaaacacacatttcaagaaatataatgttcctatcttcaaagcaattcatgctctttcccattttgtct   237300
ccttatcctcctcagtgataagcattttttctcttatgcttttatatttttccatgctttttcttttata    237370
ttttcccaaaaagaaaggcatccctgcatcgcataaattttgcttgtttggagatactaaatgaatgcaa    237440
cttcatattacttttccgatgtgttcttttcaggcataattctgttttataaaattcttacatgctgctat   237510
gtatacattcattccactactttttaattgttgtatagtgttctaaaatctgaatatatcacactccatat   237580
ttccattttattcctaattgatacagatacttttttccagtttgaggttattatggactcgtgttatgaac   237650
gttgtttttcacgcatcctcatttctcacaagcattgattttctgagatatataccactatgtaattgct   237720
ggttcaaatcttcaactatatactcttttttgcagtacaaatgcctgtttttcaccagcagtatgcatcgt  237790
tcaacatgtagcagtataagaattctgtttttcttcttctgatctaatgggtgtatgtggaaactcactgt   237860
gtgtttattgtgttttccctgggattgagatgtttccatgtatttattggccgtttgttttttcctgatta   237930
gtggaagcatctgtttgtttttgattagttttctattagattgtgtgtcttcttattgttttattttga    238000
ttagagtacttcattgattatgtatgtcacaaatttcttcttatgttttttgtttttaattatttcttat    238070
ctattttttttttttgagATGGAGTGTTGCTCTGTCACCCAGGCTGAAGTGCAGTGGCATGATCTTGG     238140
CTCACTGCAACCCTCTGCTTCCCAGGTTCAAGCAATTCTTCTGCCTCAGCATCCTGAGTAGCTGAAATTAC   238210
AGgttttgtgccaccatgcctggctaattttttgaattttttagtaaaaacgggggtttcaccatttttggtcag  238280
```

FIG. 11A-47

```
actggtcttgaactcctgaccttgtgatccacctgcctcggcctcccaaagtgctgggattacaggtgta      238350
agccacctaatgatttctttaaagttcttactcttagtttacacactttaccataattttttttcagatta    238420
gcactttgggattttgttaatggtatcttttcctactcctagatatgaagatttcctttttactttatct    238490
gcaaaaaggcttatgattttatctttgatattgaaaatacacattgatttatttattgcattctgtaaga    238560
ggtgtagtttattttccccttagaatgtcacaataccatttattttaaacaatttaacccatatcactaaa   238630
gttcaactggtctctgtctaccactgtgccagtaatcacatttttatcatcatgatttttataataatac   238700
aaaatatctagtatagcaaatattctttcctttgtcttttgcaagagagtcttggctatcttttggtgtgt   238770
tgacttttgtatgaattttggcatacccaccttgaaaaataaataagcatctgattttcaattaataatg    238840
aattgaattaattaattacttaatctcaaggctagtttgggctgattggacatctttaaacattgaacag    238910
acatattcatggaattgtacatccttatacacatttatgtattttagatttttttctatttcatattctg    238980
tactattttgaatagcagtcttttatacatttttggttaattgatttgtaagaaaagatgttttcaaaagt   239050
atggtaatgtttgttttaaaatgttcattctctgttattgctaaaatggaaaatgccattacttacttgt    239120
tgaacattaattttgcaacttgtgaaactcttgtattctttgggatttcctagaacacactcctatcaac   239190
tgtgagtaaaaacaattttgctattcctttttaattttagatgtgtttattttctctccttaacagct     239260
cattcgtgtaacccttcaagtacaatgccaaatagaacaaagacttgagcatctctttatgactttgac    239330
tttaaagacaaggtttccaacaccctaacccattaaaatgaggtcttcaattctactgactttagttgt    239400
gaattttattagattaggaaaattcccttttattttttgtttgctaaaatatttttgaagctgtgaatg    239470
aatgggtgttgcattttgttattctttactgaatgtagtgtggtttttggtttcttttttcttttcttt    239540
tctattttatttatttttttttgagacagagtcttgctctgtcacccaggctggagtgcaatggcg        239610
tgatctcagctcactgcaacctctgcctcctgggttcaagcaattctcctgtctcagcctcccagtagc    239680
tgggactacaggtgtgcaccaccacgctcaactaatttttgtatttccatagagatgggtttactgt      239750
gttgcccaggctggtctcaaactcctgagctcaggcaatccaccacctcggcctcccaaagtgctggga    239820
ttacaggcatgagacaccgcacctggccaattttttttctcttcaatgtcactgtaatgattttattat    239890
atatatattacatttttgtaacataattataatatataatatatttatatatataaaagatgactttat    239960
ataagatatataaaagatgattttatatatacataaaagatatgactttcttttatatgtgtttatatat    240030
atacataaaagatatttatagatttttaatattaattccactttgtgtgttgggatgaacctaatttgaga  240100
attatatattcatatgcttttcacgcattgccgaaaatagtccctgggtgatgttgttggcaacttctt    240170
aatcctattctttgaatttttggatagaagttcacactatcatacataaaattgaaatatatgtcttttt   240240
ttaatacttgaagagattaagattggggatatatcttcattaatatgttcctgaactaagaaataccacc   240310
gtctccgcatagttttccttgtggcttgagttttggcagcaaatttgatgtcttcctttcttttgttct    240380
ttgttttgagacagggtctcattctgtcatccacactggagtgcagtagtacaatcatagcttactgcag   240450
cctcaacttcctgggctcaagcaactaatttggtatcataaatgatgggggactgggtgtggtgtctca    240520
cacctgtaatcctagcacttgggaggctgagacaggtagatcacctgaggtcgggagttcaagatcagcc   240590
tagccaacatggtgaaactccgttctactacaaatacaaaattaaccaggtctgtggtgtgtgcctg      240660
taatcagctcctgagtaggagtttaggcaggagaatcacttgaactcaggaggcagaggttgctgtgag    240730
ccaagatcacgctgctgcactccagcctgggtgacagagcaagaatccatctcaaataaataaataaaca   240800
aacaaacaaacaaataaatgatagaaggcttattcagatgtgtacttttgaatcacttttgttctactat   240870
acttttcaaagaagtcttttttactcttttaaattttcaaattttttgaaaatgccaaggaactaatttt   240940
tggttttcctcttcattctatttttatgttgttttttccattaatcactactgctatcttaattatttactt 241010
ctgataaatcttgctgttgttttactgtcttcttgaaatgctgattttattaacttttaagatatgcttct  241080
tttctcatatgttaatatatacctggaaattttgctcaagtactgaattagctacattccacaaatcaga   241150
taaatgatactttgcttttgttcagataaactattttgtaatttctattattaatttttttagtcatgaa   241220
ttatttcacagattattctttagtttccaaatagactgttttttttttctggttgtttatatttttatact  241290
tcatttatttctcaccagtgtgctttgcatacttgagaaaagtatatatttgcaatggttggtcaata    241360
tgttatatgtctaatatctcagactgttgaagtatgttgctcacatactctatgtagttttataggtagt   241430
ttacatgttctttcagtaactaaaataggtatatgaaatttccccttgatgtttatggatgtttaaaacc   241500
tttcctatattttttcaaactttagttttttgtgtttgacgtgcttatcaatttagtggatatggtcta    241570
gaattgttattgaattgtggcaaattgaggttgttctcattataaaatgatcctctttaagttttgtggt   241640
gcttcatgcctaatgtctgtttagtctgacattaacattaccttatgttttaatgttaatgttatctta   241710
tgtttgttaataatcgaattgtgtattgtttctatgtgtttacttcaggcctttctgctggctcaggct    241780
ttgagtgttttctatgtagcatctatttgggtctcattatatttgacttttaactgcagattcactgata   241850
tttactttcatgttttatgtatttgtgttcaagtcctctatcctaaattgtgcttttaatatctcacttc   241920
tatatcttgcttgaattgcttttttaaaaaaatcattccaggccaggcacagtggctcacacctgtaatccc  241990
agcactttgggaggccaagacaggaaatcacttgaggatcctccaggagttcaagaccagcctgagcaa    242060
catgaaagatctcatcccctttgaaaaataaaaataaaaattagccaggtgtggtggtgtgcacttgtag   242130
tcctaggtactccagaggttgagtaagcaggagagtttgagcccatgagattgaggttgtagtgacctgt   242200
gatgacaccactgcactgcaacctgggcaagagccaagcctggaacaagatcctgtctcaaaaaataaac   242270
aaataaataaaattattccattttcttttactcccacttctcccactacactagctgttaaaagactgtac  242340
tactttttagtaaataatcctagaaattacaacatgggtccttaacataatcactaaatttaattaataca  242410
tttcctcttctctgaaaatagttagtaatcagtgtgttttaactccatgtttatgacctaacttacttgc   242480
tgttagtacccttcgatgttttgtgttttttaggaatcttttcagatatgattgcttattttgttattt    242550
caatattcatttgatttttgacaattacactccttcatttgtgtttcattctcttgtacctcctac       242620
tttatctgtgattattctcttacaaaatctattgtgattttaaaatatattttcagagctagtgagctgt   242690
tggaagctctcagtttgcatggctaagtatgtcttttatccacttcttgaacaattttctcgttgaatttt  242760
aatttttacttcttttcagctattcaagaaatcattctccattctctggattccactgttcctatggaaa   242830
tttagctgtcagtttaaaagttacatacttaaaaataatatatttgggtggctacggtggctcaagccta   242900
taatcccagcactttgggaggctgaggcaggtggataacctgagttcaggagttcgacaccagcctggcc   242970
aacatgatgaaacccatctctactaaaaatacaaaaattagccaggtgtgatggtgggtgcctgtaatc    243040
tcagctactggggaggctgagacagaattctgaagcccgggaagtagaggtttcagtgagccgagatca   243110
caccattgcactccatcccaggtgacaacagcaagactctgtctctctctgtatatatatatattaaata   243180
tattaaattaattaaatattatatattatacatttaatatatatatactatatacacatatacacaca    243250
tatatgtgtgtatacatattttatacatatatatatatatatatatatatatatatatatatat        243320
ttggtaaagttagtttgtatccccttgatacctttaagatagtttttgctttcagtttctgccatttcagt  243390
```

FIG. 11A-48

```
gtgatactgtttggggtttattaatctgattagaattccttgatcaccttgaaatctgccatgggctttt    243460
cttctgttctgaaaatagtcacacctcttcaaatattgctactgtttcttctgttttcagtgtgtttgta    243530
cataatttagattttctccctctggctccttttttagtttttgtgtgtgtgtgtttgcttttttaaaa      243600
atcttcatttttcaagcttcattctggattaattttcctataacctacttcactaattctctcgtttaatc    243670
tatctaatccatggctaaaccaatgtgtccaatcctaaatttgatatgtattttcattacatttcaagg      243740
ttgaattttgtttcttctcagtttccacatttttaaagttctcaattttgtattttcaggaatgctttc      243810
ttcctggttatttttaaagtctgcatctgttttcttcctttttacccccctatcactcttatgtttctt      243880
cctcttgtttgtttttggtatcactgactaatatcttcatggactaagtattagaattatgcatatat      243950
tcagcattctcattttgttttttcttatttctagctctctattttatattcttgtatattacatctcatg     244020
ttgttgcccaggctggagagcagtggcacaatcatagcttactgtagctttgatcttatgggctcatgtg     244090
aatctcttgcctcagccttctgggtaagtgggactacaggtgcacaccatcatgtctggctaatatttta    244160
tatttaatttttttttagtgactagatcttgctctgttacgcagactggtctaactcctggcttcaagca     244230
atccttctcctcagtcttgcatagtgggattacaggcctaggccactgcacccagtttcccaacgttt      244300
ttcttcttttgcatgatactctctggatcattcttctctcccaagggtatacgatatcctttt           244370
aacttttctgcccttaggcagatgcattcattttctcattttgttttatttctctgatctagaaatttgat    244440
ttgatctttatttttccattcttaatactttcttattcctggcagatgctttccaacttgttgttttcaa     244510
ggtctttgaacgcccttcagaaaattggttatcatatatatatctggtgactgcactatcataattcttt     244580
tggcatttccaccagcttttgctggtgactttttgtttcttctcttcatgggtttggtaatctttgtgaat    244650
tggctgctgtatttgcaaatggattaagggcatcttctgaacctgtggacactggaattcaaggttcttt     244720
cattcactgagccatgctgttccctgaatttcttagatgctatgaaggtagattacaagtccttgcaaga     244790
ccgaatttacttttgtttaatgcttgccttcagggggaaacctacaaggtaggaaaatgttagaggtgag     244860
tatattagattgtataccttcaggagtgactacggtttgagaattgtcccattatctgctgatgctgcaa    244930
gaaccctaactattcttcaagattggaacagtgcactaaggcaaaggctgcactgtgtgccaggcgtct     245000
agatagaccatcatttggtcatcagtgttttttgtttatttggttggttggttgttttttgaggcagg     245070
gtctctctgtcaccatgctggaatgtagtagcatgatcatggttcattgttgcctcaaactcccaggctg     245140
aagacttactcccaccacagcctcccagtagcttagaccacagatgtttgccaccaggactggctaatt    245210
tttaaaaacttttgtagacacaaggtttcaccatgttgccaggctgtgatcatcagttttgaagctat     245280
aatcttaaatataattttagcactgaaatgcttttaagagacttttcaaaaatcacacatattacaaccc    245350
actttcaattagaagggttggtctgaatgatcttctctgttactgctagatgtagacttctgatttccgct    245420
gatatccacagaaatgactaggtagaacatgaatttatagagataaattcaaatatcttattagcactcca    245490
ttatctcaagagcagttctgagttcagagaatcatgactttctttttacaggcattaaaataagttaaatc    245560
agcaatatttttctaacaactaacacttcaaagaaatgtcagacagttaatcatcacctgacaccatag     245630
ctcatgcaaatcgtgtttttatttaggatttatgttactgctagcattttggatgaaaagatactgttttt     245700
ttttgtttgtttttgtttttttgttttgagacagagtctagctctgtcgcccaggctggagtgcagtgg     245770
cgagatctcagctcactgccagctcctcctccdagtcacgccattctgcctgcctcagcctcccgagta     245840
gctgggactacaggcgcccgccaccacgccgggctaatttttttgtattttttagtagagatggggtttcac   245910
catgttagccaggttggtctcaatctcctgatctcctgacctcgcgatccgccgcctcggcctcccaaa     245980
gtgctgggattacaggcgtgagccgccgtgcacagccaaaaagatattaacattttctctgaagcactg     246050
agtcatactttgtttttttcacaagatttttttacacttttcaattagtatgtgagtgttcctcaggaaat    246120
gcatgtttggctattttgctgttttagagtgtttcatctttgaaatgcatgattaaaagccattttagaa     246190
attaacacgagtgtgtttaaatacaaattatgaagccagtgtttttgtttcaaacttagggatataatctt    246260
ttttttccaagaaaatgctctcatttatatatacatgaggttatgtaagacttttaaagattgatgatgg     246330
atttagtgccagctgttgattagtatgtctgcaatggatctacaatatggcaataacactaggtactatg     246400
cagagttactgtgaataataaataagacacgatgtatataattcacctagcagacttatttgtatactat     246470
aattattcaataaataatggcccttgtggttatttatctattgtagatatttatgttgattatctact      246540
gatcagtcctatagcagtaaattttatcttttaaaatctagacacattaggaaagaacaatgttagattta    246610
tgtcaaaaataaaaattcttagtgtactaaaataatatatttttctattaatgcaagttaggcttttat     246680
attgattattttgaatatttttactatgcttggtatgttttaaaaatttagtagttcttaatgcaattcta    246750
cttttaaaaacttttcattatctagtaagatttactagtgattaattttaatttggtagacatgaaaaa     246820
tacacaccagtttttcacacacaatcataaatcctgtacatcatattggtgaagcgggaactaaactgca    246890
tcaaatttccactaaataatagaagagcaatctatgatgtaattgaaatgttaataaatattgtagaaat    246960
gggaaattttcagaatgttcagatttgtcaagagaatctcaaagcgtgacacttttctgtaatctgtcat    247030
agataaatcaggtctttttgttatgttgtttttctcttttttatttccaattcatcacaaaaatatactttg   247100
gtttatgaatatgtaaactatagagtagtaaatttgacaaagtctacgtgttgaaaactacattcgacca    247170
ctgagggacactgatgaaggcttaaacaaatggagaaaagactgtattcacaaacacgacaccctcctaa    247240
gaagatacaatattgttaatatattttattttgtacaaattaatctacagactcattgcaatcccaaatga   247310
aataatggtagacttttagaaaatacataaattaacaagatgaatttaaaatttaaatcaaaatacaaag    247380
gatgtgcagtagccaaacatctttgtaggagtagaacatattgggaggactcctgctacttgacctcaag    247450
acttagtgtggagctatactgattgaaacagggtattattcatataaagatagacaaacagatcactatc    247520
acagactggagactccacatggaactacacatatatggacaatgaattttccaaagaaatacaaaggctt   247590
atcttttcaaatccaactggaagcaagcagctttagttatatattaaaaatttccactaactagaatattc   247660
ttgggtaaaaatgaagtgtcacctaaatggaattttcaaacttgcaccctatgtctgaacacgattctttt   247730
ttcagtcaggcatgtagttattgaggacacatttctcagctgtgcatacatcccatccagtcccatccat    247800
agatgtattgaaagcatgtgcttactgcaagagcaatgcactagcctttttcctagagttgggtctccaa    247870
agaaagggcctttactcagagtatctgcccagggtacaagattgacttaaaaccagtgttaacaacacac    247940
atggtactctgaaccatctgctggaggacctccctgtgtctgcacagtctatctattgaatgtcatgga     248010
aaagattgatggttgaagcaaatcacttttatgcagttagaaaaagaccatgctgatcttcagttttga     248080
gcccacatctacctaatccacagtcagatttgtcagcctcagcactactgatatttgggacttcataattc    248150
tttgctttgttaggcttgtcctgcgcattgtaaatgttcacagtccagataccagtacataaaatagtac    248220
agttttaccaattaaaataaataattaaaaaatcatctttacaggtaaaaataataagcagccagacac      248290
agtggctatgcctgtaatcccaacatttgggaagccaaggctggaggatcttattagcctgggattt       248360
gataccagcctgtgtcatatagttagatttgcctctaaaaaaacataaaaaattagctgctgggcatggt    248430
ggtacatgcctatagtcccagctacacaggagacagaggtgataggatcacttgagctcaggagttcaag    248500
```

FIG. 11A-49

```
gctacagtgagctattgatgattccaccacagtccgctgtaggtgacagagcaagaccctgtctccaaaa        248570
ataaaaaataagtaagctaaatacttttgaattgaaaaaatgtattctgtaagagatatctgataatca        248640
cctactatgaccatgttttcatccttcaaggatttcaaactattataaaaatcttctaaacctctatctc       248710
tttagtttaaattacttacatgaatttaatgctccagtatgtgacaacaattattgattttaaaaaataa       248780
tagatctgttttgatattcctttaccaatattcctcatgtttgtgagaaaatatgaggcagtgcagttga       248850
ctgcatttgtatgtatttaatatcatgagcaagtgggaaaaattcagaagtggcaccgagttgatcatct       248920
ctgttatcatcatgagaaggatgcacaatgtgaacattctgccatagggcttgtctctgtaaagtgcagg       248990
tcgagggcatgaagagcttctactatttttaaaaacatctttctgaacagataatggaggcttaactgt        249060
agtgtaaacacgctaatgcacaaatcttgaaaaatgtaaatcaaactgtgttgagattagaggtgatcta       249130
ttcacatttgaaggatagaaaatatgcctaccagccataaaaggggtgcatttactttattttttgagaa       249200
cagcatgagagcagaaagacacattaacaaaagggtaagagtcttcagagcagattactcccacttgaaa       249270
aaaatgagttaagtgattttacagcaggaaagatatttgcagcaagaagtttcattagtcaccaaatgag       249340
gtttctctgacatatatttttcacagaatgtgaagcatgaggaacaataaaaatttctatatttttcttgtg      249410
tttattcatttggctggaagattcccttccctagccttctggaagtttcagtcttctaatctgatttagt       249480
gacctttgttcactaggaagaacatagtccatttacgtttgccaaagagtatttacatgtatttgcagtt       249550
taaacaggaaacattctaaaaaatagagggtgtgtttgttgaaaacattatgactattaaagtcagagaa       249620
gttacctaaaacagaagatgctcagagtttgaaactggatggttattaatagatgcttctttgtgttgac       249690
tggagtttaactgccagtcctttcttaagccaagagattttcccaaaagaaacacttcagttgtaggccc       249760
agtaaagaaactggaatctgctttatgaattggcaataaaaagaaaaggtggggaggataggtgaagaaa       249830
agagagagggagtcttcagataggaaaccccccttgcttccctggagtctcatcttaagatttaaatta       249900
aattgaagaccatattaaggaatagaaaatatcaggattttctcttgtgacacataatcaactttatctc       249970
tcaaacaatttacatgatgacttacagaacgactgcatgatgttgattctacaaaagatgactgaattca       250040
ttaggactactcatttgtcttcagttatacttctgcagtttcaattatctatggtcatccatggtcagc        250110
agaaaattccagaaataaacagtgcatcagtttttacattgccctttggttctgaatagcatgatgaaatcc      250180
ccagcagtcctgctccctcccaatccatcctgtccagccagtgaatcctccctttgtttggcatctccat       250250
gctggtaaggctgcctgatctttagtcatttagtagtcttctcagtgaccagatctgtcatgttactgct       250320
gtgtttgtgctcaagtaaccccttatttcacttaacaatggtcccaaagtgcaagagtagtgatgctggca      250390
tatttttacaattatcctactgtattgttagctattattattaatctcctactgtgcctaattgataaat       250460
taagccttttcataggcatatatgtataagaaaatgcatagtacatacagggttcagtactatctgtgtt       250530
ttcaggtatccactgtgggtcttggtacatacataacagaagactactgctgtccacatttgtagcaatg       250600
atcacctttctttcattgtgcaatggcatatttctcatttgcctctgatggctcatataaatggagtttt       250670
ctgtccatatttctagtgtcattctgttcaaagttgcataggtcttccttacgatgattaaggttttctc       250740
tgcagcccttatcttttcctgagctctcattagaatcaccttcgacgttctactcatggcttcataggc        250810
tctgtcgaccatacacttcaaaactctttcagattctacttattaccaattccagagctgcttctgaat       250880
ttgtaggtgtctgttatctcaataccacactctcaggaccaattctgtcttaggtcattcaggctgcta       250950
tgatgaaataacataatctgggatggggtggaggtgggttgtaaaaaactgacatttatttctcacagt       251020
tctggaggctagtaatccaagatgaaggtactggaagtttcagtctcttgacagcccacttcctagtcca       251090
cagacagcaacttctccctgtgtccccacatgggaaaagggtgaggggctctttgagatctcttctttaa       251160
gggcactaagctcattcatgagcactccatactggatctaatgacctctcaaatacacatcctcctaa        251230
taccatctcctgggaaaggagtttaggattttaaggttgaatttgaggagaatgctaacattagtcta        251300
taaaagaagacagtacaggaaaactacagaaatcaataaactcagctattgttttgattaaaaatagagcc      251370
aagtgcattttgttttacatgttttactttatatttgttattattcttcaacaaacaaatacacatag        251440
tgatagttaattcttccatgatgttttgaaaatgtgttgttctgcattggctataagtctcctctctga       251510
cttttgaagaccttggaaagctgccaaatatctcagaacttgttatcttgagtcttaaagtgaataaaatg      251580
acctcagtactacctgccttataaaatgtctgccaattaatgcatacagtatgcatatactttgaacca       251650
agtatgttttgagactgcaggtttggatgttattggaatacacttgactctctatatttcttttttatggaaa    251720
cagatatacacacttaatgtgtcaaatagtttggatcttttatgagctaatatgattagctaatgtgatta     251790
gtagaataagcagtctcttttccatcttagtttgtgtatctgccttctcctagaactcaacacaaaatgag     251860
cttcatgattcacatttatgctaacatggagacagaaccaccttgtgcaaaacaggtaaaagcaggtata      251930
agatgccataaagggaaatgagactgaatgtgttcaattctgctttgtttggcttatcatgtatcataga      252000
aatgtgctcctacatgcagtagaaacaaaaacatcccttaacactctgtttgagcagttcaaatcatat        252070
ttttttatgttgtgcgagtttcaggtgataaatcctcttcaagatacatcagggggttcacaaaaatgtaaa    252140
aaatatgttcaaagtttgaactgactcatattttttagcattcatggcaaagaactgcttttctagcctta     252210
ataggttttcaaatggactttgatgtgttagtaaatcagaattagcttttctttttaagctcctgtgtc       252280
ttatgtaaatggctgtgttgacttttaaggaattgaatattccagaaaatgtcatggaacctaaaacaac      252350
gtaacattctgattttagatcttaaagggatatggtgttaaatatagcttttgatacccatccaaccctg      252420
tgcaaagttttctctgtacatgtgactttcaaatttgagaatttagtatgtcagtgaagggaaatctgta     252490
tacctgctgaaaacaaaatagaaatagaaattctgaaggaattattgtaatttacttaaataagaactgt      252560
aagtagtcaaagactattagtggaatgacaatagatttcttttgagaccttcaaacctttttactacca       252630
aaacagctgttatattctgaaaggcagtctctcttcacaaaaagcattatccagaactttaacttatttt     252700
cacaaagaacattctacaaaattagtgtacctttgtttaaaataagattctctacctgaggtctgaaa        252770
tttattattaatgtgaatatttaagcattttagaagaaaataattttgtaaaagatgtaagttatgaa        252840
aaataccacagtgaagtacaacattcacaaacttactggaaccttgtcctaaaaatgaactaattattgg      252910
atcatatggcaaactggttaagaaggataagaaattactttatatcattaaaaaccatatgactatccac      252980
ctgcgcttctaaaacttttttcctgttacgttctgctatttttacttagaattttttgtccattacactatta   253050
ttttaggttaaggaacaatgtgttttagacagttgctcattaaagtactaaacagaaaaggtagtagatta    253120
agcttttcaccccacaatttatatattatcttataatgtgtgagagacaacagcataaatagataaattc     253190
ttcatcagtcttagtaacaatagggcacttttttgcttttatgcctctcattttatttaaattcctttgtg    253260
aaattatgtaagttctttgaaatattgcttaaaatatatttagttttttaacatatttttaaaaatatgga   253330
aatgtataacatgtgaaatttccctatcagcgtttcctgtatattttctccagctttgtcttgaattaca    253400
gacagatattgtacaactataccacccacccacacaaatttattcatttacacatatttctttttagtgc    253470
tgtttgtcaaaattgggatattaattatacttctctgcaacttgctttacttactatttttatttttttc    253540
tatctttttgcagctttgtgataatcccaagcattaagacacattataatgtcagtggaataaattagac   ,253610
```

FIG. 11A-50

```
aatacagtgccaattaactaaggtttccagaggcaactcttttgttattgatacaatgcaaatacaagt      253680
ttttcatgcagggctgccagggccctggagtagaaatctaaatcataaccaaaacaaacattatcaccac    253750
atagaaagtaacaaaaaacatttcatgtgggtttggagtatttgaataatattttaataattaggtttta    253820
aagcagaaactgacagctttgtctacttcacccatcctgtggtgtcagatgcaggttatggatctggctg    253890
acagggaaattgaggtaggaaaataaaataaacaaaatgatattatgtacctgtgctttggtttaaggat    253960
gataaaattatttaacctatgtccacattcctggagtggttccttaccctacctaagaaaatccacct      254030
cttacttcttcaactgttcagatctcaatcaacacagcttttgtcattgctggaaatgcattgt          254100
tttcatgaaatgaattactagttacatcaaaatgaatattagcatgaactctcattggcccataatgtta    254170
aaatattcaaaatatatgaattggctaaaataatttacagaaaatccctacagtggcattatcaaggtac    254240
aaaaatccagaggtgtctttgcctttgacctggtccaatgcccatggcttgaagtctcttagccctaca     254310
ttcagatgttgacacaggagaatttctcattacctgatgctgactgaaaaagataaagaacatcactta    254380
ttttgtccttagaggactgaaaggcagagaagctacaaatagaagttgtacctcaaaatttttgaaacaa    254450
tacatatgaactgtttgcatctgctgtggggtctgatgaatgacaatgtatgtaacacatttggctct     254520
gagacacacaggatgaaatataggtggagagaaggaattaataaccatcactcatctccttttctgagg    254590
ttacttttacctaccaaaatgaacctaaaaattttacctgaacaaattggctcagatagattgcaacatt    254660
gactttattgtttgtcctagggctgcccctgggctgaacctaatgaaactcaggcgggttatatgaaaac    254730
tgcaatagcctgtatctctacactttctgcaacctggtttctgcacagagaaatgctgcatgtgtttgct    254800
gtaggcaaatcttaaataaaccatgaccccacaagaagaagagaatgatgtgcagaaatactttaggga     254870
gggataagatggcaattttgaatgggagcccacagggtacaagtactcatattccattaccaacttcaga    254940
agcttaattactttggaaaaccatttttcaccttatttagtaatatgtcaagcatttcaggtggtctgc    255010
aaaagccgtatagcccatggtcttagcctacctcgtcaaacatcaggcagaaacactttctaaacccatt    255080
aaaaagagtcaagcaggaaattgtgagtatatagtattaaggagatggacttgctattcttaaatttata    255150
gaaaaaaaaattctgtatttctctcgtcaatctccacttaatgacagatttgttttttataaaaagatgc   255220
atgacagataatacttatttaaacttacagcgggtaaacacgatgaaatattcttgttttatccagacat   255290
ctgtaagaatttcagaattattacccttgacaaattcatgtatgactttttttgtggaaatcttcaactt   255360
ttgttctcactgctccctgtcttccccaccaacaaaccctgaatacgtgggaatttctcacaagctatt    255430
atttaactgcattccacatgtccatcagatgtcctacacaagatgggttaaatcaaagcttttcttttgt   255500
gggagaagataacaactgtttatattaaatgcataaaaattttctcaatactacaggtgtgataaagac    255570
aagaaaaggccactttaaaagggagccatttgaaaaaataaaataaggcagaaatgcttcactttcctac   255640
ccaatatggaaataattttgcaaaaactaaactctaatgatggaattaaatttattttatattgagtaaa   255710
agttacgttatgcatgaagcaacataaaaattttggacaacaaagagtgattcaggacaacatagtcac     255780
tactgctcttggtgtggttttagggggttgcataattggtgagttccttaccatcacctcacctgggaa    255850
gagaaagggtcagggaactccatccccctacccaagggaagcctggagtgtgctgtgaggaacactg      255920
cactccagcccagatactaagctttcctatggtctttgcaagccccataccttaggagattccctaagt    255990
tcccaccagggccctaggttcaagcaaaaactgggcagccatttgggcagacaccaagctagcagcag     256060
gatttttttttcatacccaggtggcacctaggacccattgagacagaaccatttactctcctggaaag     256130
agggctgaagccagggagccaagtagtgtagctcagcagatcacacccacagagcccagcaagctaag     256200
atccactgacttgaaattctcactaccagcacagaagcctgaagccaacctgggatgctggcttggtg    256270
tggggaggggcgcctgccattactgaggcttgagtaggcggttttcccctcacagtgtaaacaaagcctc   256340
tggacagttagaactcatcggagtccacccacagctgggcaaaaccactgtagccagactgcctctctat   256410
attcctcctctctgggcagggcaactgtgaaagaaggcagcaacccagtcaggggactatagataaaa    256480
ctgccatctccctgggatagagcacctagggaaagggacagcagtgggcacagctttagcagacttgaac   256550
attcctgcctgctggctctgaagagacagtggatctgccagcacagcgttcaagctctgctaagcaaca   256620
gactacctcctcaagtgggtccctgaccccaggcctcttgactgggagacacctccaagtacagtttga    256690
caaacacctcacacaggagagatctaactggcatctggtggttgcccctctgtgacaaagctcccagagg   256760
aagaagaggcaacaatctttgctgtgctgcagcctccaccagtgatacccacgcaaacagggactggag   256830
tggacctccagcacgccccagcagacctgcaacagagggacatgactggtagaagaaaacctaacaaaca   256900
gaaaggaataccatcaccaccaacaaaaaggacacccacaaaacctcatccaaaagtcaccaacatc     256970
aaaaaccaaaggtagataaattcctgaatttgaggaaaaaccagcgcaaaaagcctgaaaattccaaac    257040
cagaatgcctcttcttctccaaaggatcacaacttctccaccagcaagagaacaaaaccggatggagaatg   257110
agtttgatgaactgaccaaagtaggcttcaggagctaggtaataataaactcttctgagctaaaggagca   257180
tgttctaatccaatgcaaagaagctgaggacattgaaaaaggttagaggaattgctaactagaataacc    257250
agtatagagaagaccataaaagacctgatggagctgaaaaacacagcatgagaacttcgtgaagcataca   257320
caagtgtcaatagccaaattgatcatacaaaggaaaggatatcagattgaagatcaacttaatgaaat     257390
aaagcataaagacaagattagaggaaaaaagaaggaaaatgaatgagcaaatcccccaagaaacataaga   257460
ccatgtgagaaggccaaacctacatttgcttggtgtacctgaaagtgacagcgagaatggaaccaagtgg   257530
gaaacactcttcagggtattatctaggagaacttcagcaacctagcaagacaggccaacattcaaattca   257600
ggaaatatagagatcaaagatactccttgaaaaaaggaactccaagacatataatcatcagattccacaa   257670
ggttgaaatgaaggaagtaatgttaagggcagccagagagaaagtctgggttactcaaaaggggaagccc   257740
atcagacaaacagtggatctctatgcagaaaccctacaagccagaactggcttgtagggtttattcaaca   257810
ttcttaaagaaaagaattttcaacccagaatttcttatccaaccaaagtaatctacataagtgaatgaga   257880
aataaaattccttacagacaagcaaatgctgagcgattttgtcaccaccaggtctgccttacaagagcac   257950
ctgaaggaagcactaaataaggagaggaaaaaccagtactagccactgcagaaacataccaaaatataaa   258020
gtcctgagacactgtgaagaaacagcatgaactagcaaaataagcagctagcatcataaggacaggatca   258090
gattcacagataactatattaaccttaaatgtaaacaggctaaatgccccaactaagatacacagactgg   258160
caaattggataaaaaatcaagacctatccggtgtgctatattcaggagacccatctcatgagcaaagata   258230
acatataggctcacaataaaggggatggaggtgaaaccaatgagaatgctgacacaatgtaccagaatctctg   258300
atctctgggacacaactaaagcattgtatagagggaaatttataccactaaataccccgcagtagaaagtg   258370
ggaaggtctaaagtcaacaacctaacatcacaattgaaagaactaaagaaacaagagcaagcaaattca    258440
aaagctagcagaagacaagaaatagctaagatcacggcagaactaaaggagatagagacatgaaaaaccc    258510
ttcaaaatatcaatgaatccaggagctgatatttgacaagattatcaaaatagatagactgctagctaga    258580
ctaatgaagaagaaaatagagaagaattaaatagacacagtaaaagtaataaaagggacatcaccactga   258650
tcccaaagaaataccaactaccatctgagaatactataaacagctctacacaaatgaactaaaacatcta   258720
```

FIG. 11A-51

```
caagaaattgataaattcctggacacacacatcctcctgagactaaaccaggaagaagttgaatccctga    258790
atagaccaataaaaagttctgaagttgaggcagtaattactagcctaccaaccaaaaacggcacagaatc    258860
aggcagattcacagtcgaattctaccagaggtacaaagggtagctggtaccactacttctaaaactatta    258930
caaacaatagaaaagagggattcatccctaactcattatatgaggccagcatcatcctgatattaaatc    259000
ctgacagagacaacaaaaaaataaaaatagaatttcagccaatatccctgatgaacatcgatgcaaa      259070
aatcattaattaaaatactggcaaaccgaatccagcagccctttacaaagcttatccatgatgatcaagt   259140
ctggttcatccctgagatgcaaggctgatttaacaagggcaaatcaataacataatccattgcataaaca   259210
gaaccaaagacaaaaaccacatgatatctctatagatgcagaaaaggccttcggtaaaaattcaacatcc   259280
ttttatgctaaaaattctcaaaaaattaggtattgatggaatatatctcaaaatattaagagatatttat   259350
gacaaacccacacccaatatcatactgaatgggcaaaagatggaagcatttcatttgataactggcacaa   259420
gacaaagatgccctctctcaaaactcctattcaacataatattggaagttctggccatggcaatcaagca   259490
agagaagaaataaaggatattcaaataggaagagaggaagtcaaattgtctctgtttgcagatgacatg    259560
attgtatatttagaaaaacccatcatctgagccccaaatctccttaagcaataagtaacttcagcaaag    259630
tctgaggatacaaaatcaatgtgcaaaaaatcacaaacattcctgcacaccaattgtagacaaacagaga   259700
gccaaatcatgagtgaactccattcacaattgctgcaaaggaataaaatacctgggaataaaacttaa     259770
aagggatgtgaaggacctcttcaaggagaactgcaaaccactgctcaagggaacaagagaggacacaaac   259840
aaatggaaaaacatcccatgctcatggataggaagaatcaatattgtggaattggccatactgcacaaag   259910
taattcctgagattcagtcctctccccgtcaagctaccactgactttcttcacagaattagaaaaaaaaa   259980
ctaccttaaatttcataaggaaacaaaaatgagcccatatatacaatcctaagcagaaaaaaaatagctg   260050
caggcatcacccttacctgacttcaaactatagtacaaggccatagtaaccaaaacagcatggttctcata   260120
ccaaaacagatgtatcgattagtggaacagaacagaggcctcagaaataatgccacacatctacaaccat   260190
ctgatctttgacaaacctgacaaaaacaagcaatggggaaaggatttcctaattaataaatggtgttggg   260260
aaaactggcaagccatatgcgaaaacagaaactgaccccttcttacacctttacaaaaattaactc       260330
aagatggagtaaagacttaaacatgagacttaaaacctcttttaaggacccacagcatttctgagcatca   260400
acacattcatcatcaacccaaaaccatggaggcagaaggagggaaagcatttgaaaaactagaagaaaat   260470
ctaggcagtaccatttaggacatagacatggacaaagaaaatacttcatgactaaaacaccaaaagcaat   260540
ggcaacagaagccaaaattgacaactgggatctgattaaactaaaaagcttctgcacacaaaaggaact    260610
attaccagagtgaacaggcaacctacagaacgggagaacaaatttgcaatctatccatttcaccaagggc   260680
taatatccagaatctaaaaggaacttaaacaaatgtacacacacaaaaaatcaaacaacccatcaaaaat   260750
tgggagaaggacatgaacagacacttctcaaaagaagacgtaagtgcagccaacaagcatatgaaaaaaa   260820
gctaatcatcacttgtcattagagaaatgcaaaccaaaaccacattgagataccatctcatgccagttag   260890
aatggcaatcattaaaaagtcaggaaacaacaagttctggagaggatgtggagaagtaggaatgcttta    260960
cactgtttgtgggagtgtaaattagttcatccattgtggaagacaatgtggtgattcctcaaggatctgg   261030
aacaaaaaataccatttgacccagcaattccattactgggtatatacctaaaggattataaatcattcta   261100
ccttaaagaacatgcacatgtatgttttattgtggccctgttcacaatagcaaacacttgaaccaacccac   261170
atgtccatcaatgatagactacttaaagaaatgtggcacatatacaccagggactacttctgcagccataa   261240
aaaagatgagttcatgtcttttgcagggacatggatgaagctgcaaactatgttctcagcaaactaacac   261310
aggagcagaaaccaaacactcttatgttctcagtcataagtgggagttgaacaaggagaacacatggaca   261380
caggaaggggaacatcacgcacccgggcttgtcagggcttaggggttaggggaggaatagcgtcaggaga   261450
aatacctatgtagatgatagcttgatgggtgcaagaaaccaccatggcacggtatatatacctctgtaac   261520
aagcctgcatattctgcacatgtatcccagaacttaaagtataagaaaaaaaatatgtaaacaattataa   261590
taggaaaatgtcatattcatattatgaatatgtacttcaaattagctgttgaataaaattaatgaagtca   261660
cttaaaaaataaaatgcaggttattctggagggtattaaatatttcagtaactatcatttgttaaaaa     261730
ccaggtatccccaatatgttactggatgtgtgagaaagagtttctggagacgtattttggggagtccact   261800
acaactgatgaatttcatctcttcttttgtctctctgtctctgactctgacactctctgcctctcactgat   261870
tgcttctctctgtctttacatacacacacacacacaccatacacagaatatttcagaaattctcaaca    261940
cacaccaccagtaagtactgccaacaattagattataaaactggcagtcatttctttcaatgcggcttt    262010
ctatttcattatgtcacaaataccaaagtaacaggtggacaatcaggatacattctgtcatgtttacatt   262080
atgtaataactaatctaaaacaaatgcccagtggagggtttcttagctttctgtcagttttcaaatgtt    262150
ttccctcttcctgcctccctggtctcaggttggcgatgcatgtgctggtgctcagagatgctatgggtcc   262220
ttagaagggggttttgagctggggcatagatgattatttccaaagcagtctgccaaaccctcagttcctgt   262290
aattctacacattttcaggcaatcgaaacacaatgagaaagatagtttgggtggttctcggattgcaaac   262360
ttaggcagccacagtcctcaactagcaatactaatttttctcatccttttccatttctacccagtgtataat   262430
ttatataaatttcctctgcaaaccaaaaaatgaactattccttatttatgatgttatgaatgtgtctg     262500
tgtcttagactataactgttggcatagaaaccagcttatgcttctataactttttgttgtatgatctttaa   262570
aattttgacttgctggtaaatataaatataaatatagaaataaatataaatatatttgcctgag         262640
tgtcaaaattatatatataaaatgtatgactgtgtatatatacacaaatattttgtgtagattatata     262710
tataatgtaatgtaaaacatatattacatcatatattacagattagctatatataacatatttgttttat   262780
atttatatttatatattatgtaatgtataatatatattttataattatatatatataatttcattagt     262850
tgtatcattttctccagtttgatttccagtggtgcagaacattttattcatattcctgataccaggaaag   262920
ggtgcatattgacagtgcaactcaagtaaaatatttagaagacacatggctataattagttacttgcatt   262990
tttcctgaaagcttttcatggtattgcctatttaagaatatcttgctttgctttctgagcaaataaacta   263060
cactagcagcatttcttgaatctctttgatctgtgtggtgtggtggtgtggttttacacaggattttgcc   263130
tatttttttttaagtgtggatattcctccttttatcttttaacaaatattgaaatattttaaaattttta   263200
atactagtctcattaggaatgagagtttcctataattttcctggggtaatgttatacaattcatttctta   263270
aaaaaatacttcttaaatttgttaatgttctgattattttctgtcattattttggcactttgtattgt    263340
tacattatgattccatatcctcctttgattccagcactgagaattggttttcatttctatgaactcatta   263410
ctgaggtccttgtttctttttgagatattaaacttgaccctgattttttcttccctgtgagtggaa      263480
ttatcattcttttctactggttcagcaaaaagaaatgctacttcctaaagaatatattttttctatgat    263550
taaatatgttttagataaaacaaaagcttttttacatctgtccataaagtgtaggttttgaaattctcatt   263620
ggtgatagctatgtttattttcttacctgacacatcagctaccacagttaaattcggtgaactattctg    263690
tatcacttactgatgaagaaataaatggctgtctcatgttggtaagtgtattgctgttccacaatctgaa   263760
tatattttgcttaaaccttgaggtgttaccacatggtaaggattttaaaatcacactcagatcataatag  263830
```

FIG. 11A-52

```
tagttatctactttcaatgttgtaaagtcagatataccattgcaagtttaaaaacagagagtactttgta      263900
gtttaagtatctgatttaccttgataaacactttcatcaattttgagagcatatacaagctatattctgc      263970
tcttaaattttcaaggtttgggggtgtggggagagtgggaaggggaaggaggagagggtgagtgtgagg      264040
ggggaagagggagggaggaagagaggaagagagagagagatagacagagagagacagagagagaaattgc      264110
cgtggttcatggagccatctagctacaaatgtcagtttatgagaccagacacaatggctcatgcctgtaa      264180
tcccagcactttgggatgttgaggcaggaggaatacttgagcccaggagtttgagatcagattgggcaac      264250
atagtgagaccccatcttttcaaaaaataaaaaatataaaaaattattcaggtgtggtggtgcctgcctg      264320
tagtcccaactcttgagaggctaagcctggaggatcattgagccctggagttggaggttgcagtgagct      264390
atgattgcaccactgcattccagcctgggtgacagcacaaaaccctgtctctgtataaataaataaataa      264460
ataaataaataaataaataaataactatgtatgttctttccagcttttcatagtcccccaaagcct      264530
tgcagccttccaaaacttgattttcttctaaatttctcagaaaattgaggggaaaatagcacttagaatt      264600
tgacgacagctgtctacatcacctggaatctctggcagaacaccaattcagtctcttctttgagcttcac      264670
aacgcaggcatatattacaatttttattaggttgagcacatatggcctttaccctcaggagttcctccata      264740
gttcctccatgctaatctccgtagagagaggcatttctccacttttattcaaattaacagcccataaaag      264810
aaaagacatcttaaaggctgcagcctctctgggacttgcatgggcgtctcctattattgtgcataatgc      264880
tgtgctgaaatacaggtcaaatactctaacatccttttgctcattatatgaacattatgcatattgcagt      264950
ttgaaactaggaagagagaagagcaatattacaggcgaacagtgcatcagaatatgataacttaa      265020
ttagaagagaaggctctcaattttgaattctcagtgtttctcttctaatacacacaatgatgtctttcac      265090
atgattttaattttgattattatgataaataatagatgtatatgtgatgcagtgttttcccacaggtg      265160
tgaaatgtgtaataatcaagtcacagtagttgcagcatttattacggcaggtatttattccttctctgtg      265230
ttaagagcattccagctctactctttagttatttttaaaatacacaacaaattattttttattgaatcactc      265300
tgctatgctaccaaatagtagattttttttttttttgagacaggagtctggctttgtcgcccaggctggag      265370
tgcagttttgtgatcttagctcactgccacctcgatctcctgggctcaagcaatccttccaccttagcct      265440
cctgagtagctgaggtgacaggccatgacaccatgcccagctaattagtatcattttaatttgtaca      265510
gatgaggtctcactgtgttgcccaggctggtctcaaattcctgagctcaaatgatcctcctgccttgatc      265580
tcccaatatgctcatatttcagatgtgaaactctgcccagctgataggaatctttcatagagtttcccaa      265650
taactgagctttcaaagattttggatagcgactgagtagtgcaaagtctctctaaataacaagtctga      265720
ccagggaccttgtgttacttatatgaatacactgaggttgctgtctgtctctttgttaatgtataagcag      265790
agaatggtatattgatgcttatcagattttcagtttaatattgaagcattacaaattaaaatataaggtg      265860
tgggatacatgcaatttttactttaggggtatgcaaaacctgagggcccccaaagcagaagaaggcattca      265930
gcccctactctgcatttcctccctcctgagttgccagccagccagccagcctgtcttacagattccagac      266000
ttgccagttcccagattgcgtgagtcaattccttaaaatagatcgatctaataaatttatcctatattgg      266070
tgaacaaatttagcacagaacttttgatatatattagtaccacttattattttttagaaaagttggaatttg      266140
aataacttataccaaagtttaattcgtcatctggtgtgtatgttataaatgcacacccactcacagagac      266210
ctattcatggcctcacataaaaataggcaatagatacaggaaaagacaggcagccatagaaggtcttaga      266280
taagaaacccccatccttcgcacactcactcaagaacgttgttcccaacttctacatctttgtagtttat      266350
atccactgggcacccctaacatccatccacattcttcattatcccatttggaaataagcatctgacct      266420
gcactttctctgcctgatgtggctgtatgtctttgtttctctagcaaccatctgctcgtcttccaagagt      266490
cctcactgatcacatctcaactcctcttcacctatcctttcttaaatccactccacttcaccaaactcct      266560
cttgccaattatacaattggatcttaggccccacaaaagtggagctactattcctaatgttcctaaaaaa      266630
tgaccattctgcatttccctccaatctccactgcctctatttttggaaaaaaatttcatctttgaaaaa      266700
gcatttaagaccaactttttttttcccactctggtgggaaaagaaatattgctgaatgcagaggacaactac      266770
atgaattcatactacttgctctggcaatattcccagatccttatcctggagcatttgttggtagttgggag      266840
gatggattttctagcagtatatagactgaatgtgtatgtcccccaaaaattcatatgttgaaacctagtc      266910
ctcaactgtgtaggtatttggaagtggggctttggagggtaataaggccatgagagtggagccccatgag      266980
tggaattcctaccattacaaaagggtccccagaattcctaccattacaaaaggcgccattgcaaaagaca      267050
ccctcatccctttaccatgtgaggacacagcgagaaggtgctgtctatgacccagaaagtgagtcctca      267120
ccagccactgaatctgccttgatcttggacttctggtgtccagaactgtgatcagttttttgttttttaca      267190
aaccatgggtacagtcttttgttttagcagccaaagcaggtaagataggtgatgctggaaagtaatggag      267260
atgtccacaaacaccctgaatcatgtactgcttcccaaccccctgtcctcctagcagagacagcaggaaa      267330
aagaaggcttacttcctccagatttgatgctcttctacccacagtaatgacagacaggttgccttatatt      267400
tttattgtgtttggttcatctgatcaattcacaaattgctcaaatgtcagaaaaatgggtcaaagggcca      267470
gtttggatttctgtggtagaaaaagaaaatgcaaaagactagatcctggtgtattcctagactgtaagaa      267540
agttcttatttttacaaagccataaataaatatgacatttctggtgcctgagaatttgaggcaggtagtac      267610
tcccgtgaagtaagataatgtcttatgtaaaataaaattcattcaaaaccatgggaatcattgtaact      267680
ttcattgtcaagaaagaaacacataattttggatgtaggtgaacactaattattaaagatgattgttctc      267750
agaacaagtttattccgatttgtagctacagcaatctaagagaaaagcaatacagcaaccacaaccaata      267820
tgaggcttcttataatcatgttggggtggggatgcttcttctctggtcctacatcctggagaatgactgaag      267890
gtttcctcctgtcatgcgatcttcccttcatttgctatattctagatttgctagtctagtgcactcactc      267960
caggaactctgtacttgtactcagcatttactgggtggtgtatatctgtcacaggttataagtttcatga      268030
aaagcatgtatcatgcctcccttttttcctcatgcacgcatgcagcaagccaattaagggcataaaacaca      268100
gcacataaagccctccattgattgacttaaattaatttatgaacagttgcaagggtaactgagggcccac      268170
atggttttcatgtatcatttaaaaaaattttaaatatgatgtttgatttttatctatattattct      268240
atagaaattaatctatcatatttcaatagtaacatggttgacattgaggtttaatataatgttggaac      268310
acacatgataccttgattctgaatcaacactgtatgtgcaatttgatgtctgatgtatgatttggggcag      268380
tttgaagaccagacatttctttgtactgagcctctcccattccctgtgtgtgaagggaaccgtggggaata      268450
aatcagtcttcaatggataggacagttgcctttgtccctggaaggtttcatcaactgatcacagcagtct      268520
gttttctgagtcaagatgcaacttccccttgatgtaggaacactacatatagtgtagtgtgctattccat      268590
atctattggaatcatcacacatgatcagtcaggtttaatgtcaagtcaggttttaatgtcaagggtgtgat      268660
agatagaaatggatgcagatagtcttgcaaatttagttgaaccctctcccagcatcttctgctggcctca      268730
gtgactatcttcttgaatagaatgttctgggagtaatgatttgggacttccaaggatggattataaggaa      268800
ctattaagcttccatttaggacatttggagtgctgattcttgtgacatttccttttggaacccatacctc      268870
atgctgcaagtgttcaagcccatggagaagctatgcatggtgctccaatcagtagcttttgcttcattt      268940
```

```
ccagttgacaaccagcagtgccaccatgtgagtgacccattaaggacatcccatctgattgagaactcct      269010
atcccttagctaactcaggaactctcaagagagaacttctcagctaatcccagtcaactcacagaattat      269080
gggagatcctcataaaagagtgtttgaagccatacattatgggcatgtttgttacacagcaatagctaac      269150
cattgttacacagcaatagctaaccagagcaggcattgaaaccagaagtgaggatctcttccaacagaaa      269220
cctaaagtaagtggtgttggatttgaggccaaatggtatatggaagctagaacctccatggggcgagaca      269290
aagggcttaaagaacaaggaaagaaaattggaggctggggcattggaactgatgaagagaactctttgaa      269360
tgactgactcacaacagtgagcacttttctcactattggtgagagaagtaacctttttgcattgtgcaact      269430
gcatgcaaactggatttttgtcttttgaaatagaaagatggcatctcaacacatttgtcatgtgtagttcc      269500
taataagcttaatacttaacataaagttcacaggcctgtgttatttataatcttagtatagtatagttta      269570
cactggatggcaaaaggtcacatatacaatgacaataatagattcttttaaaatttattttggttacact      269640
taaatgtaaattgtgaacatcatttctatttctattataccccatggcttttctattgtttgagtcata      269710
ctaagtctattttttattgcataaattttgcaacatatattctaacaggaaaaataaaattataaaacata      269780
tgttttatatatgtctttcctttaaacgtgagattttaactaggttttcttcttctctgttactatgcat      269850
atgtcttttattctttggatcaatatattcccacatccctggaacatttttggaaagttggcagtgc      269920
tcctataaattcttttagtctctatctgcctgacatatatttaggttccatatatatttatcattttct      269990
acttaaatatacatatttccatttttatgctcatgctattctgcaaatgtctgattttaaggatgagac      270060
atgcatttaaaaggacatctgtatcttctttcagaatattttttccttaatatgtgttactttcatatt      270130
tgaaatttcatacccacaaacatacacatacaaacatgtgtgcataatatacatctcacagaaatatcca      270200
ccactttgggaaaatgtcatttctgttgaaaatgtctttacagccacaaaatatatattatttcttggcc      270270
taagccacagatcctctgtcaccactatcaattcatcccagggtctaatcacttgaaattaatattgtt      270340
tctttgaagaatttcagaattaatttttttcctcaaaatttcatgaacttgcatgcattttttacctcag      270410
accttgaacactctggacaaattccttttatccctgtaaattttttaactaattctaaacaaaataccttt      270480
gttcacttttccctaaatttgctaactttcatgcattttgttttgtgacttgaaaatgctctggaaaca      270550
cttctttatgcccatgattctttaattctaaacaagctactttttatcaatgctgacaaggttgtagagaa      270620
taggaaatcctttataccatattggtgggagtgtaaattctttcaactattgtggaatgccgtgtgataat      270690
tccttaaagagctaaaagcagaaataccatttaacccagcaatcccataactgtgtatatacccaaacaa      270760
ttagaaattgtatcaaaaagacacatgcggccgggcgcggtggctcacgcctgtaatcccagcactttgg      270830
gaggccgaggcgggcggatcacgaggtcaggagatcgaccatcttggctaacacggtgaaacccgtc      270900
tctactaaaaatacaaaaaattagccgggcgtgttggcgggcgcctgtagtcccagctacttgggaggct      270970
gaggcaggagaatggcgtgaacccgggaggcggagcttgcagtgagccgagattgcgccaccgcactcca      271040
acctgggagacacagcgagaatccgtctcaaaaaaaaaaaaaaaaagacacatgcatgcatatgtttatt      271110
gtagcactattcacaatagctaagacatggaatcaacataaatgtccctcagtgtagactgaagaaaata      271180
tggtacatatacataatggaataatatgcagccataaaaagaacaagatcatgtcctttgcaggaacat      271250
ggatgaagctgcaggccattatccttagccaacaaatgcaggaacagagaaccaaatactgcttttctc      271320
acttgcaagtgggagctaaagatgaaaacacatgggcacagagcagagcataatagacattgtgacctat      271390
aacagggcagagggtggggagagggagaggataaggaaaaataagtatcagtgtactagtcttagtacct      271460
gtgccatgaaataatctgtttaacaaaccccctatgacagtagtttacctatataacaaacctgcacacat      271530
atccttgcaccctaaaataaaagtttaaaaaaataccagcctcactacagtcgtggacagttttcttggg      271600
tttcacctcagaaaacactgctaaaattcaagataaaattactttgattacatgggttaataatagctct      271670
ctgtgtgtgtcttagtcccctctctgtttcctatgtgtattacttgatttctaaataaactgtagaagct      271740
ccaagtacttatttgaatctctacatacaatggtgccatgttatctaattttttcctttaggatgtgtaca      271810
aagactgtacaaaatatttgaattgtgtaatggtatccagtatggataataaaggataagtaaattttg      271880
agaagtcagttaagtccgggcgcggtggctcacgcctgtaatcccagcagtttgggaggccagtgagcg      271950
aatcacgaggtcaggagatcgagaccattctggctaacacggtgaaaccccgtctctactaaaaatacaa      272020
aacattagccgggcgctgtggcggctgcctgtagtcccagctactcaggaggctgaagcaggagaatggc      272090
gtgaacctgggaggcggagcttgtagtgagctgagatcgcaccgctgctctccagcctgggcgacagagc      272160
gagactccgtctcaaaaaaaaaaaaaaaaaaaagtcaaaaataacagatgctggtgaggttgcaaa      272230
gaaaagagaacacttacacaatatcggagagagtgtaaattaaatcaatcattgtgggaaagcagtatagt      272300
gactcctcaaagagctaaaaacggaaccaaaaagaaaaaagaaaaaaaagaaaagtcagttgaaatgta      272370
atagatacatagatgtctaatttttcagttctgaactatggacatttttgcaaagatacatgcttttcac      272440
ttcaggaggtatttgtcaaggtctggaaaaaatttggctgccacagctagattatgggagtgagtacca      272510
ctcgcatttcaaggccagaggccagagatactgttaagccaccccacaaggcataggatagcccagcacat      272580
taaataatcttccatctacacatgtcaatattcctgaggttgagaaacccagatctagagtaatattgat      272650
gagcagtaagtataggccgaagcctcgttttccatatggctgtgatagatttttttaaaatagtcattgga      272720
agaaataaaccctcggttctatggaagtcataaggaatattctgcctgtgtgcttgtacaacccttggctt      272790
ggagcagcggtggatataatgcaagtggctttgcagaatcacggggttttctacaggtcatttcatcacc      272860
caggtattaagctgagtactcattagttattttcctgatactctccctgctcccaccttccaccctcaa      272930
ggaggtctcagtgtgtgttactctcctctatgtgtcgttgtgttctcgtcctttagctcccacttataag      273000
taaagacattcagtatttgctccagatagttgctggaggctattatccttacaatcttctatattaatta      273070
caatgggcatctcctgaatttcagaggaatacttgtttcctgattctgatgtatatactatcagcata      273140
tacataaatacataaatacatggctgtgaaatcacataaagcctttacttccatacttgacttcctgcag      273210
aacctccacatttctatgagcttccattttctcttcttcttggcatttatcattacttaatgagaggtt      273280
tccaaagtttagagtagtacattaattaccatttctcctcttcctcctcctgctcctcctcctcttcctc      273350
ctcctcttcccttcccttactctctttctcccccaccttctcctcttcttcctcttcttccttcatt      273420
atttatttatttatttatttctgagacagcattttgctcaccaggctagaatgcagtgaca      273490
ccatcatagcacagtgcagcctcaacctcctaggctcaagcaatcctcctgtcttggcccccaaagtgc      273560
tgggaatacaggcatgtgccacatgccagactacttttatttttattatcttttttttaagagacagtc      273630
gtgctctcttgaccacgctggttttgaactcctgggctcgaccagtcctccttccttgacctcccaaaat      273700
gctgagattacaagcatgagtcaccatgcctggccttaaattgtgtatcttctaattgatgtagacttt      273770
atgcccctatttatttgtgctttgaagtgaactgattctgaatgtcagtcactgagcactgcttagtgttt      273840
gggggtggttaggcagatatgcaagttcttagagcataaagctgctcactgctcccagtgagggggctgc      273910
aactgtttggagggttttagaatactaccatttgtgagttatgtatgaagttagggaagcctgctactcc      273980
tgattagactggcaacaacttttttgcattataagacaactgaaatttcatgtccaagccaggtgatctga      274050
```

FIG. 11A-54

```
gctaccectgttcattccagatccagggctggtgaggcaaaatggtatcccaaaacagatgggtctctt      274120
tactgaacttctgggttatctccaccatgtagagaagatatagaatcatgcatttataaactgtatggtt    274190
gaagatggcacccacagttacatttttctcccaaacttccccggcctatctcagttcttagatatattgt    274260
ctgaggattcctgattaggcatagagtaatgaggaaattttctccttagatgattatggcaagctgctat    274330
aggcctgttatttatcctcagttaatatggatattctagtaggagggcacagtaaggtaggaagaaatgg    274400
tcactctgaattcaaagtatctcttaatttagaaggcaagtttaccactctgaaagtactgagagtctca    274470
aatttcacgtaagcatattttttgagcattttctacaaatcctcatttcttcaaatccatcctttgcaac    274540
ctcaagtttatccggaggattcacactgcctgcaagtccttcttgtatgcatttcttgttgtttctgtaa    274610
caaattatctcacctgtagtggcttaaaacacacacatttattatatcgccattgtgaagttctgtagtc    274680
tgagtagcttggatggtttctcttcattgtcgaccaaggctgaattcagtgtgttggcagcagggtagtg    274750
tttcttcctccatattccagggatgcgttcacttccagaaacatctgggttgttggctacattcagttcc    274820
atcaggttgcgggtcctgcttccttgcaggctattgattggctgagggcaaattttggcttcttgaggat    274890
cgaagcattccatgactcctggcctccttcctcattcttcaaagcacagcttttaatgttctgaatctct    274960
ccaactacctttctacctcttctgtcctttccttgtcatatggcttgtctgacctgattgttctgtca     275030
ctgtttcttggttttcagtatcatacaattgtattggacacatttggttattctaggataatcagctta    275100
tcttaacatcagctgactagtaaccttaattgtatctgcaaagaccattcataacagtacctagatacat    275170
gtttaacttaatagcgaggggaataagaatcttgagtggtgtctttataattctgtttaccacacaccca    275240
tccgggtggacagactccttacaactgggtttgagtactcagaacaatggccttccatctttactcaccc    275310
agggagctcctccagggaaagctcatctaagtaagatctcaccatcattttcatgcccttttcttttttt    275380
tttttctttgttgttttgagacagagccttgttgtctctcccagactggagtgaagtgacatgatctcgg    275450
cccagtgctacctccacctcccaggttcaagcagttctgctgtttcagcctcctgagtagctgggactac    275520
aggagtgtgccaccacacctagctaattttgtactttaggagagatgaggtttcgccatgttggtcag     275590
gctgatctcaaactcctaacctcaggtgatccacctgcctcagactaccaaagttctgaaattatagtca    275660
tgagccactgtgcccagcctctcctgatcttttgaagtccaagtaataatcctcaggtggcagtgcacat    275730
aactgtggagaattaaccactcctctctgatgttgcttgtaccaccgcaaataatttgtctatttattt     275800
ttacttttatttttcattttttgagacagggtctcactctgtcacccaggcttgagtgctgtggtcaatt    275870
agagctcactgcagcctcgaccttcttggctcatgtgatcctccacctcggcttcccaagtagctggga    275940
ctaaaggtgcatgccaccacccatggttaattttaattttttttcattgatacagaatcttgttcaggct    276010
tgtcttagaactttttaggctcaagcagttcttccatctccagactcccaaagtgagccactttgctggcc    276080
tatttgtcctttttaatttaaaagactcaacatgtagaaataattttatcccttcaccttgtgcattaag    276150
agcttcctttttcttgcagatggctgaactgaagcaccataagtgatgagatgacattttgtattttac    276220
acacattcctgccctttctcagatgagtctaggcttcatcagtatttaaatgctaacttactctggcaa    276290
gacatttaggtccagaaaatagtttaaaaaaataacatcttcacagaaagaacctccagatagttaaaaa    276360
tagggggaacttgtggatacaccatattctgaacaattagtgtttgctaaataaaccacattattttaggtt    276430
tttcttcctgatttttttttttcttccttgtgttacttttaattctggaacataactgggcactgataatac    276500
tacagcagacccttatctcttttcttattatgactggaaatcgtaattagaaagatggataaaaatgga     276570
aaagcttaatgacgtatgcatattttttataagacagaaatatggaaagatacgagcaataaaataattca    276640
gtttagaataggaagggttataaaacactttttaagcagaaaaggaatcagagaatggcacttttataata    276710
tagtaattaagcctatttatttgataaaattcaaatgtcatgtcctcttttgtacctatgagtgcacatta    276780
acagtaaccataaaaaagaatacttggagctacagtgtgtgtgtgtgtgtgcatctgcacctgtc         276850
tttgggtgtgttccatctgatttgattttttcaccatatctctattttttgcactcccaaatgtaagtattt    276920
aagtgtttattatataaaatattttttgcattcttcctcccttcacatgcagtgatttacaaatttcctat    276990
ctgactatttccatcctgcaaaccccccagaatactgtggctgaggtactcctcttttctgttcccttctct    277060
atataggtggaacatcttctgggaaccatcttccatctataagtttcccattcacagaggtggctaaatc    277130
tgtagcatgcatccatccatatccaatagtgtcttttacatgggtgggttggataatgcaaaaccaagctt    277200
caacgtcaatggtgtgagaagtacacaaacacacacacacacaaataaaaaacatgcataatctctgtagatc    277270
agaagggggattgtccagagttaatattaatgtacactcttaactacaaagaggtcataacatccaaattc    277340
cgttaagtacattgactaaattactatattataaagctcccattctctaatatcttttgtgctaaaaata    277410
ttcccaagccatgttgaagatatctttcaacagttatgtttcctaaaaatatgcctagattgttaaatgt    277480
tcacttcttcatgtgtttttctggttacgattttcagtcattaaagatgaaagtgacaaggtctcagcag     277550
tgttttacctctaaacctaatactgacccctaacagaaattgaaaccttaaaactaacctgtggcctttga    277620
ccattgcttcttgatcattgagctgacccatgaccctgaacagagaatgagaacttgaacccaaattta    277690
atctgaccctaactaatgactggatatgaaacctaattctacccaaccttgaaaatgaatctaaattta    277760
gactcaaaaccaaacccaacccaacacctactttaacttcaatgtaaaattttgaactcaccttgactt    277830
ttgccagtaacccttgactcttgacccctgatttgaacactgaagcatctaccaaattctctaaaccac    277900
agactttgatcctaatcctgaccttgaccattgtccctaataacgaatataatcccttgatcataata    277970
ttgacttgtgctcctaccctgacattcaattagtgatctaaccatacccccaaattgaacttgaagccaaa    278040
tcctaacatgaacctttatcaatacctgaaaccgtcctaacccttgatctttgatctttaaccctctgt    278110
gttttgctccttgactcctgactgtgagatcccagcctggactaaaatccaaacacacactcaacatcat    278180
tcttgaccagaattgttacccaaacctgaacaggaacccaaaccctaccctaccccacttacaaatctga    278250
acacaaaacctctacctattctgaactttgggattgagtgtctcggtcctgtttggtagatgcggagtt     278320
tgcaggccttcagtcatggtggacaccacagacttgaagaactctccaatatattttttggaaaaaaa     278390
gatgcaaccatttgagagcaagatgttaaaacattcatcctcaatctctgtttgtacagacttcaaggtg    278460
aaatacatgtggttggacttgtgatatttccagccacaaaattgtatcatgtagagataatgtaggtttc    278530
cctgtctctgaaaatgcatttattcaaccagtacttacttgctccagaagtgcaccagggaccatttttag    278600
gccccctggaggcagccataagcaaaacttcccagatccctacctggaatctctgcctatggaatggaa     278670
attgtcataatggatgtagataagaaatatcctggactcaaatctgaacttcagtcacgctggaagtcca    278740
aactcctgcccagacatgttttcctattactcacagaggataggtgaggactcaggttaattaaggtggt    278810
tattttgttgccagttttatctaatgtcctttgtggatgatgtgtttttcacttggaataccaacatga    278880
gagactgggccacttctcaattcagaaatccactcaaggccaggcatggtggctcacacttgtaatccca    278950
gcactttgggagccaaggtgagaggatcgcttgagcccaaagagttcgagcccatcctgggcaacctgact    279020
aaagcctgtctctacaaaagaaaaaaaattagctcagtctggtagcacatgcctgtagtcccagctac      279090
tcaggaggcttgaggtgggaggatccctaatcccaggatgtcaaggctgctgtgagctatgattgcacca    279160
```

```
ttgcactccagcccaggaaattgatcctgtctccaaaaaaaaaaaaaaaaaaaaaaaaaaaaaaaa        279230
aaaattcaactacatgtagaagagagagagtgtgtgtgtgtgtgtgtgtgtgtgtgtgtgtgtgtg        279300
ttcattagatttaactgaggatttaaggagaaatttggaggcatattctcatatgggaaaaataggaaaa    279370
taaaccttctaaaatcaacatctagccctttttgctgatgaccttttggctatcctaacataaacttttct   279440
tctgaatgcttcaaatctcaactcagcaaatccacaatgagctataggaaattcacgatctcttctttc     279510
tttggatttcacccgccgccattcatgatttaacaaataattctttgaaggcagttctctttcaaagat     279580
gagttttgcttctctgtgttaaaataataaatatgtgtcgctgttaaaatagttttgcatacatgaggga    279650
actccttagaagcttattgggtttcttagctgtgcatgcaatttgaatttaataattactacatagcaattcc 279720
agtaacatagccaatacatcagaaccctcaggggaggcagccaggaactttcttgcaaaatatccccac     279790
atcttcatccctctctggagaccactggtaaaatttacaatcggtaataatttctacagacatggcaact    279860
gagaatggtagaacattagtttttaaaaatcattttaataaaatggctttataaatattgagacttaatta   279930
tttaatttgttccagttaatgaaagatttcatttggcacaagactaggacaaattagaatacgtataatt    280000
ttcttcattccagacaaacaattattttaatgtctactggtacttagaccacaaacttaattcattgatt    280070
tcatagtattagaaaatatagagtgagaaaattgttagcagggcacagtggctcacgccggtaatcccag    280140
cagtttgggaggccgagacgggcagatcacaaggtcaggaaatcgagaccaccctggctaacacggtgaa    280210
acctcgactctactaaaaaaacaaacagagaaaaaaaatatatagccggggtggtggtgcactcctgta     280280
atcccagttgctcaggaggctgagtcagaagaatggcctgaacccgggaggtggaccttgcagtgagcag    280350
agatcatgctgcttccccgcagtctgggtgacagagcgagaccccatctcaaaaaaaaaaaaaaaaaaa     280420
aaaaagttagaagttgttgaacagctggatttgacctaaaattactccaagaatgtatcattttttatgc    280490
ctcaagctgttttgtgcagttctattttcaacttccatagacaattgtaatctttttattttgttttctt   280560
attagagaatgtttcatgatatggatgtgaataattaaatgaacatctttctatgtacagcttgaattta   280630
aattagaacatgatggagattttggattcccttaattcctgttataaattgtatttctttaaacctgc     280700
ccaaagggtaaccatctttctgaaaccaattcattatttccttcttttactaaattttatttctacaaaa   280770
ttagcactaccagcttaacctaaagaataatattgtcatctgctttttgttctttttataaatgtcattctgt 280840
gtttttcttgacctagcacttccttttttcattgaatggtatgttttttgatattcaaccatgaaaattctt  280910
ggagctgtagttcatttatgttcactgatatgagaaaccacaccctatggttattccacaagatatttaa    280980
ctctttcagaagctgggtatttgaattggccttatgtaaacagttcaactgttagtattctgtgtatatc    281050
ttgttgaaaaaaatgaagtttctctacctagaaatagatttactggactatattttatatccatattta    281120
gatatgcatcctgatgtcaaagattgtttaagtggttgaacagttttatttacccaagaaccatatgaaa    281190
gtttcttgttctttacgttcactatactgagtccaaagttgaatagaaatgaaattagctatctttgattt   281260
gttctgtctttagacaaaaggagttttaaaaaaaattttattttgagacagtcttactctgttgccctgg    281330
ctagagtgcagcggcatgatcttgtctcactgcaacctctgcttccggggttcaagcgattctcatgcct    281400
cagcccctgagtagctgccactacaggcgttcactaccatgcctggcaaattttttgtattttcagtaga    281470
gatggctttcaccatgttggccaggctggtctcgatttcctgacctgaggtgatctgcctacttcagcc     281540
tccaaaagttctgggatcacaggtatgagccactgcatccagccagacagagaagtcttctaatgttttatc  281610
attatgtataatatttggagtaggatataaatgaactatctttttcacataaataaatgtttatctcctt    281680
aatttgataacatgaaaccataaattcattagaggtaatttttttttcatcttttaatattttccttgct    281750
ttgtgtttaatttgttcatgtagtaaattaaataagttaactttctaatatcaagcttagtttgatattc    281820
agtatactctttaatatcattttgtatttgttatatattaatcattttgtatctctgtactaaattgg     281890
ataggctgtaatttccttatgttaggcttctctggttttagcctcaacttaatagtagctgtgtagaaa    281960
tagtaagaaaacatttctgctctctgggagagttcatataaaaattccttaattaataggtggtagact    282030
tgctattcagtccaccctggacagatgatgtctttgatgtagttaaaaacatcttttatttcctgcttga    282100
tttgtgggctttattacgtattgatttcttatatatattaataacaacatgtttgcctgtatctgtctgt    282170
taacactttattatgttctcttttttcatttgtctgttgtctgtatacattttgttaaactattgtaaca    282240
aattatgagaaatgtagtaatgtaaaagagcaaccatgtagtatgtcatggttcaaaggtcagaattct     282310
tggtgcagtggagcctagcttggtcctcttcttaaggtcttccatgggtgaaatcaagagactggcaggg    282380
ctgtattcctctctgggggctggagggatgaatctgttacaacatgtagattttttaaaatctaagtattt   282450
gcactaacttctgattttaccatattagatccataggtgaattcctatttcttgatcatttgagtctta    282520
gagaagcttgatttccgtcctacaacatcgttagattattacagatttcttatctgctttaaacaagggg    282590
ttttttctctgttttttgtcaagattaacataatattttcaacatgtattatacttgagttgtatattgtg   282660
agtatataagtacacacaatgaactctcagcctttaaaaaaggagtaaataagaaataggccggcg        282730
cggtggctcacgcctgtaatcccagcactttgggaggccgaggcgggcggatcacgaggtcaggagatcg    282800
agaccatcctggctaacacagtgaaaccccgtgtctactaaaaatacaaaaaaattagccgggtgaggtg    282870
gcgggcgcctgtagtcccaggtacgcgggaggctgaggcaggagaatggcgtgaacccagagggcggag     282940
cttgcagcgagccgtgatggcgccactgcgaggctccatctaaaaaaaaaaaaaaaaaaaagaaagaaa     283010
tcatgtaattggtgacaacacagatgtacctgaaggacattatgtgaagtgaaatgagccaggcacataa    283080
aaacaaacactgcatgatgaaatgtgaaatctaaagaagtcaaactcacagaaacagagagtagacttgt    283150
agttgctataggctggaagttgtgcacatggcgaatttggtcaaagagcataaacagttttttccttcc    283220
tataatattattttcttaggttcaattttgagctattgggattttcacatcataattttttggtctta     283290
cttatgcttgcatatctttactactcttgaataattttagtctttctatatcttttggcttaaatttg     283360
tctcaaattggttgcattttcatctttggttttgttacaaacgtgtgattgtctggaattttaattta     283430
tgagttcaaaacatttatgtttgttgaatattaatttactaaggcttagtttgccatcttgtttgacat    283500
gttcaattagttacttcagaataagcataatataactgtatattttgtcttgaaaacatcagtttcca     283570
cctgtcatttaatagatatacttctactggatttaaaactatattctgttttttgttcttacactgttgt   283640
tgatcataactgagcacagatactgctacttattttcccagttttttttgttttgtttttttcttttctt   283710
tttttttttttttaaggcggagtctttctctgtccccaggctggagtgcggtggcgcgatctcagctc     283780
actgcaagctctatctcccgggtccacgctatactcctgcctcagcctcccgagtcctgggactcagg     283850
tgcctgccaccatgcccgcctaattttagcattttagtagagacggagtttcaccatgttagccagga     283920
tggtctcgatctcctgacctcgtgatctgccggcctaggcctcccatactgctgggattgcaggcctgag    283990
ccactgcacctggcccttcccagttgttttataaatttagcaacatactattggtttataccaattgtg    284060
tcccatttctatatgaaaatcaaaaatatatagaatacatcaagggatttgttgacagatctgataattt    284130
ctgtagcagtcctctaacaagacaaacatttttcaaacatgcatctccttttagtcccaccactgaatgc    284200
catttaagtagatagttcctagaatttaagttctgggctgttatctatgtataattgttgcattctttt    284270
```

FIG. 11A-56

```
tacccatttagccaaatataaattataaattattgattgtccctgcatttcatatattttccacaattc       284340
ttatcaaaatactcatattctttcataggtgttttctcaaaaatatttttgagtcattgaaattttgttt       284410
agcaaaatgtttgagtcccttttgatcaatttttgtttttactttgcctatactatttgttttctaaac       284480
aaaaaatttaaattcacagttattttcttccaactttcaaatatcactactgtatctgcagatgttctg       284550
tgctatcactggaaagtttaatgtcagtctgattcttactcattcatgactcagctattttttctccga       284620
aggctattataattttgtatttgtctttgacgtccttgaatttcatagcaatatatcaactcagggcact       284690
ctatgagctcattcaaaataaagtttttgttctgtttgtctgtttaagcatattttcattcattcatca       284760
acttagttctttctgtttttttctctcttacctattattgatatatctaccaaaactgcctttctctcct       284830
ttattcttcctggtgtttcctatgaatgttctttccatctgatcttccaattcagtaatttgttcttcaa       284900
ttctctctgttctaagatttatcttaactattatgttcttgttcatctttactattacttattccatact       284970
tactatatttaccaagttatctttttaattcttattataatctactatttgaaatatattaccttaggtga       285040
tcaagtgtattattttgtcttttgtaattcttcattgatctgttccaataattatatcttatgtagaag       285110
agttttcatctgttgagagagatagagtttggtaacttttttaaatattcaggtatataactttttaaaa       285180
aaacatttagcctatatcctccttaggtgggtgaaaactcaaccatcagcctgtttgtaattgtggattt       285250
gatatgacttaaggccatgcccaagtctatgttttattttacaagattaacattcaaaaatcactttagg       285320
ttactctggtgcactgaaaacctgcaaggaaggcttcttatttgaaatgtgcctttaaactctaaatgaa       285390
ctggcattacaaagaggcagcctcttaacatccttctgggggcatggaggggaagggctgaagcagg       285460
aaaagcccattgtggccatgagtgactggtggccctgtaggttttagccgactcctcaatgcatctgag       285530
tttcccctaggcttaccgaaatcctactacctgatggctgctgtagggttctatgttgtatggagaagag       285600
aagatggaaggtgagattagataatgataactcaagacattttgctaagagacaaggaggtgaacctaaga       285670
ctttctcttcaaactggcatcgttgtgttaccacttccaccctctgccagaaggtttagccaccccatc       285740
cgccatatatacatggttcttcaggttgtactctctgcagaatggcttatagtttactgcttttatgttc       285810
tgttattgctctttcagtagatcgatgccttcattttcttagcctctgtagtttctcaaatgtagatttt       285880
tgtggaggaagcagcattctgttctattcaccatctcaaaagaagcataaatcttttcttgttttatta       285950
gtatttttcccaacccatcaaataaatctgtacttctaccaccccccagactttgcactgaagaggattg       286020
agaaatggtgaaacacttagctattggatagcttttttcattcccacagacctcatcagttattgttagc       286090
taatatacccattaagaaaattaccgaggaaacaccacatacatccttattaattcatcacttgtcaaaa       286160
tccttctaagcacctttcatctatttctaaaaacattccaaatatttcagggacaatttcctaatattt       286230
ggttttgaatgtcacatagttcatctatcatcatatatgatagctataactacagaaaccaaaatattaa       286300
ctaattcttaatgacaattaggataatgaaggatctattagaattgctctgggtgtctttgattgtcata       286370
tgaattttttaaccaaaggcttgtatgagttccagagagcaaacccactacattttccctgccctgacttc       286440
cagcccatcactatgtagatccattgtggagctttgttactcctttgtagtgtattaaattcgaggatat       286510
aatatcatctgattatggatgaaagtaatgggacacttactgccatgagagcccctcgtgacaggtgata       286580
gttgaaccagaagtttaaagacctgtggcagacaggaggggtaaaacaataggacgcaggacccaggaa       286650
tacattagggaaggcaacaacagtgaaggaagagctagagtaattgaaaggctgataaacatatttggag       286720
ccagttctttttatgctatcattaagataaaatcagtaaatcagtaatccttgcctggtggatatttctt       286790
ctttgcaagaaaaatgttttaactaaaggaagtcattttttgataatttgatttatatacatacatatc       286860
ctctgtacaaattgcctccaagcactttggggacaggagaagaggggaaacctgtgagattgatagatgc       286930
tagatagatagatagataggtagatagatagttaggttagagatataaagatatattctctctatatata       287000
tatttttttcttgtctctcaaagacatgattaggaaacattctcttgctatatataagtatatatatta       287070
tatacatacttacatattatatataatttatataaatgtaatatatattgtatcataaatataa       287140
atatatttttatatacacattctctctacaaatagaacatatctatcgagagagacatatgcagtatatg       287210
tatatgtgtatgtgtatgtatatctaaaacaaagaaacaatataaacacaaaatccaaatgtcaagtgga       287280
agaaaactctaatcagctacaagggacaattagaacatctgtaagaataatatgtgtactggatttaaaa       287350
tgataaagacattaaaatgcatatattcatcatgtatcccagataaaactcactgttaatattactagg       287420
caatgatcacattctcctggatcttgatcaataaaaattatgattttcctacatttggaataaatactg       287490
aatttcacaataactaaaaaattgatgattacaagtaaaattccagataatatatgcaggaaaaacaata       287560
gtataagaaaatcattattttgtgaaaccccaaattaagctaagtgtgtgagtctgttctcacactgcca       287630
aaagaactgcccgagactggctaatttataaaagaaagaggtttaattgactcacagttctgcaaggctg       287700
ggaaggcttccagaaacttccaatcaaggcagaaagggaagcaaacatgtccttcttcacatggtgccag       287770
gagagagaaatcaggtatacattataattttattcctcctgttttttttttgtttgttttttgtttgttta       287840
tatttcaaaaataagaggccatatccaacacagtgaagcaaaatgaacaaagacgttcaaatactgaa       287910
gttgagcataaatttgacttcacaatttctgtcagatgaaccaaaaaaaaaaaaaaaaaagagagag       287980
agagagaaacatttgattctgggattttttatttccagaaagagaaagtttttctctttttcttctgatta       288050
ttgattaagtagttatgaagttggagataaaaggagaagatggcaatgattgttccttgttcttttctt       288120
tctgcagtggctgtcagcttcactgatgatattaagaataacacagcaaagcctgactgcctccctaaag       288190
acagatacttccattacgtgtggcggtacccttcactcctgaatctagaaaatactacttgggccatgtt       288260
aagtttattcttaaaagcctaacattgtgtagctacagctgcccaacaaatctgcccaaagcactgttcc       288330
cccaattgtgaatatgcatacaaataactttcagttttcatgcctactcctggatcataccaccagaca       288400
ttctgatttggaggtcgactgtggagcctatgcaatttaaaatttacagactacccaaggttatgtgaa       288470
tatatcccgagatagcacagccttcccaggctgttggtgccataaggacttggagagatcaccctcgctt       288540
acccacaaacaacttgcaggactaagaagagtgcttaatgaatatgtgttcaaaaaataaaggaatgcac       288610
ctgtgcttggagatacctggagagctctctctctctctcttcatctcccctctgtatctctcactctt       288680
tctctggctctcgttcactctttctctctctctgattcatttgctatgccgctgagtcatacagtgag       288750
aagcagcttaaggtcattaaaaggttgaagcatcatgggaaaaagtgaacatgttttcatttgaatctct       288820
attttaactctttctgaacttgagactgttcagtgataatgaaataagcctatggtggttcttggaaa       288890
tcattttagacacacaaatttctaacatatatagagataatatgtaagatcacattatatataaagtcac       288960
atagagtaagtataatatataatcatatataattataaaaaattacataaaaagtatattatatatcat       289030
acttatatattcatattatataaatatataatatatattaattatctataattttaaatatatttaaatt       289100
taaataaatttaaattaaaaatataatttaaatataaattatatatgtaattatatattatacattatatt       289170
atatataaaatatttcatattatggaaatatttttatatattacatattatatataataatatataaaat       289240
tgtatattatataaaaatatatcatatataaaatataatgtataattatatatacttcattatataat       289310
atgaaattattatatgtaatacacactatatatggtatatataatatataacataatttaaatataaattttt       289380
```

FIG. 11A-57

```
atataatatataattttatagaatacattatatactataagtatataattatttttacatataatatatta      289450
tatataaaatataatataatatgtattgtatatatttatataatattttatatatagaacataatataaa      289520
tttgtatatgatgtatatcatatagtatatgtaattattatatctagtttatgctatattgtatgtaatt      289590
atatataaaatataattttaaatataaactctatatgatataattatatattataatatatgattagat      289660
aatatataataagtatatatacttaatatatgtgatcttgttaagtataatacatatattatatataata      289730
tatattatatgtatataaaatatattaaacttaccatatatgatcttgtttgacatgtcttttgtatag      289800
aaaagcacttaaattaccccctacttcagcaatgaggatgttgtgtttaggccaaaaggcaatataaacac   289870
aacttgctattaaagttttttcttaatcatcactaccactgaaccattaataagtattttcctgcacaag    289940
ataataatagcatctcacatttccatggtactttataatgcctgaagctcttccacattcataattttgt    290010
tcatgtcatagaaagaatgagctttagtaacctcttccatttaaggggatcacagaatgagtaaaagcct    290080
agggtgcagttagaaaagaactaggtttcagtcatctagacatggttctaggactcttgaatgcatgtgt    290150
aactcaggctgaaaatcccggaagatacatccccatcccaagagcacctacacaatttcaataacctggt    290220
tacaactgatgcactttggatattgcactcttcacaaacatctatccaaatctaacatgaactcacatca    290290
gaacaactatcgaatccccactcctaccaaatattcacgtctggtattaccaccaaagcctgaagcaccc    290360
tgacaacatgtgtccagatgttgttgaatttttccatcctgactgcctctcaccgaaagccagaaccaa    290430
cttgctcctggatgactgcagtggacttcttccaaaggcagcctcctgcagtcacatccatcagtgcctc    290500
ttatggacttcacaaaaccataaattctatcacatactgctatcttcccattcttatgtcttgtcattgt    290570
tttataataaattccaacattttagtcacttttccaagtgtgaagtcatttatgcctaccactgtaatac    290640
cattctttcacatttccttagtcatgatgagtcagttacactgggaatccttctgttctcctcacccttt    290710
aaagttcctttggaactttgaacttataattcttttcaggaatgtttccctcttaacatcttgtggct    290780
gcttccctgtcatcatttccttccatttctacctttcagagaggctttgtttagaagaaaatataggag    290850
caaatctttgccagctaggcttatgaaaagttttcttacatagaacacaaaatacaagaactgtaagaga   290920
atgtattgattatgaggacttcaaggcaccacgaagaactcagacaaaaagcttcagattcagacaaaac   290990
atttgtaactaatagagcagagaattgacttgcatcttgaatatatataaatatctcccaactcaattgt   291060
taggcaagcgccctatagagcagcactcctgaacatttttgacatcagggactggtttcacataagtcaa   291130
ttttcccatgtcggtggatggtttctgggtgaaaatgttccacctcaaatcactaggaattacattctca   291200
tcaataagcacacaacctacatccctcgcatgtgccgtctcaataggatttccgctcctatgagaatata   291270
atgtcaccacttaactaacaggagatggagctcaggcagtcatttgggtgatgaggattggctgtaaata   291340
cagaggaagctttgctaggttgcctgcaactccccctcctgctgacccagttcctaaaaggccatggacca   291410
ggctttggtggtaatacaagatgtgaatgtgtggtaggagtggggattcaatggttgttctgacgtgtgt   291480
tcatgttagacttggatacatgtttgtgaagagtgcaatatccaacgtgtgttggttgtatctggtccag   291550
tactggaccatagcctgggggattggggatccctgctgtagaggacagaataacaaacccctatgtatgtt   291620
cacatcctacgttttgtggcaagaaggtcttaagtgatgtgataaaagactttaagatggggacagcatc   291690
ctcaagtatctaggtgagctcaatgtaatagaaatatccttataaaacgaaaactgaaacttgaaacaa    291760
tagaaaatctgaaggtgaaacagaggtcaaatagagatttaaggtgctgtgctactggctattaacgtgga   291830
agaggggtccatgtgttggaagcctctaaaaggtgggagaaacaaggaaatagttccacaattgtacgct   291900
gcagaaggtaccagcactgaagaagcattttagacctctgatttccaaaactatcagatactaagtatgt   291970
gttgggttaagccaccaagtttgtgtatgttatggcaacaactaagaaacacatacatcacattatttaa   292040
cctttgcttgtaaacaatttgtctctccatgctggagggtgaatctcctgatatcaaagatcctgtttgt   292110
attgttcattgtctgtgtcttcaacactaaggacaaaacatgactagcatattttgagcattcatgtaga   292180
cctgttaaatgaacacatggaataatctcaaatgcctgctaagtattttatctcaatttcatcttgttat    292250
attaaaacctgtggtcagctgtggtggctcacgcctgtaatcccagctatctggggaggccaaggcgagag  292320
gatcaagaggttaggagattgagactatcctgactaacacggtgaaaccccgtcttactaaaaatacac    292390
acacaaaaaatttagctgggcatggtggcaggcgcctgtagtgccagctactcaggagactgaggccgg    292460
agaatgacatgaacccgggaggtagaggtgcagtgagctgagctcatgccactgcactgcagcctgggca   292530
accatgcgagactctgcctcaaaaacaaaacaaaacaaaaacaaacagaatattaacaaaacaaa        292600
caacaacaaataaaaacctgtgctttttttcccaacaattaacttcaactcttaatcatcattcttttgcc   292670
ttgggggataatataaggttaattatatttttgtaaaacacaagagtcatgaacaaaatctaatggaccat   292740
acatagcctccatgtgctgtctactcatgatgcagtgtttcaaatataaaacatatatatagtatatatg   292810
tatacatacatatatacattcaacaagcaaacaatatatatattaccctggagaactgcctttgttgaagc   292880
ctataaaagtttgtgtgtggagcttataaaattgagtgtgataaaagttggaaaattgagataaagtgga   292950
gaattgttactgtgatagttgcttaaaatctagttttagaacaacactaagtttgaccatagctgctct    293020
ggtatgtgatccatttaatgtttttgcttttgtacattaattatcagagagatatcttagcctgagatat    293090
ttaaatctgttagtgaataaagacttccatgcaacaccgagacagagttatcaaaaatgacaaatccttg    293160
acaattatagtaacaaactttagtacagtaagagatataataggacactgtaactgctctcagatcaaac    293230
atccctcctgcttagagaaaaaaaaaaattgcacttagtgcaaatagaattgcaccaatttctctgatac    293300
agcctgaaaattaagccaacatttcaggtcttgtaagaaaagttgctgtcttctggcttagaaaaggcat    293370
cccaggtagtggctgaccattaaaagaagatgagcgttatgaggtagccatcttcaaaagaaaatgg      293440
caaagactttacaaaaccttaatgttacaatgtataaaaatagtataaataagtaagaacttaaagagac    293510
agagagtgcggttaaagcagcaagccagtaggacaattttagtgtatagcttaaggtacaatatatgcat    293580
aattgcccttccttaattctagaaaatattgtctgtcttcttcaataacctttctattaatgaaactaa    293650
acattccactgggatttttagctctcttttttatgctgtcatatttactttgctactgtatgtgattacaact  293720
aacttctaatttgtctaatatatgtgatattttatctgtatttcattcatttaatatgaattttaatta     293790
atctaatataatattgtaaaagtcttttcttatatgtatttatagtgccttttatatgtgttttatct      293860
ccatactttgatggtgaaaacttactttcaattcaagtgttttaaaatactctcattaaaaacaaatgga   293930
aatataaatgaaaaaaaacatttctgtaactttcaaagtatatatggaaatgcactcaactgtggcaa      294000
catttcccccaggtttagcatattgcttggatgattatggctacttcatacatgtttgttgaatgagaa    294070
ttttttcataaattttatagtgtatgtaaaagctatggtatgtttttgtcttgtcttttctcttttggctt   294140
taaacacatagtggctaaacacagagcaggctgaataaatacatcccccctttatgcaaaattattcact    294210
aataaatggtatctagttcattctttaaaataccataagagaacacataatatctctttaccatttgcaa    294280
aattttgaagtcagagtctaatttgaccagcagtcgatttacccttttggactcgtttaatttatttgaa    294350
gaacatttatttgttcctcatgtgtgcaggtgaagcaaaactaaagagcatggctctgatcttcatgga   294420
agcaggctagtaggcagctatttttttgtttgcttttgagatggagttttttttcttgtcactcaggct    294490
```

```
ggaatgcaatggcatgatctccgcacactacaatttctcctcccaggtccaagtgattctcatgcatcag    294560
atccccgagtagctggggttacaggcatgcaccaccacacccagctaattttgccttttagtagagat    294630
tgggtttcaccatgttggccaggcagaccttgacctcctgacctcaggtgaactgcctgccttggcaacc   294700
atttttgaacatattccacatgaggcaccatgctgtttcttgtacattgtccagttgagttcctcagctt   294770
tctatgtgaggactactattctcctccctttttcacatgtaaagaaagctgggctttgaaatcttaaata   294840
acatgtttgaggccttacaatagattacaccccaaaggtgtcagactgaatccattgaatcaataactct   294910
gacagcaattacaaagcaaatgacctttgtgtaacatggtatattctataacagaaattcattgaatgcc   294980
atttagtgtgctgagacaatacagataatcacacaggacacttctggaaagaggtctacattggtagaaa   295050
gacttggccaggtcctacctgattatgtaggtgactcctgcagaagatgcagagcctgcccttcaggtca   295120
cactgacctttcaagtggtgctgtgtgtccatgagctagccatgcagcttttttatatggccatagccacag  295190
gaagggatgctcaggcaaggtgttcaaggcaattaaaggctgcagaggccaccttagatcttgaggactt   295260
catataaaaaagcaagcatttcaaaatccaaggcatattctggaagtagttagcaagtatagtggtggat   295330
ttgcaagctcaagaacataagtagggcatcccttgagaaggtcacatgggcccacacaggatgacccttg   295400
gattccagtaatgaatttgtgtgtccagtacactcattatattgtgtgtaatgtgattgctaaaaaag    295470
aagatataaattgtgaacaaaatataaacagttattagcaataaaacatgaacatttcctataaccacct   295540
cctttgagataatcactctccactgtttgaattccttccacatttttattttttaataaaataaatgggcc   295610
acgcaaagtggctcatgctggtaatcccagcacttcaggagacagaggcaggtggatcacttgaggtcgg   295680
aagtttgagaccagcctggacaacatggcaacgtctctgcaaaaaatacaaaaattagcccacacgtggt   295750
ggcacatgcctgtaatcccacctatttgggggactgaggcaggagaattgcttgaatccaggaggtggtg   295820
gttgtagtgacccaagattgtgccactgcacttcagcctggtcgaggctctgtggcaaaaaaacaaaaaa   295890
caaaaaacaaaacaaaacaaaaccctaaaaaatataataaaatacaataaaaagtatttagcagcccact   295960
attttttttttttttcagatggagtctcactccgtcaccgaggctggagtgcagtcacatgatcttttct   296030
cacggcaacctctgccacccaggttcaagcaattatcctgcctcagcctcccaagtagctgggattacag   296100
gcagcccactattttattgagacaccatagatgtgttcctgtctccatgcatgtaaatactccttaaca   296170
cttcatgcaaacaaacagcatcccataatatgatgcaggcaagagaatccactcaagtcactgatttgt   296240
gaacactgagcttgctgctattgtttgttttaaaattacaatcaatatattcaaggagaaactgctcag   296310
ttattttttatgcatcagaataaagattttcatagaaaaaccattcaaagcattaggactcctaggtcaga  296380
agtctccaatttttaattttcctgggttttactcatcctcttacattggacagcatcatgattattttgat   296450
agtgcagaaattcagagaaagctgaaaggacataaaacccaagtgggtaggtcctgggagactgtggttc   296520
tcatctcaggcactaggatgcagacccaggggaggaacaagatgtacaagcttttttgaaaaataaaaccaa  296590
aaggatgtgacagccaattgaatgagagtcatacaaatctggagatatattcaaggagaaactgctcag   296660
ttaaaaagattcaaagttgtctgggtgtgatggctcatgcctgtaatcccagcagatcacttgagctcag   296730
gagtttgagaccaacctggccaacatggcaaaaccagatctctactgaaaatataaaaattagtcaggca   296800
tggtggtgtgcgcctataatcccagctgctcgggaggctgaggcaagataatcacttgaatttgggacat   296870
agaggttacagtgggccgaaatcatggcactgcactccatcctgggcaacagagtgagagagtctatcta   296940
aaaaaaaaaaagactcaaagttgactcaaagagaattgtttccaggcaggccattctcaaatttcattt   297010
ccatgaaactcatatatcaattatcttcaagtttttgatatattattgtttattaagcaaactgtatttat   297080
tattttatattttgctcagaaaatatccatcttggttttttttatttttatgtaattgaaactaaagcact   297150
taaaaaagcttatgcagcttcattatagatacatgtaggtggacattacctactttatgaaaatgatgca   297220
aggaatctgaataagagtttgtgggcccccagagtttgaaatctgtggtataaataccatgtgtctgtta   297290
taattgtcttagattttctctatggactttggaaactaaattttggctctgtgaaataatgatatgataa   297360
catgatacaataggaaaatagtctgctagtactcattccattttttaagtaaagtaaaaactaaaaatcaa   297430
aggcactgaatttcaaccagccttacctatcaagctacagaatttgagtgcaggacgtcacgttccctcc   297500
catccagcacactctgtatatgtatgtgctcctgtgttgaatcctacacaatttaaaacagaaaactgaa   297570
gcctcacctttaataaattgactatgaatgatttcctataaccatcaaagattagtttttaatctatt    297640
gactgattttttattttttatacctctgccttcattctcaccagatttctctttgaccacagttgtgtgac   297710
ctaaaacaaattctgtttgttctcactgaataattttttatttaaactttttcctgtttggtgtcacttctt  297780
tagttttaaaggtgcacatatgtgtgtctgtgtacatatacattcatacccatacattcatatatatggtt   297850
atatatgcatattgtatgtatgcgccagctacaggtaaatgacacacacggaaatggtcaaagatattta   297920
acttctctattcacataattatcttctggttacttgtctccaaaaaatgcctagtgtgtttatacgagga   297990
atgatctcataaagaaagtggattatggctttaatgtcatataacaatgtcttttgttaattaaaaggc   298060
caacaatatctgaccccatttggttccttaccattgacttggagggcatgcagaaacaaaagacctgcaa   298130
ttattctcctaagccttgtgatataattcaaaaggagaggaaacatctacattattatttataataaaa   298200
gtggaaacttttctattctaccaacaatattaagcccaactagaaatcctcatgtttatatgatactcat   298270
tttagtcaacatgcagaaggaaaaactgattcctgttttacggcacctttaccatgaaacatgttttaa   298340
ataaccacactaactgaatgtattagtctgttctcatgatgttaataaagatattcctgagactgggtaa   298410
tttataaagaaaacagatttaatggattcacagtttcacatcgatggggaggcctaacaatcagcaga    298480
aagtaaaagaggagcaaagtcatgtcttacgtggtggcaggcaagagagcatgtgcagggggaactgtcct  298550
tcataaaatcatcaaatcttgactatgaaaatagcatgggaaaaattcacgcccaagattaagttacctc   298620
ctggtgggtccctaccactatgggatctacaattcaagatgagatttgcctggggacacagcaaaatcat   298690
atcactgaaaatattgattgatatttcttgtgtgtatattttgttgtcgatgttccttccagagccctg   298760
gatgaaacttggcatcaatgtagccattaacatgcattaattctacatgatctcttttgcatctttcttt   298830
tgttgttcagttggtagaggagaggttgctgatttacaagcttcattttagggagagtaaaacttaaaag   298900
ccaaaatttcatcagctaacaggcttagagtatggagcctaaaggacctgtcgatgaaggaggttattcg   298970
ttgcatatctgtggttttagacaatcaagggggttgttttttttcattcacctggaatgtgtatttaaagt   299040
taagtgatctacctgagagctgagttctcaagaagagcactcatctttgatattatgcatggctctctcc   299110
aagttgatgaggtaccatcattttgctctctacaatcaggaggcaaaacccagtgatttaggtgtgcagg   299180
attcctaaaatattaattttaacttgctacaaaaaataacagggtttctggtgtctgaaaacttttgaga   299250
aatcacaccattagaatattgttaagatcactctttatttgcacttaagaagataaacttgtcaggaaaa   299320
ttttcttcttcctatcttccttccttccttccctccttccttccttccttccttccctcctccct    299390
ccttcccttccctcccacctttccctctccctgctccatcacataatatagctataatgtgctgcctttc   299460
ctctcctccagtgttattgataggaaaaactggccaggtactgatgaataaagaaaaagacaaatttata   299530
gtgagatctgattgtcacagatcaggtgcctatgaaaacaggtcatttttcttcttcaaacaataacttt   299600
```

FIG. 11A-59

```
ctgagctcagaatttcatgacaataagcccacatgcttcttaagtctcattttatataaaatgtgatttag    299670
acctcagaacactgtaactgcccaacagactcatctttactacacagatagagctgattagtcaagatag    299740
aagaattgcaataaacagtttaattcctacagagctggctaaataagtgattggagtttattattacct    299810
aaatcagccttccccaaaattcgaaggcttgagtttttcaaggatagtttggcatttaggggctaggaa    299880
tgagtgctgctggattggttgggatgcaattatagtgttttggaaaacaaccctggtgcactaagtcacc    299950
ctctacatggggatacagagatgttaatggtcccagtgggaccaatcaattgtcgcaaataaaagcctga    300020
aaaggcatctcaaaaggccaatctgtactattccttatccacctgagtaacaacaattcaagatgagattg    300090
ggtggggacacagccaaatcatatcaccgaaaatatctattgatatttcttgtgtgtatattttgtggt    300160
tgttgttccttccagagccctggatgaaatttggcaacaatgtatccattaacatgcattaattctacat    300230
gatctcttttgcatctttcttttgttattcaattgaaagaggagaggttgctgatttacaagcttcattt    300300
cagggagagtaaaacttaaaagccaaaatttcatcagctaacatgcttagagtatggagcctaaaggacc    300370
tgtcagtgaaaggtcctgtcacatgaaatttacctacataataaaacctatagttgtacccccaaacctaa    300440
aataaaaggtttttaaaggccaattttagtttctagtgattggggaagttgcagatcttgtcacctatgg    300510
aattgtgtctggagtttgttccttctggtgggttcatggtctcactgacttcaggaaccaagtttccact    300580
cgacccaggaagtccacctggcttcacataccaatagaaggtgtctcctctaaactggacaccccaaatg    300650
ctattgggaattgggtgatgaccgctctacctacttcctgatggatagggggcaaagaagtggccctgcag    300720
ttgtaatgtccttcagaggggaactctctagcccagtcttggagccacaaggtcgattcaggggtcctca    300790
gtagaagttgtgagttgagctcatttgggggttccatttgtaagaccatctgtagctgatggcctcgatc    300860
ctggaggaaacaaatttgacaaggagattaaaaatacagggcccaaatgcaagtaatagcaagatggctg    300930
tcacaggacctagaaaggggagaagccatgtcactcaacttcagatgttggtataagagtttgagaggca    301000
ttgtctgatttcacaagtcttttcctgtaaacactggatggcatctcatattatccctgactggttaata    301070
taaaaacaactcttcccctaagaaggtgcagagtcctccttttctcagcagtgctaggcctc    301140
agtagttttggagagtcactgctgccaaagagtctacttgggattgcagtgtaaggaaagattttgttat    301210
ttcttgaaaactgtctgagaaatactttagtgtgtgataggtagtaggataatggagtagataaact    301280
ggctattctgtttcctgtatcagtggccattcctaaaactataagtagggttattagttgcatggccctg    301350
cactgacgaacttgaactttaaggggcactgatagggtctgatttcctggggaaatgtcagtgttgggac    301420
ttaggaagactaagttccaggtgcctgtccaggtggggaggcagcagtaggttcaagttccacataagaa    301490
gaacatgccttggctgagtagacagaactggttgtatatgttaaaaaggcttgtgataataataataact    301560
catattattttcattttcccatactcctagagtacttgccaaggtacctccagagaatagctgaaaagga    301630
gtgttgggagaaaactgagtggctccctgtgttctatttttcccattggagaaaaaccgttttgtatcta    301700
ctaggaaccattcaagacagtgatagaaagaggggaatgagaaggctttcattagtggtgggatgctgct    301770
gcaagggtccagggatgaatggtcatgcagggagaatgtttgccattacaacacccagactgttaagca    301840
ggtaggaggtgataattttggaggccctgagaagcagacaagccatctgaatggagctgtatgggtgac    301910
tcacaagttgctatgatctgttggtggttgaagttgtagagtattattacactgatggcattgtaggttt    301980
ccaggggcaggcctgataacagattgcactggatgcataaagaggcttgaaaagttaagatggtattcgt    302050
ggttacagggccatatatgggcttttcattgctagtgtaataggtgaaagtggaaatgtaagagtgtaaa    302120
agctggattccatgtcctgttagggtattcttggtaagctttgtgataaccaaatctaggaattatttc    302190
atgaattaggactttaaccacttcctgagcattctctgtcttgcaggggaaggcttctatcaaattcta    302260
aagatatcagcacagaccaacaagtattgaaatcccttttaacttaggcataggcatgaactctaaatacc    302330
agtcctgcccaggatagtgccctattctttcttctcccagagggggcctatgatagaccatggggttttt    302400
tctttggcacacatcacaggctttgactacttgtcagatgatctagaggagacatgtccttgtaaatagg    302470
gatttggctatttgatgagtgttctcaatacacatatggagagttttggtggaggcttttaagtattttcc    302540
actggctggcttcaggtatgagtacctttccctttctgtcattaaccacccctagcatagaaaactata    302610
cccccgtgaaattttccattctgttttcatttgggggaatactgggggcttaatctcttggagagggttgttc    302680
cataccaagggtccttccacaggtacttctaatggggaggttccgcctggtagcaattttggcctcagagt    302750
ctgcctgacagtttctaccttttctccttcatcttttttaatggctttggcagcacaagactgccacccc    302820
ttggttttttgcactgtgtgcaataactccatgatttccttgtggcatttaatgggggttcccccagaagt    302890
taggaactccccttttttcttcatattgtagcattggcttgtagggttagataagcatagttttctacctata    302960
tacacatttattattttttgcttttcccatttctaaggctcgggtaagcaccagtagttctgctaactggg    303030
tgctgatccctgggtgaagagggttacttttcaaatactgttacatcactatggcataacctgcccttc    303100
atctcccattctccacaaacgaacttccatcgttctataggttaaggtcaggattagctaaggggacttc    303170
ttagagatcctcttgggtgacacagtctgggctacaatttgttggcagtcatgctagatcggtcccatgc    303240
tatgggagaaaagtcgcaggggttgagggctgcacatgtgcatactttgaagcaaagtctcaaggagtagca    303310
cctggtatctaagcaggtggttatctgatagccataaacttcctttggcacctagtgtgccatttacatc    303380
atgagtagtccagacagtgagatcctttccttgtattattttgatagcctctgacactaagatggccacc    303450
actgcaactacccgttaacagtgaggccagccttttgctactacataaatttccttacttaggtatgctg    303520
ctggttgtggggacacttagtgcgtctgaataaggactccaagagctatttccactcttttctgtgatgta    303590
taaaaataattttttttcatgtacgaaggcttaaggctacagcttgtactagggcctgctttaaggttttg    303660
aaaactgtttctgcctctggtttccattccactagatgagtatttgccctctgggtgtccttgattaaag    303730
tatagagtggcctggccatctcgccgtatccaggatccatagttggcaaaactggtgatcccaaggaac    303800
gtctgcaactgtttaaatttcttagggcaaaggataagccagtatgggctgcatttattctttgctgagg    303870
gttcctctggttaaaattaggcctggatatttgaattgttgtaggcagagctggccttcaattagatgcc    303940
ttttaccattgattagctagaaacttcaagagatctatagtagactgctggcatgtggcttccaaactgg    304010
tagcgaaaagtaaatcatccacattctcaaggaccagtgtaccttgacttgaagtgacctagatctgg    304080
gatagcacctgaccaaacagatgagggctatccctaaatgcttgaggtaagaccgtccatgtaagttggg    304150
atgtgtggtctgtgggatcctcaaaggtaaagagaaactaggagttagagtgcaggggaatggagaagaa    304220
ggcatccttgaggtccagaacagtgaacaattctttttcctctgttgagagtgtagaggtataggtcttg    304290
ggtgcacctggatatagatgaatttctgcctcattgatgaatctaagatcttgcactagtctccactaac    304360
aattcggttttgtactcctagaattggagtgttgtagagactgctgcattttcttgctaagccttgaga    304430
ttttagatgtctaacaatatcctataattgtttatgagcttcagacccttaaggggatattgcctttgataa    304500
ggaaaattggtggggtctttcagcctgatttggacagggccaacattttttgccccttccgaactgtcctt    304570
acaatgcccagactccaggggttgattcccctcaagcagtgacaacagataagtgacttgttccccat    304640
attcatatggataatagctccagctttggctaatatgtcccttcctaataagggtgtgggactttgaggc    304710
```

FIG. 11A-60

```
ataacaagaaaggcatgtgaaaagagcaaagtctcccaattacaactgaggagctgggagaaatgcctgg    304780
ttacaggctgccccaggattcctcagatggtaatggaccttcagagcagccatctgtggcaggatattaa    304850
cactgagaaggccacatccatgtccagaaggaagtcaatgtcctggtcctcaatggttaaatgtacctgg    304920
ggctcagtgagggggacaaaatgagctggtgctttccacaggcaccctcagtcctgctgttggatcacct    304990
ggttggggactgctggtcctgagaacctttgtcctctggggcagtgtgctttccagtgatgaccttggca    305060
tagtggacatggccaaggggtgacttgtttctcactggacaatcttttctaaggtgtccttgaaaacca    305130
cactaataacaaccccctaccaggtaattggtctgatccatttctgtcctctctgaagcaccaaggtttg    305200
tttgactgagggccatgactgtggcctttcactgatctccttttccttttgggcctgttcctcttggtc    305270
tctattatagaacaccaaatttgccaggtttaataatgcctccagatttgttcggggccagggctcact    305340
tttggagctttatcctgatatctgcagctgattggatatgtgttaggatcaattgaccctcgaggggagtt    305410
ggttgacaggggaatatatttttcttaaggcctcttgtagctgctcaaggaaggcagtaggattatttcc    305480
tttccctgagttatggtggacatcattgattaattcatgggcttttcctattctccttagtccttctag    305550
aacacaggtcaacagatgtttgtgactccagtccccacgatctgagtctagatcccagtggggatccata    305620
tgggttacagcttgctgaccagtagggaatttgtccctttcttcggctgttattctatcatttacttaac    305690
taaaataccagatctccaaacactcaggctgtagctaaagccatttattttcactaaaggccagggttt    305760
gatctaacaatagcatgatatctttccaagtgaagtcaaatatttgccctggaccctgtaggacatctat    305830
atacctattcaggactatctgaaaacatccccaggtctacccttatctgctttaaattggagagggagaag    305900
gggacatgtacctaggttcagtcaaattcccctcccctgacagcttgaaggggacataagccatagcctg    305970
ggggtgtttgtggtcccttggatatttctttgcttgttccccttctgggtggggagactagaggaggct    306040
tattactgataggaaagggagctgtatagatggtaggatatgaagctaaactgagaggtcctcctgtgga    306110
atgtaaatttcaagcttttgccttgttctgattatccttcagtgaaaagaaagcttagacataagatatt    306180
tcactcaatttgccttctctcttacaggtcaaaggacagtatggcattctaatttatacttccctcaggt    306250
ggtcattttccccatcagagagagaatattgaggcaggccatagtgcagaaaaaaaaataagccacttc    306320
tatttcagtgtttgcagatcaaattgttcccaatggcttaggatgcatttcaaggggtgagcttgttgatg    306390
cctgagtgattcccatctaaaagaaaaaaacaaatgtggttttggtttgccttttttccttgcccaagat    306460
cctgcaacagtccctggaccctgatgttccgaatagttgtgctcgccaaagcagcagagaaacactagt    306530
tttcctcctagatcataaggaggaccaataaaatgtcggatttagtagcccttaccaacacattcttgaaa    306600
atcaacacccttgcctttcctcttagaccacaaagaggactgagaaaaatcagatttagtggccccttagt    306670
gatgcatccttaaaaatctgtaagagtcctaagcattctcctcttagtattgggaccttatccttgtcct    306740
ataaagatgatatgcatcaaaatggagtggagggccatacccttagggagggaagggatctccagggttg    306810
gaagagtgacaccttttgtcctcacttctcatcaatgaaaagaaggatataatttctgaggctccccctt    306880
atcctagcttcaggaatagcctttgttaggcctgctagtctgaggaggggttgataaattccagatcatcc    306950
ccctcccaacaaagcttcaggtgaaaactatgttttttctgataggggagcctgggtacctaaagaaggaa    307020
cagagtcccacagtttataccataaatcatttataggagaaactagaagatcacagggacagggagttg    307090
tttttagacacagggctaccttcagagaagagaggcagtaggaaaggttgtcttacaggcgttaggaccc    307160
agaaggcaagggtcacgatagataggatagatgggcgagtctcgcttgtgcaacataactttgaaagtta    307230
tgctcatggctgcagggtcaaccaacttttttgttgggaccctggactcatgaatgaagctgctgaccttcactgt    307300
cccttggctcagccaagaaatgcaggaaaaatggaagctggttccaggcaaatcaatgctcccaactcca    307370
aagattcagtggttgttagagagcccttcccagaaagcctgacacctgagtctttagtccagcagccac    307440
gctagttgcttttaactggtcaacaggtgcctggtatttagtccccgaattctaaagaaaaataggacag    307510
aatagcaagtgaaaagggtccagcggtactcaccacatggcaatatcctggatgagccactagatgtgtc    307580
cagagttggttcctgccagtgggttcgtggtcttgctgacttcatgaatgaagctgctgaccttcactgt    307650
gagtgttacagatcttaaaggtggcatggactcaaagagtgagcagcagcaagatttactgtgaagagtg    307720
aaagaacaaagcttccacagaatggaagaggacccctagtgggttgccactgctggctgagttggcaact    307790
tttatttcttatttgtcccatcccatgttgtctgtctgtcctatcagaatgccctttttacaatcctcc    307860
ttgtgattaactacttttaggttattatagagtgcagatttgtgcatttttacagagtgctgattggtgca    307930
ttttacaatcctcttgctagctacagagtgctgattggtgttttttacagcactgattgttgcatttta    308000
caatcccttactaactacagagcgctgattggtgcattttacaatcctcgctaaagagtgcttattggt    308070
gtgctttacaattctcttgtaagactgaaaagttctccaagtccccactcgacccaggatgtccacctag    308140
gttcacctttcagataatgtttggtaattatttaactaagccaacatcttagcagaattcaggcatctgt    308210
cattttttctaacctgctggtctttcattagtttacaaaggttgtttagttttaagaagggctattatca    308280
tttaaactataagttcaatttctcccaaagttagcttggcctatgctcagcaatgatcattgtagtatgg    308350
tggtgaaagacaagatgtgttggttaggtcagatctctttcactgtcataatttttctcacagttacaag    308420
ttttgcaaaggtggtttcaagatgaaaggagtatactcttgtaaagagcgtaaaattatttcagtcattc    308490
tgtacctgaaacaggcactccccctttttgatagtttaaatttaaaagaaaattaataatccctggatg    308560
ttgcagtaaatgaaaattccaatgcagaaactgtgaaaacacatgcttcaaaacaccacattcttttgtt    308630
aaacttcagagatgcaagcattgccatttcccttggcaagcttacagaatatttggaggaaattctgaac    308700
ctcaaagatcaatccatccagtaggatgctgtttgaataactaagattttgaacacaagggacattcat    308770
tagcctgctattggaaaggttacaaaaaccccttgttttgtaaggagggaagggattgtggtggaagaaag    308840
gccagtgattcacagcatgttgaaaatcttcacgatcctctgcagaaacaaaataagccaacagatcatt    308910
ctgcagaattgtgaaagagagaacagtgagttaagaaaagatgtgctgaagacagaatcattctgttaga    308980
aaattactcgtgcctaaaaattaattaccctctctctttaataggggacgaaagcattgccctgtggtat    309050
tagagggcacccacactgacattattcatcattgtcatatgtacccctgaatgaaaggattttcttcctcca    309120
ggcaaagcctgatgctctttatgaacaaaccgtgtcaaagatttagtgatggagactggtgttgcagaac    309190
atttttttggcataaagcactaattagtaatcactaattaaatggtgggggggcttgcgtaatgtctgaacat    309260
acccactaatcacagctaatctcacatcaagtttctctgaactttaaagaaatcacattggtaggatgtg    309330
tcttaagtaagaccaacctcacagttgcaatactgcctctccttgaagctgcaggcaatggtgactcctg    309400
atttaggcttggaatttattgtcattgtaggaaaaaaaaaatcttatgactttctttgaagcctggccat    309470
ttcctccttttcctgctagctacagatcattttttccaattgttcacgaaacctaatgagaaaatctggttaact    309540
ctactggtatgcagcctcatcctctactcttttttgttttaaaagtagaagccaacactcagtctctcatt    309610
ggaatgctgtcaactttggttaggaatatgctttgaagtagttggtttggatttatgttattttagggct    309680
taaagcagtctgtcatcatacaaacaagcccctcccttatgtgacactgttgttcataaaaggcatcaga    309750
ctttgctcgggagaaatgctcaactaaggacaggaaaatggtaaaaaacaacaacgcaagaaaccttccc    309820
```

FIG. 11A-61

```
caaatactcaactataatatttgttccttacatacaatttcttttttgaagatctacgtcattaactca      309890
tttgaagggacatttagtacgtaatttatcataggagtctgttgtgtttaaagaaaaatgtgcacacaaa     309960
tggtaccttgaacctcgtaaaatttacaatgacttctgggattgcttcatgttattaatattttagattc    310030
attttgtcttctattagccacatatatacccaaagatgacaaggtatcataatgtcaacttaacaataat    310100
cattgtttatgtaattatttctgccacaaaaattttctctagttttttctttaatttcctgtaatttcc    310170
actaacactgtagatgcattttccttctacattagccacatatatacccaaagatgacatggtatcata    310240
aggtgaatgtaaacaataatcattatttgtataattatttctgccacaaaaattgttctccaggtttttc   310310
tctaatttcctataatttccactaacattttagatttattttgccttctacattagccatatatacctaa   310380
agatgacatggtatcataatgtcaacctaaacaataactattatctatgtaattatttctgccacaaaaa   310450
attttctacagttttcctctaatttgtggggacagggttgtggagagagagaatgaagaaggcaagct     310520
atgagataacttttcaaatggtggggatgtgtacacaattttttgaccaacaaaaatgtcctgtgttct    310590
tctgtagGGTTTTTAAGTACCGGTGACCAGGCAGCAAAAGGCAACTATGGGCTCCTGGATCAGATTCAAG    310660
CACTGAGGTGGATTGAGGAGAATGTCGGAGCCTTTGGCGGGGACCCCAAGAGAGTGACTATCTTTGGCTC    310730
GGGGGCTGGGGCCTCCTGTGTCAGCCTGTTGACCCTGTCCCACTACTCAGAAGgtaataatggtgtcccc   310800
gggtgggtgggcaaatgccctgaaccaagaaatgaatagtcagagttcatagctgagattcatgtccag    310870
gttgccagaagtcactgtggaaattgcaacagaaatgcccaaaagacaaaatgaacccatcttcatata    310940
ttttaactcagctttttttccatttgctctgtcactcaggctggagtgcagaggcatgatcatagctcat   311010
tgcagcctccaactcctgagcttaagccttctccaatcctcaacctgctgaatacctgggactaatggtta  311080
aattttaattttattttatagagaagtggtcttgctatgtttgctcagggtggtctcaaactcctagc    311150
ctcaagtgatcctcctcccttggcctctcaaactgctgaggtgacagaattgagccaccatgcttggtta   311220
gcaatatctcctcatttaagtgtgtgacaattaggtgtcggttacaatgataggaaaaaaataactgctt   311290
tagaagggcggacactattgtttcttttgacagtctcactgtatttgaacattttgaaattttattaactt  311360
ctagctacaatttggtaagagtaatatgtgaagagagacagtacgtcaataaggaagagaaatagtatgtc  311430
aatattgcagatttatagattttttaatcaactgggcttttaaccacgtgtttttttaaaagacacttctc  311500
taattcacattaattctttaaatcttctggaaacattaggaacatggctggtgcattcatagagaagtag   311570
attctacccataggaatagtgtctctctccctgactctgtctccctccctctctctcttcccctttcact    311640
ctcctctttccctctctcttcctgtctctccctctctatgtctctcctcacttttctctctctctctctct  311710
gttttcctctgtctctcgccctcctctctccctccttcccactgtctctcctcgatctccctctccctc    311780
acactatcctctcacctctttctccttttctcccctctctctttgtctctcttcctctctctccctctc    311850
cagttccccagtttcttcctcactgtctctcttcctctctcacttcccccccttcacactctgtctctct   311920
cccttttatttcttttctctctgtctcccttttttctccctctgtctctttccctttcttcctctcctgcaaa 311990
catgactttcagcaaaggaccaccttactggtcagttcagcatgaggcacttggaagtgtccacagtttc   312060
ctttatctctctctctaacacacttttaggaagaacctccctgctgggccagtcagcatgacatcctc     312130
tacttgtccccgtgggagctccaaacccctccctggggccctgctaataacctgtgaaaaagctgctgttgg 312200
caaaataggggaaggggaaaccgcagaaacacactcacatcatgttacctcaatcagacatgcacttgta   312270
tgtggtagttagcataggcaacccacacccaaccagatgtgcacttgggcctctaagtagtaattgctcat  312340
gctgcctaagtggtggtcagcatagacagccacacccctgagccctgccagagcacctgaggctcactca   312410
atgcaattccctgatgctaatgcaagagggaggctctctgcagtatcaaagctgaaacttcaaagagaagtc 312480
cacaggaatttgtggcaatggttctggaagctggatcaccaattcttggctgtggcctaaaaggagaaa    312550
gcaggaaaatctgcagaacagatccagccctctgttacctggccaggtacaaatgaatattcataatagc   312620
catctcagtcatcaacacagcattgtgatatgttctgtgtcattggtaggcttcagaatggcaccacact   312690
gactggaccatttacatctgaagtactcaaaatcttaatggaattttcttcttttctttttttttttt    312760
ttttttttgagacgagagtctcactctgtcactcaggcaggagtgcagcatgatgatcttcactcatgtcaa 312830
cctctgtctcccagttttaaaatgattgtcctgcgtcagcttcccaagtagctgggcttacaggtgacca   312900
tcaccatgcccagctaattttctatttttagtagagatggttttttaccatattggccaagctggtctc   312970
aaacttcttgacctgatgtgatccgcctgcctcagcctctggaattgttatttattaaagttatcagctg    313040
ggtaaggtggctcatgcctgttatcccagcagtttgggaagctgagtggggagtatggcttgagcccagg   313110
agtttgagcccagcctgtgcaacttagtgagaccacatttatacaaaaataattaaataaaaaacaagcca  313180
gggctggtggtggacgcctgtggtctcagttgcttgggaggctgaggaggggaggatcacttgagccaggg  313250
aggtcaagtcttcagtgagctctgaaggtgtcactgcacttcaccctgggtggcagagagagaccctgtc   313320
taaacataaagaaataaaattaaaaaaatacccttctttaaagtaactgcaggactttcttcacttcctg   313390
caccatctgaacaagtttctagatcactatgctcctcagtgtcttcttagcaagataggacagatgagg    313460
atttcctaaaatcctccaaactctgaattcctgagttcgtagttcataatgttttgcccaggagaccaa   313530
atgacttttgacctcaaactagtgctaataacaggggaagaggaaaggctcatatttgtagtaacttatt   313600
ttaaaaacaggaacaatgaataatctgatgaaccatttggcatagagatttctatggcattttttgaaaat  313670
acatagatattcacatttctcagttgatatgacagttgtagatttagaaagcagtcagaaccaacttcag   313740
gagtaatgaaacacatgtaagccacactaattagaggaaagtgttaattatttaagtcagcaggttggaa   313810
gttattatttgctgcaaaaataccttttgttggtcatttatgcaaggcagtgcttctaaacagcccatc    313880
agtattatcaagaattttgaaaaatatgagcccggcactgtggctcctgcctatccccagtactttgg    313950
gaggctgaggtgtgaggattgcttgagtccaggaattcaagaacaacctgggcaacaaagcaaaaccttt   314020
tctctgcaaaacattacaaaaattagccaggtgtggtggtgcacacctgtagtcccagctacttgggatg   314090
ttgaagtgggaggatcagttgggcctggatggcagaggctgcagcaagccaagatcatgccactgcactc   314160
cagcctgggtagcagagagacactctgtctgaaataaagataaagataaaaatacccaaattgttggcct   314230
taggaattctagtctaatgaaggcaaagtacctgtggaaagaagactttttatgaagatattcaccccag   314300
tattattatcatagcaaagaatgaaatggaaaagctacaagatcaaaaggagatgaaagttattagaaac   314370
catatgcaataactcaaaagaataataatttacctaagatattcaacagctggaaaaatgcagtgtagac  314440
aactatataaatattgggctcagctattcaaaacaatgtttgaatggaagagaaagatgtaagaaagaat   314510
tatgttaattcccaacatactcattttgctaaggtgagttttgctttaatgtttgacttatgggtgattt   314580
tttttcattatccaagtttttttagtgtcatcaggagtttattacttttcctaacatacaaataactgtt  314650
tatatatgttacttatatatatgtgtgtgtatatatatatgtgtgtgtatatatatgtgtgtgtgt      314720
atatatatgtgtgtgtatatatatgtgagtatatatatatatacacacaaaaatatgctgctacctagat  314790
tattgccagtagttataagaagggtaggaaaggaacatctcagagcattttatctcaattctgaatgttt   314860
taactaatgaaagtatccaacagattacatattgacattttttttcttttggacattttaaaataatcttc 314930
```

FIG. 11A-62

```
agagccaagtactcaagtcaatacttgtacatttctgacagaaatgtttccaagatggctttgctgacat      315000
aatggttaaagccatattggtttcaagttgcagtcctgtgtgtcatctttgggcaatcctttagtcttta      315070
aaaatcatatcttcctgatgacaatcacatttttcctcatatttgattgcttccatgacatgaaaaatcaa      315140
cacggcatctggacttacagctgaatgctttattcttcagtgcctgactcagtctgggatttacagaaac      315210
gtcaggaagtgatcgtaaatggaatgctgtgatttttacggcctgccgtctcttgtcctgttatgattaa      315280
aaatacagattttatacttctggacattcatgtagtagactgagctgatgagaattttaagctatacag      315350
aatttttactcctaaaattgcccatgcttttcaagttctcaccaagtgggagaattttcctatgtggca      315420
aaaaaataaaaaaaaaacaaaaacaaaaacaaaacaaaacaaaaaatctctgagttaccagtggatat      315490
agttttgaagaaaatgacaaaaaatacttgttagttgggtacctggttgaggattaggcatagctaagct      315560
aatgcatttacattaattcccaaaccgtaatatcttcattagacgcagggtagaaatgcatttctaaatt      315630
agcactctgaaattcattcaactggatttattttttcccataatgaagagacacctggatttgtttgtga      315700
gacaagatagcctttgatctttttactagtttaaggcctgtttttttgtttgtttattttccccttggaa      315770
atgggaatgtagttgctgttgcattttatgtatggcatctgaaggtaaggaagcaaaaatgacactaaa      315840
ttgtggaagaaaaaaagaaatcacatgtatttaccagtgcacgaaaagcctcaatgtggtttcatttcc      315910
ttaaactcgtgtgtgtgtgtgtgtgtgtagaataacattccctaaaatgaatgttcaggggggagggaa      315980
tcaaaatgaaatgggtaaaagagccctctgacagagctgaatgctactacatccagaaattcacatgct      316050
tgcgaaacaatcacagccttcattgctcagtaaaagctgtttctgtcctgcaggtttttcatttgcatgtc      316120
cgcaatttttgcacctgcagGTCTCTTCCAGAAGGCCATCATTCAGACGGCACTGCCCTGTCCAGCTGGG      316190
CAGTGAACTACCAGCCGGCCAAGTACACTCGGATATTGGCAGACAAGGTCGGCTGCAACATGCTGGACAC      316260
CACGGACATGGTAGAATGTCTGAAGAACAAGAACTACAAGGAGCTCATCCAGCAGACCATCACCCCGGCC      316330
ACCTACCACATAGCCTTTGGGCCGGTGATCGACGGCGACGTCATCCCAGACGACCCCCAGATCCTGATGG      316400
AGCAAGGCGAGTTCCTCAACTACGACATCATGTGGGCGTCAACCAAGGGGAAGGCCTGAAGTTCGTGGA      316470
CGGCATCGTGGATAACGAGGACGGTGTGACGCCCAACGACTTTGACTTCTCCGTGTCCAACTTCGTGGAC      316540
AACCTTTACGGCTACCCTGAAGGGAAAGACACTTTGCGGGAGACTATCAAGTTCATGTACACAGACTGGG      316610
CCGATAAGGAAAACCCGGAGACGCGGCGGAAAACCCTGGTGGCTCTCTTTACTGACCATCAGTGGGTGGC      316680
CCCCGCCGTGGCCACCGCCGACCTGCACGCGCAGTACGGCTCCCCCACCTACTTCTATGCCTTCTATCAT      316750
CACTGCCAAAGCGAAATGAAGCCCAGCTGGGCAGATTCGGCCCTATGGCGATGAAGTCCCCTATGTCTTCG      316820
GCATCCCCATGATCGGTCCCACAGAGCTCTTCAGTTGTAATTTCTCCAAGAACGACGTCATGCTCAGTGC      316890
CGTGGTGATGACCTACTGGACGAACTTCGCCAAAACTGGgtacgttcttcttcatgttggggtatcactg      316960
tcctcttcgcttgtttggttcctcagtataagtgttgcttctaccggcatgtgcaggagcacacatgcat      317030
gcacacatatacacatacagacacaagcttacacacacagcaataacaggcagcttctcccccatcatct      317100
gtgagaactcaaattttctttattaccaaagtgtttactcctaaaacactttagtgtcaaaccagattt      317170
ttactagatttctaattgcccattagaaattccacttgcaggtgcaggtgcagactttacacatata      317240
taatggttttgttaacagctgatcactttttgttttttgttcttactgttgttgaagagacacagtctcact      317310
ctgctgtccaggctggtgtgcagtgatacaacatagcacactacagccttgaactcctaggctcaagcca      317380
ttctcctgcctcagcctcctgagtagcttggattacaggtgactgccatggctggctaatgtttatttt      317450
tttatttttttgtagagacaagttctcactctgttgtctaggctggagtgcaatggtgcaagcatagctc      317520
acggtggcctagaaatcatgatttatttgatcctcacatctcaagcagctgggactacaga      317590
catgcaccaccatgcccttgcatggattttttgtagagacagggtttcctatgtgcccaagctgttctga      317660
aactcctggtctcaacggatcctccctcctcacccttctgaatagctgggactacaggtgaatgccacca      317730
tacccagctaattttaaaatttatttgttagaaacaggattttgctatgtcacctgagctaccacttgg      317800
ggaattgtttagattgcctgaccatatgaatacaaacaattgtcacaatatttatagagaaatataaata      317870
aatattcctatatatttaacatatatagagagaaaagaactattcccatatgtataatatatatta      317940
tatatatattgcatttgtatatatacacataaataccagtatatttctgtgtatatacatatacaaa      318010
tagtaatatatatatactatatatgcatatacaatatataatataaaatacaaacaactacaaatatat      318080
acatactatatatacaagtacaaatttatgtacatatacatatatatttgtatttcctttgctgtataaa      318150
tagatagagagcaaagaaaatatatgatatttatattatattgttatatgtcatgcatatataacaca      318220
tacacacacatatgtcacaggaaagctcatttattgacctaaatatagtagaaatatacaaaaaacaca      318290
catacaacagagactgccaatattctactgagtggattctcttcaaaccatgggagaaagaaacaaag      318360
catcctaaatagggtccaaatattgtggcatcttttaattttctcctgtctaataatgtaactatggaaat      318430
caatggagtatcattctgttctacctgtgtgtgccaccatcatccaccctgagtttctttaaactgaata      318500
gaagagcaacatgtgcatgtcacccagggagggtcaatcttcccatgtggaatgaggctctcagactgca      318570
gtggccctgccacgcatgagctgtacacagtaattctgataagatcagaggacacgattttttgtttgttt      318640
gtttggttggttgtttttttggcaaacatatagctgtttggcatgtttttgaagtggaaaatgtatcat      318710
ctggatatcaactttccaaaatcagactgtgtagatttggtctgagaatggctaccaggaggagaacaga      318780
ggagggaccaacagttgttggagatgctcgtctatcactgaaaggttcttcctgcatgaagaaatgatt      318850
taaatcaaattcatatttttttctaagtaaaccttgtttattagttagcttgggctgctgttaccagag      318920
tgccaaaatctgtatggctgtgccgggcagagtggcttatgcctgtaaccccagcactttgggaggccaa      318990
ggccggaggactgcctaaggaggtcaagagttaagacaaccctggcaacatagtgagagtctgtctct      319060
acaaaacaaatgatgccccacaagccgcaaaaccagcaagttttttattagggattttcaaaaggggagg      319130
gagtgtgcaaataggtgtgggtcacagacatcaagtacttacaaggtaatggaatatcacaaggcaaat      319200
ggaggcagggtgagatcacaggaccacggcagcggggcgaaattaaaattgctaatgaagtttcgagcac      319270
cattgtcattgacaacatcttatcaggagacagggttttgagagcaactggtctgaccaaatatttatta      319340
ggcaggaatttcctcttcctaataagcctgggagcgctatgggagactggggtctatttcaccccctacgg      319410
cctcaaccataagagatgggctcacctaggggggctgtttatagcctatacttccaggcgagtttctc      319480
tttcccagggatgttcctctgctgagaaaaagaattcagcaatattttcccatttgcttttgaaagaaga      319550
gaaatatggctctgttccgtctggctcactggcagtcagagtttaaggttatctctcttattccctgaac      319620
aattgctgttatcctgttcttttttcaaggtgcccagatttcatattgtttaaacgcacatgttctacaa      319690
tttgtgcagttaatgcaattattacatggtcttgaggcaacatacatcctcatcagctgacaggattaag      319760
aaattaaagtaaagacaacataggaaatcacaagcgtattgattggggaagtgataagtgcccatgaaat      319830
ctttacaatttatgtttagagattgcagtaaaggcaggcataaggaaattataaaaatattaatttgggga      319900
acaaataaatgtccatgaaatcttcagaatccatgttcttctgccatggcttcagccagtccctccgttt      319970
ggtgtccctgacttcccacaacactcagtattagggtgggagtgatccaatgtcccaggtgccatctgtt      320040
```

FIG. 11A-63

```
accccttctttgactaggaaagggaattccctgacccctttgcacttccaggtgaggcgatgcctcgcc      320110
ctgcttcagctcacacttggtgcgctgcacccactgtcctgtgaccactgtccgacactcccagtgaga      320180
tgaacccggtacctcagttggaaatgcagaaatcacccgtcttctacatcgctcatgctgggagctgtag     320250
actggagctgttcctatgcagccatcttggctccacctaccagtcttcatatattttatagaaccattaa    320320
aacaatagtgaaatctaaataatgctgttaaattctcattaactcctcctgactcccaaaggctatgata    320390
ctgaggctggctatgtcactattaaaaaaaaaaaaaagaaaaaaaaagatacgaaaagataaaggaagt     320460
taaatcattttatgaggtgactattatcatgactggcatcaaatggatgcttttaccaagatatcatgaa    320530
agtctgaaagagccgtgagaataccagtgatctctctgttactgagtgcttttaatgccatgaatctat     320600
ttcttaaagtcacctggtttagagcctgtgatttccaccctgcatttagggagtacattcacattgccat    320670
ttatggtctgtgttgagggtgcttctagcttttgtgaaggccctgacatcaccggaagagaggaggaagg    320740
aaaaaccactagaaccaccagagcagagattctctgatgctactcaaattaaaaacttcagatagagagt    320810
tcactgaggtaatgagagcctgaatgtcagtctgtctgaagtctctatttttgtttcttccatccatagg    320880
aaacatccctgaaataacagagtgtattaatgcagtgagttcttttgtttcattagaaatgtattagaat    320950
gactcaaatgattcatcaaggaagttactcagaacttacatgtcatgtgaaatgcatgatgtggattcaa    321020
atataaatgttttaagtgatcacacttgtttggcagccctataagagaaagaaatgaggaatttcactgt   321090
tgctagttatttgcttattgtaaactggatggtggcctgatccctccagggcagagaaagattccctggt   321160
cgtcaggtgcagagaacaaatgaaactgataccgtaaggagaaaacatgggatgtatctcatctgctgt    321230
catggtgtgacctggcaagtttaacaccattctacagagcacacactcagacaatgactcacagaaaagg   321300
agagggtatttctgcatatcctcactgttccctttccagcactggaggtgacaagaggaaacaagaatagc  321370
tcccagcgtgtctgtcagtacacagtgctgtggagagaggatcacattgtgccaagacatacttccccac   321440
tctcagtggtcatcatgtcatgtgtttaaacctgcaggcatagcacagtctcctgatgacaaatgtttg    321510
tggagatgaagtggatggtgcctggatgcttctttacagacatctcaaagcagatggttctgattcttac   321580
tatgagtttaaaagtacatataacctggtatgcatataacctttggaatttggatgatcacagaaaaatgat 321650
gttggaatgtgcatgtcaggaaaaattaggaaggggaggatgaaggggactgaaggaaggagagttgtgatg 321720
aaggaaagaagggaaggagggaggaaggagggaggagggtgggagggaaagaagagagagaggaagg       321790
gagggaaagaaggaaggaaggaaggaagggagggaatcaagaaaggagtaaaggaagggaggaagtaagga    321860
aagaaagagggaagagggagaagagaaatgaaagatgtaagaagggaaggaaggtgaaaggaaggaaggg    321930
aggaagggaaggggaggaaggaaggaaggaagaagtgagaggaagaaagtgagagaaagaagaga        322000
ggaagggaggaggaagaaagaagaggaaggaaggaaagagagattagggagagaggcaaggataaaaa      322070
tggatggagacaaaaaagaaggaaggggagagaggaaggaaggaagagagggagaaaaaagagggaatgga   322140
ggaggagaggaagaaaggattgagggaagggagggatgggtaagggaaagaagaaaaacagggaaaggga    322210
gggtgagagataaaagagggaaggggagtaggggaggaaggaaaggaagggagggagggacaattggat    322280
ccttgcttacaaatcatgtcacctgtatattttcatgttaataattaggtaagagggccctcccatcttag   322350
aaaggcagattcagcaagcacacacagtagaaatgagaagaaagttgctgcagaagctctaaaccatgaa   322420
agccttgatcaagacaggatgttgaaatcagtgaatgtcaggcctcaaataatccttgctattttttaa    322490
ttattattttgaataggaagcaagtgcccaggcctgtgcctgaggggggattctcccctgtagcaaggag   322560
gtgtttcaatgttagtccaggtcacgggactaaaatcatgcttgaagagaactgagtaagcccaaacatg   322630
caaagccattgtagaaataaggtagattaaaaccattttttgtaaatgagaagcaccatcaagcaaaagtg   322700
aaaactaactctgaggtttgaaaggggctctagagaattaaacttattttcctctaaaattatttgggaa   322770
ataggagaaaaggggtttgtctaagctgatcaataaaatgcaggtgcccattgatccaggattctctcat   322840
tttgagctctatgtggaaagagatcggcaaaaaggagtgggggaaccttggtctttttttttttttctt    322910
ccgagacagagtctttctgtgtcacacaggctggagtgtggtggtgcgatctcatgtgatatcagctcac   322980
tgcaacctccgcctctgggttcaagcaattatcctgtctcagcatcccaagtagctgggattacaagctc   323050
ccatcagtgtacccagctaattttttattttttagtagaaacagggtttcaccatgttgtcctggtctcaaac 323120
ttctgacctcatgatctgtgcaccccagcctcctaagtgctgggattataggcttgagccactgcgcc     323190
agccaaatcttggtcttttttataagatatgacaaagagcagtgctttaaagtaatcaaacaatacattat  323260
aatatgtaatagaagaagttgtgtgctattggaagtcagaaatgggaaaagagtttgtaatgggaaaatc   323330
agatcaacatgtatttcattttttatgttgttgcactgagtctgaggcttgtacatcagattgatttct    323400
atctttttgtcatcagacaccatcactgctgttgaatgttctctattctatcgataatttatattcaacc   323470
attgctaaatctgttgaggaaaaaagaagtcccaatgaagtgtttagcagggattggttacagagagttg   323540
cagcataattctagttgtaaaggtgacctttagtaccaaaaaggggattttaagctgaatgaatgaacatc   323610
ctccccctggtgtggtggaggagtcactgaatgtataataaactagtttgctaacaatgttttggatataa  323680
ggaaaacctgtactacttaaaggaacagctgagagtgttcatggatattttagagagatcatagtacta    323750
tatccatctctagctaaagaaatgaacaagaccttagaaatgcacttgagtctctcctgccaagattaca   323820
tctcaaatagaacaggtggaaatggctgtgttaggtgctaggggataaggaagacaggcattgagtc     323890
ttttactagagacaccaactagtgtttctatcctcagtcattacaatcttaattttactcacaggaatt    323960
taaacatttcttatgctgaataaaaactaaaaaaataaaacactgatatcacacatctagacctcactgt   324030
ctgcagggtttggtaagggagaatgacgtgggctgtcataatctccacaagcttatcagtgcttaagaat   324100
tctggctatgcatccctgagatctttaatagacagattacatcgggcagcagctcacttatctggatttc   324170
ccaaatcctctcctttattcttcaagaatacatgttttttattttttttaaagaacagaataaatgtt    324240
ttttcttttacctttcgaatataccctgaatccttcaaaaattgcctaatagtcaacatgaacagaatact  324310
ccttttcctagattctcactgcttagtagatgagatagccacacatctaatagacccaatttagaaaaat   324380
tggatccatgaaaaaacgaggaatcttcacttccatttgtttctttagaacactaaaaattaataacaa    324450
atattagtacgaagttttcctaaaatatttattcatttattttctttcaacacacattaagtaaaaat     324520
tttataattatttcagaaggcttaaagaagcaaaagaaacatgagatgataaaatgaatccagtgttttt   324590
tcaaagccgtatcaaaatgtatgcataacaaataaaaagcagtagacttttcaaatatatttttttatgaa  324660
taaatatgagatctcatggtattcaaacttatgtgattttatatatatatttgttttcaccctcttagta   324730
acgtgaaagcacggcagtagtgtgcattcaagtaaaaggtagaggtcaacattctttttcttctctatt    324800
acattatacatcttatatctgtatctatagatagatatacatgtacacatatgtacatatgttatacata   324870
catatatatactgcatatagtatatggttagtatacagtataaactctggtacacagtatacttatatat  324940
agtatgtaatatacagtataccattatactctataatgtacataatatagaattatagtatgtactat    325010
gatacacagtatatcactccatcactcccttagttcccccctcccttgcaatattgtaggtgttctaatttt  325080
tatattggaagagaagggataatatttcctgaattcttaccatatgtcagacattttgtcattatctttc   325150
```

FIG. 11A-64

```
aaccttcatcacgtgtctccaagcctgatattcttattctctatgtagatgggtaagttaaggccaacag    325220
tggctggaaaatttgctcaatatttcacagctgttaatgagccagagcttcagaaatttgaatacaggga    325290
cattatttcctttacgaccaccacagactcagattgaggggagaaaatcttcctttatcacatgtggcat    325360
ctctgagtcaagtatattgttcaaatcctgcacaatatctgacaatgactagacatatgctcttccttgg    325430
tcctgtagccttctgccatacaggtcaatatgcaatggttggaggcaacttcacaaaagtcccctaagg    325500
aggagttacctggaggatggactttagattacacctggaaccattgatcaggatgttgcaactccctgcc    325570
tgcctgggtctgcacattacatctcaatgctgagtactaaccattagatgacattttaccatgcacaatc    325640
tcaattttttgtaacaattaaaccttaagatgtaattggttttatagcttactttatcaaccataaggaa    325710
aggtagaaatgagaatttggtatatttgttttttgaaggggaagtgttatcttaaaagggttagttgcaa    325780
agatgtttaaaggctctatgctttatgaattatctccaaattttatgattctccttctacctctgccca    325850
cttgtgcaaataataataagataattcttcagtgtatagcttccaagcacaatttagcatctgcagcagc    325920
cctcagcttgtttctgggtgtcttatttatactaaatatgttaaccttggcgtaaatatatgtaccattt    325990
taacaaacttcttacagctgctgtaatgtgctttcatctttctggactctgtcttcaaaaattgtccac    326060
gtgtgtatgtatttcactttcaaatagagagcaaacaaatgatgcatgtgttgacttgcagctttttaatt    326130
ataaatcctattttattttgagtgttaatatcaatttttcattgctgtaactgcaatatctgttcatttac    326200
ttcaaatgcaattattgagtaagaaagagaatgcccacttgttgaaaaattcttaatcagaatttctcag    326270
cctgagtactgttaacatttgggtccagataacttctttgctgtgggggtctctccagtgcaccagaggg    326340
tgtttagtagcatccctaacctccaccccttcataggaactgccctctgtctacaaaaaccaaaaatgtct    326410
ccagaccttcccaaataccccctctggggcaaatcactcctggatgagttttgcagttcagaaacagtgaa    326480
acttgaaatactgaaattttttcccagagacacttagttttccttttattttttgaagatcatttgatgcatt    326550
aaaaaatagtaaacatgttataaaaattgaataatgatgctgtcaggattttatatttaaaagaaaaataa    326620
gagcaattttttaaaggaaaagacaacatgatagacatgcctaggatgaaagcagaatgtacctttgctgc    326690
ttgggtattttgtgctcattgataaatatatatgaagagcagattgtaacttcctgatttattggtttaa    326760
gataatttcatatcacatgtggaagaatatgacctttcttttttttcttccttctatcccagTGATCCAA    326830
ACCAACCAGTTCCTCAGGATACCAAGTTCATTCATACAAACCCAATCGCTTTGAAGAAGTGGCCTGGTC    326900
CAAGTATAATCCCAAAGACCAGCTCTATCTGCATATTGGCTTGAAACCCAGAGTGAGAGATCACTACCGG    326970
GCAACGAAAGTGGCTTTCTGGTTGGAATTGGTTCCTCATTTGCACAACTTGAACGAGATATTCCAGTATG    327040
TTTCAACAACCACAAAGGTTCCTCCACCAGACATGACATCATTTCCCTATGGCACCGGCGATCTCCCGC    327110
CAAGATATGGCCAACCACCAAACGCCCAGCAATCACTCCTGCCAACAATCCCAAACACTCTAAGGACCCT    327180
CACAAAACAGGGCCCGAGGACACAACTGTCCTCATTGAAACCAAACAGAGATTATTCCACCGAATTAAGTG    327250
TCACCATTGCCGTCGGGGCGTCGCTCCTCTTCCTCAACATCTTAGCCTTTGCGGCGCTGTACTACAAAAA    327320
GGACAAGAGGCGCCATGAGACTCACAGGCACCCCAGTCCCCAGAGAAACACCACAAATGATATCACTCAC    327390
ATCCAGAACGAAGAGATCATGTCTCTGCAGATGAAGCAGCTGGAACACGATCACGAGTGTGAGTCGCTGC    327460
AGGCACACGACACGCTGAGGCTCACCTGCCCTCCAGACTACACCCTCACGCTGCGCCGGTCGCCGGATGA    327530
CATCCCATTTATGACGCCAAACACCATCACCATGATTCCAAACATTGATGGGGATGCAGCCTTTACAC    327600
ACTTTTAAAACCTTCAGTGGAGGACAAAACAGTACAAATTTACCCCACGGACATTCCACCACTAGAGTAT    327670
AGcttttccctatttcccctcctatccctctgcccctactgctcagcaatgtaaaagagacaaataagga    327740
gaaagaaaatctccaaaccaggaatgttttttgtgccactgactttagataaaaatgcaaaagggcagtca    327810
tcctgtcccagcagaccccttctcattggcatttccagtattgtgagatcaatttctgaccatatgaaat    327880
gtgaaaagtatatgtttctgttacaatactgcttaagatctaaaacccatgccaacagatgtttcgtgtga    327950
ctaggacatcaccatttcaaggaactgtgtgtttccaacatcatgtgtagcagcacacacttccaaagctc    328020
agccaggacacttaatatttttttaattacaatggaaatttaaacattttttatgtgggctacacaatgga    328090
tggctcttcttaagtgaagaaagactctataggcttttacacagcacatgaagcagtaatccagaaagaa    328160
ggaaatgcagaatttttattatcaaagtaagcgaattgactgtgcagaaaaattgtagggttctgtggaag    328230
gaggtattctgccagcctgaactatatttaagaaactttgtaaaaaataaaaatgtatatagctgtgagc    328300
tcaaacaaaaactgcagacaaacaaaaaagagaaaagcttttatttgttttcagtttgaaagaactttt    328370
tagcaaggttgtgctttcaaacacatattagtcctaccaccttagttcctctacagcaaaagaggcttt    328440
cttcttaattacatgtaaacaaagacatgggattttctgacgtaagattttcatttgtaggaatatgtga    328510
tgtcaaatggaagactcagaagttttgtgtggcctatttctccctgtcaggttgcacagatgcatgtaga    328580
gcattcttaggagaccattgttttagaaaactttgatttgtacatgttagttttcatgaaattgcaacac    328650
agagataggtcctaaaagtggaatgtatttaaaacttgttgaattagacacacacacagacacacaca    328720
aagaatcagcagagaaaacaaaatacaagtcctgttctgtagttcttgcccctttgaatatatttgggaag    328790
agttgcttcctatttcaggaccctgccaaaaaagaagaaagcttgcctttggtggggctatgccccttgg    328860
agtaaatacagctctgtgttccctagcagctgccggagggatttggctgatgaagtacctgctcagcttag    328930
ctaatcagattaaaggaagacatgtatgtcttttgtttaagcacctagtcccttatgtatcagtaaacag    329000
gtttttaaaaatctttttatgtcattttataggataaaacatatgcttgtctgaaaatataccctttttgtga    329070
atttatctgatcaccaaataataaatattaagaagaatgggggaaaaggatagaatattaaaactgctt    329140
tgcataggttttggggaaattaggatatcttcactgacaagacactgaatgaatttattcacccattt    329210
taaattggttacttggggatcagagatttgtctctccaacagcttgtggttttcttattactcattttca    329280
ggaaagtttgtagtattacaaggcagaaggaaacacagtagcaatggttgctctatattttgtctttcaa    329350
agattactgcattaccaagaaacagtagccaaagatgtttgaagatcagtgtccctagctgcattgtgag    329420
ttattctagaaatccaatgttaaatgcctctactaaagtggggattccccataaaaattgtccagctacc    329490
tgactcttttgcaataacaactttgattactgaatccatacactcaaactatagtgatatatcagtgttt    329560
gggagtgacctctagaaaaaagaaaactgttttagaaatacataaaatcacttccaaatcctgttgctt    329630
atgttgggttaaatttgaaagcaattctctatatataaatatgtgaaatattatgatctgaacttagcac    329700
acatgaagcaacatttcttttgctacacagaggtgtcttggaaagatttcattcccaattcattttttcata    329770
gatctataatcaggcaatttctgcaagcaatgtatgaccccacctgagcaaccacaaataggctctccat    329840
gaaactgcaaaggaactgatgtgtgtggcatccatgctggtttttgtctgtctataatatgaattcaagtatc    329910
tgttcatatttccaattgtctcctgctagcaatatgtgccacaacatgacagtcttgtgacatcttaagg    329980
aaaagaagagttcctgttaaatgaatagctttagcttttacaggggattatgattaaagtgatttagta    330050
catcttacatgatatctcatttctacgtgaaaagaagttatagaatcttcatagagttccatgagaaaaa    330120
tatacttgctatttatgaaaacgagaaaaaagaaaaaaatgagaaacaagtaagaaaaaatccttttcct    330190
aggcttttccttgatcttcagaggcacacaggggtttaatggttccttaggttattattttgaggttttgt    330260
```

FIG. 11A-65

```
tctttcttttgccttaagtaatgacagaagatatatatggccagacacatatgtataaacttttcagcag    330330
cattttaataataaaatatcacactattttctaatgctttgtacaaacaattatgcatctgttcttctt    330400
ggtaggtggaatattttattttactttttgccattcttttgaatgccttttctttgtaaatgctacatggta  330470
gctctcacataggctacaaatggataaatacatttggtaatgggatggtttctttagctttggccagctg    330540
cacagttgaggaggctctgctggcctgattttggaaaaccaagccctgtttggtgaagctcctgagatga    330610
cactgcctgaaaatgagtatttggttgtgttatttctaccactgttcattcttgtgtctctgtgttttga    330680
tttgtgttcaacaaactgatgccttaatggtttcaaatagaaagccttaggtgagtaaaccttctagtga    330750
cagtaagaaattctactgaatgaaactccagaggcagaaaatcattgtcattccaatgggagctcaattg    330820
tcaattccttcctgtgcattcagccatcacgaacttatttcacattcacagtagctctaaggggcaggca    330890
cctgcattactccccttcataatgaagatgttctgactttgaaacatgccccttggacaggaaaatt     330960
tgatggataacaggatagcatatcctcatatcccaatctttcaccaagaagttatacagcaaacacttgt    331030
aagtcaaggtcttgcatgataatctttgctaagtagcaagtaaagaaatatagcaaggacccagactctt    331100
tggaatatgtgaactaaatccttcagatgttgttggcctcaatcatgttgtgaaggcacacaggagaata    331170
catacacacacatatgcatatatgtatatatgtacatgtatgtgtacattatatatgagtatacatgtac    331240
ctatcctatatatgtatgtatgtatagagtcacagactgcataatgttttggacaaatatagatcacata    331310
tatgatgatagtgtcttgagattaaaataccatgtttttattgtaccttttcagtgttcagatatgttta    331380
gacaaacaaatgcttatcattgtgttacagttgcctaaggtcttctctccagtcacatgctgtacaggtt    331450
tgtagactggaagaactaggctataccatagagcctaggtgtgctataggctacacatcggttttgtgta    331520
agtatactacatgatgtttgcacaatgatgaaattgcctaacgaaacttttctcagaaacctattgatac    331590
atgactgtgtatgtttacattatatatactgtatatgcacacatgcatatatgcatatatatgttataca    331660
tttacatatgtacatggatatcacatactttaaattcctgaagatgtcatttttcattaaatacatatgca    331730
cacacactcataaacacacacagactcatatatacacacaaatctataacacatttgtgctcacatatac    331800
attcctctgtgtgtgtgtgtattacattactgcttttatctgtgaaatcacattctgcagtttcatt      331870
tactgtgatcaactatgatctaaaaatatatggaaatctcaataagatattttgaaagaaaccacattca    331940
cataacatttatgacattataattgttctattttattagctattgttcatctcttactccatctacttta   332010
taaattaagcttcataataagtgtgtatatttaataaaatatatagtatataaagggtttggtactatct    332080
gtggtttcaggtatccactgggagtcttggaatgcattcttttggaaaaggagcgttacactatatact    332150
tacatatagacacagatgcatatatacacatatacataatttacatatatagacatattcgcagatatgaat   332220
gtacttaaatctctaagaatggcactttattaaatgtacacaaataaacattgtatacacatacatatat    332290
atatatatatatatatacacacacacacacatttaactgaatgtcatcttcaggcattcaaagcctaatttt    332360
tagcaaatttcagctggagggagaatcactcttgttttgactattttatgcattcttgttcattttgaat    332430
aactcaaggaatgctaaaaattatatgcatccattcagtgaaactttactgaatatcttcactgcctcag    332500
gccctgtgctgggctggtgttaaaattgaagaacaaacttctcacaccacaaaacttgaggggaaggcag    332570
agaaacacagaagcaaggagaggcaagggtgctggcaccatgttaataagggtgtcctgaagtca        332640
atgtctggacactgcccttaacctagtctgggaagatcaggaatacattctgtctgaagaaaccctaag    332710
ccaggtcttctccaactctgtagaaaaaatactagtggggtggtgtgttgtggggaggatagaattacacat    332780
ctttgaagtaagaagacagacgaagacataggaagacatggctcctgcatcatgggtgaaaaatataagg   332850
tgtttttagaaaggtgtgaaaaatgagacagaaagaaattggctgataaaaaacctccaacaaatgaga    332920
cagaaaggaactggctgataaaaaaacctccaactgcaagacagggatttgggcttttgtcctgaagtca    332990
attgagagacaccaaatgattgcaccaaagtggattatgagtgtatttagttgagacatttagcagtaat   333060
tctcaaaagttcacatgcttaggaatacacgggatgtcaacttaaagtacagatccttactgaattgtgg    333130
tttggtgaacctgtgtctgaatttccaagacgatctctaagtgatgcacttgttgctcattctcaattaa    333200
ccccaacttatttaggttgcaaaggatggagaactgttcactttagaagtaaccatgaggataatctgca    333270
ttggaatgagagggttctggatgcaaggacaacattaaagagccaggacaatcagaaattaattactgtc    333340
ctcttttaagggtgatggagaccgtaataagacaagaagtaaaaaagaaaaaaaaaacgataagaaatg    333410
catccttatagctgcatgtaccagaactgataaagcgtagtcatcaaaaaccacctggaaccacatttgtc    333480
cttaagcttttgtttaggaacttgtttcaacagagagaggagaatgatgagataccttggagagagtttc    333550
agacaggctggtcaaggtttgggcttagactggggttgttttataagtgctaagagggccaaaaacttgt    333620
tcctgcattggttactgtcatgataatggggatgtcaatatcctttagcaagaaagtgacaggaccagag    333690
aatgactagcattgtcttcagtaaaaataagcagtggaagagaagggggatttggggtcattttcagtgtt   333760
tccagactgttcatgtttctggcttgtcccatgctggccgtgggctgccttcatctaatgaggaagttcg    333830
ttcaattattttttatgtgcagccagatgcacctgacttagcaattaattatcaggctaattctagcagc    333900
cagatataagggctgtttttttgttgtttctcagaacttccaggaaatatgcatatgtcacatctccta    333970
ggccacctggttcaaaaaaaaaaaagttatgctaaggaagtaaaagtgatacttttctctgcaaaatctt    334040
attaatatattgaaagaaattgagatataaaaaaggtccactgtacctctaccttttctctaaaatgatca    334110
tacatgtaaattcttagaacacccacaaataatctggtttcctctactggcaaaagaattagaaaaaaaa   334180
aaatgagaaaattagccaggagaaaaccctgcctgaaattaacaggtgacattcattaaagtggaatgt    334250
tccaactagttctcaaagtcactgattcctaaaagggccggagagggagtccttggagactaagacaaat    334320
tgccaacagccatagctggaaggttacaaaaaagaaaatcttctcaccccgggcccctaaacacaaga     334390
acttggactcagcagaaaggaagtgggaagatgcatttctggcaccaaaatataaacctaacaactcc    334460
tgtaaaaactgagaaatcagatggtgcccaatttataatattagacgccactattacgcttcagtggtaca   334530
attggtcaaactggtttcttgtgggctcagatgttagcttcatttttatgcaacacctgtttctacaagt    334600
atatacgttatgatcacagctttcaaactaacatgcttggcctgcctgggttattggatgttatttctag    334670
tatttaaagagcaattacagttttttagattataataatagaaaagcacataacaatttataagtatatgc   334740
attacctacagacaaacttttcaaataaatgtttaagagattttgtaaaagcattgattcaaccatttac    334810
agagcaatcacttgtttcaagttttaaaactttcagataatcatcaaaatgtattgttctgcgtaagtta    334880
tatgcattaagtcatttaatccttttactagttccagggtgcagactctcattttacagatgaggaaact    334950
ggggtacagaaaattaaataaattgctcaaggttgcagacttagaacataaaattttatagcgttcacaat   335020
catattgttttgtttttaagagcatgtgcttgtcaactattctctaaaaaacctggttattgcagaaata    335090
tatgcctccctgtagacattttggggaagaaaaaaatcactataatctgtttgtagagaacattgatagc    335160
tttatatcttaaaaacttgtcatgtacacacacacaaac                                    335199
```

FIG. 11A-66

```
aaaaaaaaaaaaaaaaagatccaccacaagcctgctatttctgaatttaccttatctttttttttctttcacattaagac
tataattatgatttcaacttcctcatctgattcccagtcatgaatctatctaacatattcagctgaaggctgtcaatgtt
gtactgattccaaaatgcaatgatactctcccattttccttcactcctaaaatctctgaagactgtgacacaattgactc
ctgcctactccttgagaaggttacaatcctccttgaattccatgccatgttttctcttgccagagatctttgcagatgg
gacaatgaccctatttcaggttgctatcaagaccctacccagtgtcacttcctccaaagatttgccttttccttttaagtg
aacgctttctctattttacaccaaaatgttaagtatcatatccacagggtttgtgctcagatctacagatcctactttaa
gatccctattcagatcaaatctcctctcccaaagatctcaggtctgtgggtcattggtatttctatgatccacaagcatc
tcatttttcttcccatacaagtgactttgggtgaatgcactatcactcatcatatccttcccatagcaccacatcaaagc
tatctttagtctttctcattttagggctccatcccgttttactcaacttttgcaactatgcatatagtcaaatgccat
ccatagtgaaaaaaatttactactactctgaaatttccctattactgggtattttcactactaatatcctaatttatgaa
tgctgcagtatcactgtcctcttttgttctagaatgtcccggatcttaaattccctcagagtaaattctctgaaaggtaa
tctctgccaccatcccccactaacaccaataaggattccagtcaatgaatattcataatcctctgtagtccagccttctt
attctcctctttgaatcacaagaacctacaagtagctcaccaccattcctgttctcagagtttaacttgagtattatcta
ataaaacaacctcatgtagcagggtggccccacatattcaggttcccagaactcactcgagacctgtgaagtttgaatcc
tggtgtttagctctagaggcatggattttgtaaccatcttcctgggtcatccttgttgaccttgaagttccaaagcctct
gctcactccatatctatttctcttctctagatattattaacttggaataatttcccatatctactctccaattccccaga
aaaaacttgttctgtgaaccttttctcatcatcccaataggatgcttgttatgccttctgtatgctttggagatggcat
atatcacacattgagttgcattttaataattgaagagtttaattattcccttattagattttaagcatcttttatgcta
tacatatttatctttccaataatgattaataacatagtatatattattattgcactaacaattatcctactgaaaatatt
tgtttcaatttgaccattgtattaggagagtcaataggaatcagtagtgcccctatagtgtatctggcttcaccagtattg
tatttcgagttccacatattgatcccataggagcattaacataatagtatgtatgaatgtatgtatgttcataatagtat
gaacataacagtatgtagaatgtagttgatgaagacactgagatgaaaatcagagagaacaagtaatgtggtatagatt
atgtctcatgtttcatccagttctttgtaccaaacccagcttatatatccttctaggaaccctactgttttatttcattt
tatgaatcctcctagctcccacatctcaccatactccacaattagatttcaagtggaaacatgaagaatgatatccttat
ctcttccaggaattcagaatttaaacctccgaagctcttctgtctgtatcgtaatcctgtggctcagttgttaagaactg
gtgttttaggttcatcctggtcacttatgagggattttggattagggaaaattataaactcataatatcttatattcac
ttttcttataagcatgattccatttgtctaagatgctttcttaatttttttttttttttgagggagggtttcattctgca
acacaggctggggtacagtggcatgatcatggctcactgcagcctcaacctctctggctcaagtggcccaaccttcagcc
tcttgaatagctggtaccacaagcatgcactaccactcttattttaattttttggtagaaacaggatctcactacattgc
ccagggtgatatcgaactcctgggctctagtgttcccctgcctcagcctcccaaagtgcagagattccaggcatgatcc
actgctcctggcctttttttttttttaagaaattaattaattaattttaaaagtcttagtgaagtaattcagacagaa
gtgacttgtctgctctctcccaggtcacatgtctcagggaagagatctgctacccaaccaatgcacccacaaactaagcc
aagcattcagattttgcccaaaatctccctcccaatctcactttatcatgctgccttaaagtatttagagttgatgtctc
cccacagcaatctccactcccttcccttcccctctccctcccctcatctcccctgccctccactcccctccacttcttt
tctgtcccttcttttctccttttctctctctgtctctctcattcaggacttgatttgtcacagccattcttgc
aacaaccttacaaacattttctttgctttccacattggccctcttcaactagttctccatgttgccatcacagtgattgt
cctaaaacataaatctgattatttcttcttccctcactgcagaaaatgtgttattggctttcccactgcctactggataa
attccacctttcagcatgacatttaaaactcttcacaattaggtctctaatcctttcctcactaccttcttttcaaatt
caatgtcctgccatgccaaaccctcccctatttctagatctccacacatacagtattgctgcgatgtctttagcccatggct
tcttttcaacttcttcaaccaatcagtgtcgatgtaccattccttccctactctgaatgttcttcctttgcaaacccctt
ggttaattattttaacctctatgggtccctattaatttatatgtattccttgtacacaccttcctgtaatcacattttttt
tctcatgcttttcattatcttgtctactataatgtatgctttctcaaaaataaatggataagtctcactcacagttacat
gtctgtgcttaggactgtgtcagtgctaaaaaaaaaaaccctgaacttatgaataagtcaatgaattaatacattcttg
gcaaagtccatgactttgtggcctattataaattagtgtgttcaagttgaggttctggttttagtttaggacatagatatc
tatatatagtccatatatctacatatatatgtctacatccatgtatatcactgatttgggggataagctgtatttataaa
caatactatcatgttaatgggtcttcaatatctacacaataatggaaaaaagtatatgtatatttctaaatatctaatgg
gaacacacacacatatatgtatgtatgtatatacattttttctattattggctatagatatcttttaatagataagtgtat
atctatgtaccaatcttgttggcaaaggatgctttcatgcatattatctcatttagtccccacaaggaaaagcaacccac
aggaaaggtaataataatgtcagctcaacagagtcacagaacataactgactttatgacaaggcaaaatttgtgaggata
```

FIGURE 11B

```
gagtcttaacatgaaaccaggtccccagattcatgtccatcatcttccccattattgctcatgttgtccaaaatccttcg
catcatcatggaaggcttcatgcttaggtttacttcctaaagcagaagcaattaggagaatgtcctatgtgttgtggaca
ttatcttttttccttccataaatgaattaatgggcaatgaaataattttaagaaaagctaacttttatagccaggtagaa
taaaagtaatcaccatgaaatattgtgaagataagcaggccccacacactagctcagctaatcaatatgacaatattaca
tggagattatctgttccatttttacagatgcagaaatggaggcgaatattaaaattcattcctaaggtcacatgcaactta
aacccaagcaatctcattttagaatctgtgttcattgccacaacattctatgatgtactctgatctttgcattgccaatt
taaatccaactttcttgaagccaactttaaatactgggaactttaagcattgtcaatttcaagccaactttctccaaccc
aattttaaatacaggggtcacaccctcctcctcgcccccctgcaacttgaaactccctgggaaagataacctcctggacct
gggaaatgaggagtatttagaaacaactgcctcttggtaagcacacctcctatattttatccaaatcatgaaattataac
aatagaagtaaacaaaaagccttcattcatcctctttcaaccataacctcggcataaaaagctcctgtactttacagagc
tgtattccaatttccgctgctcttaaaattttttttaatatcattgcttcccaattgactcacaataacgcagacatagg
gactgctggagactgtgaccttaaacagttaaagatgtctgcatatacgacatcatgtttggtgtggagagtacctagag
attcctaaaaaagcaaagaggaagaaggtttgctgtgcgcatctgggtaccctgctctatctccagggttcccaggatct
ctctgttacagctggtttgcactggattagttgctctttgcatgaggttgtagctgtggacgtgggttttgtagcgatt
gggacgactctggagatctattggctgctgggtttgtaaatttcattcattttggtccaatggcagaaggagagcgccgg
aagcagaaggacctctctcccctagctctctttttcttgcagagacatctttctcccatctctgtctgttagtacagagc
tcttattcagccactagctcggcctttcctgcttcaattgtaatgcttgttctgcccggggacacactattgacagcaga
aacaatgaatttcctccaaacccggcaaTGTTGGTGGCTCTTGCATTCCTCTGGATGAGCGAATCTAGTTGGGGGGTTCC
CGAAGGGGAAGGCGCCTGGGCTTTCAATACATCCTCCTGAATCATACTGCGTTTCAGGTTCCTTAGAAAAATTTGGATGT
GTAAAAAGAACTCTTAACGGCGATGCAGGTCTTCCACAGCTAAGgtaggtgcagttttaagacgtgtctttcgcatatta
ttatccttatttaaaaagccgtttaaacaatttgacttgcagtggctctccagcaaaggagggaaagcctcactggcga
tatttgagcttcatttcatctaatatttatttattttttcctttattattattattattggacaatttgggctggactc
tctcccatctgtctcgctccatttctttggtgtggatgggaatgtggacatcgatgtatggcttttacatgcaatctctc
cacaggaacatttggttttatttcacttaaaaataaaaatgcagaccaccaatgttgtttggaagcattttgctgcaat
cagctgtttgaacagctctggggccatgtgcggtgtgtttaaaaagtagcgctgccttccatacaaattaaaggaagact
gtggcggggaaaggaggggaaaatatatatatatatacacacagacatatatatgcgtatgtgtgagtttgtgagtgta
cacatacacacacacatatatatgtacacacacacacatacatgcagtacaggggaaaaggagggaaaaggccagggc
tggagatggcgaaagcaggaggacttctgcaaactgtgagcatgaaggcttttcttctcttttctccccactccaaagc
cctcgtcttctttaagaaaaccaccactgcctggggtgcttcttttgggaggctggggttgggggttggtgccattaacc
agagagaaaaggggaaataaagcttggttggggttgcattatgagattttttttccctTCCTTCATCTCCTGGCCTCGG
ATAAGATAAGGCTTGGGGGATGCACGAAATAATCCAAGTGATTGATTAGACCTGGCATGGCTTGGTTGGGCTGGAGAAAG
ATCGGGGCGCGCTGGAAACCCCGCGTGAAGATGAAATGACTgtagctccgtgctgctcctccaaactcgggagcggtatc
catgcacccctttcccgtgtgtgtgggttacgacgtgggtgggagtggtgaggcaagccgcaaaagtggggtagagctgg
tggttttgcttcttcggaagcctttgagtgtggcctggaccttagatgggggtgcagggcggttttgccgctgccaccctc
ggcaccatctctgaactgcccgcttttccggaggagcggaaaagttggaagccgaaaagacaggcgcccggagccctggt
ctaggtatcaggtgatccggagccctagtcggtgcccactaagaacacccttctcccatcggggttcggaggagtgtt
aagcctgcgggtctgccagtccctaaggtagggatgggggagggggtctgaggaatccgttccaataggcacaccatcccc
acagccctagaaaaggcaaccaccaccgctccttcctcccgcaccatcccatctcaaggctctctgctgacccgggccg
atttcatctggtctcttctccccgcttcccacctcccaattcccgcgcagctcggctccgttccctcccactcccctag
gcggaactgaaagcgaagatcagccaagagcacagtcggaggcggcagagacggtggcgggtgagctaggggctgtgaga
cgaagcagggagagagtgaacttcagccccgtcccctcccactgccacggctggggcaacccaaccgcgcctgaagcg
gcttggcttgacctgcggaagcgcgggccgggatggcgtggggagagggaggtaggtgccactgggctgcagatgacgag
tggggttgggggcttgctgtgggacaagaggttcaggttccggcctgc
```

FIGURE 11B(continuing)

>HNL4Y cDNA (SEQ ID NO:5)

Exon 1 (1-153)
Exon 2 (154-724)
Exon 2bis (725-784)
Exon 3 (785-937)
Exon 3bis (938-1048)
Exon 3ter (-)
Exon 4 (1049-1234)
Exon 5 (1235-2024)
Exon 6 (2025-5338)

ORF (253-2871)

```
ttttttcccttccttcatctcctggcctcggataagataaggcttgggggatgcacgaaataatccaagtgattgatta
gacctggcatggcttggttgggctggagaaagatcggggcgcgctggaaaccccgcgtgaagatgaaatgactttttcga
aagacttatctttctgcaggctcgcctctgagctttgtctccttggagccacctcacttagacagcttcggatgtggatg
cagatttgaaccATGTTGCGTCCCCAGGGACTGCTATGGCTCCCTTTGTTGTTCACCTCTGTCTGTGTCATGTTAAACTC
CAATGTTCTTCTGTGGATAACTGCTCTTGCCATCAAGTTCACCCTCATTGACAGCCAAGCACAGTATCCAGTTGTCAACA
CAAATTATGGTAAAATCCAGGGCCTAAGAACACCATTACCCAGTGAGATCTTGGGTCCAGTGGAGCAGTACTTAGGGGTC
CCCTATGCCTCACCCCCAACTGGAGAGAGGCGGTTTCAGCCACCAGAATCCCCATCCTCCTGGACTGGCATCCGAAATGC
TACTCAGTTTTCTGCTGTGTGCCCCCAGCACCTGGATGAAAGATTCTTATTGCATGACATGCTGCCCATCTGGTTTACCA
CCAGTTTGGATACTTTGATGACCTATGTTCAAGATCAAAATGAAGACTGCCTTTACTTAAACATCTATGTGCCCATGGAA
GATGGAACCAACATAAAGAGAAATGCAGACGATATAACCAGTAATGACCATGGTGAAGATAAAGATATTCATGAACAGAA
CAGTAAGAAGCCTGTTATGGTCTATATCCATGGGGGATCTTACATGGAGGGAACCGGTAACATGATTGATGGCAGCATTT
TGGCCAGCTATGGGAACGTCATCGTTATCACCATTAACTACCGTCTGGGAATACTAGCACAAAACACCCTGGCTCATGGA
AACTGCAAGCATCGTTGTCAGCTGCACCTGCAGGCACCACGGGATTGCAAGTCAGCATACCCTTTCAGAAATGAGGATGA
AATTAGAGGGTTTTTAAGTACCGGTGACCAGGCAGCAAAAGGCAACTATGGGCTCCTGGATCAGATTCAAGCACTGAGGT
GGATTGAGGAGAATGTCGGAGCCTTTGGCGGGGACCCCAAGAGAGTGACTATCTTTGGCTCGGGGGCTGGGGCCTCCTGT
GTCAGCCTGTTGACCCTGTCCCACTACTCAGAAGGTCTCTTCCAGAAGGCCATCATTCAGACGGCACTGCCCTGTCCAG
CTGGGCAGTGAACTACCAGCCGGCCAAGTACACTCGGATATTGGCAGACAAGGTCGGCTGCAACATGCTGGACACCACGG
ACATGGTAGAATGTCTGAAGAACAAGAACTACAAGGAGCTCATCCAGCAGACCATCACCCCGGCCACCTACCACATAGCC
TTTGGGCCGGTGATCGACGGCGACGTCATCCCAGACGACCCCCAGATCCTGATGGAGCAAGGCGAGTTCCTCAACTACGA
CATCATGCTGGGCGTCAACCAAGGGGAAGGCCTGAAGTTCGTGGACGGCATCGTGGATAACGAGGACGGTGTGACGCCCA
ACGACTTTGACTTCTCCGTGTCCAACTTCGTGGACAACCTTTACGGCTACCCTGAAGGGAAAGACACTTTGCGGGAGACT
ATCAAGTTCATGTACACAGACTGGGCCGATAAGGAAAACCCGGAGACGCGGCGGAAAACCCTGGTGGCTCTCTTTACTGA
CCATCAGTGGGTGGCCCCCGCCGTGGCCACCGCCGACCTGCACGCGCAGTACGGCTCCCCCACCTACTTCTATGCCTTCT
ATCATCACTGCCAAAGCGAAATGAAGCCCAGCTGGGCAGATTCGGCCCATGGCGATGAAGTCCCCTATGTCTTCGGCATC
CCCATGATCGGTCCCACAGAGCTCTTCAGTTGTAATTTCTCCAAGAACGACGTCATGCTCAGTGCCGTGGTGATGACCTA
CTGGACGAACTTCGCCAAAACTGGTGATCCAAACCAACCAGTTCCTCAGGATACCAAGTTCATTCATACAAAACCCAATC
GCTTTGAAGAAGTGGCCTGGTCCAAGTATAATCCCAAAGACCAGCTCTATCTGCATATTGGCTTGAAACCCAGAGTGAGA
GATCACTACCGGGCAACGAAAGTGGCTTTCTGGTTGGAATTGGTTCCTCATTTGCACAACTTGAACGAGATATTCCAGTA
TGTTTCAACAACCACAAAGGTTCCTCCACCAGACATGACATCATTTCCCTATGGCACCCGGCGATCTCCCGCCAAGATAT
GGCCAACCACCAAACGCCCAGCAATCACTCCTGCCAACAATCCCAAACACTCTAAGGACCCTCACAAAACAGGGCCCGAG
GACACAACTGTCCTCATTGAAACCAAACGAGATTATTCCACCGAATTAAGTGTCACCATTGCCGTCGGGGCGTCGCTCCT
CTTCCTCAACATCTTAGCCTTTGCGGCGCTGTACTACAAAAAGGACAAGAGGCGCCATGAGACTCACAGGCACCCCAGTC
CCCAGAGAAACACCACAAATGATATCACTCACATCCAGAACGAAGAGATCATGTCTCTGCAGATGAAGCAGCTGGAACAC
GATCACGAGTGTGAGTCGCTGCAGGCACACGACGCGCTGAGGCTCACCTGCCCTCCAGACTACACCCTCACGCTGCGCCG
GTCGCCGGATGACATCCCATTTATGACGCCAAACACCATCACCATGATTCCAAACACATTGATGGGGATGCAGCCTTTAC
ACACTTTTAAAACCTTCAGTGGAGGACAAAACAGTACAAATTTACCCCACGGACATTCCACCACTAGAGTATAGctttc
cctatttcccctcctatccctctgcccctactgctcagcaatgtaaaagagacaaataaggagaaagaaatctccaaac
caggaatgttttgtgccactgactttagataaaaatgcaaaagggcagtcatcctgtcccagcagaccttctcattgg
catttccagtattgtgagatcaatttctgaccatatgaaatgtgaaagtatatgtttctgttacaatactgctttaag
atctaaaccatgccaacagatgtttcgtgtgactaggacatcaccatttcaaggaactgtgtgtttccaacatcatggta
gcagcacacacttccaaagctcagccagggacacttaatatttttaattacaatggaaatttaaacattttatgtggg
ctacacaatggatggctcttcttaagtgaagaaagactctataggcttttacacagcacatgaagcagtaatccagaaag
```

FIGURE 12

```
aaggaaatgcagaatttttattatcaaagtaagcgaattgactgtgcagaaaaattgtagggttctgtggaaggaggtatt
ctgccagcctgaactatatttaagaaactttgtaaaaaataaaaatgtatatagctgtgagctcaaacaaaaactgcaga
caaacaaaaagagaaaagcttttatttgtgttttcagtttgaaagaacttttagcaaggttgtgctttcaaacacatat
tagtcctaccaccttagttcctctacagcaaaagaggcttttcttcttaattacatgtaaacaaagacatgggattttct
gacgtaagattttcatttgtaggaatatgtgatgtcaaatggaagactcagaagtttttgtgtggcctatttctccctgtc
aggttgcacagatgcatgtagagcattcttaggagaccattgttttagaaaactttgatttgtacatgttagttttcatg
aaattgcaacacagagataggtcctaaaagtggaatgtatttaaaacttgttgaattagacacacacacacagacacaca
caaagaatcagcagagaaaacaaaatacaagtcctgttctgtagttcttgcccttttgaatatatttgggaagagttgctt
cctatttcaggaccctgccaaaaaagaagaaagcttgcctttggtggggctatgccccttggagtaaatacagctctgtg
ttccctagcagctgccggaggatttggctgatgaagtacctgctcagcttagctaatcagattaaaggaagacatgtatg
tcttttgtttaagcacctagtcccctatgtatcagtaaacaggttttttaaaaatcttttatgtcatttataggataaaac
atatgcttgtctgaaaatatcaccttttgtggatttatctgatcaccaaataataaatattaagaagaatggggggaaaaa
ggatagaatattaaaactgctttgcataggttttttggggaaattaggatatcttcactgacaagacactgaatggaattt
attcacccatttttaaattggttacttggggatcagagatttgtctctccaacagcttgtggttttcttattactcatttt
caggaaagtttgtagtattacaaggcagaaggaaacacagtagcaatggttgctctatattttgtcttttcaaagattact
gcattaccaagaaacagtagccaaagatgtttgaagatcatgtcccttagctgcattgtgggttattctagaaatccaat
gttaaatgcctctactaaagtggggattccccataaaaattgtccagctacctgactcttttgcaataacaactttgatt
actgaatccatacactcaaactatagtgatatatcagtgtttgggagtgacctctagaaaaaagaaaactgtttttagaa
atacataaaatcacttccaaatcctgttgcttatgttgggttaaatttgaaagcaattctctatatataaatatgtgaaa
tattatgatctgaacttagcacacatgaagcaacatttcttttgctacacagaggtgtcttggaaagatttcattcccaat
tcatttttcatagatctataatcaggcaatttctgcaagcaatgtatgaccccacctgagcaaccacaaataggctctcc
atgaaactgcaaaggaactgatgtgtggcatccatgctggttttgtctgtctataatatgaattcaagtatctgttcata
tttccaattgtctcctgctagcaatatgtgccacaacatgacagtcttgtgacatcttaaggaaaagaagagttcctgtt
aaatgaatagctttagcttttacaggggattatgattaaaagtgatttagtacatcttacatgatatctcatttctacgt
gaaaagaagttatagaatcttcatagagttccatgagaaaaatatacttgctatttat
```

FIGURE 12(continuing)

>HNL4Y protéine (SEQ ID NO:6)

Signal peptide (1-43)
Esterase domain (44-654)
Transmembrane domain (732-753)
Required for binding to PDZ domains (871-873)
Extracytoplasmique domain (1-731)
Intracytoplasmique domain (754-873)

MLRPQGLLWLPLLFTSVCVMLNSNVLLWITALAIKFTLIDSQAQYPVVNTNYGKIQGLRTPLPSEILGPVEQYLGVPYAS
PPTGERRFQPPESPSSWTGIRNATQFSAVCPQHLDERFLLHDMLPIWFTTSLDTLMTYVQDQNEDCLYLNIYVPMEDGTN
IKRNADDITSNDHGEDKDIHEQNSKKPVMVYIHGGSYMEGTGNMIDGSILASYGNVIVITINYRLGILAQNTLAHGNCKH
RCQLHLQAPRDCKSAYPFRNEDEIRGFLSTGDQAAKGNYGLLDQIQALRWIEENVGAFGGDPKRVTIFGSGAGASCVSLL
TLSHYSEGLFQKAIIQSGTALSSWAVNYQPAKYTRILADKVGCNMLDTTDMVECLKNKNYKELIQQTITPATYHIAFGPV
IDGDVIPDDPQILMEQGEFLNYDIMLGVNQGEGLKFVDGIVDNEDGVTPNDFDFSVSNFVDNLYGYPEGKDTLRETIKFM
YTDWADKENPETRRKTLVALFTDHQWVAPAVATADLHAQYGSPTYFYAFYHHCQSEMKPSWADSAHGDEVPYVFGIPMIG
PTELFSCNFSKNDVMLSAVVMTYWTNFAKTGDPNQPVPQDTKFIHTKPNRFEEVAWSKYNPKDQLYLHIGLKPRVRDHYR
ATKVAFWLELVPHLHNLNEIFQYVSTTTKVPPPDMTSFPYGTRRSPAKIWPTTKRPAITPANNPKHSKDPHKTGPEDTTV
LIETKRDYSTELSVTIAVGASLLFLNILAFAALYYKKDKRRHETHRHPSPQRNTTNDITHIQNEEIMSLQMKQLEHDHEC
ESLQAHDTLRLTCPPDYTLTLRRSPDDIPFMTPNTITMIPNTLMGMQPLHTFKTFSGGQNSTNLPHGHSTTRV

FIGURE 13

HNL4Y cDNA (SEQ ID NO:7)

Exon 1    (1-153)
Exon 2    (154-724)
Exon 2bis (725-784)
Exon 3    (785-937)
Exon 3bis (938-1048)
Exon 3ter (1049-1170)
Exon 4    (1171-1356)
Exon 5    (1357-2146)
Exon 6    (2147-5460)

ORF (253-1074)

```
tttttttcccttccttcatctcctggcctcggataagataaggcttgggggatgcacgaaataatccaagtgattgatta
gacctggcatggcttggttgggctggagaaagatcggggcgcgctggaaaccccgcgtgaagatgaaatgactttttcga
aagacttatctttctgcaggctcgcctctgagctttgtctccttggagccacctcacttagacagcttcggatgtggatg
cagatttgaaccATGTTGCGTCCCCAGGGACTGCTATGGCTCCCTTTGTTGTTCACCTCTGTCTGTGTCATGTTAAACTC
CAATGTTCTTCTGTGGATAACTGCTCTTGCCATCAAGTTCACCCTCATTGACAGCCAAGCACAGTATCCAGTTGTCAACA
CAAATTATGGTAAAATCCAGGGCCTAAGAACACCATTACCCAGTGAGATCTTGGGTCCAGTGGAGCAGTACTTAGGGGTC
CCCTATGCCTCACCCCCAACTGGAGAGAGGCGGTTTCAGCCACCAGAATCCCCATCCTCCTGGACTGGCATCCGAAATGC
TACTCAGTTTTCTGCTGTGTGCCCCCAGCACCTGGATGAAAGATTCTTATTGCATGACATGCTGCCCATCTGGTTTACCA
CCAGTTTGGATACTTTGATGACCTATGTTCAAGATCAAAATGAAGACTGCCTTTACTTAAACATCTATGTGCCCATGGAA
GATGGAACCAACATAAAGAGAAATGCAGACGATATAACCAGTAATGACCATGGTGAAGATAAAGATATTCATGAACAGAA
CAGTAAGAAGCCTGTTATGGTCTATATCCATGGGGGATCTTACATGGAGGGAACCGGTAACATGATTGATGGCAGCATTT
TGGCCAGCTATGGGAACGTCATCGTTATCACCATTAACTACCGTCTGGGAATACTAGCACAAAACACCCTGGCTCATGGA
AACTGCAAGCATCGTTGTCAGCTGCACCTGCAGGCACCACGGGATTGCAAGTCAGCATACCCTTTCAGAAATGAGGATGA
AATTAGAGATGGAGTGTTGCTCTGTCACCCAGGCTGAagtgcagtggcatgatcttggctcactgcaacctctgcttccc
aggttcaagcaattcttctgcctcagcatcctgagtagctgaaattacagggttttttaagtaccggtgaccaggcagcaa
aaggcaactatgggctcctggatcagattcaagcactgaggtggattgaggagaatgtcggagcctttggcgggacccc
aagagagtgactatctttggctcgggggctggggcctcctgtgtcagcctgttgaccctgtcccactactcagaaggtct
cttccagaaggccatcattcagagcggcactgccctgtccagctgggcagtgaactaccagccggccaagtacactcgga
tattggcagacaaggtcggctgcaacatgctggacaccacgcacatggtagaatgtctgaagaacaagaactacaaggag
ctcatccagcagaccatcaccccggccacctaccacatagcctttgggccggtgatcgacggcgacgtcatcccagacga
cccccagatcctgatggagcaaggcgagttcctcaactacgacatcatgtgggcgtcaaccaagggggaaggcctgaagt
tcgtggacggcatcgtggataacgaggacggtgtgacgcccaacgactttgacttctccgtgtccaacttcgtggacaac
ctttacggctaccctgaagggaaagacactttgcgggagactatcaagttcatgtacacagactgggccgataaggaaaa
cccggagacgcggcggaaaaccctggtggctctcttactgaccatcagtgggtggccccgccgtggccaccgccgacc
tgcacgcgcagtacggctcccccacctacttctatgccttctatcatcactgccaaagcgaaatgaagcccagctggca
gattcggcccatggcgatgaagtcccctatgtcttcggcatccccatgatcggtcccacagagctcttcagttgtaattt
ctccaagaacgacgtcatgctcagtgccgtggtgatgacctactggacgaacttcgccaaaactggtgatccaaaccaac
cagttcctcaggataccaagttcattcatacaaaacccaatcgctttgaagaagtggcctggtccaagtataatcccaaa
gaccagctctatctgcatattggcttgaaacccagagtgagagatcactaccgggcaacgaaagtggctttctggttgga
attggttcctcatttgcacaacttgaacgagatattccagtatgtttcaacaaccacaaaggttcctccaccagacatga
catcatttccctatggcacccggcgatctcccgccaagatatggccaaccaccaaacgcccagcaatcactcctgccaac
aatcccaaacactctaaggaccctcacaaaacagggcccgaggacacaactgtcctcattgaaaccaaacgagattattc
caccgaattaagtgtcaccattgccgtcggggcgtcgctcctcttcctcaacatcttagcctttgcggcgctgtactaca
aaaaggacaagaggcgccatgagactcacaggcaccccagtccccagagaaacaccacaaatgatatcactcacatccag
aacgaagagatcatgtctctgcagatgaagcagctggaacacgatcacgagtgtgagtcgctgcaggcacacgacacgct
gaggctcacctgccctccagactacacactccacgctgccggtcgccggatgacatcccatttatgacgccaaacacca
tcaccatgattccaaacacattgatggggatgcagccttttacacacttttaaaaccttcagtggaggacaaaacagtaca
aatttaccccacggacattccaccactagagtatagcttttccctatttcccttcctatccctctgccctactgctcag
caatgtaaagagacaaataaggagaaagaaaatctccaaaccaggaatgtttttgtgccactgactttagataaaaatg
caaaagggcagtcatcctgtcccagcagacccttctcattggcattttccagtattgtgagatcaattctgaccatatg
aaatgtgaaaagtatatgtttctgttacaatactgctttaagatctaaaccatgccaacagatgtttcgtgtgactagga
catcaccatttcaaggaactgtgtgtttccaacatcatggtagcagcacacacttccaaagctcagccagggacacttaa
tatttttaattacaatggaaatttaaacatttttatgtgggctacacaatggatggctcttcttaagtgaagaaagact
ctataggcttttacacagcacatgaagcagtaatccagaaagaaggaaatgcagaattttattatcaaagtaagcgaatt
```

FIGURE 14

```
gactgtgcagaaaaattgtagggttctgtggaaggaggtattctgccagcctgaactatatttaagaaactttgtaaaaa
ataaaaatgtatatagctgtgagctcaaacaaaaactgcagacaaacaaaaaagagaaaagcttttatttgtgttttcag
tttgaaagaacttttagcaaggttgtgctttcaaacacatattagtcctaccaccttagttcctctacagcaaaagaggc
ttttcttcttaattacatgtaaacaaagacatgggatttctgacgtaagattttcatttgtaggaatatgtgatgtcaa
atgaagactcagaagttttgtgtggcctatttctccctgtcaggttgcacagatgcatgtagagcattcttaggagacc
attgttttagaaaactttgatttgtacatgttagttttcatgaaattgcaacacagagataggtcctaaaagtggaatgt
atttaaaacttgttgaattagacacacacacacagacacacacaaagaatcagcagagaaaacaaaatacaagtcctgtt
ctgtagttcttgcccctttgaatatatttgggaagagttgcttcctatttcaggaccctgccaaaaaagaagaaagcttgc
ctttggtggggctatgccccttggagtaaatacagctctgtgttccctagcagctgccggaggatttggctgatgaagta
cctgctcagcttagctaatcagattaaaggaagacatgtatgtcttttgtttaagcacctagtcccttatgtatcagtaa
acaggttttaaaaatctttatgtcatttataggataaaacatatgcttgtctgaaaatatcacctttttgtggatttat
ctgatcaccaaataataaatattaagaagaatgggggaaaaaggatagaatattaaaactgctttgcataggttttggg
gaaattaggatatcttcactgacaagacactgaatggaatttattcacccattttaaattggttacttggggatcagaga
tttgtctctccaacagcttgtggttttcttattactcattttcaggaaagtttgtagtattacaaggcagaaggaaacac
agtagcaatggttgctctatattttgtctttcaaagattactgcattaccaagaaacagtagccaaagatgtttgaagat
catgtcccttagctgcattgtgggttattctagaaatccaatgttaaatgcctctactaaagtggggattccccataaaa
attgtccagctacctgactcttttgcaataacaactttgattactgaatccatacactcaaactatagtgatatatcagt
gtttgggagtgacctctagaaaaaagaaaactgttttagaaatacataaaatcacttccaaatcctgttgcttatgttg
ggttaaatttgaaagcaattctctatatataaatatgtgaaatattatgatctgaacttagcacacatgaagcaacattt
ctttgctacacagaggtgtcttggaaagatttcattcccaattcattttttcatagatctataatcaggcaatttctgcaa
gcaatgtatgaccccacctgagcaaccacacaaataggctctccatgaaactgcaaaggaactgatgtgtggcatccatgct
ggttttgtctgtctataatatgaattcaagtatctgttcatatttccaattgtctcctgctagcaatatgtgccacaaca
tgacagtcttgtgacatcttaaggaaaagaagagttcctgttaaatgaatagctttagcttttacaggggattatgatta
aaagtgatttagtacatcttacatgatatctcatttctacgtgaaaagaagttatagaatcttcatagagttccatgaga
aaaatatacttgctatttat
```

FIGURE 14(continuing)

HNL4Y (SEQ ID NO:8)

MLRPQGLLWLPLLFTSVCVMLNSNVLLWITALAIKFTLIDSQAQYPVVNTNYGKIQGLRTPLPSEILGPVEQYLGVPYAS
PPTGERRFQPPESPSSWTGIRNATQFSAVCPQHLDERFLLHDMLPIWFTTSLDTLMTYVQDQNEDCLYLNIYVPMEDGTN
IKRNADDITSNDHGEDKDIHEQNSKKPVMVYIHGGSYMEGTGNMIDGSILASYGNVIVITINYRLGILAQNTLAHGNCKH
RCQLHLQAPRDCKSAYPFRNEDEIRDGVLLCHPG

FIGURE 15

Protéine HNL4X mutée (SEQ ID NO:9)

MSRPQGLLWLPLLFTPVCVMLNSNVLLWTALAIKFTLIDSQAQYPVVNTNYGKIRGLRTPLPNEILGPVEQYLGVPYAS
PPTGERRFQPPEPPSSWTGIRNTTQFAAVCPQHLDERSLLHDMLPIWFTANLDTLMTYVQDQNEDCLYLNIYVPTEDDIH
DQNSKKPVMVYIHGGSYMEGTGNMIDGSILASYGNVIVITINYRLGILGFLSTGDQAAKGNYGLLDQIQALRWIEENVGA
FGGDPKRVTIFGSGAGASCVSLLTLSHYSEGLFQKAIIQSGTALSSWAVNYQPAKYTRILADKVGCNMLDTTDMVECLRN
KNYKELIQQTITPATYHIAFGPVIDGDVIPDDPQILMEQGEFLNYDIMLGVNQGEGLKFVDGIVDNEDGVTPND

FIGURE 16

Famille 1
HNL3 R451C
*Neurologins*

```
                                          451
Variant            PEGKDTLRETIKFMYTDWADRD-NPETR C KTLVALFTDHQWVEP
Human              PEGKDTLRETIKFMYTDWADRD-NPETR R KTLVALFTDHQWVEP
Bos taurus         PEGKDTLRETIKFMYTDWADRD-NPETR R KTLVALFTDHQWVEP
Rat                PEGKDTLRETIKFMYTDWADRD-NPETR R KTLVALFTDHQWVEP
Mouse              PEGKDTLRETIKFMYTDWADRD-NPETR R KTLVALFTDHQWVEP
Droso neuroligin   HLNE---IFAVLKNEYTDWEKAIRNPLSS R DATLQFLSDGHTASP
Droso gliotactin   TLNPNGVYEAIKYIYTFWPDPN-NNTII R DQYINMLSDLYYRAP
```

*Acetylcholine esterase*

```
Human         PQVSDLAAEAVVLHYTDWLHPE-DPARL R EALSDVVGDHNVVCP
Bovin         PQASDLAAEAVVLHYTDWLHPE-DPARL R EALSDVVGDHNVVCP
Rabbit        PQASDLAAEAVVLHYTDWLHPE-DPARL R DALSDVVGDHNVVCP
Cat           PQASDLAAEAVVLHYTDWLNPE-DPARL R EAMSDVVGDHNVVCP
Mouse         PQASDLAAEAVVLHYTDWLHPE-DPTHL R DAMSAVVGDHNVVCP
Rat           PQASDLAAEAVVLHYTDWLHPE-DPAHL R DAMSAVVGDHNVVCP
Chicken       PQATELAAEAVVLHYTDWLDAD-NPVKN R EALDDIVGDHNVVCP
Snake         PHANDIATDAVVLQYTDWQDQD-NREKN R EALDDIVGDHNVICP
Electrophorus PHANEIGLEAVILQYTDWMDED-NPIKN R EAMDDIVGDHNVVCP
Torpedo       PHANDLGLDAVTLQYTDWMDDN-NGIKN R DGLDDIVGDHNVICP
Zebra         PHANDIGLEAVILQYTDWMDEN-NGQKN R DAMDDIVGDQNVICP
Hagfish       PQGNEVSVDAIVLQYTDWLAQN-DALKN R DAIEDIVGDYNVICP
Amphoxius     PRLNDITVERTAFEYTDWLHMD-QDTMY R DALDSVFGDPFFVCP
Aphis gossypii PNADAAVKSAIEFEYTDWFNPN-DPEKN R NALDKMVGDYQFTCN
```

*Butyrylcholine esterase*

```
Human    PGVSEFGKESILFHYTDWVDD-QRPENY R EALGDVVGDYNFICP
Mouse    PGVSRLGKEAVLFYYVDWLGE-QSPEVY R DALDDVIGDYNIICP
Horse    PRVSEFGRESILFHYMDWLDD-QRAENY R EALDDVVGDYNIICP
Rabbit   PGVSEFGKESILFHYTDWVDE-QRPENY R EALDDVVGDYNFICP
```

Family 2
HNL3 N796S

```
                                 796
Variant     PDDIPLMTPNTITMIP S SLVGLQTLHPYNTFAAGFNSTG
Human       PDDIPLMTPNTITMIP N SLVGLQTLHPYNTFAAGFNSTG
Bos taurus            PNTITIIP N SLVGLQTLHPYNTFAAGFNSTG
Rat         PDDIPLMTPNTITMIP N SLVGLQTLHPYNTFAAGFNSTG
Mouse       PDDIPLMTPNTITMIP N SLVGLQTLHPYNTFAAGFNSTG
Zebra fish  PDDIPLMTPNTITMIP N SMPGLTSLHPFNSYSSGQNNT
```

FIGURE 18

```
gcacgaggctgcgtgcggagcctgggcctcctcggccgccgcgcccgccccgccccccgtgaccccgtgaccccggggt
cggaggccgcaggcaggccccgccccacacaggaagtgggtggagaccaggtcgcccggcggccatgatggatccggag
cggtgacgtcgcctggccccgccctaactcagcctacgctgtgattgacgggtggcctgccccacccccccacgccgcg
gtgacgtcacaggaagtggcagggctgcggcaggaagtgttgcgctgagccagaagcggtcggaacggacaggaagtgac
ctcaccctaggccgtggttgccgtgacgaaacaggaagtgacctcaggagggaccggaagtgacccgggtcacccacgaa
cccgcccacccgcgacaggaagtgaccgtgcagtcgcagggagcagccaggggggcgaccggaagtgacgtcgccgtgaca
ggaagtgacgtcgccttgacaggaagtggctgcgtgaccggaagtgacgtcgccgtgaccggaagtggctgcgtgaccgg
aagtgacgtcgccgtgaccagatgtgacgtcgccgtgacaggaagtgacatcaccgtgacaggaagtctctgccggccgc
CATGCCCGCCCCCGTCCCCGCCCTTTTGTGCCTCGCCCTCGCCTGGCATCCGCCCAGCCGTCCCCGCCGCCGCCGCCGC
CGTTCCCCGTGGTGGCCACGAACTACGGGAAGCTGCGCGGGGTGCGGGCGGCGCTGCCGGGCGACGTGCTGGGCCCCGTG
ACGCAGTTCCTGGGCGTGCCCTACGCGGCCCCGCCCACCGGCGAGCGCCGCTTCCAGCCGCCCGAGCCGCCGTCCTCCTG
GGCCGGCGTCCGCGACGCCACGCGGTTCGCGCCCGTCTGCCCGCAGCACCTGGACGAGCGCGCGCTGCTGCGCGACTGCC
TCCCCGCCTGGTTCGCCGCCAACCTCGACGCCATCGCCGCCGACGTCCAGGACCAGAGCGAGGACTGCCTGTACCTCAAC
CTCTACGTGCCCGGCGGAGCCAACGGTAAGAAAATGGCCGACGATGTCACCGGCAACGACCACGGTGACGACCAAGACTC
CCGTGACCCCGGCGTGGGCGGCGCGGCGGCGGCGGCGGCGAGGAAGCCGGTCATGGTTTACATCCACGGCGGCTCCTACA
TGGAGGGCACCGCGAACATCGTGGACGGCAGCGTCCTCGCCAGCTACGGCGACGTCATCGTCGTCACCGTCAACTACCGG
CTCGGCGTGCTCGGCTTCCAGAGCACGGGCGACCAGGCCGCCAAGGGCAACTACGGGCTGCTGGACCAGATCCAGGCGCT
GCGCTGGGTGGAGGAGAACGCGGGCGCCTTCGGCGGGGACCCCGACCGCGTCACCGTCTTCGGCTCCGGCGCCGGCGCCT
CCTGCGTCAGCCTCCTCACGCGTGTCGCACTACTCGGAGGGCGTCGTTCCAGAAGGCCATCATCCAGAGCGGGACGGCGCTG
TCGAGCTGGGCGGTGAACTACCAGCCGGCCCGGTACGCGCGGGCGCTGGGCGAGCGCGTGGGCTGCGCGACCCCCGACCC
GGGGTCGCCGCCGGGGTCGCCGCCGGGTTGGGACTCGGCGTCGCTGGTGTCCTGCCTGCGGGGCAAGGCGGCGGGCGAGC
TGGCGCGGGCCCGCGTGACGCCCGCGACCTACCACGTGGCGTTCGGGCCGACGGTGGACGGCGACGTCATCCCCGACGAC
CCCCAGATCCTGATGGAGCAGGGCGAGTTCCTCAACTACGACATCATGCTCGGCGTCAACCAGGGCGAGGGCGCGCGCTT
CGTCGACGGCCTCGGCGGCGGCCACGACGGCGGCTACGGCGGATACGGCGGCGGCGTCGAGGACGACG
AGGTCCAAGATGGCGGCCCGGACGGCGCCGGGGCGGCGGTGTCGGCGGGCGAGTTCGACCTGGCGGTGTCCGGCTTCATC
AACGACCTCTACGCCGCCCCGAGGGCCGCGGCGACGCCCTGCGCGAGACGGTGAAGTTCATGTACACCGACTGGGCCGA
CCGCGACAGCCCCGAGGCGCGGCGCAAGACGCTCGTGGCGCTCTTCACCGACCACCAGTGGGTGGCGCCCGCCGTGGCCA
CCGCCGACCTCCACGCCCGCTACGGCTCCCCCACCTACTTCTACGCCTTCTACCACCGGTGCCACGCGGCGTCCCGCGGT
GATGACGTCGTCGTCGATGGCGTCGGGCTCGGGGATGACGTCGTCGTCCGGCTCGGGGATGACGTCGTCGTCGGGGTAGN
NTCGGCGTCCGCGGTGCTGATCGAGACGCGGCGCGACTACTCGACGGAGCTGAGCGTGACGATCGCGGTGGGGGCCCTCGC
TGCTCTTCCTCAACGTCCTCGCCTTCGCCCGCGCTCTACTACAAGAAGGACAAGCGCCGGCACGAGACGCACCGCAGGCCG
CCCCCGCCACGCCCCCGCAGGCCCCGCCCTCCGCCGCCGCCGCCGACCGGAACCCGCGACCCGACCCCGGGCCGGCCGG
CCGGCGTGGCGGGGAGTGCGGTGCAGTGGTCACCGCGATGGCGGCGGAGGCGTCGGCGGGCGGCCTGGGCCACGACGGCG
TCGGCGGGGTCGGGGTCGGCGGGGTCATCGGCGGGGTCGCCGGCCTGCGCCTGGCCTGCCCGCCCGACTACGCGCTGACC
CTGCGGCGCTCGCCCGACGACGTCCCCCGGGCCGGGGCCGGGCCGGGCGCCATGACGCTCATCCCCGGGCGCTGGGTGG
AGGCGGCGGCGGCCGTGCACGGGTTCAACACCTTTGGGAGCGGGGTCGGCGTCGCCGGGGTCGCGGGGTCGCGACCT
CGCAGGCCGGGCCGGGGCTGCCCCACGGACACTCGACCACCCGGGTATAGcgtggcgagcgcgggagcttggcggggggcg
gagcgtggactcctgtgaagccccgcccaccccgcccaaaagcccccgcccgcccgccgagcccccgcccacagccgcgg
acatgcaggggccttggctacggcaggcgatgacgtcaccgccctgaccacgcccccttcccgtcgcgggacatgaggt
cgactgaggggcggagtcagggcagtgcgtgggtccggatggtaacggggaaccggatagaaccggatgggaccgcatt
gatccggagggaaccggatggaactggattgagccgggtcagcacgggttggactggattgaaccggattaatccggatg
gagccggtgatgccaggcctgagctgagcagcctggtgtggccggaaccggatgagaccggataaaaccggcctgaaccc
gcgcgcgcgaccagcaccgagctggtcgatgtggaccaaacctgaatggaccggattggaccgggctacgccggctggat
ccggatccgactgggcgggaccgagaccggatgggaccggatgaaccggttcagaccgggctcggctggatcagactgg
acggaggggttggcgcggaccaaggcaagggcgccgggtcggacctgacgcagccggacaagaccggttcggaccagc
ggaaccggattgggctgtgtccctgtgggcagaaccggatttactggattttaccggatgggacaggaatggacgagag
cagcgtgaactgcatgaaaccgctttagaccggaatgaaccggaatgaaccggatcaagtgggagaccggatggcatcca
gggcactggacagatccggactgaactggaacggaccggatcgatccgatgggaccggatggagccgcgtcgcctcgca
cggccccgggcacgcggacggcggacatttacattttatcgtcaatgacgctcacggccgcgagtgaggtcatcgggga
gcggtgggggatggaggggggcggagtcttattttttattagaattcggatcgcgtcgtttcctccctggcgcccgacag
agccgggtgcgcggttgccgccacgattctatctttcctcattttttaattttatttctatttattttggttatattttt
aattttttattatacttttttatttattgtgtatctttattttttaaattattttttagcgccgcgtcggcgcaccgacgttt
ccggattttttgttatatgttaaatgacccagatttgaaacttaattttgttacagtgtcacgtttacattgatattagg
ggctaaaataatttgtatgtccacgttgaaaagtgagaccttggaaattcggggaaacttctagtttgcagagatctgt
gagaagaggtgggatctcaagggttcaatgttgggcaaattctgtgtaaacggatttagatgtatggtagattaacgttc
gcctttattggagagttaatatagag
```

FIGURE 19A

MPAPVPALLCLALALASAQPSPPPPPPPFPVVATNYGKLRGVRAALPGDVLGPVTQFLGVPYAAPPTGERRFQPPEPPSSW
AGVRDATRFAPVCPQHLDERALLRDCLPAWFAANLDAIAADVQDQSEDCLYLNLYVPGGANGKKMADDVTGNDHGDDQDS
RDPGVGGAAAAAARKPVMVYIHGGSYMEGTANIVDGSVLASYGDVIVVTVNYRLGVLGFQSTGDQAAKGNYGLLDQIQAL
RWVEENAGAFGGDPDRVTVFGSGAGASCVSLLTLSHYSEGLFQKAIIQSGTALSSWAVNYQPARYARALGERVGCATPDP
GSPPGSPPGWDSASLVSCLRGKAAGELARARVTPATYHVAFGPTVDGDVIPDDPQILMEQGEFLNYDIMLGVNQGEGARF
VDGLGGGHDGGYGGYGGGYGGGVEDDEVQDGGPDGAAGGVSAGEFDLAVSGFINDLYGRPEGRGDALRETVKFMYTDWAD
RDSPEARRKTLVALFTDHQWVAPAVATADLHARYGSPTYFYAFYHRCHAASRGDDVVVDGVGLGDDVVVRLGDDVVVGVX
SASAVLIETRRDYSTELSVTIAVGASLLFLNVLAFAALYYKKDKRRHETHRRPPPPRPPQAPPSAAAADRNPRPDPGPAG
RRGGECGAVVTAMAAEASAGGLGHDGVGGVGVGGVIGGVAGLRLACPPDYALTLRRSPDDVPRAGAGPGAMTLIPGALGG
GGGGAVHGFNTFGSGVGVAGVAGVATSQAGPGLPHGHSTTRV

FIGURE 19B

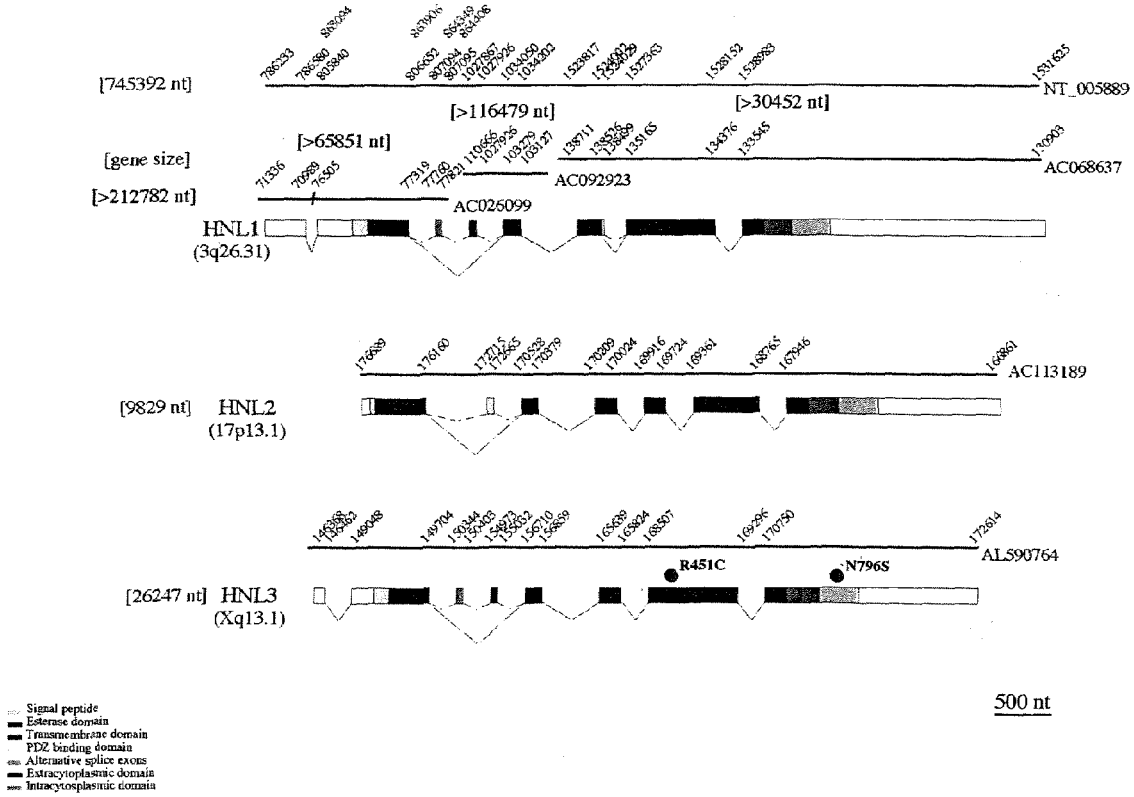

FIGURE 20

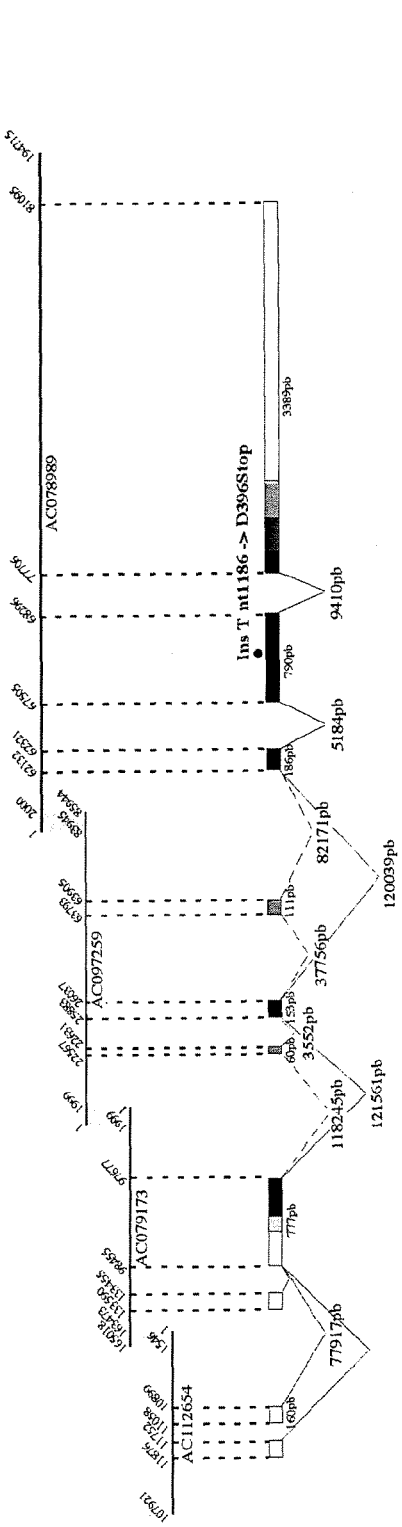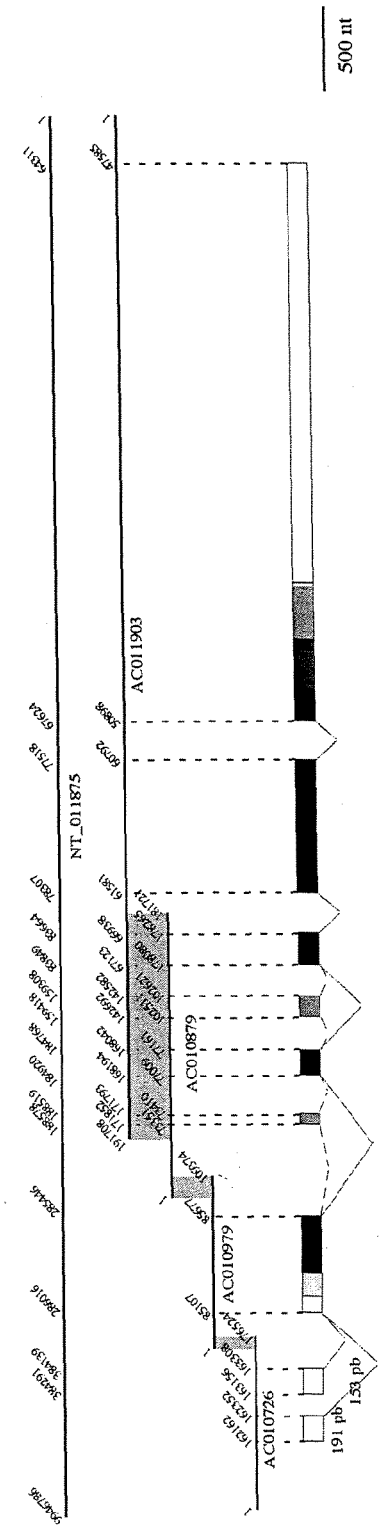
FIG. 21

SEQ ID NO: 10

PEGKDTLRETIKFMYTDWADRDNPETR C KTLVALFTDHQWVEP

FIGURE 22

SEQ ID NO: 11

PDDIPLMTPNTITMIP S SLVGLQTLHPYNTFAAGFNSTG

FIGURE 23

SEQ ID NO: 12

```
ctgatctcggggattcgggtgcggagcccttggcctggaggcgatatgggtggtccgtggcccggttcagtcgcttgcag
cagcccggggaacaggcctgtctggccctgagggagtccccttctgaagctgtggtgcttggacgacctgctctctaca
ttgctgggcacctgtaggtgtccctcgagagctcagttttgaggttcaagtcagtgtggccatgaaggggctgcctattg
ggctgatgctgtgaccctggagtctgcctctcctgccagtcccctgcccggaacATGTGGCTGCGGCTTGGCCCGCCCT
CGCTGTCCCTGAGCCCAAGCCCACGGTTGGCAGGAGCCTGTGCCTCACCCTGTGGTTCCTCAGTTTGGCGCTGAGGGCC
AGTACCCAGGCCCCAGCACCCACAGTCAACACTCACTTTGGGAAGCTAAGGGGTGCCCGAGTACCACTGCCCAGTGAGAT
CCTGGGGCCTGTGGACCAATACCTGGGGGTGCCCTACGCAGCTCCCCGATCGGCGAGAAACGTTTCCTGCCCCCTGAAC
CACCCCCATCCTGGTCGGGCATCCGGAACGCCACACACTTTCCCCCAGTGTGCCCCCAGAACATCCACACAGCTGTGCCC
GAAGTCATGCTGCCGGTCTGGTTCACTGCCAACTTGGATATCGTCGCTACTTACATCCAGGAGCCCAACGAAGACTGTCT
CTACCTGAACGTCTATGTGCCGACGGAGGATGGATCCGGCGCTAAGAAACAGGGCGAGGACTTAGCGGATAATGACGGGG
ATGAAGATGAAGACATCCGGGACAGTGGTGCTAAACCCGTCATGGTCTACATCCACGGAGGCTCTTACATGGAAGGGACA
GGCAACATGATTGATGGCAGCATCCCCGCCAGTTATGGCAATGTCATAGTCATCACCCTCAACTATCGGGTTGGAGTGCT
AGGTTTCCTGAGTACTGGAGATCAGGCTGCCAAGGGCAACTATGGGCTCCTTGACCAGATCCAGGCCCTCCGCTGGGTGA
GCGAGAATATTGCCTTCTTCGGGGGAGACCCCCGCCGGATCACTGTCTTTGGCTCGGGCATTGGTGCATCCTGCGTCAGC
CTCCTCACGTTGTCACATCACTCAGAGGGACTTTTCCAGAGAGCCATCATCCAAAGTGGCTCTGCTCTGTCCAGCTGGGC
TGTGAACTACCAACCAGTGAAGTACACCAGCCTGCTGGCAGACAAAGTGGGCTGTAATGTGCTGGACACCGTGGATATGG
TGGACTGTCTTCGGCAAAAGAGTGCCAAGGAGCTGGTAGAGCAGGACATCCAGCCAGCCCGCTACCACGTGGCCTTTGGC
CCTGTGATTGATGGTGATGTCATTCCTGATGACCCTGAGATCCTCATGGAGCAGGGCGAGTTCCTCAACTATGACATCAT
GCTAGGTGTCAACCAGGGCGAGGGTCTCAAGTTTGTGGAAGGGGTGGTGGACCCTGAGGATGGTGTCTCTGGCACTGACT
TTGACTATTCCGTCTCCAATTTTGTGGACAATCTGTATGGCTATCCTGAGGGTAAGGACACCCTGCGAGAGACCATCAAG
TTCATGTATACAGACTGGGCAGACCGTGACAACCCTGAGACCCGCCGTAAAACACTGGTGGCACTCTTCACTGACCACCA
GTGGGTGGAGCCCTCAGTGGTGACAGCCGATCTGCATGCCCGCTACGGCTCGCCTACCTACTTCTACGCCTTCTATCATC
ACTGCCAGAGCCTCATGAAGCCTGCTTGGTCAGATGCAGCTCATGGGATGAAGTACCCTATGTTTTTGGGGTTCCTATG
GTAGGCCCCACTGACCTTTTCCCCTGCAACTTCTCCAAGAATGATGTTATGCTCAGTGCTGTCGTCATGACCTATTGGAC
CAACTTTGCCAAGACTGGGGATCCCAACAAGCCGGTCCCCCAGGACACCAAGTTCATTCACACCAAGGCCAACCGCTTTG
AGGAAGTGGCCTGGTCCAAATACAATCCCCGAGACCAGCTCTACCTTCACATCGGGCTGAAACCAAGGGTCCGAGATCAT
TACCGGGCCACTAAGGTGGCCTTTTGGAAACATCTGGTGCCCCACCTATACAACCTGCATGACATGTTCCACTATACGTC
CACCACCACCAAAGTGCCGCCTCCGGATACCACCCACAGCTCCCACATCACCCGCAGGCCCAATGGCAAGACCTGGAGCA
CCAAGCGGCCAGCCATCTCACCTGCCTACAGCAACGAGAATGCCCAGGGGTCCTGGAACGGGGACCAGGATGCAGGGCCA
CTCCTGGTGGAGAACCCTCGTGACTACTCCACTGAATTAAGTGTCACCATCGCCGTGGGGCCTCCCTCCTGTTCCTTAA
CGTTCTGGCCTTCGCTGCCCTCTACTACCGTAAGGACAAACGGCGCCAGGAGCCCCTGCGGCAGCCTAGCCCTCAGCGGG
GAGCCGGGGCCCCGGAGTTGGGAGCTGCTCCAGAGGAGGAGCTGGCAGCATTACAACTGGGCCCCACCCACCACGAGTGT
GAGGCCGGTCCCCCCCATGACACGCTGCGCCTCACTGCATTGCCCGACTACACCCTGACCCTGCGGCGCTCCCCGGATGA
CATCCCACTCATGACCCCCAACACCATCACTATGATCCCCAACTCCCTGGTAGGGCGGCAGACATTGCACCCCTATAACA
CCTTTGCCGCAGGGTTCAACAGTACCGGGCTGCCCCACTCACACTCCACTACCCGGGTATAGctccaactcagagcacag
ccaatctccaggctccctccctcccagatccaggaacacatgcacacacacacacacacacacgcagacacacacacaca
cacacatatatgtatacgcacgcacccacacccctacagcagatccacctgcacaaacatagacagatgtggacatgcacc
cgcatgtacaaaaacacaaatacggaagtaaacctgaacaaaccctttaaatggggacgcagatgagtcctcggtaaacc
gaggacccatgaaacagcagctgaagccagctccctgaatctgaccacagacactcctgggggcctgaaagcaacagct
ggacacccccttggtgctcgccttcggcctctcttggaactgcaccaccgaccaactccagacttgggagctttaaagag
caggatagctcttcctcccaggacttggtcttttttctgggtcttgttttgttgatttttcttttttaattttggaaca
aatgcttttccaacccatgagtgctaagagcctctggaagggagggcttcaggcccgaaggtctctctggctctaggacc
cccagtgctcacacaatcagaccaaggaacaagaccccaggaaggaaacagatttaagcaagaccatgggtggaagga
gaaaggggctagcactggatggagctggagggtcgtaggggagagatctccaactctctctgtgtccgtgtggagggctg
cagagcctgcaggtgacctgcttccccaaaggccaacagcattggcctggccagaccaggtgaccttagatttggtgaa
caacgtactatggaagccacatcactattgggccccaggtctgatctgggttttgcctctgcccttggggaaatgctat
cagaaattcgccccatttttctttacagtcttttgtgtctgtcatttctctttcaaaaggcggtgttttttgttgttgtt
ggtttttttttttttttaaagaaaagttcttaaaacactaacgaaaaaaaaa
```

FIGURE 24

SEQ ID NO: 13

```
ctgatctcggggattcgggtgcggagcccttggcctggaggcgatatgggtggtccgtggcccggttcagtcgcttgcag
cagcccggggaacaggcctgtctggccctgagggagtccccttctgaagctgtggtgcttggacgacctgctctctaca
ttgctgggcacctgtaggtgtccctcgagagctcagttttgaggttcaagtcagtgtggccatgaagggctgcctattg
ggctgatgctgtgaccctggagtctgcctctcctgccagtcccctgcccggaacATGTGGCTGCGGCTTGGCCCGCCCT
CGCTGTCCCTGAGCCCCAAGCCCACGGTTGGCAGGAGCCTGTGCCTCACCCTGTGGTTCCTCAGTTTGGCGCTGAGGGCC
AGTACCCAGGCCCCAGCACCCACAGTCAACACTCACTTTGGGAAGCTAAGGGGTGCCCGAGTACCACTGCCCAGTGAGAT
CCTGGGGCCTGTGGACCAATACCTGGGGGTGCCCTACGCAGCTCCCCGATCGGCGAGAAACGTTTCCTGCCCCCTGAAC
CACCCCCATCCTGGTCGGGCATCCGGAACGCCACACACTTTCCCCCAGTGTGCCCCCAGAACATCCACACAGCTGTGCCC
GAAGTCATGCTGCCGGTCTGGTTCACTGCCAACTTGGATATCGTCGCTACTTACATCCAGGAGCCCAACGAAGACTGTCT
CTACCTGAACGTCTATGTGCCGACGGAGGATGGATCCGGCGCTAAGAAACAGGGCGAGGACTTAGCGGATAATGACGGGG
ATGAAGATGAAGACATCCGGGACAGTGGTGCTAAACCCGTCATGGTCTACATCCACGGAGGCTCTTACATGGAAGGGACA
GGCAACATGATTGATGGCAGCATCCCCGCCAGTTATGGCAATGTCATAGTCATCACCCTCAACTATCGGGTTGGAGTGCT
AGGTTTCCTGAGTACTGGAGATCAGGCTGCCAAGGGCAACTATGGGCTCCTTGACCAGATCCAGGCCCTCCGCTGGGTGA
GCGAGAATATTGCCTTCTTCGGGGGAGACCCCCGCCGGATCACTGTCTTTGGCTCGGGCATTGGTGCATCCTGCGTCAGC
CTCCTCACGTTGTCACATCACTCAGAGGGACTTTTCCAGAGAGCCATCATCCAAAGTGGCTCTGCTCTGTCCAGCTGGGC
TGTGAACTACCAACCAGTGAAGTACACCAGCCTGCTGGCAGACAAAGTGGGCTGTAATGTGCTGGACACCGTGGATATGG
TGGACTGTCTTCGGCAAAAGAGTGCCAAGGAGCTGGTAGGACAGGACATCCAGCCAGCCCCGCTACCACGTGGCCTTTGC
CCTGTGATTGATGGTGATGTCATTCCTGATGACCCTGAGATCCTCATGGAGCAGGGCGAGTTCCTCAACTATGACATCAT
GCTAGGTGTCAACCAGGGCGAGGGTCTCAAGTTTGTGGAAGGGGTGGTGGACCCTGAGGATGGTGTCTCTGGCACTGACT
TTGACTATTCCGTCTCCAATTTTGTGGACAATCTGTATGGCTATCCTGAGGGTAAGGACACCCTGCGAGAGACCATCAAG
TTCATGTATACAGACTGGGCAGACCGTGACAACCCTGAGACCCGCTGTAAAACACTGGTGGCACTCTTCACTGACCACCA
GTGGGTGGAGCCCTCAGTGGTGACAGCCGATCTGCATGCCCGCTACGGCTCGCCTACCTACTTCTACGCCTTCTATCATC
ACTGCCAGAGCCTCATGAAGCCTGCTTGGTCAGATGCAGCTCATGGGGATGAAGTACCCTATGTTTTGGGGTTCCTATG
GTAGGCCCCACTGACCTTTTCCCCTGCAACTTCTCCAAGAATGATGTTATGCTCAGTGCTGTCGTCATGACCTATTGGAC
CAACTTTGCCAAGACTGGGGATCCCAACAAGCCGGTCCCCCAGGACACCAAGTTCATTCACACCAAGGCCAACCGCTTTG
AGGAAGTGGCCTGGTCCAAATACAATCCCCGAGACCAGCTCTACCTTCACATCGGGCTGAAACCAAGGGTCCGAGATCAT
TACCGGGCCACTAAGGTGGCCTTTTGGAAACATCTGGTGCCCCACCTATACAACCTGCATGACATGTTCCACTATACGTC
CACCACCACCAAAGTGCCGCCTCCGGATACCACCCACAGCTCCCACATCACCCCGCCAGGCCCAATGGCAAGACCTGGAGCA
CCAAGCGGCCAGCCATCTCACCTGCCTACAGCAACGAGAATGCCCAGGGGTCCTGGAACGGGGACCAGGATGCAGGGCCA
CTCCTGGTGGAGAACCCTCGTGACTACTCCACTGAATTAAGTGTCACCATCGCCGTGGGGGCCTCCCTCCTGTTCCTTAA
CGTTCTGGCCTTCGCTGCCCTCTACTACCGTAAGGACAAACGGCGCCAGGAGCCCCTGCGGCAGCCTAGCCCTCAGCGGG
GAGCCGGGGCCCCGGAGTTGGGAGCTGCTCCAGAGGAGGAGCTGGCAGCATTACAACTGGGCCCCACCCACCACGAGTGT
GAGGCCGGTCCCCCCCATGACACGCTGCGCCTCACTGCATTGCCCGACTACACCCTGACCCTGCGGCGCTCCCCGGATGA
CATCCCACTCATGACCCCCAACACCATCACTATGATCCCCAACTCCCTGGTAGGGCTGCAGACATTGCACCCCTATAACA
CCTTTGCCGCAGGGTTCAACAGTACCGGGCTGCCCCACTCACACTCCACTACCCGGGTATAGctccaactcagagcacag
ccaatctccaggctccctccctcccagatccaggaacacatgcacacacacacacacacacgcagacacacacaca
cacacatatatgtatacgcacgcacccacaccctacagcagatccacctgcacaaacatagacagatgtggacatgcacc
cgcatgtacaaaaacacaaatacggaagtaaacctgaacaaaccctttaaatggggacgcagatgagtcctcggtaaacc
gaggacccatgaaacagcagctgaagccagctccctgaatctgaccacagacactcctgggggcctgaaagcaacagct
ggacacccccttggtgctcgccttcggcctctcttggaactgcaccaccgaccaactccagacttgggagctttaaagag
caggatagctcttcctcccaggacttggtctttttctgggtcttgttttgttgattttctttttaattttggaaca
aatgcttttccaacccatgagtgctaagagcctctggaagggagcgcttcaggcccgaaggtctctctggctctaggacc
cccagtgctcacacaatcagaccaaggaacaagaccccaggaaggaaacagattt̲aagcaagaccatgggtggaagga
gaaaggggctagcactggatggagctggagggtcgtaggggagagatctccaactctctctgtccgtgtggagggctg
cagagcctgcagggtgacctgcttccccaaaggccaacagcattggcctggccagaccaggtgaccttagatttggtgaa
caacgtactatggaagccacatcactattgggccccaggtctgatctgggttttgcctctgcccttggggaaatgctat
cagaaattcgcccccatttttctttacagtcttttgtgtctgtcatttctctttcaaaaggcggtgttttttgttgttgtt
ggttttttttttttttaaagaaaagttcttaaaacactaacgaaaaaaaaa
```

FIGURE 25

SEQ ID NO: 14

```
MWLRLGPPSLSLSPKPTVGRSLCLTLWFLSLALRASTQAPAPTVNTHFGKLRGARVPLPSEILGPVDQYLGVPYAAPPIG
EKRFLPPEPPPSWSGIRNATHFPPVCPQNIHTAVPEVMLPVWFTANLDIVATYIQEPNEDCLYLNVYVPTEDGSGAKKQG
EDLADNDGDEDEDIRDSGAKPVMVYIHGGSYMEGTGNMIDGSIPASYGNVIVITLNYRVGVLGFLSTGDQAAKGNYGLLD
QIQALRWVSENIAFFGGDPRRITVFGSGIGASCVSLLTLSHHSEGLFQRAIIQSGSALSSWAVNYQPVKYTSLLADKVGC
NVLDTVDMVDCLRQKSAKELVEQDIQPARYHVAFGPVIDGDVIPDDPEILMEQGEFLNYDIMLGVNQGEGLKFVEGVVDP
EDGVSGTDFDYSVSNFVDNLYGYPEGKDTLRETIKFMYTDWADRDNPETRRKTLVALFTDHQWVEPSVVTADLHARYGSP
TYFYAFYHHCQSLMKPAWSDAAHGDEVPYVFGVPMVGPTDLFPCNFSKNDVMLSAVVMTYWTNFAKTGDPNKPVPQDTKF
IHTKANRFEEVAWSKYNPRDQLYLHIGLKPRVRDHYRATKVAFWKHLVPHLYNLHDMFHYTSTTTKVPPPDTTHSSHITR
RPNGKTWSTKRPAISPAYSNENAQGSWNGDQDAGPLLVENPRDYSTELSVTIAVGASLLFLNVLAFAALYYRKDKRRQEP
LRQPSPQRGAGAPELGAAPEEELAALQLGPTHHECEAGPPHDTLRLTALPDYTLTLRRSPDDIPLMTPNTITMIPNSLVG
LQTLHPYNTFAAGFNSTGLPHSHSTTRV
```

FIGURE 26

SEQ ID NO: 15

```
MWLRLGPPSLSLSPKPTVGRSLCLTLWFLSLALRASTQAPAPTVNTHFGKLRGARVPLPSEILGPVDQYLGVPYAAPPIG
EKRFLPPEPPPSWSGIRNATHFPPVCPQNIHTAVPEVMLPVWFTANLDIVATYIQEPNEDCLYLNVYVPTEDGSGAKKQG
EDLADNDGDEDEDIRDSGAKPVMVYIHGGSYMEGTGNMIDGSIPASYGNVIVITLNYRVGVLGFLSTGDQAAKGNYGLLD
QIQALRWVSENIAFFGGDPRRITVFGSGIGASCVSLLTLSHHSEGLFQRAIIQSGSALSSWAVNYQPVKYTSLLADKVGC
NVLDTVDMVDCLRQKSAKELVEQDIQPARYHVAFGPVIDGDVIPDDPEILMEQGEFLNYDIMLGVNQGEGLKFVEGVVDP
EDGVSGTDFDYSVSNFVDNLYGYPEGKDTLRETIKFMYTDWADRDNPETRCKTLVALFTDHQWVEPSVVTADLHARYGSP
TYFYAFYHHCQSLMKPAWSDAAHGDEVPYVFGVPMVGPTDLFPCNFSKNDVMLSAVVMTYWTNFAKTGDPNKPVPQDTKF
IHTKANRFEEVAWSKYNPRDQLYLHIGLKPRVRDHYRATKVAFWKHLVPHLYNLHDMFHYTSTTTKVPPPDTTHSSHITR
RPNGKTWSTKRPAISPAYSNENAQGSWNGDQDAGPLLVENPRDYSTELSVTIAVGASLLFLNVLAFAALYYRKDKRRQEP
LRQPSPQRGAGAPELGAAPEEELAALQLGPTHHECEAGPPHDTLRLTALPDYTLTLRRSPDDIPLMTPNTITMIPNSLVG
LQTLHPYNTFAAGFNSTGLPHSHSTTRV
```

FIGURE 27

POLYNUCLEOTIDE AND PROTEIN INVOLVED IN SYNAPTOGENESIS, VARIANTS THEREOF, AND THEIR THERAPEUTIC AND DIAGNOSTIC USES

CROSS-REFERENCE TO RELATED APPLICATIONS

The present application is a continuation of U.S. Ser. No. 10/496,011 filed on May 28, 2004, which is a National Stage (371) of PCT/FR02/04134, filed on Dec. 2, 2002, which claims priority to CA 2 364 106, filed on Nov. 30, 2001.

CONTEXT OF THE INVENTION a) Field of the Invention

The present invention relates to the identification of a human gene encoding a protein involved in synaptogenesis and of its murine orthologs, the mutation of which is associated in humans with the development of neurological diseases and/or with a predisposition to the development of mental disorders or psychiatric diseases such as autism and Asperger syndrome.

The invention also relates to the diagnostic and therapeutic uses associated with identifying the gene and its mutations.

The invention also relates to the diagnostic and therapeutic uses associated with identifying the involvement of a defect in a protein of the neuroligin family in the development of mental disorders or psychiatric diseases such as autism and Asperger syndrome.

b) Brief Description of the Prior Art

Autism is a disease which affects around one child in 1000 and mainly boys (from 4 to 23 boys to one girl according to the selected clinical criteria). The clinical symptoms of autism are described in the DSM-IV-TR™ manual (Diagnostic and statistical manual of mental disorders, 2000, pages 70-75).

The molecular bases of autism are currently unknown. Studies have already suggested the existence of a genetic component in autism. Based on linkage analysis results, Philippe et al. (Human Molecular Genetics, 1999, 8:805-812) describes 11 chromosomal regions which may be involved in the development of autism, among which is a region of chromosome Xp. In addition, Thomas et al. (Hum. Genet., 1999, 104:43-48) describes deletions of the short arm of the X chromosome in patients suffering from autism, and Milunsky et al. (Clin. Genet., 1999, 55:455-460) describes deletions in Xp22 in patients suffering from schizophrenia and suggests, more precisely, the involvement of a deletion in Xp22.3 in the development of this psychiatric disease. However, neither the gene involved in the disease nor the nature of the mutation are mentioned.

The neuroligins (HNLs) are cell adhesion proteins which can trigger, by themselves, synaptogenesis, i.e. the formation of synapses (Scheiffele et al., Cell, 2000, 101:657-669). The neuroligins NL1, NL2 and NL3 were originally cloned in rats (Ichtchenko et al., Cell., 1995, 81(3):435-43; Ichtchenko et al., J. Biol. Chem., 1996, 271(5):2676-82). The neuroligins HNL1 and HNL2 are located on autosomes (3q26 and 17 p13). These genes are targets for susceptibility to psychiatric diseases and several protein variations in HNL2 have been demonstrated by the inventors in autistic patients (R734H, G754R, A755V). A protein HNL4X (human neuroligin-4) has been described by Bollinger et al. (Biochem. J., 2001, 356:581-588), without any genomic description or related biological function. In addition, the LOCUSLINK™ database of Sep. 13, 2001 provides, under the accession numbers KIAA1260 and KIAA0951, incomplete sequences of a neuroligin gene, the function of which is also unknown. All neuroligins have an extracellular domain homologous with acetylcholine esterase (ACHE). Neuroligins interact with β-neurexins, at the level of this extracellular component (Ichtchenko et al., Cell., 1995, 81(3):435-43). This interaction can be modulated by ACHE itself (Grifman et al., Proc. Natl. Acad. Sci. USA, 1998, 95(23):13935-40). At the cytoplasmic level, neuroligins interact with several proteins containing PDZ domains (Irie et al., Sciences, 1997, 277(5331):1511-5; Hirao et al., J. Biol. Chem. 1998, 273(33), 21105-10; Kurschner et al., Mol. Cell Neurosci., 1999, 11(3):161-72; Bolliger et al., Biochem J., 2001, 356:581-8; Toyooka et al., J. Neurochem., 2002, 83(4):797-806). Among these proteins, are the proteins of the DLG1-5 family (3q29, 11q13, Xq13.1, 17 p13.1 and 10q22.3), the S-SCAM protein (7q21.11), the proteins of the CIPP family (MPDZ, 9p23 and INADL, 1p31) and the CASK protein (Xp11).

In view of the above, it is clear that knowledge of the molecular bases of autism, and most particularly of the gene involved in the disease, is greatly desired in order to make it possible to develop novel therapeutic approaches, novel medicinal products and diagnostic tests.

A need also exists concerning identification of the biological function of neuroligins and also identification of the nucleic acid and protein sequence of neuroligins, in particular that of HNL3 and HNL4X.

The present invention satisfies these needs and other needs, as will be apparent to those skilled in the art upon reading the present description of the invention.

SUMMARY OF THE INVENTION

The present invention relates to the identification of human genes and of their murine ortholog encoding a protein involved in synaptogenesis, the mutation of which is associated, in humans, with the development of neurological diseases and/or with a predisposition to the development of mental disorders or psychiatric diseases such as autism and Asperger syndrome.

More particularly, a subject of the present invention is an isolated or purified polynucleotide encoding a polypeptide involved, in its wild-type form, in synaptogenesis. The polynucleotide of the present invention is characterized in that at least one mutation in the nucleic acid sequence of said polynucleotide is associated with the development of neurological diseases and/or with a predisposition to the development of mental disorders or psychiatric diseases.

Preferably, the present invention relates to a polynucleotide encoding a protein belonging to the family of human neuroligins (HNLs), and more particularly the HNL4X protein (previously called HNL4) and its functional homolog HNL4Y (previously called HNL5) encoded by a gene on the Y chromosome.

The present invention also relates to a polynucleotide encoding the mouse protein MNL4, which is the orthologs of the HNL4X and HNL4Y proteins.

According to another subject, the present invention is directed toward an isolated or purified polypeptide, characterized in that it is encoded by a polynucleotide as defined above. More particularly, the polypeptide according to the present invention is characterized in that it is involved in synaptogenesis, and in that the presence of at least one mutation in the amino acid sequence of said polypeptide is associated with a predisposition to the development of mental disorders or psychiatric diseases.

According to another subject, the present invention proposes a method for detecting biochemical disorders which alter synapse formation, and/or a predisposition to the development of psychiatric pathologies and/or a mental disease, comprising at least one of the following steps:

- detecting a mutation in the sequence of a polynucleotide as defined above, in the sequence of a fragment of said polynucleotide or in the sequence of a messenger RNA of said polynucleotide;
- detecting the presence of a polypeptide as defined above;
- detecting a mutation in a polypeptide as defined above;
- measuring the activity of a polypeptide as defined above or the interaction thereof with one of its protein partners.

Another object of the invention is to provide a kit for detecting biochemical disorders which alter synapse formation, and/or a predisposition to the development of psychiatric pathologies and/or a mental disease, and/or for diagnosing a mental disease, the kit comprising at least one of the elements chosen from the group consisting of: a probe, an antibody, a reagent and a solid support for:

i) detecting a mutation in the sequence of a polynucleotide as defined above, in the sequence of a fragment of said polynucleotide or in the sequence of a messenger RNA of said polynucleotide; and/or ii) measuring the biological activity of a polypeptide as defined above or the interaction thereof with one of its protein partners.

The invention also relates to the use of a nonmutated polynucleotide encoding a protein involved, in its wild-type form, in synaptogenesis, for treating or preventing biochemical pathologies or mental diseases.

The invention also relates to the use of a nonmutated polypeptide involved, in its wild-type form, in synaptogenesis, for treating or preventing biochemical pathologies or mental diseases.

The present invention also proposes a method for sorting molecules which makes it possible to modulate the biological activity of the polypeptide encoded by the polynucleotide defined above or the biological activity of the polypeptide defined above, comprising:

a) bringing said polypeptide or a recombinant cell containing it into contact with a molecule capable of modulating its biological activity;

b) measuring the biological activity of said polypeptide or its interaction with one of its protein partners; and c) evaluating the activity measured in step b) relative to a measurement of the biological activity of said polypeptide in the absence of said molecule.

Another subject of the present invention is directed toward a method for treating a mental or neurological disease, comprising the insertion into at least one portion of the cells from an affected patient of a polynucleotide encoding a polypeptide as defined above.

The present invention also proposes a method for transforming stem cells from a patient exhibiting a mutation of a gene encoding a protein involved in synaptogenesis, characterized by a) the use of stem cells from said patient;

b) the insertion into the genome of said stem cells of a polynucleotide as defined above; and c) the reimplantation into the patient of cells transformed according to step b).

The invention also relates to a cloning or expression vector comprising one of the polynucleotides of the invention or a fragment thereof; a host cell containing a polynucleotide and/or a vector according to the invention; or purified monoclonal or polyclonal antibodies which recognize specifically at least one of the polynucleotides of the invention and/or at least one of the polypeptides of the invention.

The invention is also directed toward a composition containing at least one element chosen from the group consisting of a) a polypeptide, b) a polynucleotide, c) a vector, d) a host cell and e) an antibody, and a pharmaceutically acceptable vehicle.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8A represents the genomic sequence (SEQ ID NO:1) of the wild-type (nonmutated) human HNL4X gene.

FIG. 8B represents the nucleic acid sequence (SEQ ID NO:16) of exon 1 of FIG. 8A.

FIG. 9 represents the complementary DNA sequence (SEQ ID NO:2) of the wild-type (nonmutated) human HNL4X gene.

FIG. 10 represents the amino acid sequence (SEQ ID NO:3) of the wild-type (nonmutated) human HNL4X protein.

FIG. 11A represents the genomic sequence (SEQ ID NO:4) of the human HNL4Y gene.

FIG. 11B represents the nucleic acid sequence (SEQ ID NO:17) of exon 1 of FIG. 11A.

FIG. 12 represents the complementary DNA (cDNA) sequence (SEQ ID NO:5) of the wild-type human HNL4Y gene.

FIG. 13 represents the amino acid sequence (SEQ ID NO:6) of the wild-type human HNL4Y protein.

FIG. 14 represents the complementary DNA (cDNA) sequence (SEQ ID NO:7) of an alternative transcript of the wild-type human HNL4Y gene.

FIG. 15 represents the amino acid sequence (SEQ ID NO:8) corresponding to the alternative sequence of FIG. 14.

FIG. 16 represents the amino acid sequence (SEQ ID NO:9) of the mutated human HNL4X protein.

FIG. 18 is a diagram which shows the conservation of the HNL3 mutations (Neuroligins-SEQ ID NOS:68-74; Acetylcholine esterase-SEQ ID NOS:75-88; Butyrylcholine esterase-SEQ ID NOS:89-92; HNL3 N796S-SEQ ID NOS: 93-98)

FIG. 19A shows the nucleic acid sequence of the cDNA of MNL4 (SEQ ID NO:62) (orthologs of HNL4X and HNL4Y).

FIG. 19B represents the amino acid sequence of the MNL4 protein (SEQ ID NO:63).

FIG. 20 is a diagram which shows the genomic structure of the HNL1, HNL2 and HNL3 genes, and also the location of the mutations observed in HNL3.

FIG. 21 is a diagram which shows the genomic structure of HNL4X and HNL4Y.

FIG. 22 shows a portion of the amino acid sequence (SEQ ID NO:10) of the HNL3 protein mutated at position 451.

FIG. 23 shows another portion of the amino acid sequence (SEQ ID NO:11) of the HNL3 protein mutated at position 796.

FIG. 24 represents the complementary DNA (cDNA) sequence (SEQ ID NO:12) of the wild-type HNL3 transcript.

FIG. 25 represents the complementary DNA (cDNA) sequence (SEQ ID NO:13) of the mutated HNL3 transcript.

FIG. 26 represents the amino acid sequence (SEQ ID NO:14) of the wild-type human HNL3 protein.

FIG. 27 represents the amino acid sequence (SEQ ID NO:15) of the mutated human HNL3 protein.

DETAILED DESCRIPTION OF THE INVENTION

Figure 1:
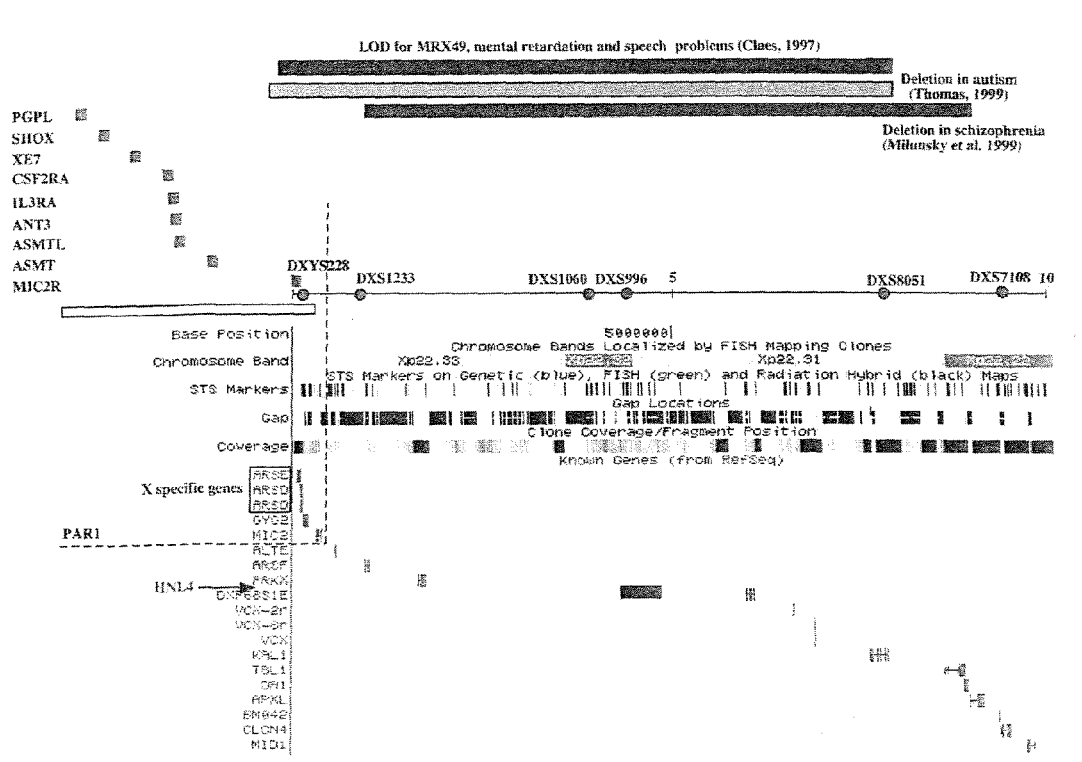
FIG. 1 shows the region of chromosome Xp22.3 containing the HNL4X gene.
Figure 2:
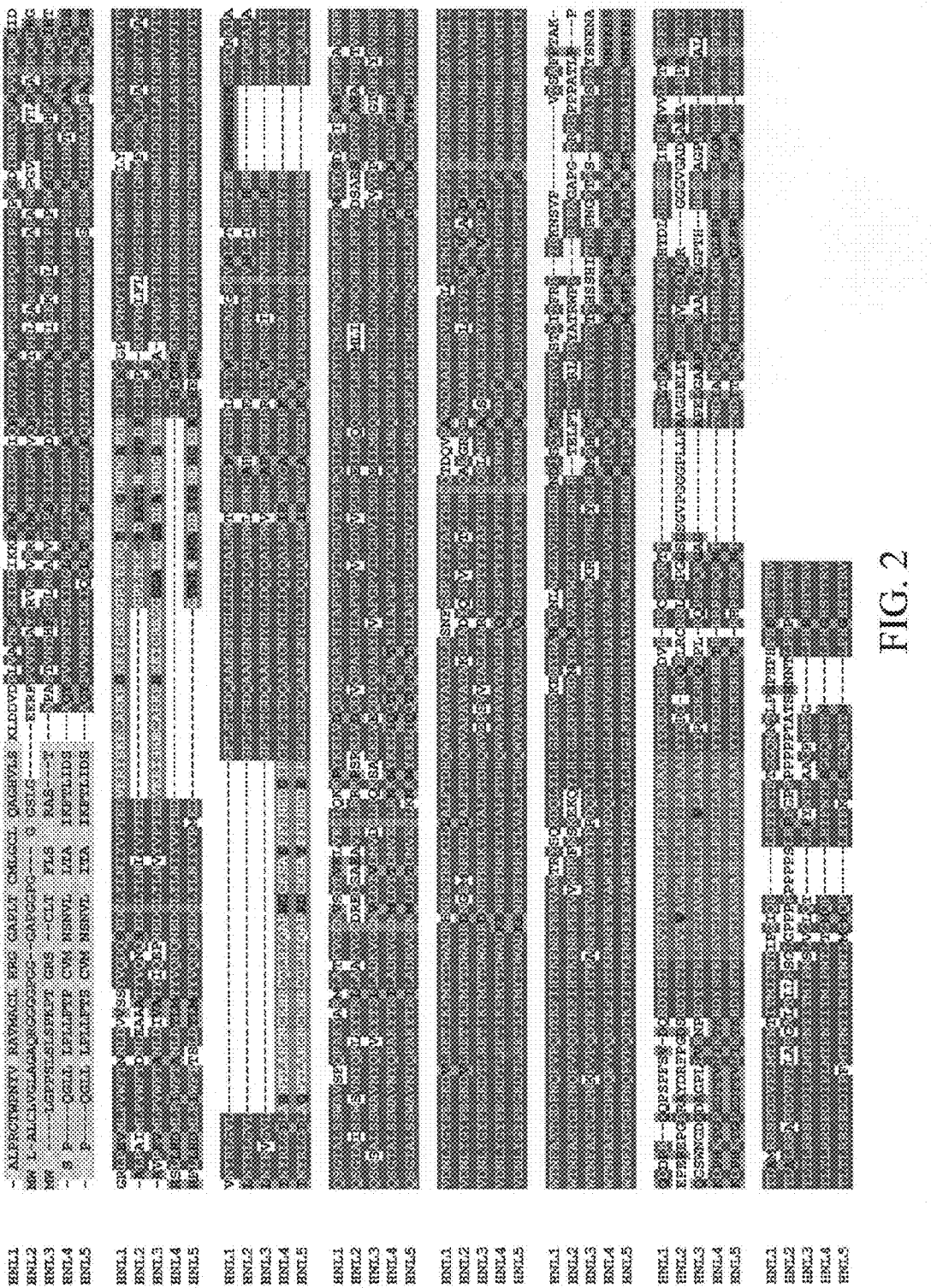
FIG. 2 shows a protein alignment for human neuroligins (HNL1-SEQ ID NO:64; HNL2-SEQ ID NO:65; HNL3-SEQ ID NO:66; HNL4-SEQ ID NO:67; HNL5-SEQ ID NO:6)
Figure 3:
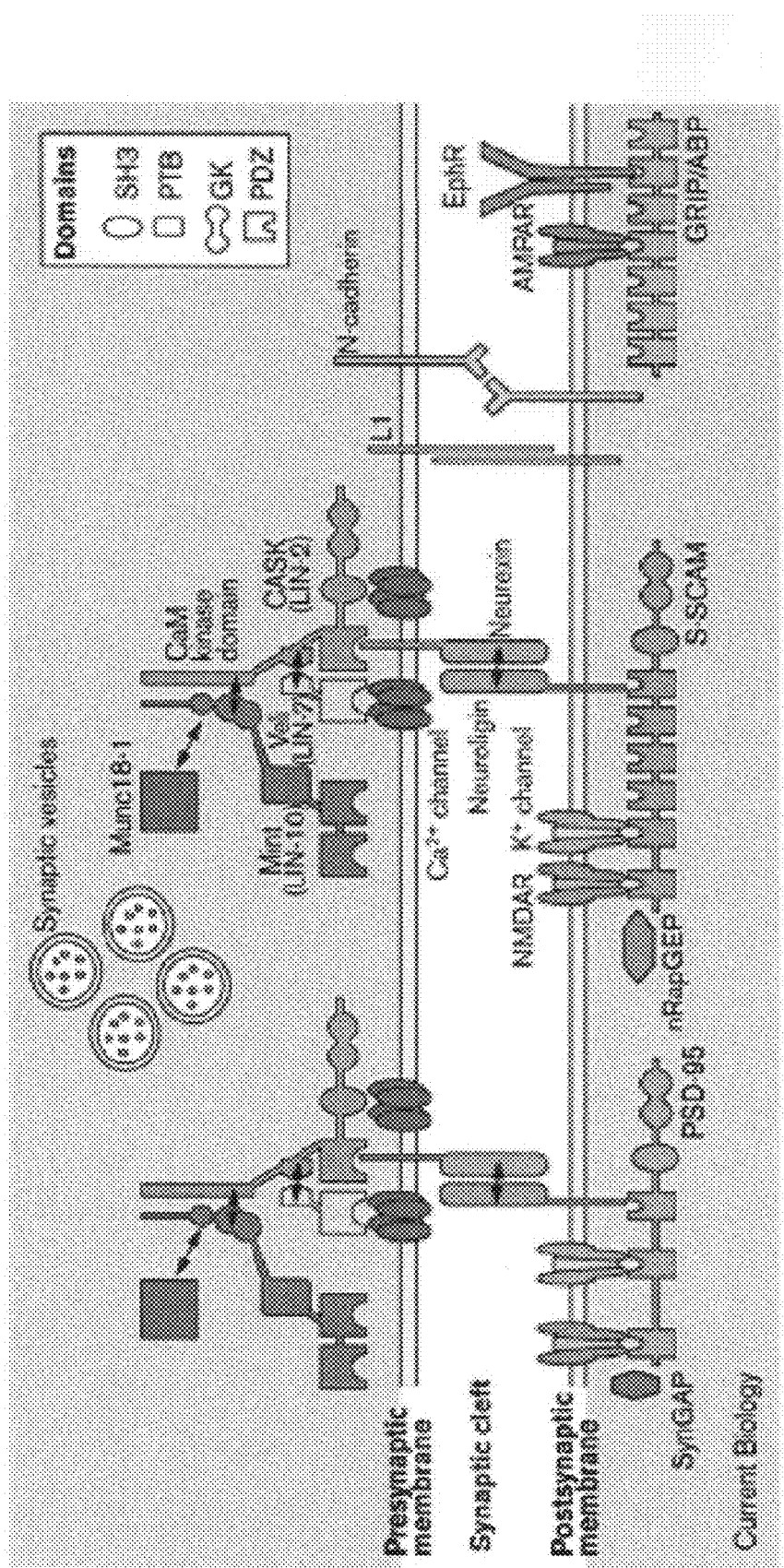
FIG. 3 is a diagram which shows the protein architecture of the synapse with the location and the known partners of neuroligins.
Figure 4:
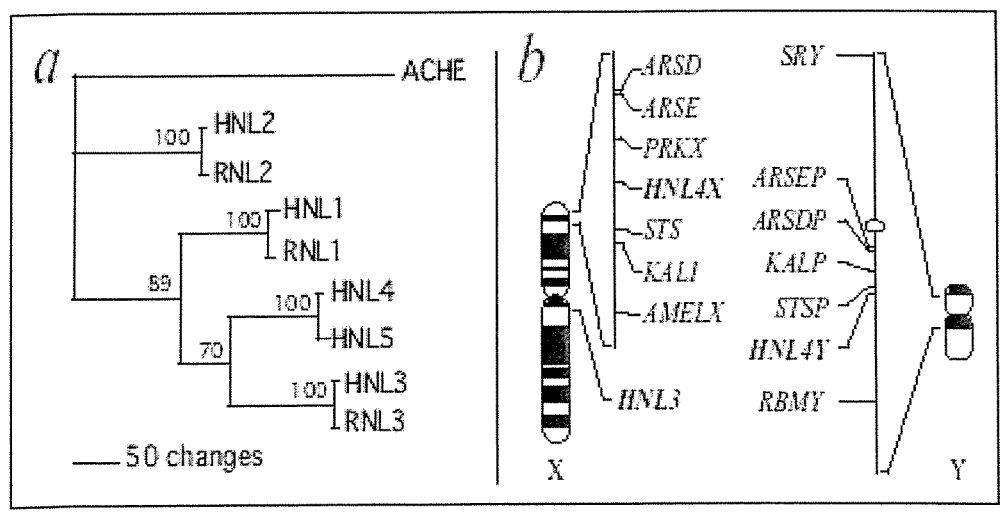
FIGS. 4A and 4B represent a diagram which shows the chromosomal location and the evolution of the HNL4X and HNL4Y genes.
Figure 5:
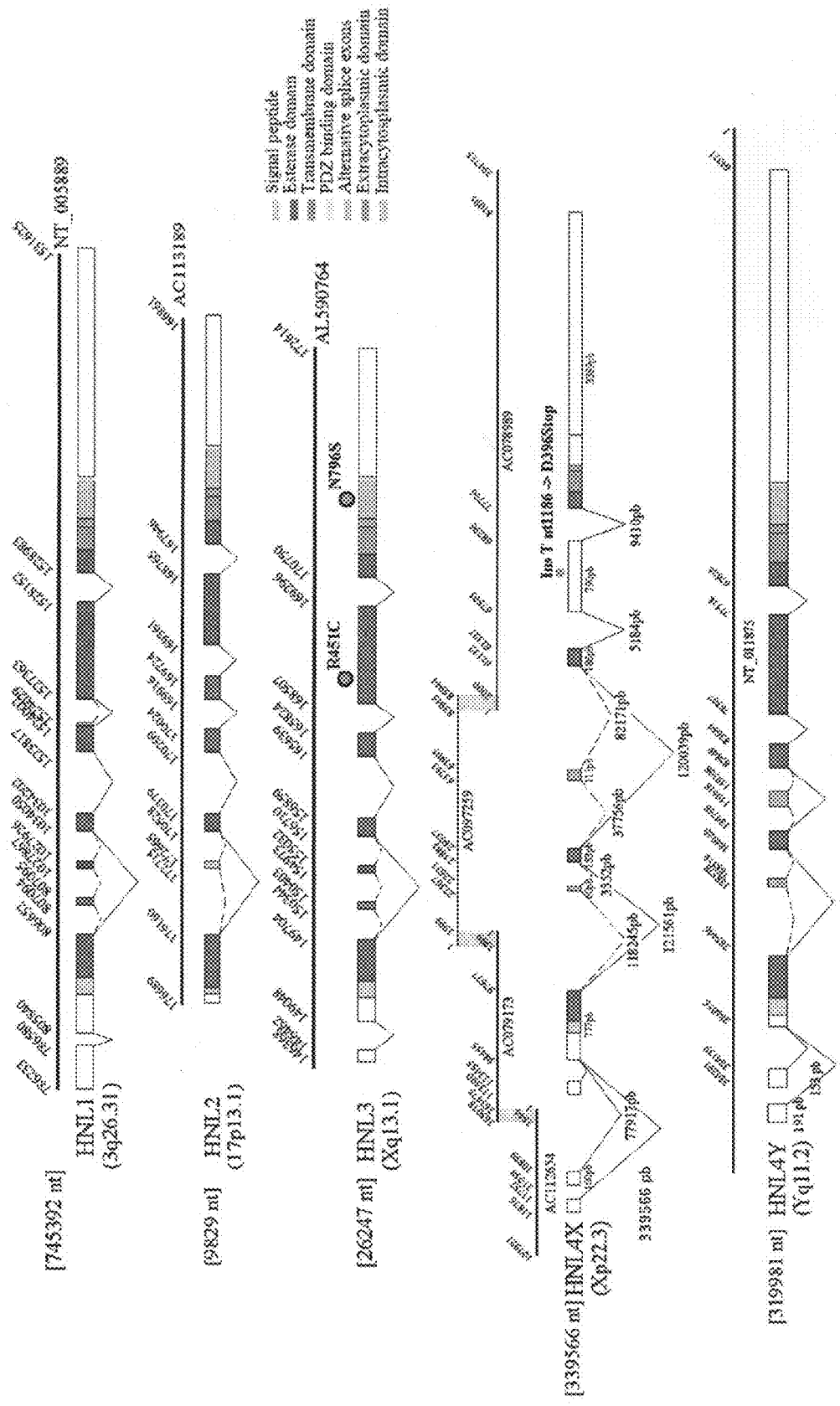
FIG. 5 is a diagram which shows the genomic structure of the human neuroligin genes.

The originality of the present invention relates to the identification of the genomic sequence of the HNL4X gene located at Xp22.3 and of a functional homolog HNL4Y placed on the Y chromosome, located at Yq11.22, and also their murine orthologs MNL4.

The invention also relates to the identification of the involvement of the proteins of synaptogenesis, in particular HNL3 and HNL4, in the development of mental disorders or psychiatric diseases such as autism.

1. Polypeptide and Polynucleotide

According to a first aspect, the present invention is directed toward an isolated or purified polypeptide which, in its wild-type (i.e. nonmutated) form, is involved in synaptogenesis, in which at least one mutation in the amino acid sequence is associated with the development of neurological diseases and/or with a predisposition to the development of mental disorders or psychiatric diseases.

The expression "mental disorders or psychiatric diseases" is intended to mean diseases such as autism, Asperger syndrome, schizophrenia and ADHD (attention deficit hyperactivity disorder) syndrome.

Preferably, the polypeptide consists of a cell adhesion protein, more preferably of a protein belonging to the human neuroligin family, and even more preferably the polypeptide consists of the HNL3 protein, HNL4X or the HNL4Y protein. Advantageously, when the polypeptide is HNL3, it comprises an amino acid sequence according to SEQ ID NO:14 and sequences of at least 20, of at least 50 and of at least 100 consecutive amino acids or more derived from SEQ ID NO:14. When the polypeptide of the invention is HNL4X or the HNL4Y protein, it comprises a sequence chosen from the group consisting of: SEQ ID NO:3, SEQ ID NO:6, SEQ ID NO:8 and the sequences of at least 20, of at least 50 and of at least 100 consecutive amino acids or more derived from SEQ ID NO:3, SEQ ID NO:6 or SEQ ID NO:8.

The invention also relates to the "mutated" polypeptides and the polypeptides "derived" from the wild-type protein, preferably a neuroligin such as HNL3, HNL4X or HNL4Y.

The term "polypeptide derived" from a wild-type protein or "variant" of a wild-type protein is intended to mean all peptides which have a peptide sequence substantially identical, at least in part, to the peptide sequence of the wild-type protein. They may, for example, be chemically modified polypeptides having a peptide sequence 100% identical to a portion of the wild-type protein. They may also be hybrid polypeptides having a first portion 100% identical to a first portion of the wild-type protein and a second portion in no way/partially identical to a second portion of the wild-type protein. They may also be polypeptides having complete/partial homology with a portion of the wild-type protein.

The term "mutated" polypeptides derived from a wild-type protein is intended to mean all peptides which have been obtained following modification of said wild-type protein, whether this is modification by addition, deletion or substitution of one or more of the amino acids of the wild-type protein. It may also be a modification introduced by the addition of carbon chains attached to at least one of the amino acids of the wild-type protein or to at least one of the amino acids of the peptides for which there exists a substitution or a modification of one of the amino acids compared to the wild-type protein. More particularly, the present invention covers the peptides which derive from the human protein HNL3, HNL4X or HNL4Y.

According to a preferred embodiment, and when the polypeptide is a mutated HNL3 according to the present invention, it has SEQ ID NO:10, SEQ ID NO:11 or SEQ ID NO:15, and a sequence of at least 20, of at least 50 and of at least 100 consecutive amino acids or more derived from SEQ ID NO:10, SEQ ID NO:11 or SEQ ID NO:15. When the polypeptide is a mutated HNL4X or a mutated HNL4Y according to the present invention, it has SEQ ID NO:9 or a sequence of at least 20, of at least 50 and of at least 100 consecutive amino acids or more derived from SEQ ID NO:9.

The invention is also directed toward the polypeptides (and the fragments thereof) which are encoded by the nucleotide sequences mentioned hereinafter.

In the context of the present invention, the term "polypeptide" is defined as being any peptide or protein comprising at least two amino acids linked by a modified or unmodified peptide bond. The term "polypeptide" refers to short-chain molecules such as peptides, oligopeptides or oligomers or to long-chain molecules such as proteins. A polypeptide according to the present invention can comprise modified amino acids. Thus, the polypeptide of the present invention can also be modified by a natural process such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, bonding with a lipid or a lipid derivative, covalent bonding with a phosphotidylinositol, crosslinking, cyclization, disulfide bond formation, demethylation, cysteine molecule formation, pyroglutamate formation, formylation, gamma-carboxylation, hydroxylation, iodination, methylation, oxidation, phosphorylation, racemization, hydroxylation, etc. Thus, any modification of the polypeptide which does not have the effect of eliminating the biochemical characteristics of the polypeptide of origin, i.e. the ability to form functional synapses, is covered within the scope of the present invention.

According to a related aspect, the invention is directed toward an isolated or purified polynucleotide encoding a polypeptide as defined above, and more particularly an isolated or purified polynucleotide encoding a polypeptide involved in synaptogenesis, in which at least one mutation of this polypeptide is associated with the development of neurological diseases and/or with a predisposition to the development of mental diseases or psychiatric diseases.

The term "isolated or purified" is intended to mean the molecules which have been altered, by man, from their natural state, i.e., if such a molecule exists naturally, it has been changed and/or removed from its initial environment. For example, a polynucleotide or a polypeptide naturally present in a living organism is not "isolated". However, the same polynucleotide or polypeptide, when separated from its normal environment and/or obtained by cloning, amplification and/or by chemical synthesis, is considered according to the present invention as being "isolated". Moreover, a polynucleotide or polynucleotide which is introduced into an organism by transformation or genetic manipulation or by any other method of recombination is "isolated" even if it is present in said organism.

The term "polynucleotide" is intended to mean any DNA or RNA molecule or sequence having two nucleotides or more, including the nucleic acid sequences encoding an entire gene. The term "polynucleotide" encompasses all nucleic acid molecules which are in the natural or artificial state. This includes DNA molecules, RNA molecules, cDNAs, expressed sequences (ESTs), artificial sequences and all the fragments thereof. It goes without saying that the "derived", "variant" and "mutated" definitions also apply to the polynucleotides according to the present invention. Any polynucleotide which has been chemically, enzymatically or metabolically modified but which has conserved the biochemical properties of the polypeptide of origin, i.e. which has conserved its ability to form functional synapses, is included in the scope of the present invention.

According to a preferred embodiment, when the polynucleotide according to the invention encodes an HNL3 protein or a fragment of this protein, the latter advantageously comprises SEQ ID NO: 14. Preferably, the polynucleotide comprises a sequence chosen from the group consisting of: SEQ ID NO: 12 and the sequences of at least 20, of at least 50 and of at least 100 consecutive nucleotides or more derived from SEQ ID NO: 12.

According to a preferred embodiment, when the polynucleotide according to the invention encodes an HNL4X or HNL4Y protein or a fragment of this protein, the latter advantageously comprises SEQ ID NO:3, SEQ ID NO:6 or SEQ ID NO:8. Preferably, the polynucleotide comprises a sequence chosen from the group consisting of: SEQ ID NO:1, SEQ ID NO:2, SEQ ID NO:4, SEQ ID NO:5, SEQ ID NO:7, SEQ ID NO:16, SEQ ID NO:17 and the sequences of at least 20, of at least 50 and of at least 100 consecutive nucleotides or more derived from these sequences.

Figures 6A, 6B:
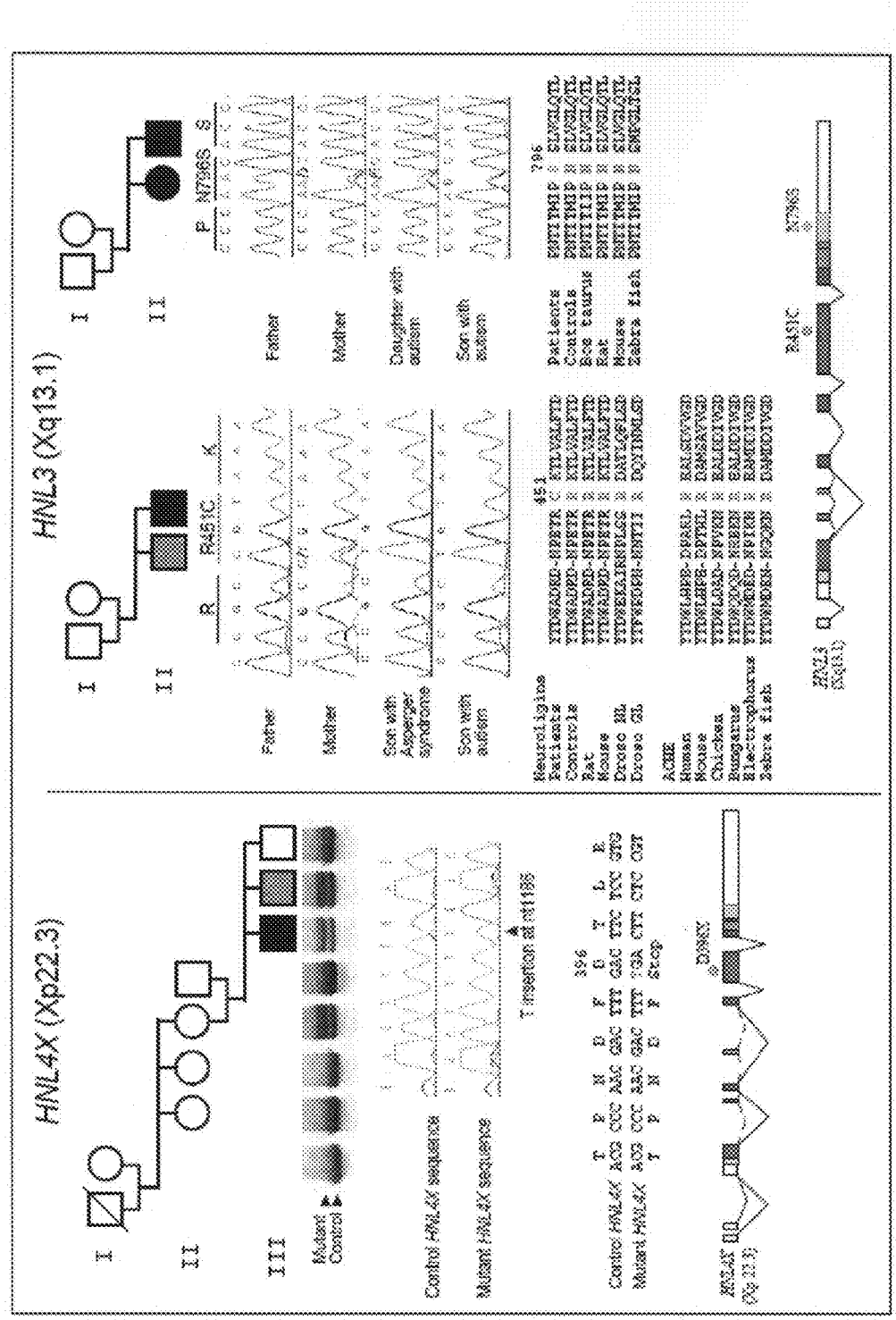
FIGS. 6A and 6B show the result of SSCP (single strand conformational polymorphism) analysis of a mutation of the gene encoding the HNL4X protein and also the sequence of this mutation.
Figure 7:
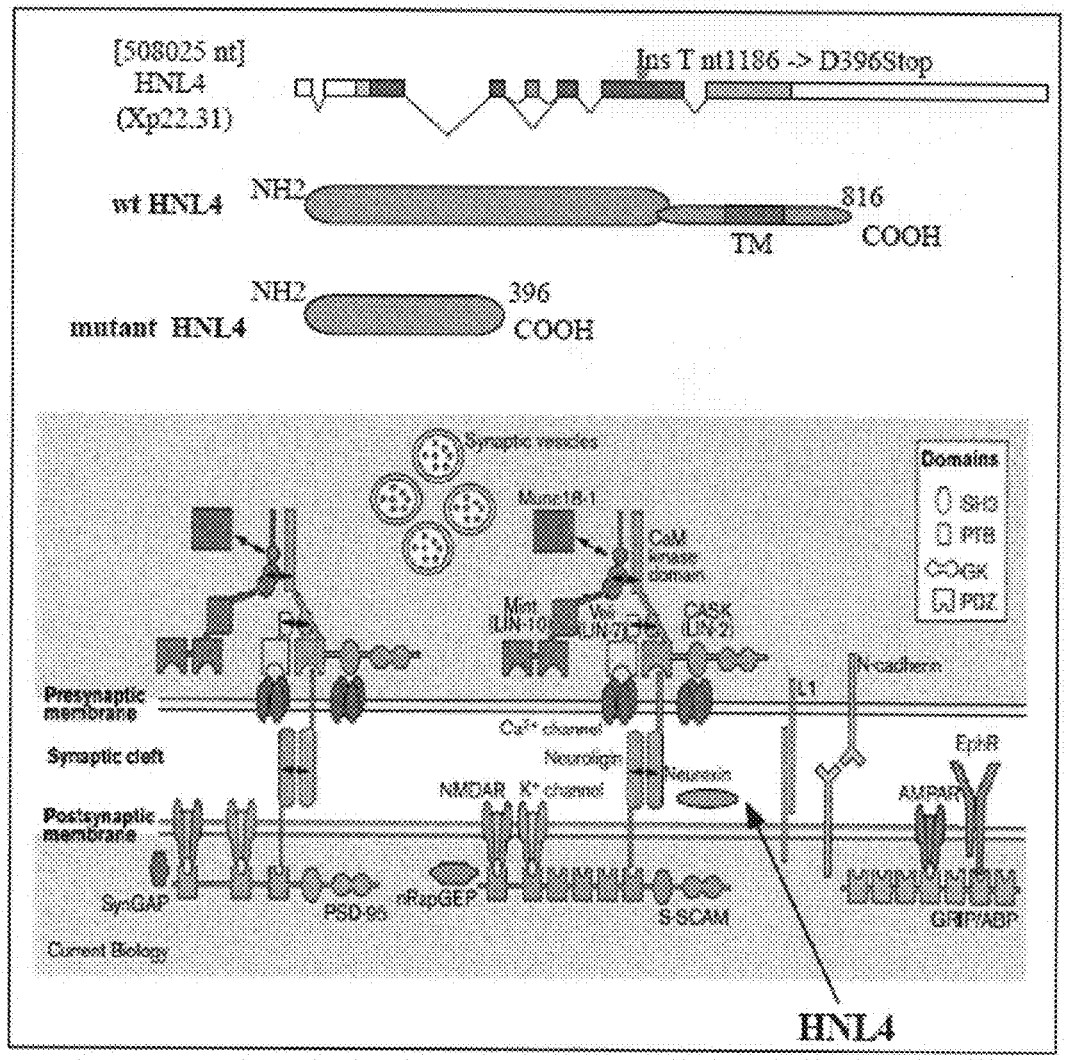
FIG. 7 is a diagram which shows the location of the HNL4X protein and the effects of the mutation on HNL4X.

According to another embodiment, the polynucleotide encodes a nonfunctional mutated protein. Preferably, the polynucleotide encodes a mutated HNL3 or mutated HNL4X protein. When the protein is HNL4X, the polynucleotide is mutated such that the mutation causes early termination of the protein. More preferably, the polynucleotide of the invention comprises SEQ ID NO:1 and the mutation is an insertion of a thymine at position 1186, from position 465 of FIG. 9 (ORF). This mutation causes the production of a defective protein lacking its transmembrane portion since this mutation causes early termination of the protein (D396stop). When the mutated protein is HNL3, the mutation causes a modification of the protein sequence such as an amino acid substitution at position 451 and/or 796 of FIG. 18 or 21. More particularly, the mutation produced at position 451 consists of the substitution of an arginine with a cysteine, while the mutation produced at position 796 consists of the substitution of an asparagine with a serine. This amino acid, arginine R451, is located in the acetylcholine esterase domain of the neuroligins and is extremely conserved in all the neuroligins sequenced to date and in fish, bird and reptile acetylcholine esterases (FIGS. 6A and 6B).

The polypeptides and polynucleotides according to the present invention can be prepared by any suitable method. They can in particular be obtained by chemical synthesis, but it is also possible to obtain them biologically, using in particular various vectors in suitable cell cultures, as will be described hereinafter. The peptides according to the present invention can be in deglycosylated or glycosylated form, if this is necessary. Those with knowledge in the field of the invention will be able to obtain various polynucleotides/polypeptides and will also be able to determine which, among the polynucleotides/polypeptides obtained, are those which have an appropriate biological activity.

2. Vector, Antibody and Cell

According to another aspect, the invention relates to any vector (cloning and/or expression vector) and any cellular host (procaryotic or eukaryotic) transformed with such a vector, and comprising the regulatory elements for expression of the nucleotide sequence encoding a peptide according to the invention.

According to another aspect, a subject of the invention is a method for preparing a peptide of the invention, by transformation of a cellular host using an expression vector (plasmid, cosmid, virus, etc.) comprising the DNA sequences encoding the peptides of the invention, followed by culturing of the cellular host thus transformed, and recovery of the peptide from the culture medium. The use of vectors for the expression of proteins and peptides in the cells of host, in particular humans, is well known and will not be described in further detail.

The polypeptides and polynucleotides of the present invention can also be used to prepare polyclonal or monoclonal antibodies capable of binding (preferably specifically) to at least one polypeptide/polynucleotide which is a subject of the invention. The present invention is therefore also directed toward such purified antibodies which can be obtained by very well-known techniques such as, for example, the technique described by Kohler and Milstein (Continuous cultures of fused cells secreting antibody of predefined specificity, Nature, 1975, 262:495-497). According to a preferred embodiment of the invention, the antibodies are of the "humanized" type. Those skilled in the field, by virtue of their general knowledge, will know how to prepare these types of antibodies.

In the context of the present invention, the term "vector" refers to a polynucleotide construct designed to be transfected into various cell types. As a result, these vectors are directed toward expression vectors designed for the expression of a nucleotide sequence in a host cell; cloning vectors designed for the isolation, propagation and replication of inserted nucleotides; viral vectors designed for the production of recombinant virus or of viral particle (viral-like particle); or shuttle vectors which comprise attributes of more than one vector.

3. Methods and Process for Use

According to another aspect, the invention relates to the treatment or prevention of biochemical pathologies or mental diseases such as autism or Asperger syndrome. More particularly, the invention is directed toward the use of a nonmutated polynucleotide encoding a protein involved in synaptogenesis. Preferably, the protein consists of a cell adhesion protein, more preferably of a protein belonging to the human neuroligin family, and even more preferably the polypeptide consists of the HNL3 protein, HNL4X or the HNL4Y protein. Examples of nonmutated polynucleotides are given above.

The invention is also directed toward a method of treatment comprising the insertion into at least one portion of the cells from an affected patient of a polynucleotide encoding a polypeptide involved in synaptogenesis, such as the HNL3 or HNL4X protein. Preferably, the cells into which the polynucleotide is inserted are stem cells. Examples of satisfactory polynucleotides are given above.

According to a related aspect, the invention is directed toward a method for transforming stem cells from a patient exhibiting a mutation of a gene encoding a protein involved in synaptogenesis, the method comprising:

a) the use of stem cells from the patient;
b) the insertion into the genome of the stem cells, of a polynucleotide encoding a functional polypeptide involved in synaptogenesis, such as the HNL3 or HNL4X protein; and
c) the reimplantation into the patient of cells transformed according to step b).

Those skilled in the field will be able to adapt the treatment methods mentioned above and to determine, according to several factors, the polynucleotides which should be used, the means for inserting them into the cells and the method and the amount of polynucleotides or of cells which should be administered. Among the factors which can influence their choices are: the nature of the treatment; the exact sequence of the polynucleotides; the stage of the disease; the condition, the age and the weight of the patient, etc.

According to another aspect, the invention also relates to a method for detecting biochemical disorders which alter synapse formation, stabilization and/or recognition, a predisposition to the development of psychiatric pathologies and/or a mental disease such as autism or Asperger syndrome.

Thus, the method comprises at least one of the following steps:
  detecting a mutation in the sequence of a gene encoding a protein involved in synaptogenesis, in the sequence of a fragment of this gene or in the sequence of a messenger RNA of this gene;
  detecting the presence of a protein involved in synaptogenesis;
  detecting a mutation in a protein involved in synaptogenesis;
  measuring the biological activity of a protein involved in synaptogenesis or its interaction with one of its protein partners. A method for measuring such an interaction is, for example, described in Ichtchenko et al. (J. Biol. Chem., 1996, 271(5):2676-82) or Grifman et al. (Proc. Natl. Acad. Sci. USA, 1998, 95(23):13935-40).

According to a preferred embodiment, the method comprises:
a) amplifying a gene encoding a protein involved in synaptogenesis, amplifying a fragment of said gene or amplifying a messenger RNA of said gene; and
b) detecting a mutation in the sequence of said gene, in the sequence of said fragment or in the sequence of said messenger RNA.

A related aspect of the method of the invention concerns a kit (set) for detecting biochemical disorders which alter synapse formation, a predisposition to the development of psychiatric pathologies and/or a mental disease, and/or for diagnosing a mental disease. According to a preferred embodiment, the kit comprises at least one of the elements chosen from the group consisting of: a probe, an antibody, a reagent and a solid support, these elements allowing:
i) detection of a mutation in the sequence of a gene encoding a protein involved in synaptogenesis, in the sequence of a fragment of this gene or in the sequence of a messenger RNA of this gene; and/or
ii) measurement of the biological activity of a protein involved in synaptogenesis or of its interaction with one of its protein partners.

Preferably, the gene to which reference is made in the method and the kit encodes, in its wild-type form, a cell adhesion protein, more preferably a protein belonging to the human neuroligin family, and even more preferably the HNL3 protein, the HNL4X protein or the HNL4Y protein.

Advantageously, the gene encodes, in its wild-type form, a protein comprising SEQ ID NO:3, SEQ ID NO:6, SEQ ID NO:8 or SEQ ID NO:14. More preferably, the gene comprises SEQ ID NO:1, SEQ ID NO:4 or SEQ ID NO:12.

Knowledge of the gene involved in a predisposition to the development of autism or of Asperger syndrome opens the door to the discovery of novel molecules for preventing, controlling or treating the disease. Thus, according to another aspect, the invention is directed toward a method for sorting molecules which can make it possible to modulate the biological activity of a polypeptide encoded by the polynucleotide as defined above, or the biological activity of the polypeptide as defined above. According to a preferred embodiment, the sorting method comprises:
a) bringing said polypeptide into contact with a molecule capable of modulating its biological activity;
b) measuring the biological activity of said polypeptide; and
c) evaluating the activity measured in step b) relative to a measurement of the biological activity of said polypeptide in the absence of said molecule.

4. Compositions

The present invention also relates to the use of these polypeptides and of the polynucleotides encoding them, for preparing therapeutic compositions that are useful in the treatment of a mental or neurological disease, such as autism, Asperger syndrome, schizophrenia or ADHD syndrome.

In a preferred embodiment, the composition of the present invention also contains a pharmaceutically acceptable vehicle, and an element chosen from the group consisting of:
  a polynucleotide according to the present invention;
  a polypeptide according to the present invention;
  an antibody according to the present invention;
  a vector according to the present invention; and
  a host cell according to the present invention.

The compositions according to the present invention can be in any solid or liquid form that is usual for pharmaceutical administration, i.e., for example, liquid administration forms or administration forms consisting of a gel, or any other support allowing, for example, controlled release. Among the compositions which can be used, mention may in particular be made of injectable compositions more particularly intended for injections into the blood circulation in humans.

Those skilled in the field will be able to prepare pharmaceutically acceptable compositions and to determine, according to several factors, the preferred mode of administration and the amount which should be administered. Among the factors which can influence their choices are: the nature of the treatment; the exact nature of the active or non-active ingredients which make up the composition; the stage of the disease; the condition, the age and the weight of the patient, etc.

The examples hereinafter will make it possible to demonstrate other characteristics and advantages of the present invention.

EXAMPLES

The examples which follow serve to illustrate the extent of the use of the present invention and not to limit its scope. Modifications and variations can be made thereto without departing from the spirit or from the scope of the invention. Although other methods or products equivalent to those which are found above may be used for testing or implementing the present invention, the preferred materials and methods are described.

Introduction

A locus for predisposition to autism has been suggested in Xp22.3 by the observation of several independent and de novo chromosomal deletions in this region. The size of the critical region deleted in these patients was approximately 10 Mb, delimited by DXYS232X (6 cM) and DXS7103 (16 cM). In support of these results, the overall analysis of the genome carried out by the Paris study (Philippe et al., 1999) indicates that the maximum LOD for the X chromosome is located in this region (11 cM).

Within this interval, we have identified the human neuroligin 4 (HNL4X gene encoding a new member of the neuroligin family (Scheiffele et al., 2000; Song et al., 1999). These cell adhesion molecules possess a homology with acetylcholine esterases and are specifically located in the postsynaptic membrane of excitatory synapses (Song et al., 1999). They are essential factors for the formation of functional synapses since the expression of neuroligins in HeLa cells or kidney cells can trigger the development of presynaptic structures in neurons which are in contact (Scheiffele et al., 2000). We have identified five HNL genes in the human genome, located on chromosomes 3q26 (HNL), 17 p13 (HNL), Xq13 (HNL), Xp22.3 (HNL4X) and Yq11.2 (HNL4Y). Neuroligin phylogeny suggests that HNL is the common ancestor of HNL4X and HNL4Y. The expression profile for the HNLs has been determined by specific RT-PCRs in various adult (male and female) brain tissues. Expression of the HNL genes and of their alternative transcripts is found in all brain regions. HNL4X and HNL4Y are expressed at similar levels in the male brain without significant differences between the various tissues. As expected, HNL4Y is not expressed in the female brain, whereas HNL4X is expressed.

Example 1

Characterization of the HNL4X and HNL4Y Genes and their Involvement in Psychiatric Syndromes The phylogenetic study shows that the HNL4X genes located on the X chromosome and the HNL4Y gene located on the Y chromosome began to diverge approximately 40 million years ago, during the evolution of primates. While all the genes of the Y chromosome which diverged at this date became pseudogenes (inactive genes), HNL4Y is strongly conserved (table 1).

This table includes the synonymous substitution rates (KS) and nonsynonymous substitution rates (KA) of all the known genes of the X chromosome having homology on the Y chromosome. The KS/KA ratio is an indication of the gene conservation. KS is the rate of synonymous substitution per synonymous site which represents the modifications which do not change the sequence of the protein. KA is the rate of nonsynonymous substitution per nonsynonymous site which represents the modifications which change the sequence of the protein. If the KS/KA ratio=1, then the gene is not conserved since there are as many synonymous modifications as there are nonsynonmyous modifications. This is the case for the X/Y pairs having a nonfunctional pseudogene on the Y chromosome (for example, KAL1/KALP*). If KS/KA>1, then the gene varies in the course of evolution but the protein is well conserved. This is the case for the HNL4/5 pair indicating that the genetic variation between these genes is subjected to a selection pressure which conserves the protein sequences of HNL4X and HNL4Y.

For the detection of mutations on the HNL4X gene, the following steps were used:
Materials and Methods
Identification of the Sequence of the HNL4X, HNL4Y and MNL4 Genes The HNL4X and HNL4Y genes were isolated by computer analysis of the sequences of the Xp22.3 and Yq11.22 region and amplification of the complete transcripts from brain mRNA.
Computer Analysis A systematic study of the genes of the Xp22.3 region, close to the DXS996 microsatellite, was carried out using the human genome sequencing data available through publicly available databases. The DXS996 microsatellite is the genetic marker which shows the most significant linkage with autism in the analysis by Philippe et al. (1999, mentioned above). We identified that this genetic marker was located in a putative gene (KIAA1260, and that a putative homolog, KIAA0951,

TABLE 1

Conservation of the HNL4X and HNL4Y genes during evolution

| Gene pair | Ks | KA | Ks/KA | DNA divergence (%) | Protein divergence (%) | Compared sequence (nucleotides) |
|---|---|---|---|---|---|---|
| GYG2/GYG2P* | 0.11 | 0.06 | 1.8 | 7 | 12 | 525 |
| ARSD/ARSDP* | 0.09 | 0.07 | 1.3 | 7 | 13 | 846 |
| ARSE/ARSEP* | 0.05 | 0.04 | 1.2 | 4 | 9 | 615 |
| PRKX/Y | 0.07 | 0.03 | 2.3 | 5 | 8 | 1020 |
| HNL4X/4Y | 0.079 | 0.012 | 6.456 | 3 | 2 | 2451 |
| STS/STSP* | 0.12 | 0.10 | 1.2 | 11 | 18 | 852 |
| KAL1/KALP* | 0.07 | 0.06 | 1.2 | 6 | 12 | 1302 |
| AMELX/Y | 0.07 | 0.07 | 1.0 | 7 | 12 | 576 |
|  |  |  | 3 |  |  |  |
| TB4X/Y | 0.29 | 0.04 | 7.3 | 7 | 7 | 135 |
| EIF1AX/Y | 0.32 | 0.01 | 32 | 9 | 2 | 432 |
| ZFX/Y | 0.23 | 0.04 | 5.8 | 7 | 7 | 2394 |
| DFFRX/Y | 0.33 | 0.05 | 6.6 | 11 | 9 | 7671 |
| DBX/Y | 0.36 | 0.04 | 9.0 | 12 | 9 | 1932 |
| CASK/CASKP* | 0.24 | 0.22 | 1.1 | 15 | 32 | 156 |
| UTX/Y | 0.26 | 0.08 | 3.3 | 12 | 15 | 4068 |
|  |  |  | 2 |  |  |  |
| UBE1X/Y | 0.58 | 0.07 | 8.3 | 16 | 13 | 693 |
| SMCX/Y | 0.52 | 0.08 | 6.5 | 17 | 15 | 4623 |
|  |  |  | 1 |  |  |  |
| RPS4X/Y | 0.97 | 0.05 | 19 | 18 | 18 | 792 |
| RBMX/Y | 0.94 | 0.25 | 3.8 | 29 | 38 | 1188 |
| SOX3/SRY | 1.25 | 0.19 | 6.6 | 28 | 29 | 264 |
| PCDHX/Y | 0.006 | 0.008 | 0.809 | 1 | 2 | 2850 | of this gene existed, located on the Y chromosome. The partial sequence of the cDNAs of the genes encoding KIAA1260 and KIAA0951 was deduced from the genomic sequence. A (BLAST) sequence alignment analysis and a phylogenetic tree grouping together the other human neuroligins were effected so as to define that KIAA1260 and KIAA0951 are new members of the neuroligin family which we henceforth call HNL4X and HNL4Y.

Analysis of the HNL4X and HNL4Y Transcripts

Total RNA from human brains coming from various men (n=5) and women (n=5) was isolated from biopsies of frontal cortex. The complete cDNAs of the HNL4X and HNL4Y mRNAs were reverse transcribed, amplified and directly sequenced. The oligonucleotides used for the amplification and sequencing are indicated in tables 2 and 3.

Sequencing of the HNL4X and HNL4Y Genes in Autistic and Asperger Individuals

Each exon of the HNL4X and HNL4Y genes was amplified and sequenced from the genomic DNA. The name and the sequence of each primer are indicated in table 3.

TABLE 2

Names and sequences of the primers used to amplify and sequence the HNL4X and HNL4Y cDNAs

| Exons | Primer | Sequence | SEQ ID NO |
|---|---|---|---|
| Exons 1-6 | HNLXY1 | ACCCCGCGTGAAGATGAAATG | SEQ ID NO: 18 |
|  | HNLXYE6dR | GAGGGATAGGARGGGAAATAG | SEQ ID NO: 19 |
| Exons 2-5 | HNLXYE2F | GGATGTGGATGCAGATTTGAA | SEQ ID NO: 20 |
|  | HNLXY4 | GCTCTGAATGATGGCCTTCTG | SEQ ID NO: 21 |
| Exons 4-6 | HNLXY10 | TCCTGGATCAGATTCAAGCAC | SEQ ID NO: 22 |
|  | HNLXYE6dR | GAGGGATAGGARGGGAAATAG | SEQ ID NO: 23 |
| Exons 2-6 | HNLXYE2F | GGATGTGGATGCAGATTTGAA | SEQ ID NO: 24 |
|  | HNLXYE6dR | GAGGGATAGGARGGGAAATAG | SEQ ID NO: 25 |

For the degenerate primers, use of the universal code: M(AC), R(AG), W(AT), S(CG), Y(CT), K(GT), V(ACG), H(ACT), D(AGT), B(CGT), N(ACGT)

TABLE 3

Names and sequences of the primers used to sequence the HNL4X and HNL4Y genes

| Exons | Primers | Sequences | SEQ ID NO: |
|---|---|---|---|
| Exon 1a HNL4X | HNLXYE1aF | GAAACAACGAATTTCCTCCAAA | 26 |
|  | HNLXYE1aR | AGTGAGGCTTTCCATCCTTTGC | 27 |
| Exon 1b HNL4X | HNLXE1F | ATTCTTTAAGAAAACTGTCAGC | 28 |
|  | HNLXYE1R | CACGGGAAAGGGGTGCATGGA | 29 |
| Exon 1 HNL4Y | HNLYE1F | GGGGTGCTTCTTTTGGGAGGCT | 30 |
|  | HNLXYE1R | CACGGGAAAGGGGTGCATGGA | 31 |
| Exon 2 HNLX/Y | HNLXYE2F | GGATGTGGATGCAGATTTGAA | 32 |
|  | HNLXE2Rbis | GTATTGTTTTCTGTTCCAGTG | 33 |
| Exon 3 HNL4X/Y | HNLXYE3F | TGTGTTTCCGTACTTGGCTTT | 34 |
|  | HNLXYE3R | GCTTAGTCATTCACATGATGAA | 35 |
| Exon 4 HNL4x | HNLXYE4F | ACCAAAAATCTCTTGTGTTCT | 36 |
|  | HNLXYE4R | TTCTTGGTTCAGGGTATTTGC | 37 |
| Exon 4 HNL4Y | HNLYE4F | AACAAAAATGTCCTGTGTTCT | 38 |
|  | HNLXYE4R | TTCTTGGTTCAGGGTATTTGC | 39 |
| Exon 5 HNL4X/Y | HNLXYE5dF | TGTCCRCAATTTTGCACCTGC | 40 |
|  | HNLXYE5dR | AGGAYAGTGATACCCCAACA | 41 |
| Exon 6 HNL4X/Y | HNLXYE6Fbis | AGAGCAGATTGTAACTTCCTG | 42 |
|  | HNLXYE6dR | GAGGGATAGGARGGGAAATAG | 43 |

For the degenerate primers, use of the universal code: M(AC), R(AG), W(AT), S(CG), Y(CT), K(GT), V(ACG), H(ACT), D(AGT), B(CGT), N(ACGT).

TABLE 4

Names and sequences of the primers used for the amplification of the MNL4 cDNA (57BL6 mouse)

| Primer | Sequence | SEQ ID NO: |
|---|---|---|
| MNL4F8 | CGTGACGAAACAGGAAGTGACC | 44 |
| MNL4R8 | GTAGCCAAGGCCCCTGCATGTC | 45 |

TABLE 5

Names and sequences of the primers used for the amplification of MNL4 in three PCRs of approximately 1 kb

| Primer | Sequence | SEQ ID NO: |
|---|---|---|
| MNL4F8 | CGTGACGAAACAGGAAGTGACC | 46 |
| MNL4R2 | AGCCGAAGACGGTGACGCGGTC | 47 |
| MNL4F12 | AGGAAGCCGGTCATGGTTTACA | 48 |
| MNL4R5 | ACGCTCAGCTCCGTCGAGTAGT | 49 |
| MNL4F14 | AGACGCTCGTGGCGCTCTTCAC | 50 |
| MNL4R8 | GTAGCCAAGGCCCCTGCATGTC | 51 |

TABLE 6

Names and sequences of the primers used for the amplification of HNL3

| PRIMER | SEQUENCE | SEQ ID NO: |
|---|---|---|
| HNL3E2F | CCTATTGGGCTGATGCTGTGACC | 52 |
| HNL3E2R | AGGGCACACAACCACATGCAAG | 53 |
| HNL3E3Fbis | TTGAGCTCCAGGTTGAGCAACC | 54 |
| HNL3E3RBIS | CCCCTTGCGAAGCCAGTCTTCC | 55 |
| HNL3E4F | CTGCGTGCTCATTCTCTATTCC | 56 |
| HNL3E4R | GTAGAAGAGCTGGCCGATTC | 57 |
| HNL3E5F | ATGGCTATGTGTGACACGACAG | 58 |
| HNL3E5R | GGAAGATGAGTGAAGGGGTACC | 59 |
| HNL3E6F | TTTCCTCATCCAGATAGAGTGG | 60 |
| HNL3E6R | CATGTGTTCCTGGATCTGGGAG | 61 |

In order to test this gene in autistic individuals, the genomic structure of the various HNLs was defined and the coding portions (Exon 2-Exon 6) were amplified.

Thus, 140 autistic boys and 18 autistic girls were tested for most of the HNL4X/4Y coding portion.

Figure 17:
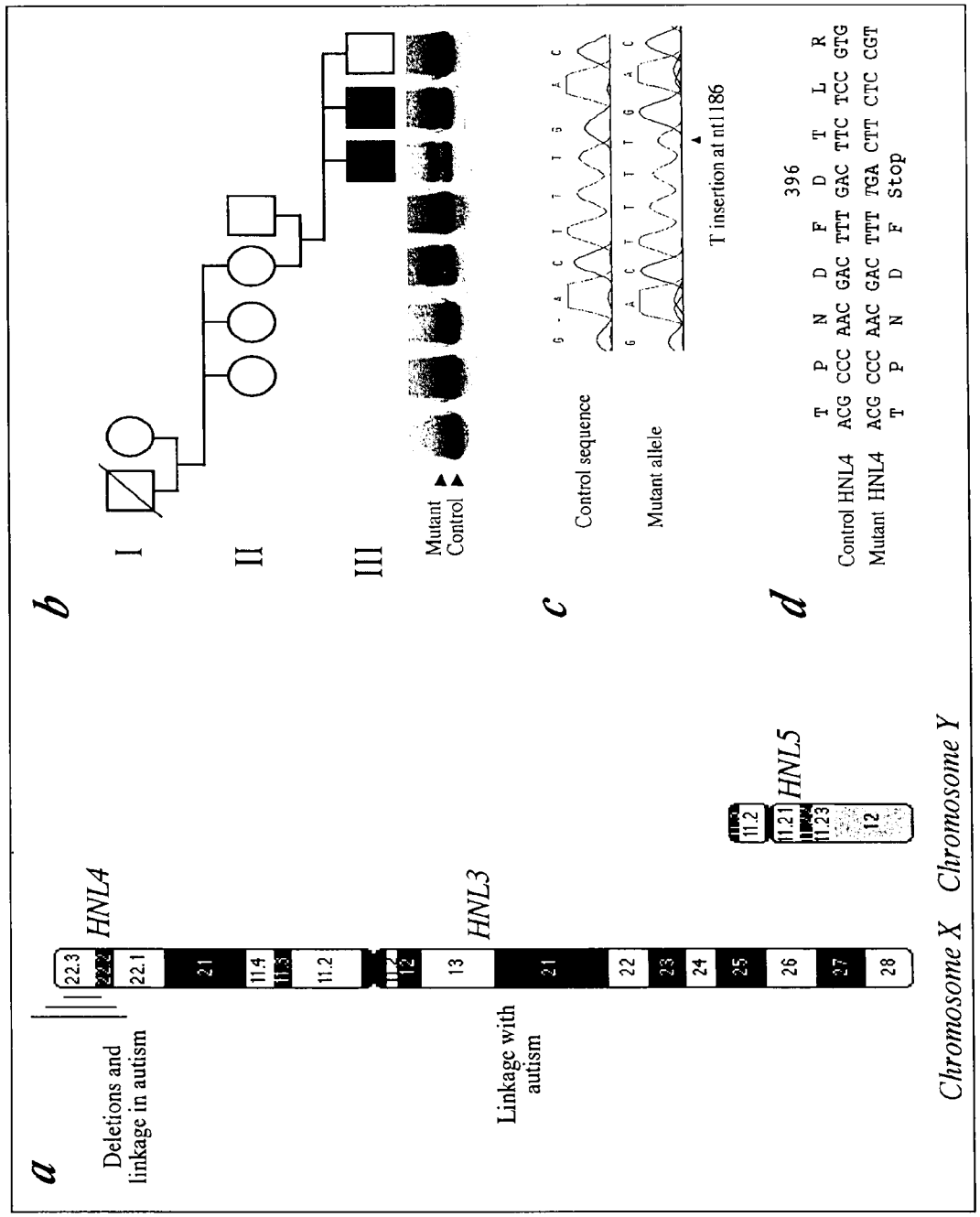
FIG. 17 shows the chromosomal location of the HNL3, HNL4X and HNL4Y genes and the pedigree of a family exhibiting a mutation in HNL4X in an autistic boy and a boy suffering from Asperger syndrome.

In a Swedish family with two affected brothers, one with autism and the other exhibiting Asperger syndrome, an additional thymidine was identified at nucleotide 1186 of the HNL4X gene, creating a stop codon (FIG. 17). This mutation (D396stop) is located in the esterase domain, producing a premature termination of the protein and deleting the transmembrane domain. This change is inherited from the mother, but is absent in the maternal grandmother, in the two maternal aunts and in the unaffected child, indicating the de novo status of this mutation in the mother of the affected boys. In addition, this mutation was not found in 350 controls (250 women and 100 men).

In addition, the boy/girl ratio, which is four for autism and nine for Asperger syndrome, corroborates this observation according to which HNL4X/4Y influences synaptogenesis and the mutation of HNL4X/4Y constitutes a factor for predisposition to mental diseases, in particular autism and Asperger syndrome.

The identification of this stop mutation in a primate-specific gene carried by the X chromosome in two autistic individuals, and involved in synaptogenesis, is one of the first functional mutations identified in a psychiatric disease. This mutation is also the first mutation described which is associated with autism without any other clinical sign (fragile X, tubercular sclerosis, etc.).

Example 2

Characterization of the HNL3 Gene and of its Involvement in Psychiatric Syndromes During the search for mutations in HNL, the ancestral gene for HNL4X/Y located in the Xq13 region, in two independent families, two amino acid changes located in highly conserved regions of the protein were identified. One of the two families is very similar to the first family mutated in HNL4X. The two affected brothers, the first affected with autism and the second with Asperger syndrome, received the mutation from their mother. Interestingly, the mother also has a brother with Asperger syndrome and other relatives with psychiatric disorders. The mutation (R451C) is located in the esterase domain of the protein and concerns an amino acid that is conserved during evolution since it is present in all neuroligins (including in *D. melanogaster*) and in all the mammalian, fish, reptile and bird acetylcholine esterases sequenced to date (see FIG. 6). The mutation is absent in 200 controls (100 women and 100 men). These results support the role of neuroligins in the etiology of mental disorders or psychiatric diseases such as autism and Asperger syndrome. MNL4, the orthologs of HNL4X in mice, was also identified. This new gene should make it possible to understand the deficiency induced by a mutation such as the HNL4X mutation in autism (see FIG. 19).

The final examination of the genome carried out on Finnish families with members suffering from autism (Auranen, et al., 2002) identified two very significant linkage peaks at 3q26 (exactly where HNL is located) and at Xq13-21 (exactly where HNL is located). The Xp22.3 region, containing HNL4X, is also deleted in two patients with schizophrenia. It is therefore possible that neuroligins are also responsible for susceptibility to this syndrome (schizophrenia affects 1% of the population).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07906640B2). An electronic copy of the "Sequence Listing" will also be available from the USPTO upon request and payment of the fee set forth in 37 CFR 1.19(b)(3).

The invention claimed is:

1. A kit for diagnosing autism linked to a mutation in the polynucleotide of SEQ ID NO: 12 or the polypeptide of SEQ ID NO: 14, or a propensity therefor, in a human, wherein said mutation results in altered synapse formation, the kit comprising
 a probe for detecting mutations in the polynucleotide of SEQ ID NO: 12, wherein said probe is specific for detecting a mutation in the polynucleotide of SEQ ID NO: 12, wherein said mutation results in a mutation in the polypeptide encoded thereby at position 451 or 796, or a combination thereof, or
 an antibody specific for detecting mutations at position 451 or 796, or a combination thereof, in the polypeptide of SEQ ID NO: 14 and
 at least one of the elements selected from the group consisting of a reagent and a solid support for:
 (a) detecting a mutation in
  (i) the polynucleotide of SEQ ID NO: 12, wherein said mutation results in a mutation in the polypeptide encoded thereby at position 451 or 796, or a combination thereof, or
  (ii) the polypeptide of SEQ ID NO: 14, wherein said mutation is at position 451 or 796, or a combination thereof,
 wherein said detecting comprises comparing the sequence of the polynucleotide or polypeptide obtained from said human with the polynucleotide of SEQ ID NO: 12 or the polypeptide of SEQ ID NO: 14 and identifying mutations in said polynucleotide or polypeptide from said human; and
 (b) correlating said mutations in said polynucleotide or polypeptide from said human with autism or a propensity for autism.

2. The kit as claimed in claim 1, wherein said kit comprises a probe for detecting mutations in the polynucleotide of SEQ ID NO: 12.

3. The kit as claimed in claim 1, wherein said kit comprises an antibody specific for detecting mutations in the polypeptide of SEQ ID NO: 14.

* * * * *